(12) United States Patent
Gullotti et al.

(10) Patent No.: US 11,540,767 B2
(45) Date of Patent: Jan. 3, 2023

(54) INTRAOPERATIVE ALIGNMENT ASSESSMENT SYSTEM AND METHOD

(71) Applicant: GLOBUS MEDICAL, INC., Audubon, PA (US)

(72) Inventors: David Michael Gullotti, Newtown Square, PA (US); Amir Hossein Soltanianzadeh, Malibu, CA (US); Nicholas Theodore, Ruxton, MD (US); Edward Frederick Ruppel, III, Saratoga, CA (US); Nicholas Griesmer Franconi, Pittsburgh, PA (US); Sritam Parashar Rout, Bhubaneswar (IN); Saki Fujita, Baltimore, MD (US); Marc Chelala, Montreal (CA); Kyle Robert Cowdrick, Lilburn, GA (US); Maria Fernanda Torres, Caracas (VE)

(73) Assignee: Globus Medical Inc., Audubon, PA (US)

( * ) Notice: Subject to any disclaimer, the term of this patent is extended or adjusted under 35 U.S.C. 154(b) by 628 days.

(21) Appl. No.: 16/237,443

(22) Filed: Dec. 31, 2018

(65) Prior Publication Data
US 2019/0209080 A1 Jul. 11, 2019

Related U.S. Application Data

(63) Continuation-in-part of application No. 16/026,754, filed on Jul. 3, 2018, now abandoned.
(Continued)

(51) Int. Cl.
*A61B 5/00* (2006.01)
*A61B 17/70* (2006.01)
(Continued)

(52) U.S. Cl.
CPC .......... *A61B 5/4566* (2013.01); *A61B 5/1072* (2013.01); *A61B 17/7032* (2013.01);
(Continued)

(58) Field of Classification Search
CPC combination set(s) only.
See application file for complete search history.

(56) References Cited

U.S. PATENT DOCUMENTS

| 6,340,363 B1 | 1/2002 | Bolger et al. |
| 6,956,202 B2 | 10/2005 | Sabczynski et al. |

(Continued)

FOREIGN PATENT DOCUMENTS

| DE | 102015102776 A1 | 9/2016 |
| JP | 2005030911 A | 2/2005 |

(Continued)

OTHER PUBLICATIONS

International Search Report and Written Opinion for International Application No. PCT/US2018/068212, dated Jun. 26, 2019, 19 pages.

(Continued)

*Primary Examiner* — Sameh R Boles

(57) ABSTRACT

Some embodiments provide systems, assemblies, and methods of analyzing patient anatomy including providing an analysis of a patient's spine. The systems, assemblies, and/or methods can include obtaining initial patient data, and acquiring spinal alignment contour information. Further, the systems, assemblies, and/or methods can assess localized anatomical features of the patient, and obtain anatomical region data. The system, assemblies, and/or method can analyze the localized anatomy and therapeutic device location and contouring. Further, the system, assemblies, and/or method can output localized anatomical analyses and therapeutic device contouring data and/or imagery on a display.

1 Claim, 222 Drawing Sheets

Related U.S. Application Data

(60) Provisional application No. 62/528,390, filed on Jul. 3, 2017.

(51) Int. Cl.

| | | |
|---|---|---|
| *A61B 34/20* | (2016.01) | |
| *A61B 5/107* | (2006.01) | |
| *A61B 90/00* | (2016.01) | |
| *A61B 90/90* | (2016.01) | |
| *A61B 46/10* | (2016.01) | |
| *A61B 17/88* | (2006.01) | |
| *A61B 90/98* | (2016.01) | |
| *G09B 23/30* | (2006.01) | |
| *A61B 17/86* | (2006.01) | |
| *A61B 17/58* | (2006.01) | |
| *A61B 17/60* | (2006.01) | |
| *A61F 2/00* | (2006.01) | |
| *A61B 90/92* | (2016.01) | |
| *A61B 90/50* | (2016.01) | |
| *A61B 34/10* | (2016.01) | |
| *A61B 17/00* | (2006.01) | |

(52) U.S. Cl.
CPC ...... *A61B 17/7035* (2013.01); *A61B 17/7076* (2013.01); *A61B 17/7077* (2013.01); *A61B 17/7086* (2013.01); *A61B 17/7091* (2013.01); *A61B 17/8615* (2013.01); *A61B 17/8863* (2013.01); *A61B 34/20* (2016.02); *A61B 46/10* (2016.02); *A61B 90/39* (2016.02); *A61B 90/90* (2016.02); *A61B 90/98* (2016.02); *G09B 23/30* (2013.01); *A61B 90/92* (2016.02); *A61B 2017/00477* (2013.01); *A61B 2017/00707* (2013.01); *A61B 2017/00725* (2013.01); *A61B 2034/105* (2016.02); *A61B 2034/207* (2016.02); *A61B 2034/2048* (2016.02); *A61B 2034/2055* (2016.02); *A61B 2034/2057* (2016.02); *A61B 2034/2059* (2016.02); *A61B 2034/2065* (2016.02); *A61B 2090/036* (2016.02); *A61B 2090/061* (2016.02); *A61B 2090/067* (2016.02); *A61B 2090/363* (2016.02); *A61B 2090/376* (2016.02); *A61B 2090/378* (2016.02); *A61B 2090/3916* (2016.02); *A61B 2090/3937* (2016.02); *A61B 2090/3966* (2016.02); *A61B 2090/3983* (2016.02); *A61B 2090/3991* (2016.02); *A61B 2090/502* (2016.02)

(56) References Cited

U.S. PATENT DOCUMENTS

| | | |
|---|---|---|
| 2005/0004451 A1 | 1/2005 | Vilsmeier |
| 2005/0165292 A1* | 7/2005 | Simon ............... A61B 6/583 |
| | | 600/407 |
| 2006/0009780 A1 | 1/2006 | Foley et al. |
| 2006/0084867 A1 | 4/2006 | Tremblay et al. |
| 2007/0167787 A1 | 7/2007 | Glossop et al. |
| 2008/0167547 A1 | 7/2008 | Bova |
| 2008/0200794 A1 | 8/2008 | Teichman et al. |
| 2009/0118742 A1 | 5/2009 | Hartmann et al. |
| 2010/0160771 A1 | 6/2010 | Gielen |
| 2012/0201421 A1 | 8/2012 | Hartmann et al. |
| 2014/0316420 A1 | 10/2014 | Ballard et al. |
| 2015/0051489 A1 | 2/2015 | Caluser et al. |
| 2015/0088093 A1 | 3/2015 | Goetz |
| 2016/0242857 A1 | 8/2016 | Scholl |
| 2016/0256225 A1 | 9/2016 | Crawford et al. |
| 2016/0331479 A1 | 11/2016 | Crawford |

FOREIGN PATENT DOCUMENTS

| | | |
|---|---|---|
| JP | 2006081569 A | 3/2006 |
| JP | 2007508901 A | 4/2007 |
| JP | 2013512762 A | 4/2013 |
| JP | 2015502766 A | 1/2015 |
| KR | 1020130094295 A | 8/2013 |
| WO | 2013044157 A1 | 3/2013 |
| WO | 2017077356 A1 | 5/2017 |

OTHER PUBLICATIONS

International Search Report and Written Opinion for International Application No. PCT/US2018/040754, dated Oct. 26, 2018, 9 pages.

* cited by examiner

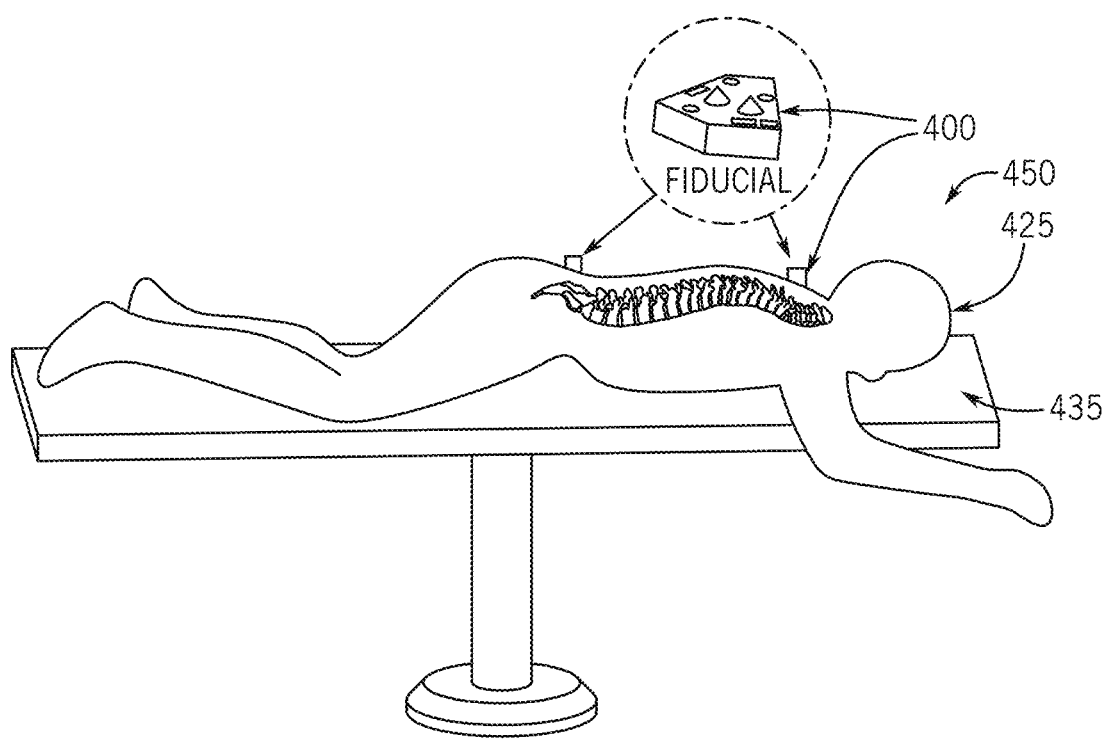
FIG. 4A
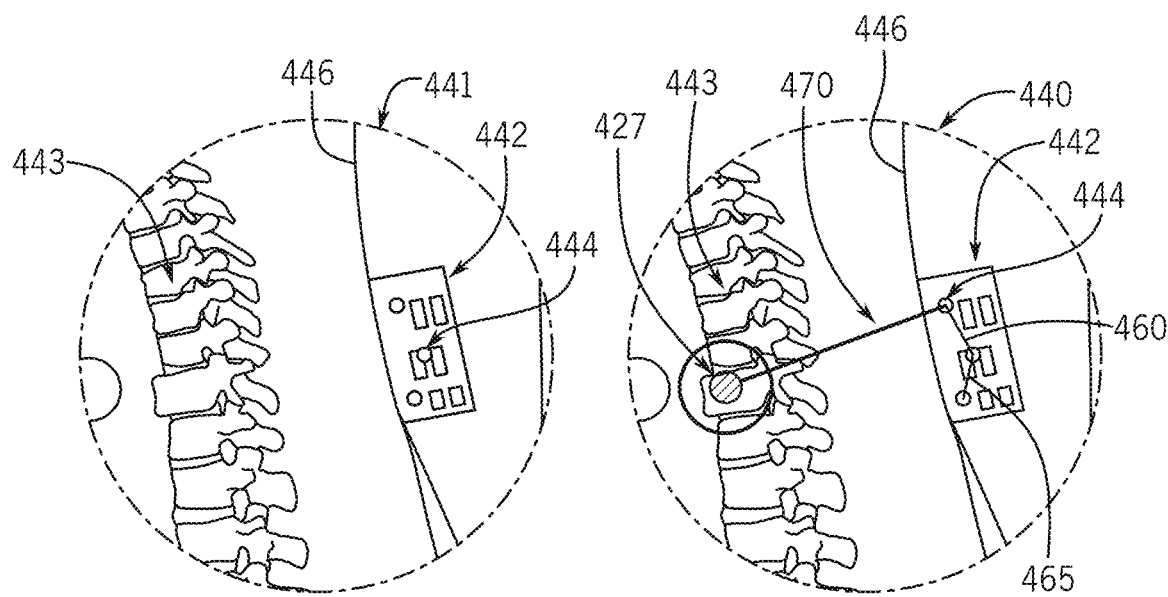
FIG. 4B
FIG. 4C

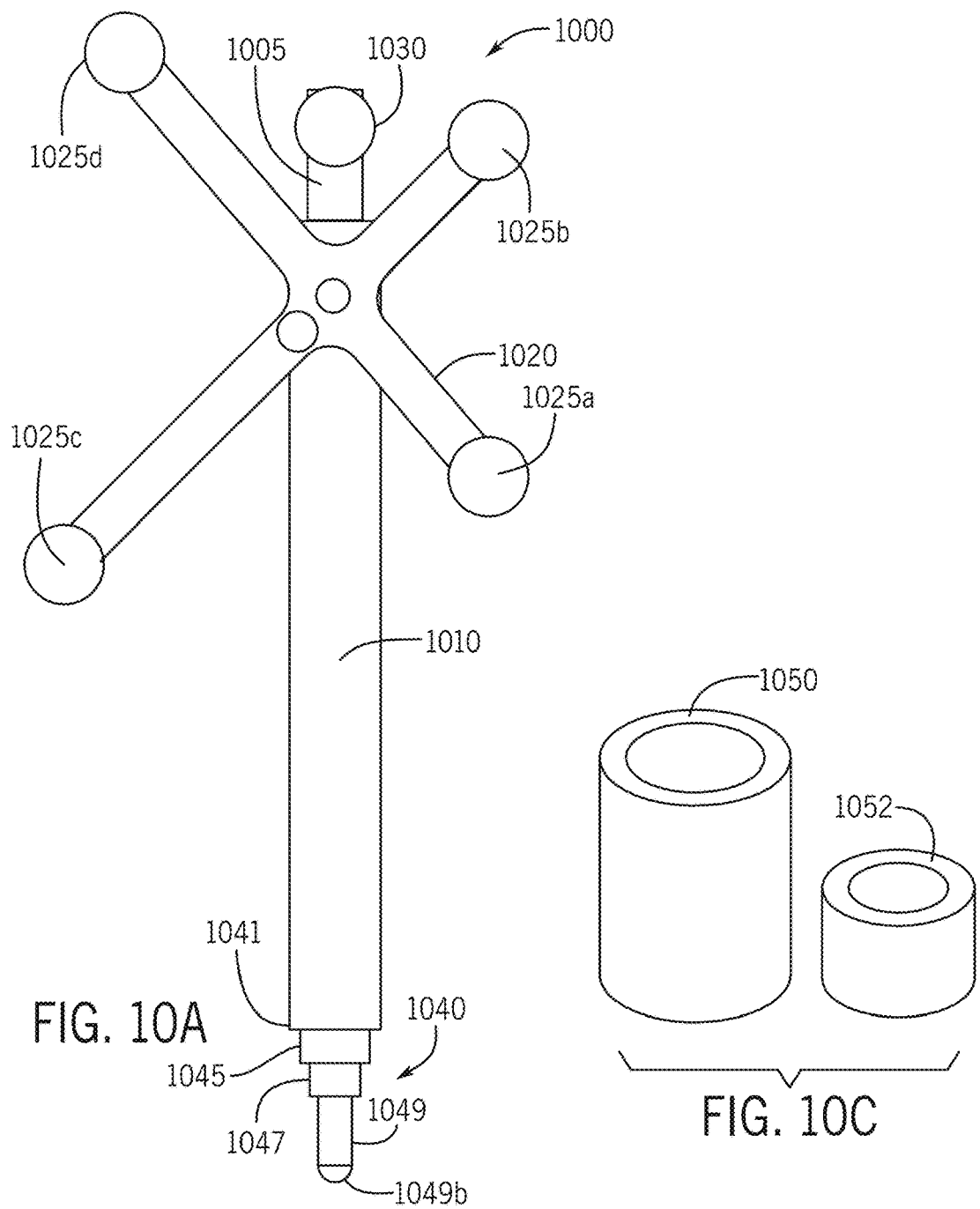
FIG. 10A
FIG. 10C
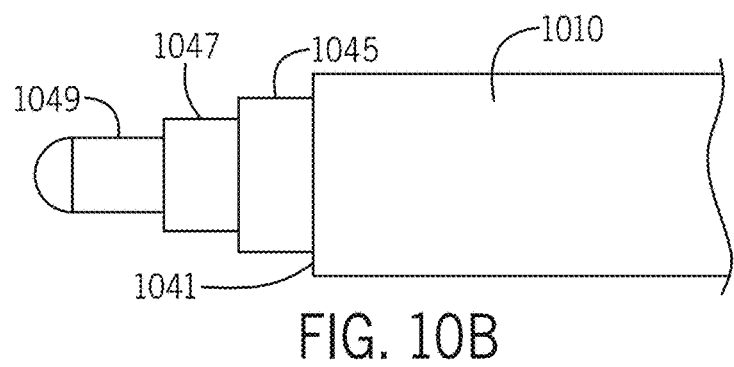
FIG. 10B

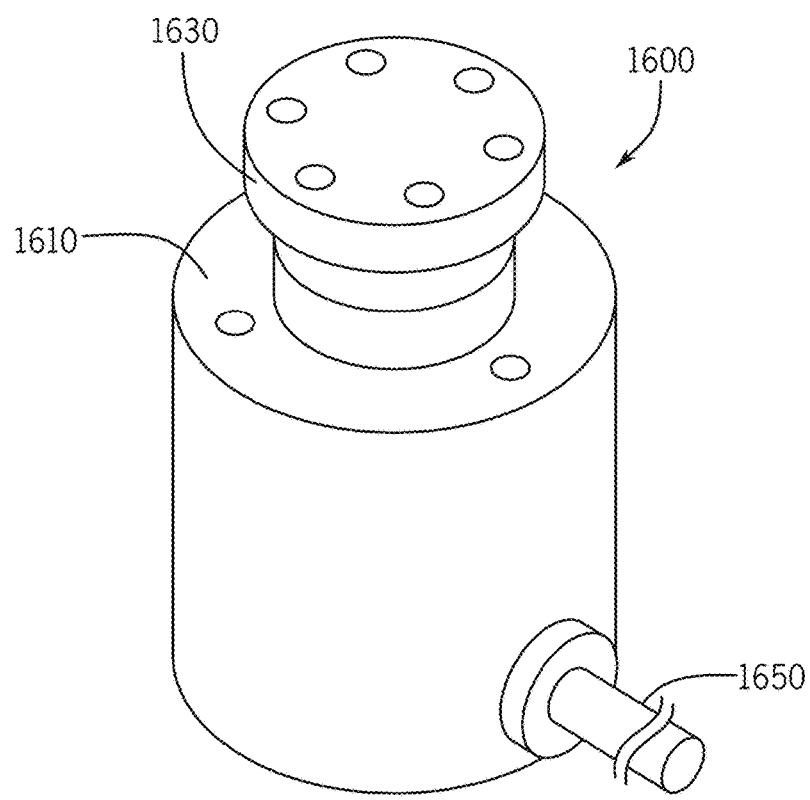
FIG. 16
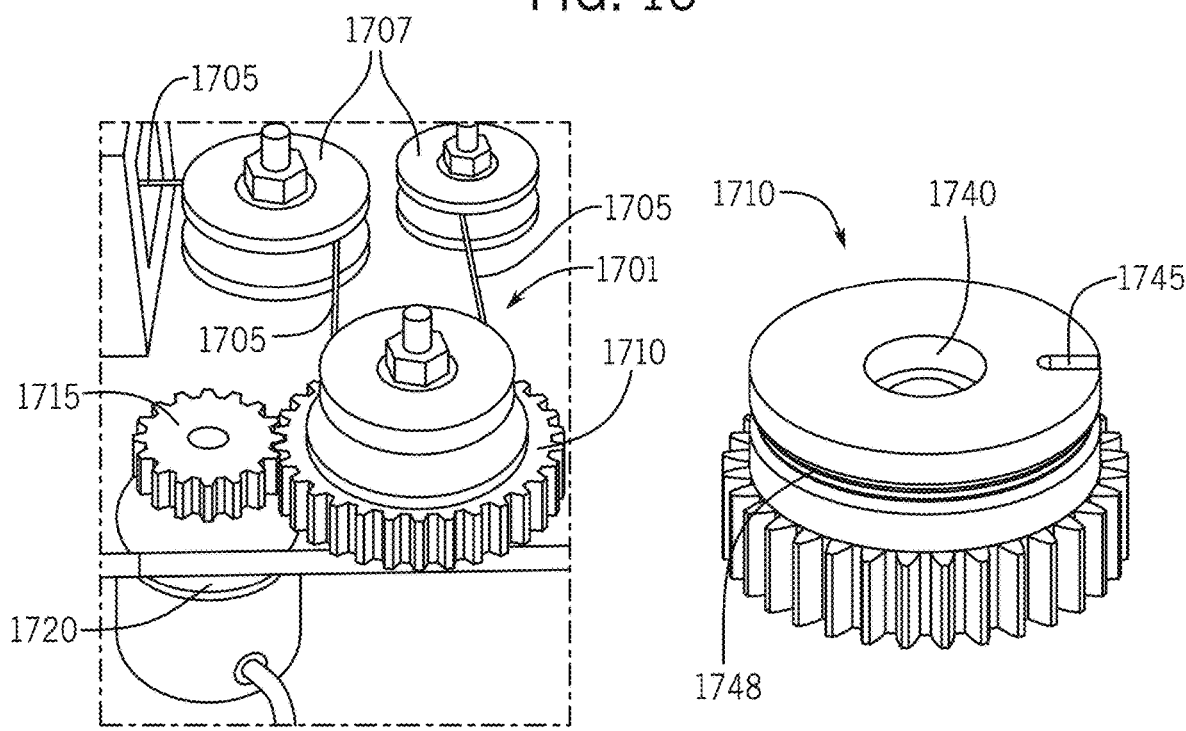
FIG. 17A
FIG. 17B

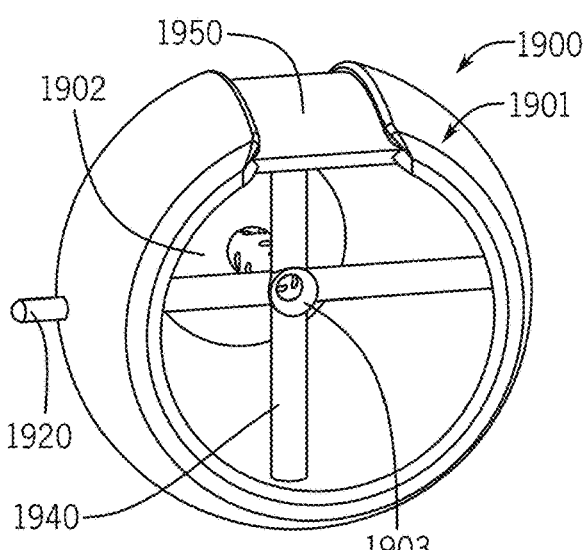
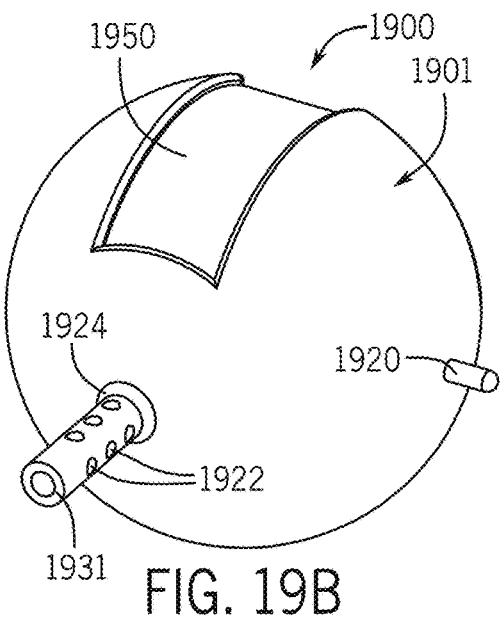
FIG. 19A  FIG. 19B
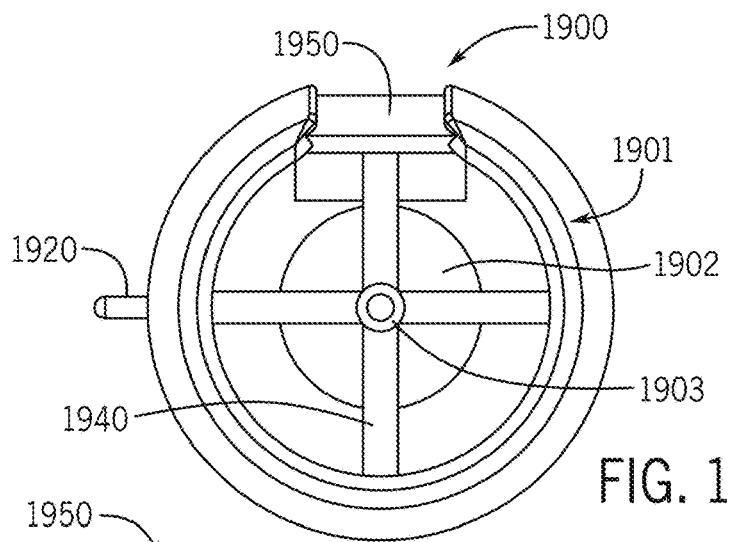
FIG. 19C
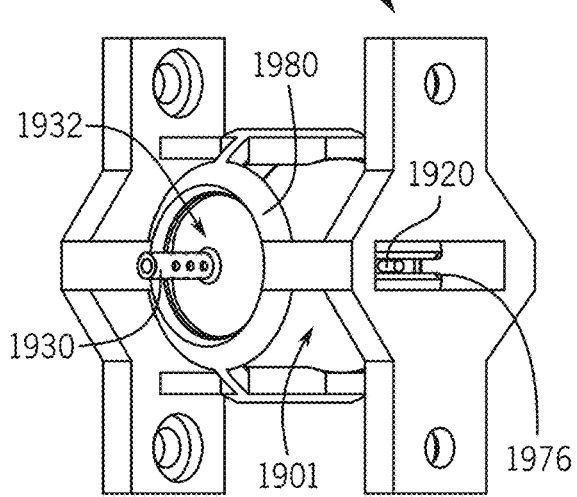
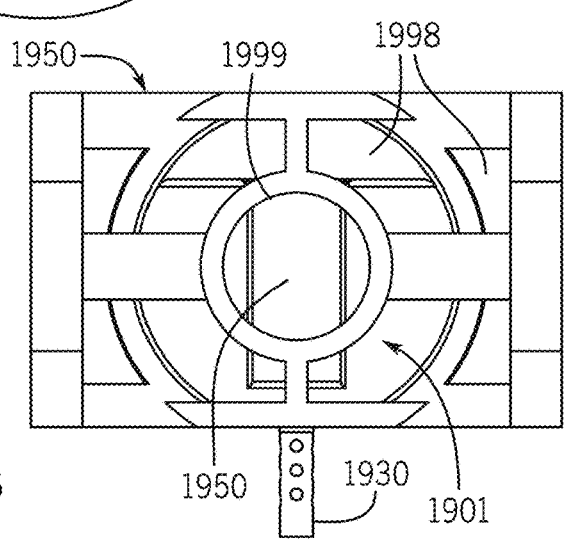
FIG. 19D  FIG. 19E

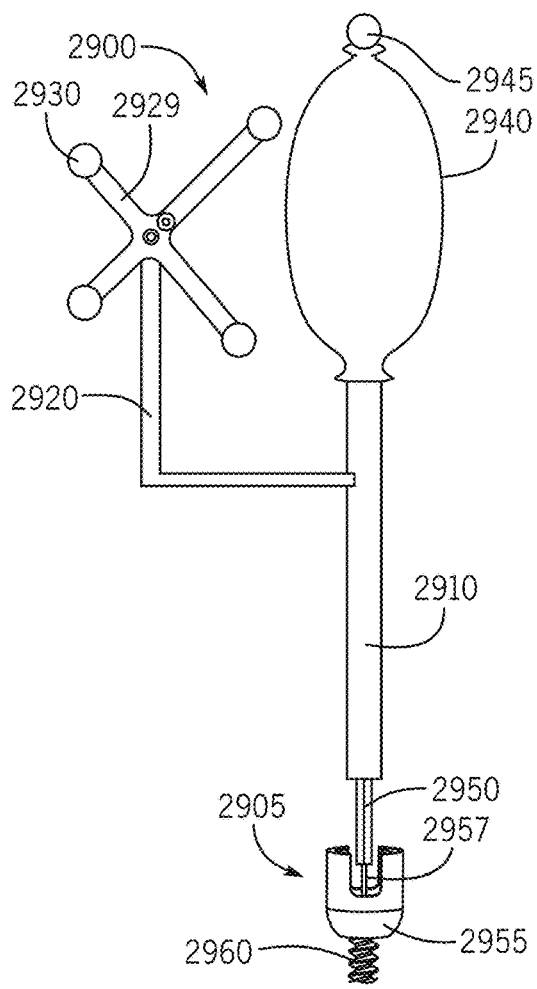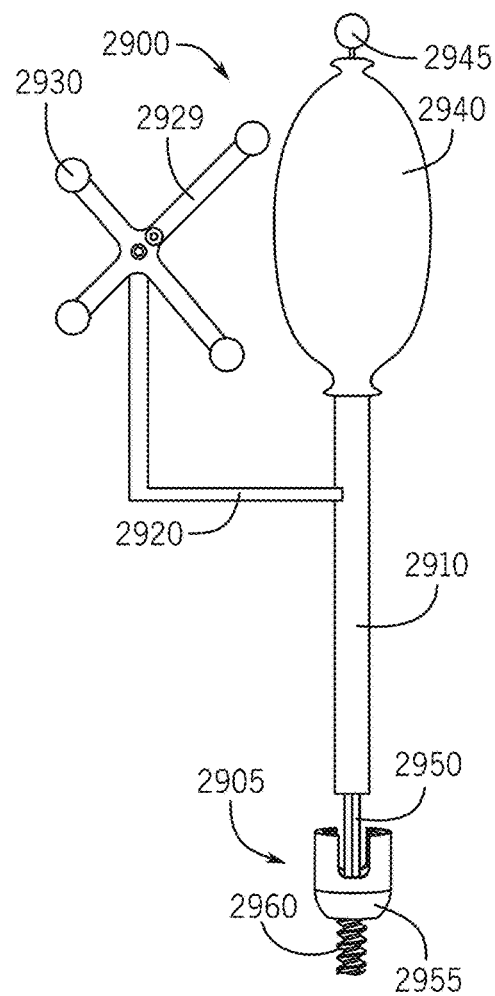# FIG. 29A
FIG. 29B
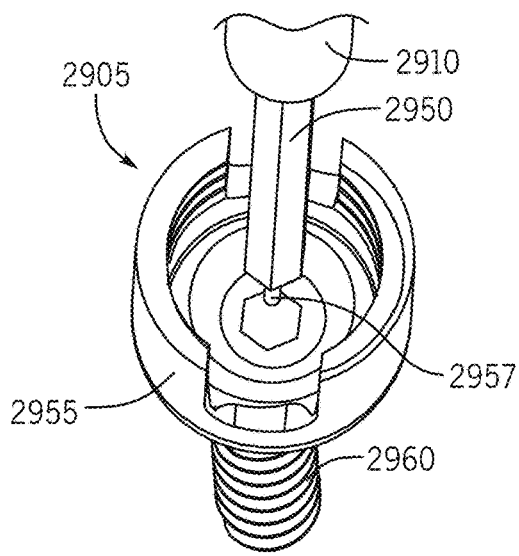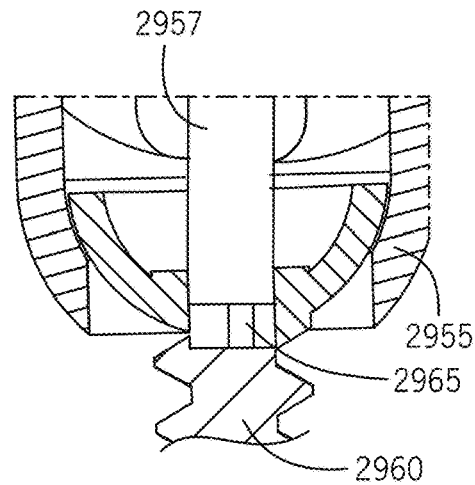
FIG. 29C
FIG. 29D

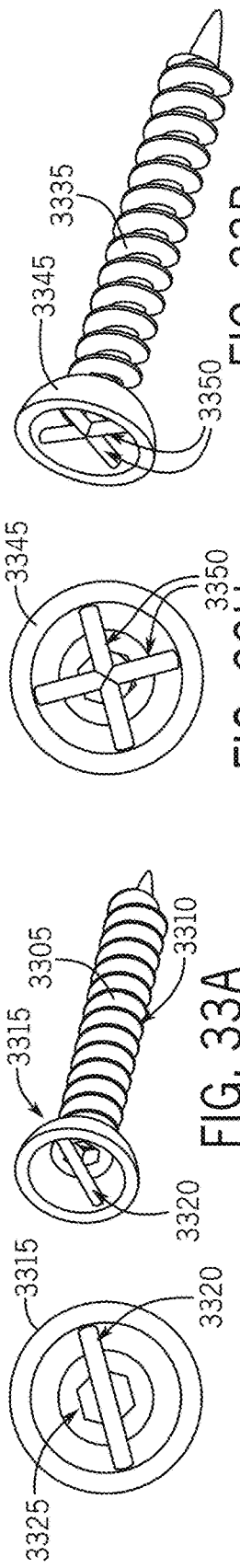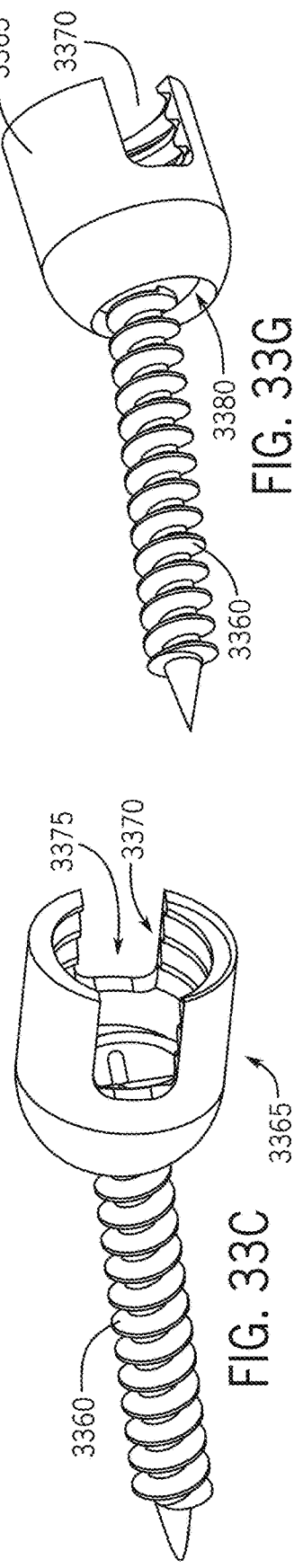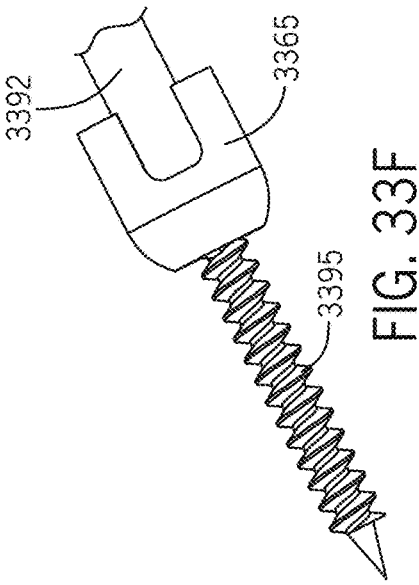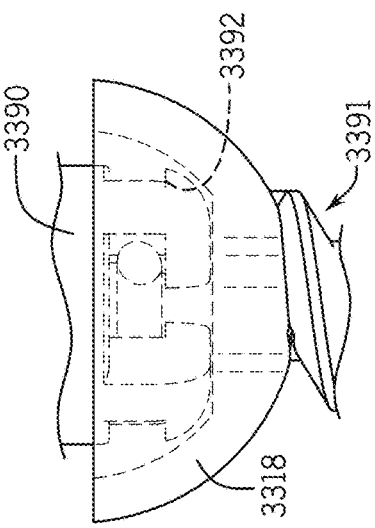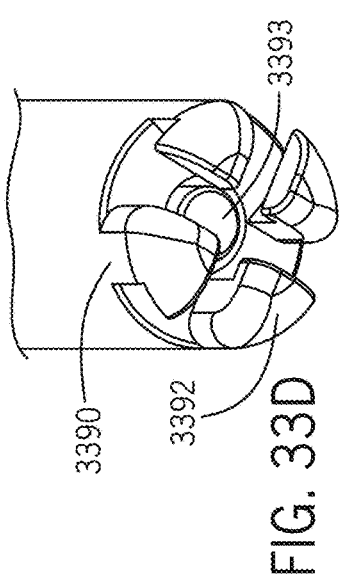
FIG. 33A, FIG. 33B, FIG. 33C, FIG. 33D, FIG. 33E, FIG. 33F, FIG. 33G, FIG. 33H, FIG. 33I

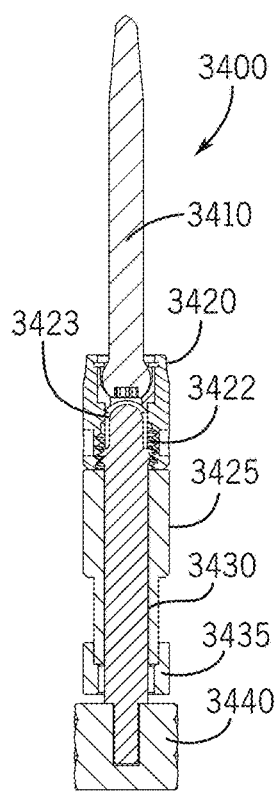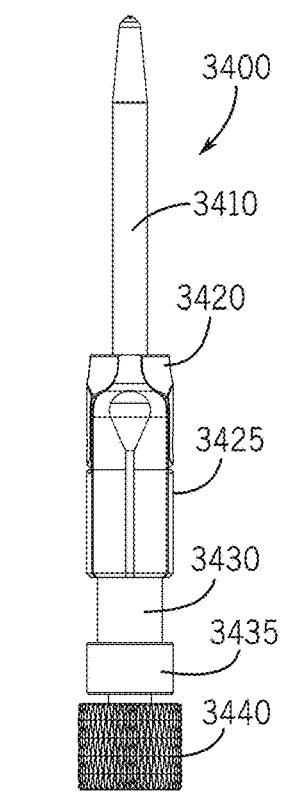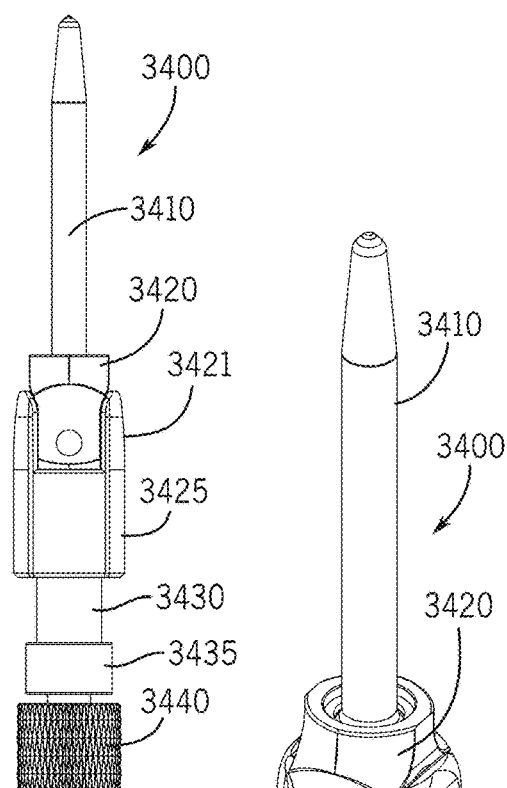
FIG. 34A  FIG. 34B  FIG. 34C
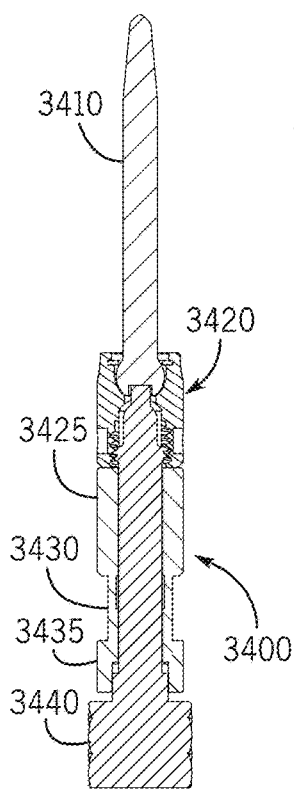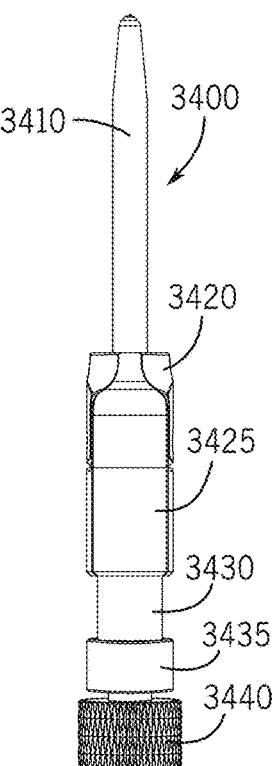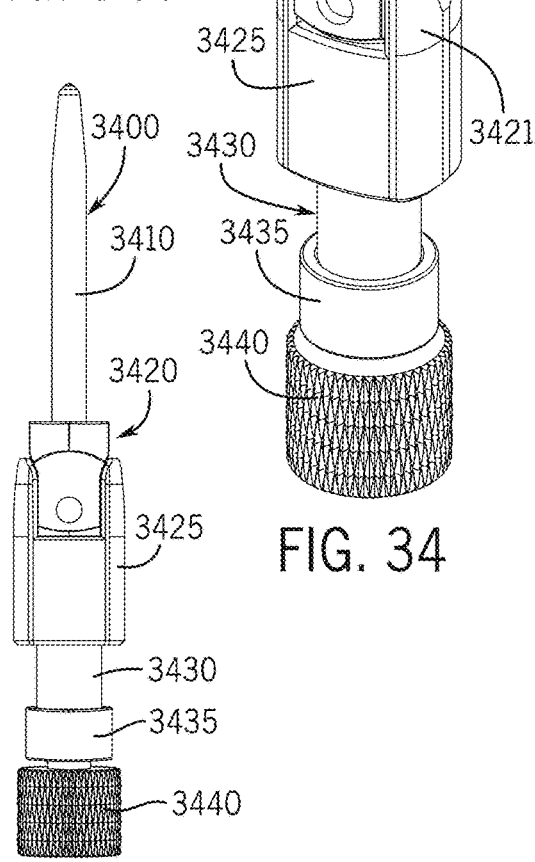
FIG. 34D  FIG. 34E  FIG. 34F
FIG. 34

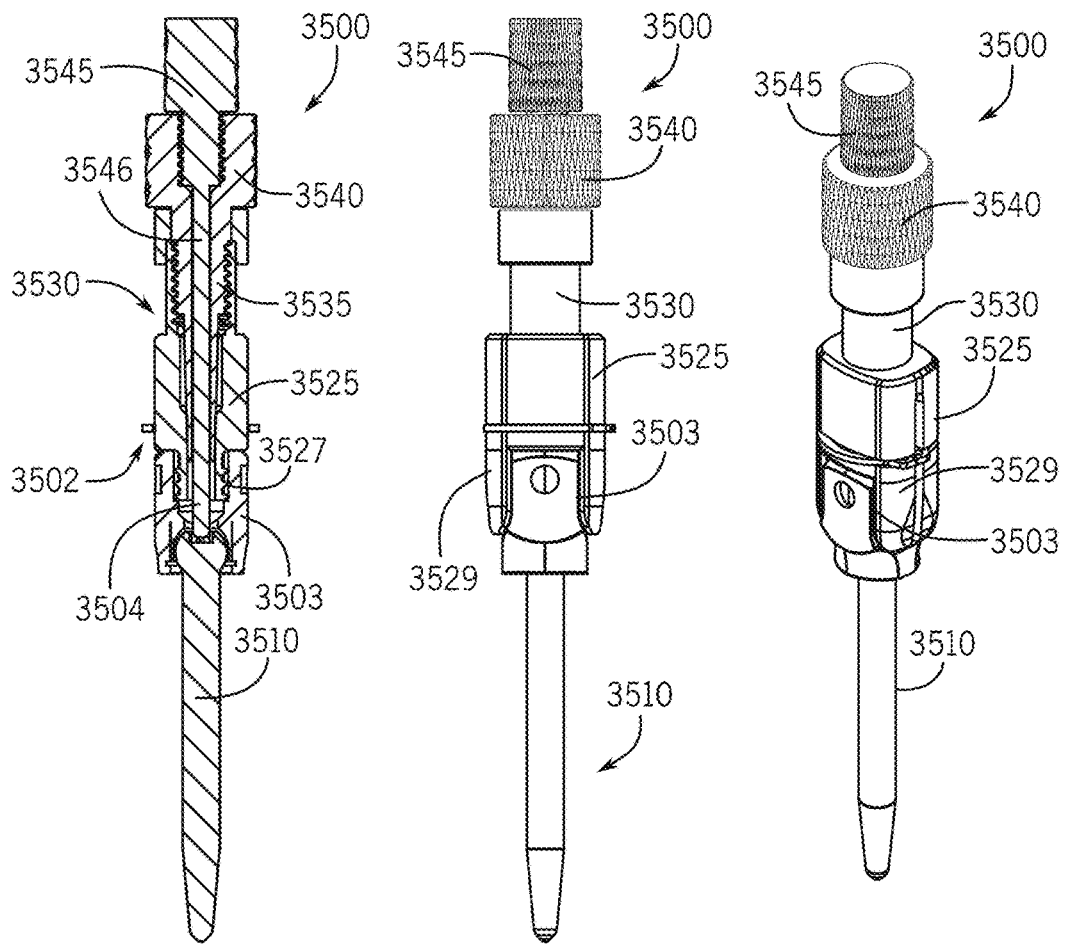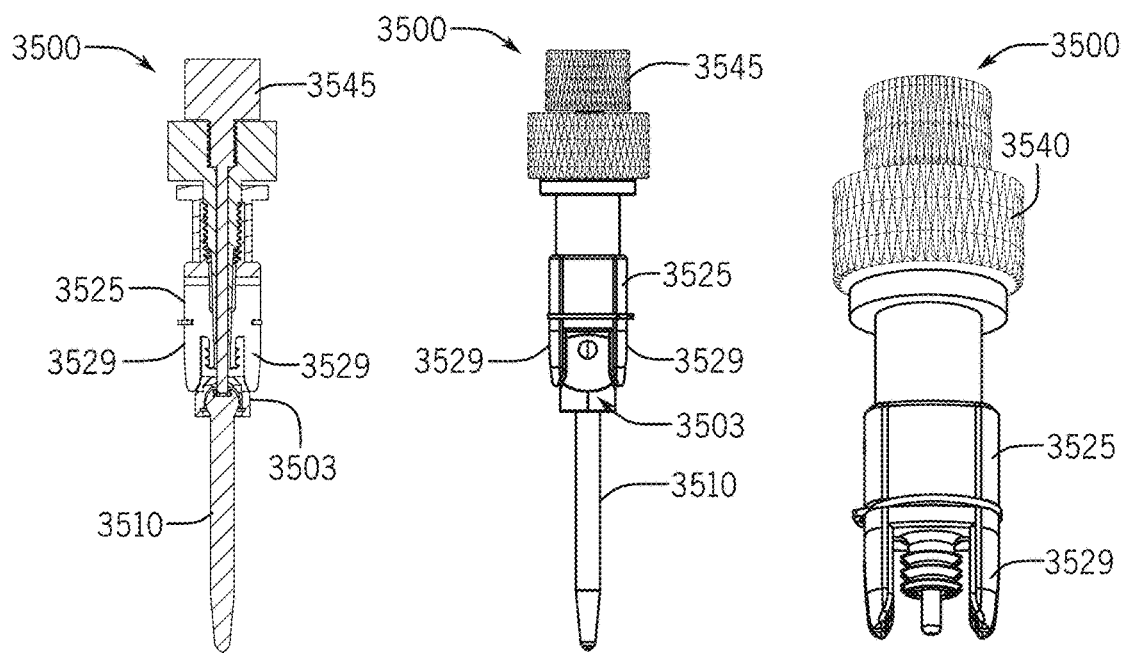
FIG. 35A  FIG. 35B  FIG. 35C
FIG. 35D  FIG. 35E  FIG. 35F

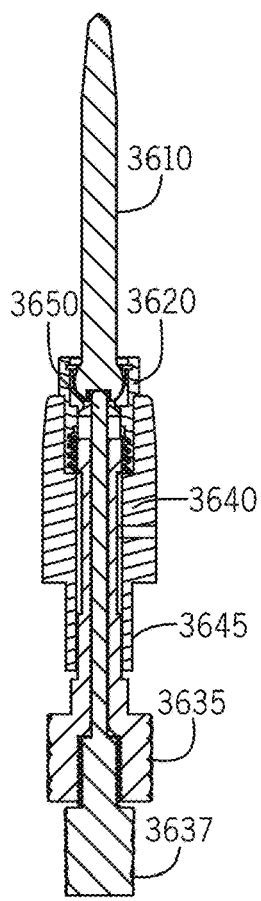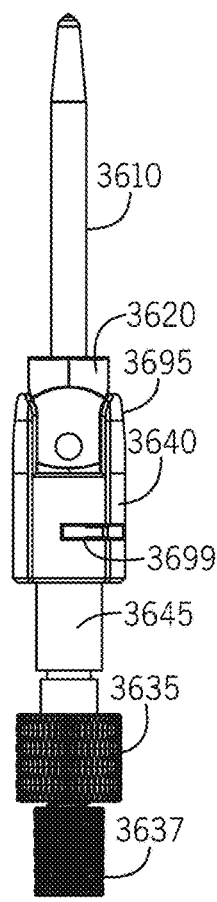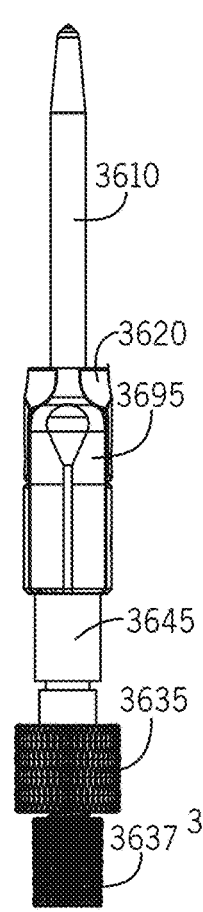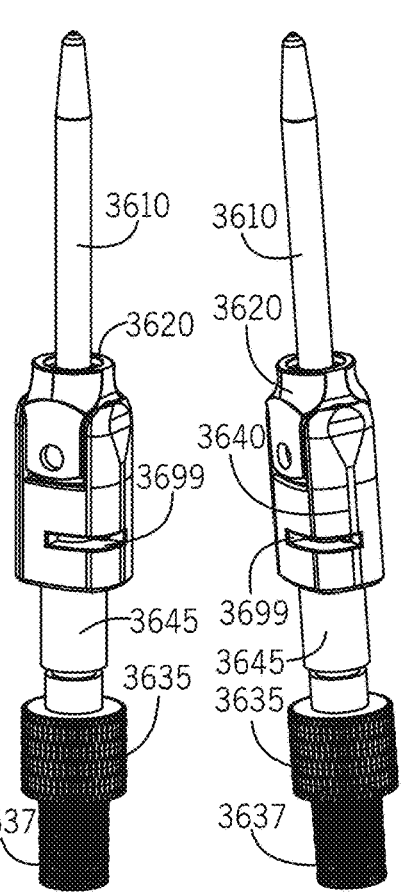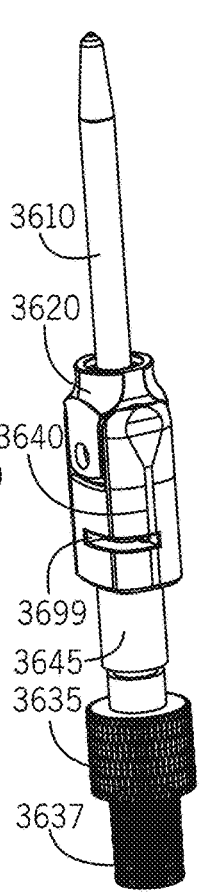
FIG. 36A  FIG. 36B  FIG. 36C  FIG. 36D  FIG. 36E
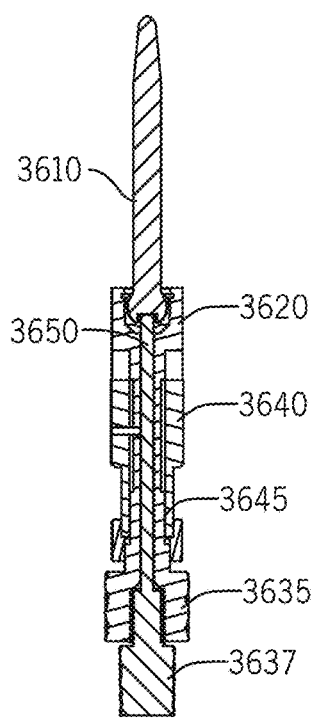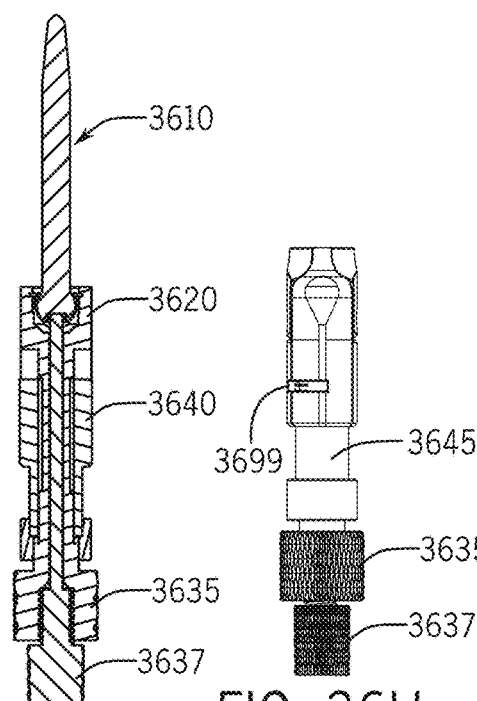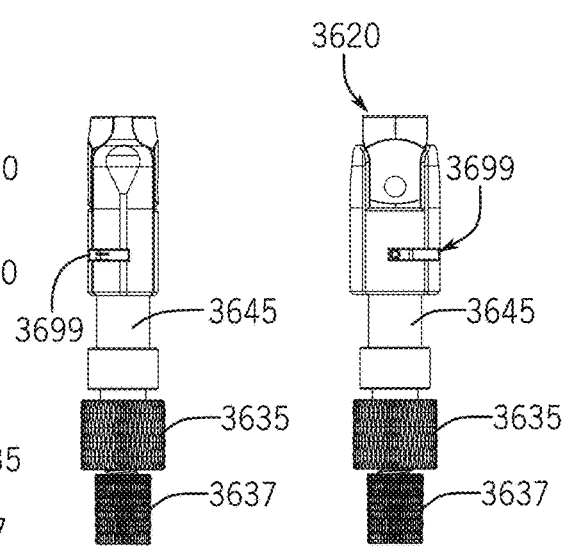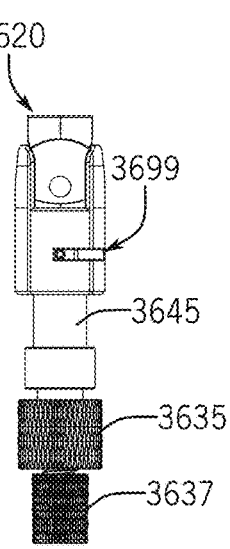
FIG. 36F  FIG. 36G  FIG. 36H  FIG. 36I

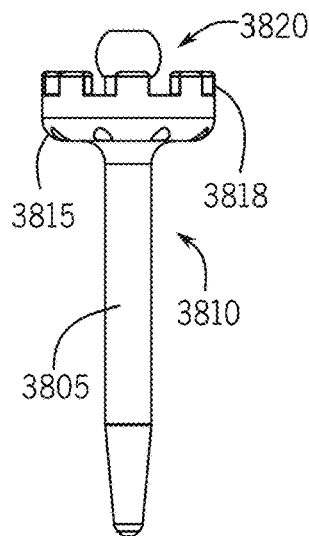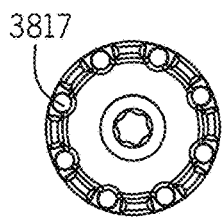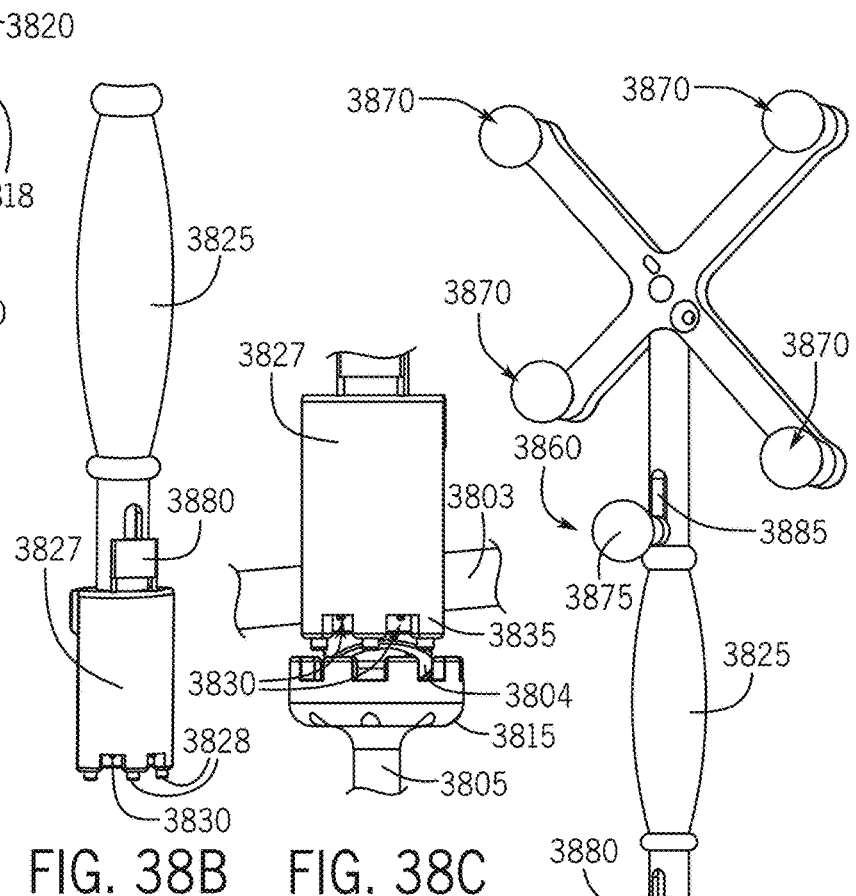
FIG. 38  FIG. 38A  FIG. 38B  FIG. 38C  FIG. 38D  FIG. 38E  FIG. 38F  FIG. 38G

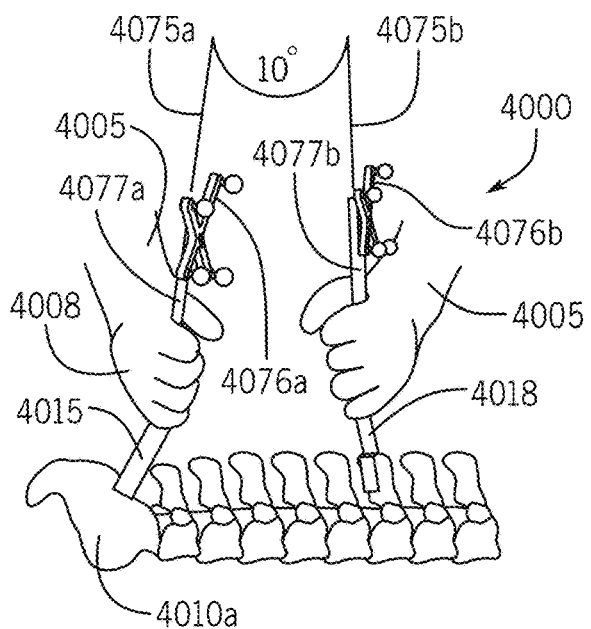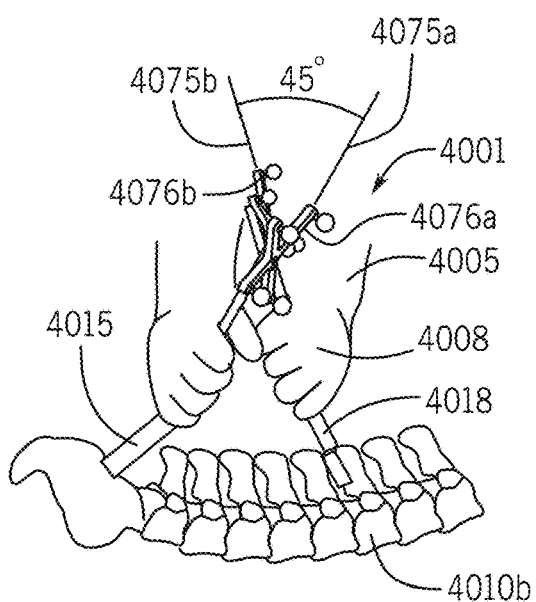
FIG. 40A   FIG. 40B
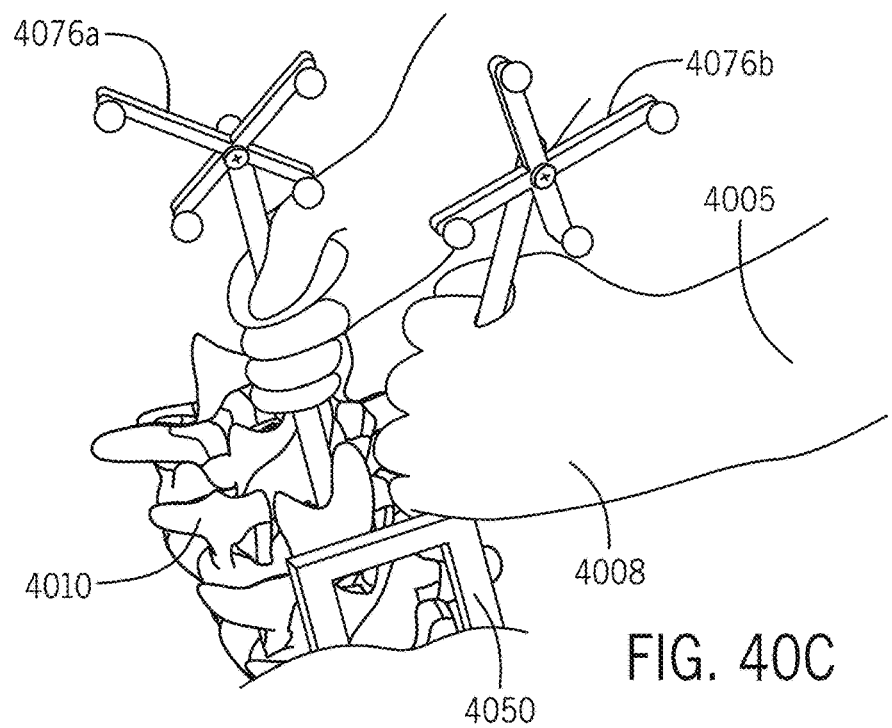
FIG. 40C

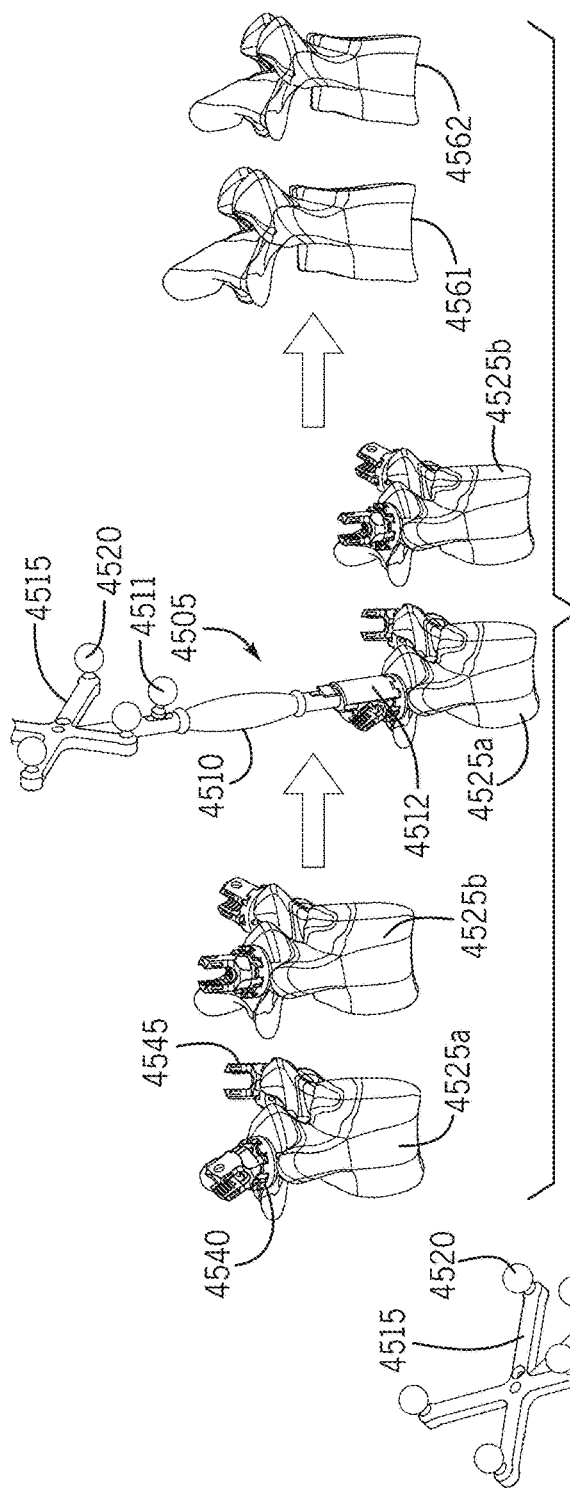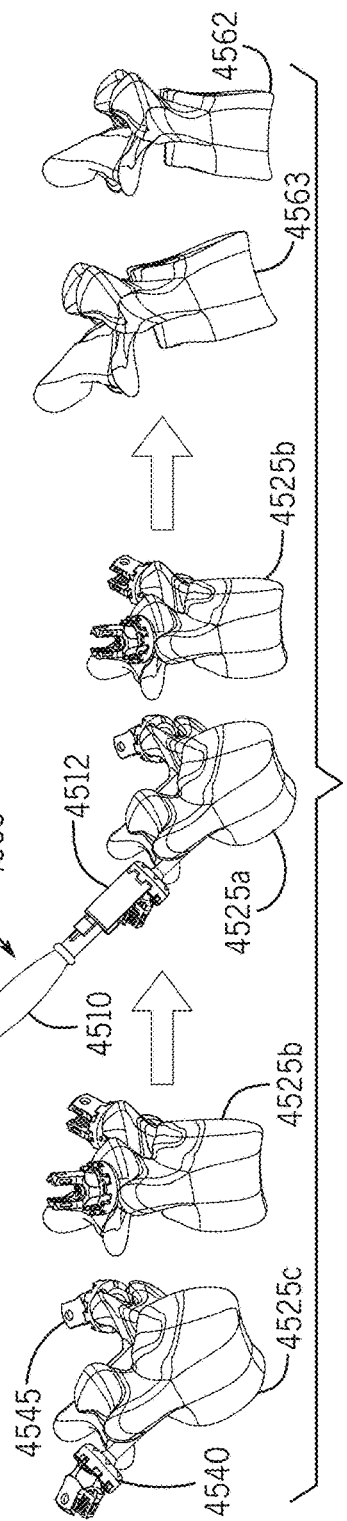
FIG. 45A
FIG. 45B

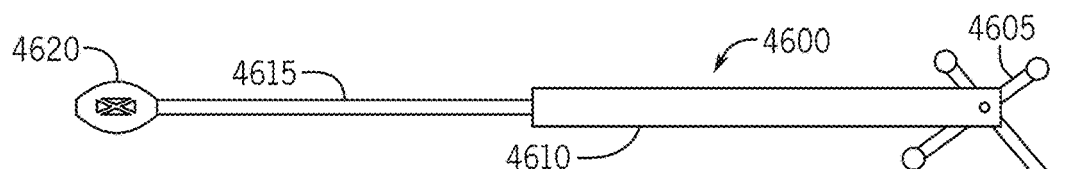
FIG. 46A
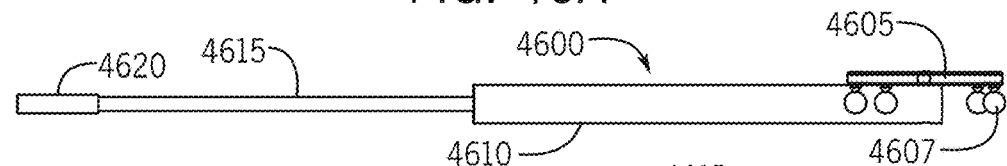
FIG. 46B
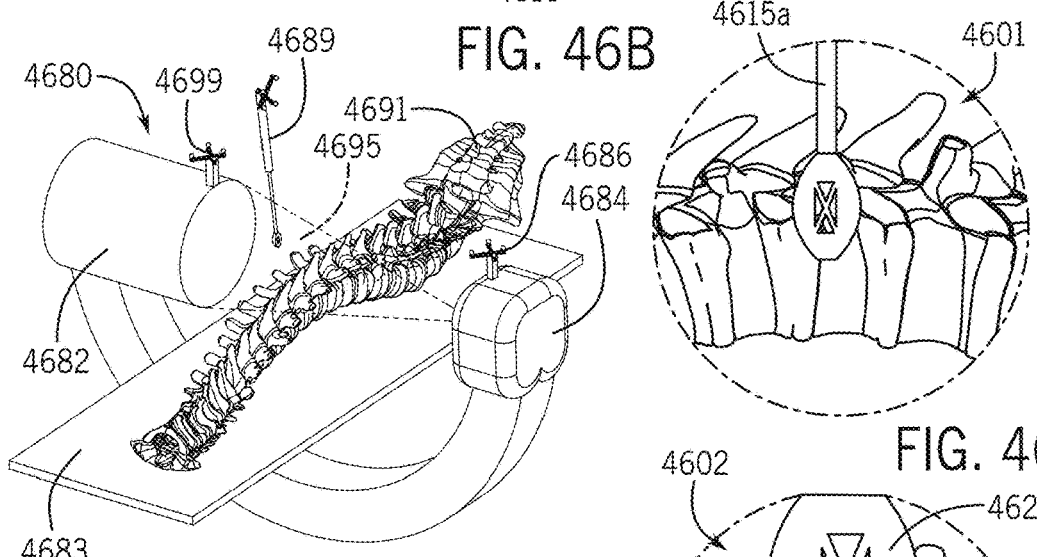
FIG. 46C
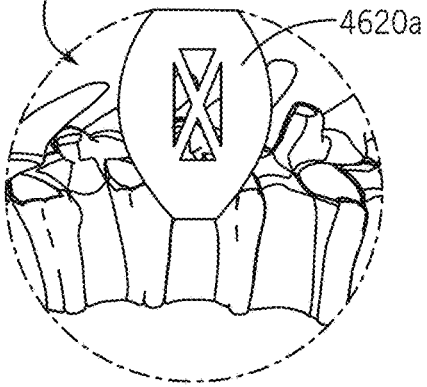
FIG. 46D
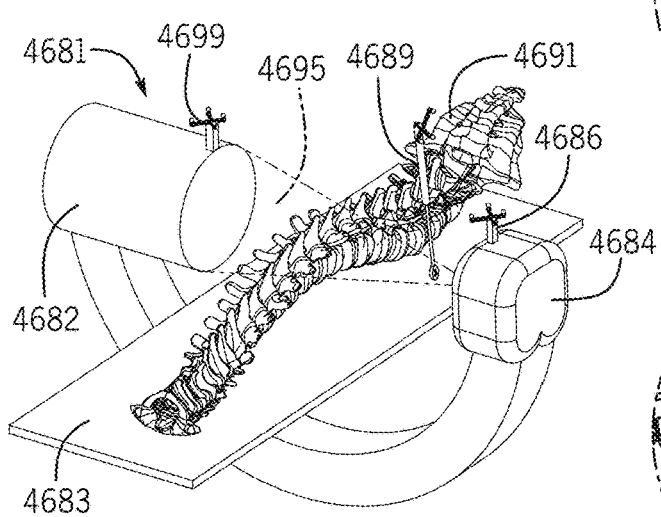
FIG. 46E
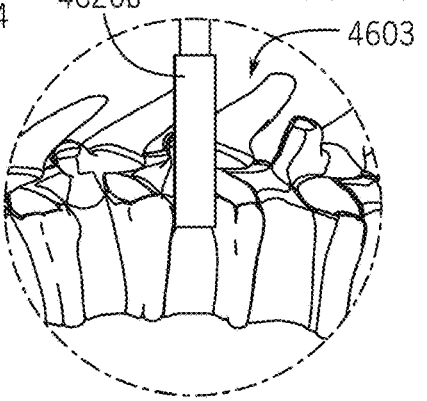
FIG. 46F
FIG. 46G

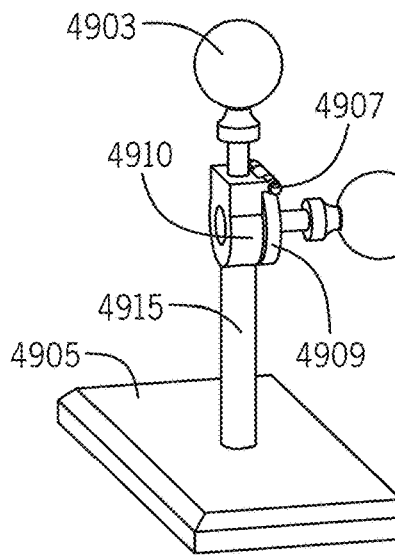
FIG. 49A
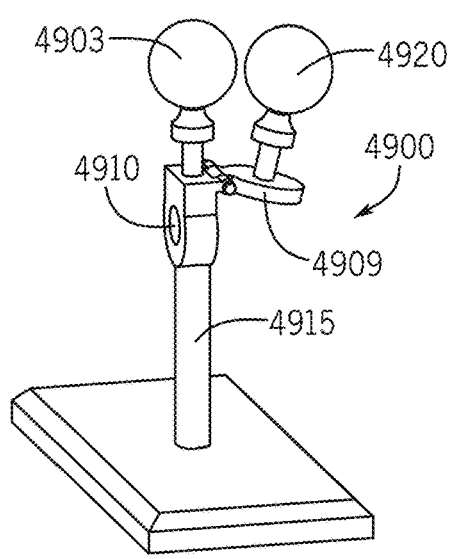
FIG. 49B
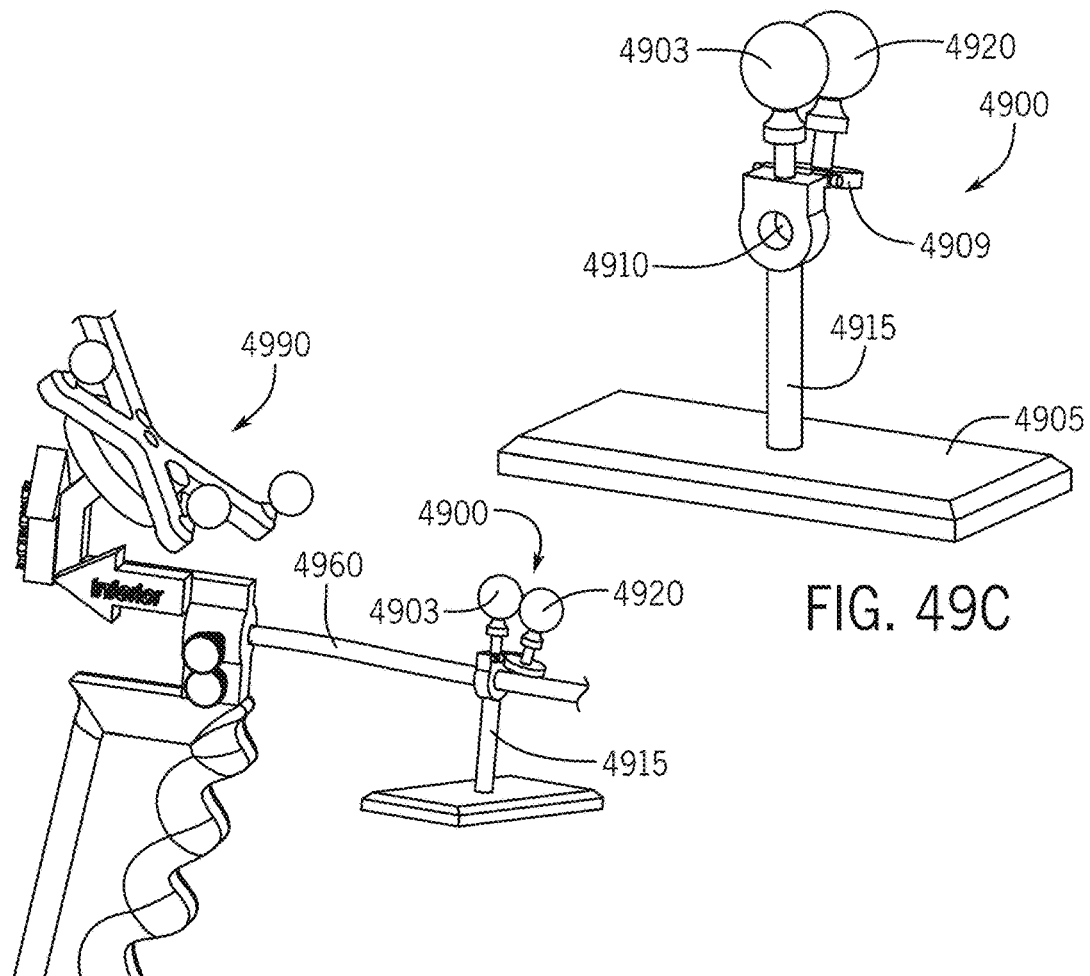
FIG. 49C
FIG. 49D

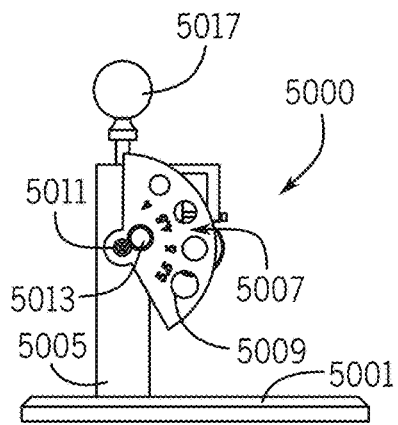
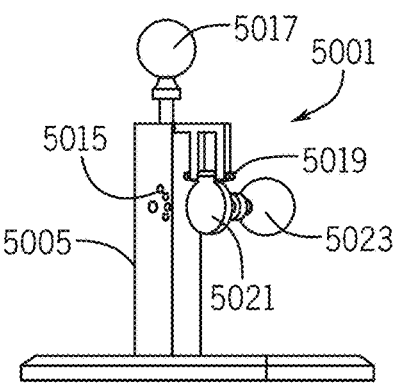
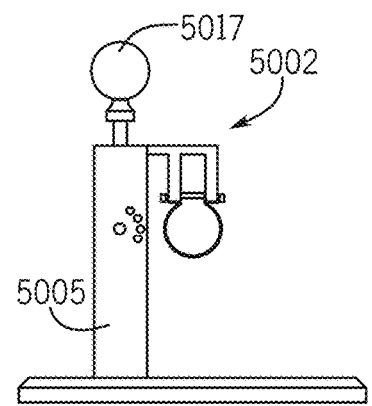
FIG. 50A  FIG. 50B  FIG. 50C
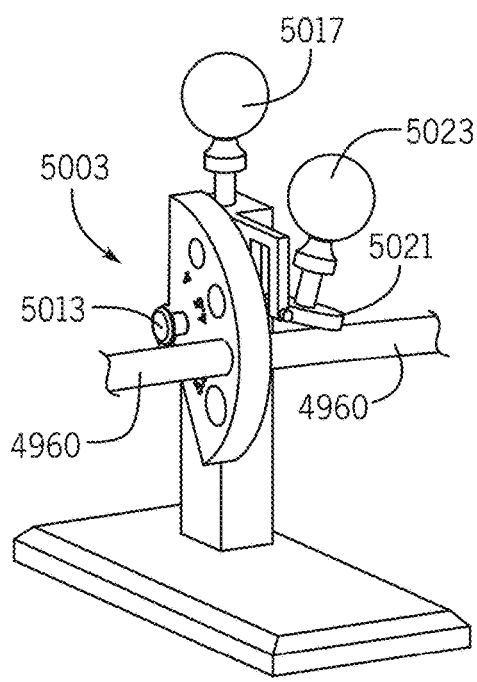
FIG. 50D
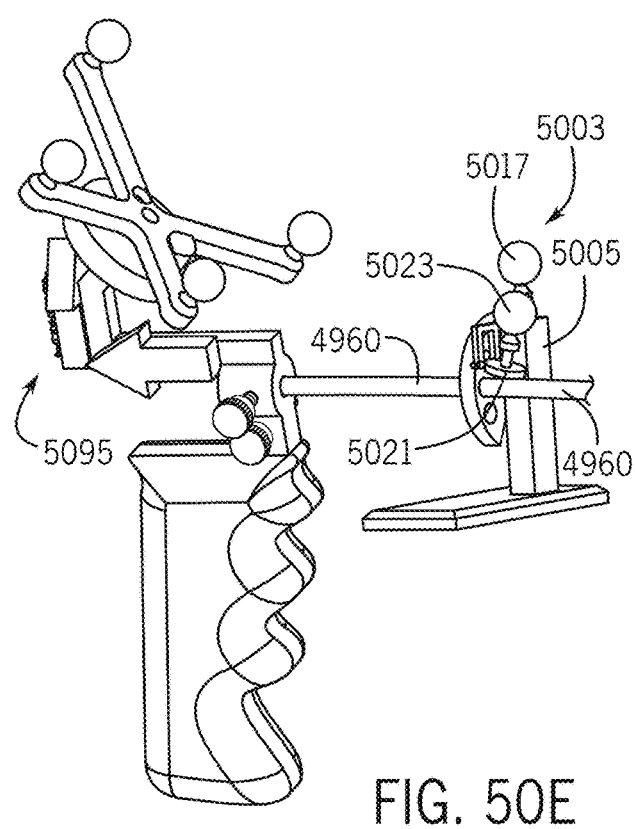
FIG. 50E

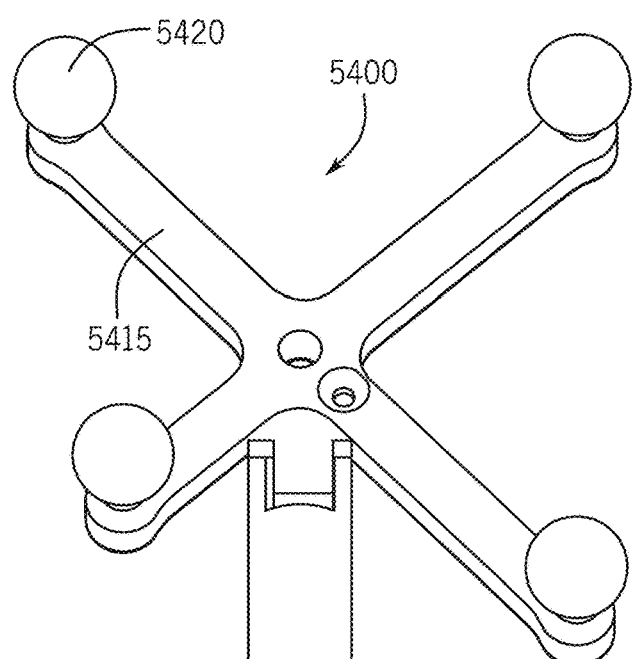
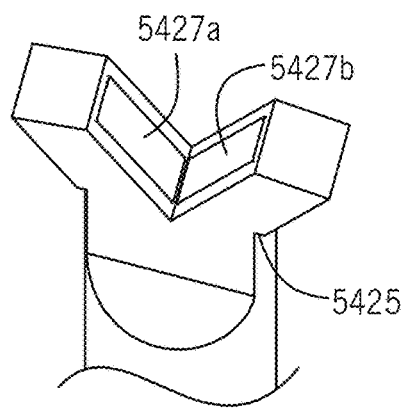
FIG. 54B
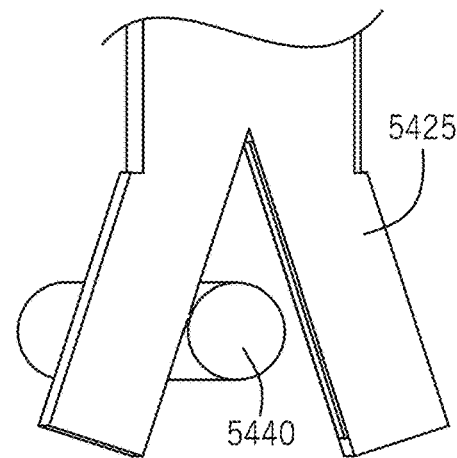
FIG. 54C
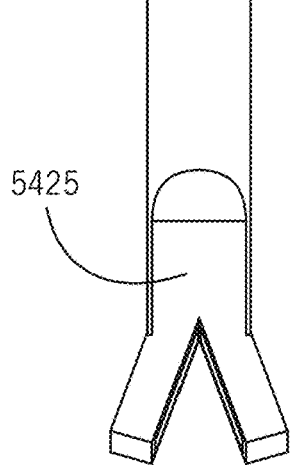
FIG. 54A
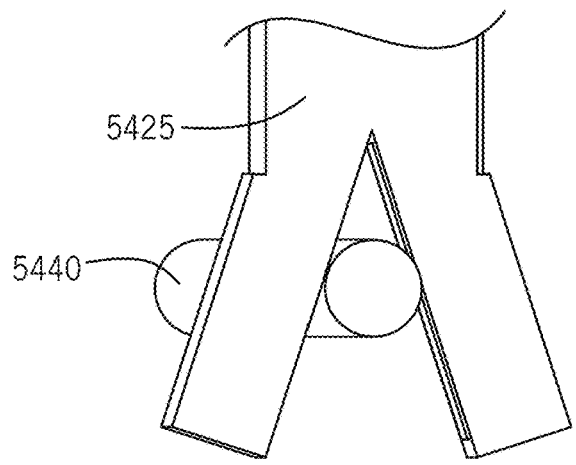
FIG. 54D

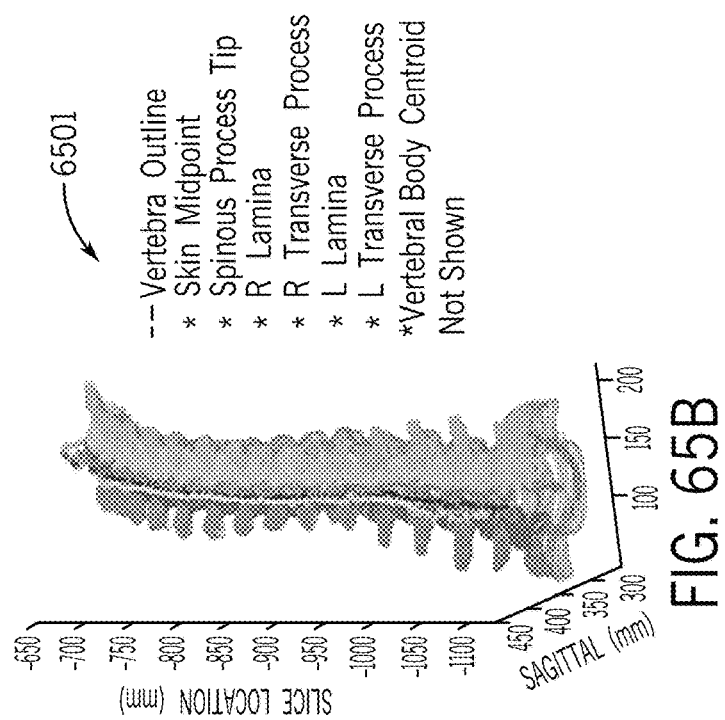
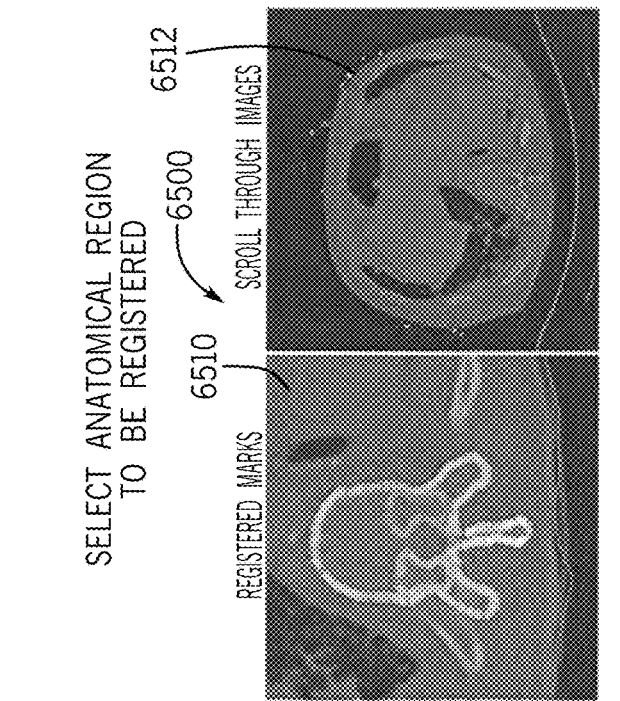
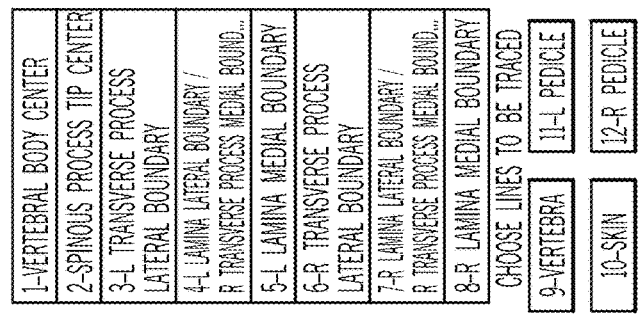
FIG. 65A
FIG. 65B

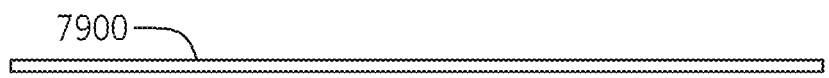
FIG. 79A
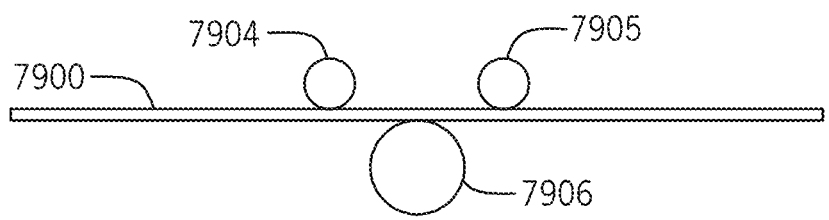
FIG. 79B
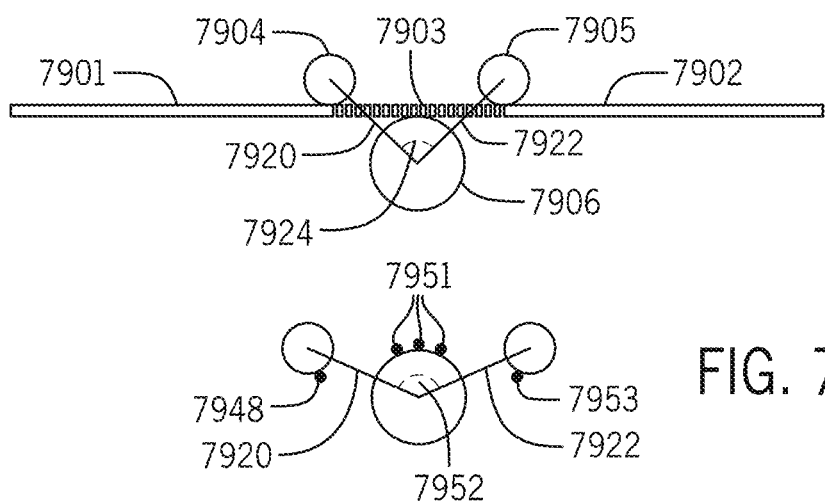
FIG. 79C
FIG. 79D
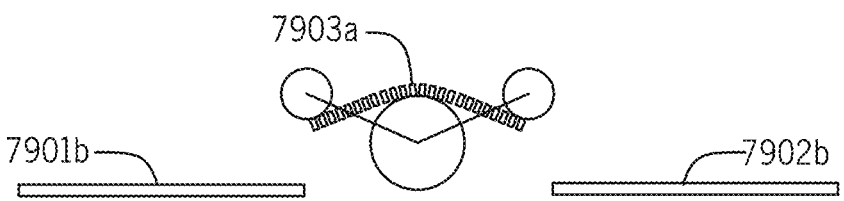
FIG. 79E
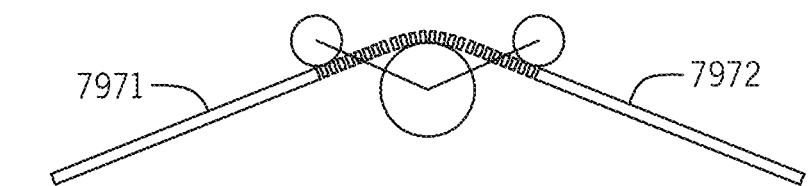
FIG. 79F
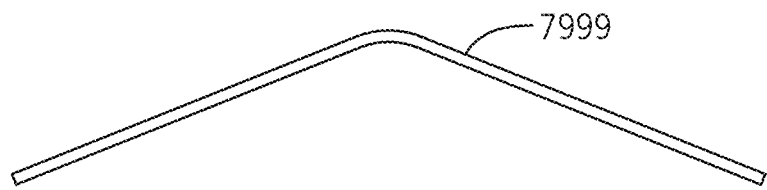
FIG. 79G

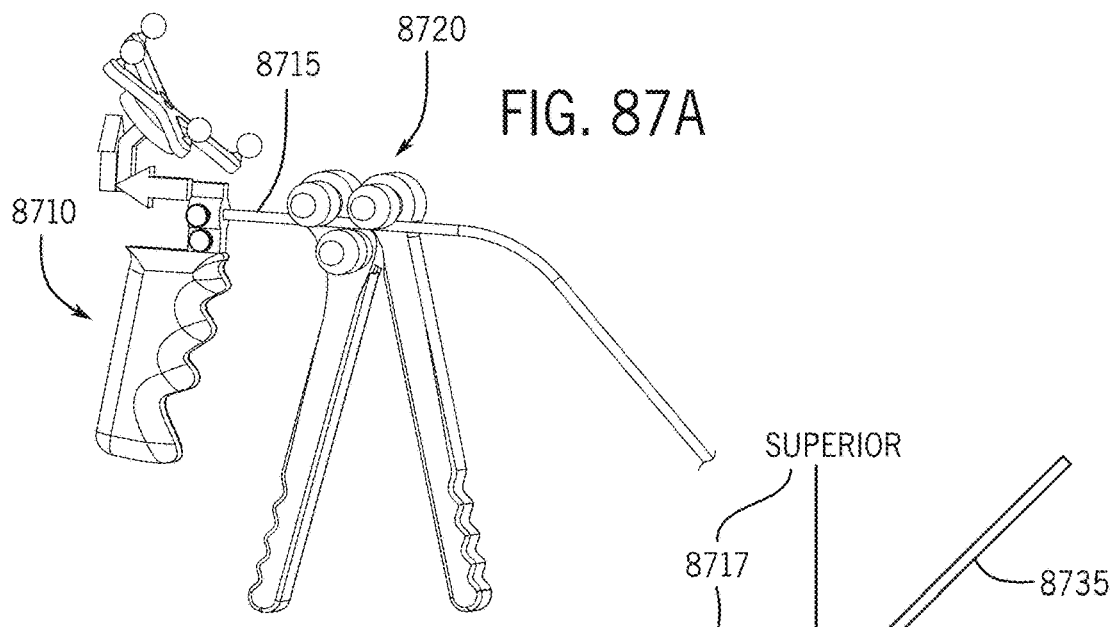
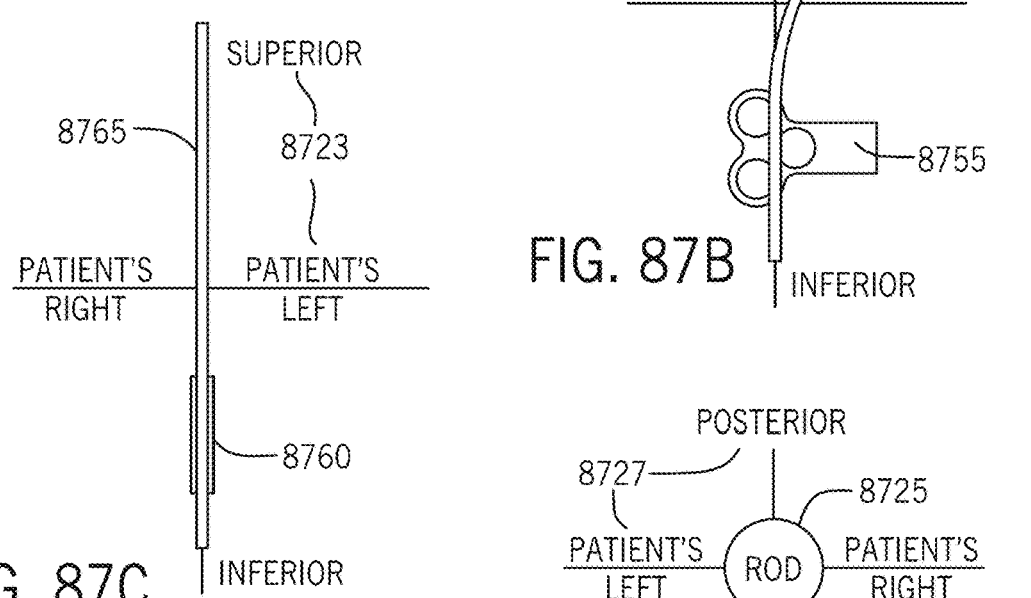
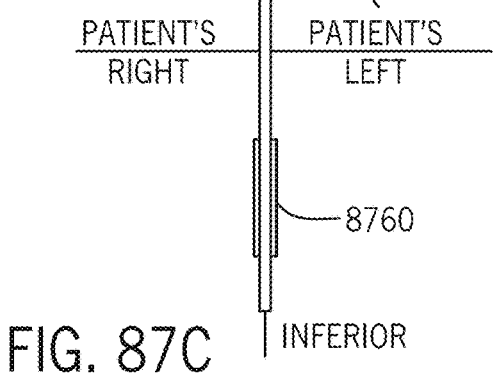
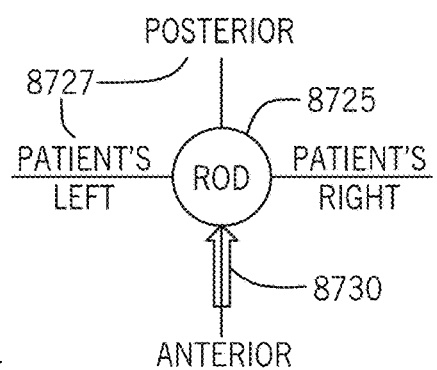
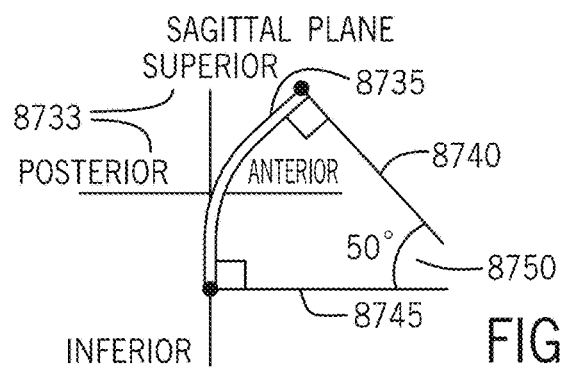

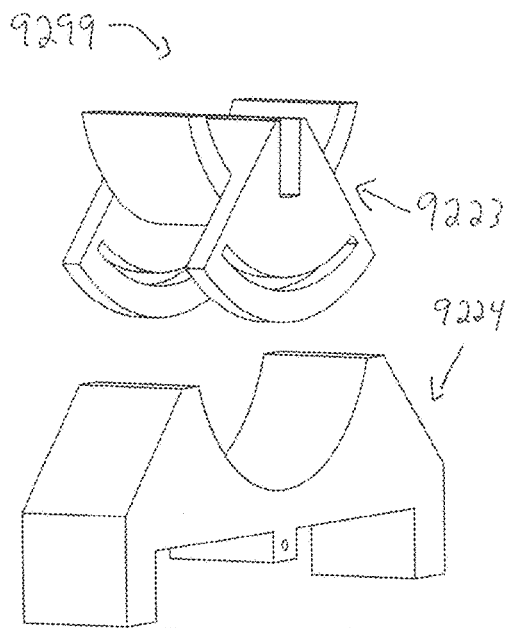
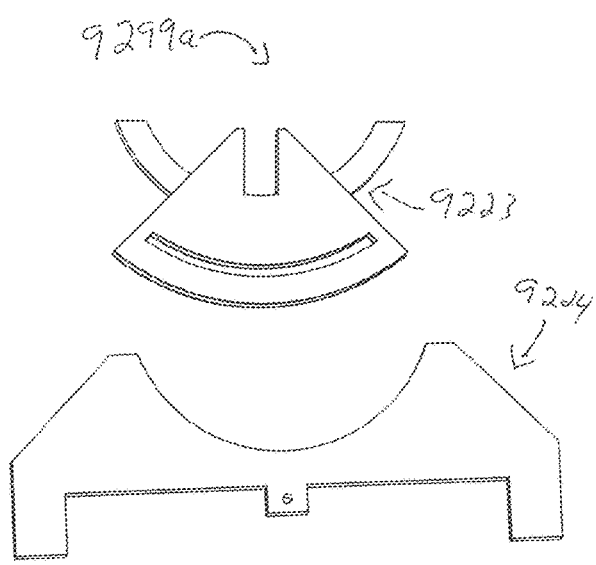
Fig. 92AB
Fig. 92AC
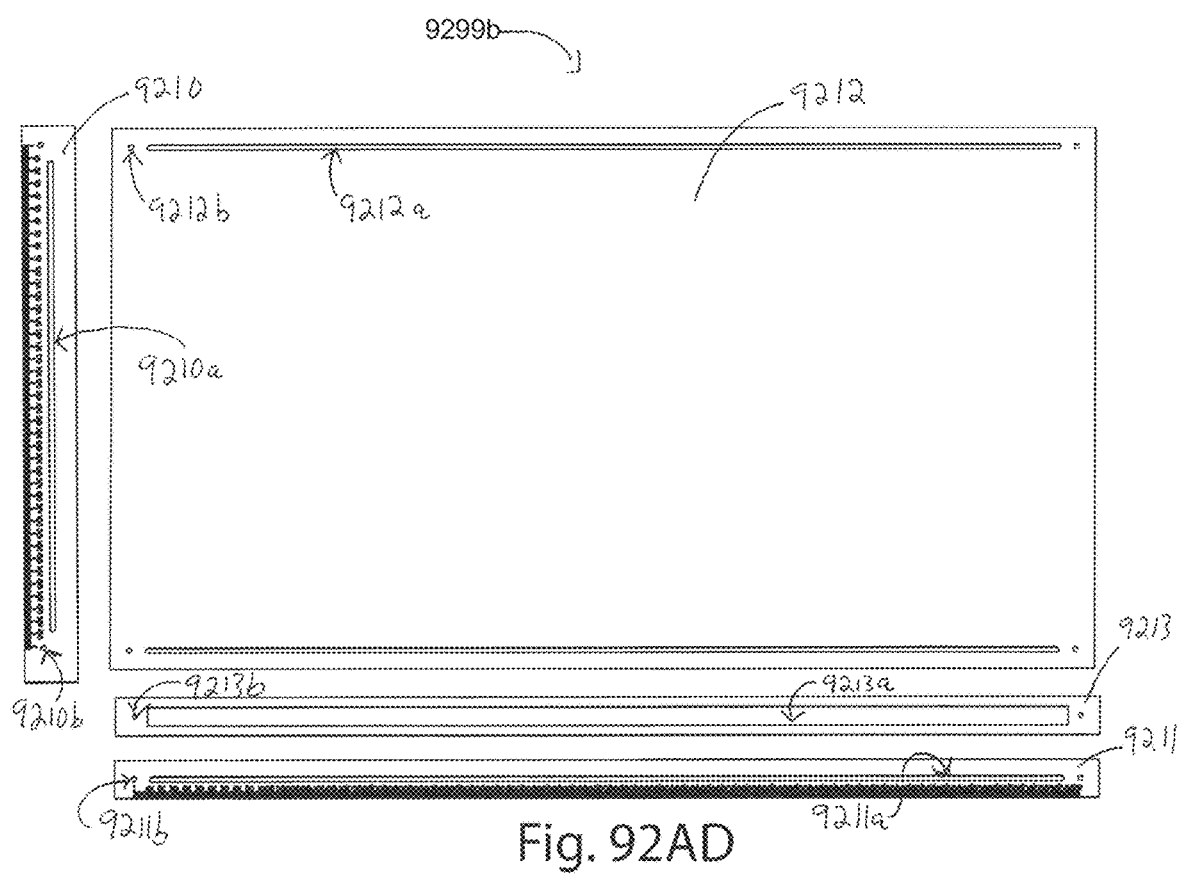
Fig. 92AD

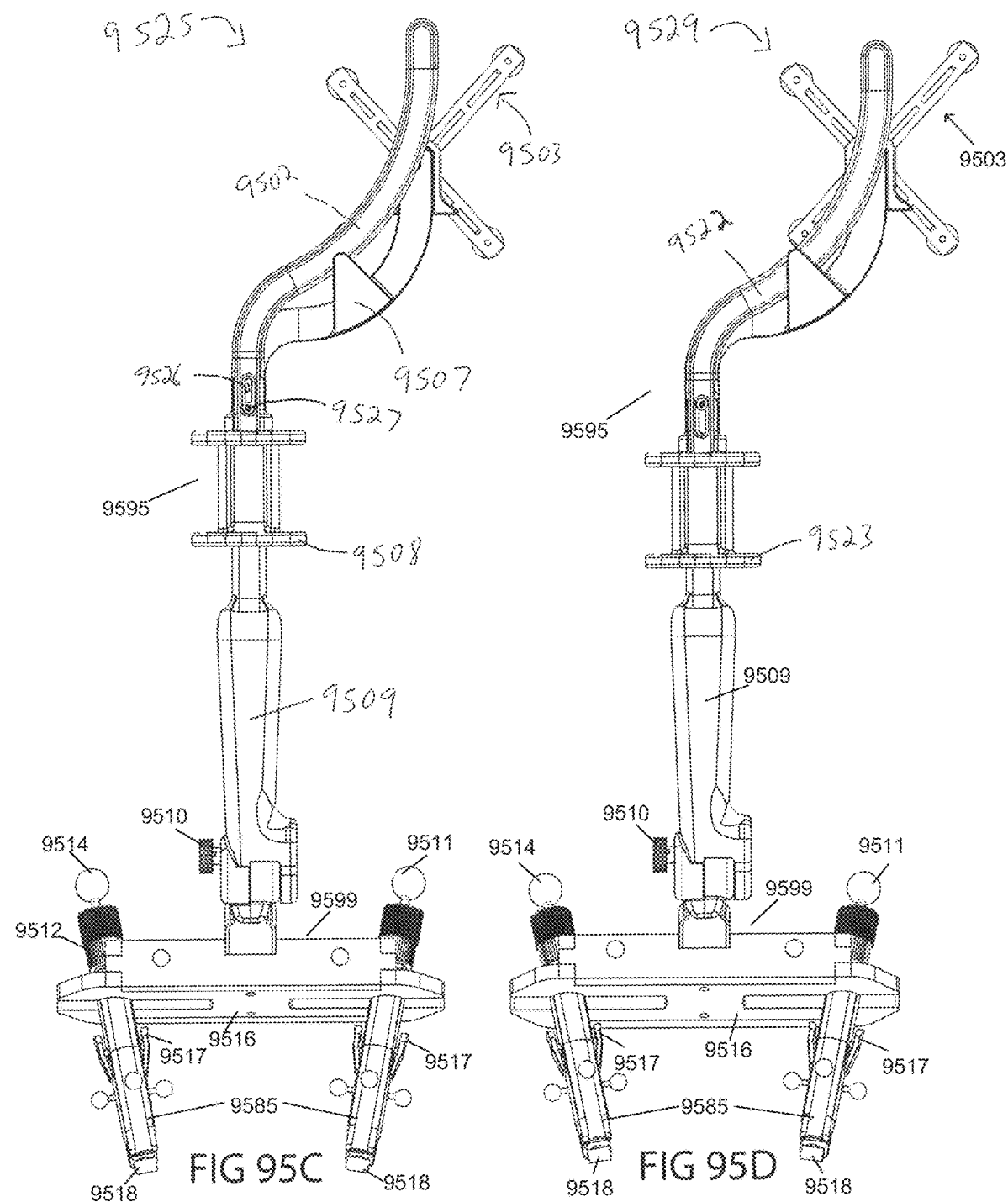

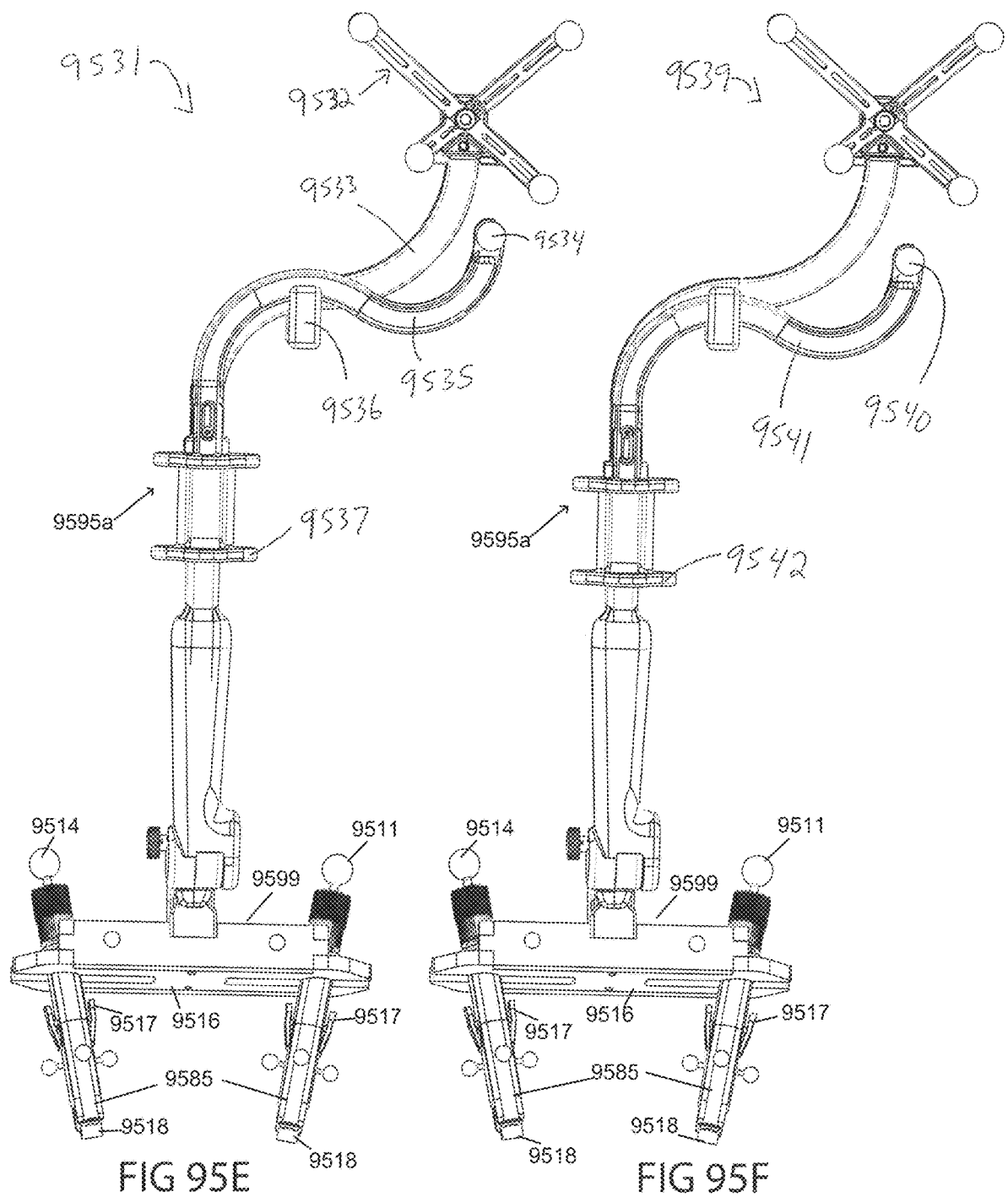

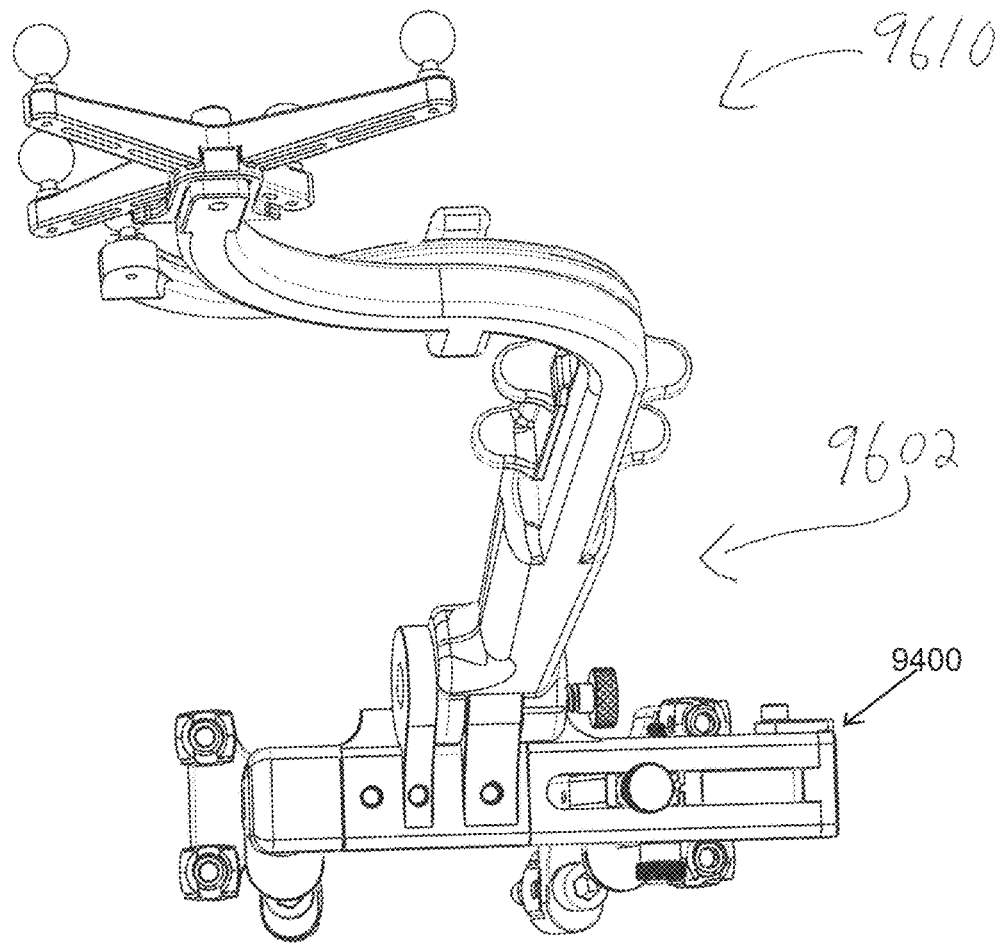
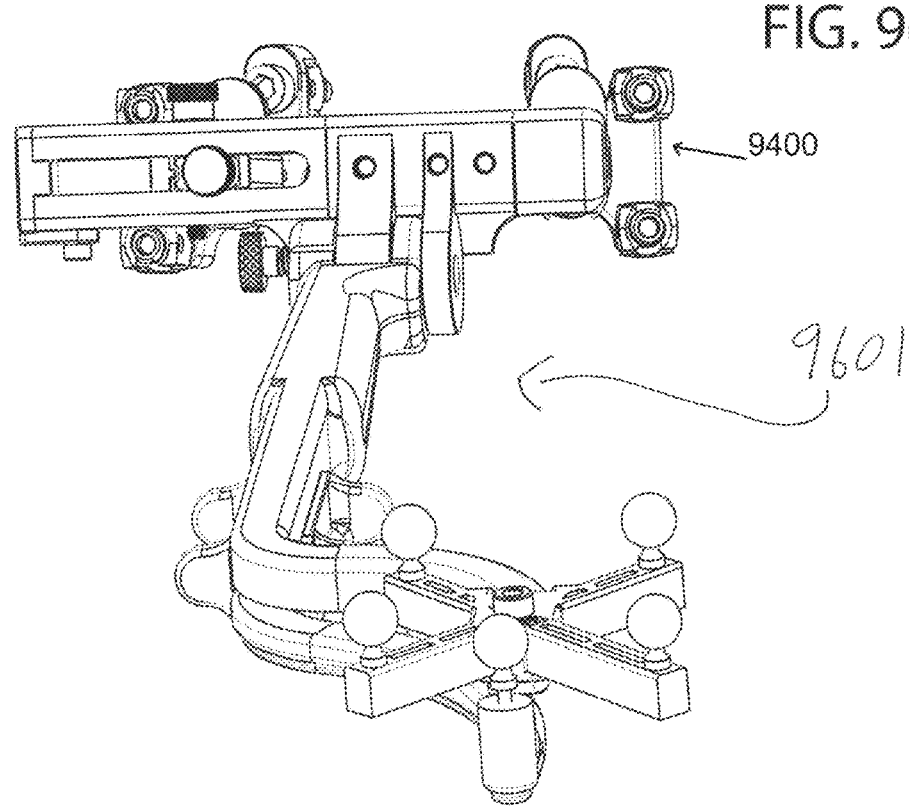
FIG. 96E

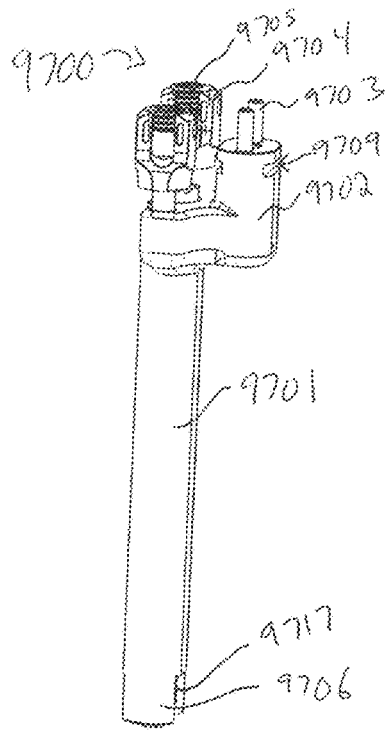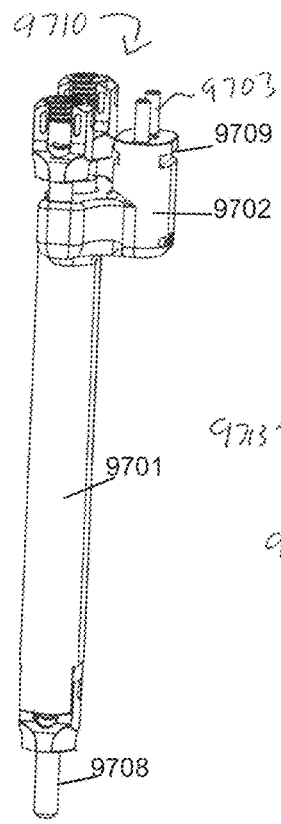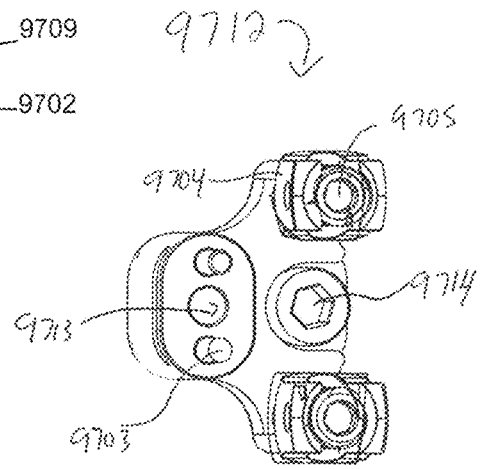
FIG. 97A  FIG. 97B  FIG. 97C
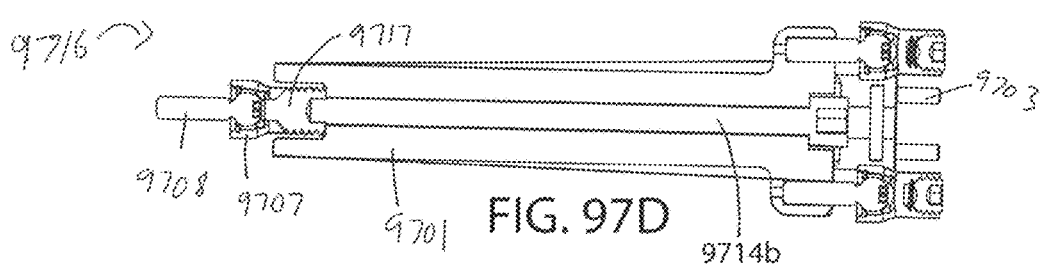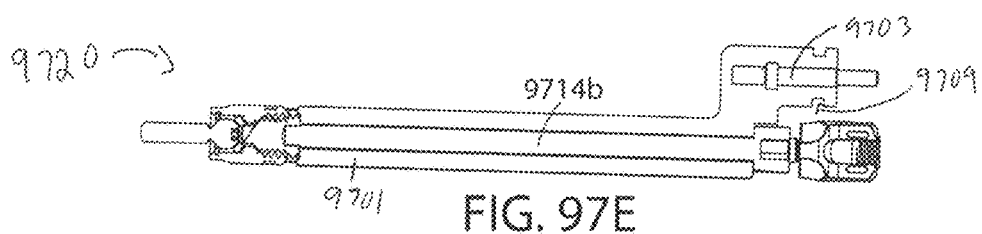

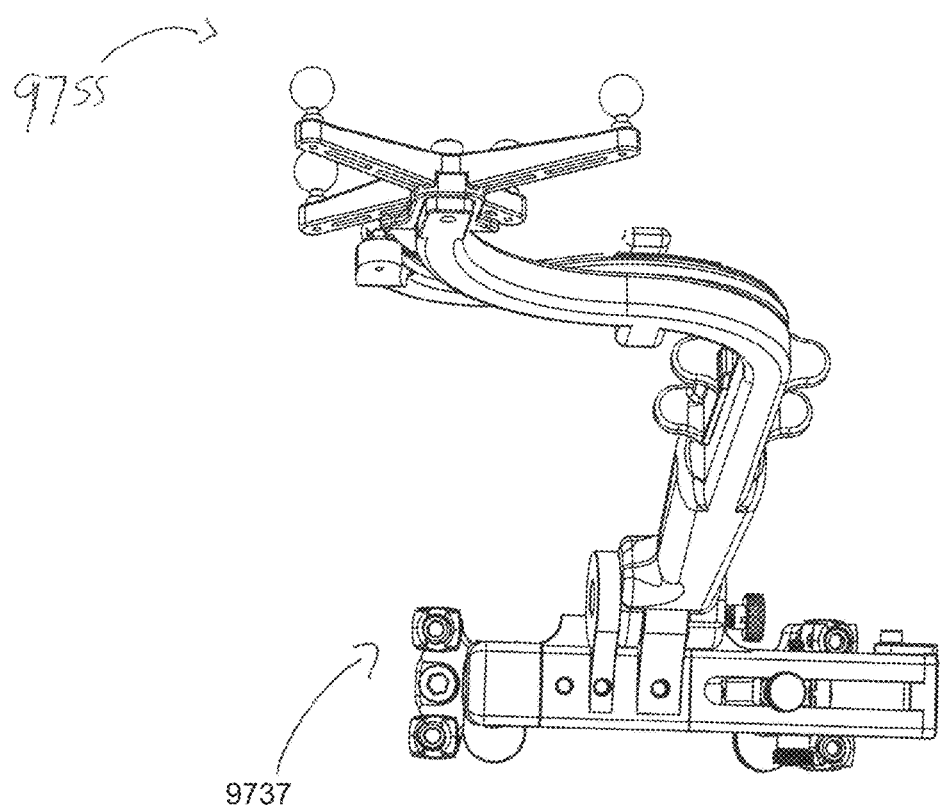
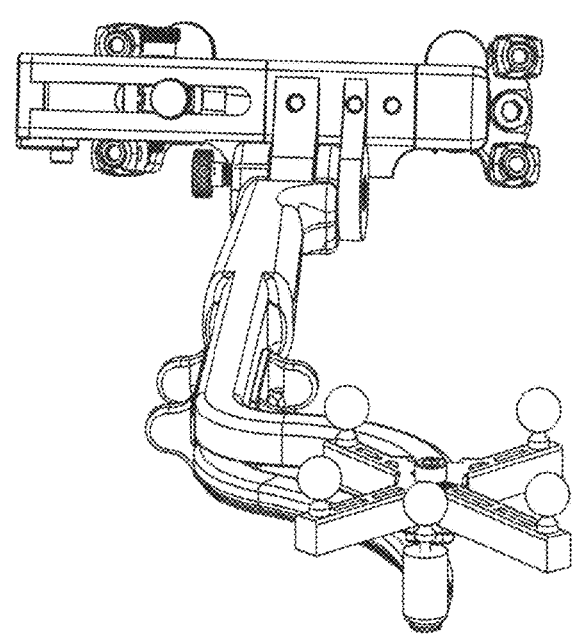
FIG. 97K

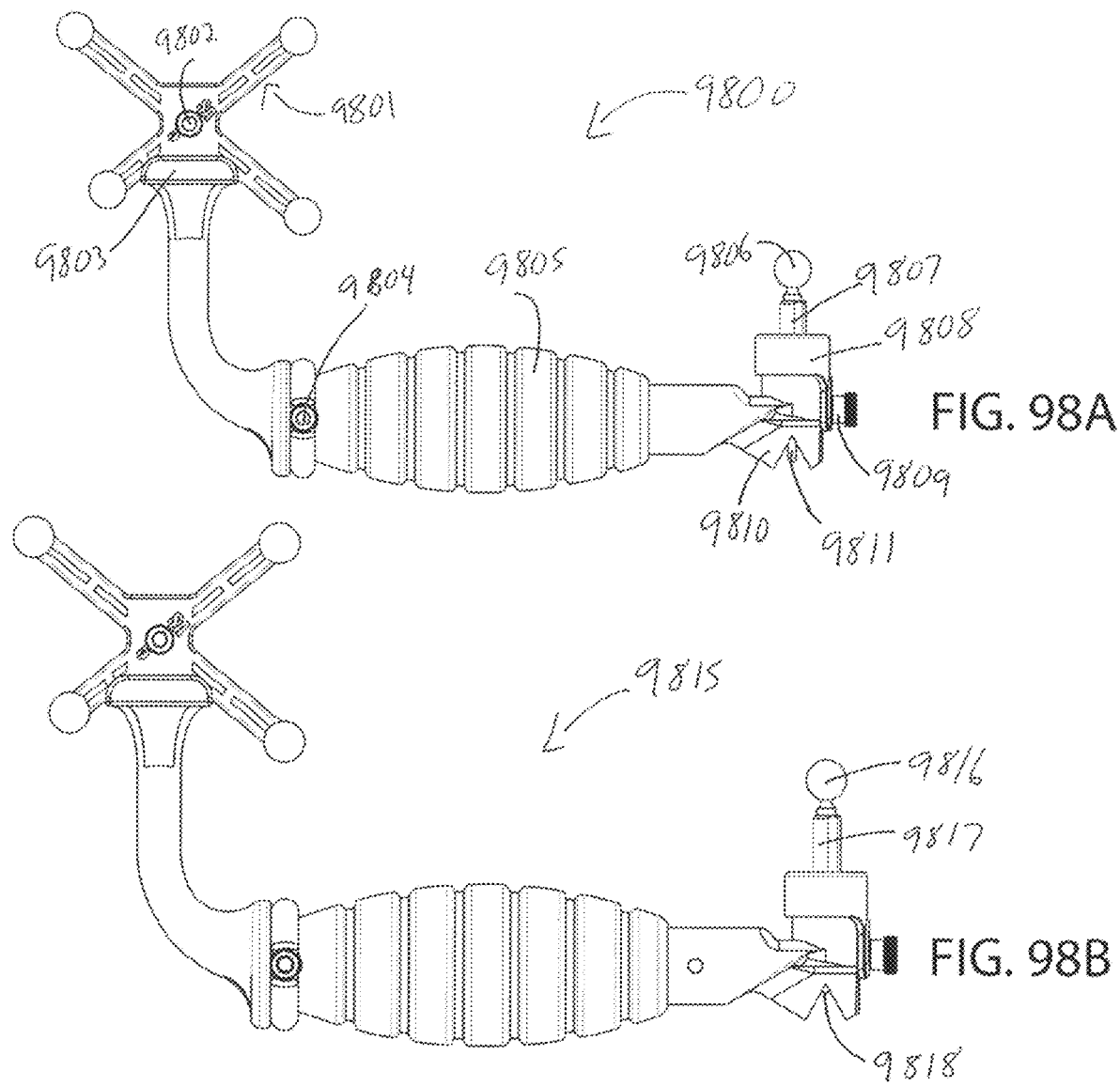
FIG. 98A
FIG. 98B
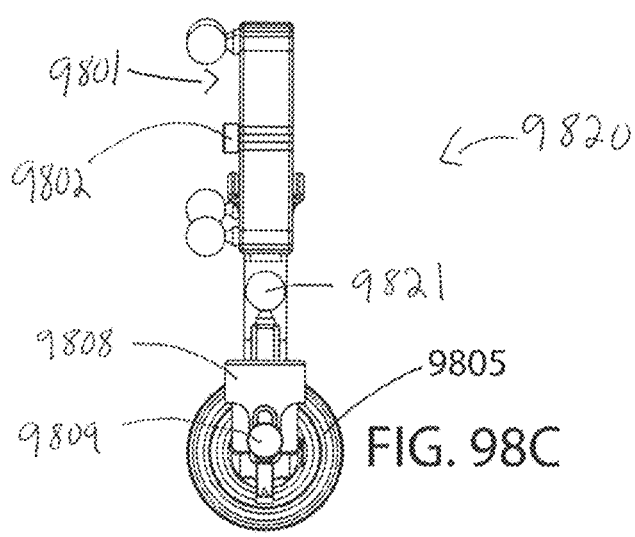
FIG. 98C

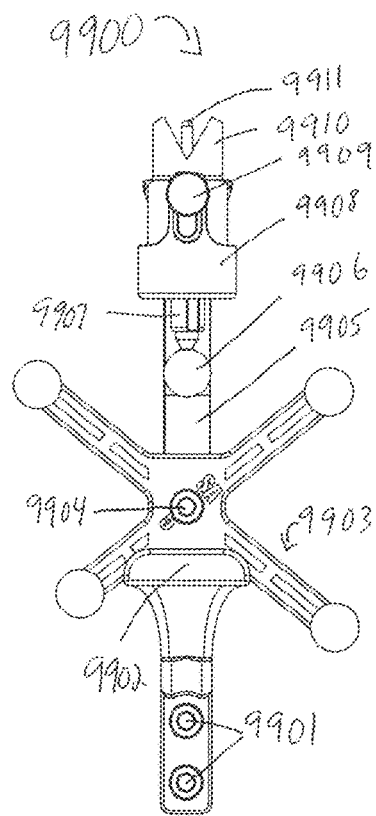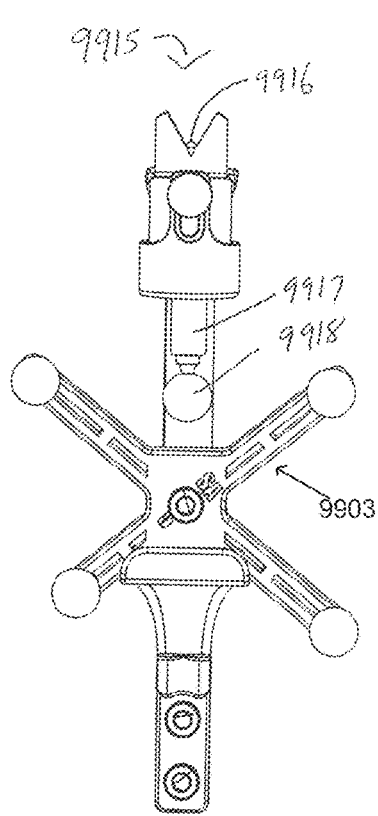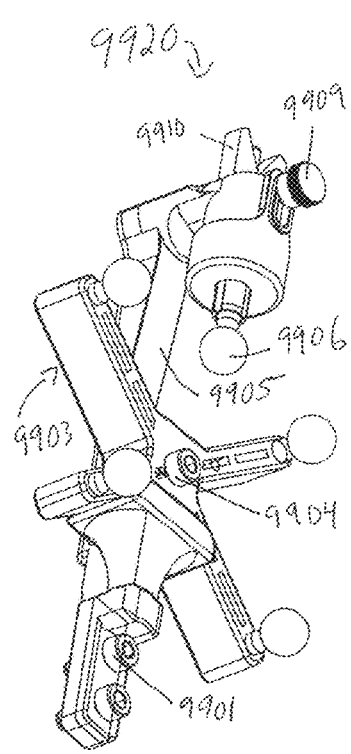
FIG. 99A  FIG. 99B  FIG. 99C
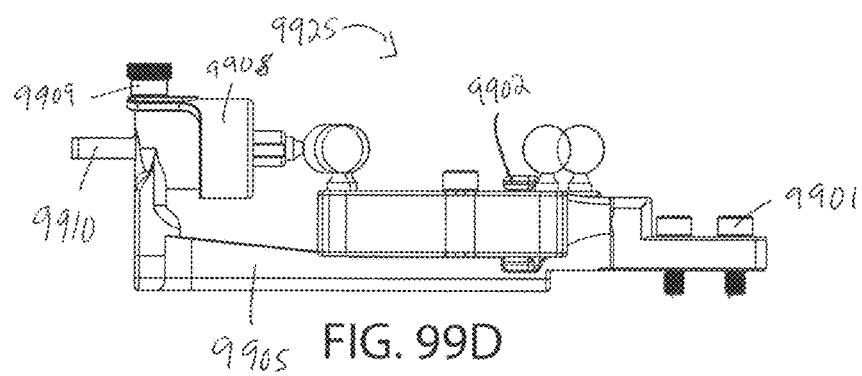
FIG. 99D

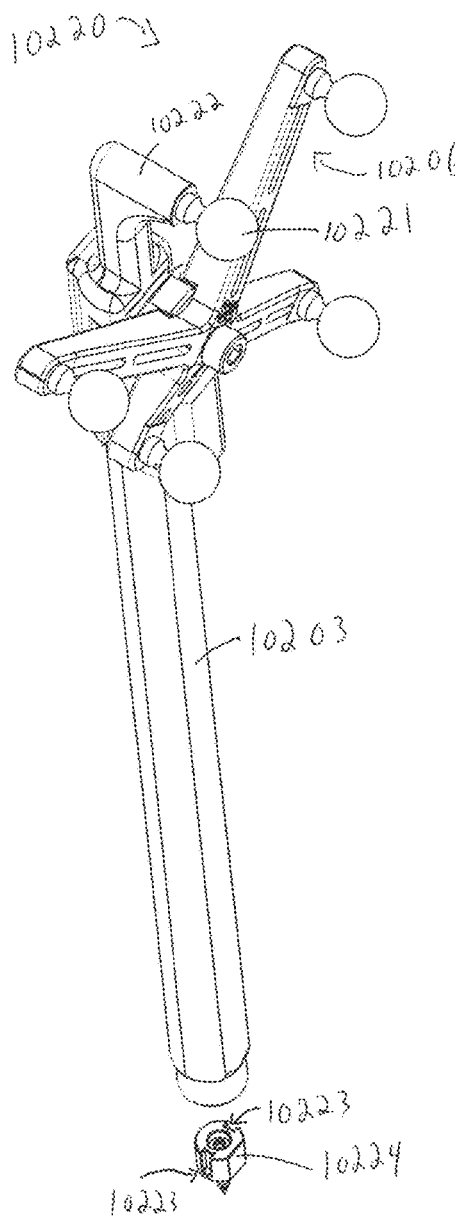
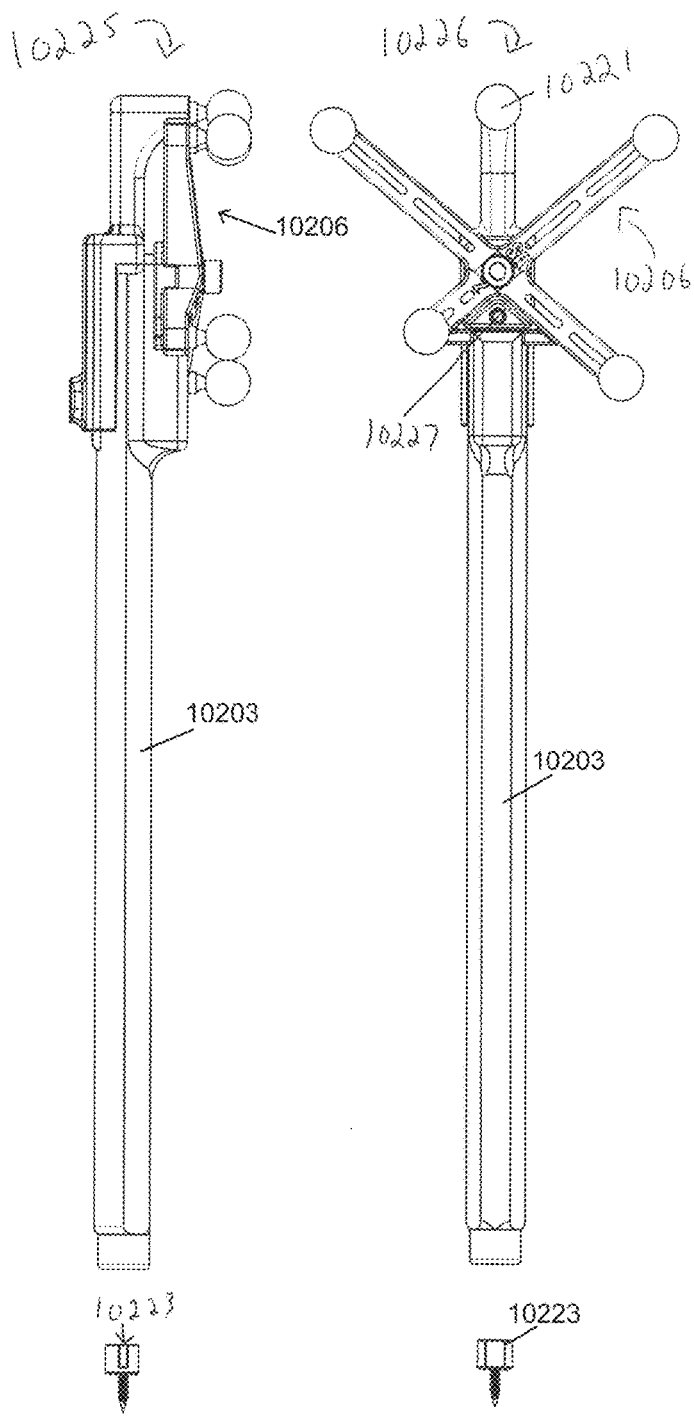
FIG 102D  FIG 102E  FIG 102F

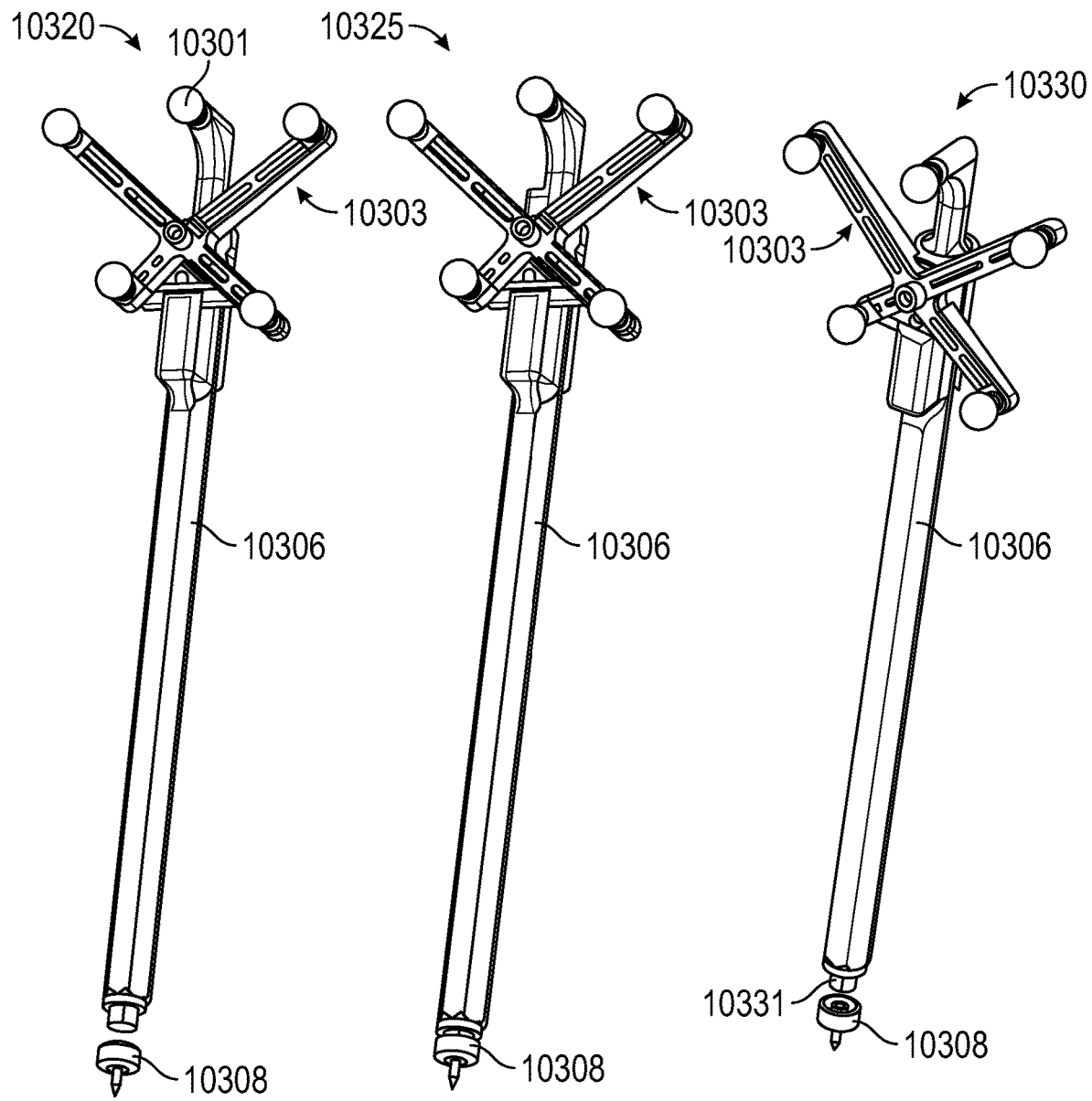

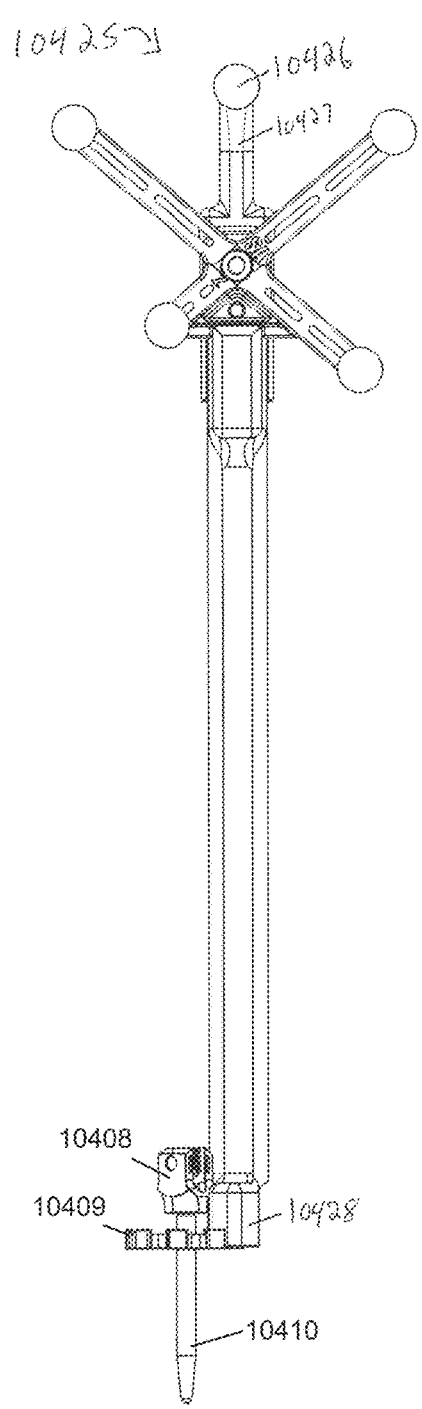
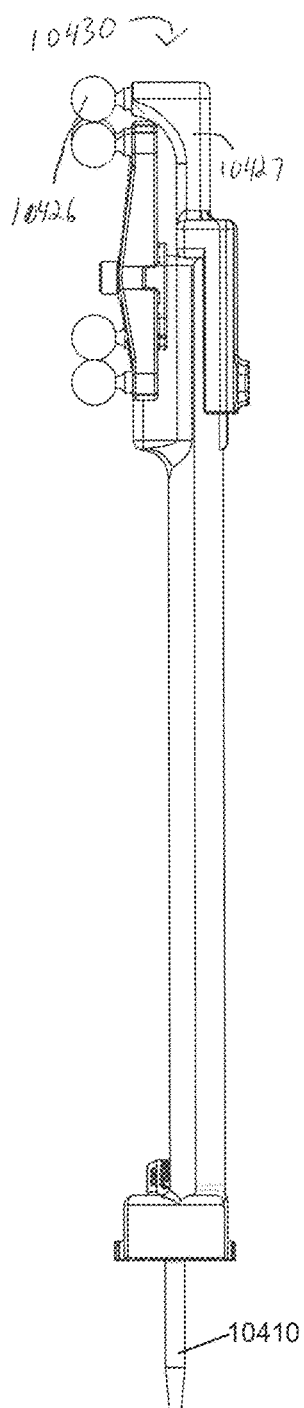
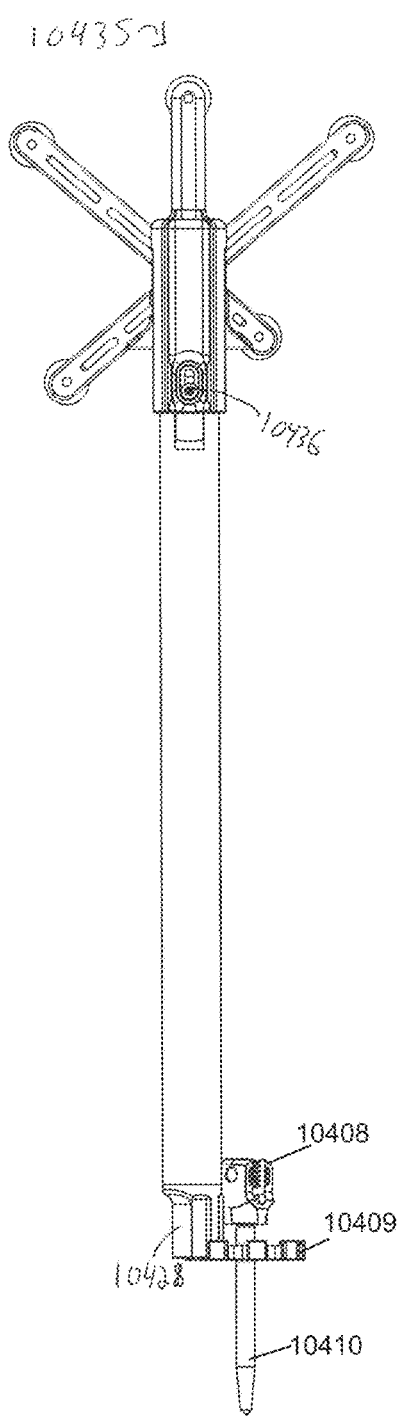
FIG. 104D
FIG. 104E
FIG. 104F

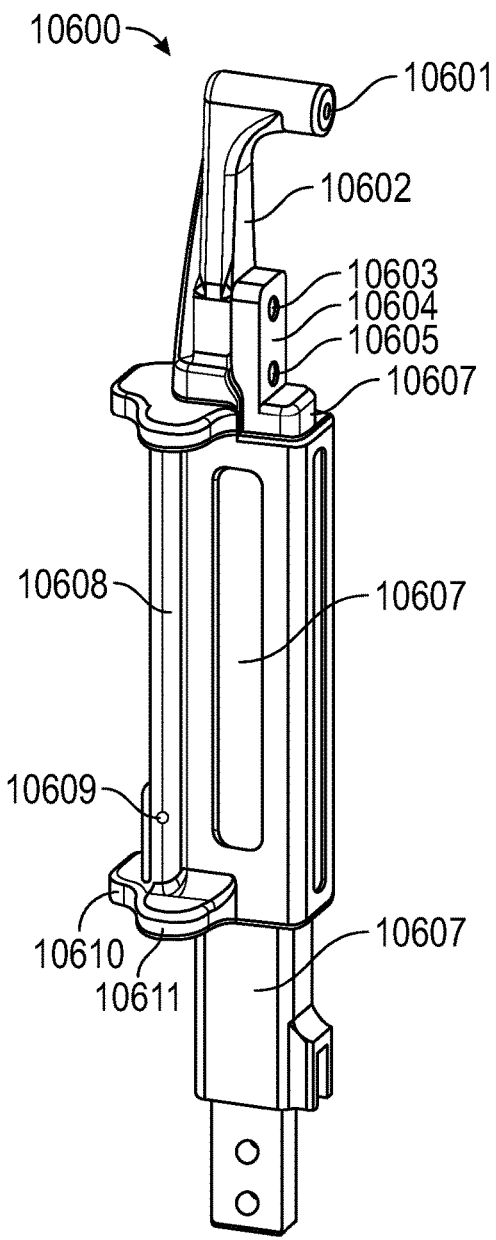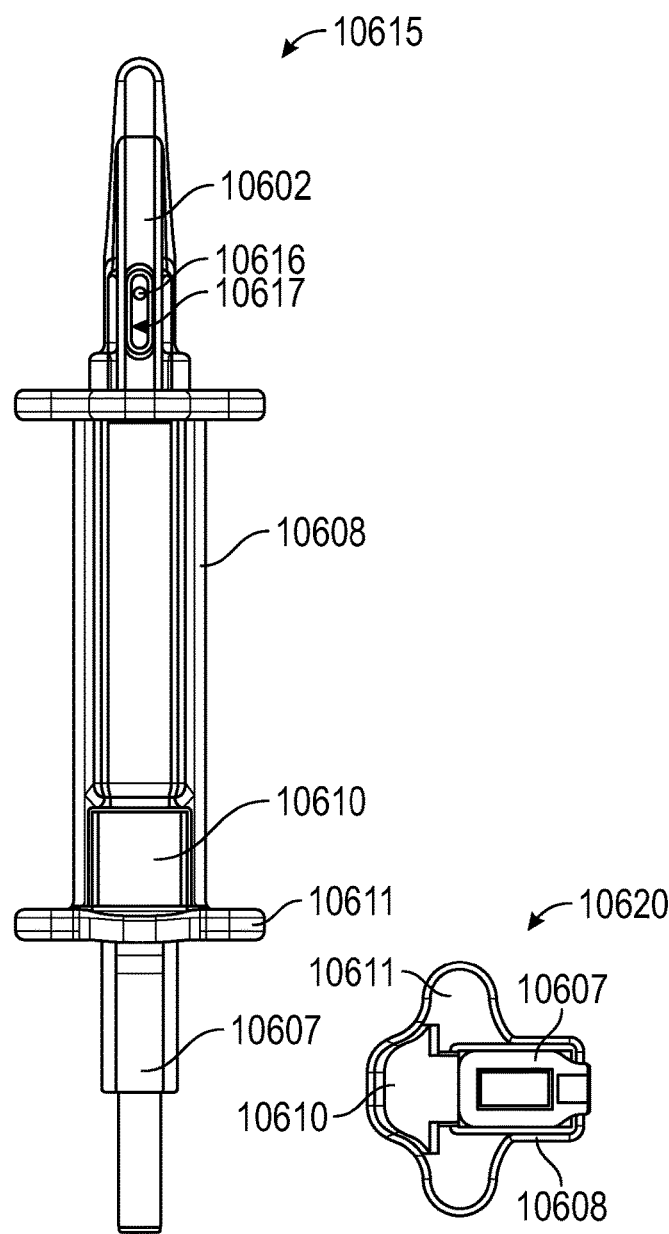
FIG. 106A  FIG. 106B  FIG. 106C

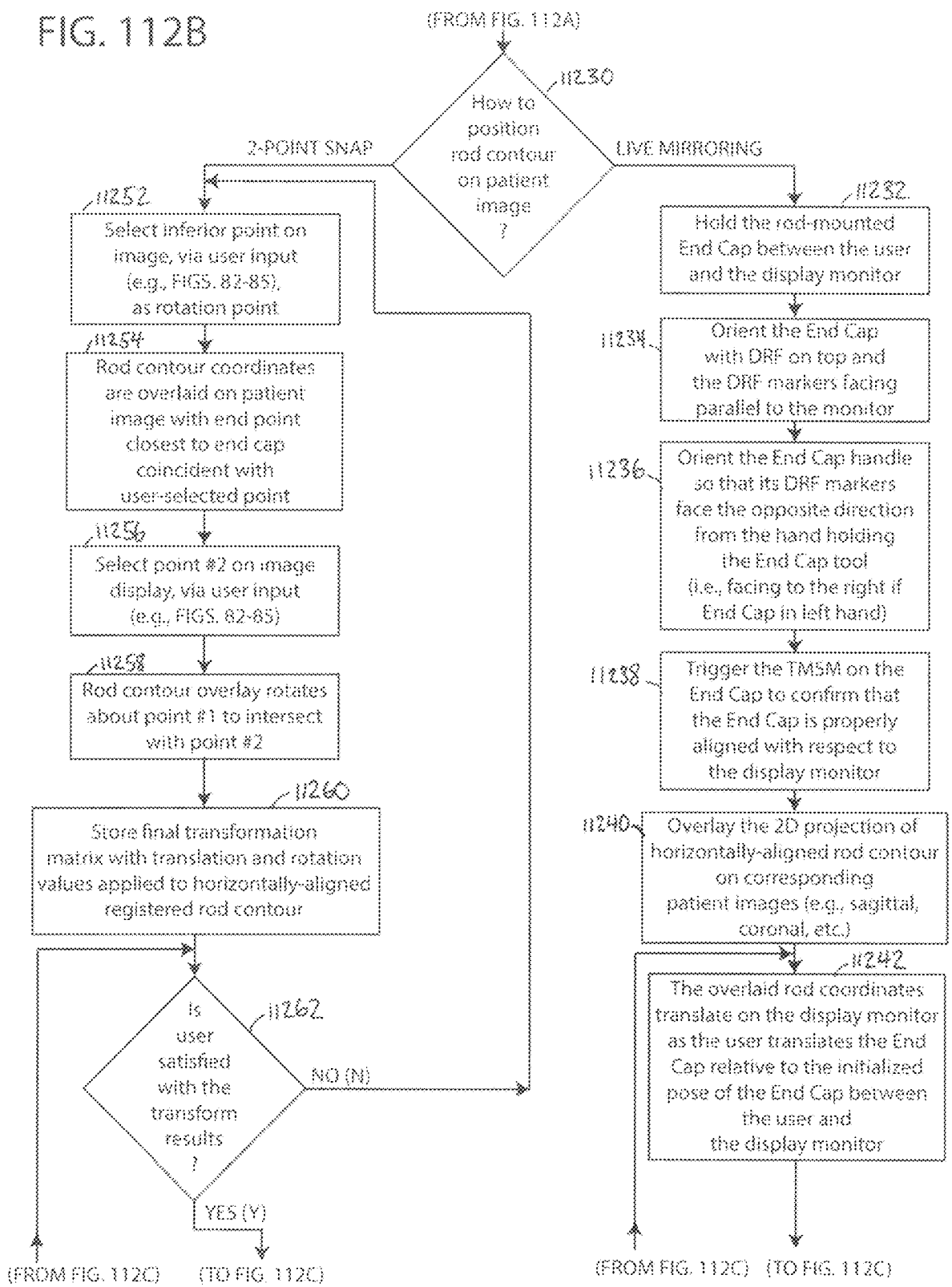

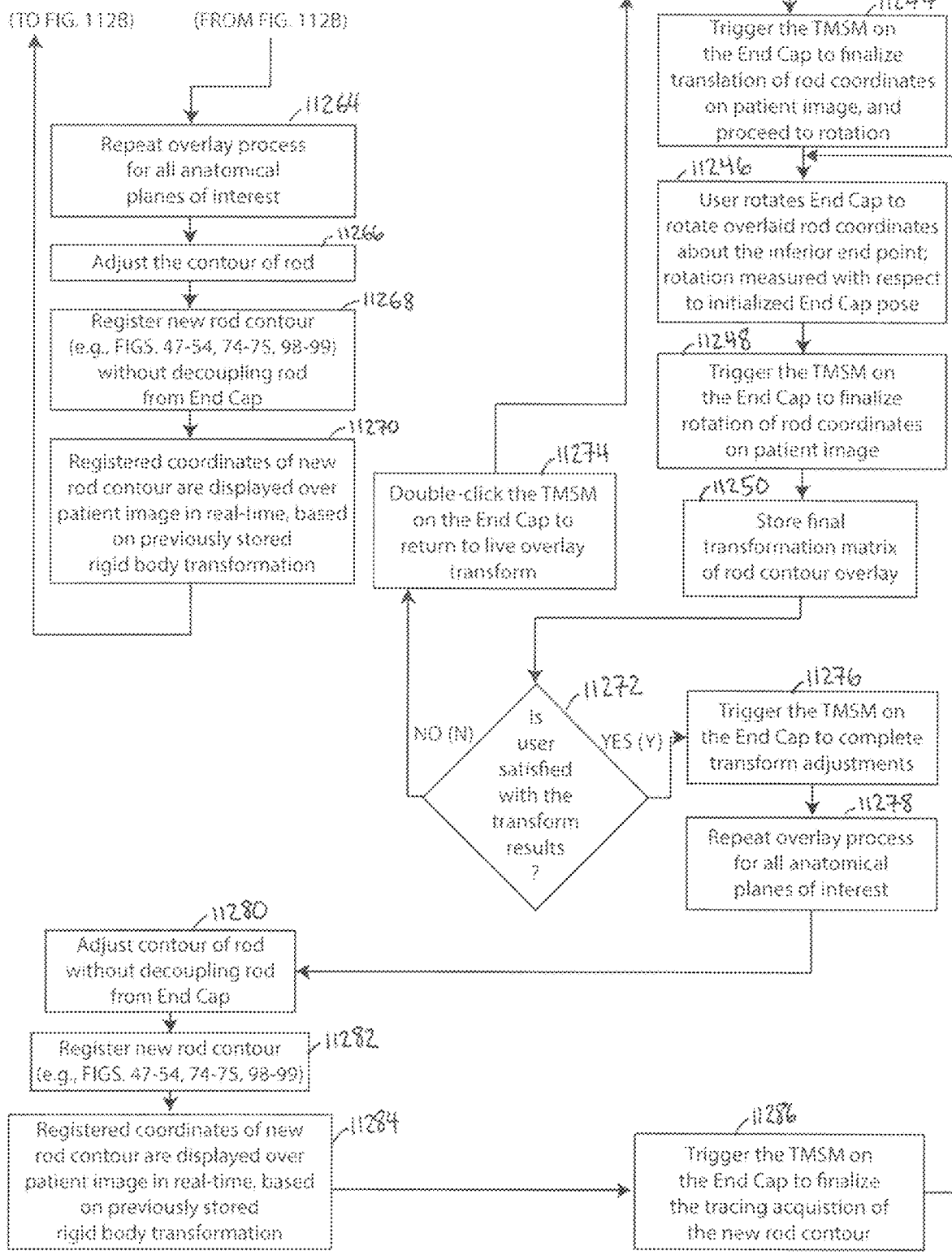

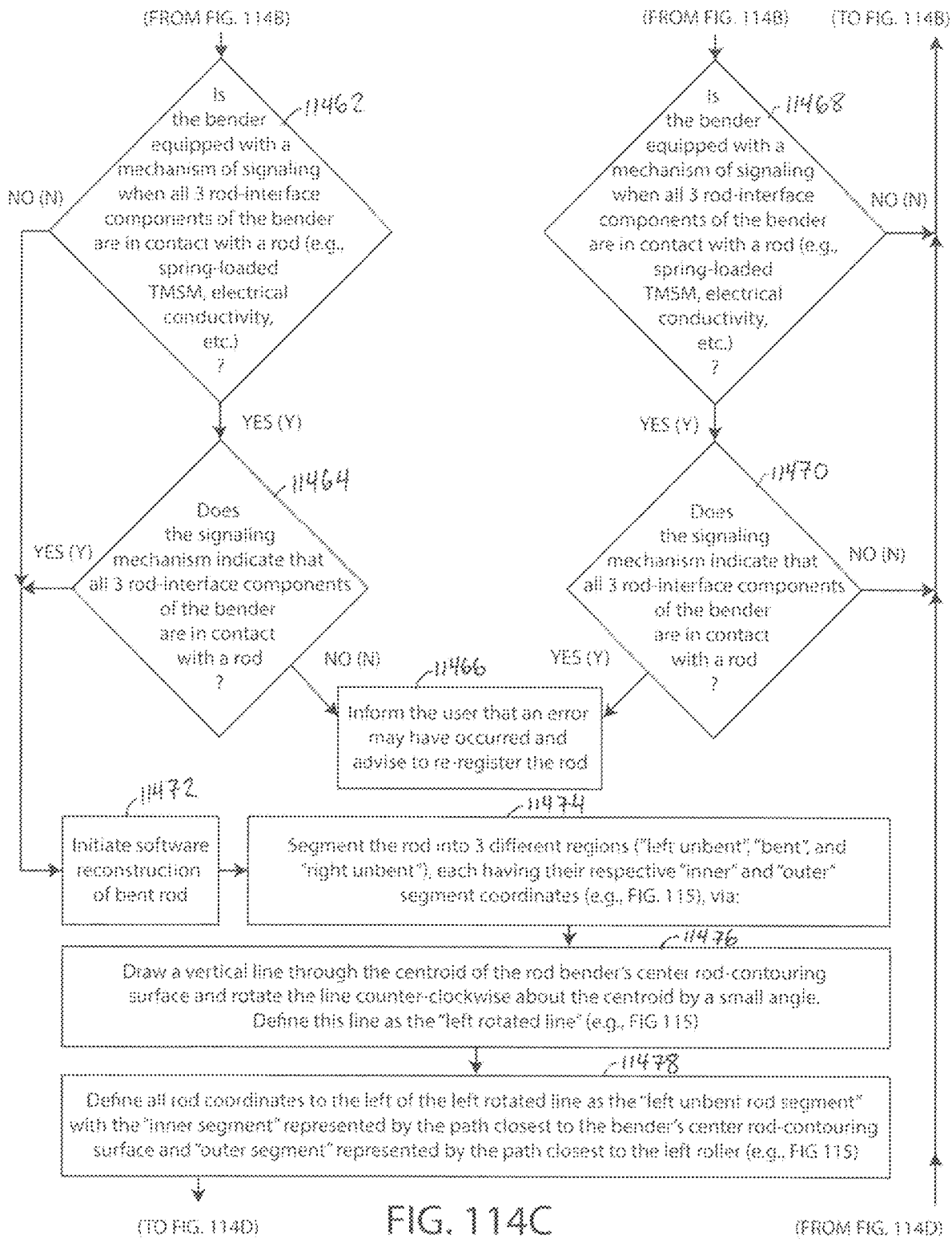

INTRAOPERATIVE ALIGNMENT ASSESSMENT SYSTEM AND METHOD

RELATED APPLICATIONS

This application is a continuation-in-part application of U.S. patent application Ser. No. 16/026,754, entitled "Intraoperative Alignment Assessment System and Method", filed on Jul. 3, 2018, which claims priority to U.S. provisional application Ser. No. 62/528,390, filed on Jul. 3, 2017, the entire contents of which are incorporated herein by reference.

BACKGROUND

Current tools limit a surgeon's ability to quickly and accurately assess the intraoperative alignment of their patient's spine, especially after the spine has been manipulated during a correction. In addition, most of the state-of-the-art options introduce or rely on excessive radiation exposure, inadequate visualization of anatomical landmark(s) of interest, and lengthy disruptions to the surgical workflow.

SUMMARY

Some embodiments include a system comprising at least one dynamic reference frame (DRF) configured so that any fixed or mobile portion of the DRF, or any assembly or component coupled to the DRF can be registered in 3D space using a plurality of trackable markers. In some embodiments, the plurality of trackable markers includes at least one moveable or triggerable marker. Some embodiments include at least one user-actuation trigger or actuator coupled to the at least one moveable or triggerable marker that can trigger or actuate the at least one moveable or triggerable marker. Some further embodiments include at least one 3D tracking camera or imaging system configured to track one or more of the plurality of trackable markers. In some embodiments, the system includes a processor and a memory coupled to the processor, wherein the memory stores instructions executable by the processor to track one or more 3D coordinates of one or more of the plurality of trackable markers.

Some further embodiments include a method of analyzing and providing spinal alignment anatomical information and therapeutic device data, comprising obtaining initial patient data, acquiring alignment contour information, assessing localized anatomical features, obtaining anatomical region data, analyzing localized anatomy, analyzing therapeutic device location and contouring, and/or outputting on a display the localized anatomical analyses and therapeutic device contouring data.

Some further embodiments include an anatomical marking or tracking system comprising a lower fiducial alignment assembly and a complementary upper fiducial alignment assembly. In some embodiments, the lower fiducial alignment assembly is configured to couple to an anatomy, and the upper fiducial alignment assembly is configured to align to at least a portion of the lower fiducial assembly using at least one characteristic of the lower fiducial alignment assembly and the upper fiducial alignment assembly.

Some embodiments include radiopaque markers configured to be visually observable using an X-ray source or imager, where the radiopaque markers are at least partially embedded in at least one of the lower fiducial alignment assembly and a complementary upper fiducial alignment assembly.

In some embodiments, the at least one characteristic comprises at least one magnet. In other embodiments, the at least one characteristic comprises at least one protrusion configured to at least partially insert or mate with at least one mating aperture. In some embodiments, the at least one protrusion comprises at least one protrusion extending from a mating surface of the lower fiducial alignment assembly. In some further embodiments, the at least one mating aperture is positioned through a mating surface of the upper fiducial alignment assembly.

In some embodiments of the invention, the lower fiducial alignment assembly and complementary upper fiducial alignment assembly are configured to be at least partially aligned and coupled at an interface through surgical drapes or towels, where the interface comprises at least a portion of the surgical drapes or towels positioned between at least a portion of the lower fiducial alignment assembly and complementary upper fiducial alignment assembly.

In some further embodiments, the upper fiducial alignment assembly comprises at least one groove positioned in an upper surface, where the at least one groove is configured to be tracked by a tracking probe to determine a unique identity of the system as well as interpret its location and pose in space.

In some embodiments, the at least one groove comprises a "z" geometry configured to accommodate and/or guide a tracking probe. In some further embodiments, the at least one groove comprises a sloped decline configured to facilitate a user tracing a probe from the upper surface of the upper surface of the upper fiducial alignment assembly down to a body surface onto which the system is placed.

In some embodiments, the lower fiducial alignment assembly is configured and arranged to adhere to a skin surface. In some further embodiments, the lower fiducial alignment assembly and/or upper fiducial alignment assembly can comprise a guide indicative of how a user should position the system. In some embodiments, the guide comprises an arrow shape indicative of a position or orientation. In some embodiments of the system, the radiopaque markers comprise three or more markers positioned with respect to each other to enable calculation of 3D pose information.

Some further embodiments comprise a tracking probe configured to couple to at least a portion of the upper fiducial alignment assembly. In some embodiments, the tracking probe is configured to couple to at least one groove of the upper fiducial alignment assembly to determine a unique identity of the system as well as interpret its location and pose in space.

Some embodiments include a tracking system comprising a lower fiducial alignment assembly and a complementary upper fiducial alignment assembly, where the lower fiducial alignment assembly is configured to couple to an anatomy, and the upper fiducial alignment assembly is configured to align to at least a portion of the lower fiducial assembly using at least one characteristic of the lower fiducial alignment assembly and the upper fiducial alignment assembly. In some further embodiments, the radiopaque markers are configured to be visually observable using an X-ray source or imager, and the radiopaque markers are at least partially embedded in at least one of the lower fiducial alignment assembly and a complementary upper fiducial alignment assembly. Some embodiments also include at least one tracking probe assembly configured to couple to at least a portion of the upper fiducial alignment assembly, and at least one groove positioned in the upper fiducial alignment assembly. In some embodiments, the at least one groove is configured to be tracked by the at least one tracking probe assembly to determine a unique identity of the system as well as interpret its location and pose in space.

In some embodiments of the tracking system, the at least one characteristic comprises at least one magnet. In some embodiments of the tracking system, the at least one characteristic comprises at least one protrusion configured to at least partially insert or mate with at least one mating aperture, where the at least one protrusion extends from the mating surface of the lower fiducial alignment assembly, and the at least one mating aperture is positioned through a mating surface of the upper fiducial alignment assembly.

Some embodiments of the tracking system include at least one groove that comprises a "z" geometry configured to accommodate and/or guide the tracking probe. In some embodiments, the at least one groove comprises a sloped decline configured to facilitate a user tracing a probe from the upper surface of the upper surface of the upper fiducial alignment assembly down to a body surface onto which at least the lower fiducial alignment assembly is placed.

Some embodiments include a tracking system comprising a tracking probe assembly comprising a probe shaft with a depressible sliding shaft tip, and a mount with a trackable mobile stray marker at one end of the probe shaft, and a plurality of depth-stops at the opposite end of the probe shaft. Further, some embodiments include a dynamic reference frame coupled to the probe shaft adjacent the mount.

Some embodiments further comprise at least one depth-stop fiducial. In some embodiments, the plurality of depth-stops comprises a series of concentrically-oriented, varying diameter protrusions. In some embodiments, the one or more of the plurality of depth-stops are configured to actuate the depressible sliding shaft tip. Further, in some embodiments, the one or more of the plurality of depth-stops are configured to actuate the depressible sliding shaft tip when forced against a depth-stop fiducial with specific inner diameters, the actuation configured to provide identifiable deflections of the trackable mobile stray marker.

In some embodiments, the probe shaft is spring-loaded. In some embodiments, the dynamic reference frame comprises at least one tracking marker. In some embodiments, the dynamic reference frame comprises four tracking markers, with two of the four tracking markers extending to one side of the probe shaft and two of the four tracking markers extending to an opposite side of the probe shaft. Some other embodiments further comprise an asymmetric protruding extrusion configured to engage with a corresponding slot of a depth-stop fiducial.

In some embodiments of the invention, an engagement of the asymmetric protruding extrusion with a corresponding slot of a depth-stop fiducial can enable the system to register a unique orientation of the coordinate axes of the depth-stop fiducial, and/or detect how the depth-stop fiducial rotates and translates in 3D space between one or more registrations.

Some further embodiments comprise a fiduciary assembly comprising a lower fiducial alignment assembly and a complementary upper fiducial alignment assembly, where the lower fiducial alignment assembly is configured to couple to an anatomy, and the upper fiducial alignment assembly is configured to align to at least a portion of the lower fiducial assembly using at least one characteristic of the lower fiducial alignment assembly and the upper fiducial alignment assembly. In some embodiments, the at least one groove is positioned in the upper fiducial alignment assembly, and the at least one groove is configured to be tracked by tracking probe to determine a unique identity of the system as well as interpret its location and pose in space.

In some embodiments, the tracking system comprises radiopaque markers configured to be visually observable using an X-ray source or imager, where the radiopaque markers are at least partially embedded in at least one of the lower fiducial alignment assembly and a complementary upper fiducial alignment assembly. In some embodiments, the at least one characteristic comprises at least one magnet. In some other embodiments, the at least one characteristic comprises at least one protrusion configured to at least partially insert into or mate with at least one mating aperture, and the at least one protrusion extends from the mating surface of the lower fiducial alignment assembly, and further, the at least one mating aperture is positioned through a mating surface of the upper fiducial alignment assembly.

Some embodiments include a tracking system comprising a tracking probe assembly comprising a probe shaft with a depressible sliding shaft tip, and a mount with a trackable mobile stray marker at one end of the probe shaft, and a plurality of depth-stops at the opposite end of the probe shaft. Further, some embodiments include a dynamic reference frame coupled to the probe shaft adjacent the mount, and a lower fiducial alignment assembly and a complementary upper fiducial alignment assembly. In some embodiments, the lower fiducial alignment assembly is configured to couple to an anatomy, and the upper fiducial alignment assembly is configured to align to at least a portion of the lower fiducial assembly using an embedded or coupled element of the lower fiducial alignment assembly and the upper fiducial alignment assembly. Further, some embodiments include at least one groove positioned in the upper fiducial alignment assembly, where the at least one groove is configured to be tracked by the tracking probe assembly. Further, some embodiments of the tracking system further comprise radiopaque markers configured to be visually observable using an X-ray source or imager, and where the radiopaque markers are at least partially embedded in at least one of the lower fiducial alignment assembly and a complementary upper fiducial alignment assembly. In some embodiments, the at least one embedded or coupled element comprises at least one magnet. In other embodiments, the at least one embedded or coupled element comprises at least one at least one protrusion configured to at least partially insert or mate with at least one mating aperture, where the at least one protrusion extends from the mating surface of the lower fiducial alignment assembly, and the at least one mating aperture is positioned through a mating surface of the upper fiducial alignment assembly.

Some embodiments include a marker system comprising a lower fiducial alignment assembly and a complementary upper fiducial alignment assembly, where the lower fiducial alignment assembly is configured to couple to an anatomy, and the upper fiducial alignment assembly is configured to align to at least a portion of the lower fiducial assembly, and the radiopaque markers are configured to be visually observable using an X-ray source or imager, and extend from the complementary upper fiducial alignment assembly.

In some embodiments, the radiopaque markers comprise three radiopaque markers. In some further embodiments, the radiopaque markers are positioned on corners of the upper fiducial alignment assembly. In some embodiments, the lower fiducial alignment assembly/or a complementary upper fiducial alignment assembly include slots. In some further embodiments, an upper surface of the upper fiducial alignment assembly comprises a depression or contour configured to be probed by a tracking probe shaft or tip.

In some embodiments, the lower fiducial alignment assembly and complementary upper fiducial alignment assembly are configured to be at least partially aligned and coupled at an interface through surgical drapes or towels, where the interface comprises at least a portion of the surgical drapes or towels positioned between at least a portion of the lower fiducial alignment assembly and complementary upper fiducial alignment assembly.

Some embodiments further comprise a tracking probe assembly comprising a probe shaft and at least one coupled dynamic reference frame including optically trackable markers.

Some embodiments include an anatomy analysis method comprising providing at least one trackable surgical tool including a tool dynamic reference frame and at least one trackable marker, where the at least one trackable surgical tool is configured so that any fixed or mobile portion of the at least one trackable surgical tool can be registered in 3D space. In some embodiments, the method includes providing at least one 3D tracking camera or imaging system configured to track the at least one trackable marker. In some embodiments, the method includes providing a topological optical surface registration system. In some embodiments, the method includes providing a malleable contour element coupled to at least a portion of a patient. In some other embodiments, the method includes providing an electromechanical 3D-tracking system, where the electromechanical 3D-tracking provides a system including at least one physically coupled probe, where the at least one physically coupled probe is configured to be tracked in 3D space while coupled to the malleable contour element and/or at least a portion of a patient, and tracing at least a portion of an anatomy of a patient. In some embodiments, the method includes registering the location of one or more fiducial markers inside or outside a surgical site of the patient. In some further embodiments, the method includes registering a contour of at least a portion of the patient using the malleable contour element. In some other embodiments, the method includes providing a processor and a memory coupled to the processor, where the memory stores anatomy contour measurement instructions executable by the processor to track 3D coordinates of one or more of the fiducial markers. In some embodiments, the instructions executable by the processor including outputting on a display an anatomical imaging analysis of at least a portion of the patient, and one or more anatomical landmarks registered by the electromechanical 3D-tracking system that are adjusted in position and orientation to the registered contour.

Some embodiments of the invention include a trackable probe assembly comprising a trackable dynamic reference frame coupled or integrated to a probe shaft, where the dynamic reference frame includes at least one marker. Some embodiments include a user actuable marker coupled to a user triggerable assembly including a trigger, and at least one probe tip extending from the probe shaft.

In some embodiments, the trigger comprises a depressible tab positioned at one end of a pivotable arm, where the user actuable marker is coupled to the opposite end of the pivotable arm, the pivotable arm configured and arranged to enable rotation of the user actuable marker. In some further embodiments, the trigger comprises a trigger tab mounted to an extension of a rotatable trigger arm, where the user actuable marker is coupled to the opposite end of the rotatable trigger arm, and is configured and arranged to be rotated in an arc pathway determined by angular displacement of the trigger arm following user actuation of the trigger tab.

In some embodiments, the user triggerable assembly includes a two-link arm link coupled to a slidable shaft, where the user actuable marker is coupled to the slidable shaft, and is configured and arranged to enable movement of the user actuable marker that is coaxial with the probe shaft when the two-link arm link is actuated by user actuation of the trigger.

Some embodiments include an implantable rod analysis system comprising a trackable slider assembly comprising a handle including a dynamic reference frame mounting arm extending from one end, and a rod engagement assembly at an opposite end, the rod engagement assembly configured to slide along a surface of the implantable rod. Some embodiments further comprise a dynamic reference frame (DRF) coupled to the dynamic reference frame mounting arm or configured to be coupled onto the dynamic reference frame mounting arm. Some embodiments include a trackable end cap assembly comprising a rod mounting assembly that can engage and secure one end of the implantable rod, and a dynamic reference frame including trackable markers.

In some embodiments, the system further comprises a 3D tracking camera or imaging system configured to track the at least one trackable marker, and a processor and a memory coupled to the processor, where the memory stores anatomy contour measurement instructions executable by the processor to track 3D coordinates of at least one fixed or mobile marker, and output on a display an anatomical imaging analysis of at least a portion of a patient, and one or more anatomical landmarks and registered contour of the implantable rod.

Some embodiments include an implantable rod adjustment and measurement system comprising a trackable rod bender assembly comprising a roller assembly including three rollers arranged on a pair rotatable handles and at least one trackable marker, where the roller assembly can grip a surface of an implantable rod, slide along a surface of the implantable rod, and/or bend the implantable rod. Some embodiments include a trackable end cap assembly comprising a rod mounting assembly that can engage and secure one end of the implantable rod, and a dynamic reference frame including trackable markers. In some embodiments, at least one of the handles includes a coupled dynamic reference frame including at least one trackable marker. Some further embodiments include a 3D tracking camera or imaging system configured to track the at least one trackable marker, a processor and a memory coupled to the processor, where the memory storing anatomy contour measurement instructions executable by the processor. In some embodiments, the instructions operate a method including tracking 3D coordinates of at least one fixed or mobile marker, and outputting on a display an anatomical imaging analyses of at least a portion of a patient, one or more anatomical landmarks and registered contour of the implantable rod and to display an illustration of a bending of the implantable rod.

Some embodiments include an assembly comprising an adjustable bracket including a fixed shoulder at one end and an adjustable channel at an opposite end, where the adjustable channel extends at least partially to the fixed shoulder. Further, some embodiments include a first side arm extending from the fixed shoulder, and a second side arm extending from the adjustable channel, where the first and second side arms each configured to couple with a pedicle screw. In some embodiments, the second side arm is configured and arranged to be moveable in the adjustable channel enabling the distance between the first and second side arms to be adjusted. Some further embodiments include a handle extending from the adjustable bracket, and at least one dynamic reference frame (DRF) coupled to the handle, where the DRF includes at least one trackable marker.

Some embodiments include a system comprising an assembly comprising an adjustable bracket including a fixed shoulder at one end and an adjustable channel at an opposite end, where the adjustable channel extends at least partially to the fixed shoulder. Some further embodiments include a first side arm extending from the fixed shoulder, and a second side arm extending from the adjustable channel, where the first and second side arms are each configured to couple to a pedicle screw. Some embodiments include a handle extending from the adjustable bracket, and at least one dynamic reference frame (DRF) coupled to the handle, where the DRF includes at least one trackable marker, and where the second side arm is configured and arranged to be moveable in the adjustable channel enabling the distance between the first and second side arms to be adjusted. Further, some embodiments include at least one 3D tracking camera or imaging system configured to track the at least one trackable marker, and a processor and a memory coupled to the processor. In some embodiments, the memory stores instructions executable by the processor to track 3D coordinates of one or more of trackable markers, and output on a display an anatomical imaging analysis of at least a portion of a patient, and one or more anatomical landmarks and representation of at least a portion of the assembly based on the 3D coordinates.

Some embodiments include a fiducial system comprising a probe assembly comprising, and a trackable dynamic reference frame coupled or integrated to a probe shaft. Some embodiments include a moveable post with trackable marker that is slidably positioned in the probe shaft. Some embodiments include at least one probe tip extrusion tab configured and arranged to engage a mating portion of an implantable mating screw. Some embodiments include a spring-loaded plunger movable positioned in the probe shaft, and configured to be actuated against a surface of the mating screw, elevating the moveable post with trackable marker to a triggered state defined by mating of the probe assembly with the mating screw.

Some embodiments of the invention include an assembly comprising an adjustable bracket including a fixed shoulder at one end and an adjustable channel at an opposite end, where the adjustable channel extending at least partially to the fixed shoulder, and a first side arm extending from the fixed shoulder, and a second side arm extending from the adjustable channel, the first and second side arms each configured to couple with a pedicle screw. Some further embodiments include at least one adjustable screw interface extending from at least one of the first side arm and the second side arm, and including a tool mating tip configured to engage a screw mating attachment comprising a depth-stop, and where the second side arm is configured and arranged to be moveable in the adjustable channel enabling the distance between the first and second side arms to be adjusted.

Some embodiments further comprise a handle extending from the adjustable bracket, and at least one dynamic reference frame (DRF) coupled to the handle, where the DRF includes at least one trackable marker.

In some embodiments, the system comprises an assembly comprising an adjustable bracket including a fixed shoulder at one end and an adjustable channel at an opposite end, where the adjustable channel extends at least partially to the fixed shoulder, and a first side arm extending from the fixed shoulder, and further, a second side arm extending from the adjustable channel, the first and second side arms each configured to couple with a pedicle screw. Some embodiments include at least one adjustable screw interface extending from at least one of the first side arm and the second side arm, where the at least one adjustable screw interface includes a tool mating tip configured to engage a screw mating attachment comprising a depth-stop. Further, some embodiments include a handle extending from the adjustable bracket, and at least one dynamic reference frame (DRF) coupled to the handle, where the DRF includes at least one trackable marker. In some embodiments, the second side arm is configured and arranged to be moveable in the adjustable channel enabling the distance between the first and second side arms to be adjusted. Further, some embodiments include providing at least one 3D tracking camera or imaging system configured to track the at least one trackable marker, and a processor and a memory coupled to the processor. In some embodiments, the memory stores instructions executable by the processor to track 3D coordinates of one or more of trackable markers, and output on a display an anatomical imaging analysis of at least a portion of a patient, and one or more anatomical landmarks and representation of at least a portion of the assembly based on the 3D coordinates.

Some embodiments include a method comprising acquiring at least one X-ray image from a patient, where the patient is positioned with at least one dynamic reference frame and at least one trackable marker enabling any portion of the patient to be registered in 3D space and any portion of the acquired X-ray image to include at least one tracked 3D coordinate. Further, the method includes calculating the position and orientation of at least one portion of the patient from the at least one X-ray image and the at least one tracked 3D coordinate. Further, the method includes calculating and scaling 3D coordinates of the at least one X-ray image to a phantom model. Further, the method includes transforming 3D coordinates to cartesian coordinates of the phantom model. Further, the method includes providing a phantom model mounting assembly including at least one dynamic reference frame. Further, the method includes positioning at least one portion of the phantom model onto the phantom model mounting assembly based on one or more of the cartesian coordinates and a position of the at least one dynamic reference frame.

Some embodiments include a 3D trackable probe system comprising a probe assembly comprising a trackable dynamic reference frame coupled or integrated to a probe shaft, where the dynamic reference frame includes at least one marker. Some embodiments include a user actuable marker coupled to a user triggerable assembly including a trigger, and at least one probe tip extending from the probe shaft, and at least one 3D tracking camera or imaging system configured to track the at least one trackable marker. Some embodiments include a processor and a memory coupled to the processor, where the memory stores instructions executable by the processor to track 3D coordinates of one or more of trackable markers, and calculate a 3D position and pose of the probe assembly.

In some embodiments, the trigger comprises a depressible tab positioned at one end of a pivotable arm, where the user actuable marker is coupled to the opposite end of the pivotable arm, the pivotable arm configured and arranged to enable rotation of the user actuable marker.

In some embodiments, the trigger comprises a trigger tab mounted to an extension of a rotatable trigger arm, where the user actuable marker is coupled to the opposite end of the rotatable trigger arm, and is configured and arranged to be rotated in an arc pathway determined by angular displacement of the trigger arm following user actuation of the trigger tab.

In some embodiments, the user triggerable assembly includes a two-link arm link coupled to a slidable shaft, where the user actuable marker is coupled to the slidable shaft, and is configured and arranged to enable movement of the user actuable marker that is coaxial with the probe shaft when the two-link arm link is actuated by user actuation of the trigger.

Some embodiments include a probe assembly comprising a probe shaft including one or more coaxial depth-stops proximate one end of the probe shaft and a trackable dynamic reference frame integrated or coupled proximate an opposite end of the probe shaft, where the one or more of the coaxial depth-stops are configured to couple or mate with one or more depth-stop fiducials. Some further embodiments include a moveable shaft slidably positioned at least partially within the probe shaft, where the moveable shaft includes a probe tip at one end and a trackable marker at an opposite end.

In some embodiments, the probe assembly is configured and arranged so that during use, coupling of the probe-tip with a body surface with movement of the moveable shaft comprises movement of the trackable marker away from the body to a distance determined by the one or more depth-stop fiducials. In some further embodiments, one or more of the coaxial depth-stops comprise an alignment protrusion configured and arranged to mate, interlock, or couple with a complementary slot, cavity, or receptable of the one or more depth-stop fiducials.

Some embodiments include a system comprising a trackable surgical tool including a tool dynamic reference frame and at least one trackable marker, where the trackable surgical tool is configured so that any fixed or mobile portion of the trackable surgical tool can be registered in 3D space. Some embodiments include a processor and a memory coupled to the processor, where the memory stores instructions executed by the processor to acquire at least one X-ray image from a patient wherein the location and pose of the emitter and detector are known or determined, and using at least one X-ray imager mounted dynamic reference frame, determine a conical imaging volume of an X-ray imager coupled to the processor. Further, in some embodiments, the memory stores instructions executed by the processor to record pose of the trackable surgical tool, and visually display, on an external display or device, in response to a calculated position of the trackable surgical tool in the conical imaging volume, a scaled projection of the trackable surgical tool over at least a portion of the X-ray image displayed on the external display or device.

Some embodiments include a trackable probe comprising at least one trackable dynamic reference frame (DRF) including at least one trackable marker, and at least one movable trackable marker coupled to the DRF. Some embodiments include a mating protrusion extending from the DRF including a mating slot or cavity. Some embodiments include at least one probe extension including a mating element, where the mating element is configured for insertion and/or sliding in the mating slot or cavity.

In some embodiments, the at least one movable trackable marker is positioned coupled to a slidable insert of the mating protrusion. In some embodiments, the at least one movable trackable marker is spring-loaded, where movement of the at least one movable trackable marker is governed by the spring-loading.

Some embodiments include a fiducial patch comprising a body-surface mountable article including a plurality of radiopaque markers arranged between a plurality of radiopaque grid lines. In some embodiments, the radiopaque markers comprise at least one of colors or shades of grey, letters, numbers, symbols, and icons. Some embodiments further comprise adhesive at least partially covering one side of the body-surface mountable article, the one side being a side intended for coupling to a body surface. Some other embodiments further comprise at least one radiopaque lining that at least partially matches one or more of the plurality of radiopaque markers.

Some embodiments include a probe assembly comprising a trackable probe including a trackable dynamic reference frame integrated or coupled to a first end of the probe, and rod-centering fork positioned at a second end of the probe, the rod-centering fork comprising a bifurcating structure configured to engage an implantable or implanted rod. Some embodiments include a depressible shaft positioned at least partially within the probe, where the depressible shaft includes a probe tip at one end and a trackable marker at an opposite end.

Some embodiments include an adjustable depth-stop positioned adjacent the first end of the probe, where the adjustable depth-stop is configured to control a maximum extension of the depressible shaft and probe tip. Some embodiments include at least one shaft guide configured to prevent rotation of the depressible shaft;

Some embodiments further comprise a spring assembly coupled to the first end of the probe, where the spring assembly is configured to spring-load the depressible shaft. In some embodiments, the trackable dynamic reference frame includes at least one coupled trackable marker.

Some embodiments include an electromechanical 3D tracking system comprising an extensible cord system including two or more extensible cords retractable or extendible from a spool, and two or more ball-in-socket assemblies, where each extensible cord extends from a ball-in-socket assembly. Further, some embodiments include at least one position or movement sensor configured for measuring a position or movement of each ball-in-socket assembly, and at least one sensor configured for determining an extended length of each extensible cord. Some embodiments include a data acquisition system configured to receive sensor data from the at least one position or movement sensor and the at least one sensor, and to calculate movement and/or at least one 3D coordinate of at least a portion of a probe coupled to the extensible cords.

Some embodiments include an implanted rod manipulator comprising a handle, and a dynamic tracking frame positioned extending from a first end of the handle, where the dynamic tracking frame includes at least on trackable marker. Some embodiments include a rod interface head positioned extending from a second end of the handle opposite the first end, where the rod interface head includes a concave surface configured to couple to a surface of an implantable or implanted rod. Further, some embodiments include a moveable sliding tip positioned extending through the rod interface head. In some embodiments, the moveable sliding tip is coupled to a spring-load the depressible shaft.

Some embodiments further comprise a moveable trackable marker coupled to the moveable sliding tip, where a position of the moveable trackable marker relative to the first end of the handle is dependent on at least one of a rod coupled to the rod interface head and the position of the moveable sliding tip in the rod interface head.

Some embodiments include a method comprising positioning a trackable probe in-line and/or parallel to an anatomical alignment of a patient, and triggering the trackable probe to communicate a reference plane initialization. Further, in some embodiments, the method comprises calculating a 3D pose of a dynamic reference frame as analogous for the patient's anatomical planes, and registering three or more points to establish anatomical planes on which to project acquired data.

In some embodiments of the method, the dynamic reference frame is attached to the patient. In other embodiments of the method, the dynamic reference frame is coupled to a surgical table or adjacent surface, where the dynamic reference frame is adjacent to the patient.

DESCRIPTION OF THE DRAWINGS

FIG. 4A illustrates an assembly or operation process for a skin-surface-mounted fiducial being applied to a patient's posterior skin as they are positioned prone on an operative table in accordance with some embodiments of the invention.

FIG. 4B illustrates a sample lateral radiograph of skin fiducials applied to an anatomical model in accordance with some embodiments of the invention.

FIG. 4C illustrates the sample lateral radiograph of FIG. 4B with annotated vectors in accordance with some embodiments of the invention.

FIG. 10A illustrates a 3D-trackable probe equipped with a substantially rigidly attached trackable dynamic reference frame in accordance with some embodiments of the invention.

FIG. 10B illustrates a close-up perspective of an actuating tip and variable height selection depth-stops of the probe of FIG. 10A in accordance with some embodiments of the invention.

FIG. 10C illustrates receptacles designed to mate with the probe of FIGS. 10A-10B in accordance with some embodiments of the invention.

FIG. 16 illustrates a rotary encoder in accordance with some embodiments of the invention.

FIG. 17A illustrates a pulley-gear system for use with the encoder of FIG. 16 in accordance with some embodiments of the invention.

FIG. 17B illustrates a gear of the pulley-gear system of FIG. 17A in accordance with some embodiments of the invention.

FIGS. 19A-19C illustrates a ball assembly of a 3D-tracking system of FIG. 23A in accordance with some embodiments of the invention.

FIGS. 19D-19E illustrate a ball and socket assembly of the 3D-tracking system of FIG. 23A accordance with some embodiments of the invention.

FIGS. 29A-29B illustrates a screw-head-registering screwdriver equipped with a tracked dynamic reference frame in accordance with some embodiments of the invention.

FIG. 29C illustrates a close-up perspective view of a screwdriver head and depressible tip of the screwdriver of FIGS. 29A-29B in accordance with some embodiments of the invention.

FIG. 29D illustrates a cross-sectional view of the screwdriver-screw interface in accordance with some embodiments of the invention.

FIG. 33A illustrates pedicle screw in accordance with some embodiments of the invention.

FIG. 33B illustrates a pedicle screw in accordance with another embodiment of the invention.

FIG. 33C illustrates pedicle screw mated with a polyaxial tulip head in accordance with some embodiments of the invention.

FIG. 33D illustrates a tool designed to interface with the pedicle screw of FIG. 33B in accordance with some embodiments of the invention.

FIG. 33E illustrates a visualization of a couple between the tool of FIG. 33D and the screw of FIG. 33C in accordance with some embodiments of the invention.

FIG. 33F illustrates a screwdriver coupled to a pedicle screw in accordance with some embodiments of the invention.

FIG. 33G illustrates a top view of the screw of FIG. 33A in accordance with some embodiments of the invention.

FIG. 33H illustrates a top view of the screw of FIG. 33B in accordance with some embodiments of the invention.

FIG. 33I illustrates a top view of the screw of FIG. 33A in accordance with some embodiments of the invention.

FIG. 34 illustrates a tool for interfacing with a pedicle screw accordance with some embodiments of the invention.

FIGS. 34A-34F illustrate various views of the tool of FIG. 34 in accordance with some embodiments of the invention.

FIGS. 35A-35E illustrate various views of a tool for interfacing with a pedicle screw in accordance with some embodiments of the invention.

FIG. 35F illustrates a close-up perspective view of the tool of FIGS. 35A-35E without a coupled pedicle screw or tulip head in accordance with some embodiments of the invention.

FIGS. 36A-36G illustrate a tool designed to interface directly with tulip heads of pedicle screws in accordance with some embodiments of the invention.

FIGS. 36H-36I illustrate perspective views of the tool of FIGS. 36A-36G without pedicle screw shaft in accordance with some embodiments of the invention.

FIG. 38 illustrates a pedicle screw shaft with depth-stop in accordance with some embodiments of the invention.

FIG. 38A illustrates a top view of the pedicle screw shaft with depth-stop of FIG. 38 in accordance with some embodiments of the invention.

FIG. 38B illustrates a screw interface region with coupled handle in accordance with some embodiments of the invention.

FIG. 38C illustrates an example assembly view coupling between the screw interface region of FIG. 38B and the pedicle screw shaft with depth-stop of FIGS. 38-38A in accordance with some embodiments of the invention.

FIGS. 38D-38G illustrates view of the screw interface region of FIG. 38B coupled with the pedicle screw shaft with depth-stop of FIGS. 38-38A in accordance with some embodiments of the invention.

FIG. 40A illustrates a lateral view of a spine model with a straight curve, and two flexibility assessment tools engaged with the model in accordance with some embodiments of the invention.

FIG. 40B illustrates one embodiment of two flexibility assessment devices interfacing with a spine model with a lordotic curve in accordance with some embodiments of the invention.

FIG. 40C illustrates an embodiment of the invention from a 3D-tracking camera perspective in accordance with some embodiments of the invention.

FIGS. 45A-45B illustrate a vertebra engagement and rendering process in accordance with some embodiments of the invention.

FIGS. 46A-46B illustrate a 3D tracking tool in accordance with some embodiments of the invention.

FIG. 46C illustrates an X-ray imaging and tracking system in accordance with some embodiments of the invention.

FIG. 46D illustrates a virtual overlay of a tracked surgical tool positioned close to the X-ray detector on top of an X-ray image of the spine in accordance with some embodiments of the invention.

FIG. 46E illustrates an X-ray imaging and tracking system in accordance with some embodiments of the invention.

FIG. 46F illustrates a virtual overlay of a tracked surgical tool positioned close to the emitter as shown in FIG. 46E in accordance with some embodiments of the invention.

FIG. 46G illustrates a virtual overlay of a tracked surgical tool that has been turned 90 degrees from the tool position previously described in FIGS. 46D-46F in accordance with some embodiments of the invention.

FIG. 47A illustrates components of a tracked end cap in accordance with some embodiments of the invention.

FIG. 47B illustrates components of a tracked slider designed to interface with a rod fixed to a tracked end cap, described previously in relation to FIG. 47A in accordance with some embodiments of the invention.

FIG. 48A illustrates a close-up view of a portion of an end cap in accordance with some embodiments of the invention.

FIG. 48B illustrates a perspective view of an end cap assembled from components of FIG. 47A in accordance with some embodiments of the invention.

FIG. 48C illustrates a side view of the end cap of FIG. 48B in accordance with some embodiments of the invention.

FIGS. 49A-49C illustrates a single-ring rod assessment device assembly in accordance with some embodiments of the invention.

FIG. 49D illustrates the assembly of FIGS. 49A-49C coupled with a rod and tracked end cap previously described in relation to FIGS. 47A, and 48A-48B in accordance with some embodiments of the invention.

FIGS. 50A-50D illustrates a fixed-base, variable-ring, mobile rod assessment device in accordance with some embodiments of the invention.

FIG. 50E illustrates the fixed-base, variable-ring, mobile rod assessment device of FIGS. 50A-50D engaged with a rod coupled to an end cap in accordance with some embodiments of the invention.

FIGS. 51A-51G illustrates various views of a handheld, mobile rod contour assessment device in accordance with some embodiments of the invention.

Figure 51A:
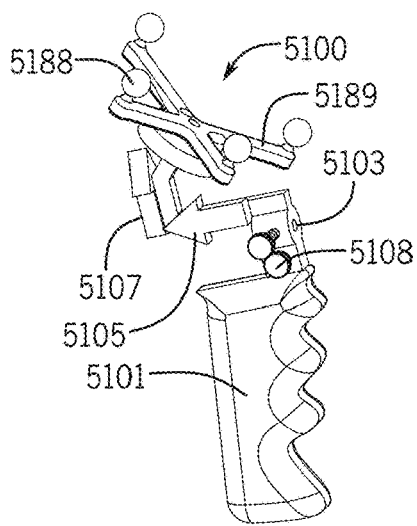
Figure 51B:
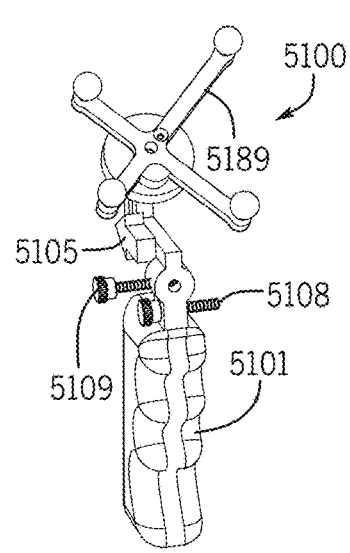
Figure 51C:
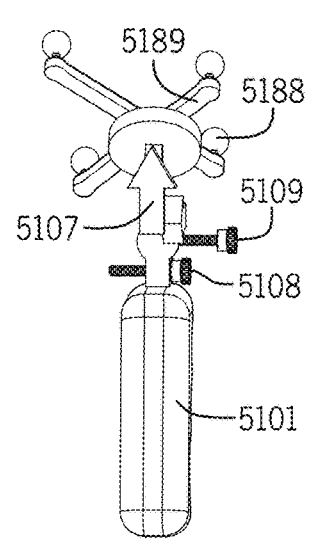
Figure 51D:
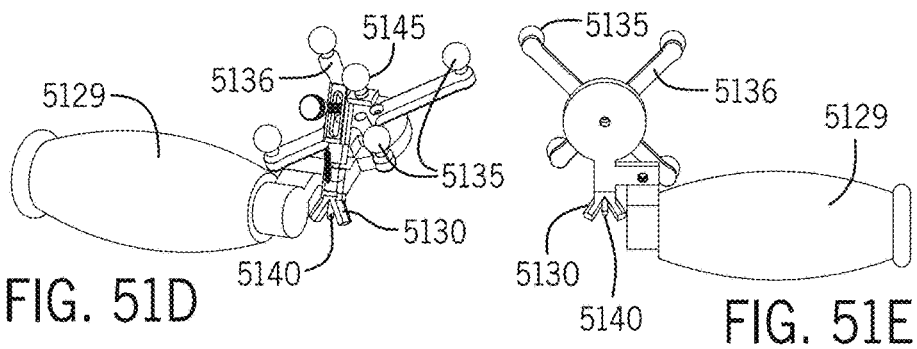
Figure 51E:
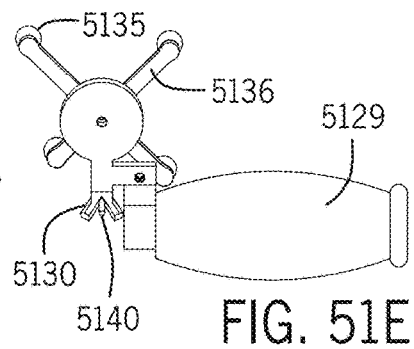
Figure 51F:
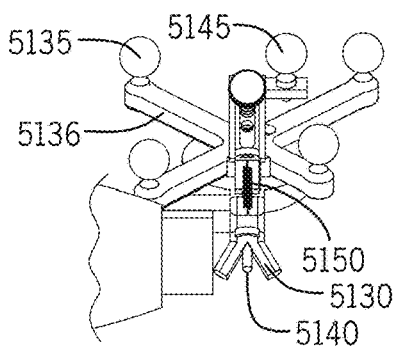
Figure 51G:
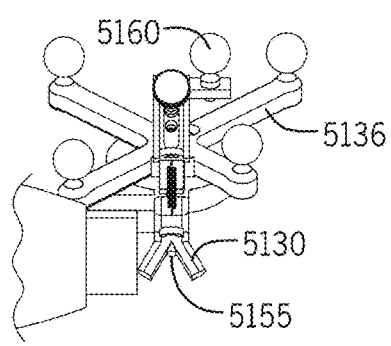
Figure 51H:
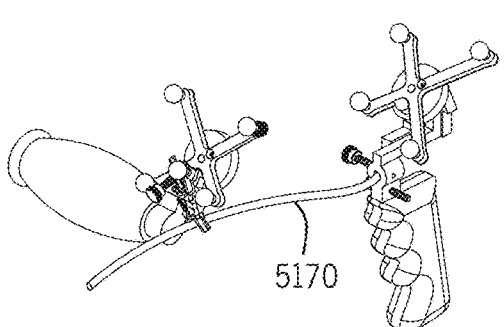
Figure 51I:
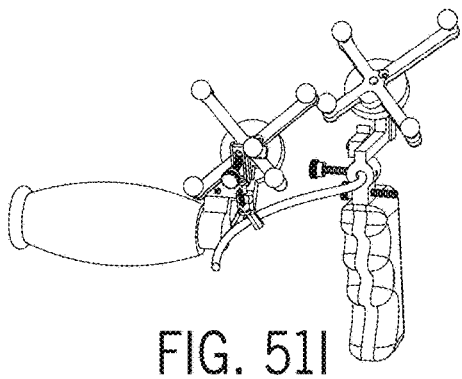

FIG. 51H-51I illustrates views of a process or method of registering the contour of a rod prior to implantation with the handheld, mobile rod contour assessment device of FIGS. 51A-51G in accordance with some embodiments of the invention.

Figure 52A:
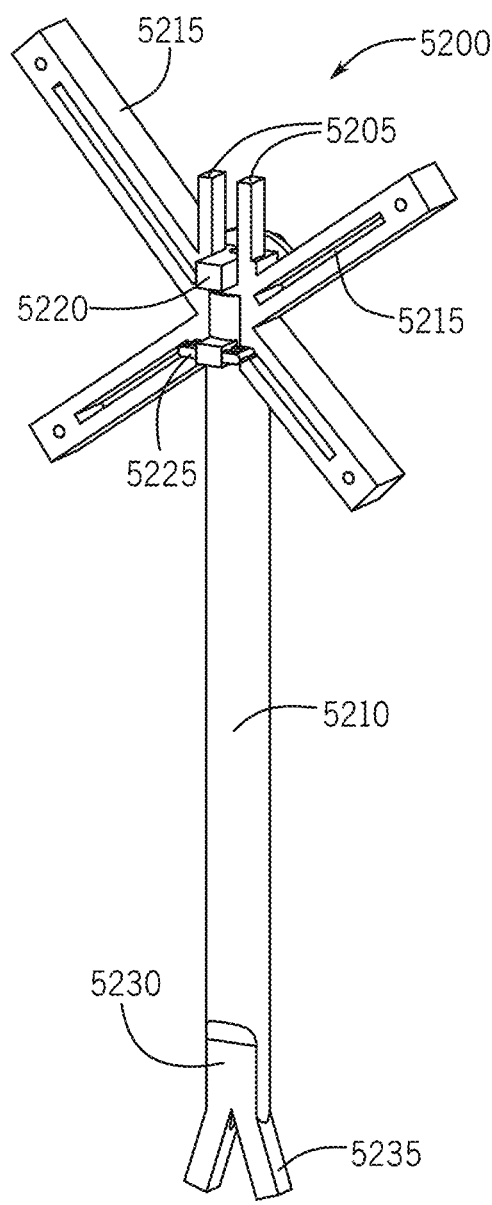

FIG. 52A illustrates a component of a TMSM-based, implanted rod contour assessment device in accordance with some embodiments of the invention.

Figure 52B:
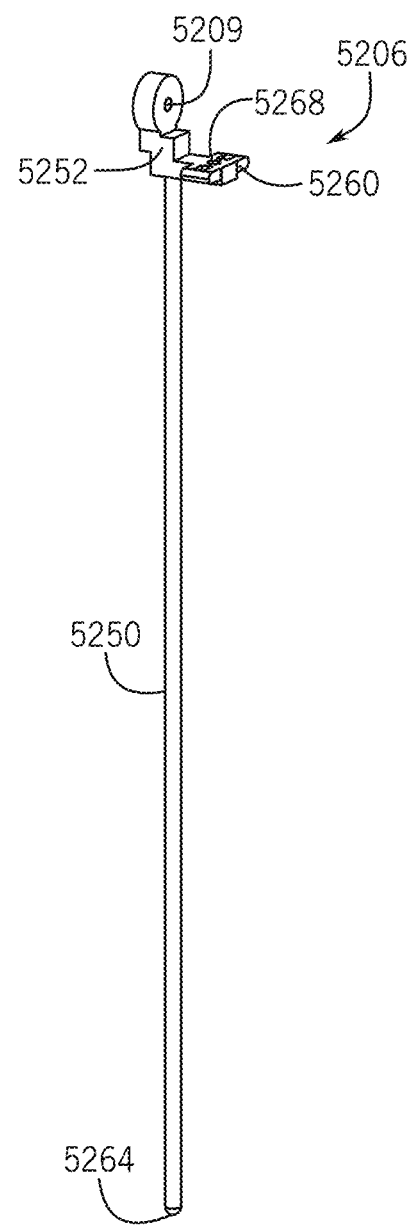

FIG. 52B illustrates a depressible sliding shaft for coupling to the component of FIG. 52A in accordance with some embodiments of the invention.

Figure 52C:
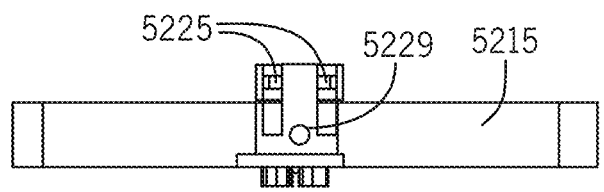

FIG. 52C illustrates a top view of the component of FIG. 52A in accordance with some embodiments of the invention.

Figure 52D:
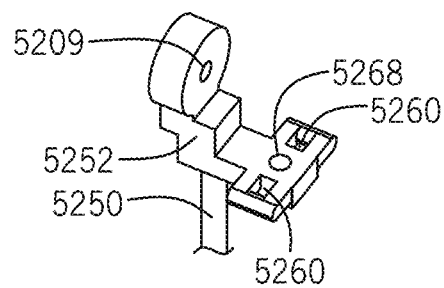

FIG. 52D illustrates a close-up perspective view of the depressible sliding shaft of FIG. 52B in accordance with some embodiments of the invention.

Figures 53A, 53B:
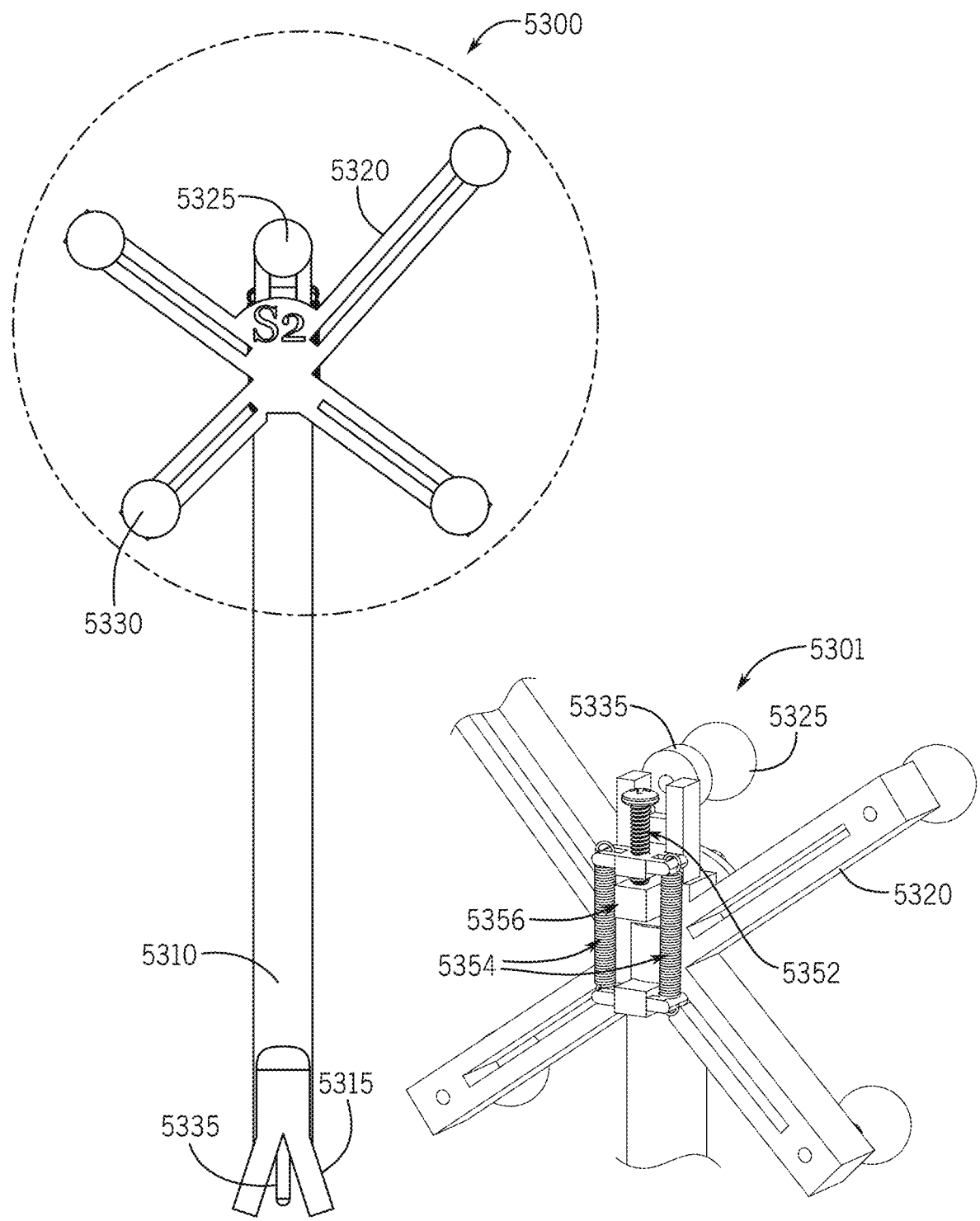

FIG. 53A illustrates an assembly of components of FIGS. 52A and 52B used to assess the contour of a rod after it has been implanted within the surgical site in accordance with some embodiments of the invention.

FIG. 53B illustrates a close-up rear view of a portion of the assembly of FIG. 53A in accordance with some embodiments of the invention.

Figure 53C:
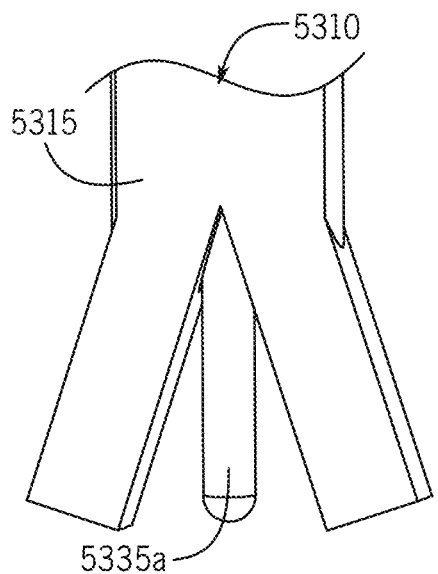

FIG. 53C illustrates a close-up view of the rod-interface region of the assembly of FIGS. 53A-53B in accordance with some embodiments of the invention.

Figure 53D:
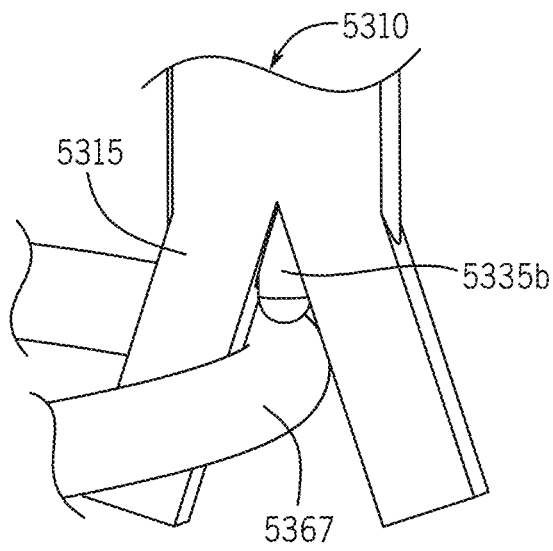

FIG. 53D illustrates the assembly of FIGS. 53A-53C interfacing with a rod in accordance with some embodiments of the invention.

Figure 53E:
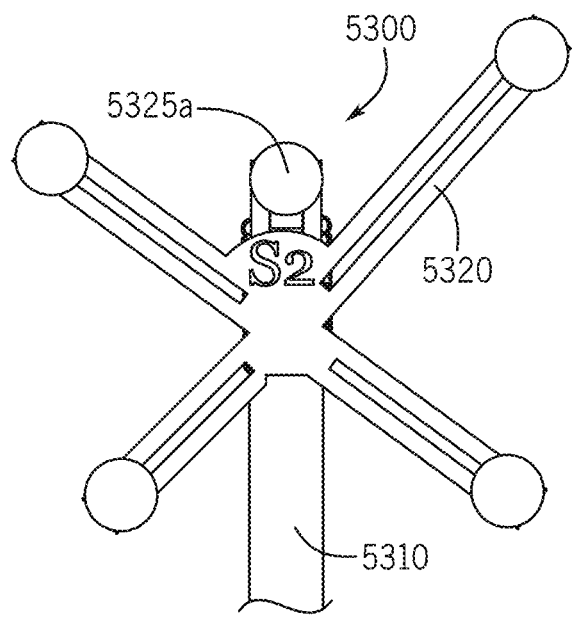
Figure 53F:
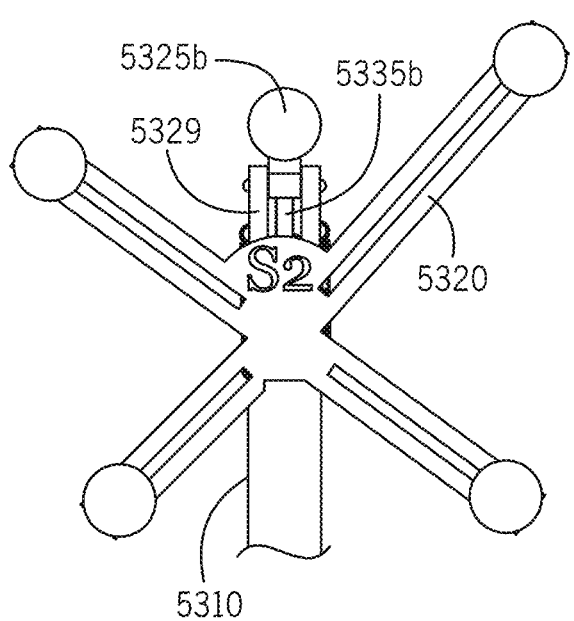

FIGS. 53E-53F illustrates close-up views of a trackable DRF portion of the assembly view of FIGS. 53A-53D in accordance with some embodiments of the invention.

FIG. 54A illustrates a conductivity-based rod contour assessment device in accordance with some embodiments of the invention.

FIG. 54B illustrates a rod-centering fork and electrical contact pads of the device of FIG. 54A in accordance with some embodiments of the invention.

FIGS. 54C-54D illustrates the rod-centering fork of FIG. 54B interacting with a rod in accordance with some embodiments of the invention.

FIGS. 55A-55I illustrates various views of a 3D-tracked, manual mobile rod bender in accordance with some embodiments of the invention.

FIGS. 56A-56F illustrate various views of a tracked DRF-equipped end cap, pre-registered rod, and manual bender equipped with TMSMs accordance with some embodiments of the invention.

Figure 57A:
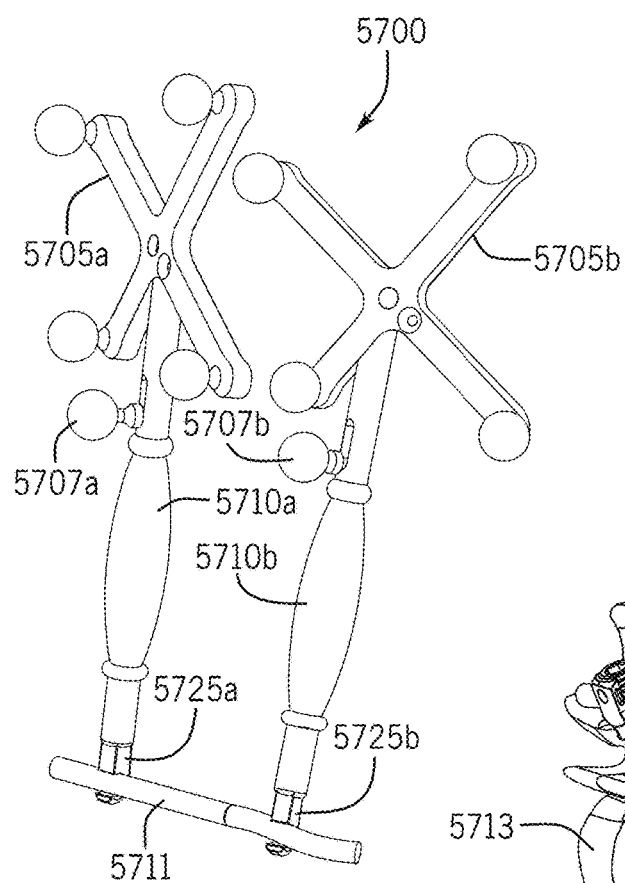

FIG. 57A illustrates a DRF-tracked and trigger-equipped in-situ benders coupled to a rod in accordance with some embodiments of the invention.

Figure 57B:
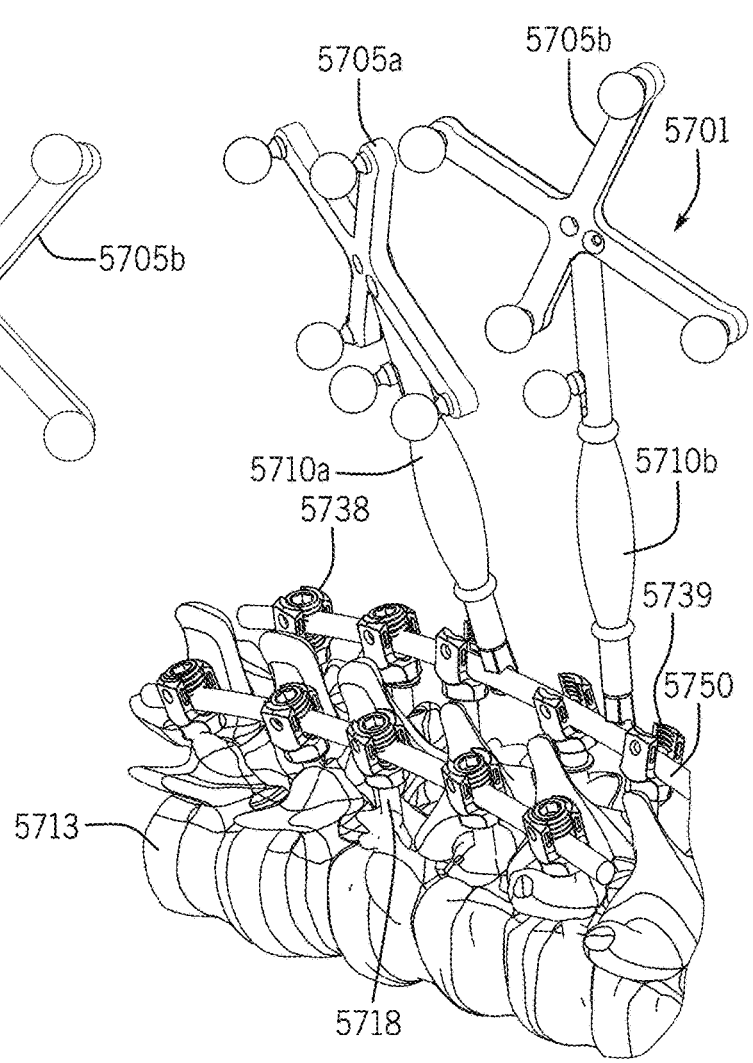

FIG. 57B illustrates a DRF-tracked and trigger-equipped in-situ benders coupled to a rod coupled to a spine in accordance with some embodiments of the invention.

Figure 57C:
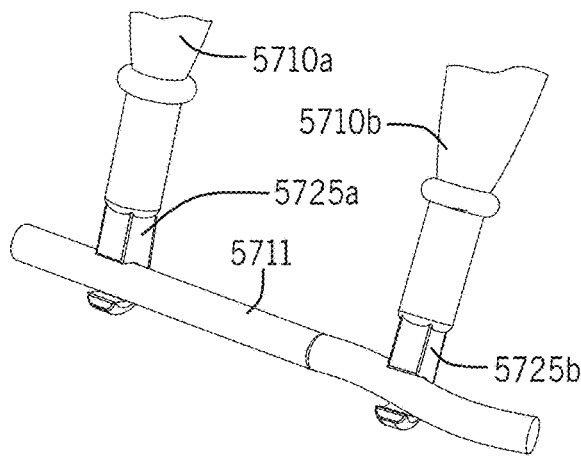

FIG. 57C illustrates a close-up assembly view of the rod of FIG. 57A in accordance with some embodiments of the invention.

Figure 57D:
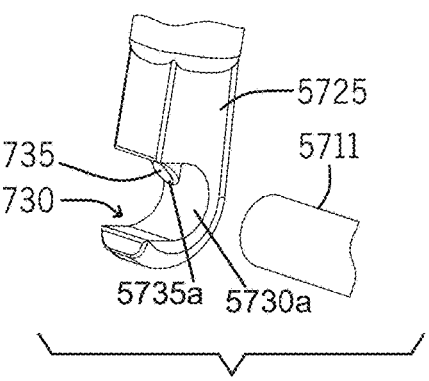

FIG. 57D illustrates a close-up view of a rod interface head of the bender shown in FIG. 57A including a view of a depressible sliding shaft tip in an extended position in accordance with some embodiments of the invention.

Figure 58:
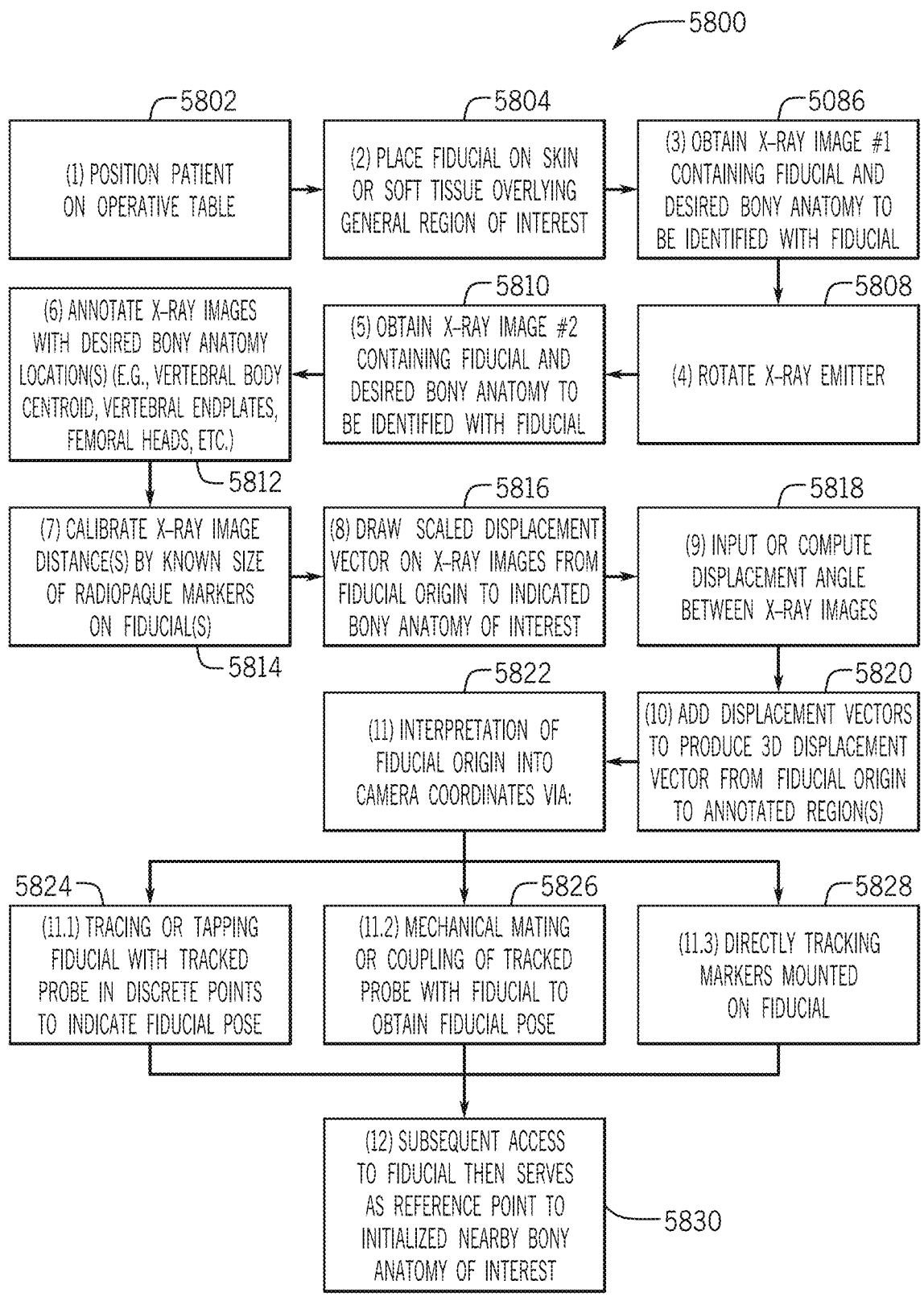

FIG. 58 illustrates a workflow to initialize skin-mounted, or percutaneous, fiducials with two or more X-ray images intraoperatively in accordance with some embodiments of the invention.

Figure 59:
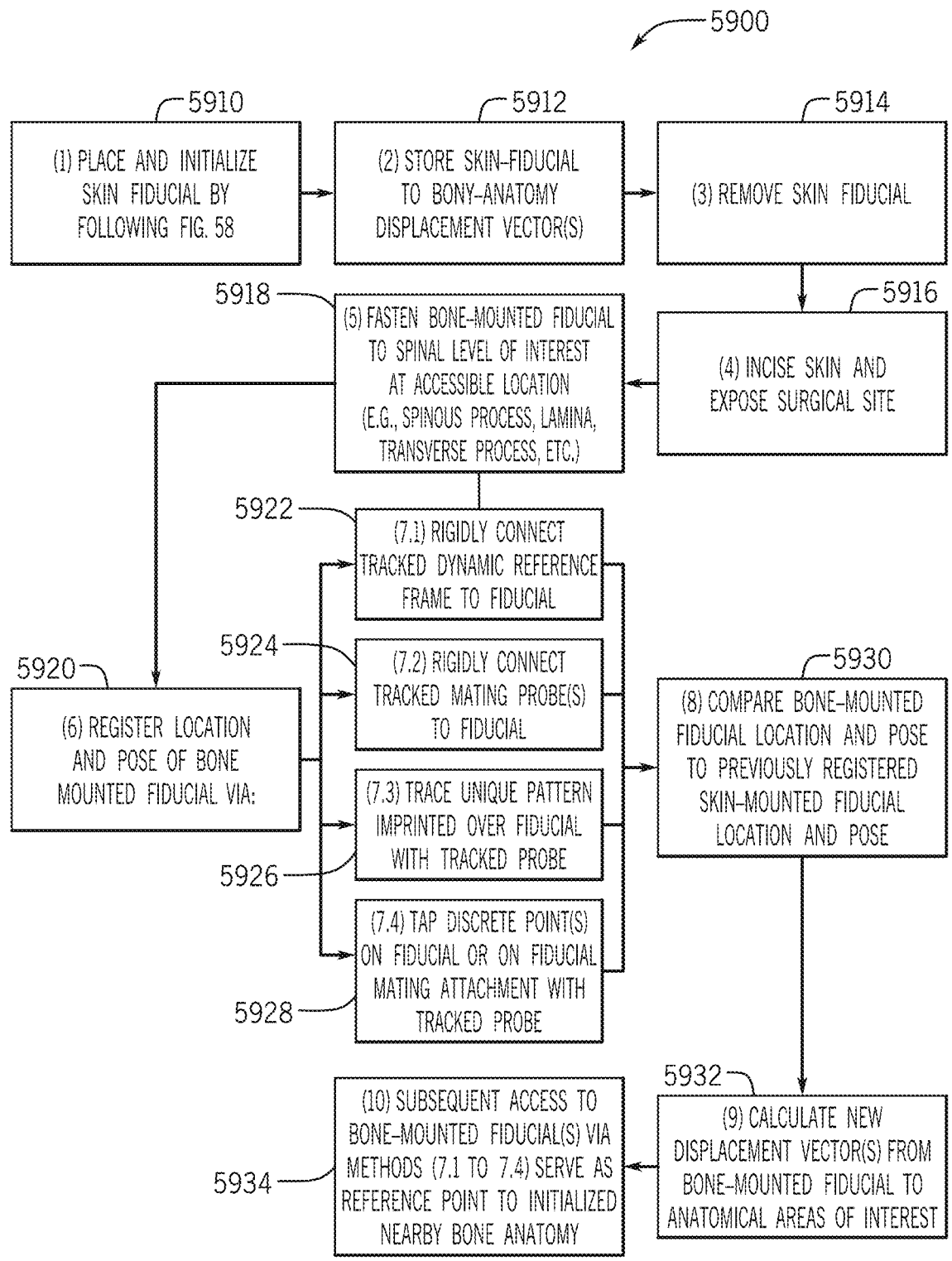

FIG. 59 illustrates a workflow to initialize one or more bone-mounted fiducials placed intraoperatively with 2 or more X-ray images taken before placement of the bone-mounted fiducials in accordance with some embodiments of the invention.

Figure 60:
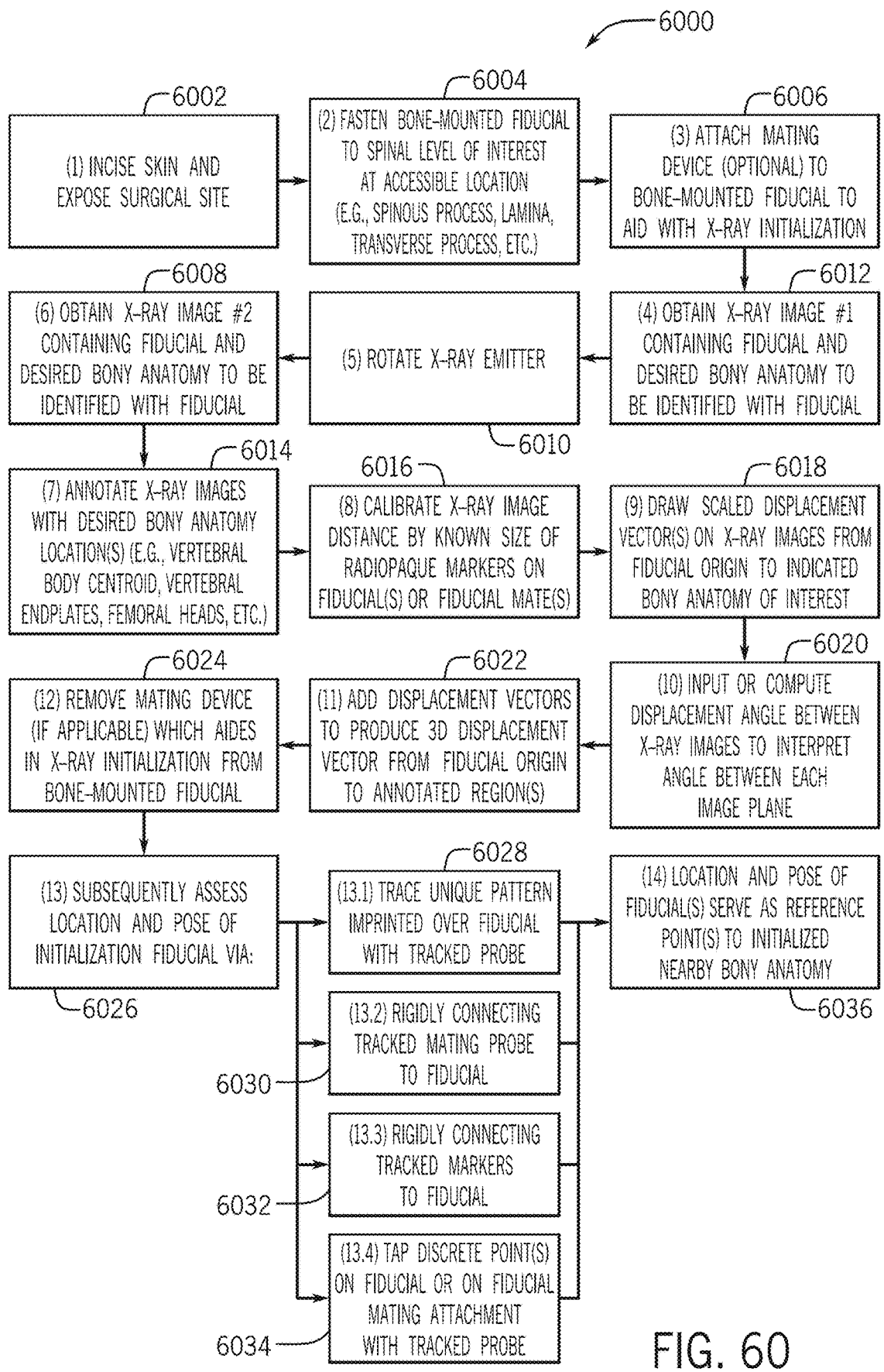

FIG. 60 shows a workflow to initialize one or more bone-mounted fiducials placed intraoperatively with 2 or more X-ray images taken after placement of the bone-mounted fiducials in accordance with some embodiments of the invention.

Figure 61:
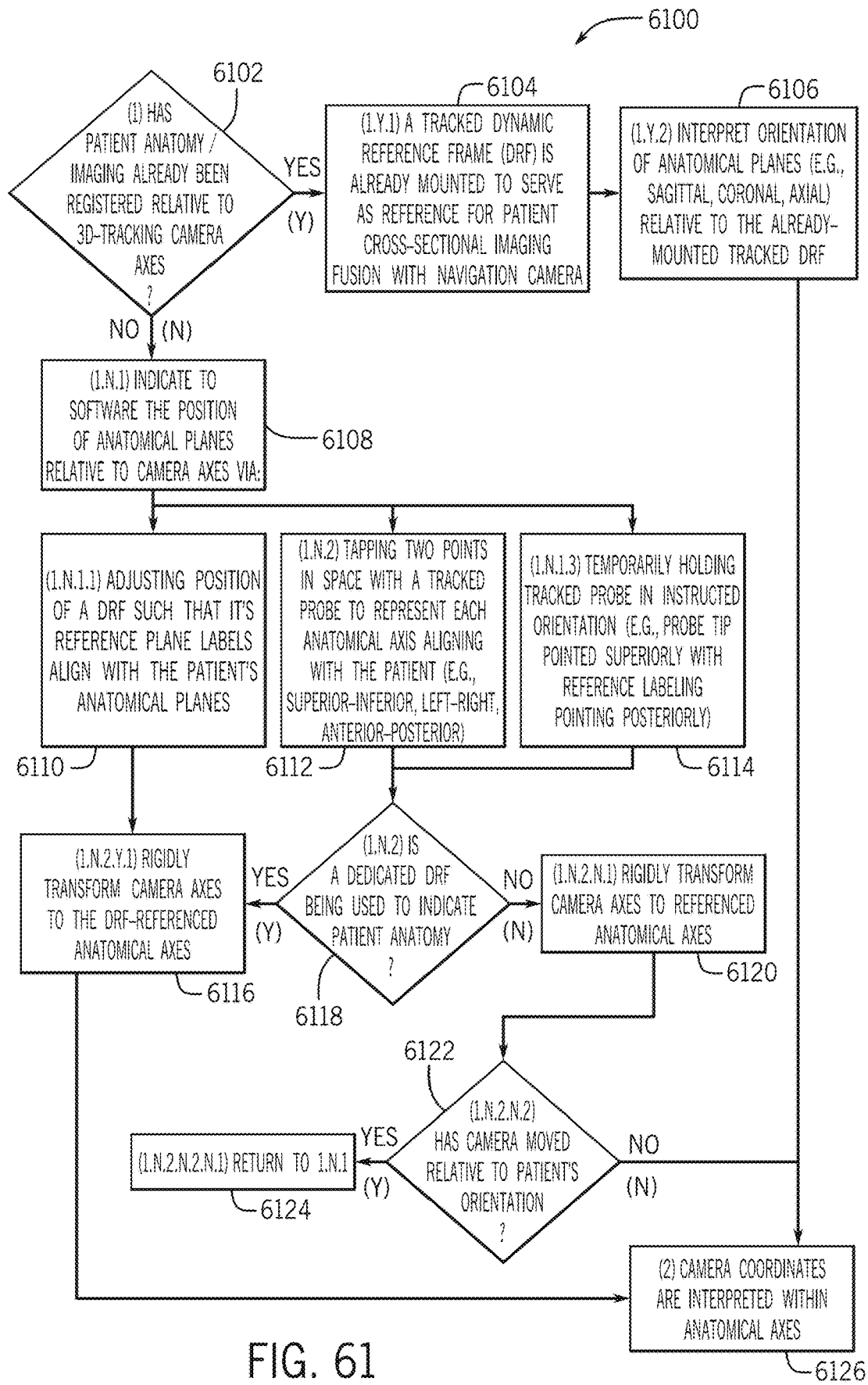

FIG. 61 illustrates methods of registering anatomical reference planes intraoperatively in accordance with some embodiments of the invention.

Figure 62A:
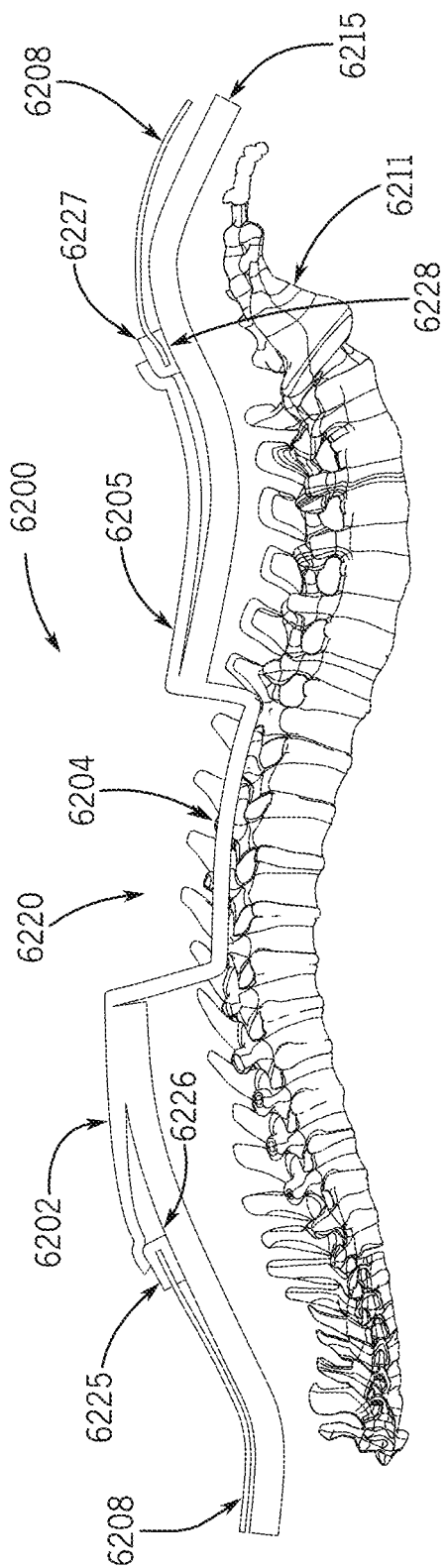

FIG. 62A illustrates an arrangement for acquiring information regarding the contour of the spine via tracing over body surfaces using a tracked probe in accordance with some embodiments of the invention.

Figure 62B:
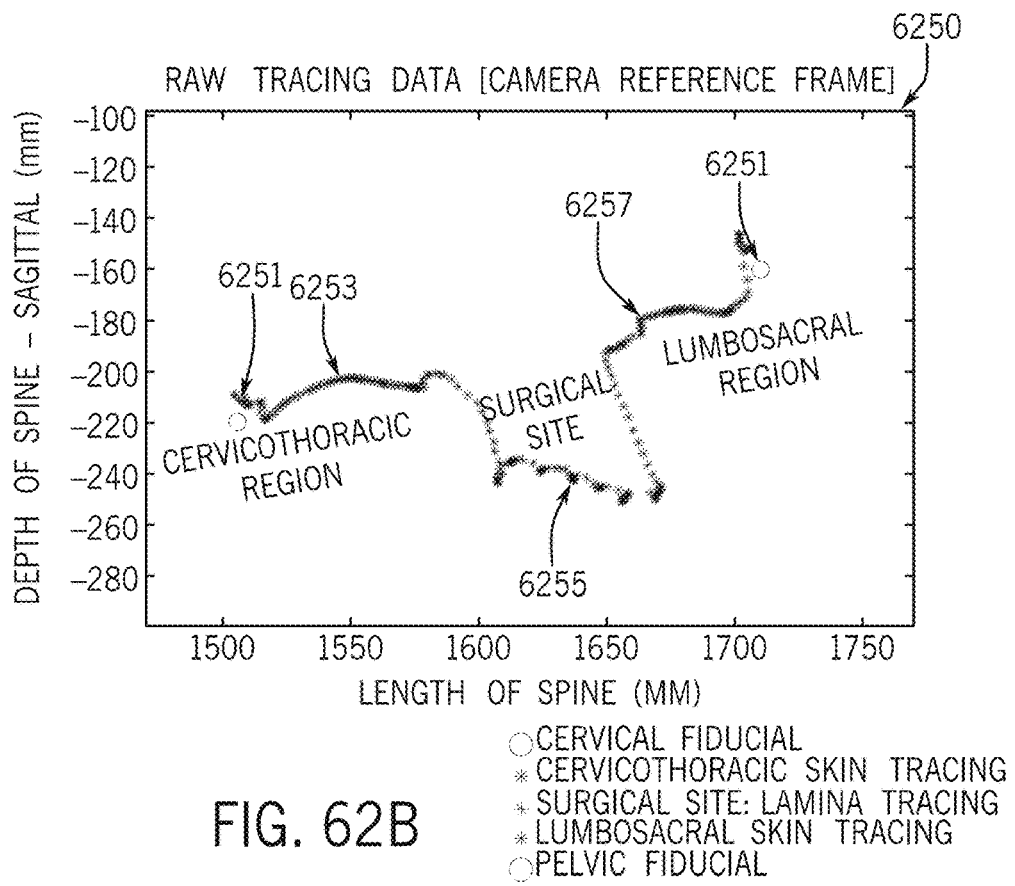

FIG. 62B illustrates a display of the acquired body surface contours via tracing with a 3D-tracked probe in accordance with some embodiments of the invention.

Figure 62C:
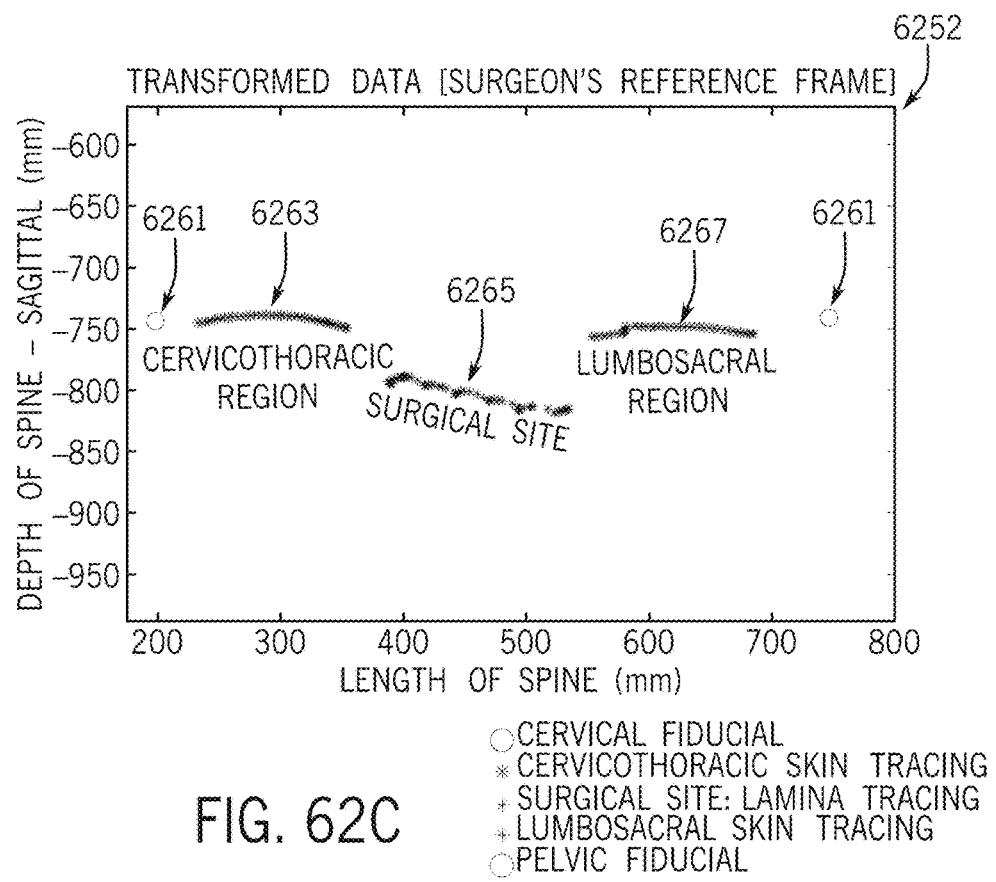

FIG. 62C illustrates a display of transformed tracing data in accordance with some embodiments of the invention.

Figure 62D:
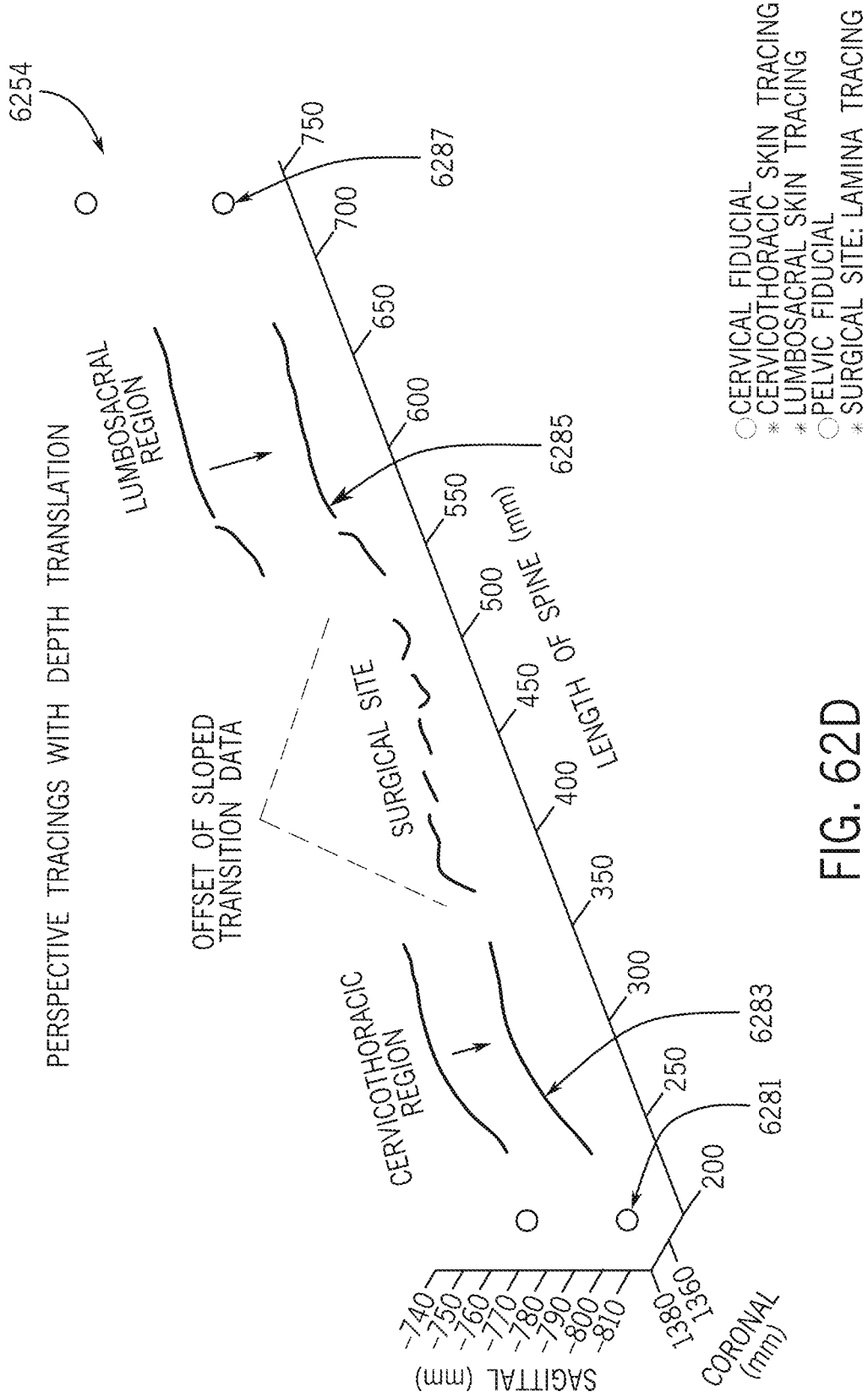

FIG. 62D illustrates a display of the data of FIGS. 62B-62C with depth translation in accordance with some embodiments of the invention.

Figure 63:
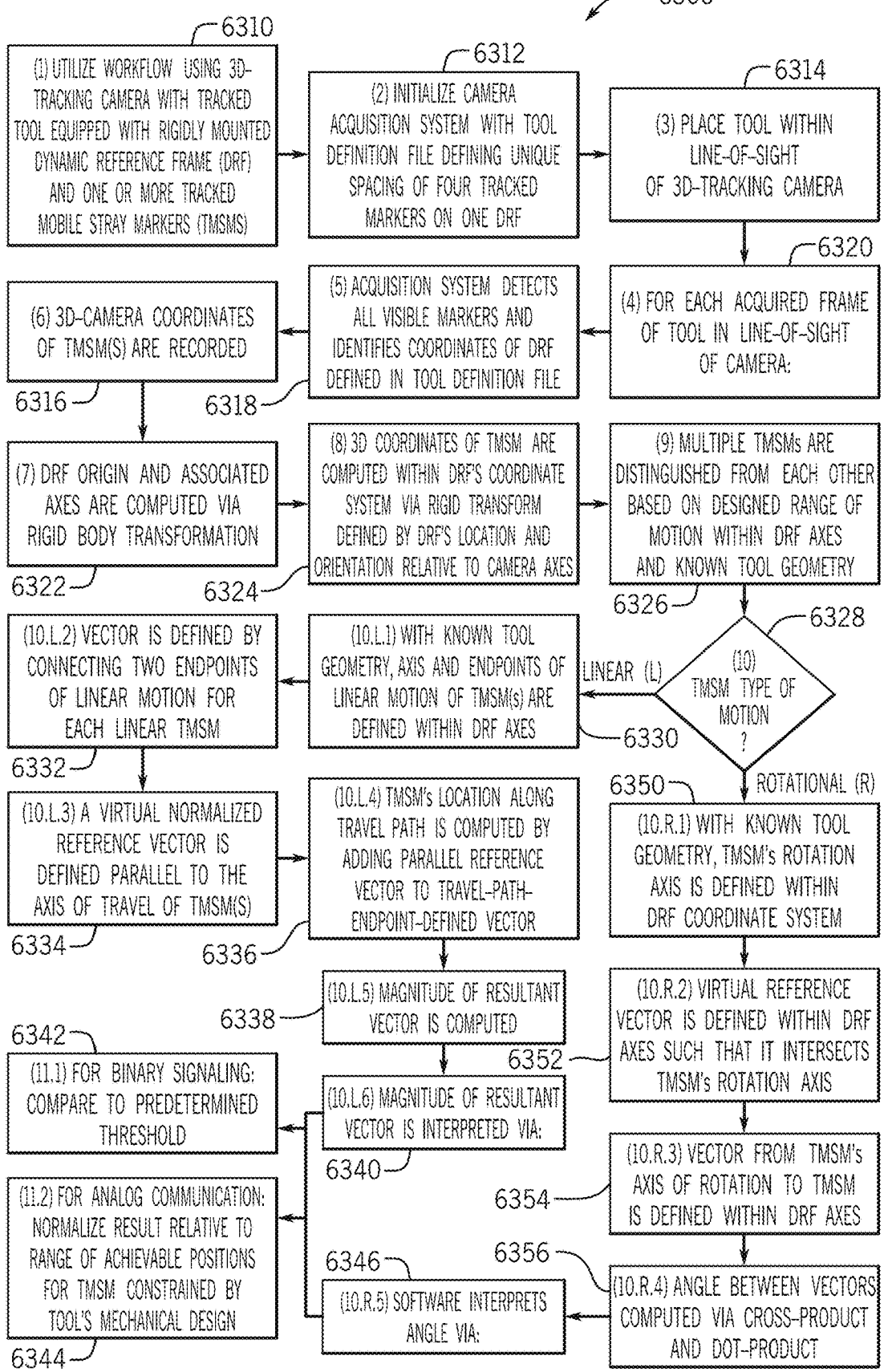

FIG. 63 shows a workflow for analog triggering detection of one or more tracked mobile stray marker (TMSM) relative to a tracked tool with a dynamic reference frame (DRF) in accordance with some embodiments of the invention.

Figure 64A:
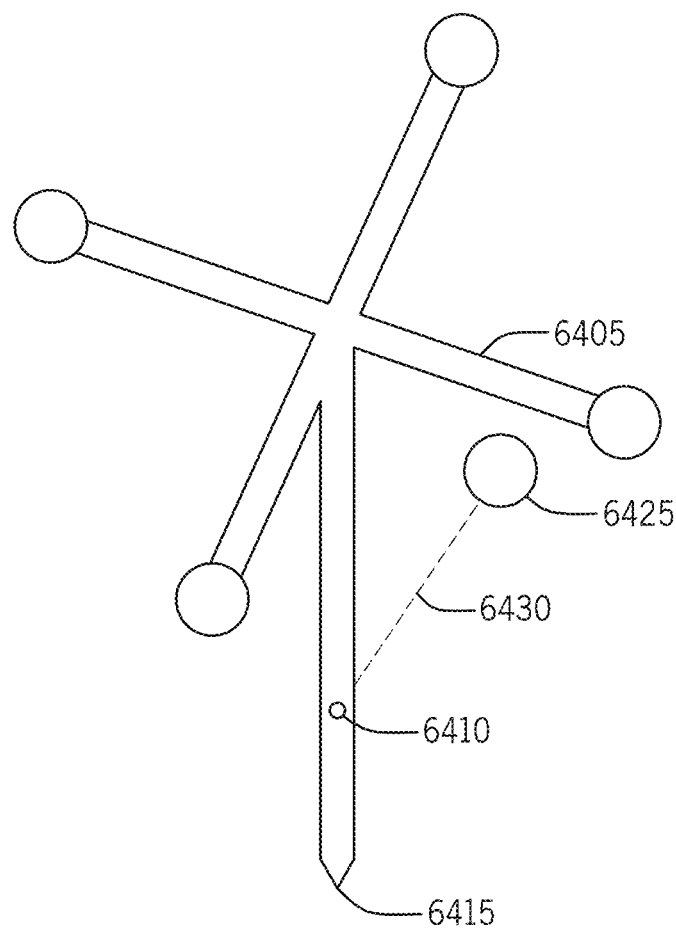

FIG. 64A illustrates a tracking probe assembly in accordance with some embodiments of the invention.

Figure 64B:
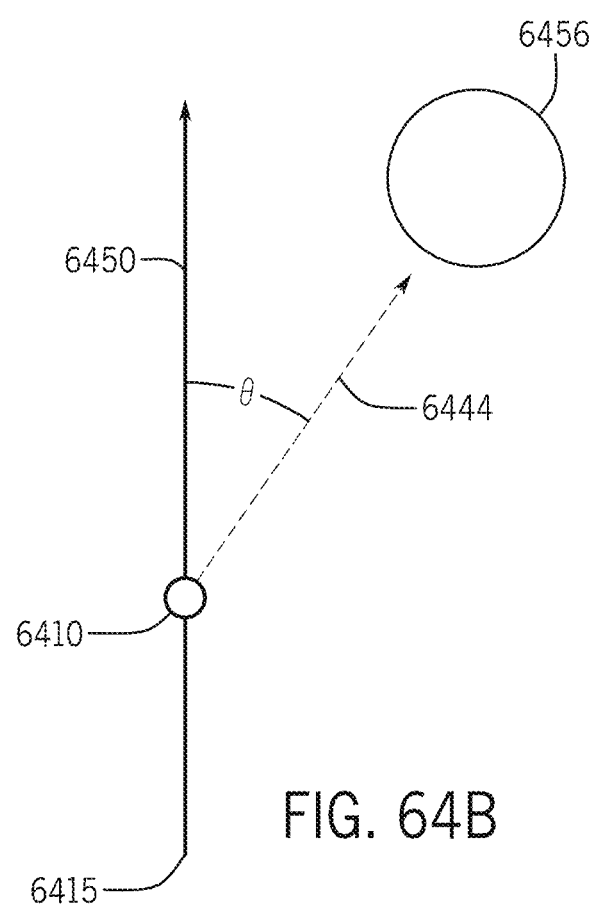

FIG. 64B illustrates an interpretation and calculation of the position of a rotating TMSM relative to the DRF on a probe as described previously in relation to FIG. 64A in accordance with some embodiments of the invention.

FIG. 65A illustrates displays of a discrete body surface or bony surface annotations on cross-sectional images used for initialization of patient-specific interpretation of body and bony surface tracings with a 3D-tracked probe in accordance with some embodiments of the invention.

FIG. 65B illustrates 3D perspective of cross-sectional annotations from the CT scan in accordance with some embodiments of the invention.

Figure 65C:
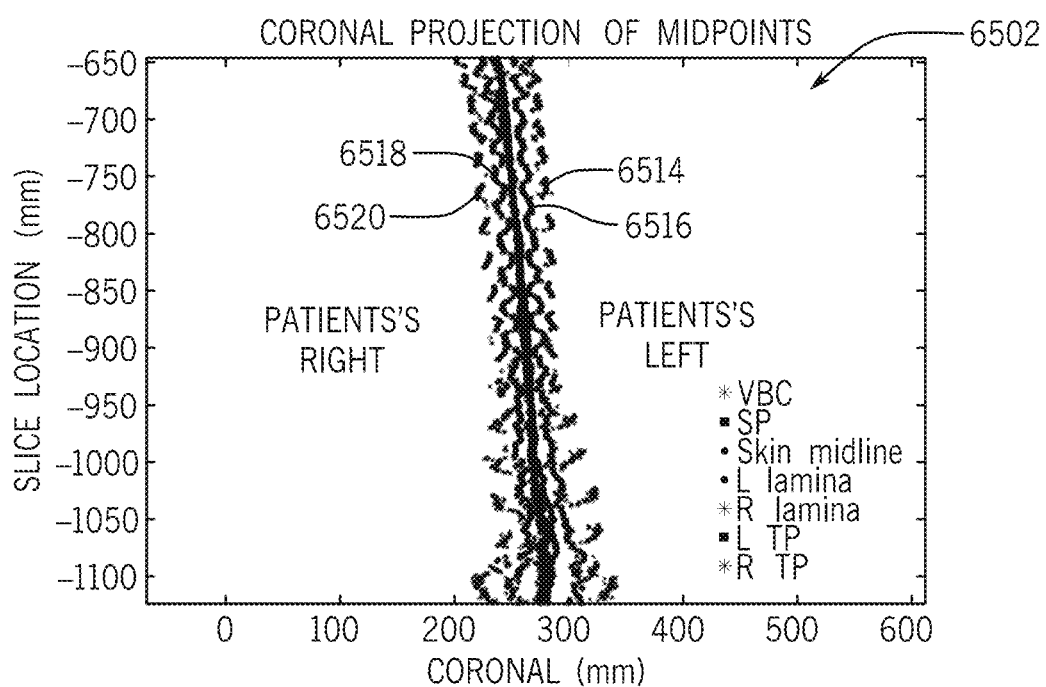

FIG. 65C illustrates a plot of coronal projected coordinates in accordance with some embodiments of the invention.

Figure 65D:
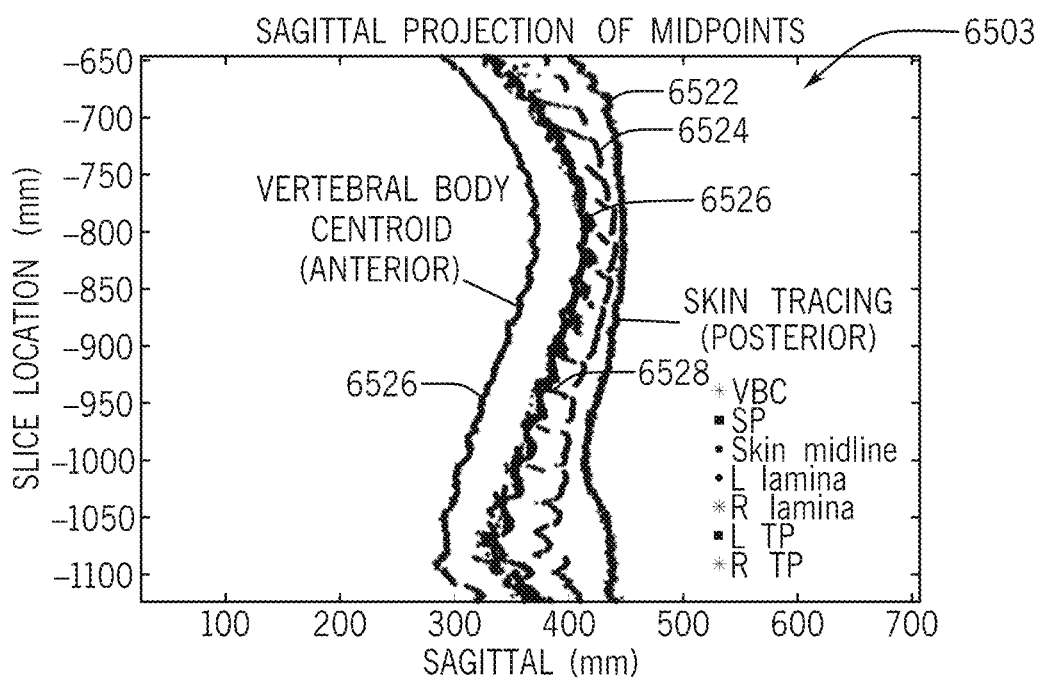

FIG. 65D illustrates a plot of sagittal projected coordinates in accordance with some embodiments of the invention.

Figure 65E:
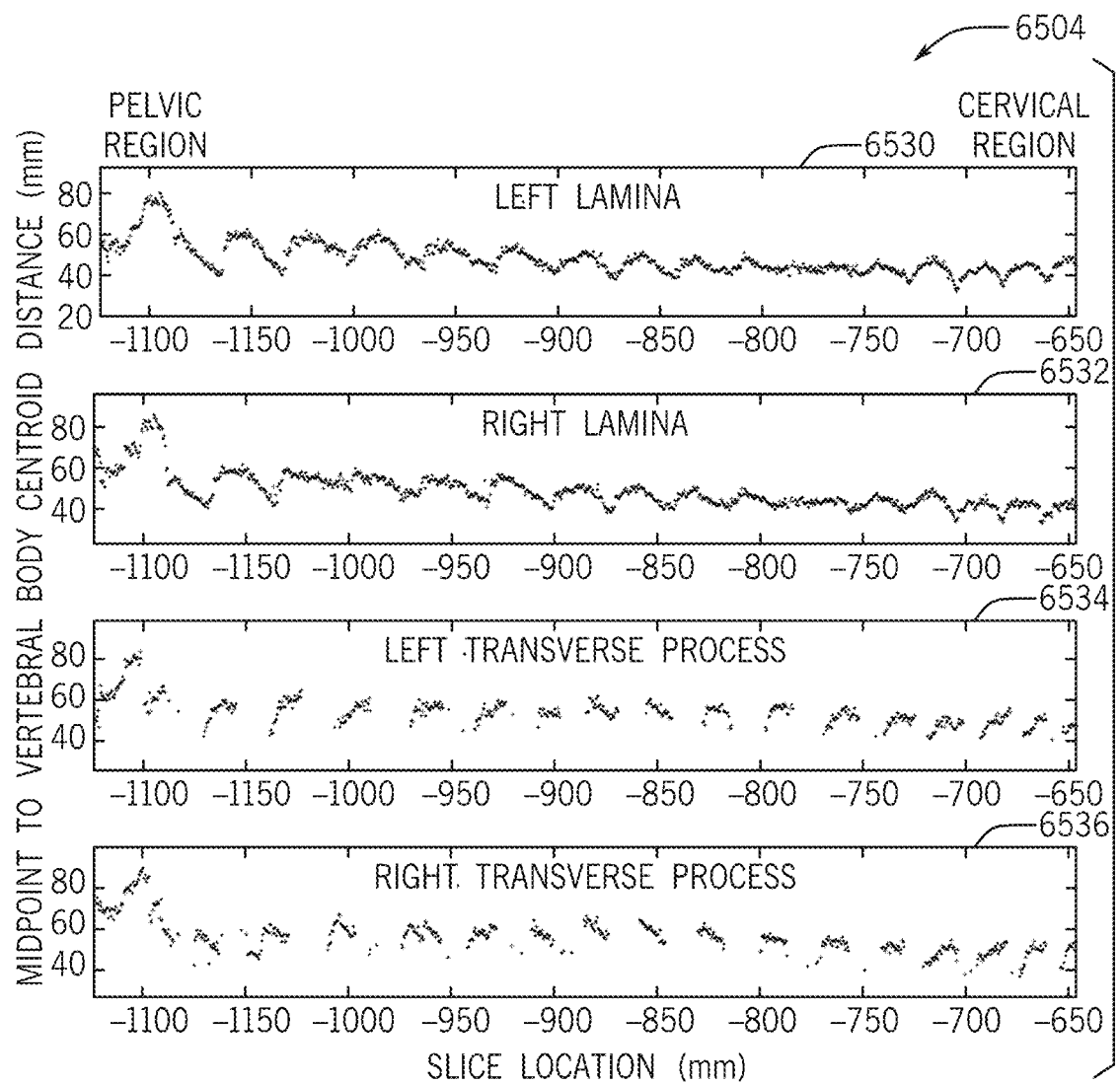

FIG. 65E illustrates computed cross-sectional distances between corresponding anatomical landmarks and vertebral body centroids in accordance with some embodiments of the invention.

Figure 66A:
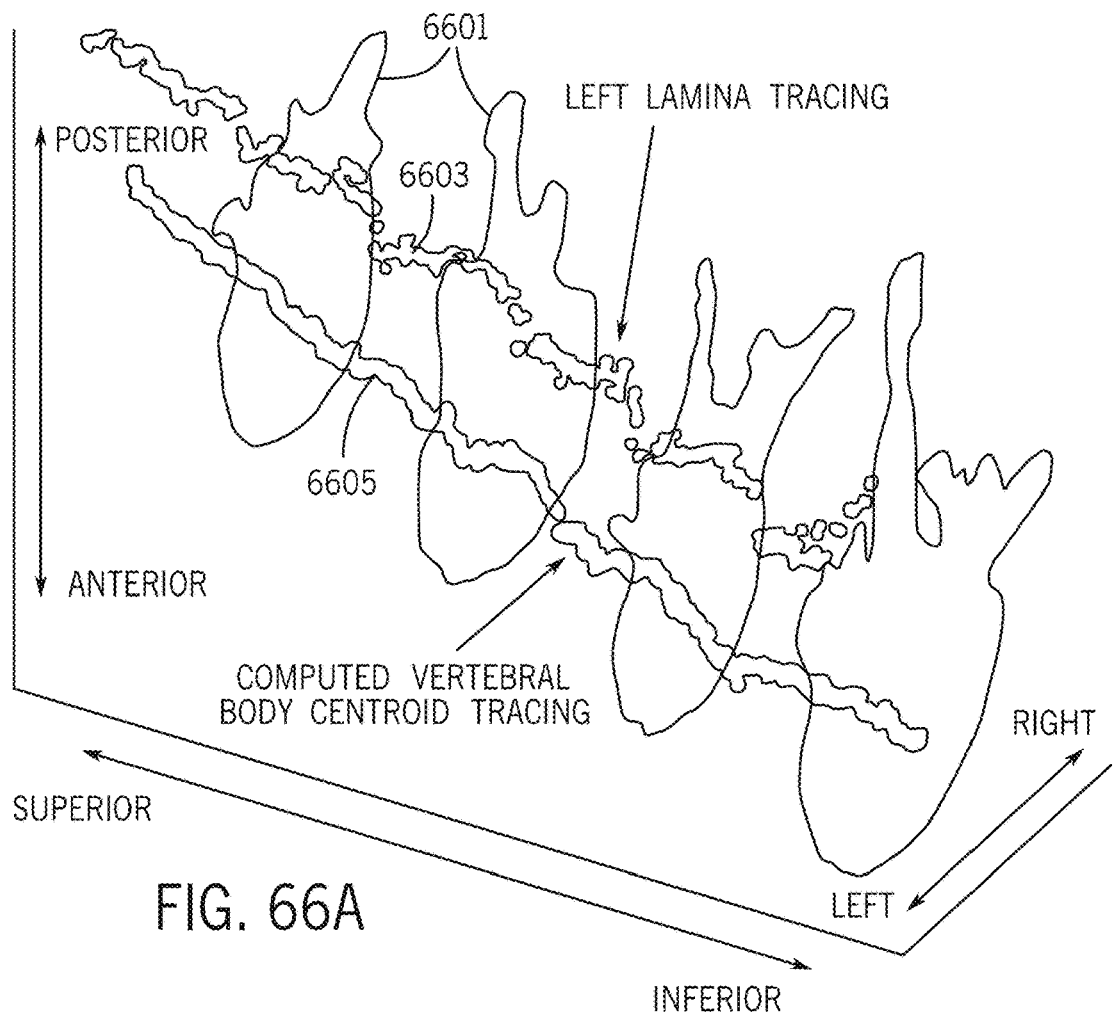

FIG. 66A illustrates a display of cross-sectional slices of vertebra (a) in their relative anatomical axes in accordance with some embodiments of the invention.

Figure 66B:
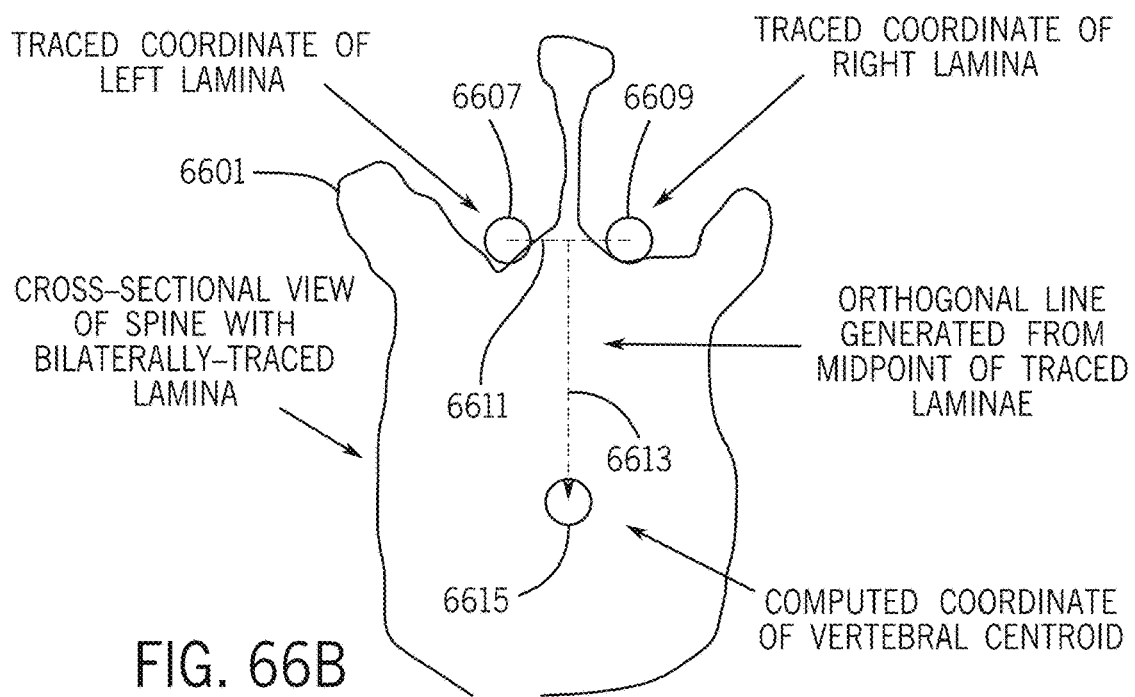

FIG. 66B illustrates a display of a vertebral body calculated via bilaterally traced coordinates and patient initialization data in accordance with some embodiments of the invention.

Figure 67:
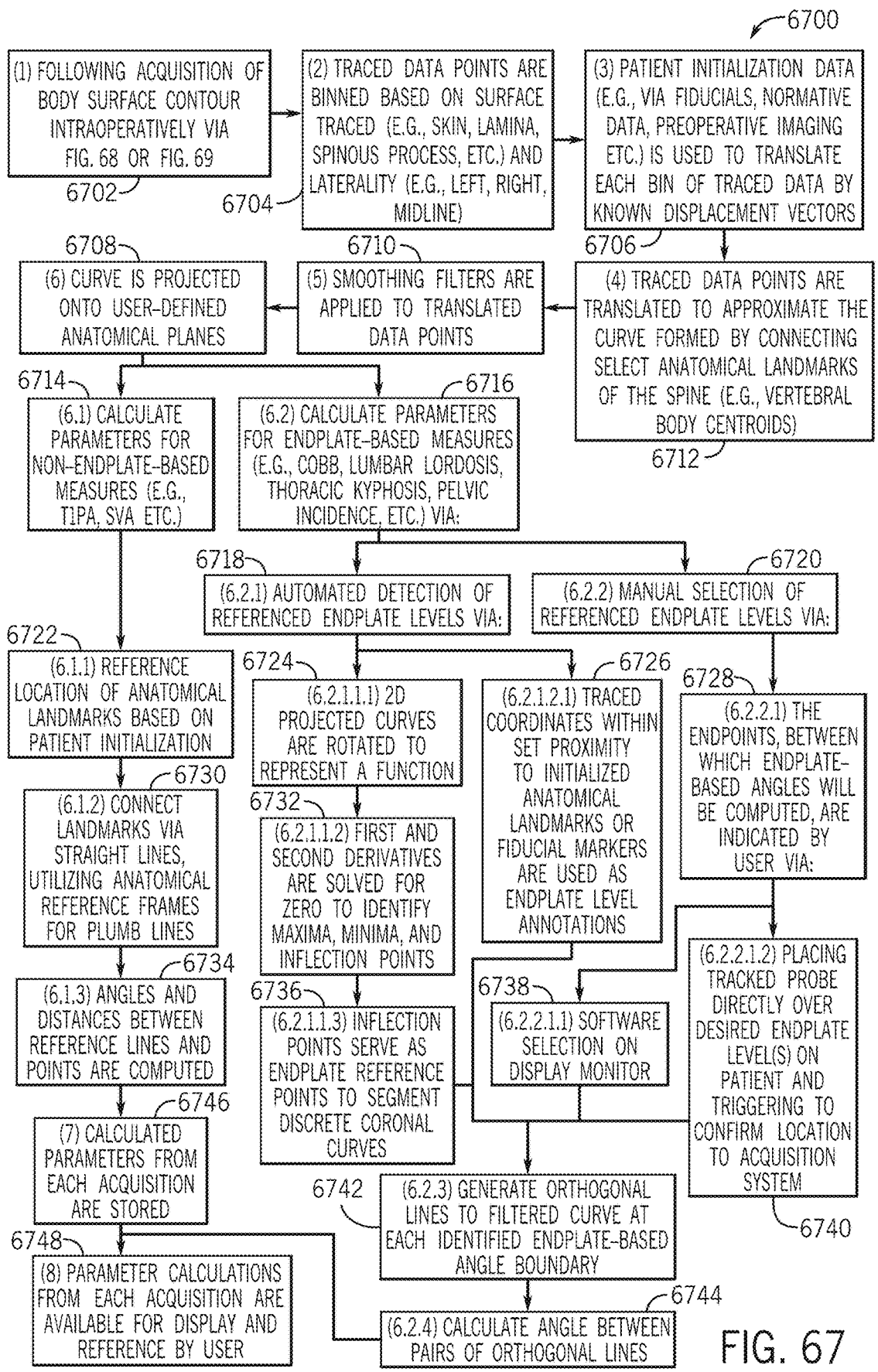

FIG. 67 illustrates a workflow to calculate spinal alignment parameters based on intraoperative tracing in accordance with some embodiments of the invention.

Figure 68:
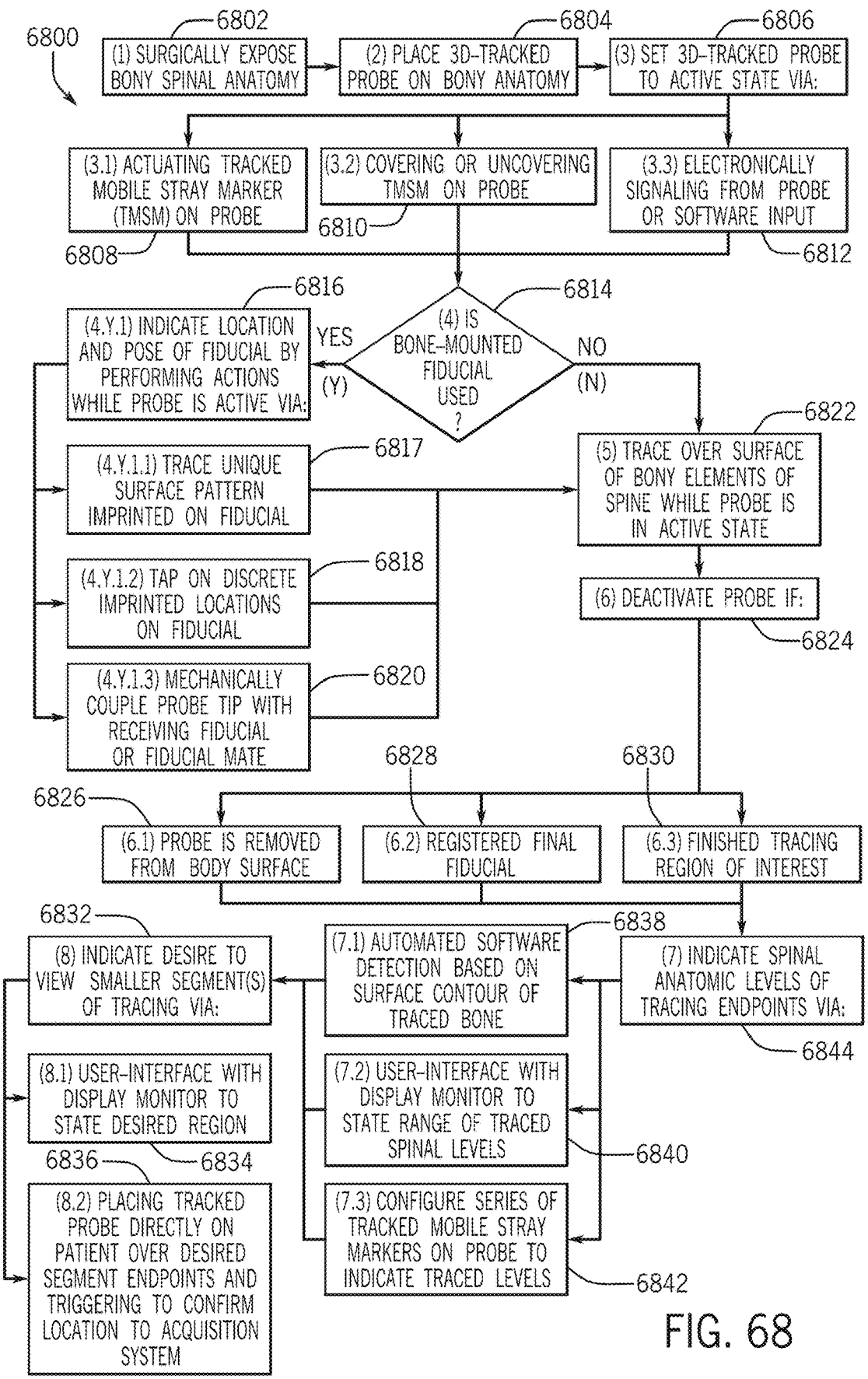

FIG. 68 illustrates a workflow to acquire a spinal alignment curve using probe-based tracing within only the surgical site in accordance with some embodiments of the invention.

Figure 69:
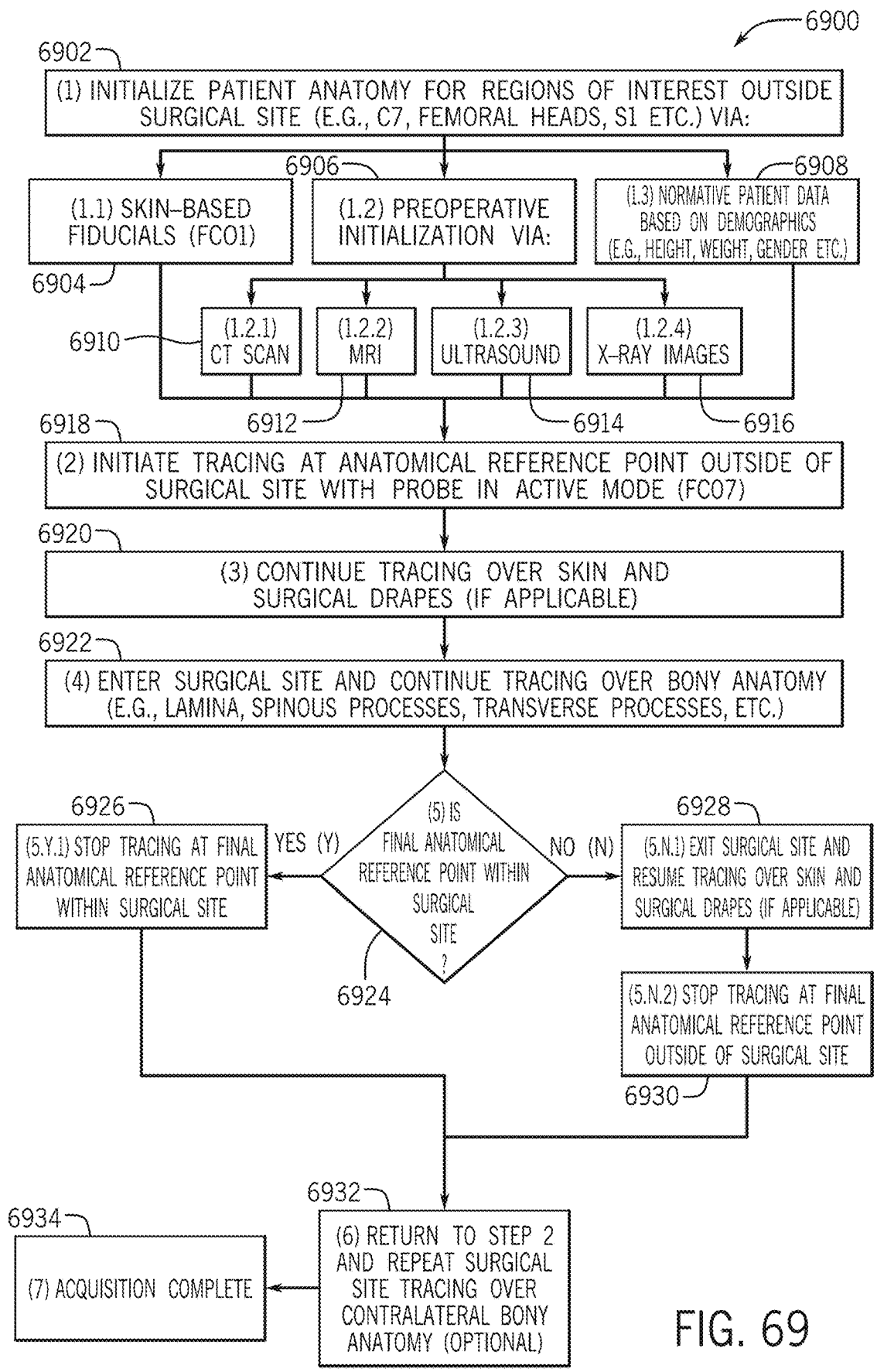

FIG. 69 illustrates a workflow to acquire a spinal alignment curve using probe-based tracing data spanning beyond the surgical site in accordance with some embodiments of the invention.

Figure 70:
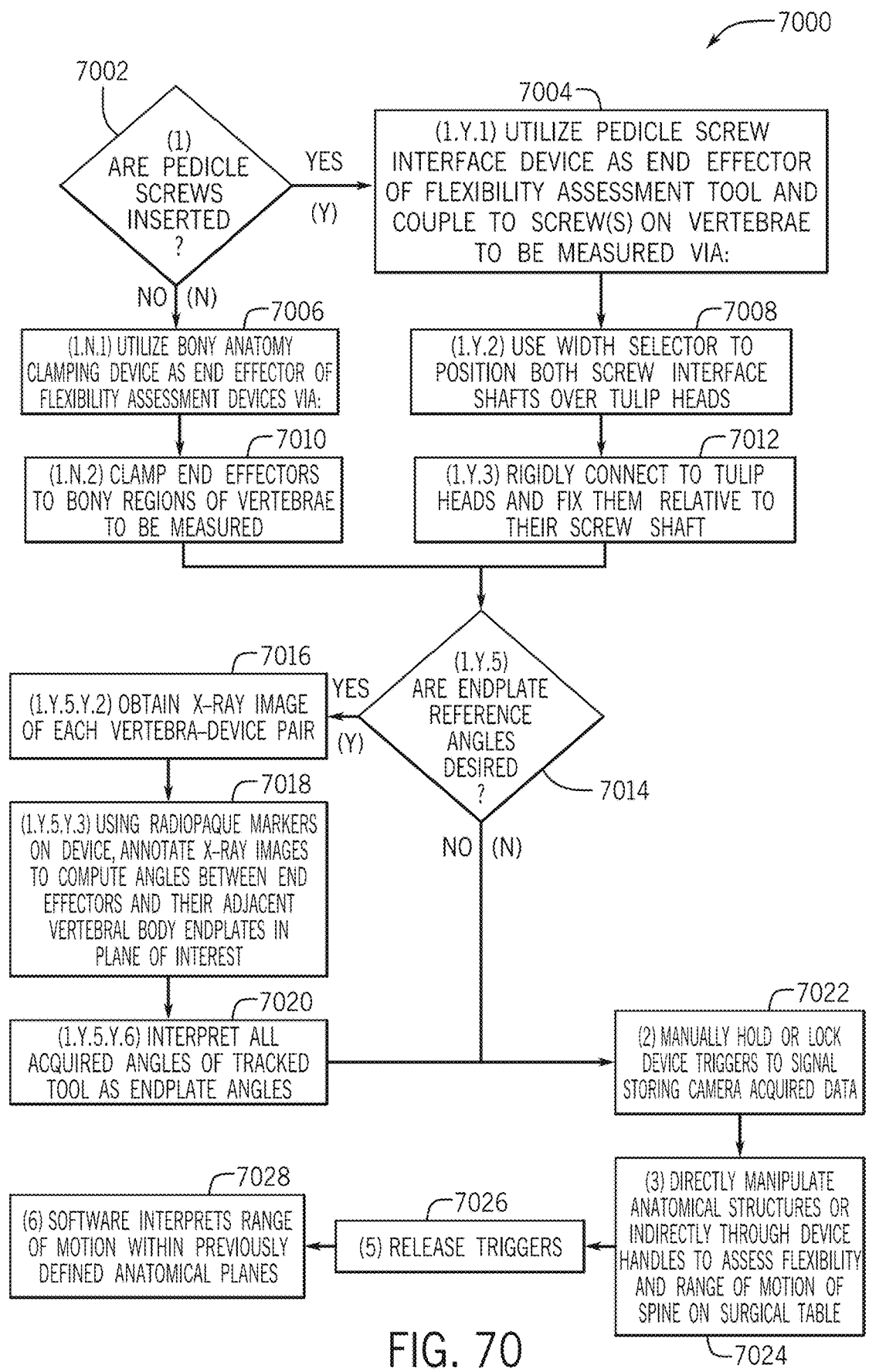

FIG. 70 illustrates a workflow to assess flexibility of the spine intraoperatively using flexibility assessment device in accordance with some embodiments of the invention.

Figure 71:
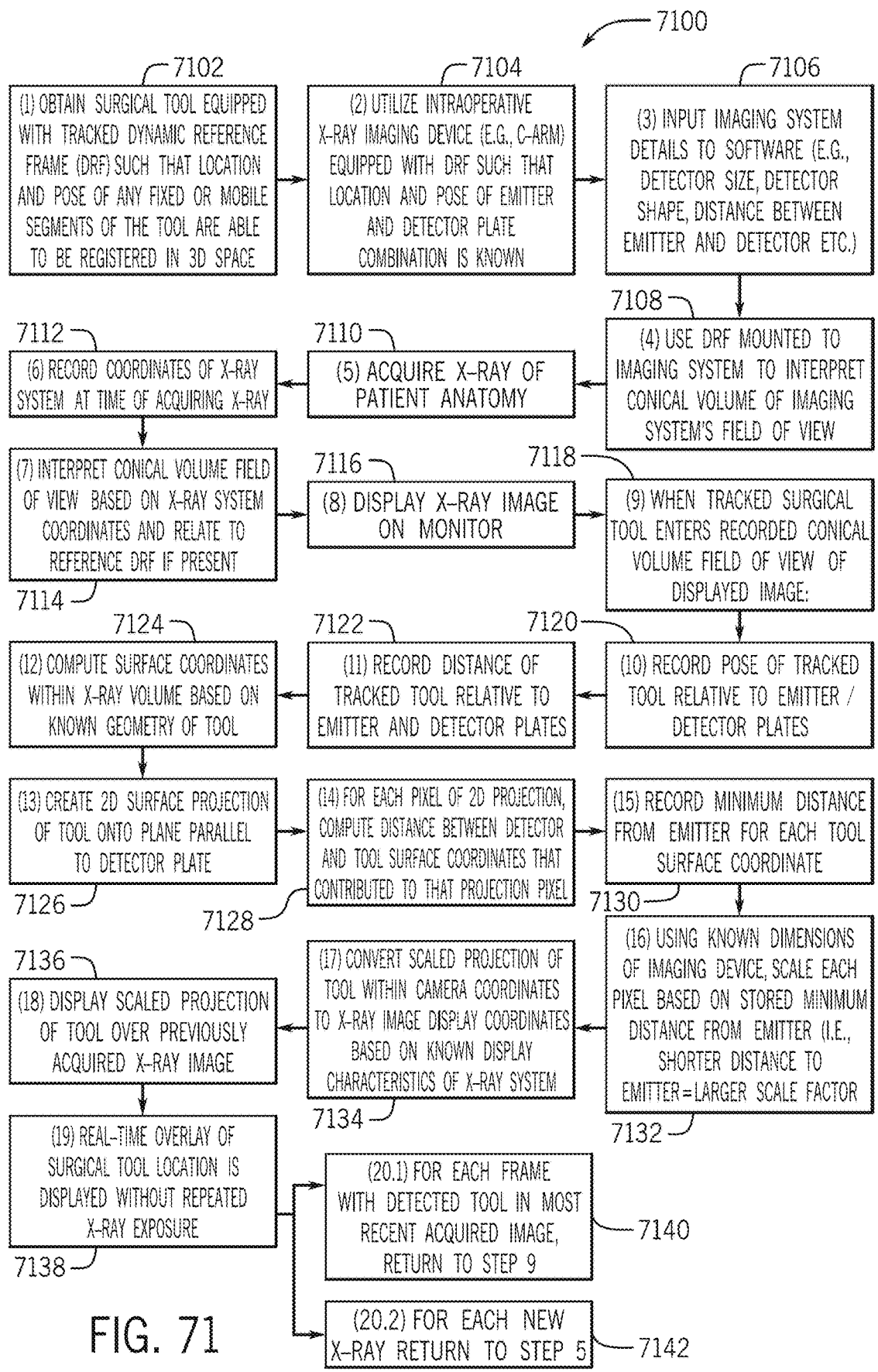

FIG. 71 illustrates a workflow of producing real-time overlays of surgical instruments over intraoperative X-rays in accordance with some embodiments of the invention.

Figure 72:
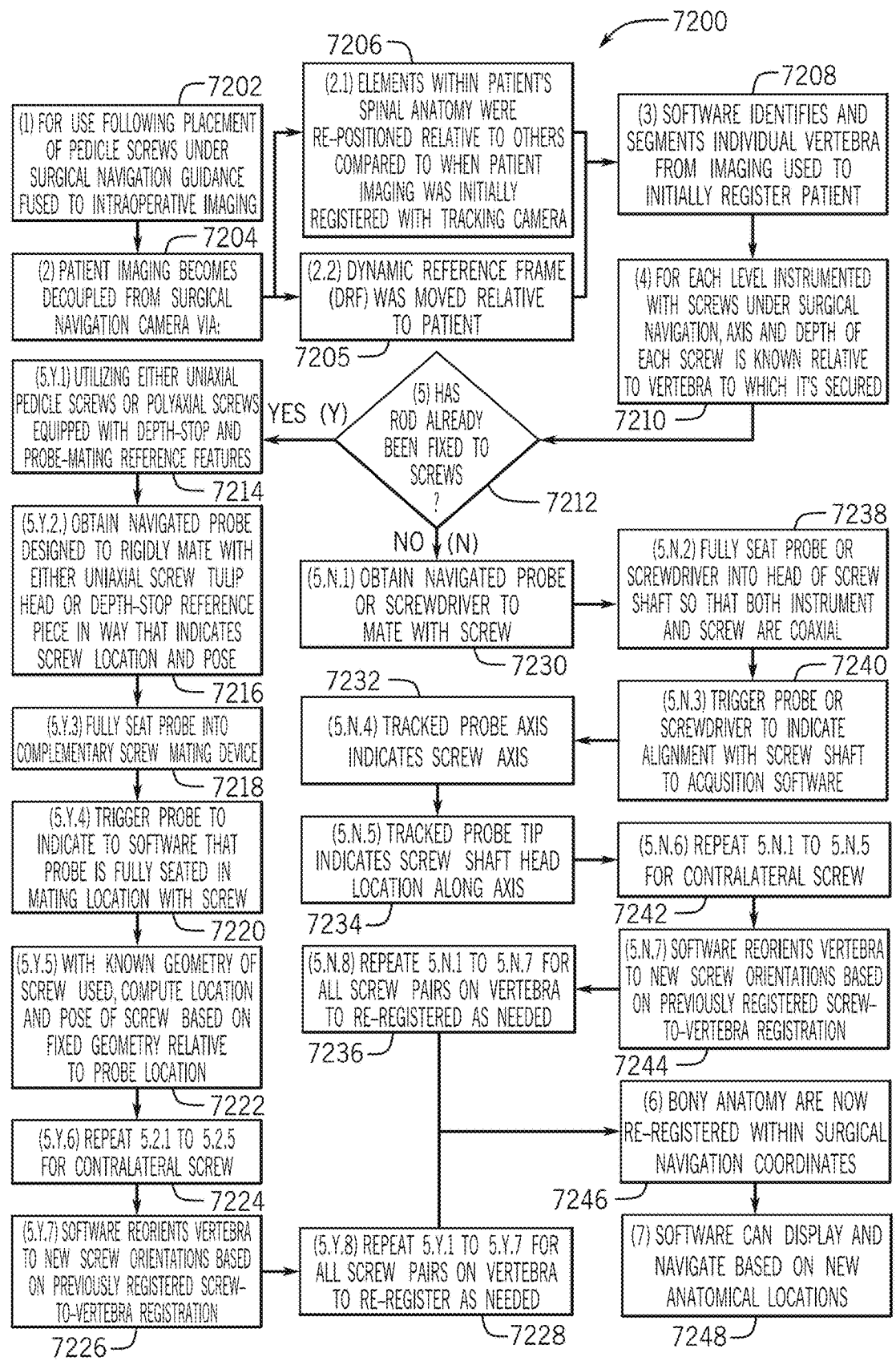

FIG. 72 shows a workflow to rapidly re-register a surgical navigation system after a navigated/registered screw insertion in accordance with some embodiments of the invention.

Figure 73A:
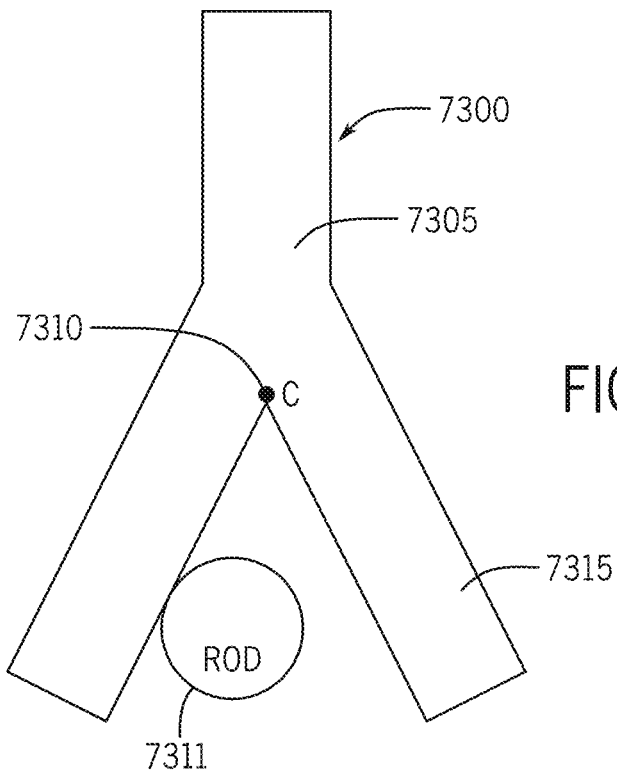

FIG. 73A illustrates a rod-centering fork on the end of a tool shaft in accordance with some embodiments of the invention.

Figure 73B:
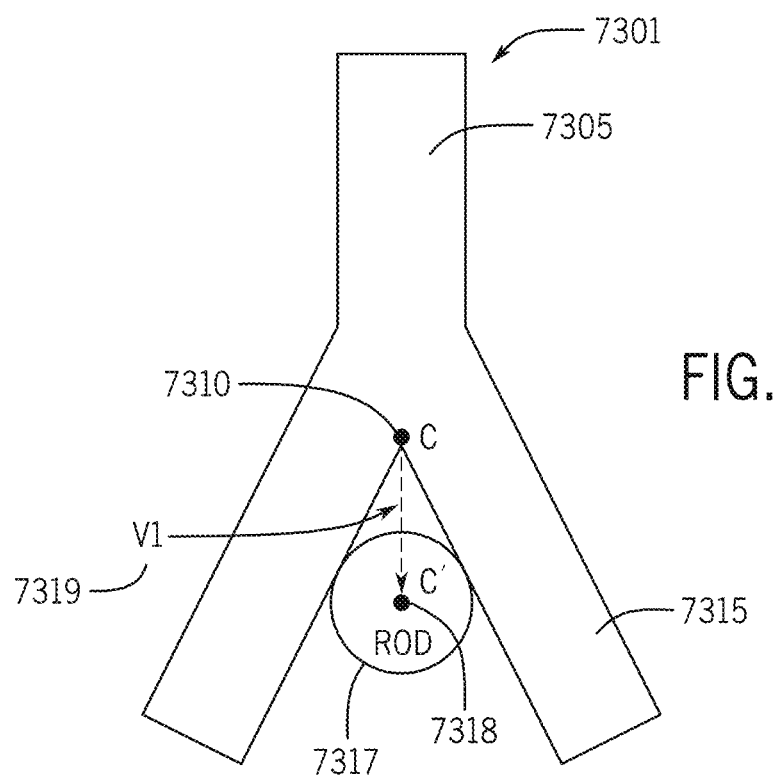

FIG. 73B illustrates the fork of FIG. 73A fully engaged with a rod in accordance with some embodiments of the invention.

Figure 74:
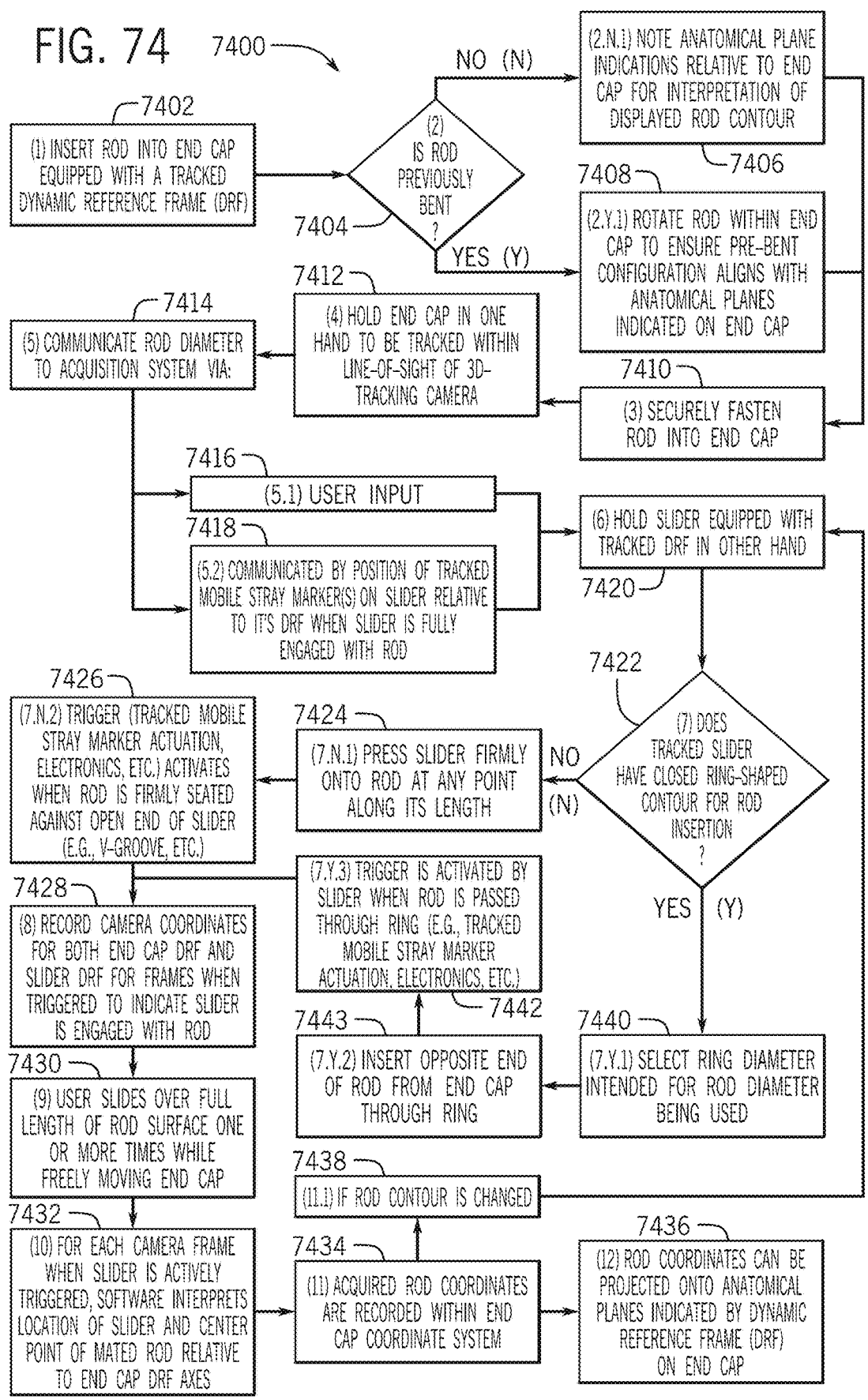

FIG. 74 illustrates a workflow to assess the contour of a rod prior to implantation using two handheld tracked tools in accordance with some embodiments of the invention.

Figure 75:
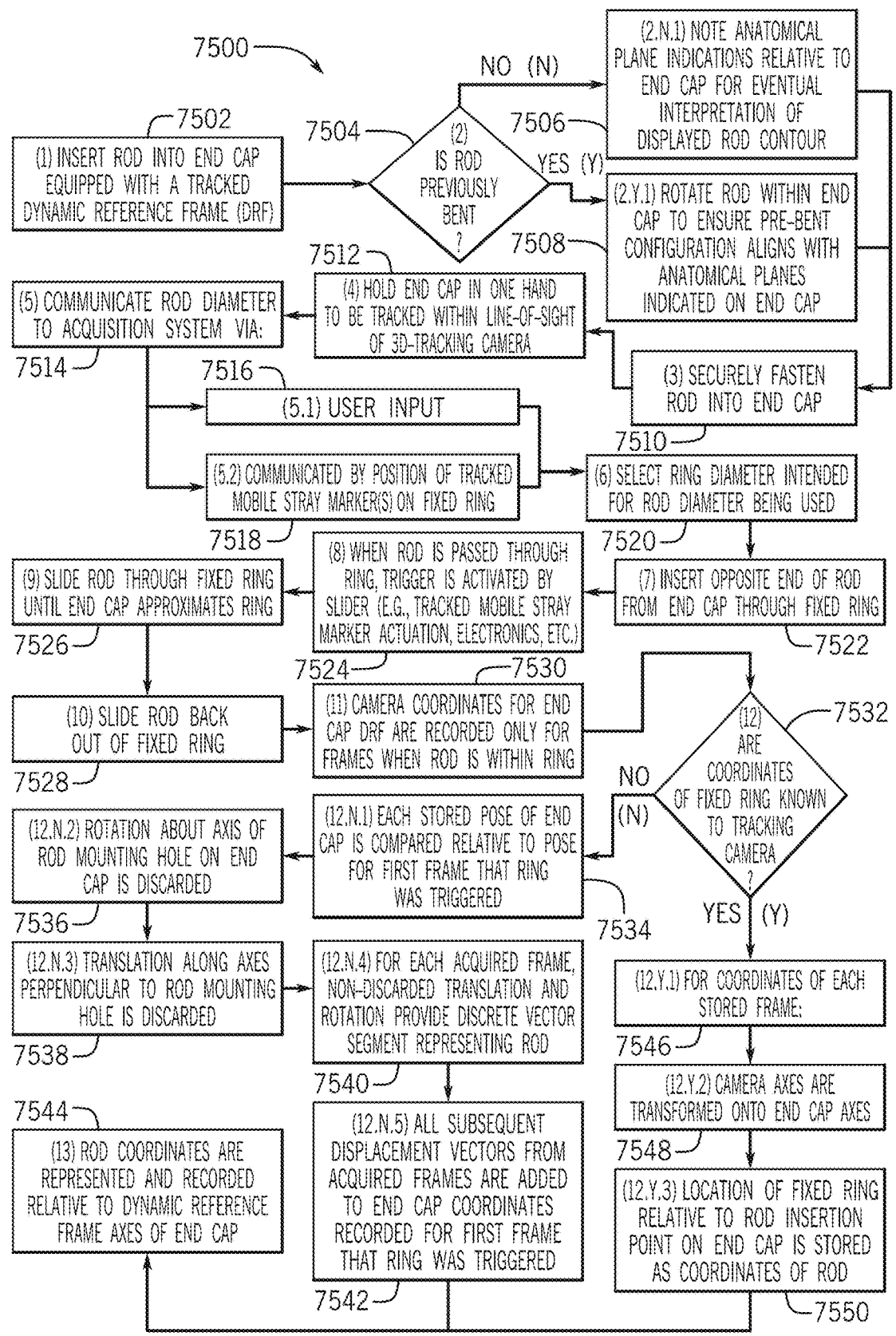

FIG. 75 illustrates a workflow to assess the contour of a rod prior to implantation using one handheld tracked tool and one substantially rigidly fixed ring in accordance with some embodiments of the invention.

Figure 76:
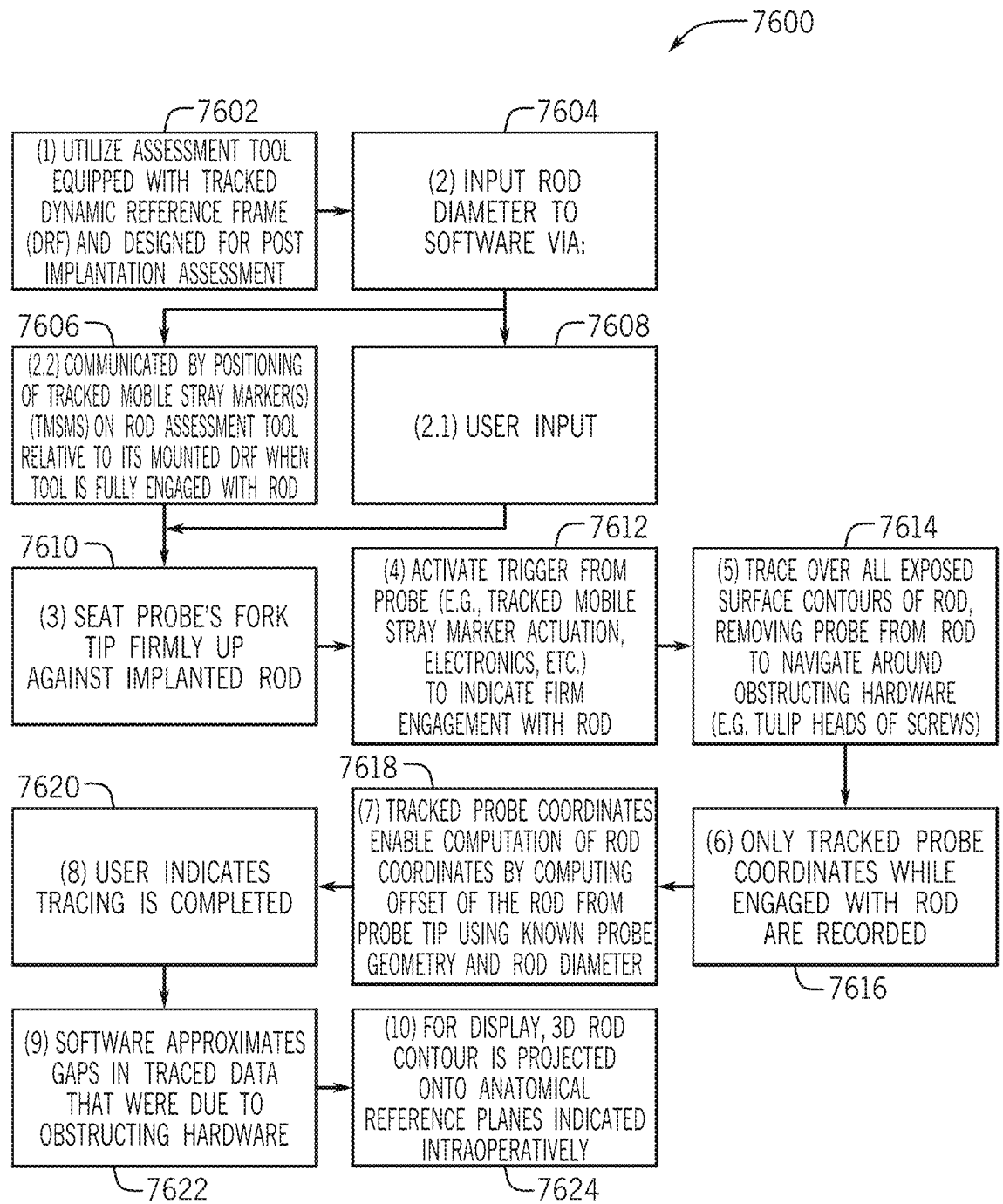

FIG. 76 illustrates a workflow to assess the contour of a rod after implantation in accordance with some embodiments of the invention.

Figure 77C:
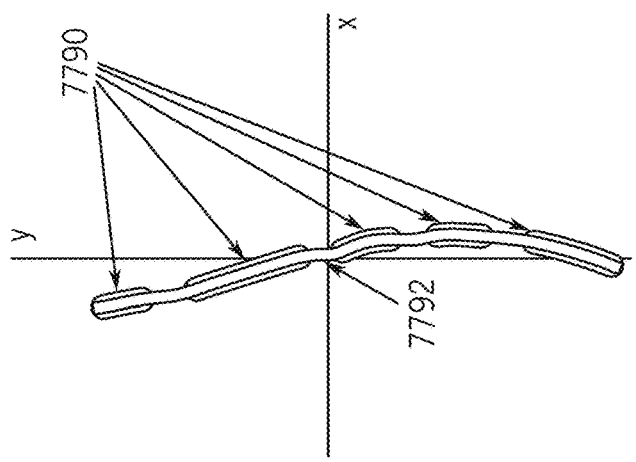
Figure 77B:
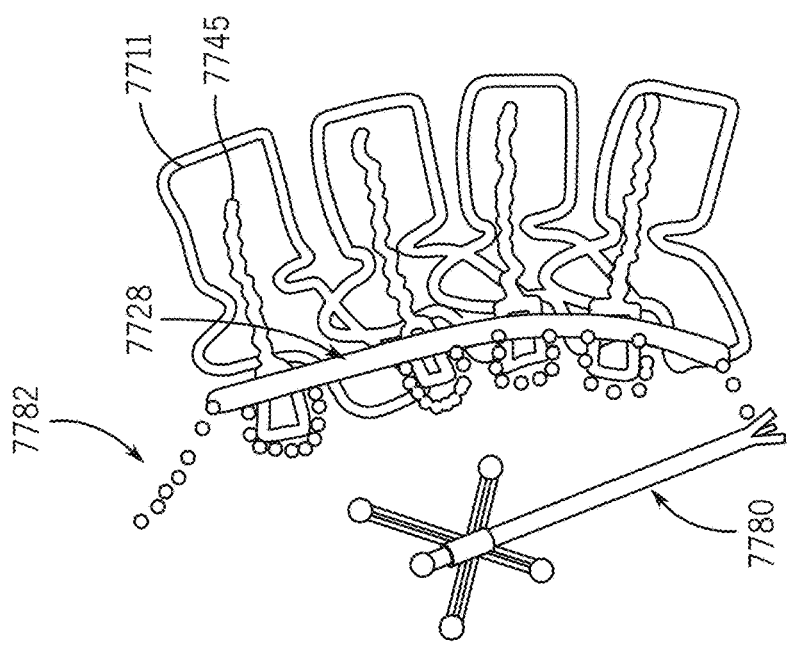
Figure 77A:
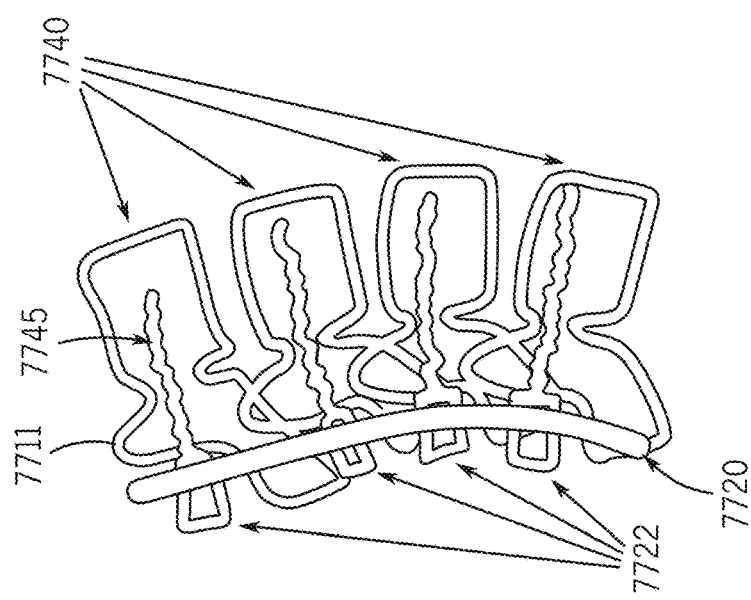

FIGS. 77A-77C illustrate various displays of interpretation of data generated by assessment of a rod contour after a rod has been implanted to tulip heads within a surgical site in accordance with some embodiments of the invention.

Figure 78:
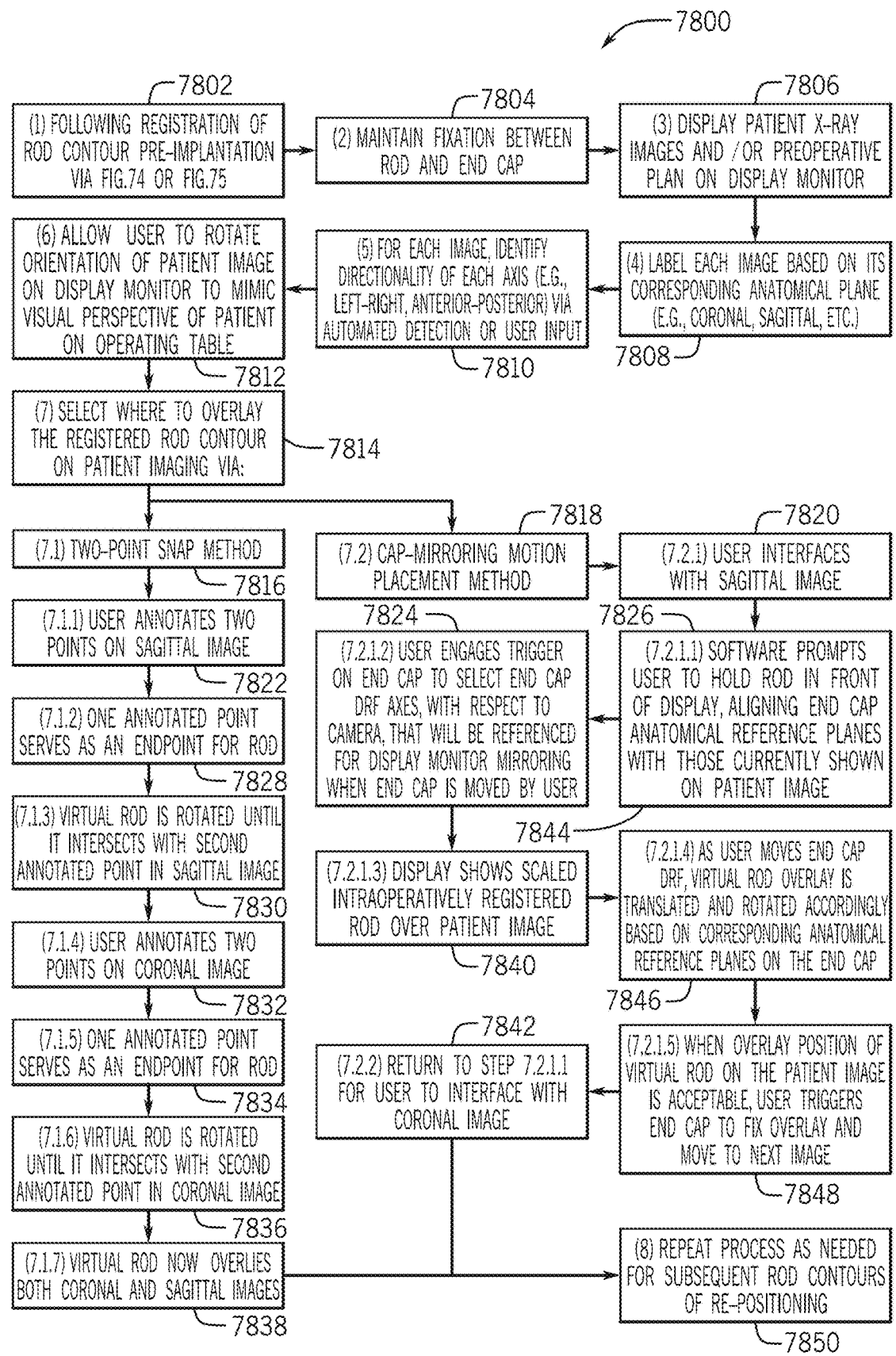

FIG. 78 illustrates a workflow for interactive user placement of a registered rod as an overlay on patient images on a display monitor in accordance with some embodiments of the invention.

FIGS. 79A-79G display processes of interpreting and calculating a tracked rod bending device in accordance with some embodiments of the invention.

Figure 80:
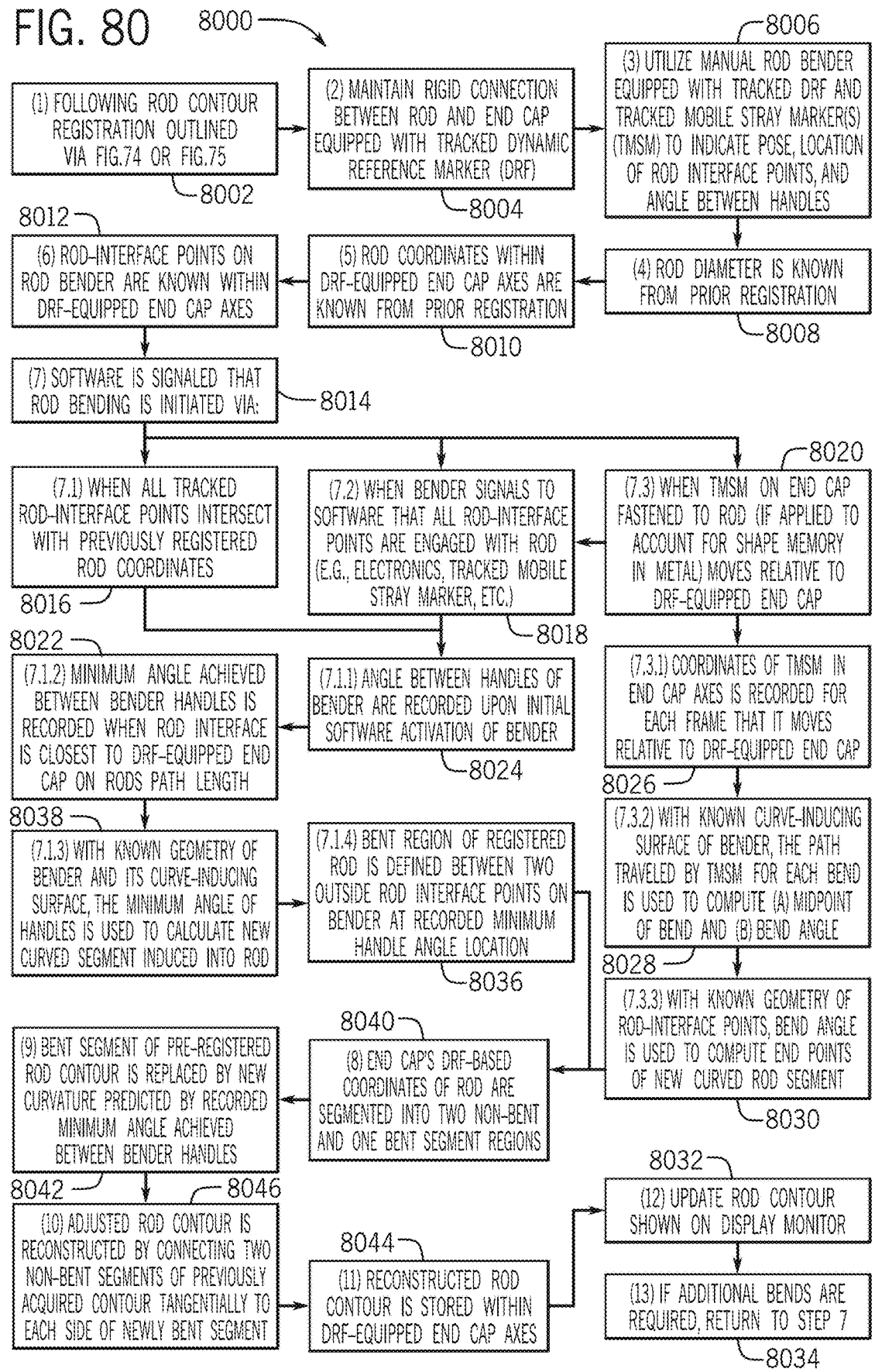

FIG. 80 illustrates a workflow for manually bending a rod prior to its implantation with real-time feedback of its dynamic contour in accordance with some embodiments of the invention.

Figure 81:
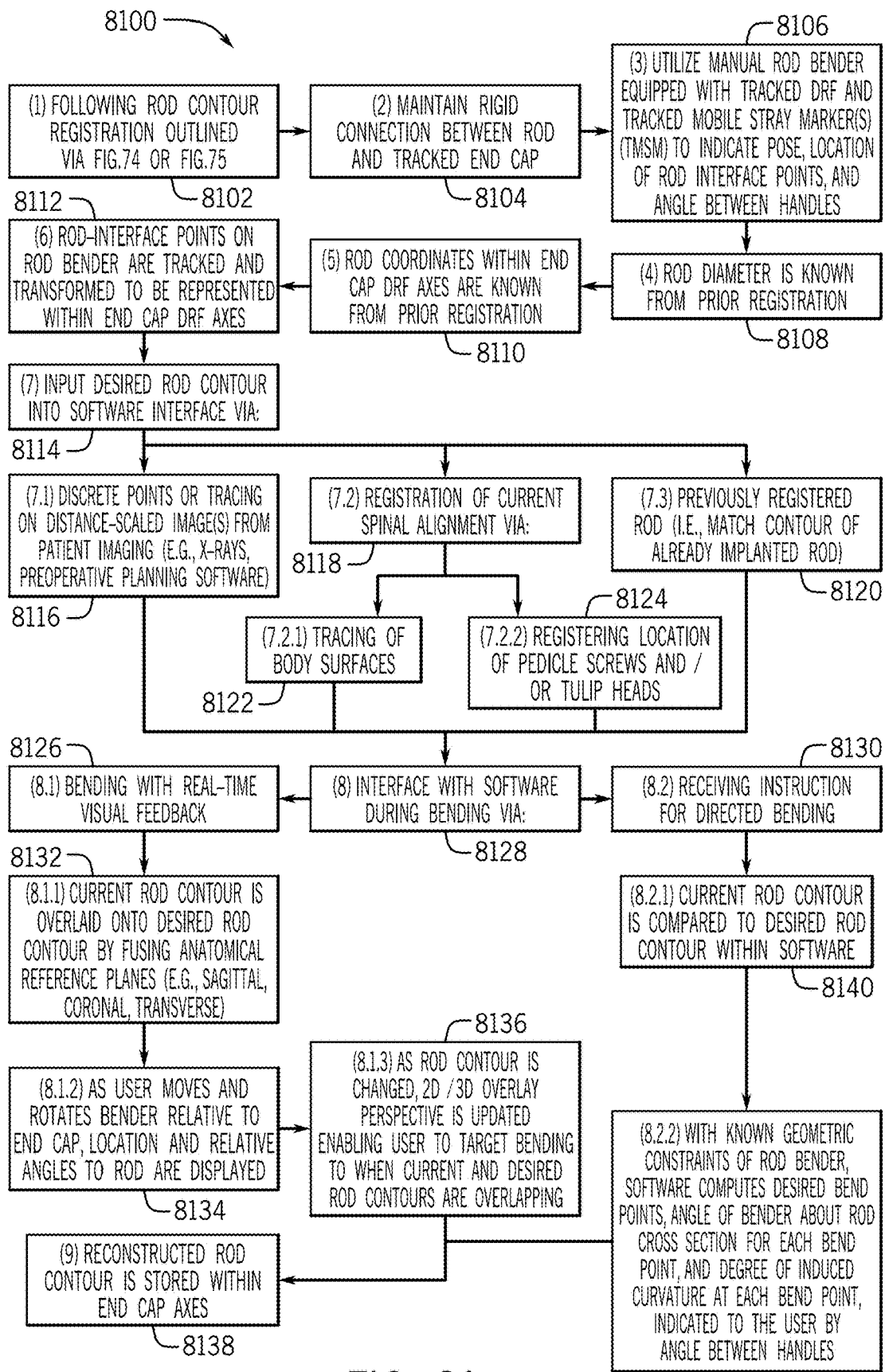

FIG. 81 shows a workflow for manually bending a rod prior to its implantation with directed software input to overlay a projection of the dynamic rod contour onto an intraoperative X-ray image in accordance with some embodiments of the invention.

Figure 82B:
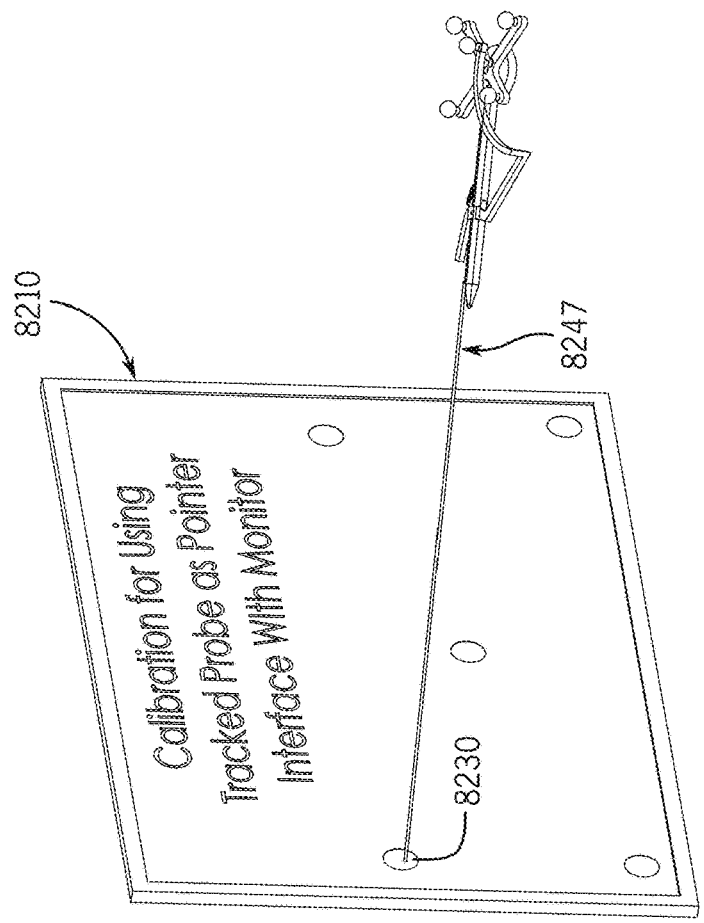
Figure 82A:
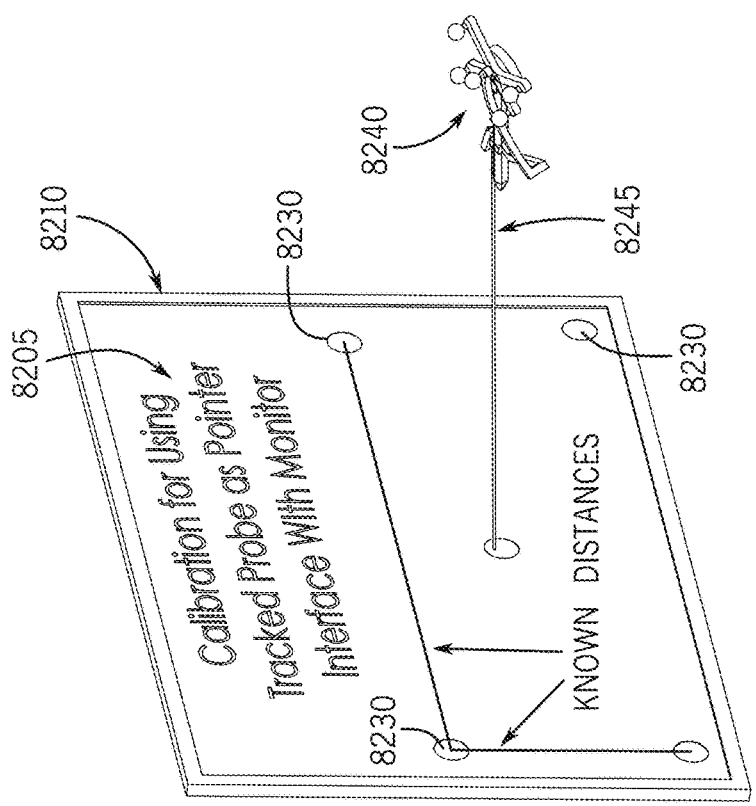

FIGS. 82A-82B illustrates processes or methods of a probe calibration in accordance with some embodiments of the invention.

Figure 83:
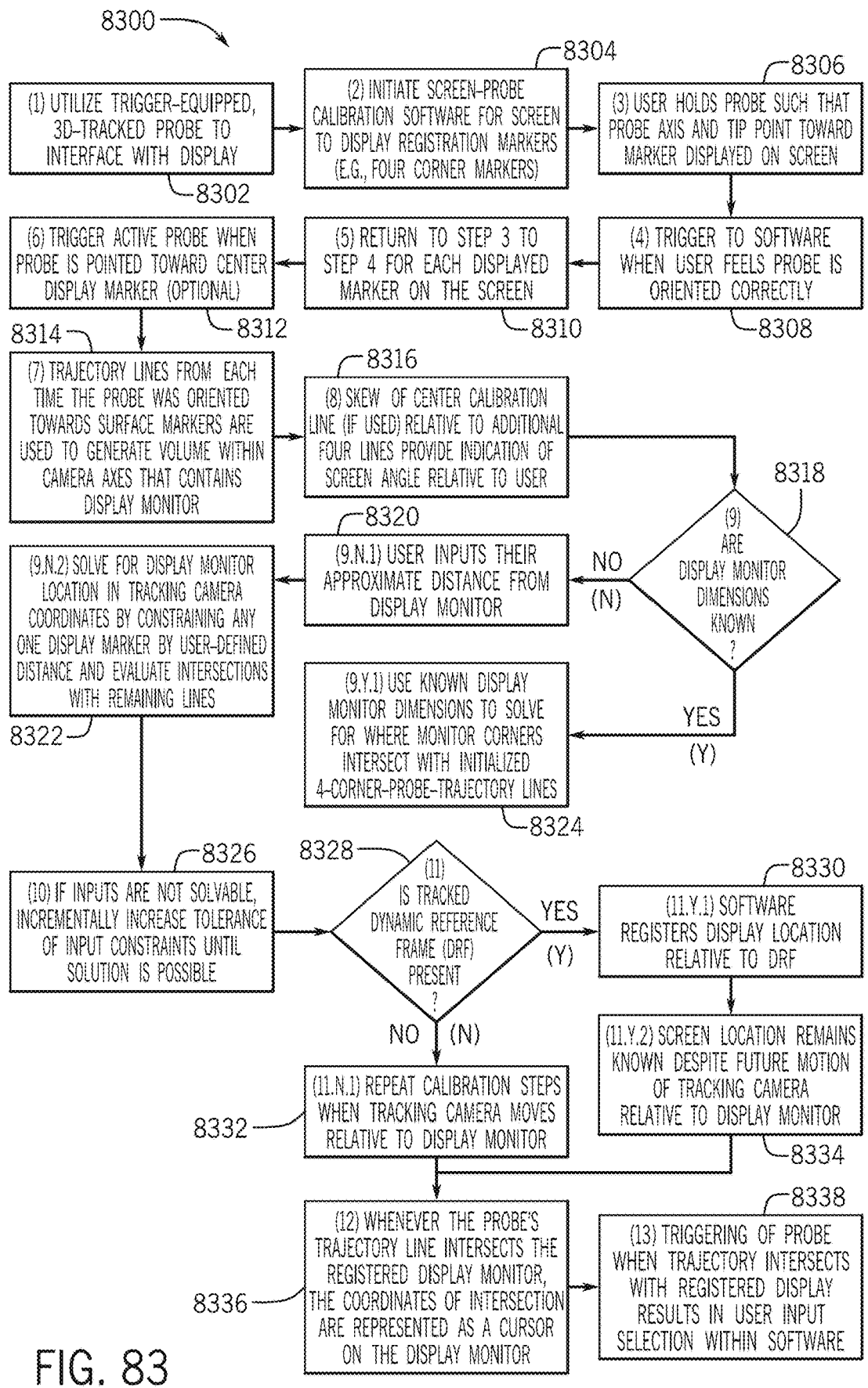

FIG. 83 illustrates a workflow to utilize a trigger-equipped probe to serve as a laser pointer analog for a user-interface system with a non-tracked display in accordance with some embodiments of the invention.

Figure 84A:
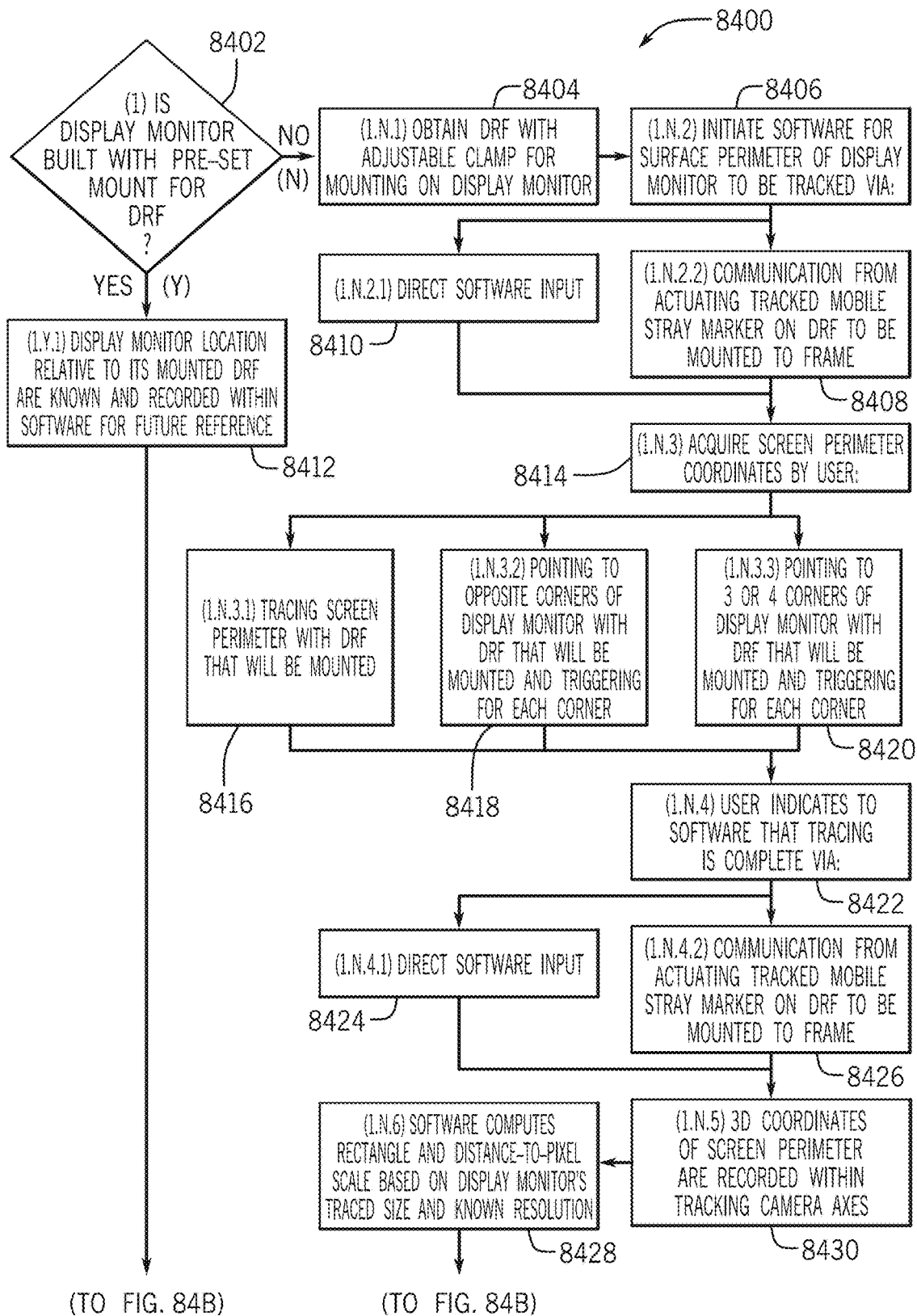
Figure 84B:
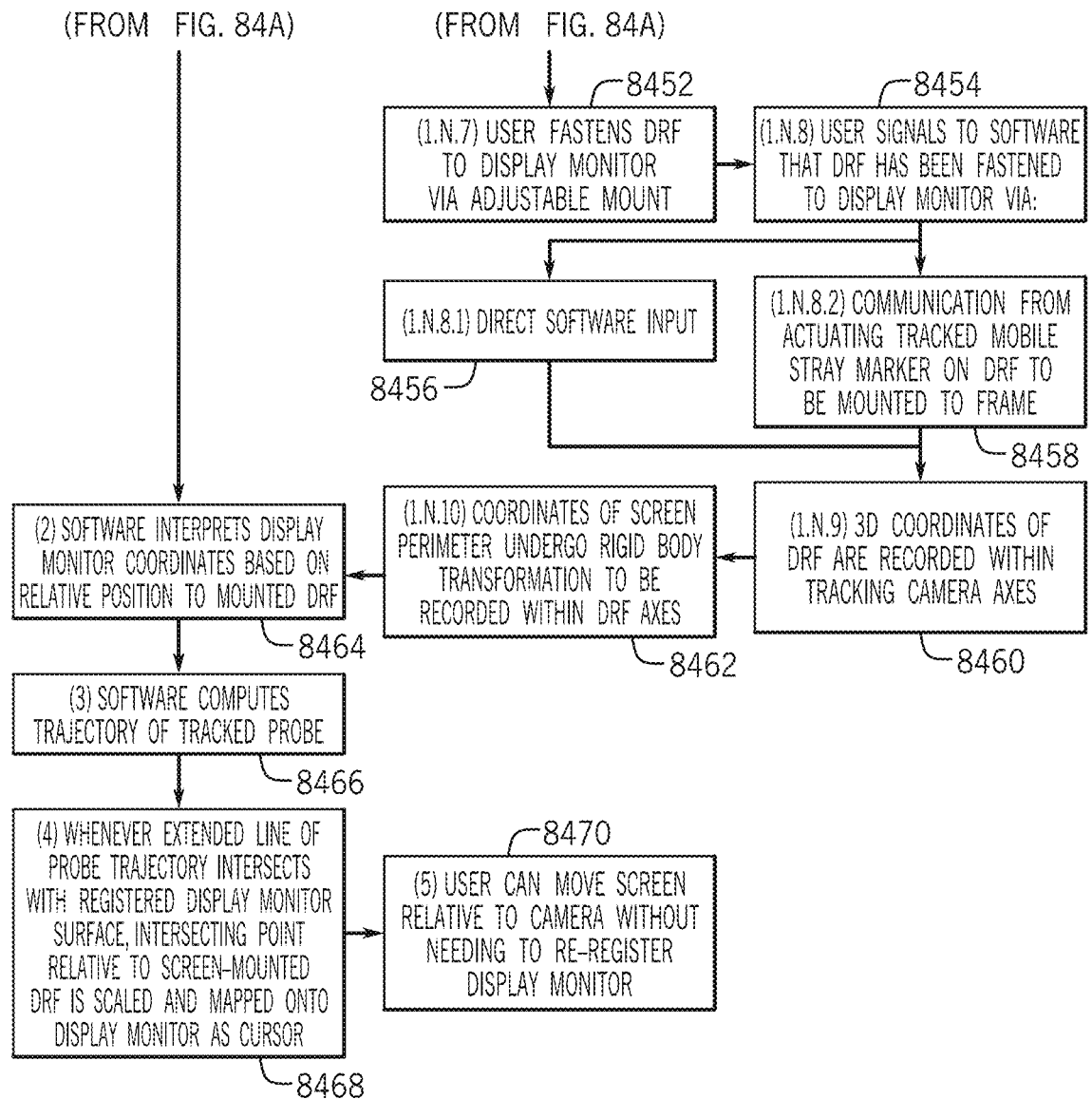

FIGS. 84A-84B illustrates a workflow to utilize a trigger-equipped probe to serve as a laser pointer analog for a user-interface with a 3D-tracked display monitor in accordance with some embodiments of the invention.

Figure 85:
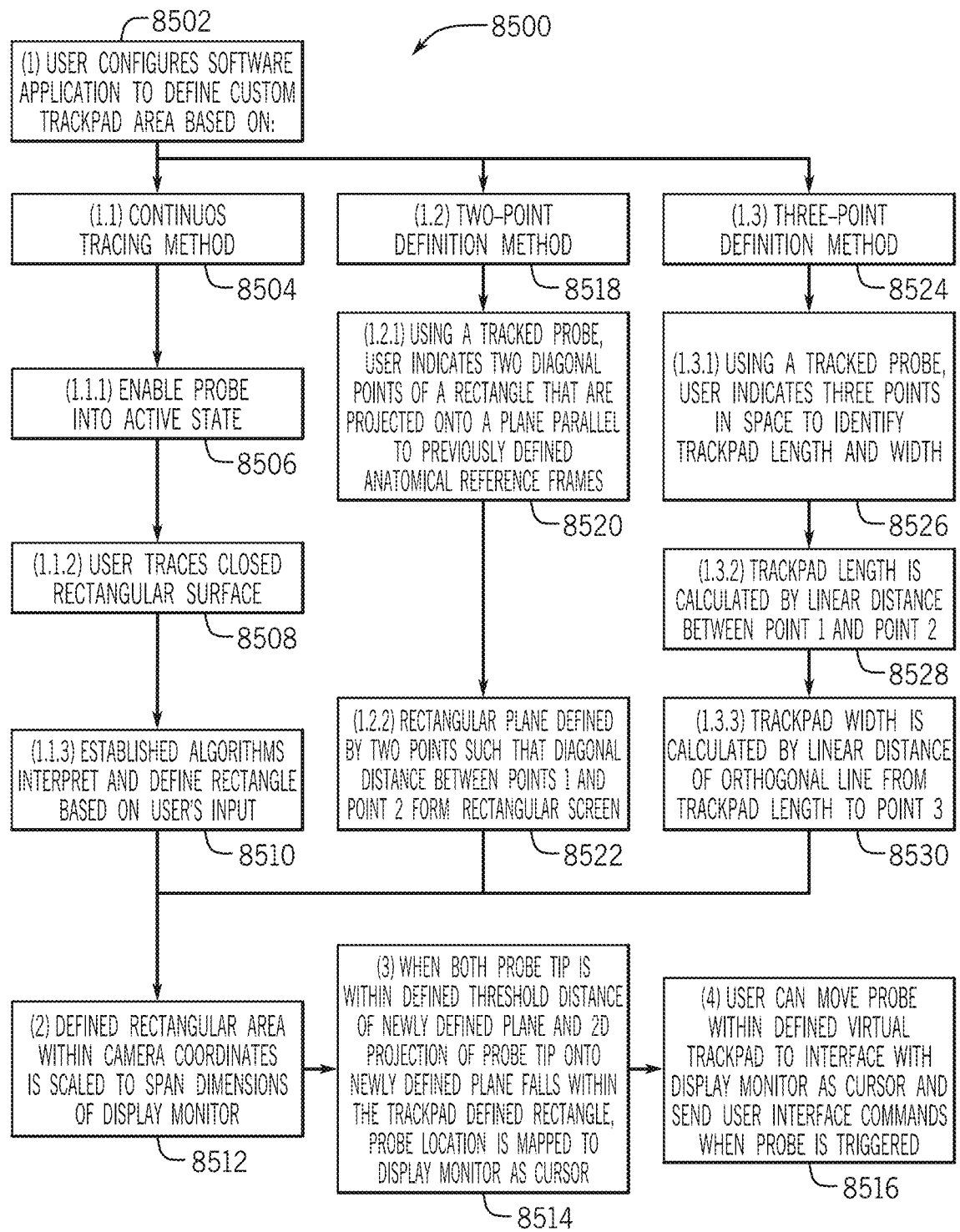

FIG. 85 illustrates a workflow to utilize a trigger-equipped probe to serve as an interface device for a non-tracked display via a user-defined trackpad analog in accordance with some embodiments of the invention.

FIGS. 86A-86D illustrates output displays of alignment assessments in accordance with some embodiments of the invention.

FIG. 87A illustrates a rod with previously registered contour fixed to a tracked DRF-equipped end cap and interacting with a tracked rod bender in accordance with some embodiments of the invention.

FIG. 87B illustrates a sagittal projection of the registered rod contour in accordance with some embodiments of the invention.

FIG. 87C illustrates a coronal projection of the registered rod contour in accordance with some embodiments of the invention.

FIG. 87D illustrates a display of the location of a rod bender's center rod contouring surface relative to a cross-sectional view of the rod in accordance with some embodiments of the invention.

FIG. 87E illustrates a display of a sagittal projection of the registered rod contour in accordance with some embodiments of the invention.

Figure 87F:
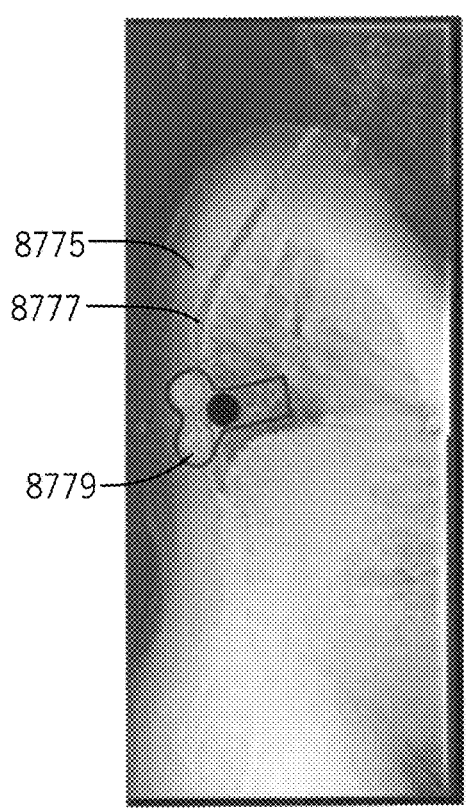

FIG. 87F illustrates a sagittal patient image with an overlay of a registered rod contour as well as an overlay display of the location of a tracked rod bender relative to the previously registered rod in accordance with some embodiments of the invention.

Figure 87G:
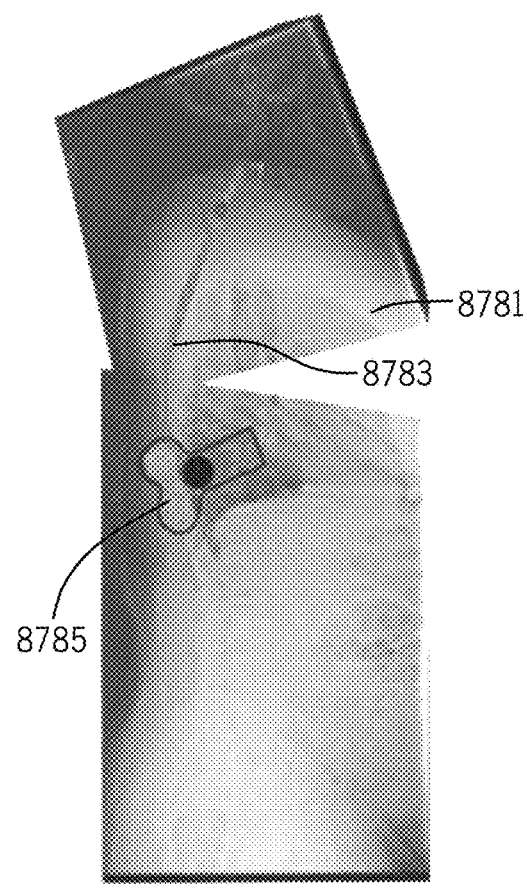

FIG. 87G illustrates a sagittal patient image adjusted for operative planning with an overlay of a registered rod contour as well as an overlay display of the location of a tracked rod bender relative to the previously registered rod in accordance with some embodiments of the invention.

Figure 87L:
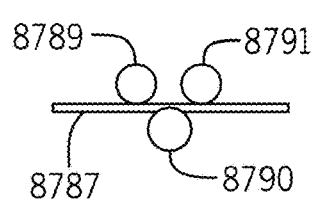
Figure 87M:
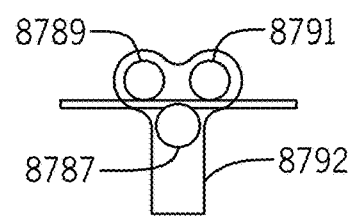
Figure 87J:
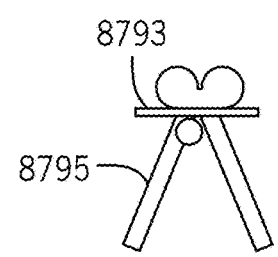
Figure 87H:
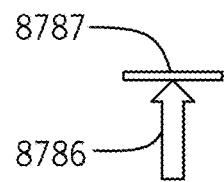
Figure 87I:
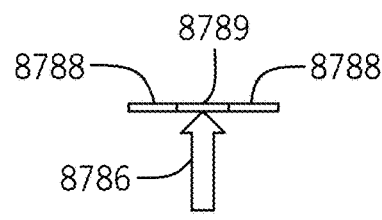

FIGS. 87H-87I include displays of a rod and rod bender's location on display monitor in accordance with some embodiments of the invention.

FIGS. 87J-87M illustrates a display of a bender and rod in accordance with some embodiments of the invention.

Figure 88A:
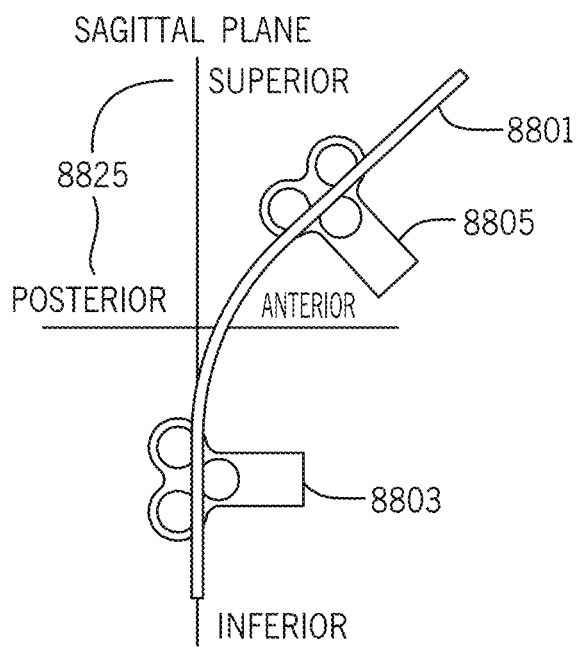

FIG. 88A illustrates a sagittal projection of a registered rod contour, a display of the current location of the rod bender relative to the registered rod contour, a display of the software-instructed location where the user should place the rod-bender, and anatomical axes labels in accordance with some embodiments of the invention.

Figure 88B:
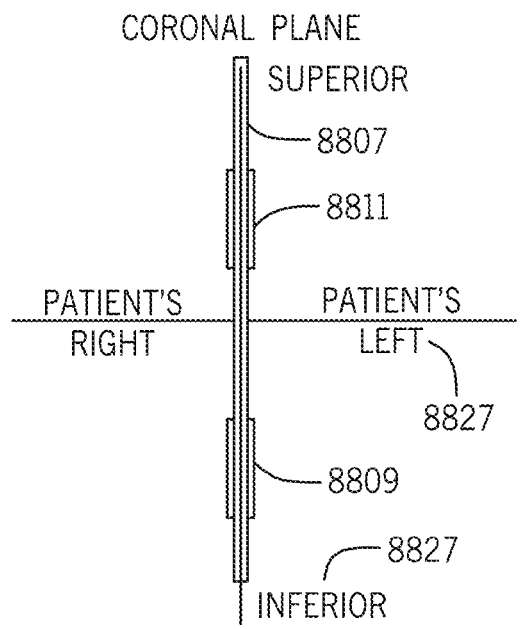

FIG. 88B illustrates a display of FIG. 88A as applied to the coronal plane in accordance with some embodiments of the invention.

Figure 88C:
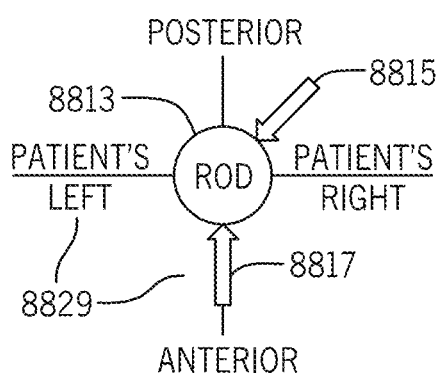

FIG. 88C illustrates a cross-sectional display of the rod, the current location of the rod bender's center contouring surface, the software-instructed location of where the rod bender's center contouring surface should be placed, and anatomical axes labels in accordance with some embodiments of the invention.

Figure 88D:
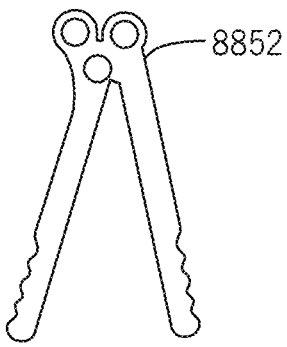

FIG. 88D illustrates a display representation of the current relative position of the bender's handles, directly related to the degree of bending induced on a rod of known diameter in accordance with some embodiments of the invention.

Figure 88E:
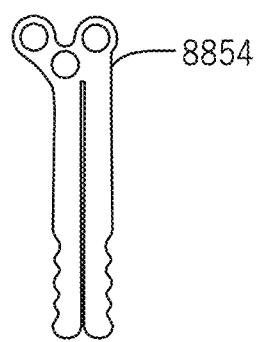

FIG. 88E illustrates a display representation of the software-instructed relative position of the bender's handles (k), directly related to the degree of bending induced on a rod of known diameter in accordance with some embodiments of the invention.

Figure 88F:
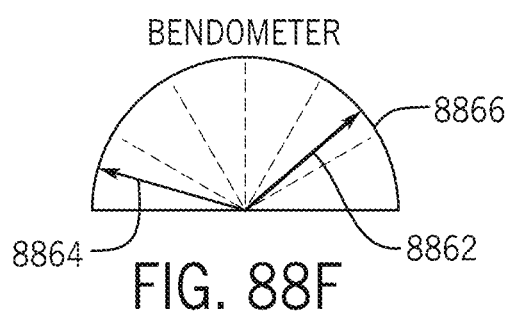

FIG. 88F illustrates a bend angle display gauge in accordance with some embodiments of the invention.

Figure 89:
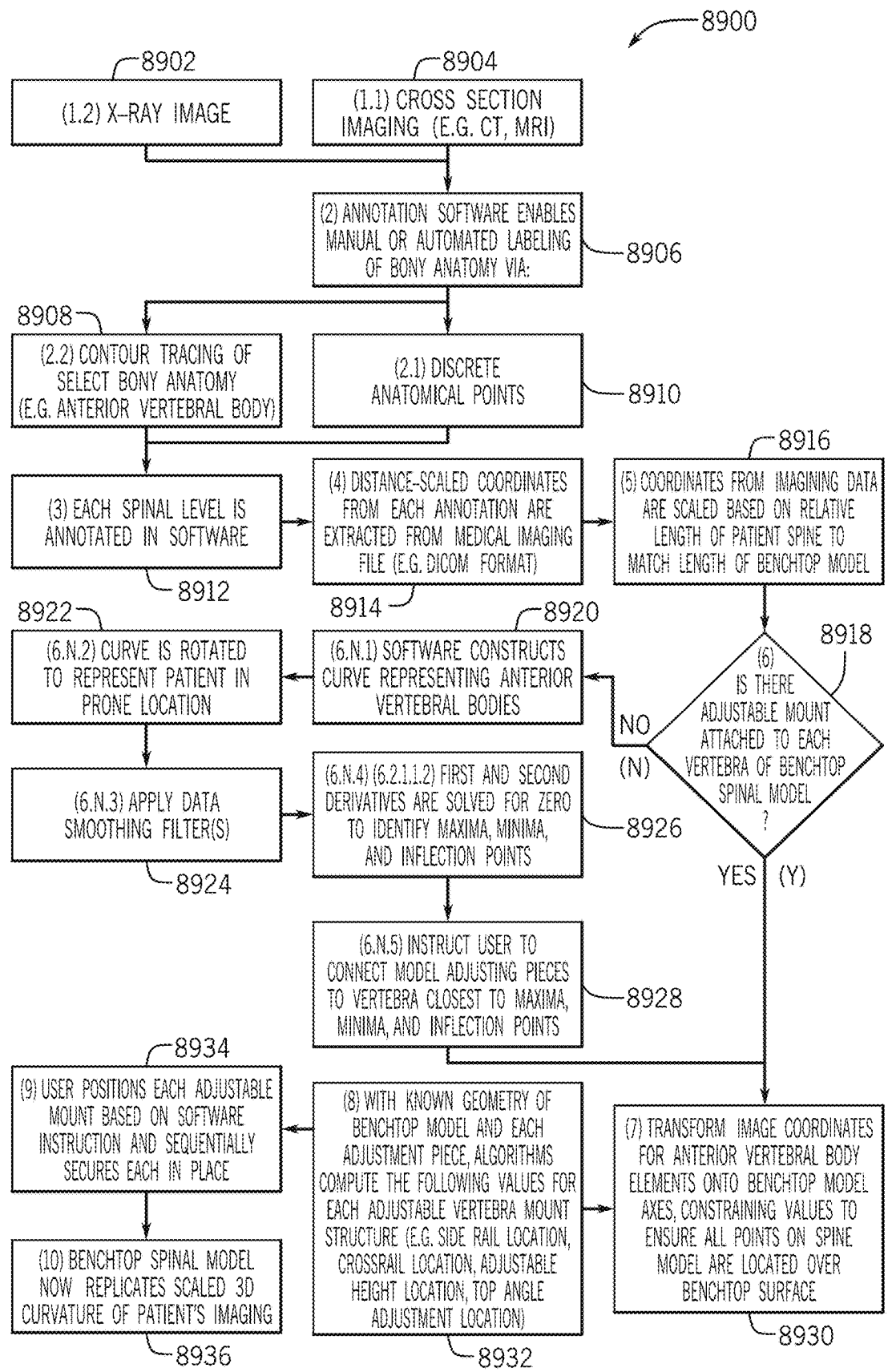

FIG. 89 shows a workflow to match the adjustable benchtop spinal model to mimic alignment parameters from patient-specific imaging in accordance with some embodiments of the invention.

Figure 90A:
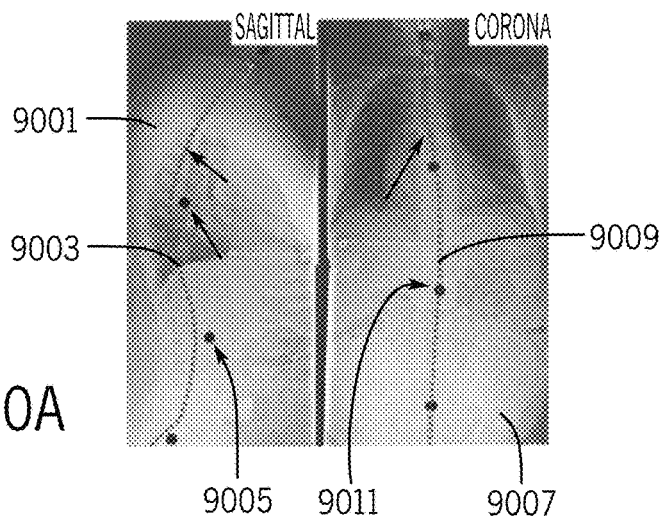

FIG. 90A illustrates sagittal and coronal patient images with overlaid sagittal and coronal contour tracings of the spine, discrete software-instructed placement of adjustable mounts onto the anatomical model, and instructions for the coordinates of each of those adjustable mounts to be positioned on the adjustable benchtop model in accordance with some embodiments of the invention.

Figure 90B:
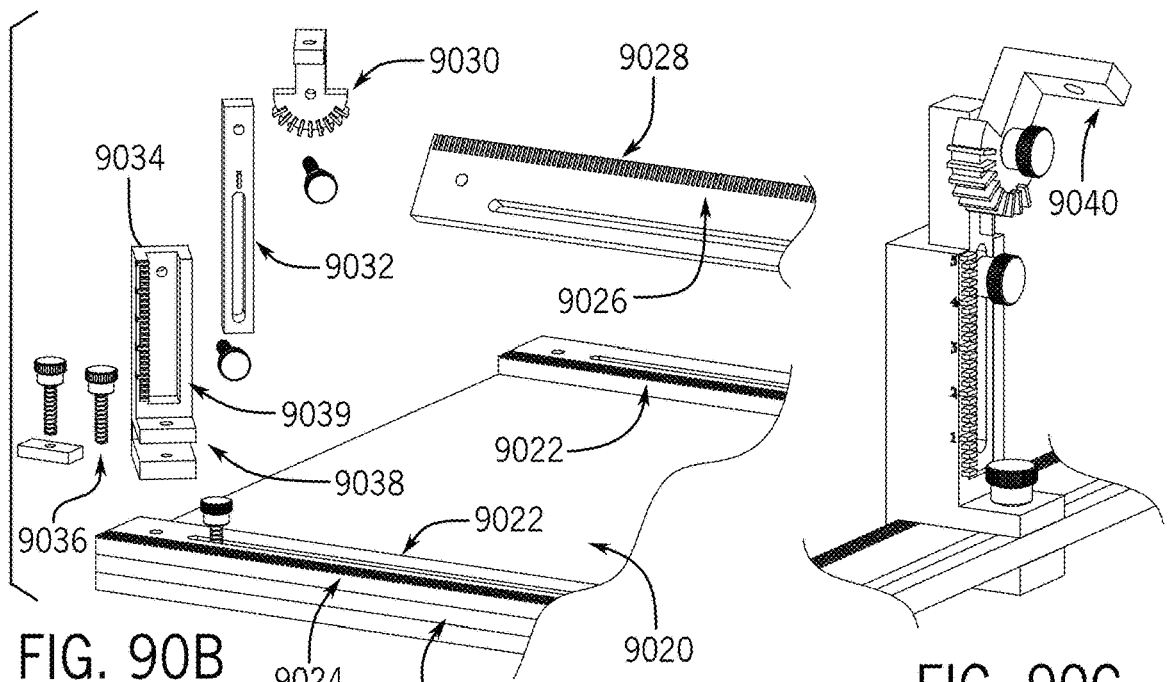

FIG. 90B illustrates an anatomical model mounting exploded assembly in accordance with some embodiments of the invention.

Figure 90C:
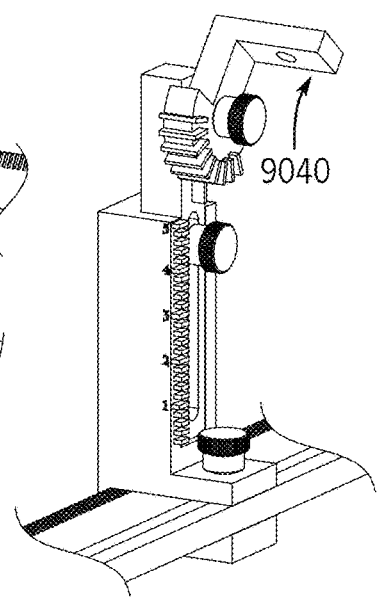

FIG. 90C illustrates a fastening interface for anatomical model in accordance with some embodiments of the invention.

Figure 90D:
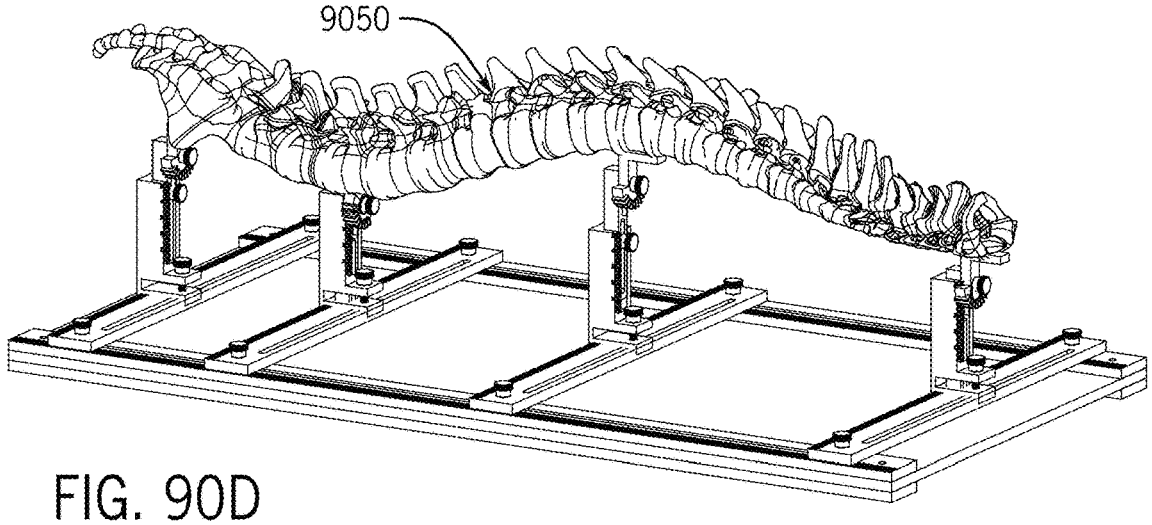

FIG. 90D illustrates a mounted spine anatomical model in accordance with some embodiments of the invention.

Figure 91A:
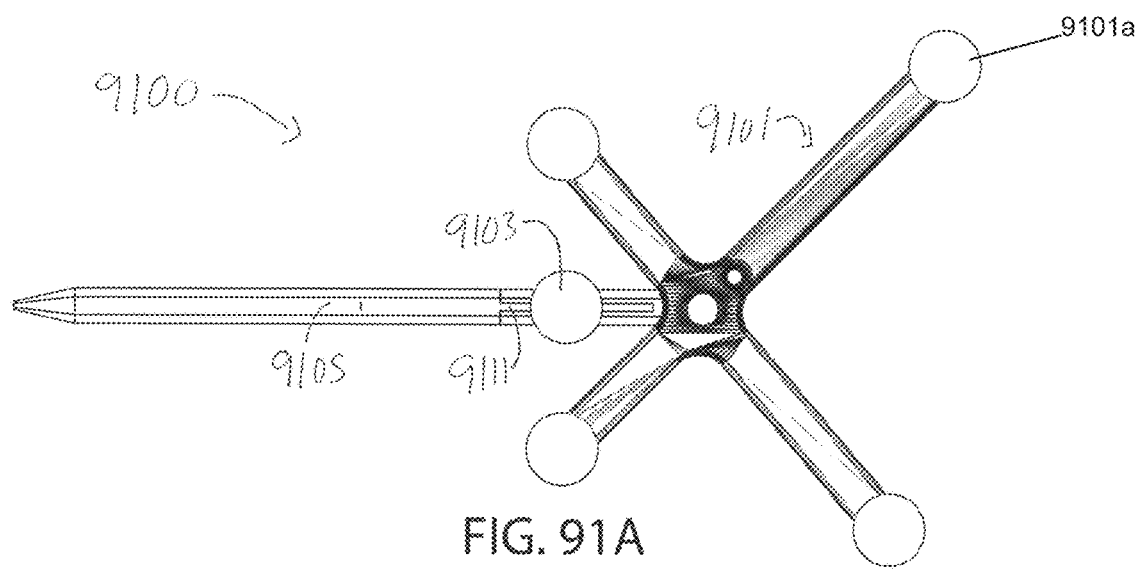

FIG. 91A illustrates a top view of a modular 3D-tracked tool with a straight extension that is fully engaged into the tool's base in accordance with some embodiments of the invention.

Figure 91B:
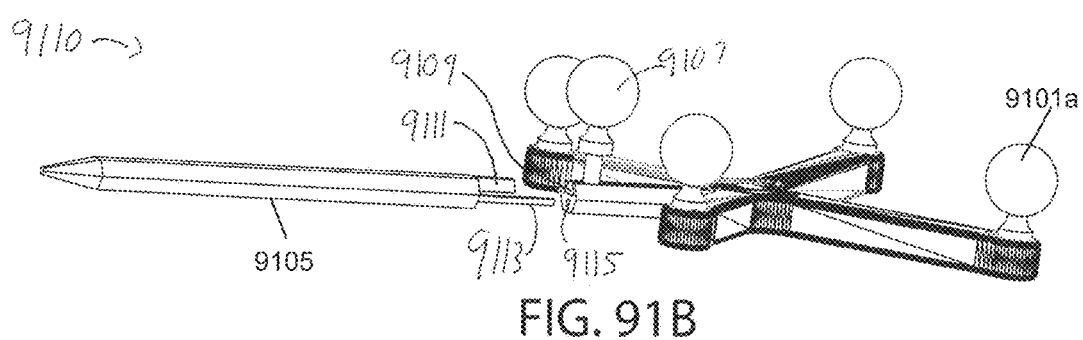

FIG. 91B illustrates a perspective view of a modular 3D-tracked tool with a straight extension that is disengaged with the tool's base as described previously in relation to FIG. 91A in accordance with some embodiments of the invention.

Figure 91C:
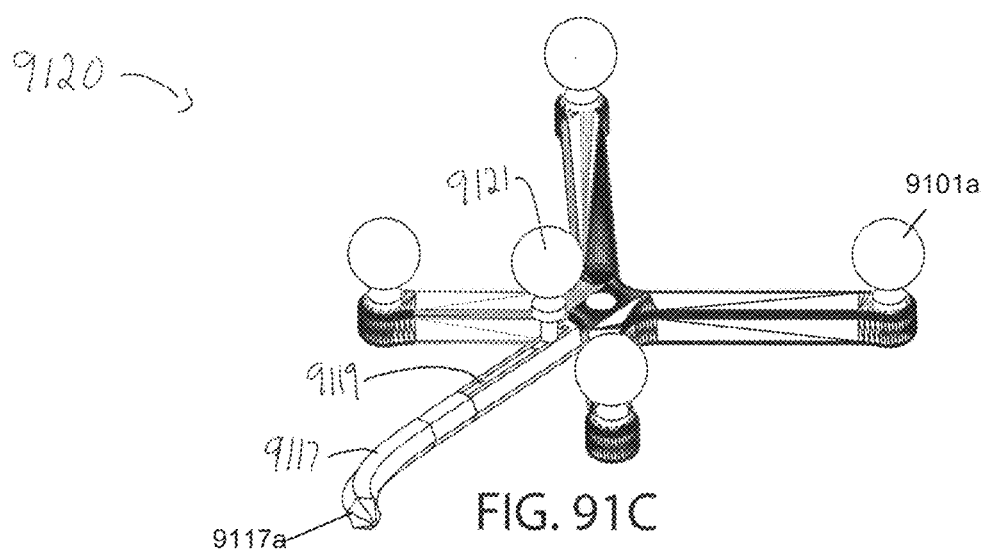

FIG. 91C illustrates a perspective view of a modular 3D-tracked tool with a curved extension that is fully engaged into the tool's base as described previously in relation to FIGS. 91A-91B in accordance with some embodiments of the invention.

Figure 92A:
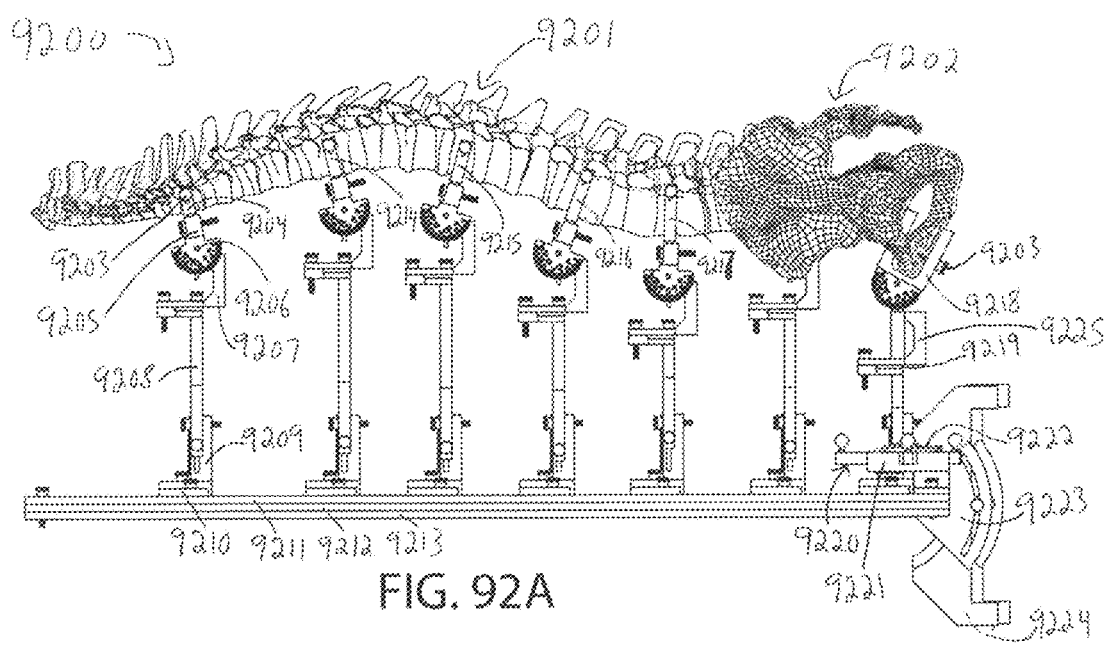
Figure 92B:
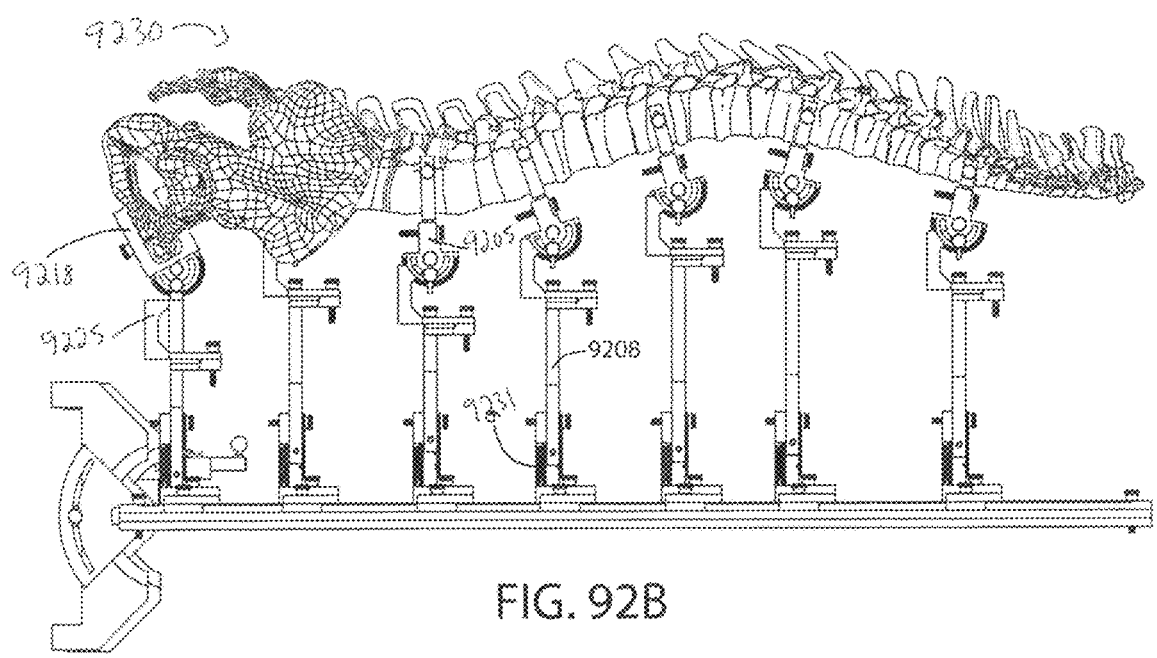

FIGS. 92A-92B illustrate side views of an adjustable phantom spine model holder with vertebral holders substantially rigidly engaged with select vertebrae and the pelvis of the model in accordance with some embodiments of the invention.

Figure 92C:
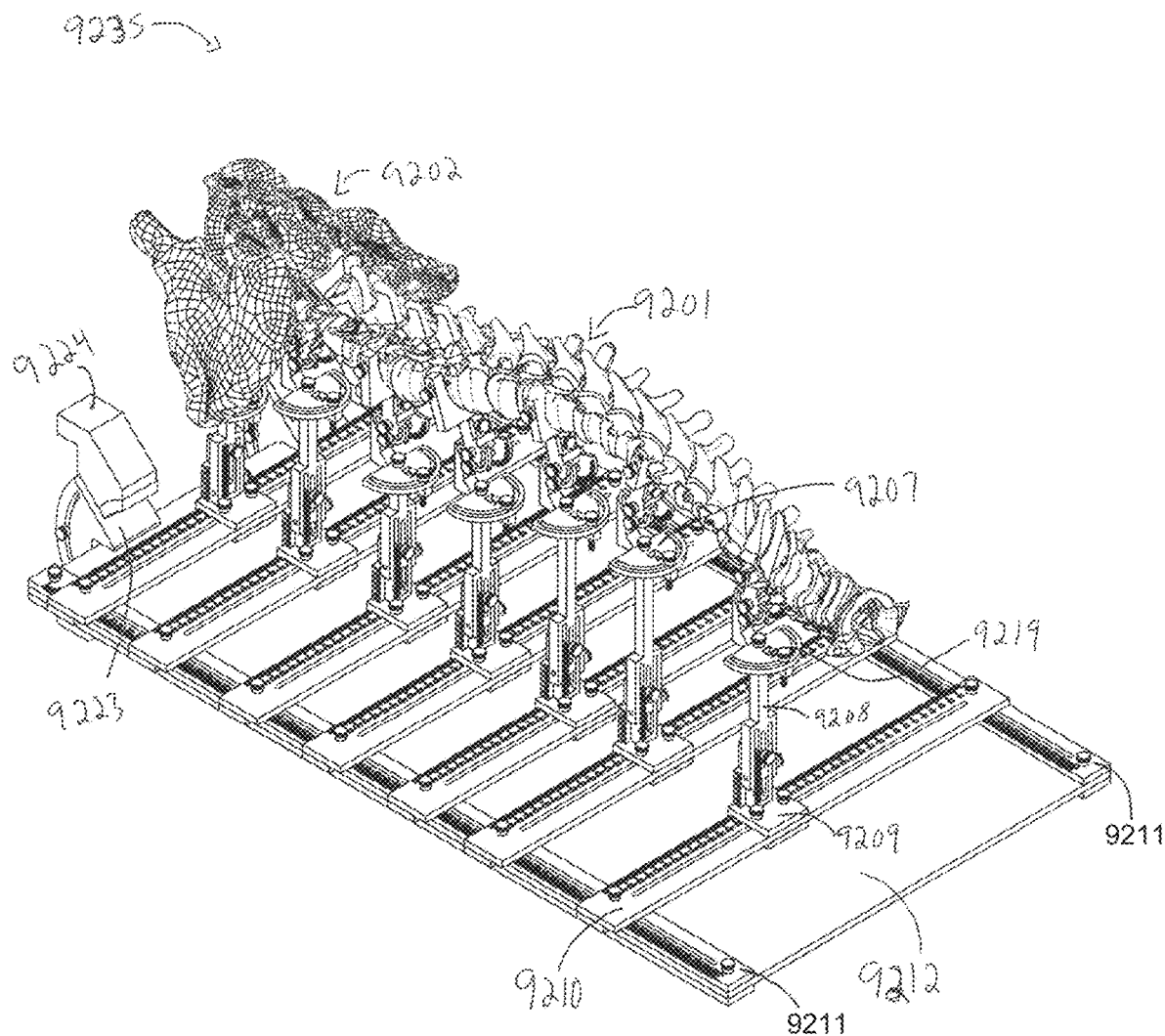

FIG. 92C illustrates a perspective view of an adjustable phantom spine model holder with vertebral holders substantially rigidly engaged with select vertebrae and the pelvis of the model as described previously in relation to FIGS. 92A-92B in accordance with some embodiments of the invention.

Figure 92D:
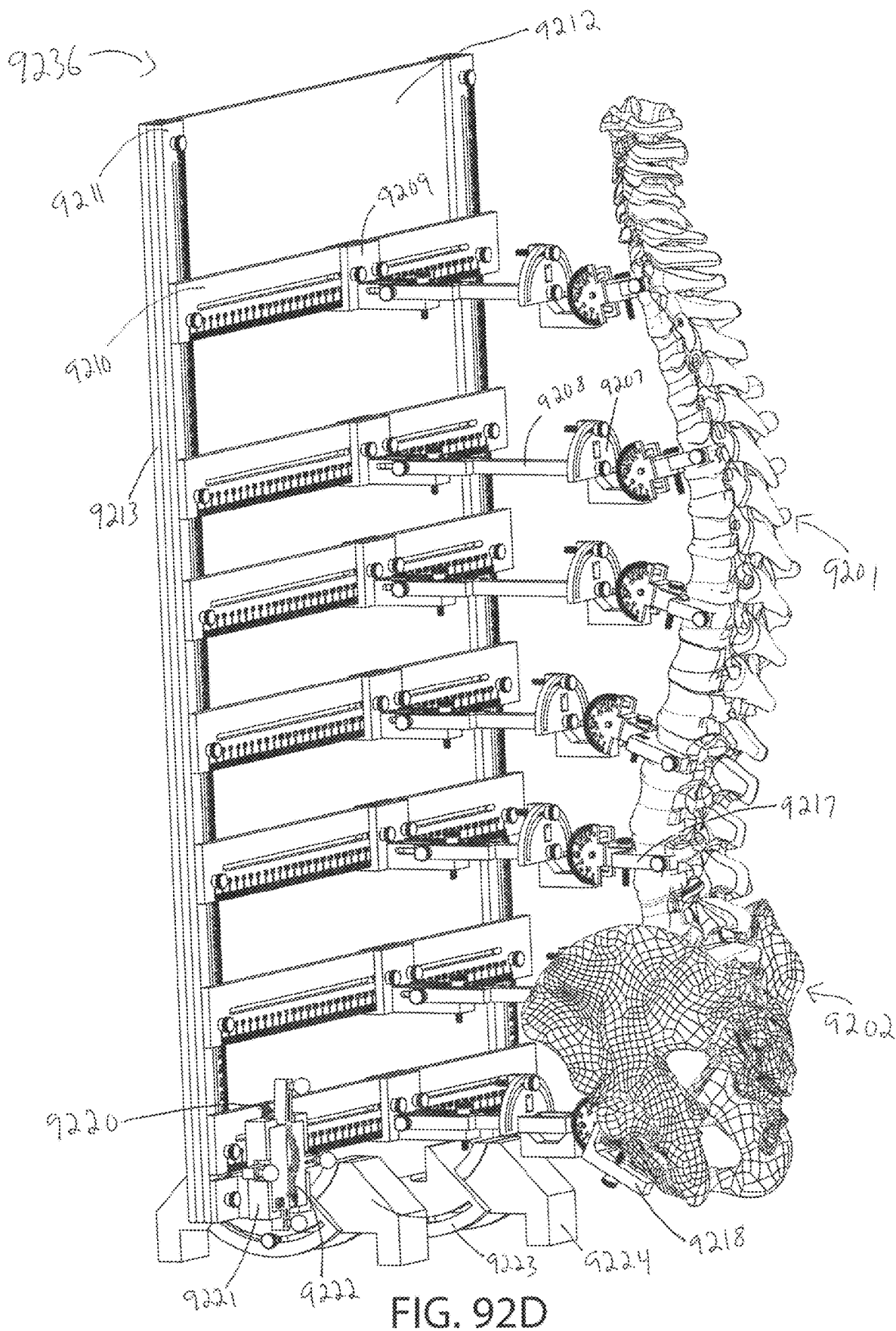

FIG. 92D illustrates a perspective view of an adjustable phantom spine model holder in an upright position via an adjustable base holder as described previously in relation to FIGS. 92A-92C in accordance with some embodiments of the invention.

Figure 92E:
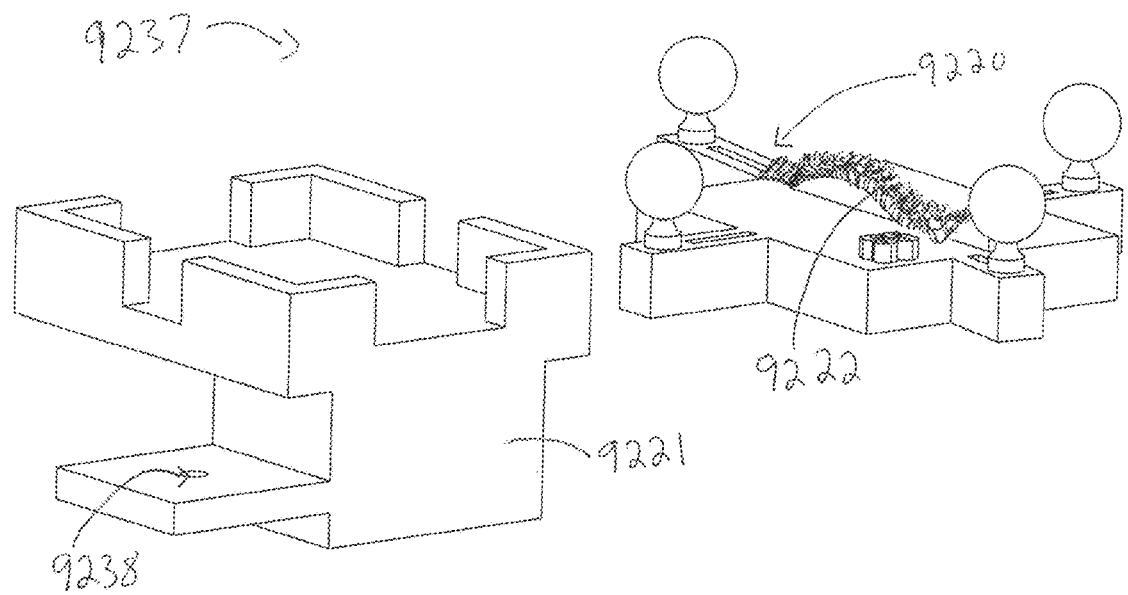
Figure 92F:
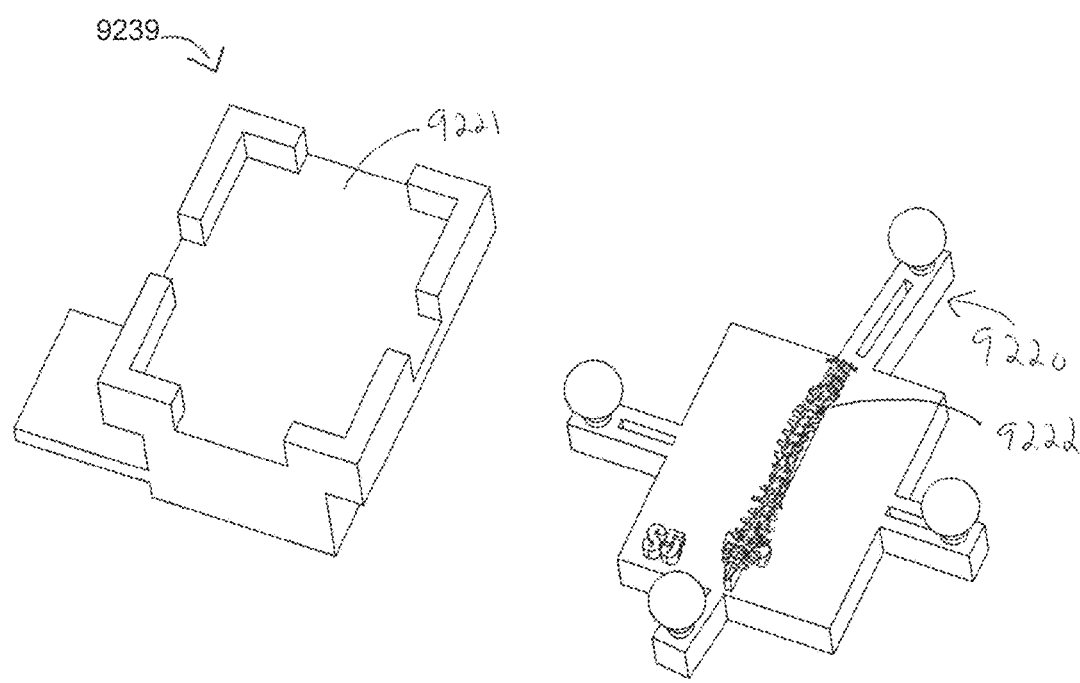

FIGS. 92E-92F illustrate perspective assembly views of a DRF and associated mount for attaching the DRF to an adjustable phantom spine model holder's base platform as described previously in relation to FIGS. 92A-92D in accordance with some embodiments of the invention.

Figure 92G:
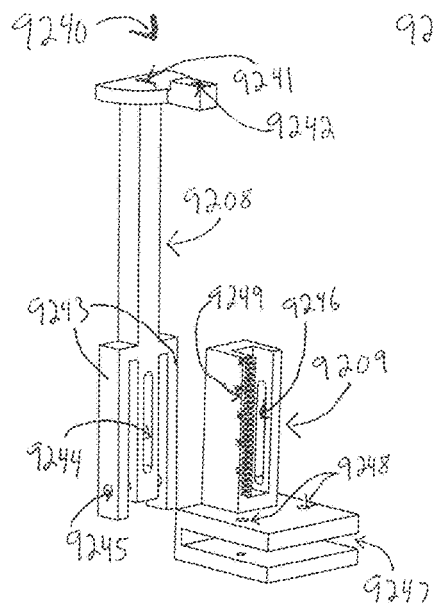
Figure 92H:
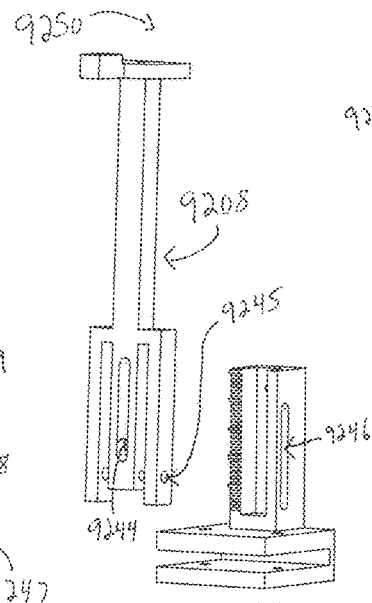
Figure 92I:
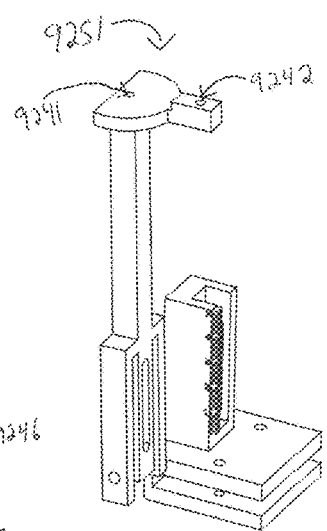

FIGS. 92G-92I illustrate perspective assembly views of a base mount and vertical height adjustment for attaching to an adjustable phantom spine model holder as described previously in relation to FIGS. 92A-92F in accordance with some embodiments of the invention.

Figure 92J:
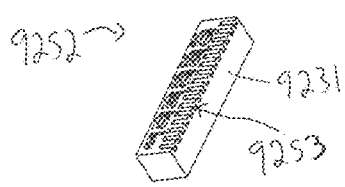

FIG. 92J illustrates a perspective view of a vertical height indicator for a base mount of an adjustable phantom spine model holder as described previously in relation to FIGS. 92A-92I in accordance with some embodiments of the invention.

Figure 92K:
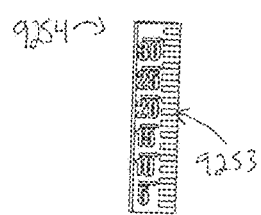

FIG. 92K illustrates a front view of a vertical height indicator for a base mount of an adjustable phantom spine model holder as described previously in relation to FIGS. 92A-92J in accordance with some embodiments of the invention.

Figure 92L:
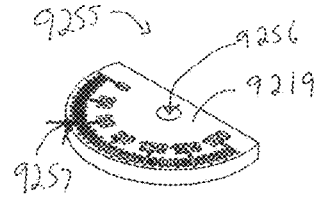

FIG. 92L illustrates a perspective view of a sagittal angle indicator for a pelvis mount of an adjustable phantom spine model holder as described previously in relation to FIGS. 92A-92K in accordance with some embodiments of the invention.

Figure 92M:
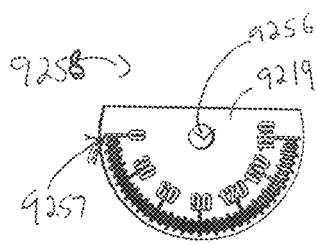

FIG. 92M illustrates a front view of a sagittal angle indicator for a pelvis mount of an adjustable phantom spine model holder as described previously in relation to FIGS. 92A-92L in accordance with some embodiments of the invention.

Figure 92N:
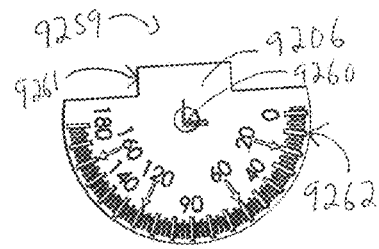

FIG. 92N illustrates a front view of a sagittal angle indicator for a vertebral holder of an adjustable phantom spine model holder as described previously in relation to FIGS. 92A-92M in accordance with some embodiments of the invention.

Figure 92O:

FIG. 92O illustrates a perspective view of a sagittal angle indicator for a vertebral holder of an adjustable phantom spine model holder as described previously in relation to FIGS. 92A-92N in accordance with some embodiments of the invention.

Figure 92P:
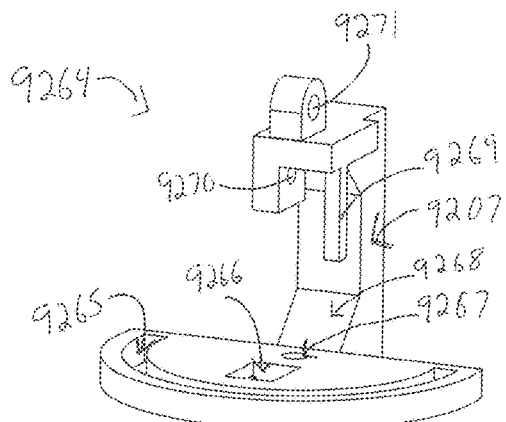
Figure 92Q:
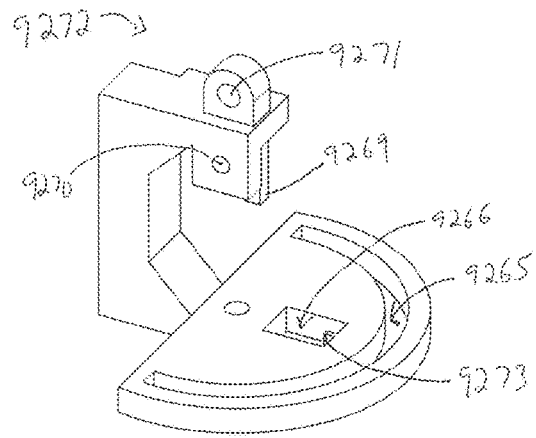

FIGS. 92P-92Q illustrate perspective views of a sagittal angle adjustment component for a vertebral holder of an adjustable phantom spine model holder as described previously in relation to FIGS. 92A-92O in accordance with some embodiments of the invention.

Figure 92R:
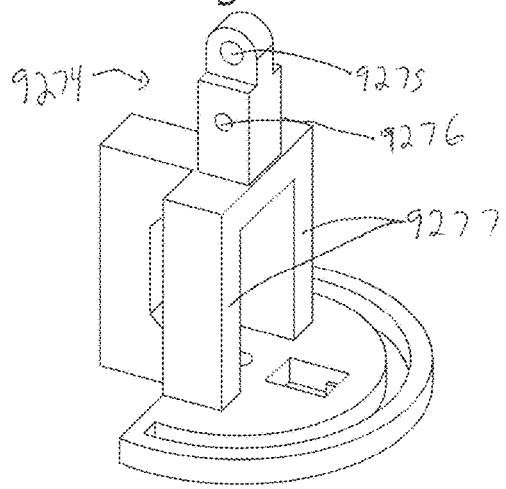
Figure 92S:
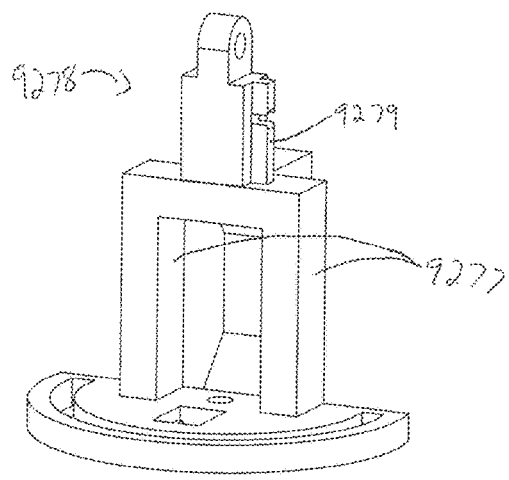

FIGS. 92R-92S illustrate perspective views of a sagittal angle adjustment component for a pelvis mount of an adjustable phantom spine model holder as described previously in relation to FIGS. 92A-92Q in accordance with some embodiments of the invention.

Figure 92T:
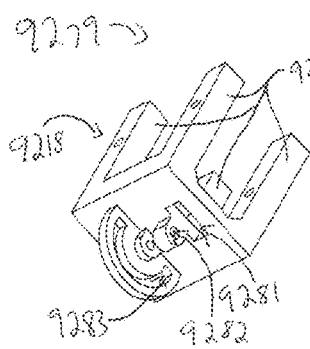
Figure 92U:
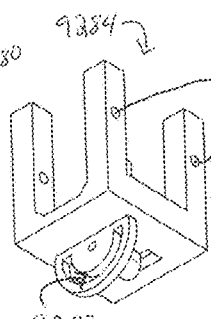

FIGS. 92T-92U illustrate perspective views of a pelvic angle adjustment component for a vertebral holder of an adjustable phantom spine model holder as described previously in relation to FIGS. 92A-92S in accordance with some embodiments of the invention.

Figure 92V:
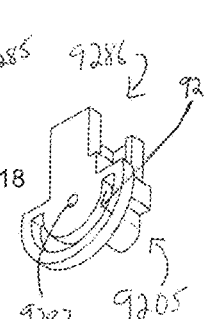
Figure 92W:
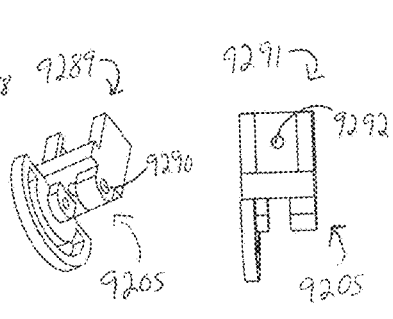
Figure 92X:
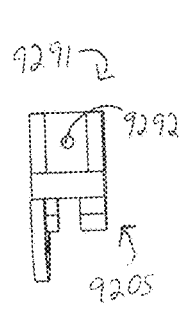

FIGS. 92V-92X illustrate perspective views of a sagittal angle adjustment component for a vertebral holder of an adjustable phantom spine model holder as described previously in relation to FIGS. 92A-92U in accordance with some embodiments of the invention.

Figure 92Y:
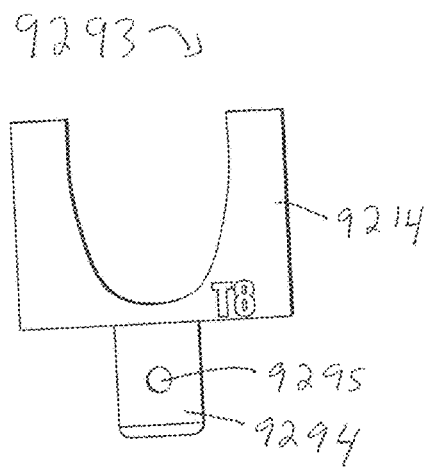

FIG. 92Y illustrates a front view of a vertebral interface component for a vertebral holder of an adjustable phantom spine model holder as described previously in relation to FIGS. 92A-92X in accordance with some embodiments of the invention.

Figure 92Z:
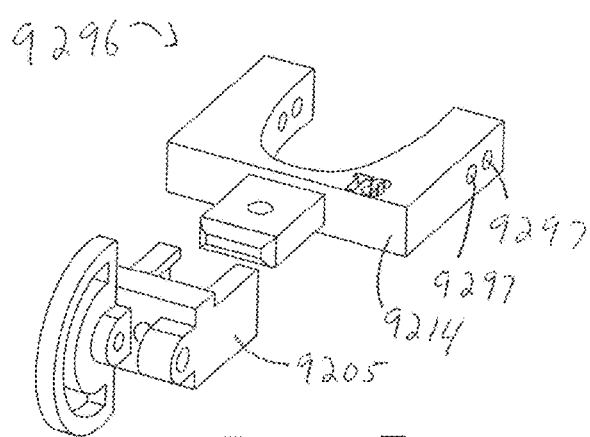
Figure 92A:
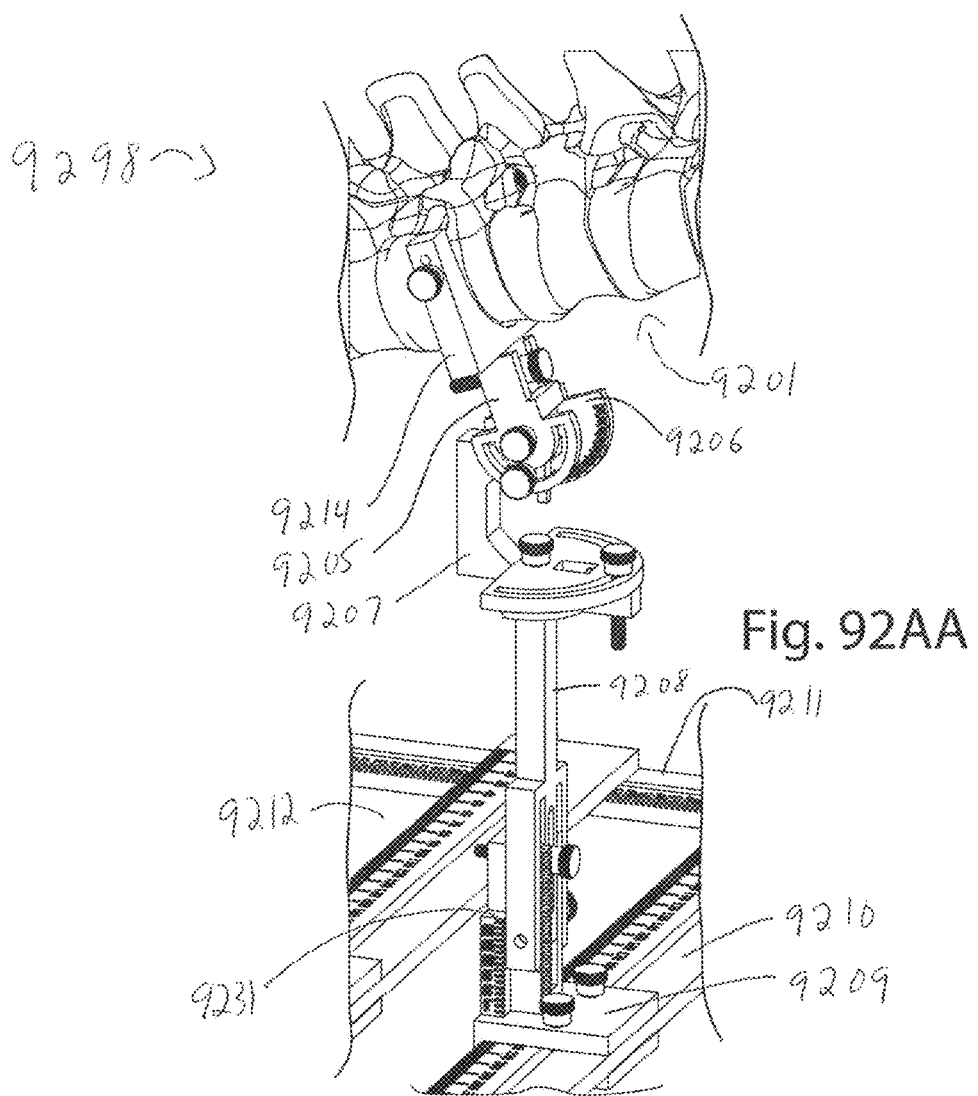

FIG. 92Z illustrates a perspective view of a vertebral interface component and sagittal angle adjustment component for a vertebral holder of an adjustable phantom spine model holder as described previously in relation to FIGS. 92A-92Y in accordance with some embodiments of the invention.

FIG. 92AA illustrates a perspective view of an adjustable vertebral holder substantially rigidly engaged with a phantom spine model holder as described previously in relation to FIGS. 92A-92Z in accordance with some embodiments of the invention.

FIG. 92AB illustrates a perspective assembly view of an adjustable vertical base holder of an adjustable phantom spine model holder as described previously in relation to FIGS. 92A-92AA in accordance with some embodiments of the invention.

FIG. 92AC illustrates a front assembly view of an adjustable vertical base holder of an adjustable phantom spine model holder as described previously in relation to FIGS. 92A-92AB in accordance with some embodiments of the invention.

FIG. 92AD illustrates a front assembly view of a base platform and cross-rails of an adjustable phantom spine model holder as described previously in relation to FIGS. 92A-92AC in accordance with some embodiments of the invention.

Figure 93A:
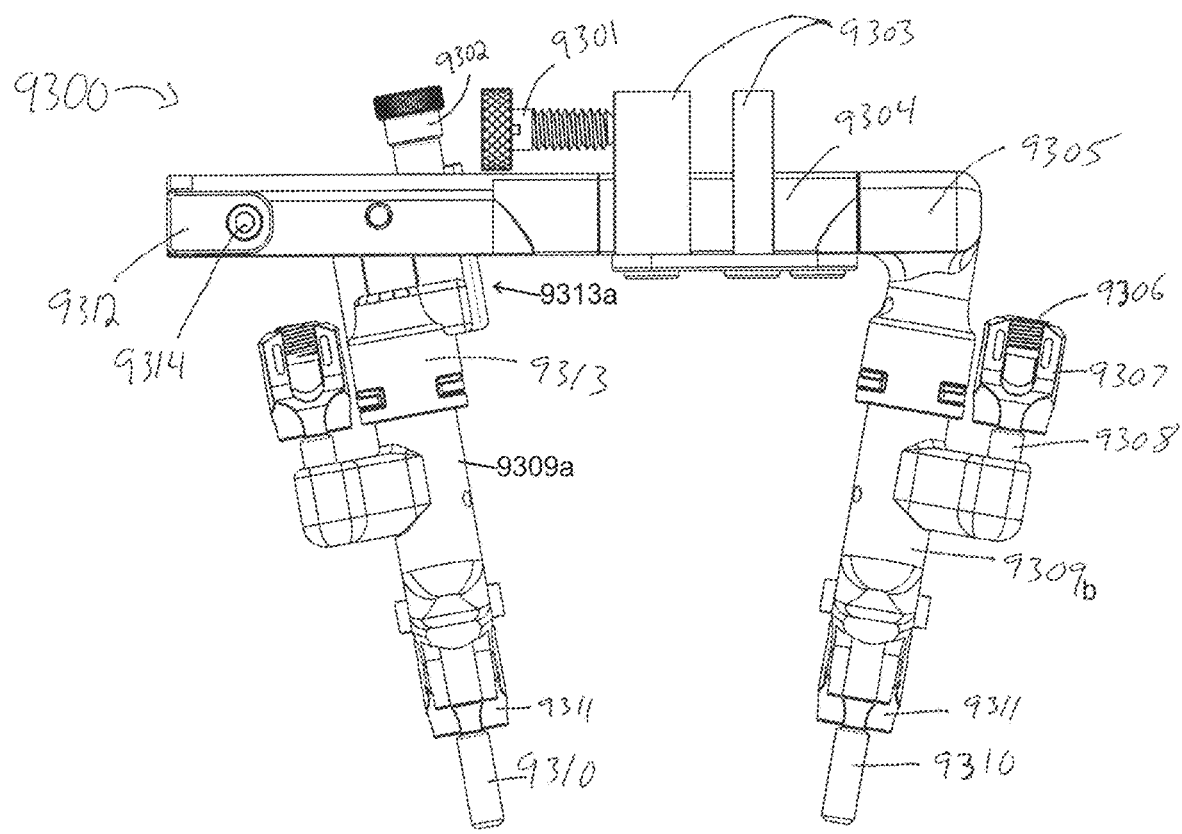

FIG. 93A illustrates a rear view of an adjustable pedicle screw interface base, with one fixed side arm and one side arm with height and angle adjustments, of a flexibility assessment device.

Figure 93B:
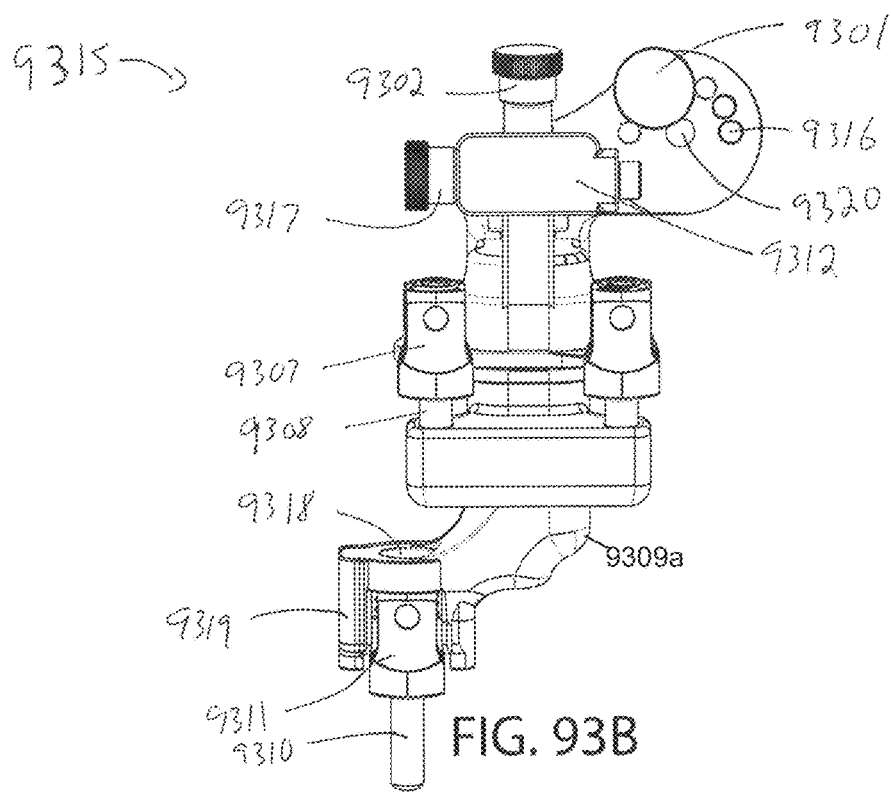

FIG. 93B illustrates a side view of an adjustable pedicle screw interface base, with one fixed side arm and one side arm with height and angle adjustments, of a flexibility assessment device as described previously in relation to FIG. 93A in accordance with some embodiments of the invention.

Figure 93C:
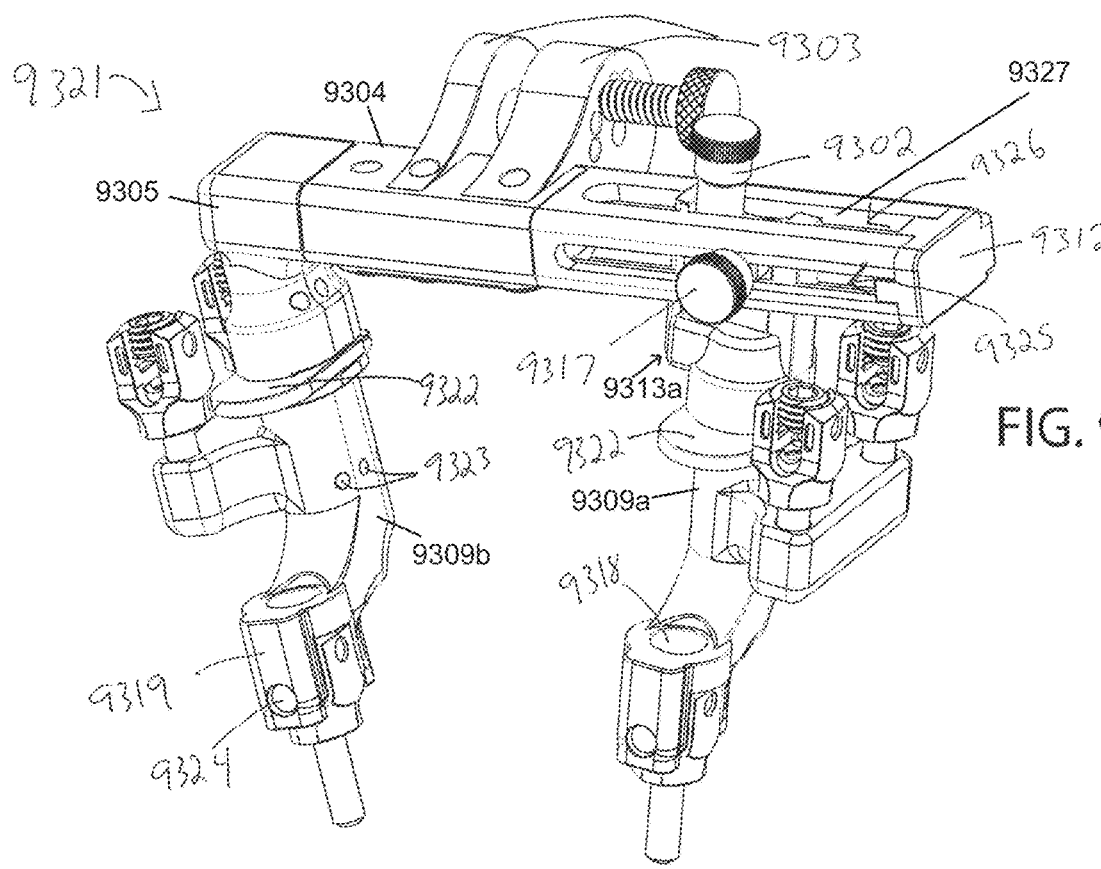

FIG. 93C illustrates a perspective view of an adjustable pedicle screw interface base, with one fixed side arm and one side arm with height and angle adjustments, of a flexibility assessment device as described previously in relation to FIGS. 93A-93B in accordance with some embodiments of the invention.

Figure 93D:
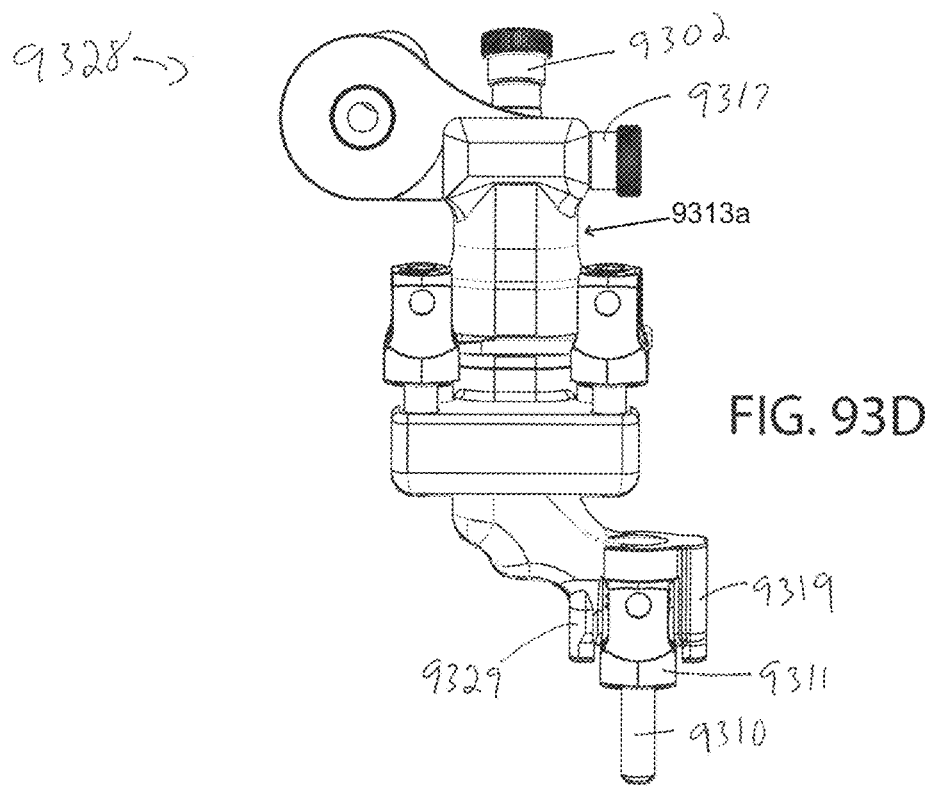

FIG. 93D illustrates a side view of an adjustable pedicle screw interface base, with one fixed side arm and one side arm with height and angle adjustments, of a flexibility assessment device as described previously in relation to FIGS. 93A-93C in accordance with some embodiments of the invention.

Figure 93E:
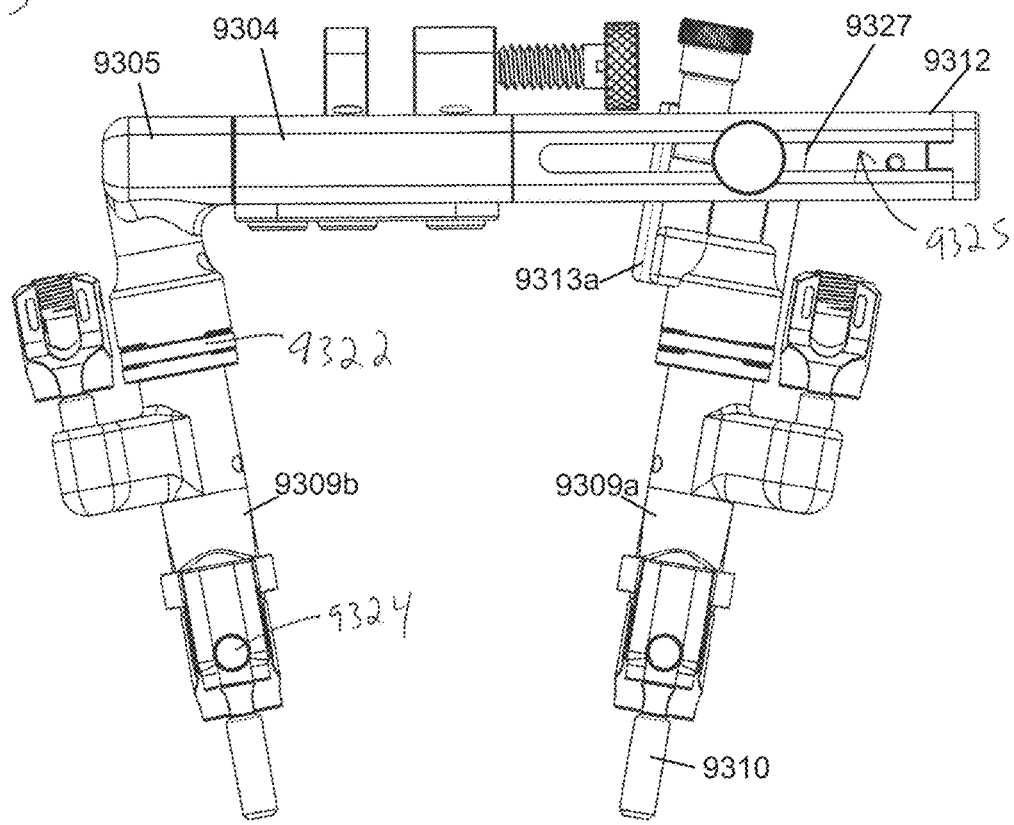

FIG. 93E illustrates a front view of an adjustable pedicle screw interface base, with one fixed side arm and one side arm with height and angle adjustments, of a flexibility assessment device as described previously in relation to FIGS. 93A-93D in accordance with some embodiments of the invention.

Figure 93F:
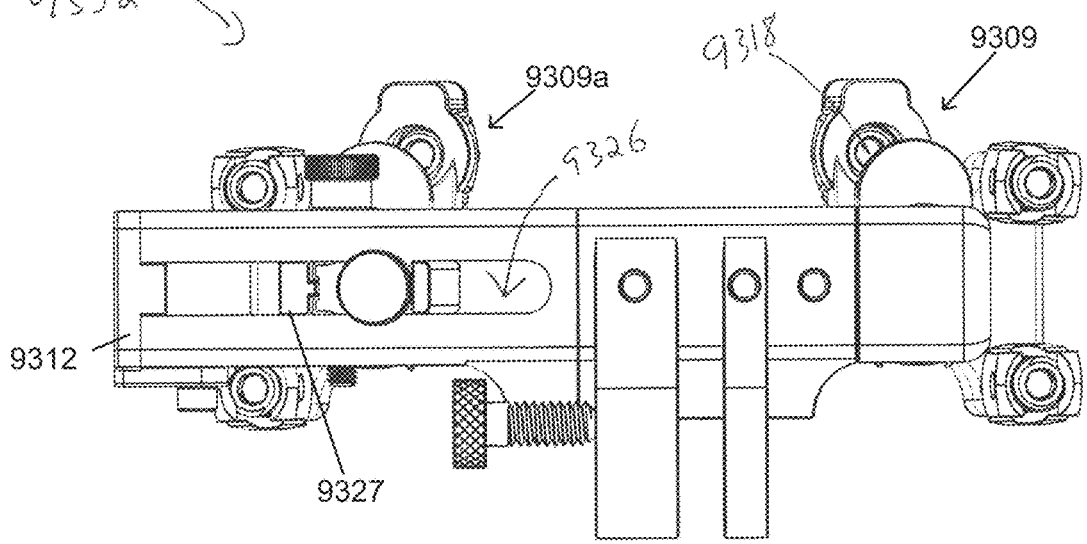

FIG. 93F illustrates a top view of an adjustable pedicle screw interface base, with one fixed side arm and one side arm with height and angle adjustments, of a flexibility assessment device as described previously in relation to FIGS. 93A-93E in accordance with some embodiments of the invention.

Figure 93G:
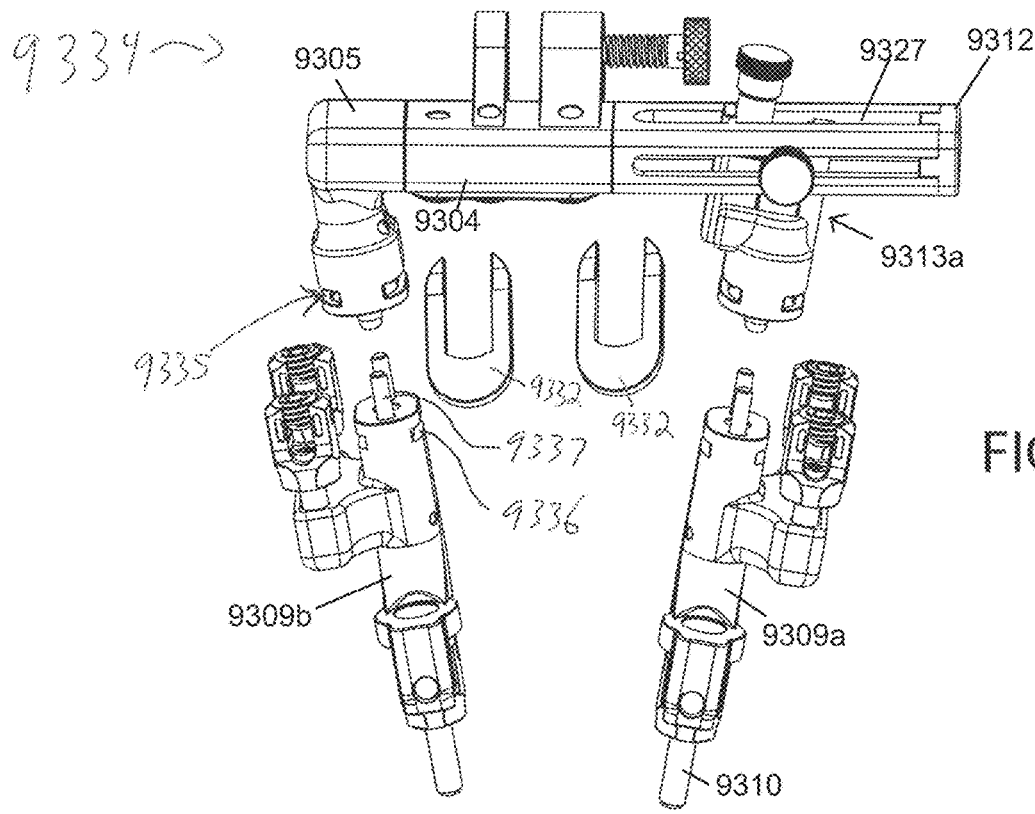

FIG. 93G illustrates an assembly view of an adjustable pedicle screw interface base, with one fixed side arm and one side arm with height and angle adjustments, of a flexibility assessment device as described previously in relation to FIGS. 93A-93F in accordance with some embodiments of the invention.

Figure 93H:
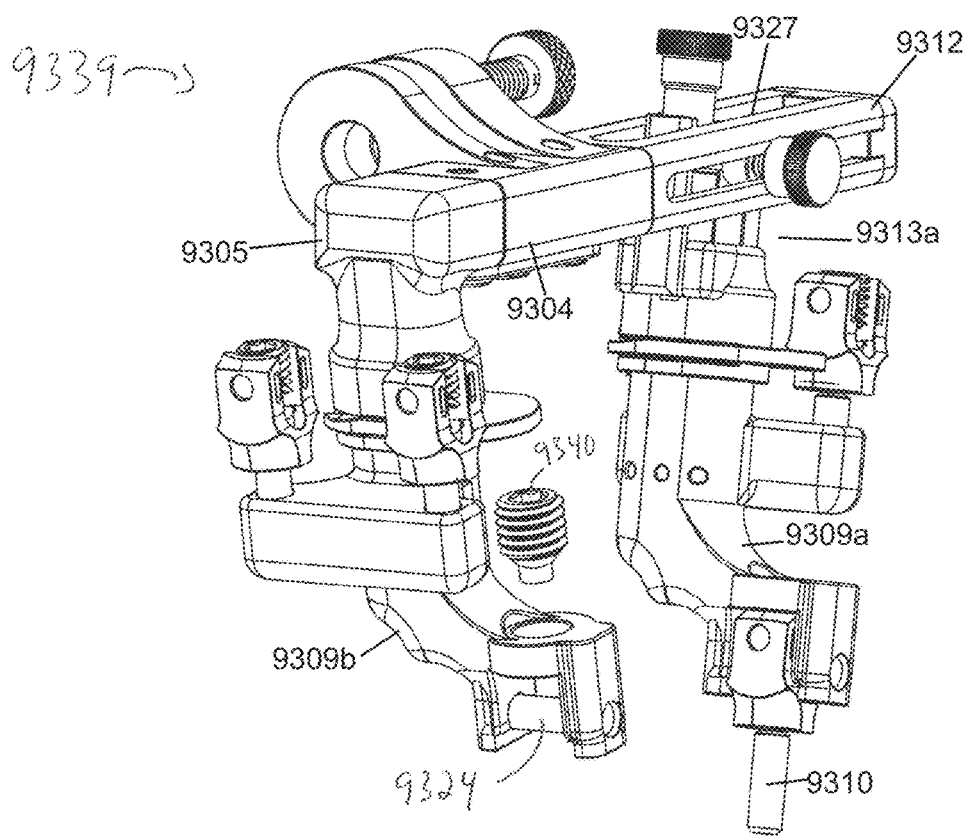

FIG. 93H illustrates a perspective view of an adjustable pedicle screw interface base, with one fixed side arm and one side arm with height and angle adjustments, of a flexibility assessment device as described previously in relation to FIGS. 93A-93G in accordance with some embodiments of the invention.

Figure 93I:
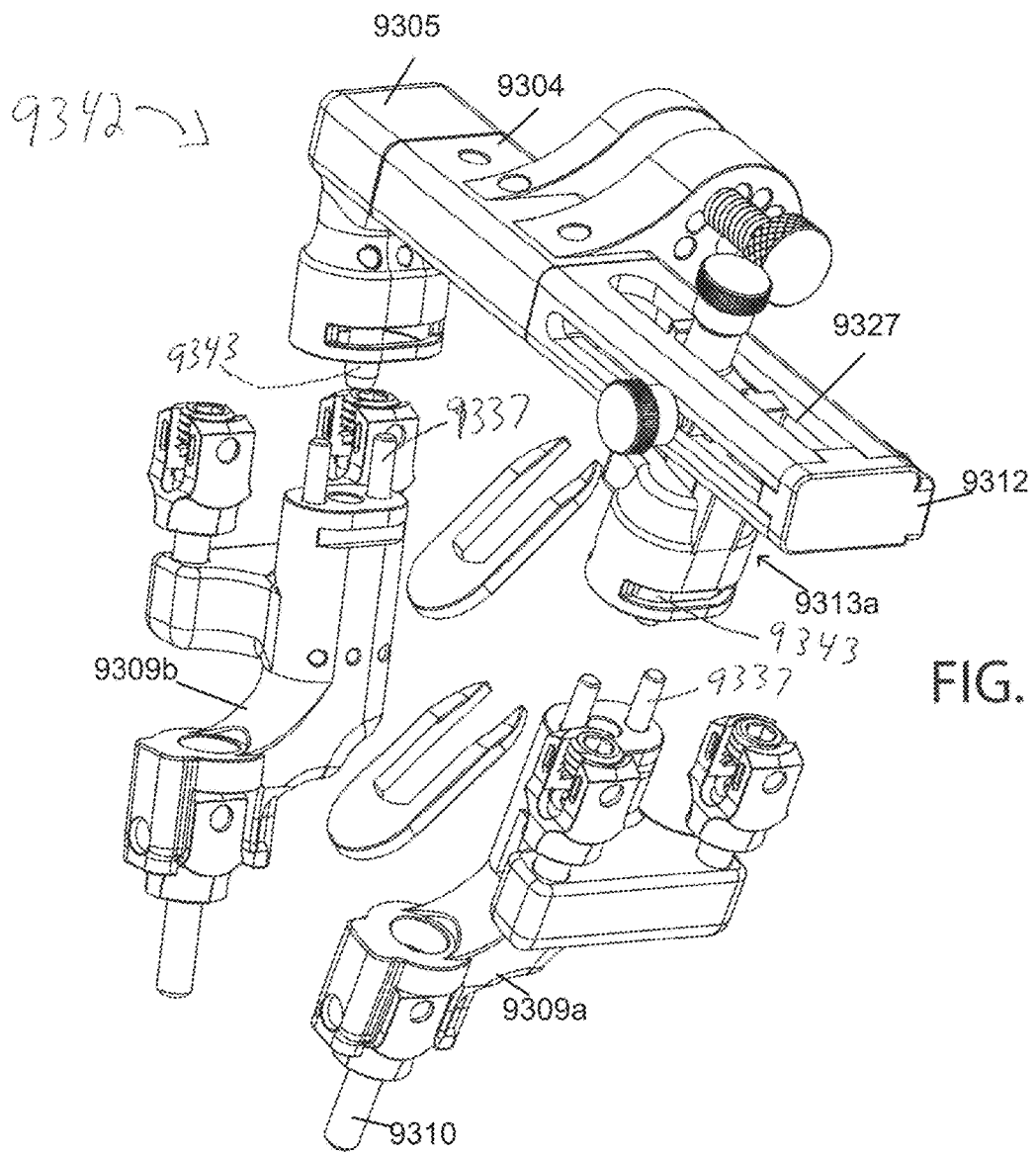

FIG. 93I illustrates a perspective assembly view of an adjustable pedicle screw interface base, with one fixed side arm and one side arm with height and angle adjustments, of a flexibility assessment device as described previously in relation to FIGS. 93A-93H in accordance with some embodiments of the invention.

Figure 93J:
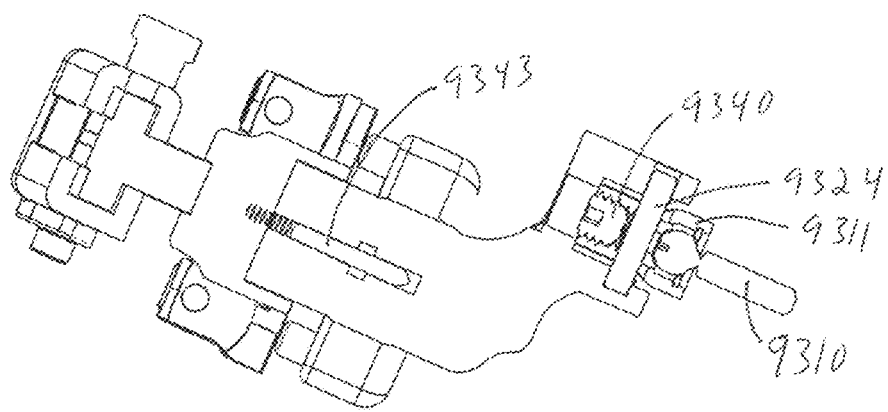

FIG. 93J illustrates a cross-sectional view of the side arm of an adjustable pedicle screw interface base, with one fixed side arm and one side arm with height and angle adjustments, of a flexibility assessment device as described previously in relation to FIGS. 93A-93I in accordance with some embodiments of the invention.

Figure 94A:
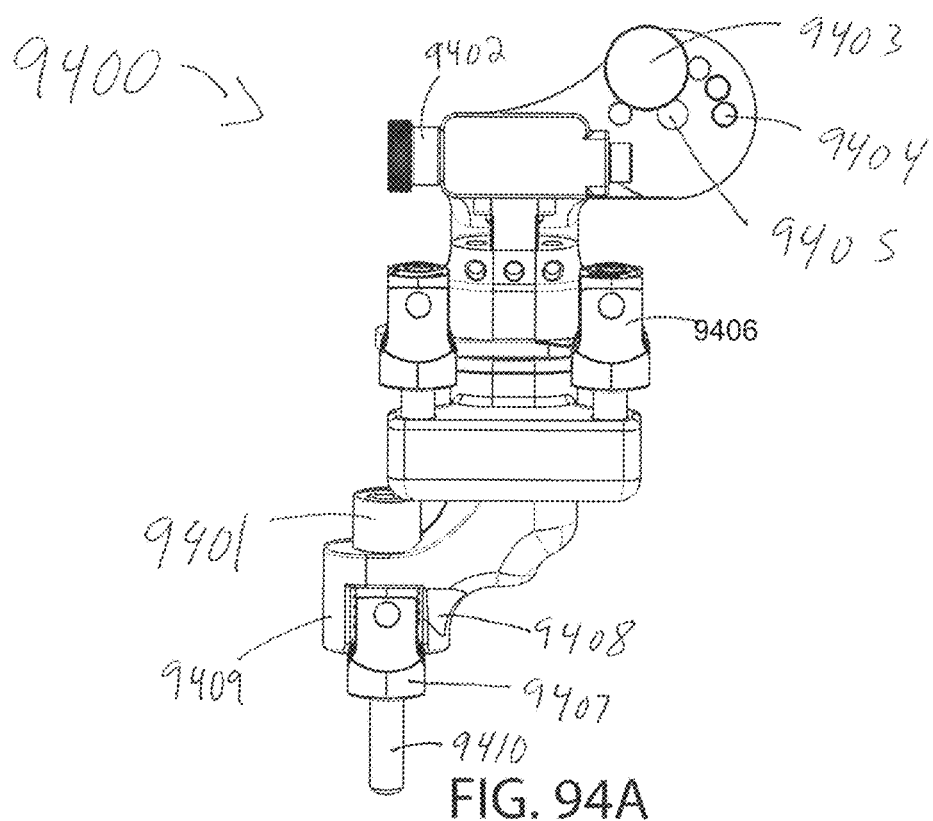

FIG. 94A illustrates a side view of an adjustable pedicle screw interface base, with one fixed side arm and one side arm with angle adjustment, of a flexibility assessment device in accordance with some embodiments of the invention.

Figure 94B:
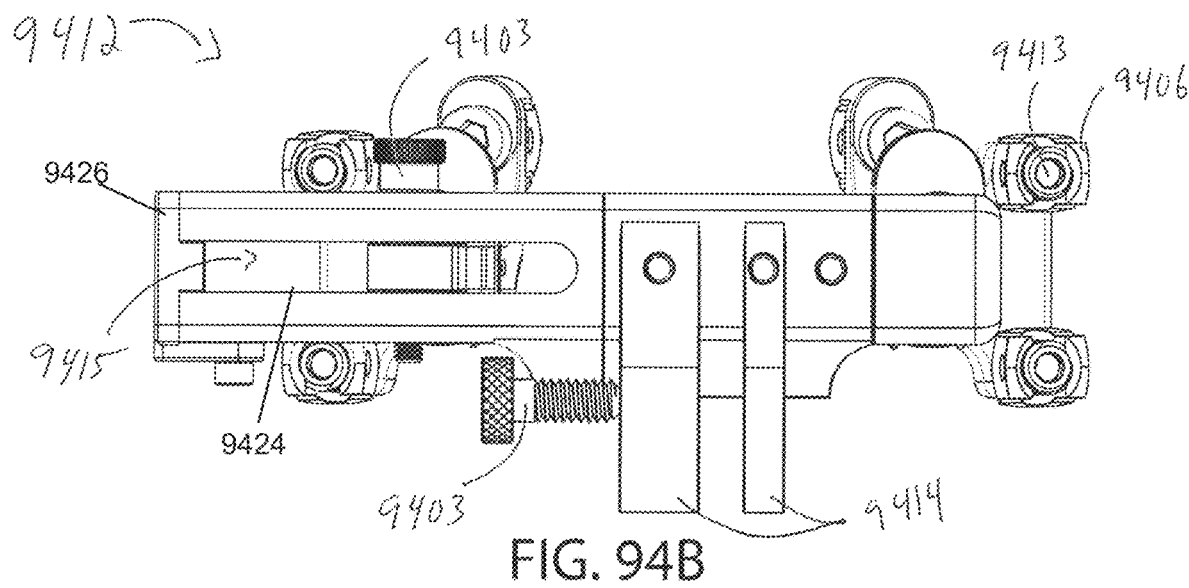

FIG. 94B illustrates a top view of an adjustable pedicle screw interface base, with one fixed side arm and one side arm with angle adjustment, of a flexibility assessment device as described previously in relation to FIG. 94A in accordance with some embodiments of the invention.

Figure 94C:
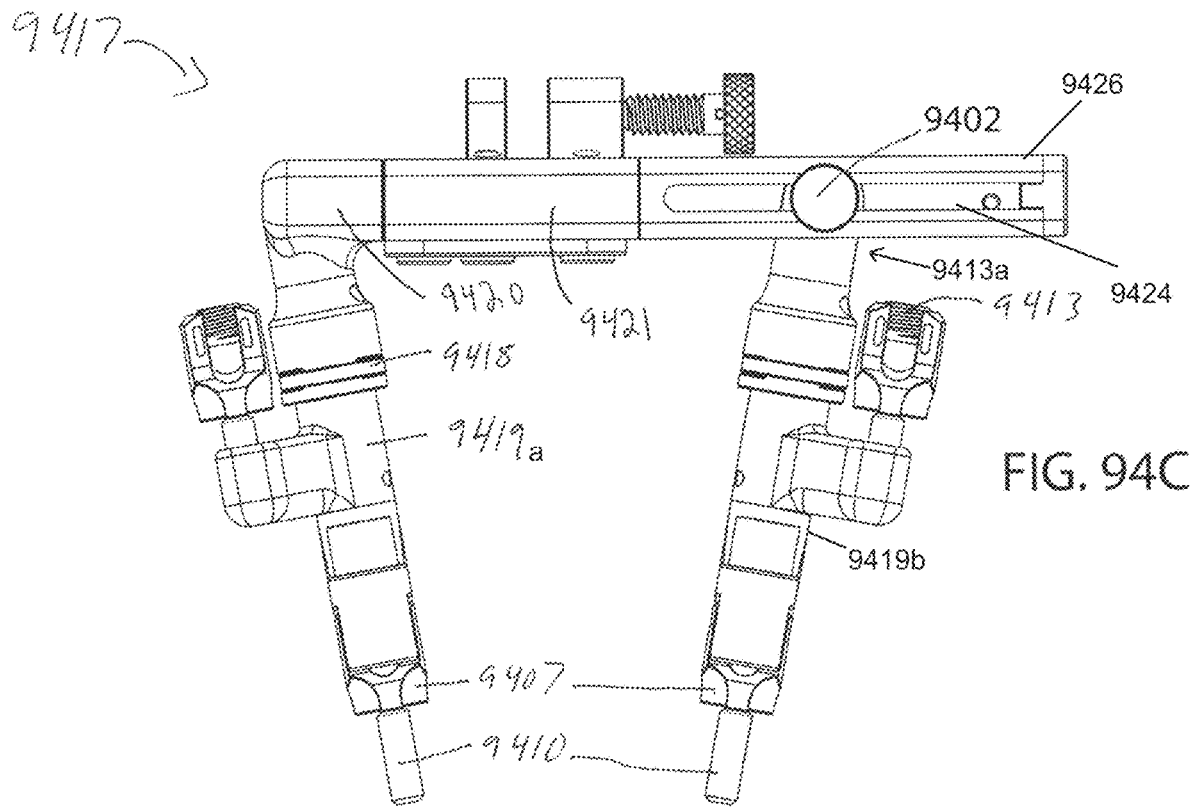

FIG. 94C illustrates a front view of an adjustable pedicle screw interface base, with one fixed side arm and one side arm with angle adjustment, of a flexibility assessment device as described previously in relation to FIGS. 94A-94B in accordance with some embodiments of the invention.

Figure 94D:
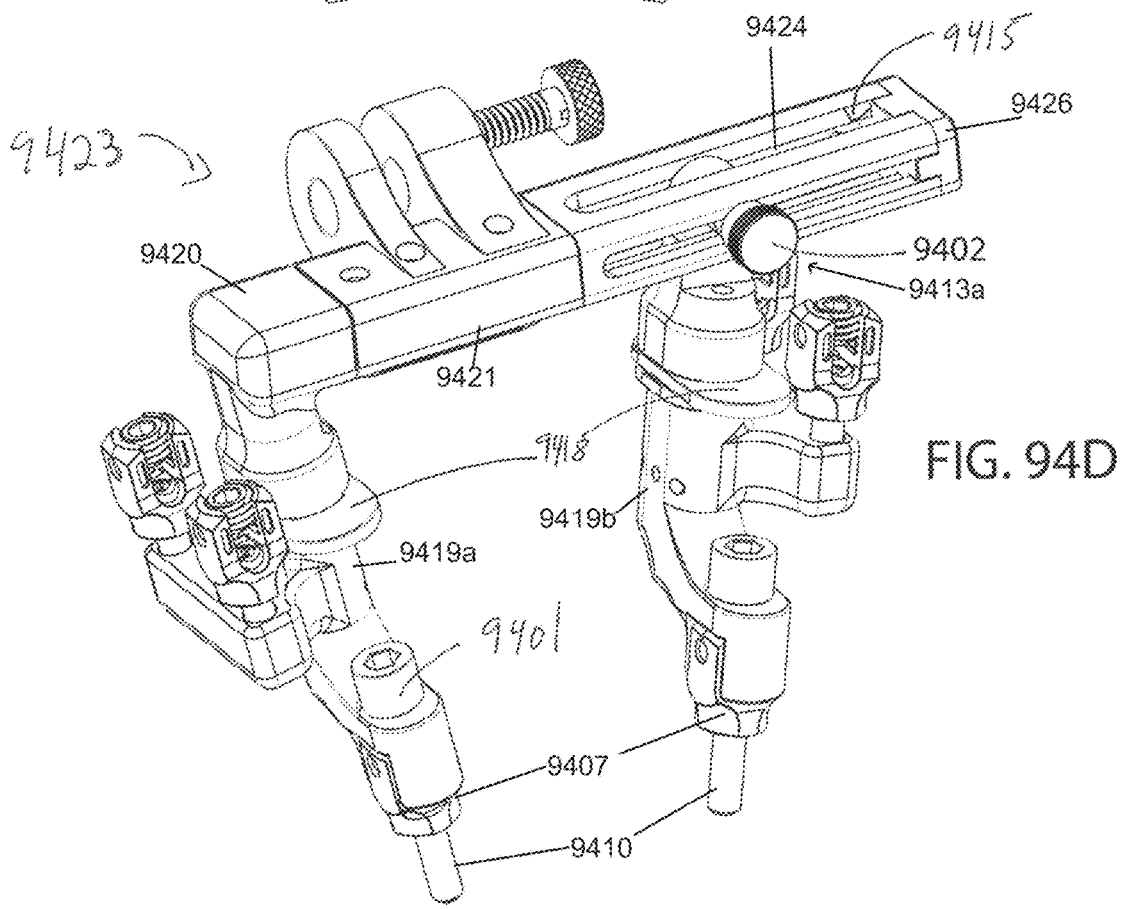

FIG. 94D illustrates a perspective view of an adjustable pedicle screw interface base, with one fixed side arm and one side arm with angle adjustment, of a flexibility assessment device as described previously in relation to FIGS. 94A-94C in accordance with some embodiments of the invention.

Figure 94E:
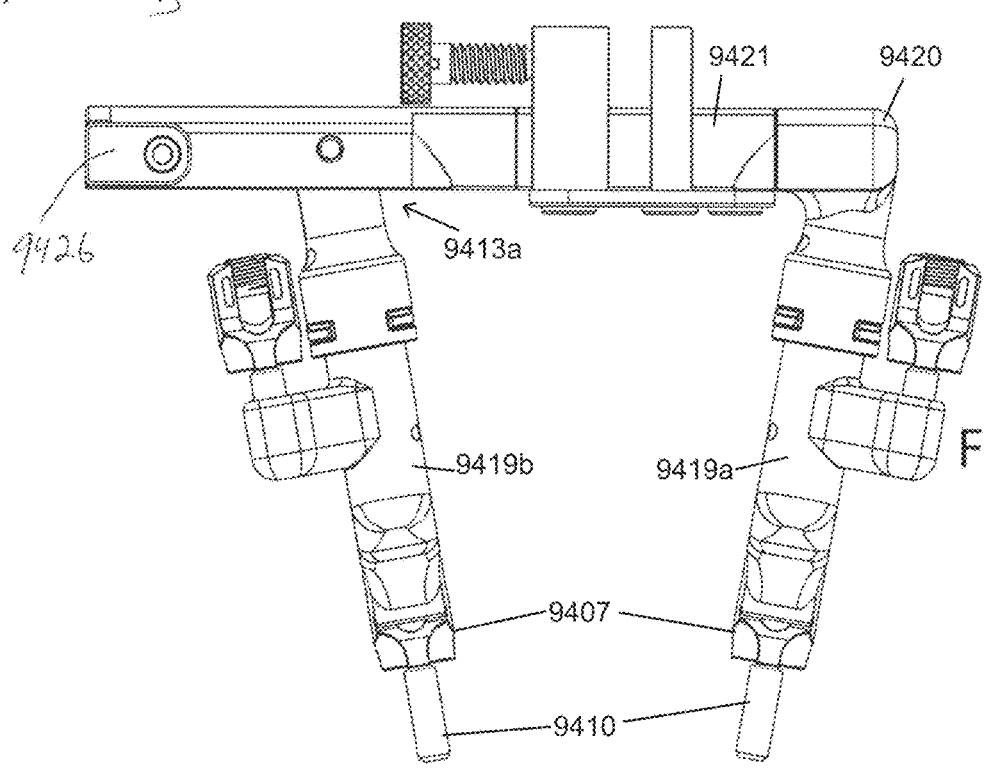

FIG. 94E illustrates a rear view of an adjustable pedicle screw interface base, with one fixed side arm and one side arm with angle adjustment, of a flexibility assessment device as described previously in relation to FIGS. 94A-94D in accordance with some embodiments of the invention.

Figure 94F:
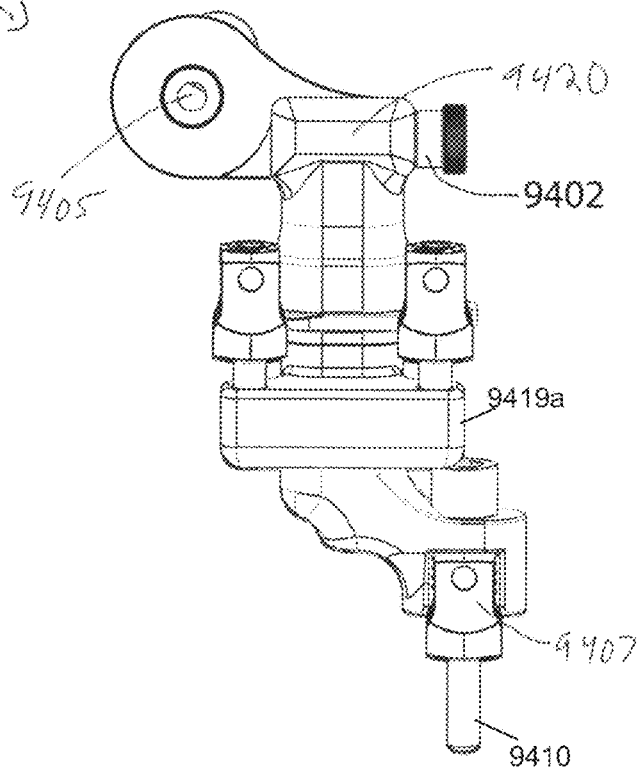

FIG. 94F illustrates a side view of an adjustable pedicle screw interface base, with one fixed side arm and one side arm with angle adjustment, of a flexibility assessment device as described previously in relation to FIGS. 94A-94E in accordance with some embodiments of the invention.

Figure 94G:
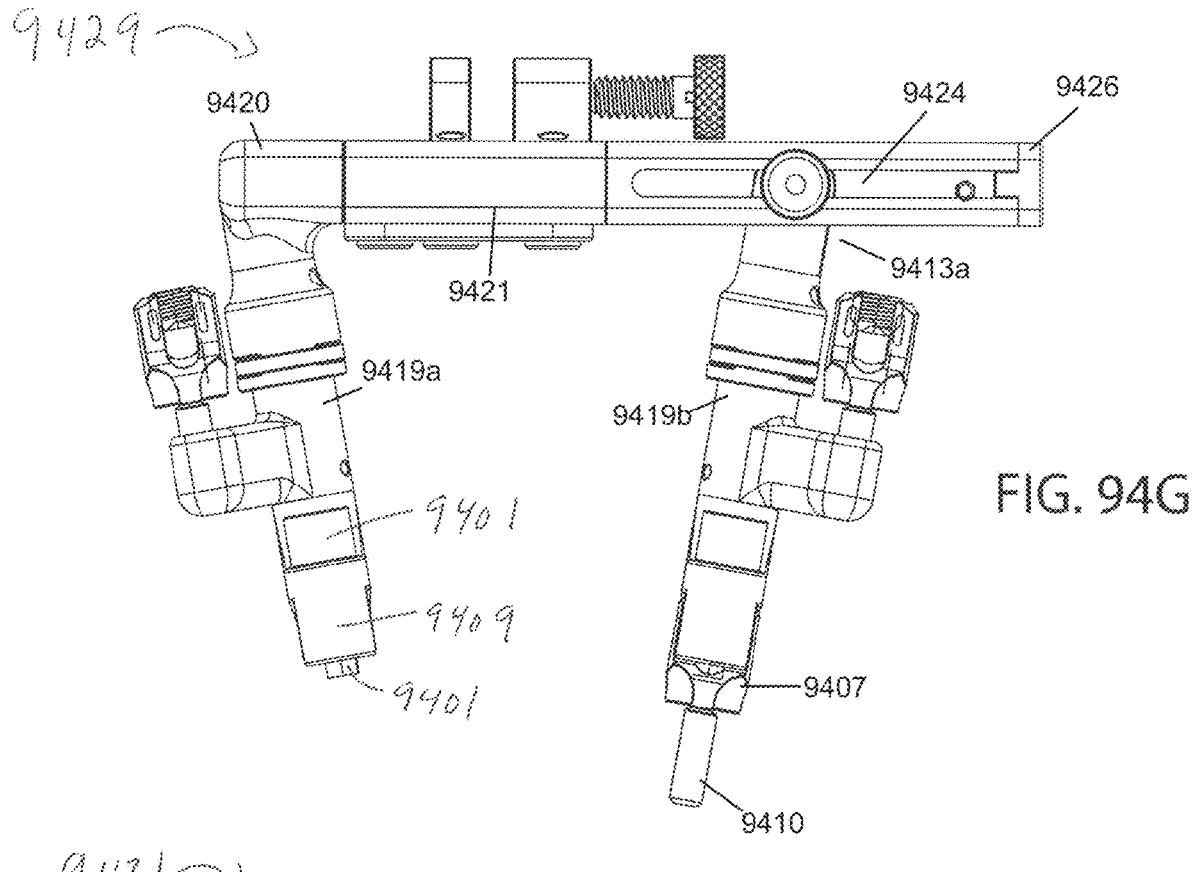

FIG. 94G illustrates a front view of an adjustable pedicle screw interface base, with one fixed side arm without an attached pedicle screw and one side arm with angle adjustment that is attached to a pedicle screw, of a flexibility assessment device as described previously in relation to FIGS. 94A-94F in accordance with some embodiments of the invention.

Figure 94H:
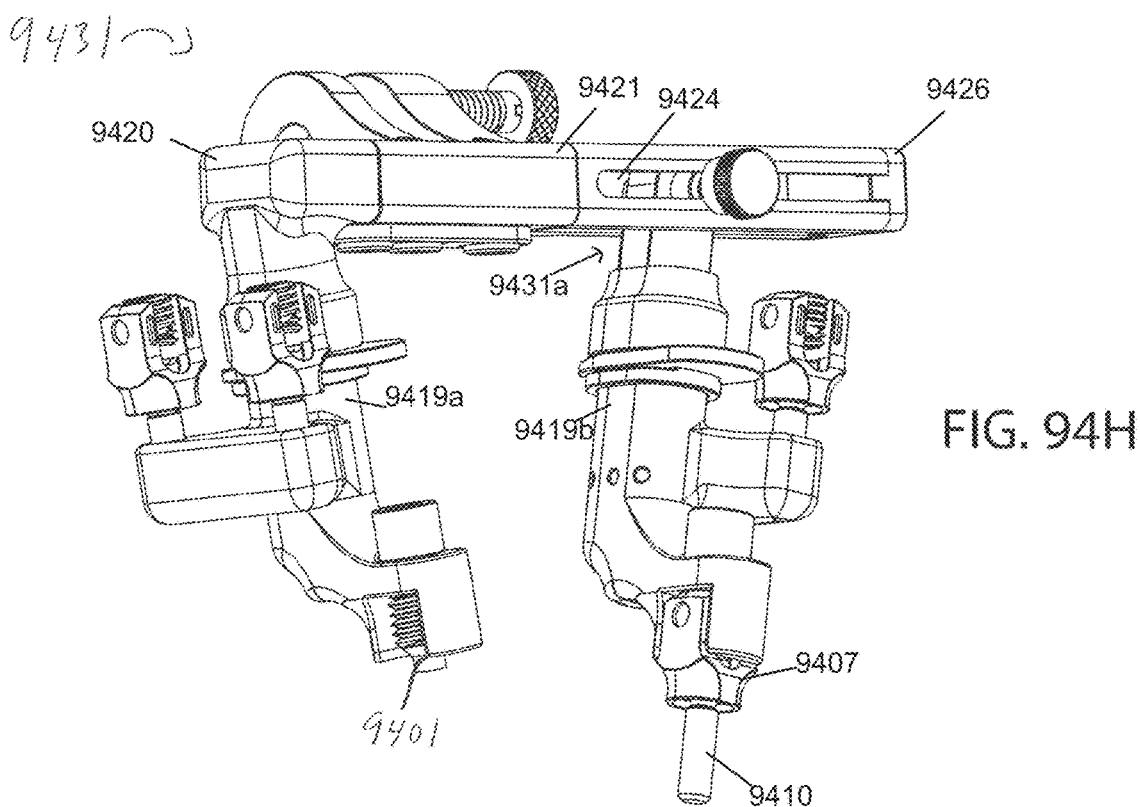

FIG. 94H illustrates a perspective view of an adjustable pedicle screw interface base, with one fixed side arm without an attached pedicle screw and one side arm with angle adjustment that is attached to a pedicle screw, of a flexibility assessment device as described previously in relation to FIGS. 94A-94G in accordance with some embodiments of the invention.

Figure 95A:
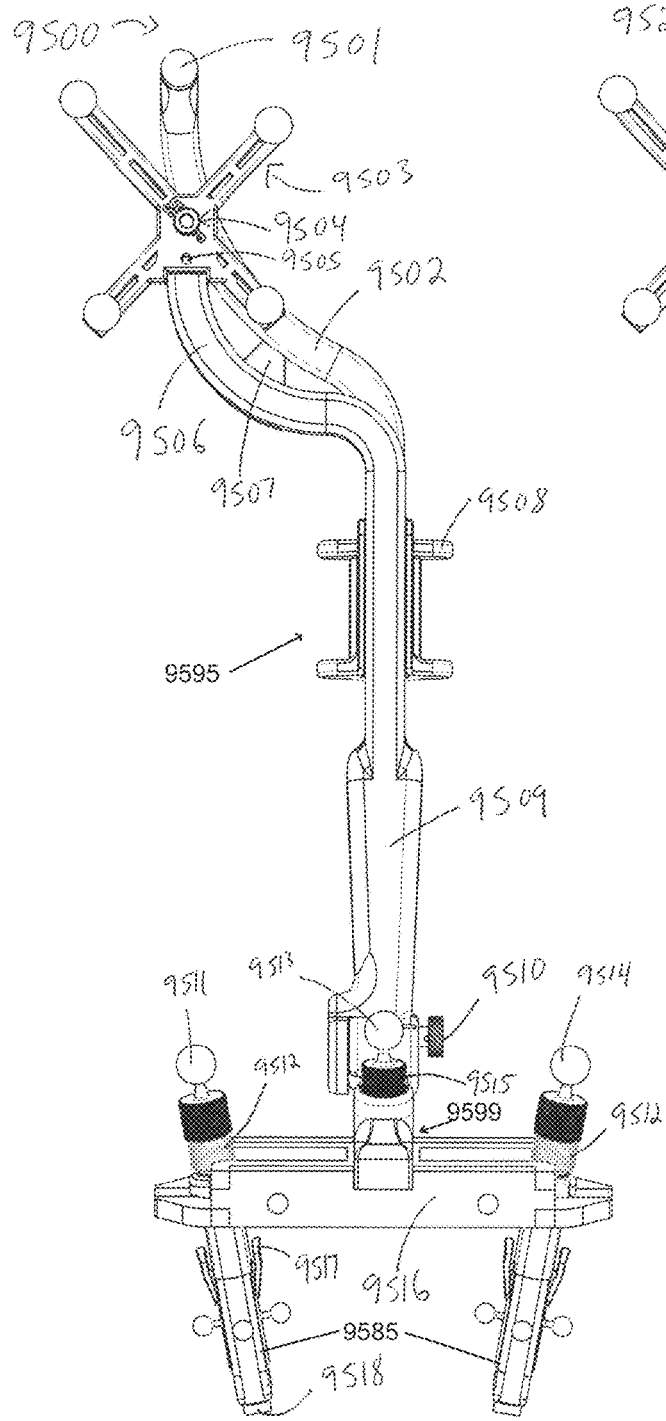
Figure 95B:
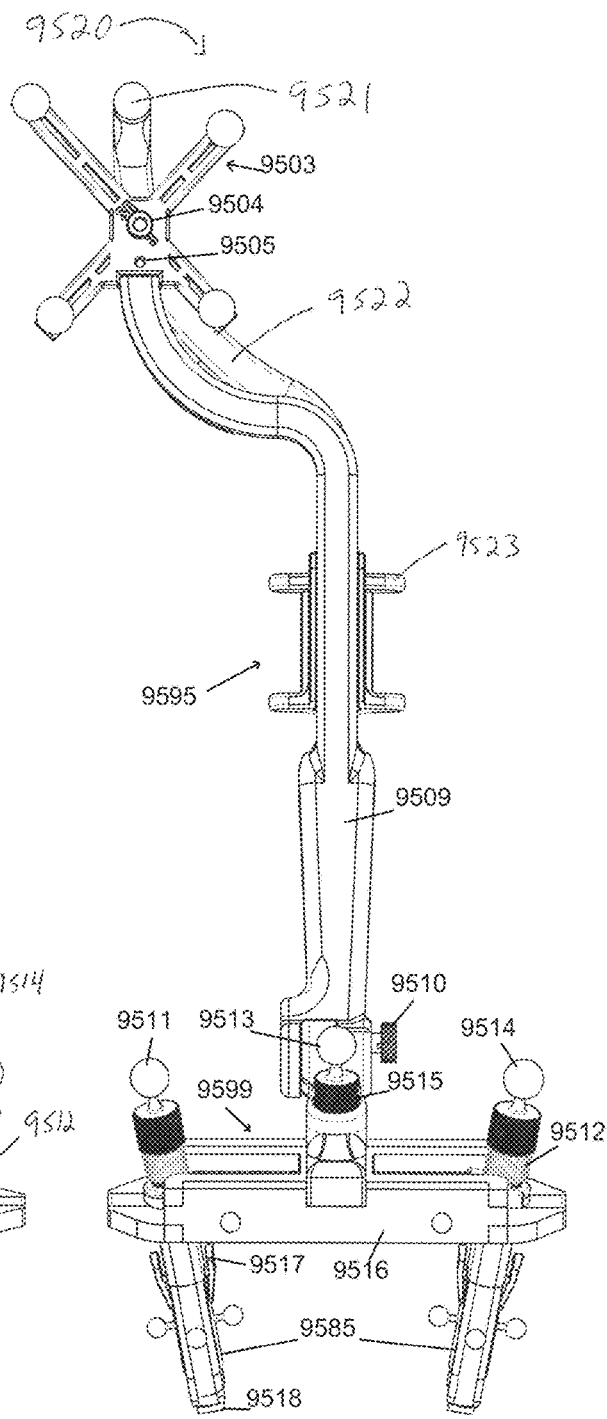

FIGS. 95A-95B illustrate front views of a front-facing flexibility assessment device in a triggered and untriggered state in accordance with some embodiments of the invention.

FIGS. 95C-95D illustrate rear views of a front-facing flexibility assessment device in a triggered and untriggered state as described previously in relation to FIGS. 95A-95B in accordance with some embodiments of the invention.

FIGS. 95E-95F illustrate front views of a back-facing flexibility assessment device in a triggered and untriggered state as described previously in relation to FIGS. 95A-95D in accordance with some embodiments of the invention.

Figure 95G:
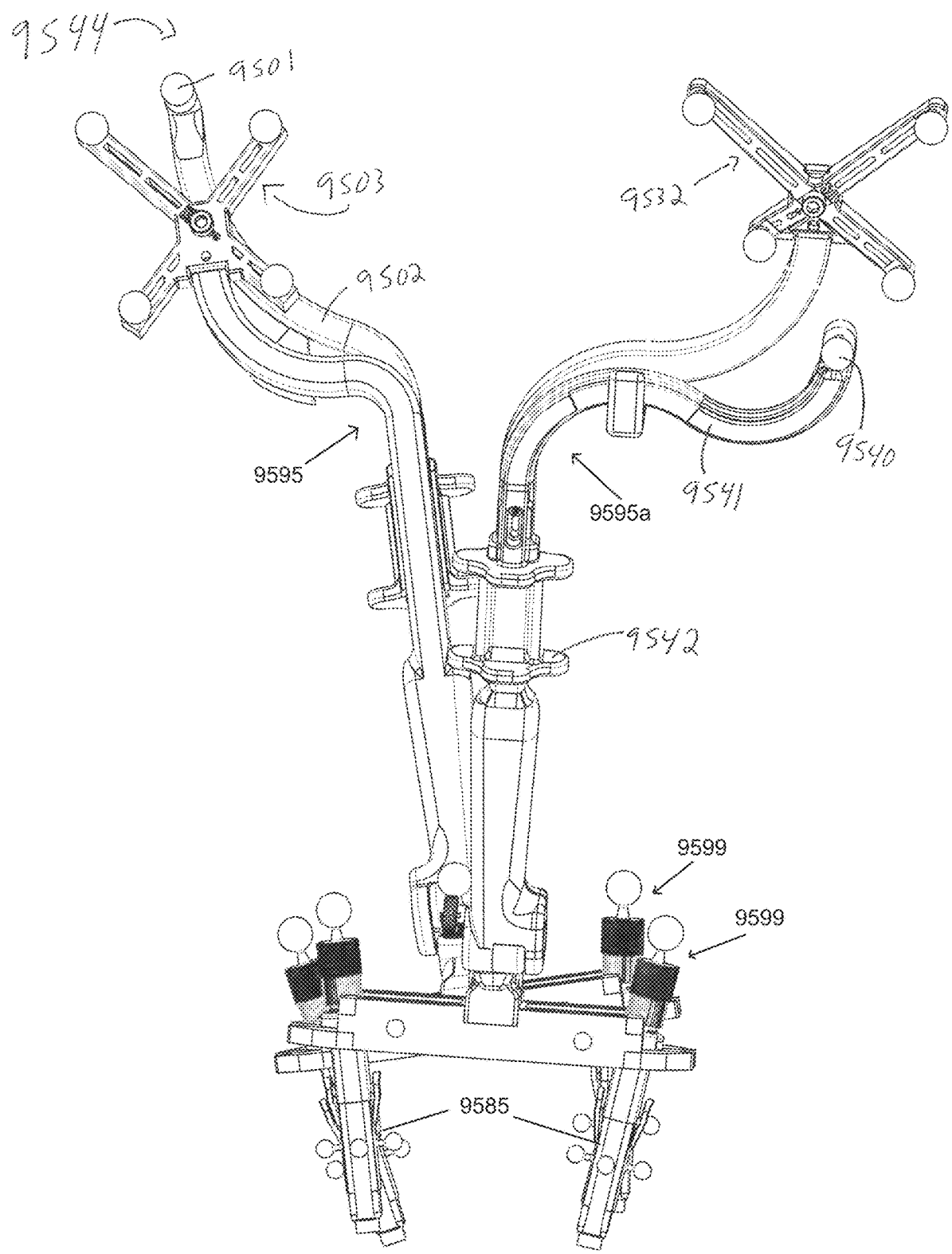

FIG. 95G illustrates a front view of both back-facing and front-facing flexibility assessment devices as described previously in relation to FIGS. 95A-95F in accordance with some embodiments of the invention.

Figure 95H:
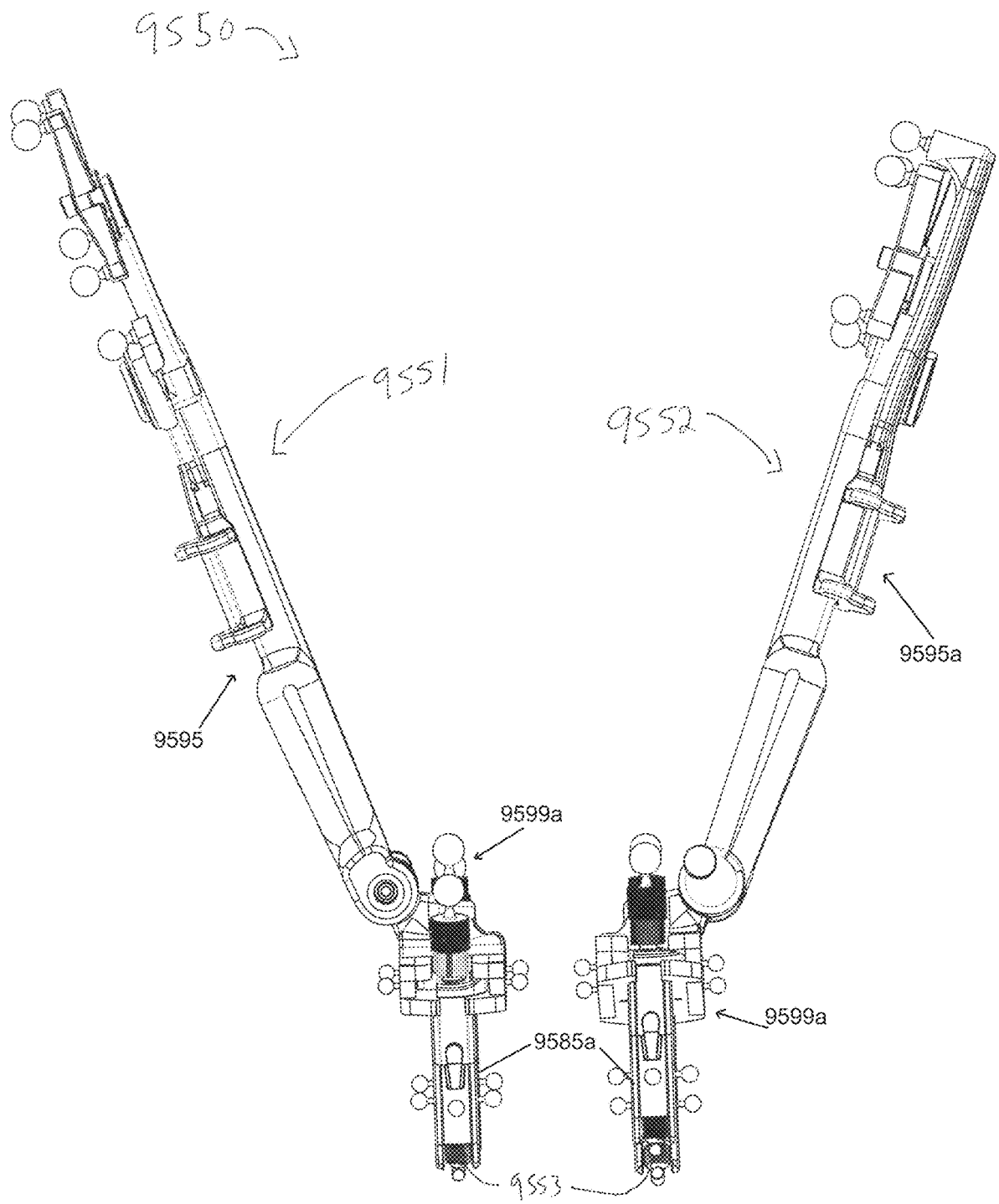
Figure 951:
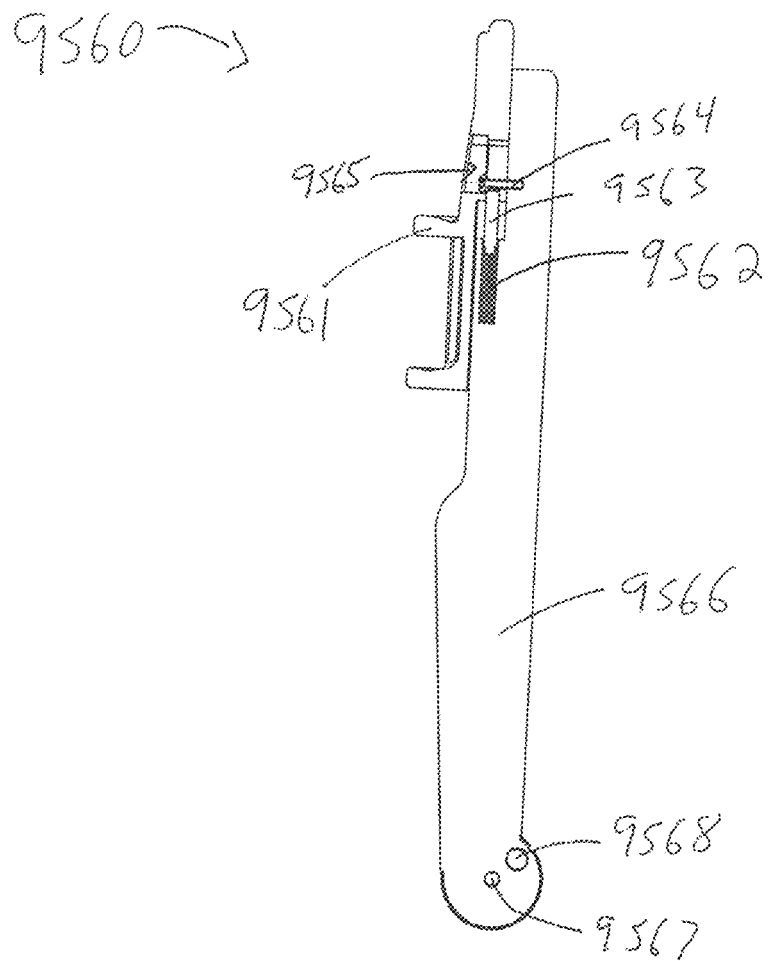

FIG. 95H illustrates a side view of both back-facing and front-facing flexibility assessment devices as described previously in relation to FIGS. 95A-95G in accordance with some embodiments of the invention.

FIG. 95I illustrates a cross-sectional view of a triggering mechanism of a handle of a flexibility assessment device as described previously in relation to FIGS. 95A-95H in accordance with some embodiments of the invention.

Figure 96A:
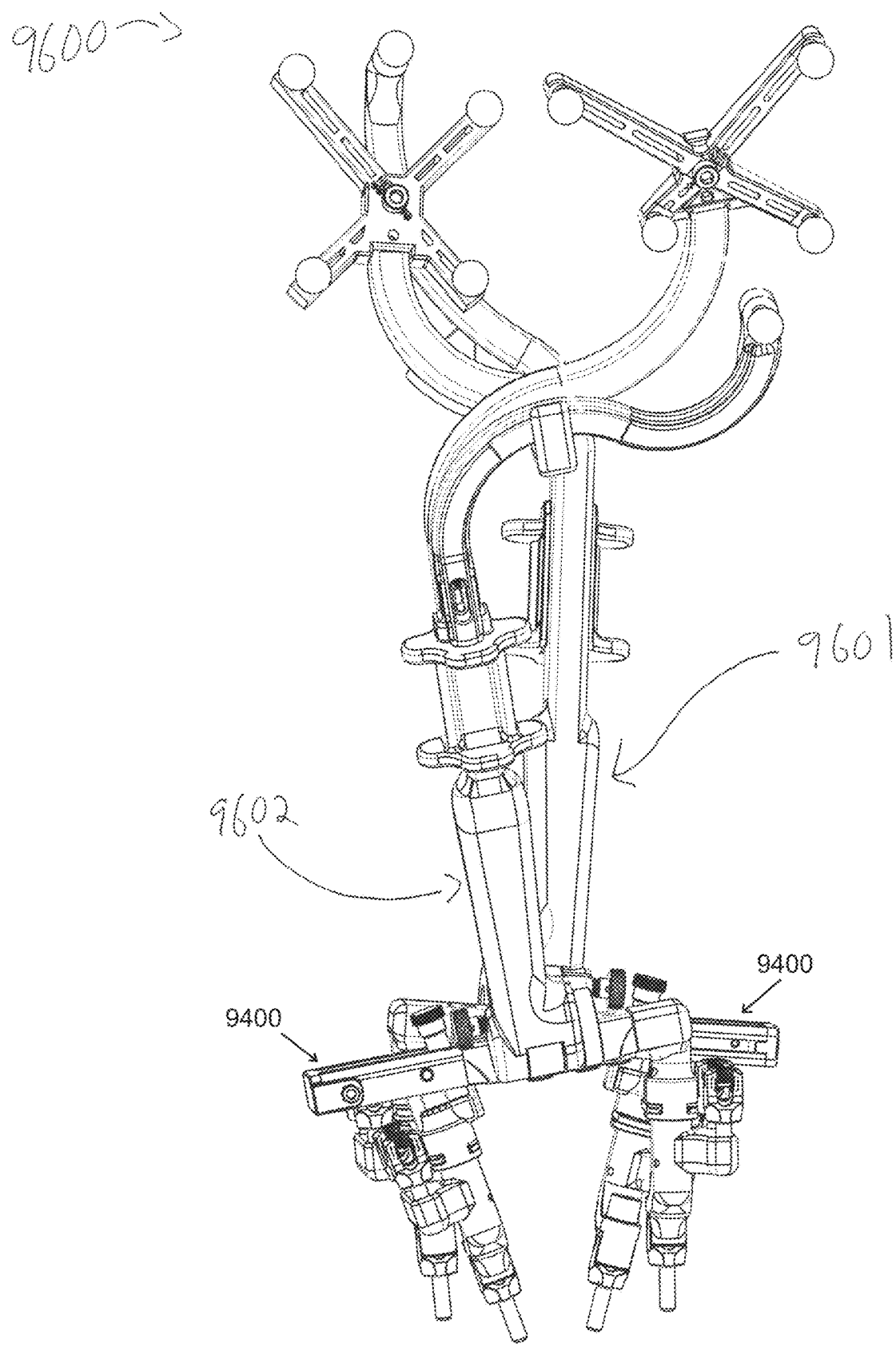

FIG. 96A illustrates a front view of both back-facing and front-facing flexibility assessment devices attached to an adjustable pedicle screw interface with accessory pedicle screw mounts in accordance with some embodiments of the invention.

Figure 96B:
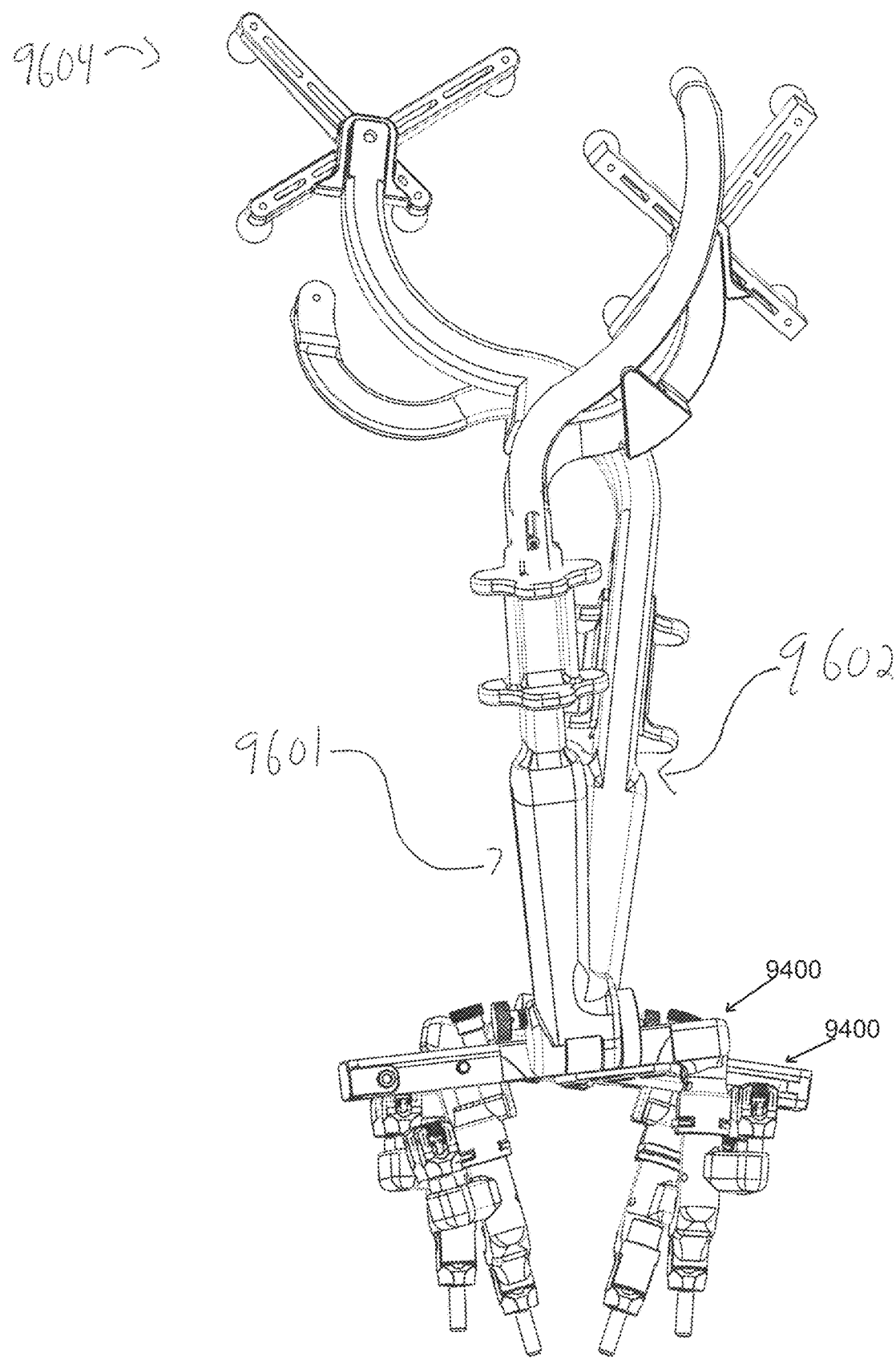

FIG. 96B illustrates a rear view of both back-facing and front-facing flexibility assessment devices attached to an adjustable pedicle screw interface with accessory pedicle screw mounts as described previously in relation to FIG. 96A in accordance with some embodiments of the invention.

Figure 96C:
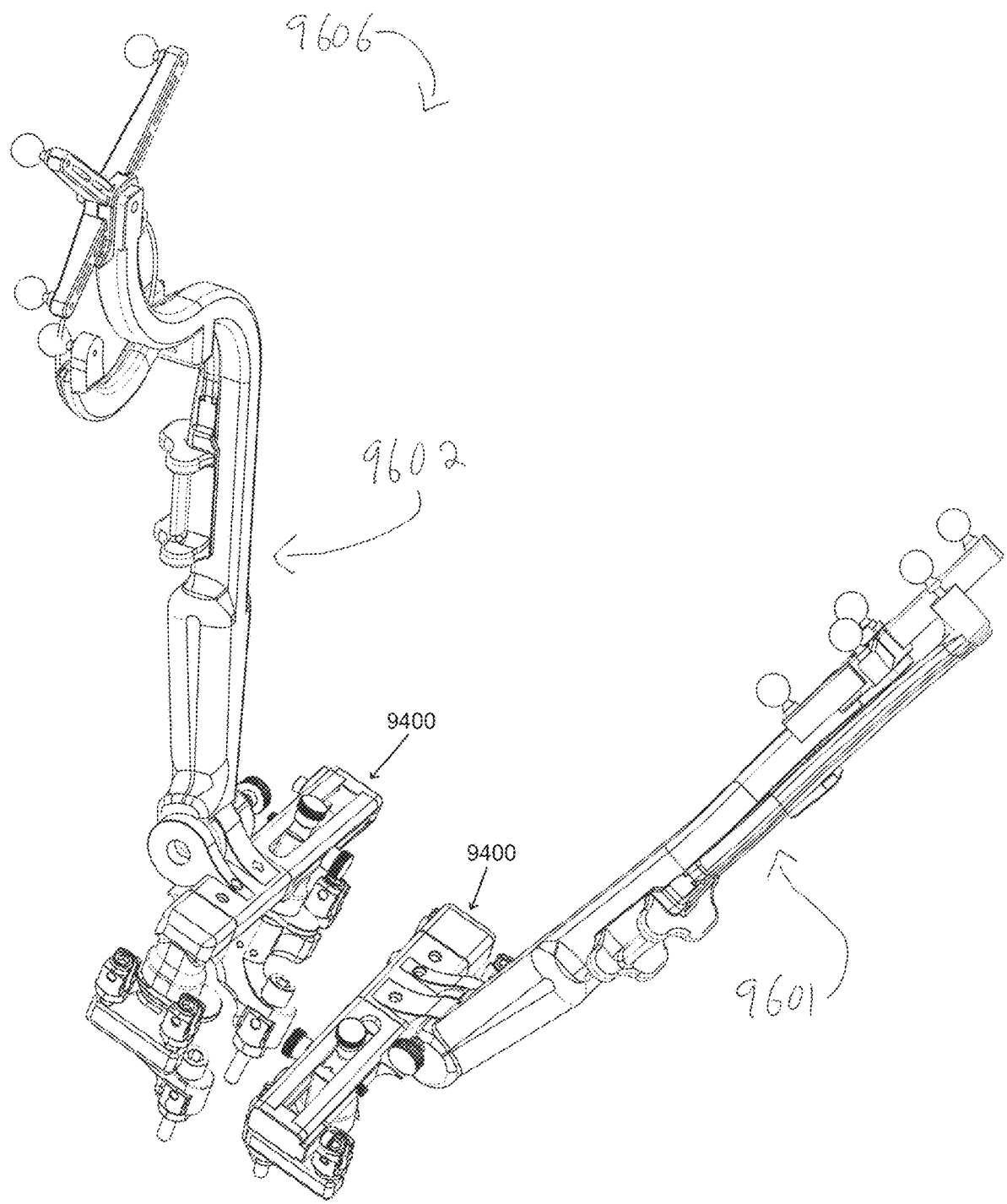

FIG. 96C illustrates a perspective view of both back-facing and front-facing flexibility assessment devices attached to an adjustable pedicle screw interface with accessory pedicle screw mounts as described previously in relation to FIGS. 96A-96B in accordance with some embodiments of the invention.

Figure 96D:
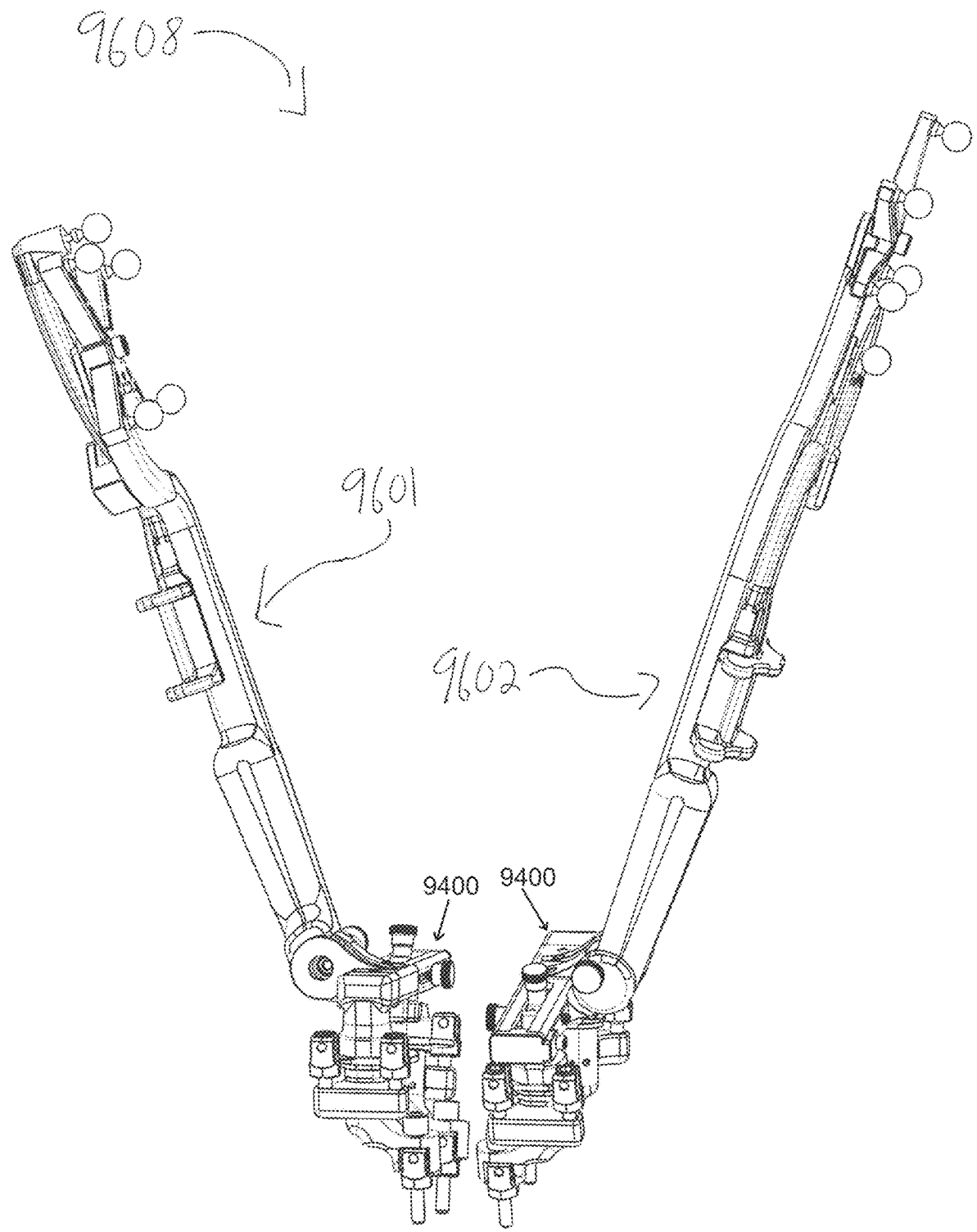

FIG. 96D illustrates a side view of both back-facing and front-facing flexibility assessment devices attached to an adjustable pedicle screw interface with accessory pedicle screw mounts as described previously in relation to FIGS. 96A-96C in accordance with some embodiments of the invention.

FIG. 96E illustrates a top view of both back-facing and front-facing flexibility assessment devices attached to an adjustable pedicle screw interface with accessory pedicle screw mounts as described previously in relation to FIGS. 96A-96D in accordance with some embodiments of the invention.

Figure 96F:
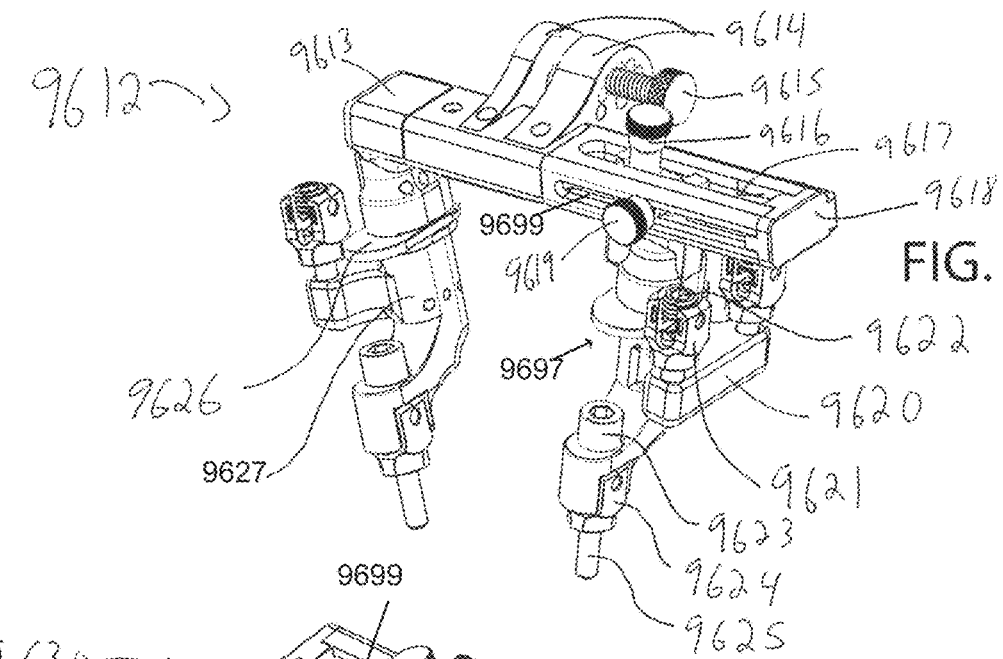
Figure 96G:
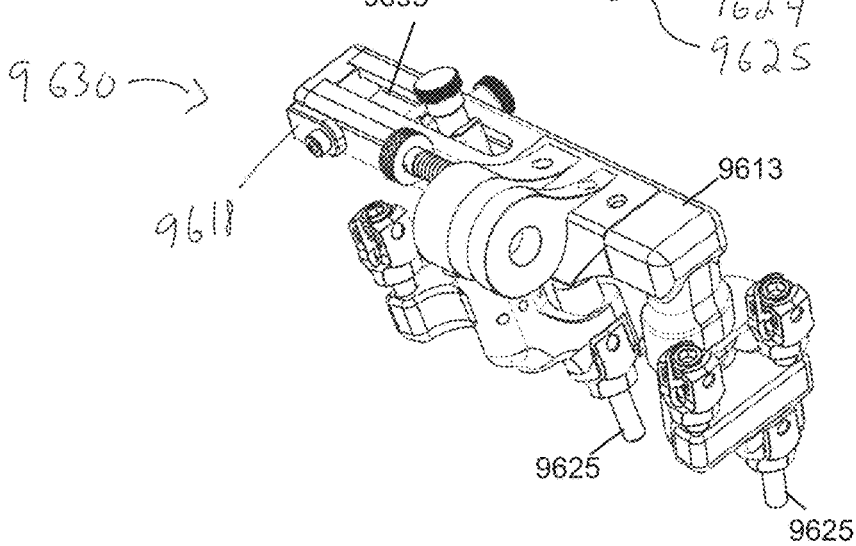
Figure 96H:
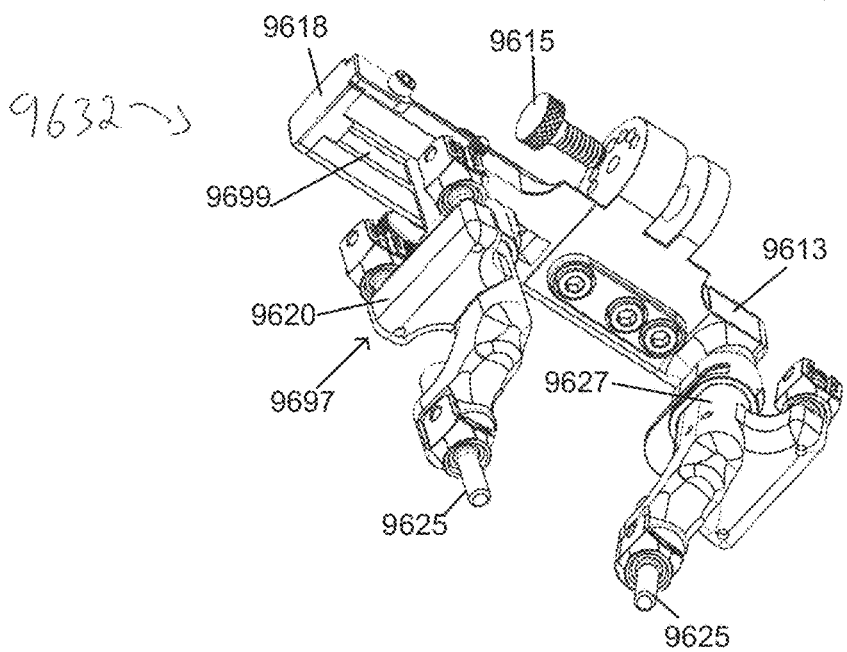

FIGS. 96F-96H illustrate perspective views of an adjustable pedicle screw interface with embedded screw-mating fasteners and accessory pedicle screw mounts as described previously in relation to FIGS. 96A-96E in accordance with some embodiments of the invention.

Figure 96I:
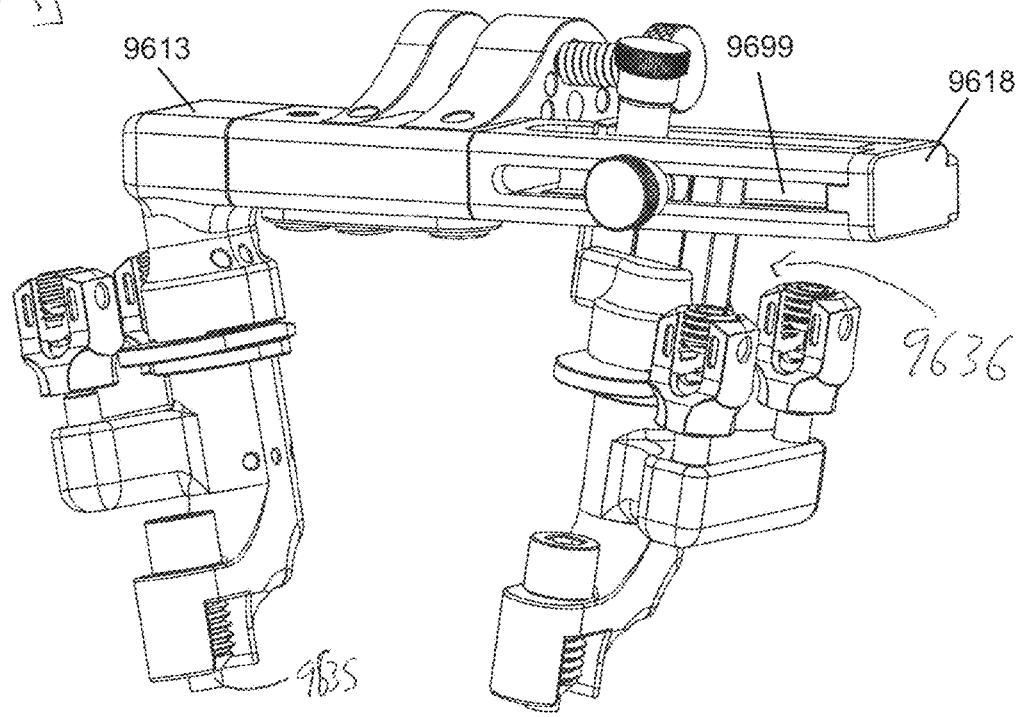
Figure 96J:
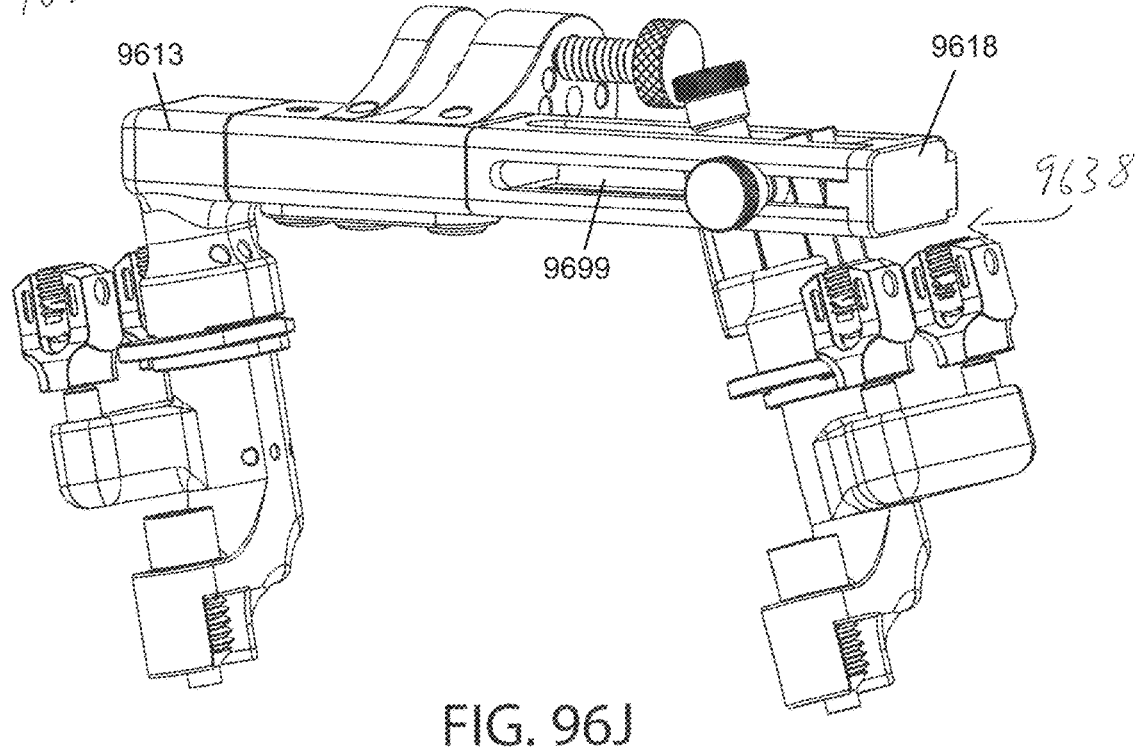

FIGS. 96I-96J illustrate perspective views of an adjustable pedicle screw interface with embedded screw-mating fasteners and accessory pedicle screw mounts, with the pedicle screw interfaces of the side arms not engaged with a pedicle screw, as described previously in relation to FIGS. 96A-96H in accordance with some embodiments of the invention.

Figure 96K:
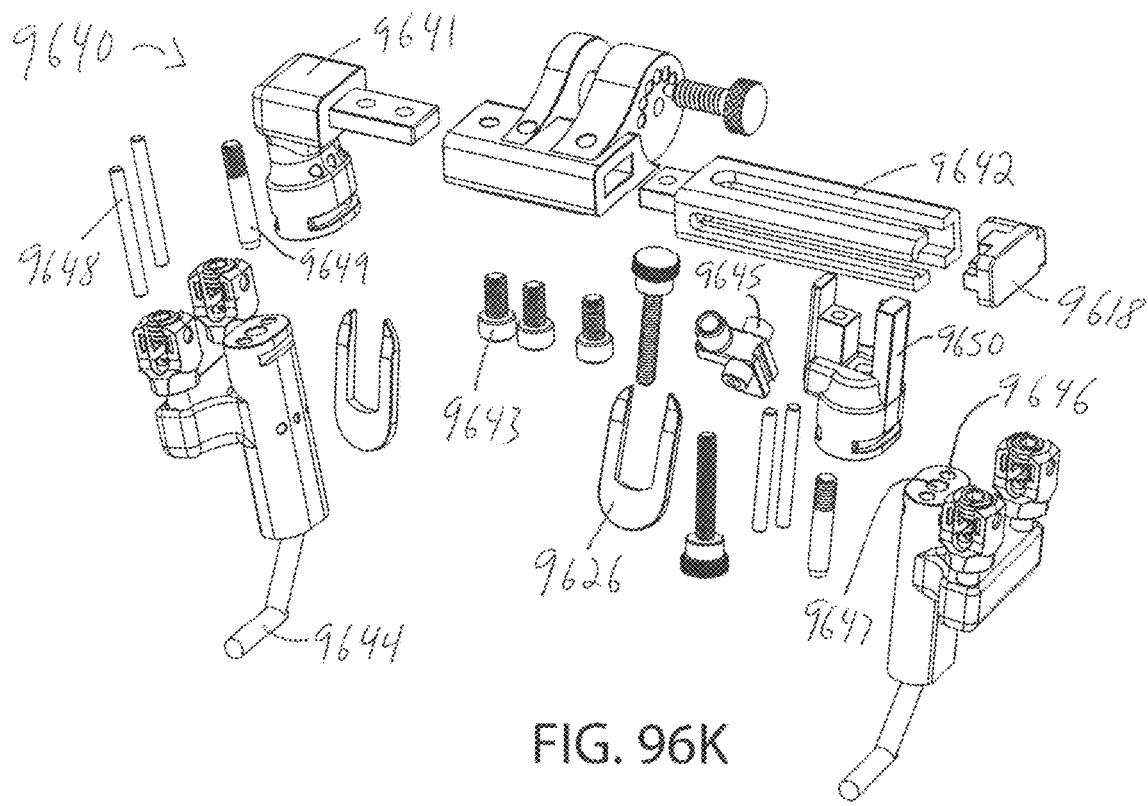
Figure 96L:
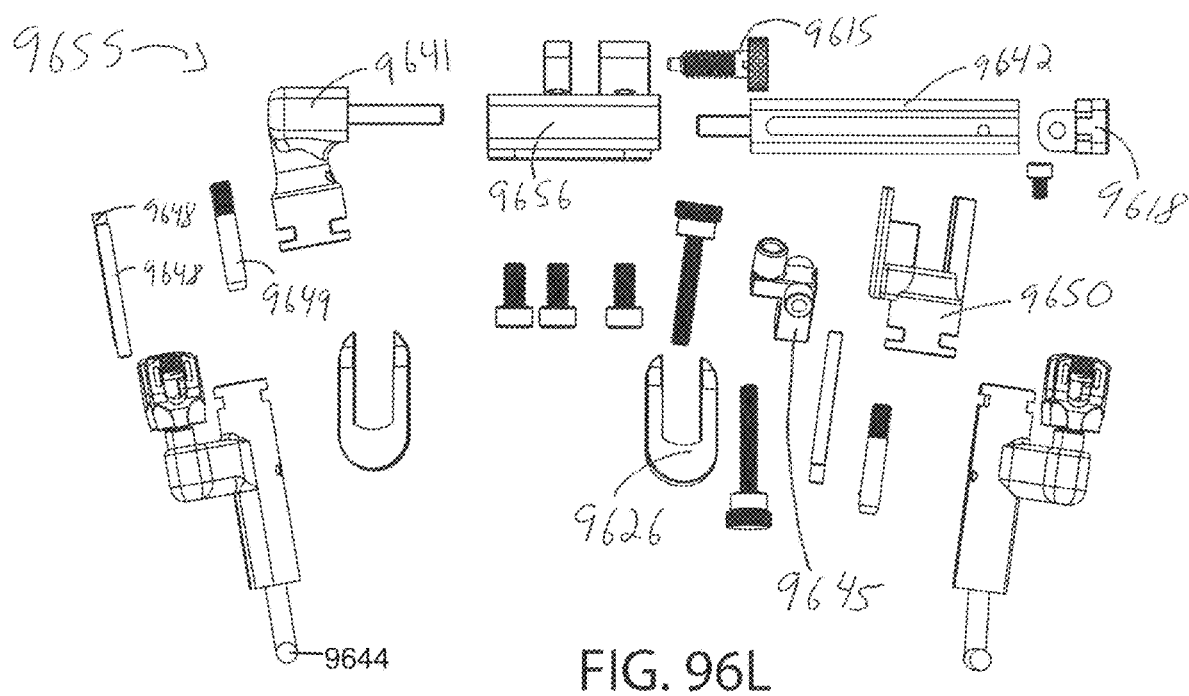

FIGS. 96K-96L illustrate exploded assembly views of an adjustable pedicle screw interface with embedded screw-mating fasteners and accessory pedicle screw mounts, with the pedicle screw interfaces of the distal end of the side arms containing a rod extension for mating with pedicle screw tulip heads, as described previously in relation to FIGS. 96A-96J in accordance with some embodiments of the invention.

Figure 96M:
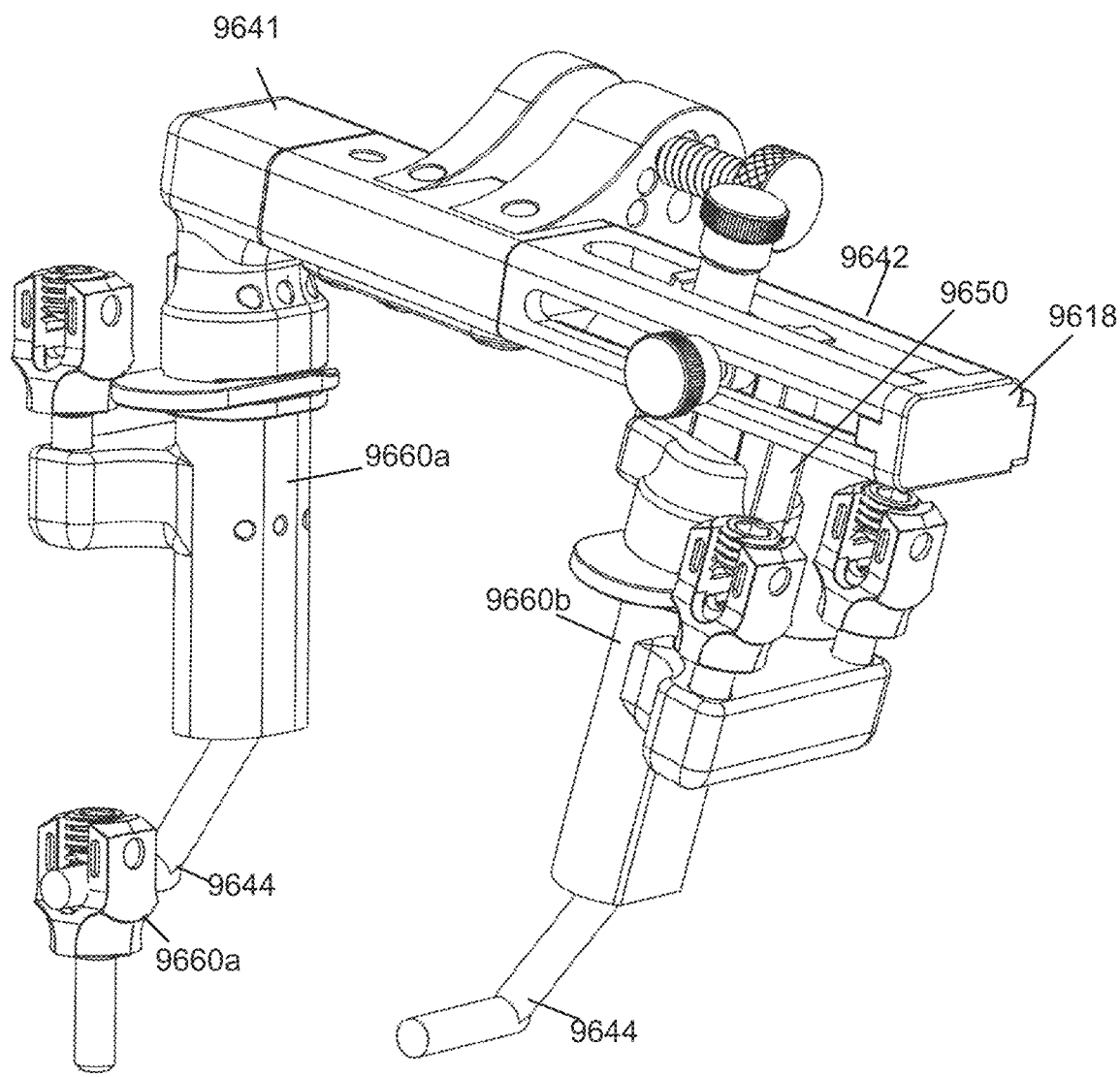

FIG. 96M illustrates a perspective view of an adjustable pedicle screw interface with embedded screw-mating fasteners and accessory pedicle screw mounts, with the pedicle screw interfaces of the distal end of the side arms containing a rod extension for mating with pedicle screw tulip heads, as described previously in relation to FIGS. 96A-96L in accordance with some embodiments of the invention.

Figure 96N:
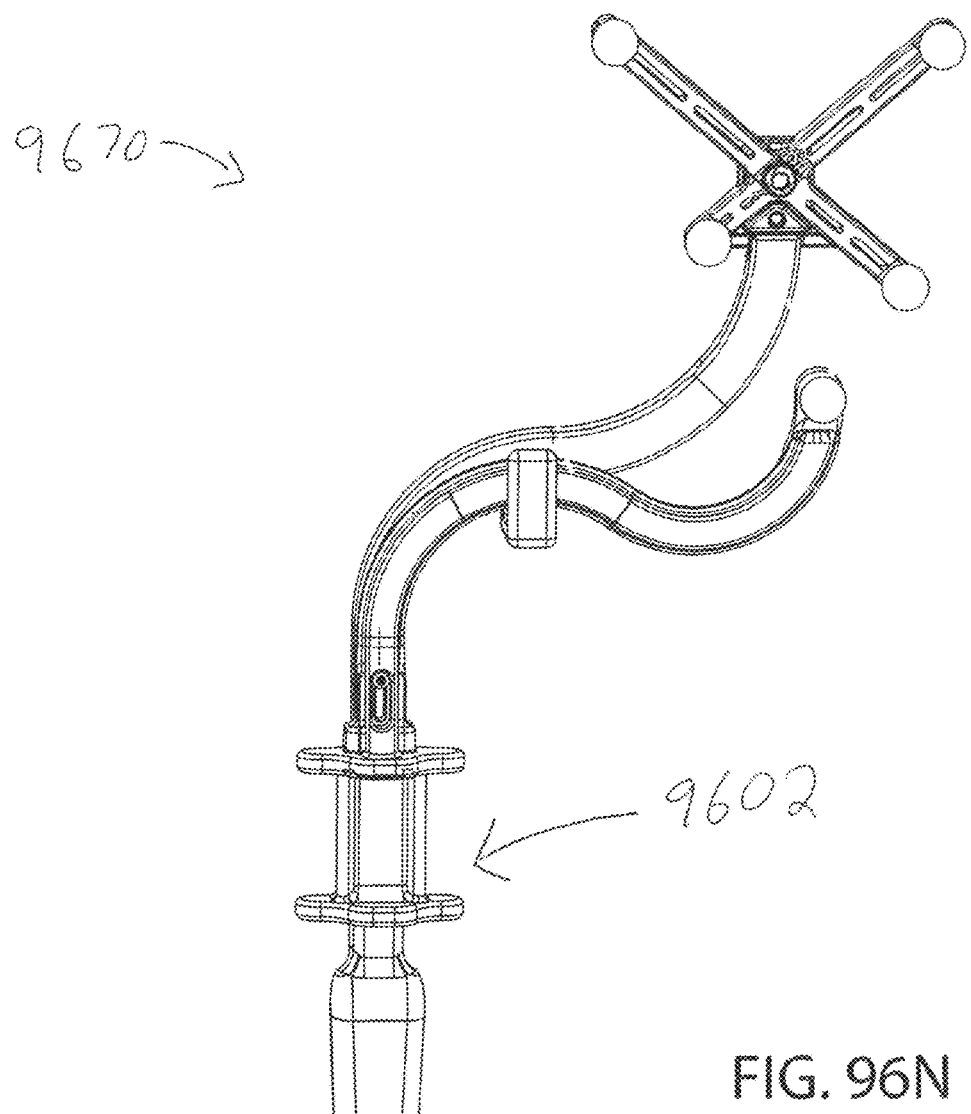

FIG. 96N illustrates a rear view of a back-facing flexibility assessment device in a triggered state with an adjustable pedicle screw interface as described previously in relation to FIGS. 96A-96M in accordance with some embodiments of the invention.

Figure 96O:
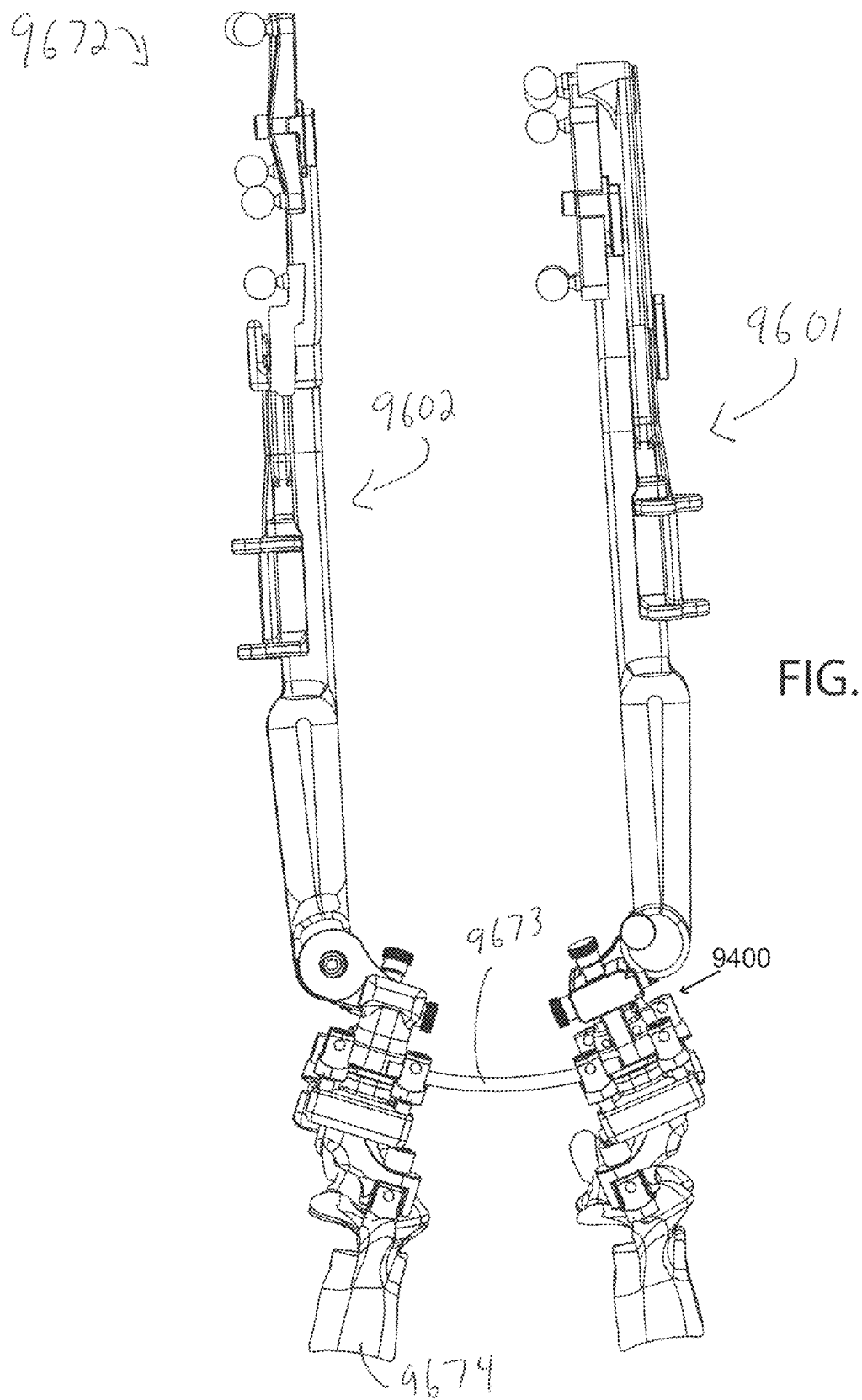

FIG. 96O illustrates a side view of both back-facing and front-facing flexibility assessment devices with adjustable pedicle screw interfaces that are substantially rigidly fixed in their relative orientations to one another while the devices are substantially rigidly engaged with vertebrae, as described previously in relation to FIGS. 96A-96N in accordance with some embodiments of the invention.

Figure 96P:
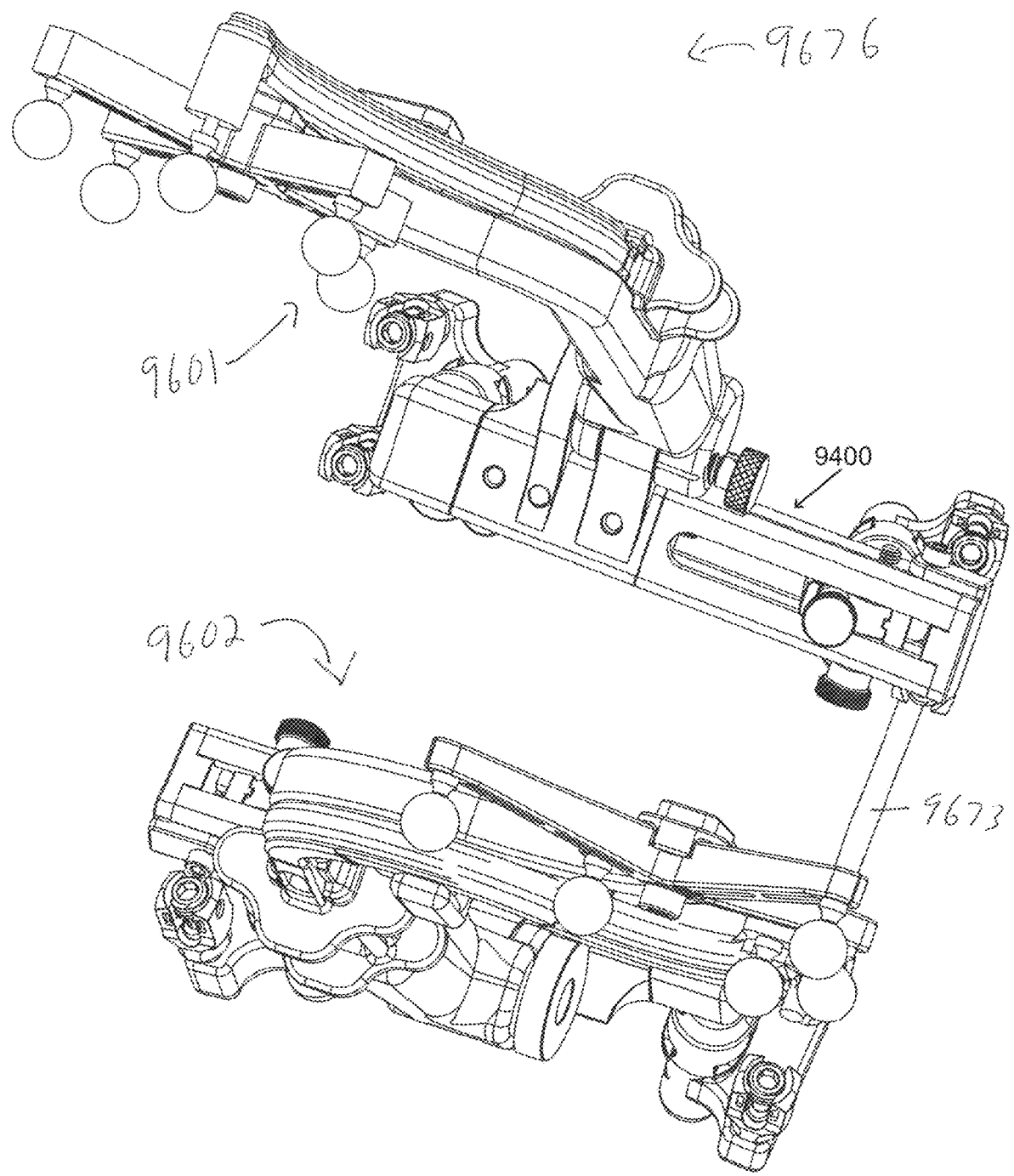

FIG. 96P illustrates a perspective view of both back-facing and front-facing flexibility assessment devices with adjustable pedicle screw interfaces that are substantially rigidly fixed in their relative orientations to one another, as described previously in relation to FIGS. 96A-96O in accordance with some embodiments of the invention.

Figure 96Q:
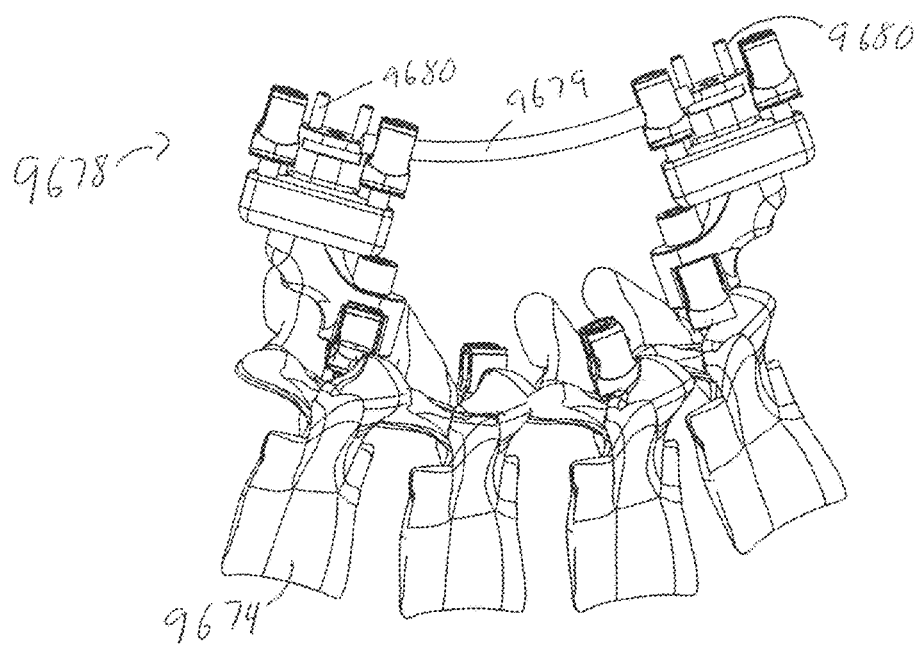

FIG. 96Q illustrates a side view of the bottom half side arm components of the flexibility assessment devices that are substantially rigidly linked to one another and engaged with the vertebrae, as described previously in relation to FIGS. 96A-96P in accordance with some embodiments of the invention.

Figure 96R:
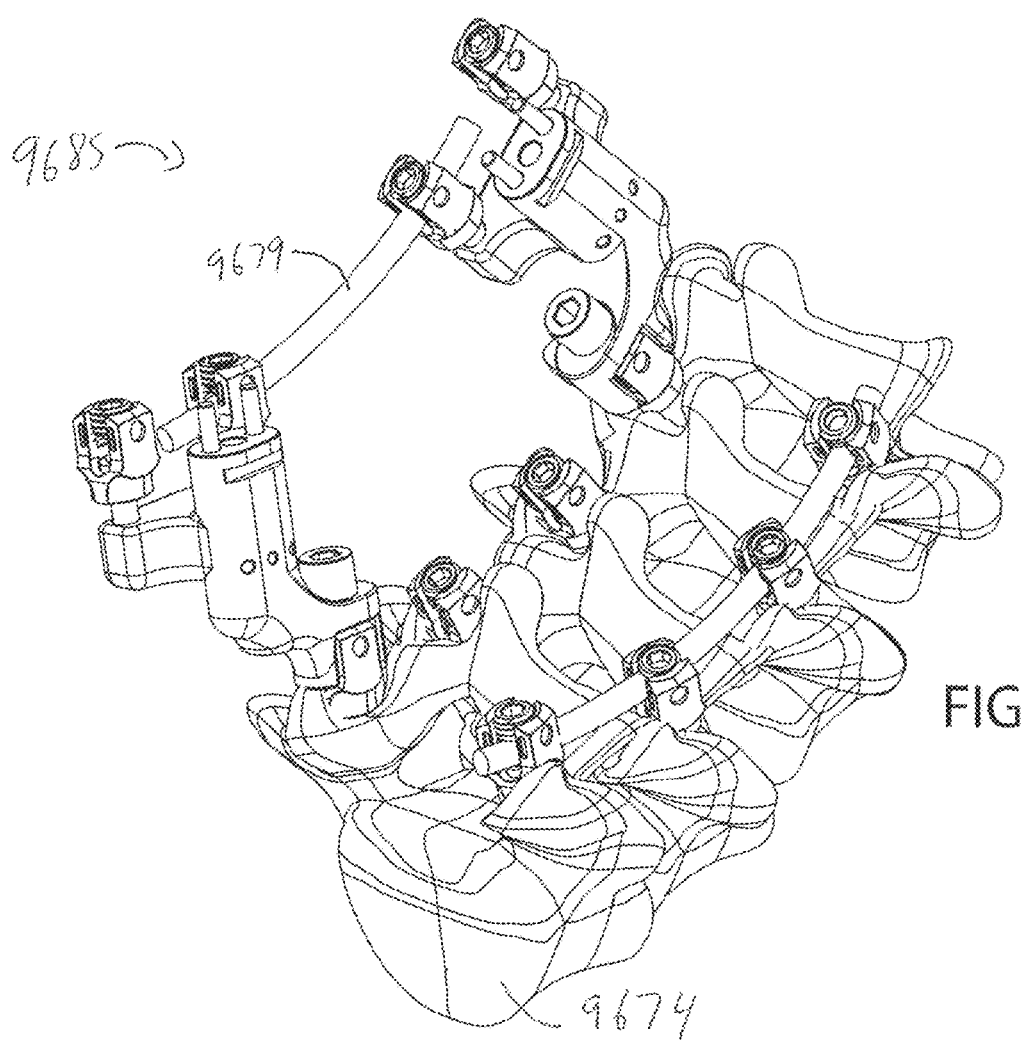

FIG. 96R illustrates a perspective view of the bottom half side arm components of the flexibility assessment devices that are substantially rigidly linked to one another and engaged with the vertebrae, as described previously in relation to FIGS. 96A-96Q in accordance with some embodiments of the invention.

Figure 96S:
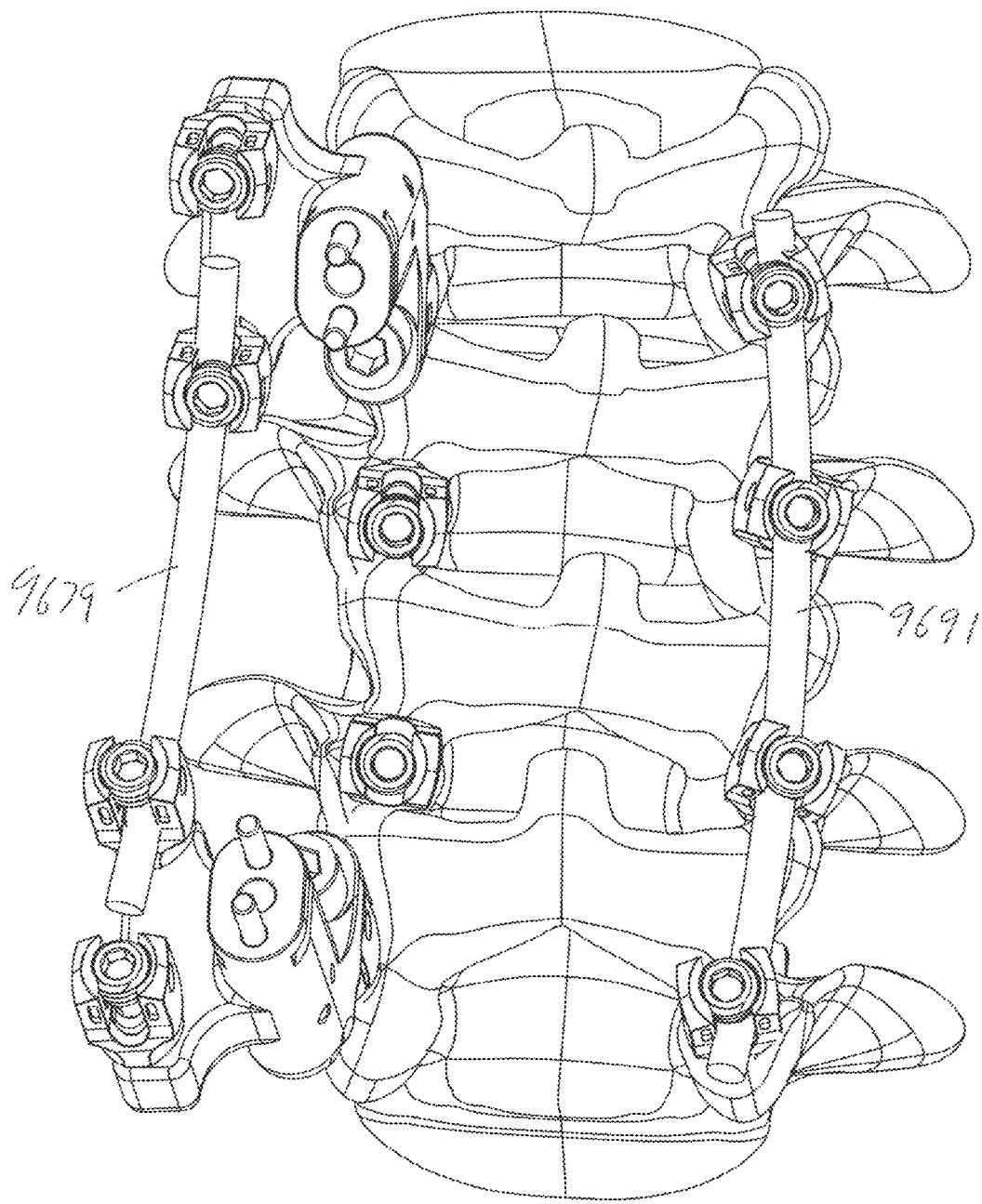

FIG. 96S illustrates a top view of the bottom half side arm components of the flexibility assessment devices that are substantially rigidly linked to one another and engaged with the vertebrae, as described previously in relation to FIGS. 96A-96R in accordance with some embodiments of the invention.

FIGS. 97A-97B illustrate side views of an extended side arm of a flexibility assessment device that is substantially rigidly attached and unattached to a pedicle screw in accordance with some embodiments of the invention.

FIG. 97C illustrates a top view of an extended side arm of a flexibility assessment device as described previously in relation to FIGS. 97A-97B in accordance with some embodiments of the invention.

FIGS. 97D-97E illustrate cross-sectional views of an extended side arm of a flexibility assessment device that is substantially rigidly attached to pedicle screw as described previously in relation to FIGS. 97A-97C in accordance with some embodiments of the invention.

Figure 97F:
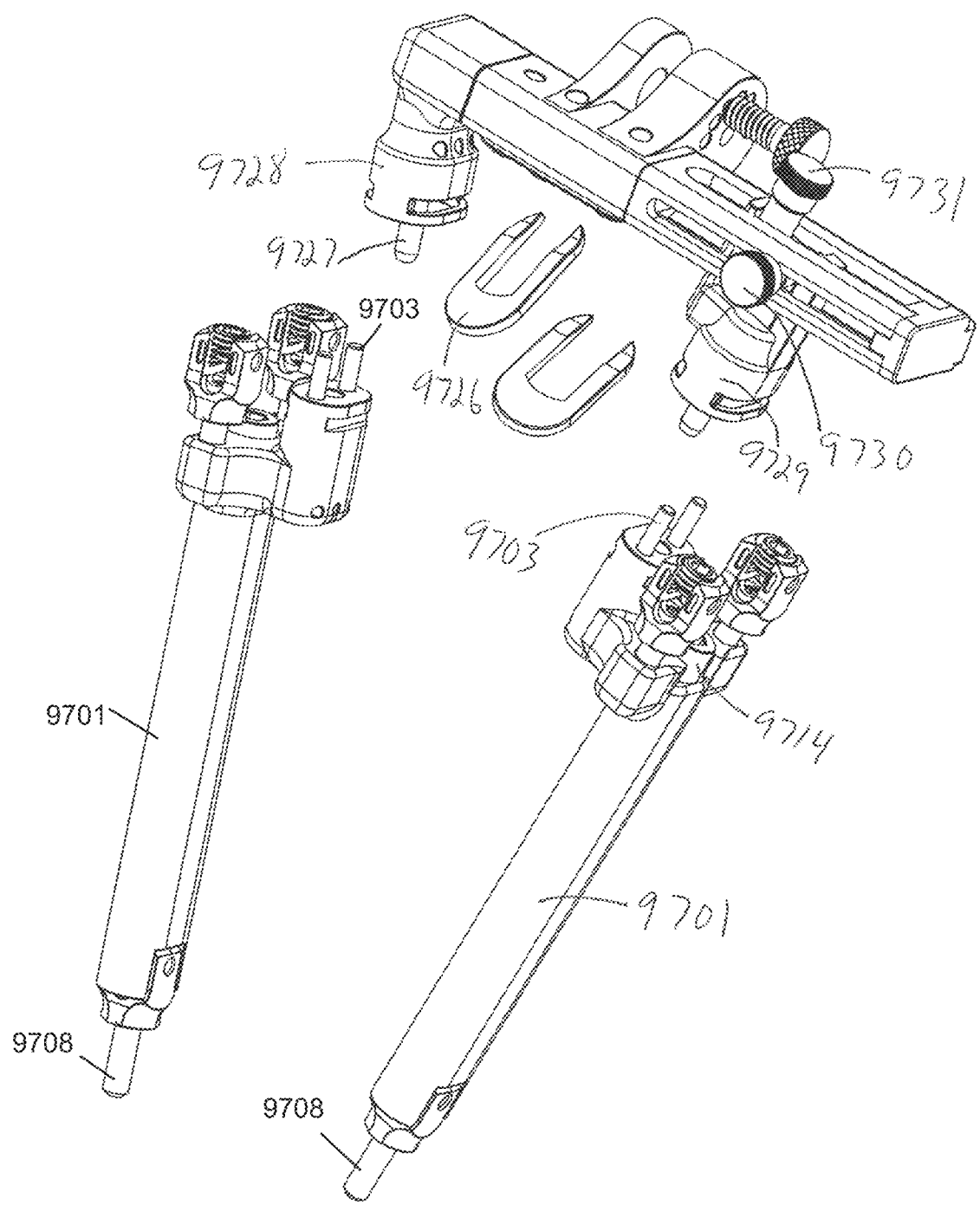

FIG. 97F illustrates an exploded assembly view of extended, adjustable screw interfaces of the flexibility assessment device that are substantially rigidly attached to pedicle screws as described previously in relation to FIGS. 97A-97E in accordance with some embodiments of the invention.

Figure 97G:
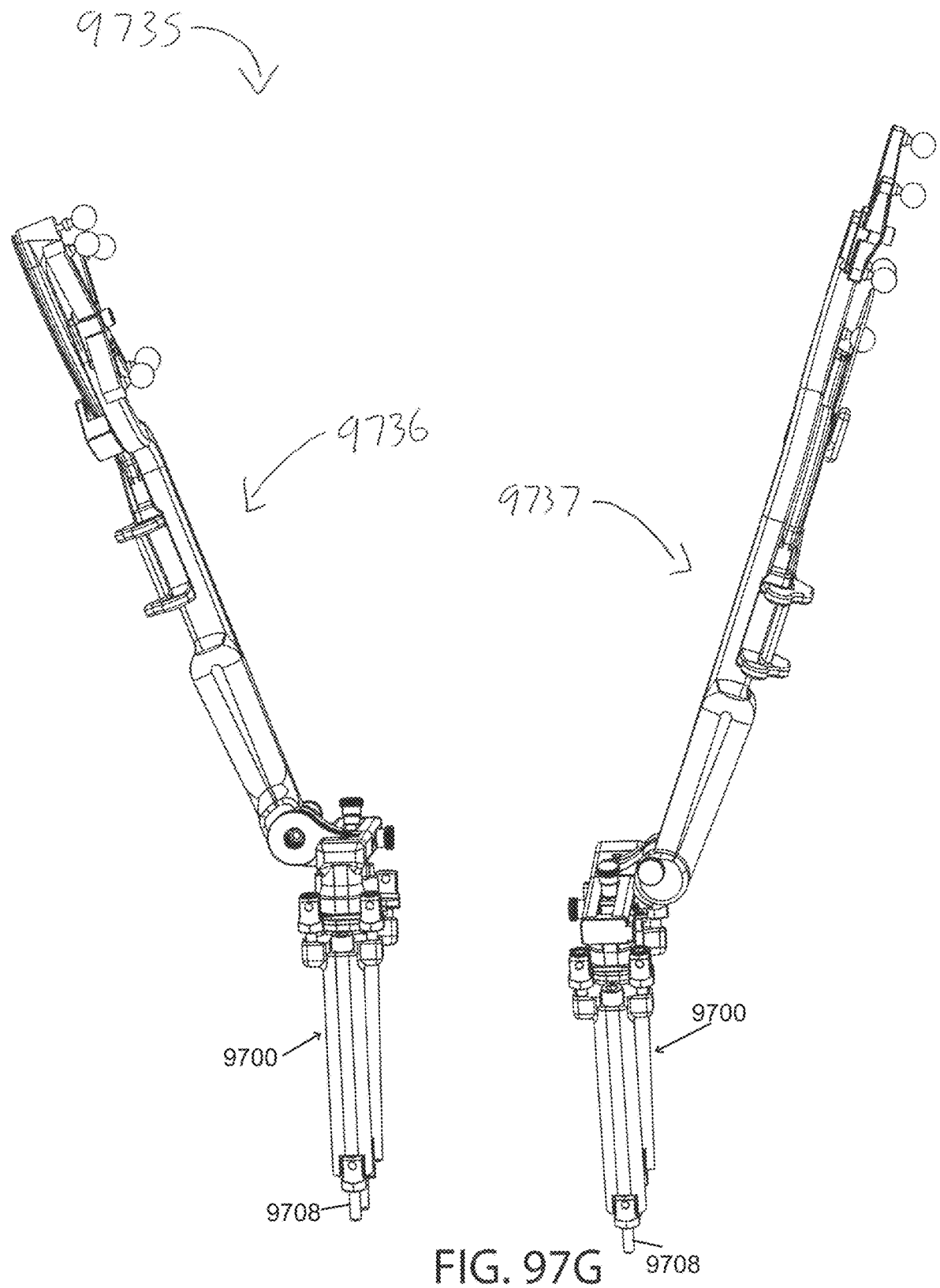

FIG. 97G illustrates a side view of extended, adjustable screw interfaces of the flexibility assessment devices that are substantially rigidly attached to pedicle screws as described previously in relation to FIGS. 97A-97F in accordance with some embodiments of the invention.

Figure 97H:
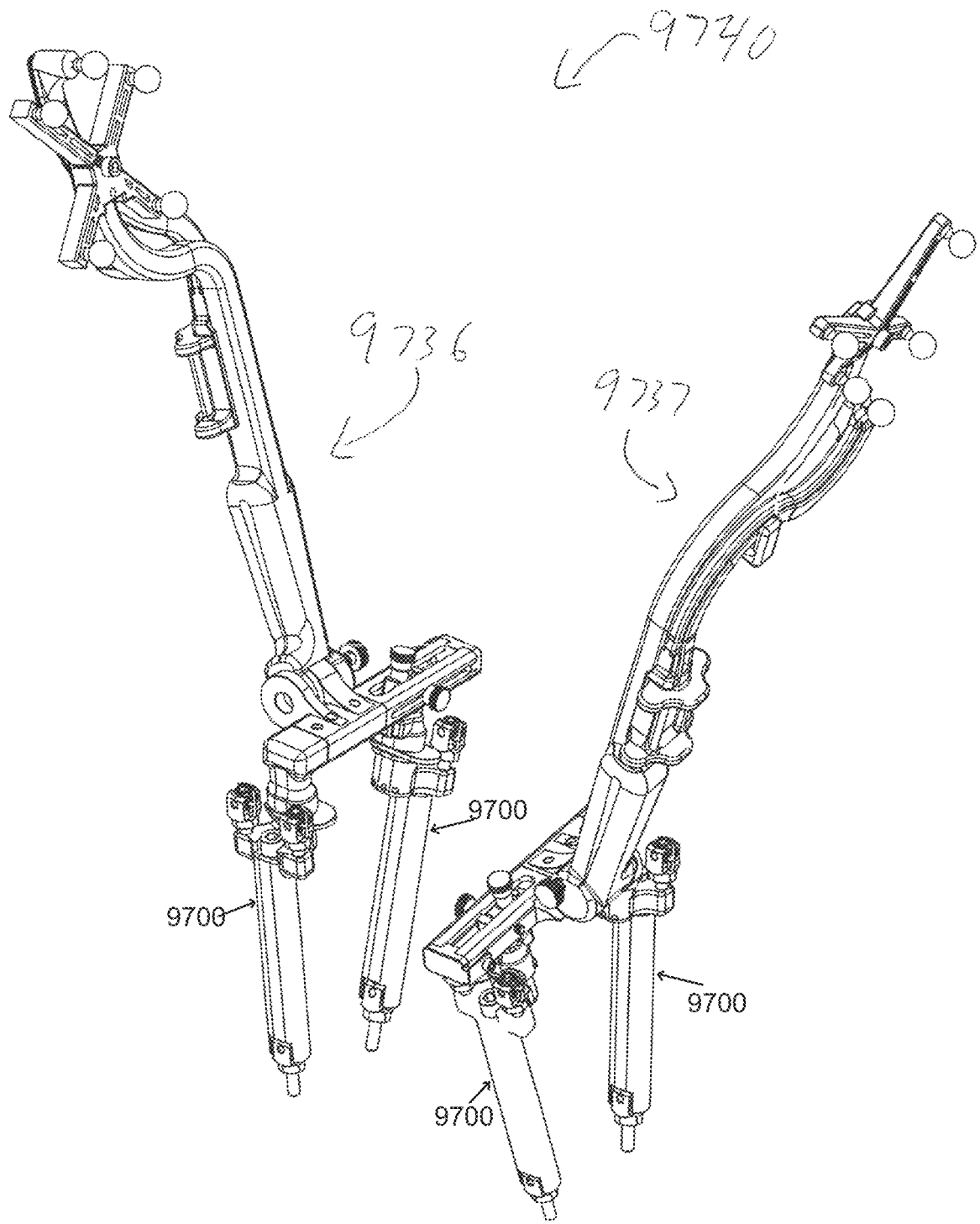

FIG. 97H illustrates a perspective view of extended, adjustable screw interfaces of the flexibility assessment devices that are substantially rigidly attached to pedicle screws as described previously in relation to FIGS. 97A-97G in accordance with some embodiments of the invention.

Figure 97I:
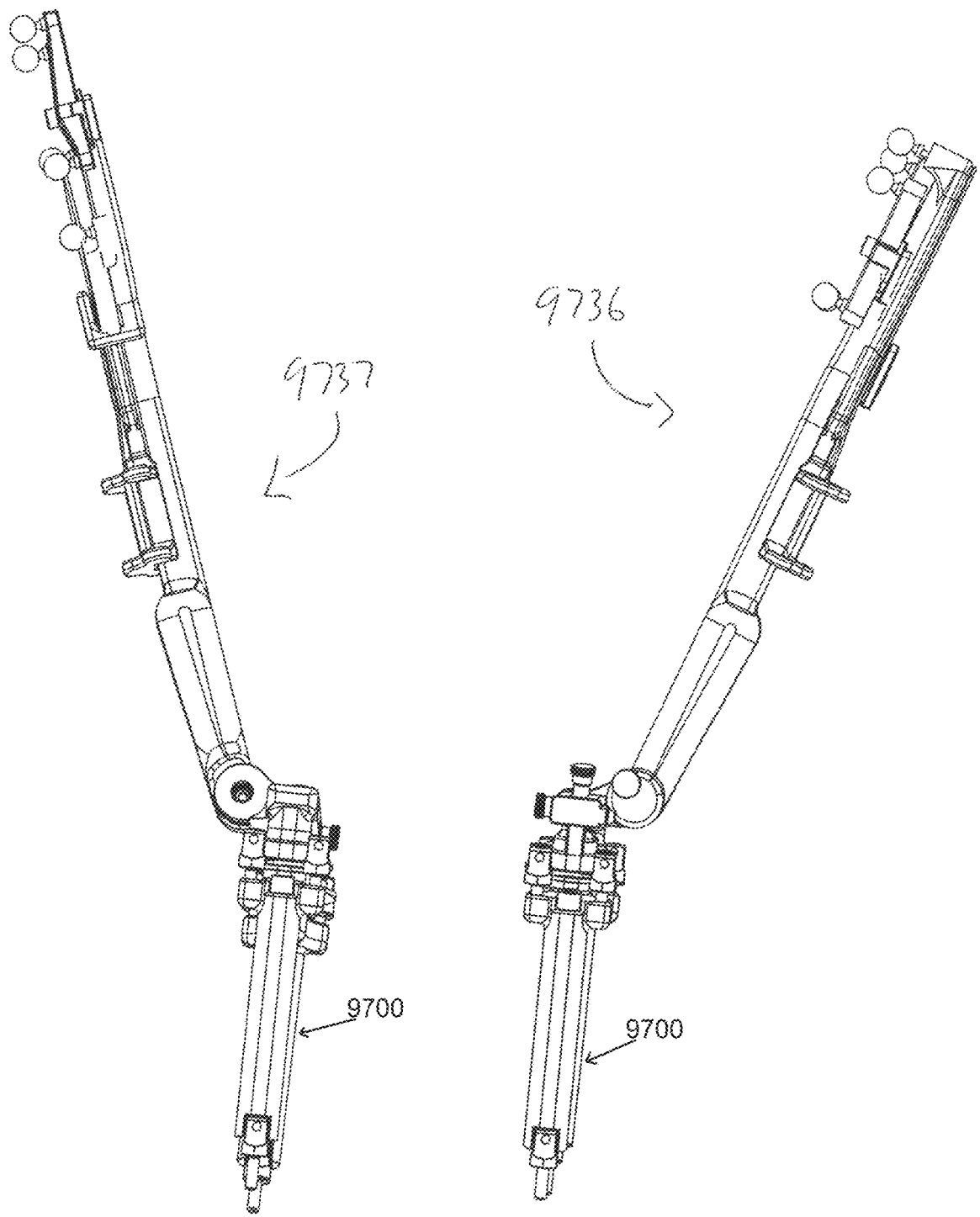

FIG. 97I illustrates a side view of extended, adjustable screw interfaces of the flexibility assessment devices that are substantially rigidly attached to pedicle screws as described previously in relation to FIGS. 97A-97H in accordance with some embodiments of the invention.

Figure 97J:
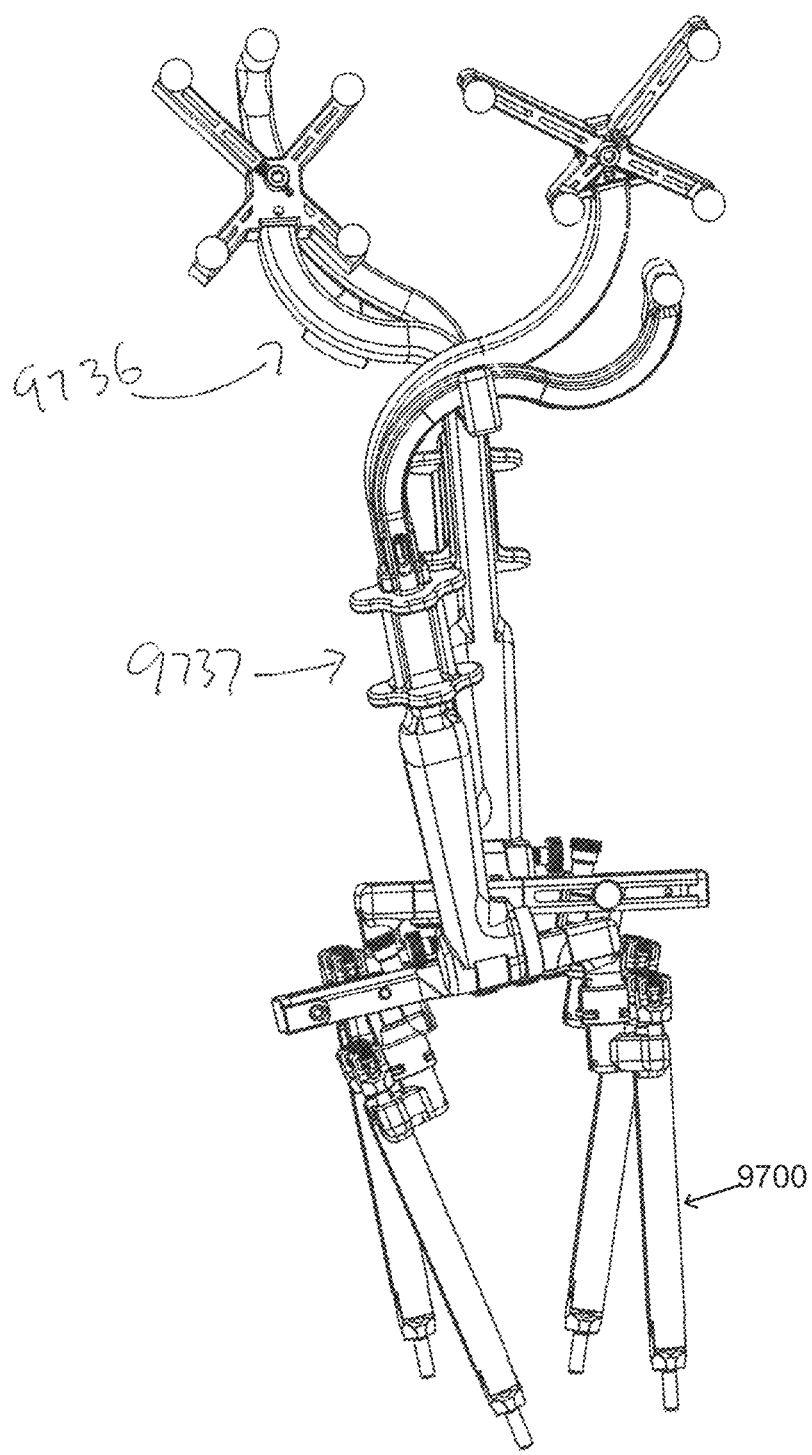

FIG. 97J illustrates a front view of extended, adjustable screw interfaces of the flexibility assessment devices that are substantially rigidly attached to pedicle screws as described previously in relation to FIGS. 97A-97I in accordance with some embodiments of the invention.

FIG. 97K illustrates a top view of extended, adjustable screw interfaces of the flexibility assessment devices that are substantially rigidly attached to pedicle screws as described previously in relation to FIGS. 97A-97J in accordance with some embodiments of the invention.

Figure 97L:
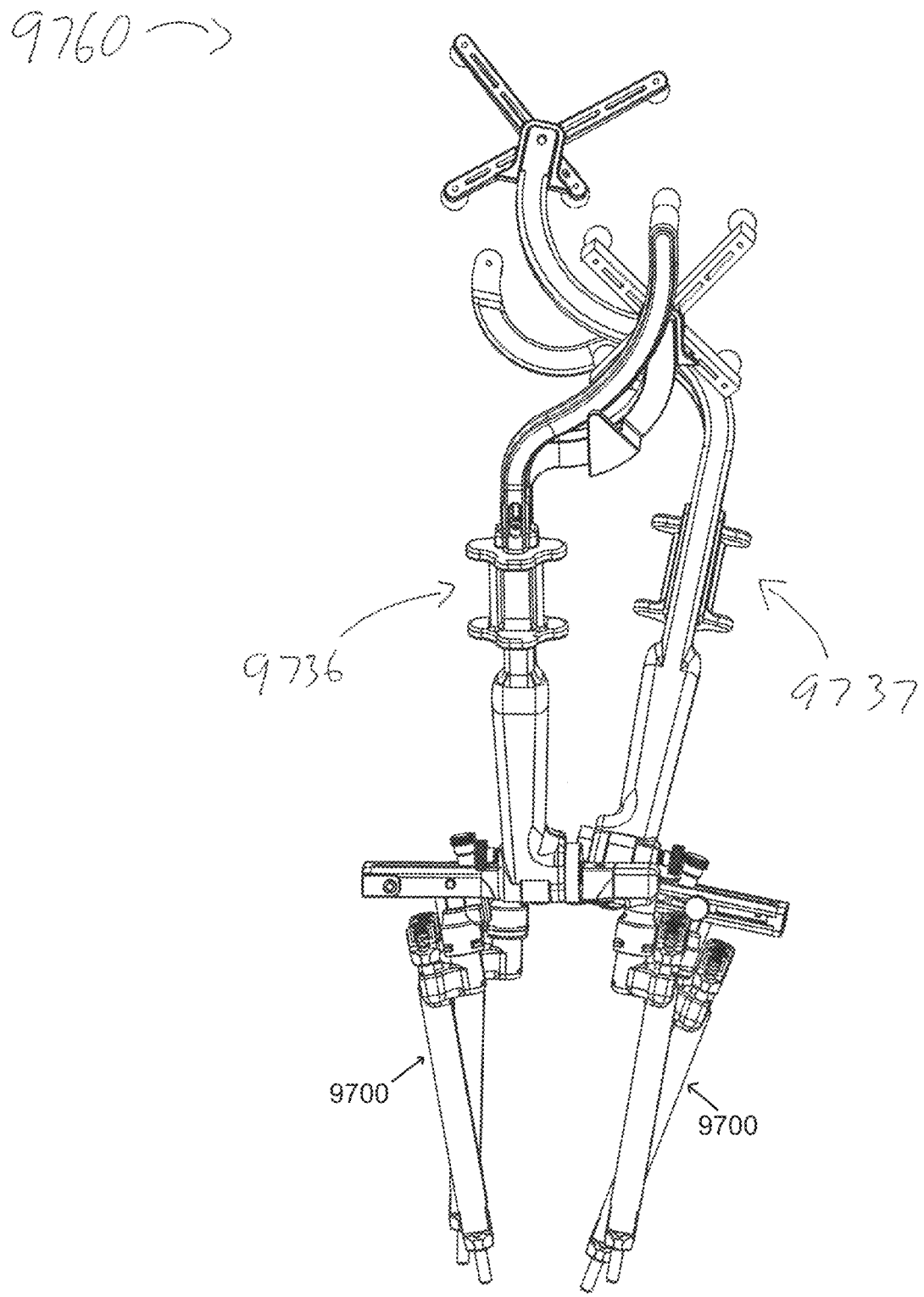

FIG. 97L illustrates a rear view of extended, adjustable screw interfaces of the flexibility assessment devices that are substantially rigidly attached to pedicle screws as described previously in relation to FIGS. 97A-97K in accordance with some embodiments of the invention.

FIGS. 98A-98B illustrate front views of a rod contour registration tool in an active and inactive triggering state in accordance with some embodiments of the invention.

FIG. 98C illustrates a side view of a rod contour registration tool as described previously in relation to FIGS. 98A-98B in accordance with some embodiments of the invention.

Figure 98D:
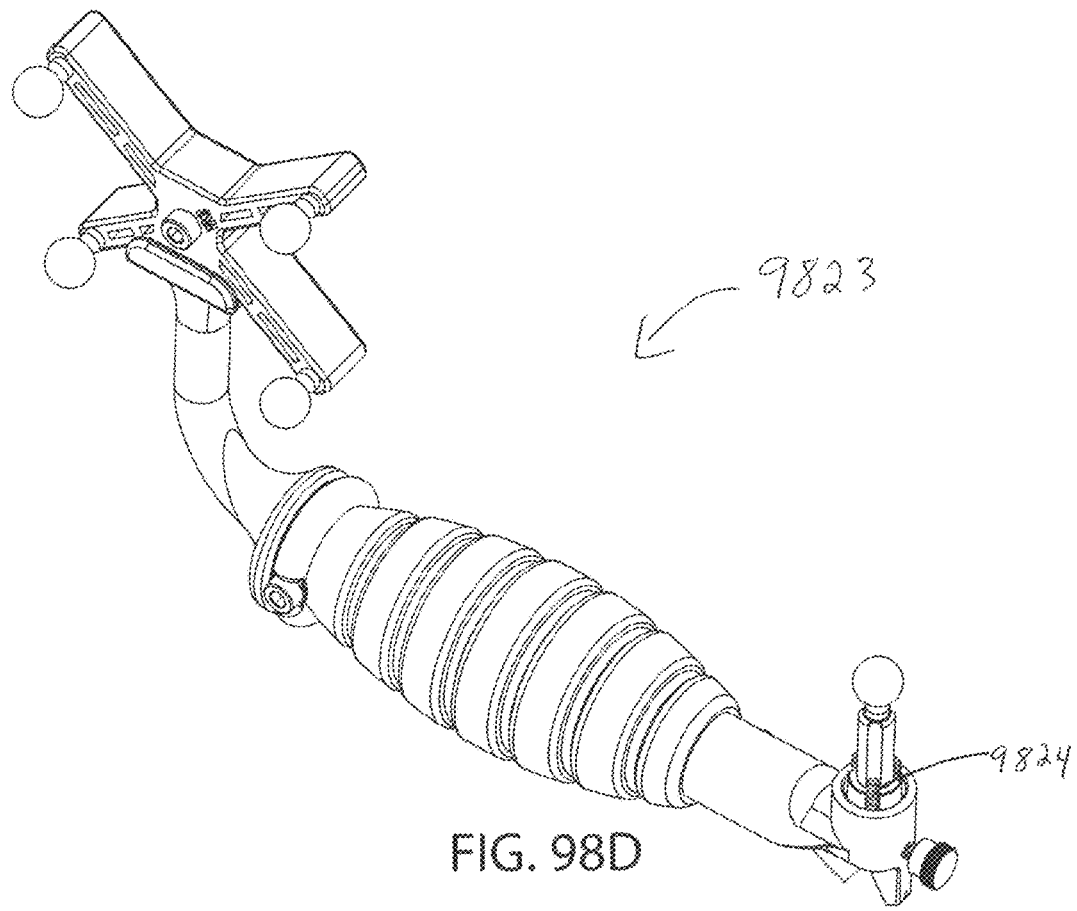

FIG. 98D illustrates a perspective view of a rod contour registration tool as described previously in relation to FIGS. 98A-98C in accordance with some embodiments of the invention.

Figure 98E:
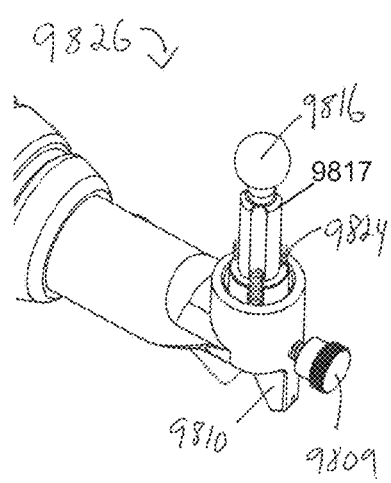
Figure 98F:
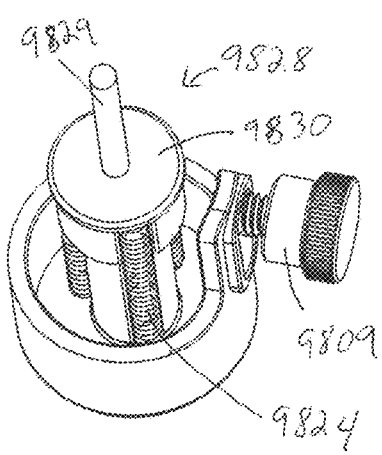

FIGS. 98E-98F illustrate perspective views of a triggering mechanism of a rod contour registration tool as described previously in relation to FIGS. 98A-98D in accordance with some embodiments of the invention.

Figure 98G:
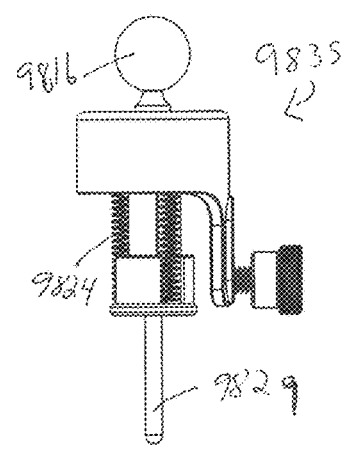

FIG. 98G illustrates a side view of a triggering mechanism of a rod contour registration tool as described previously in relation to FIGS. 98A-98F in accordance with some embodiments of the invention.

Figures 98H, 98I, 98J, 98K:
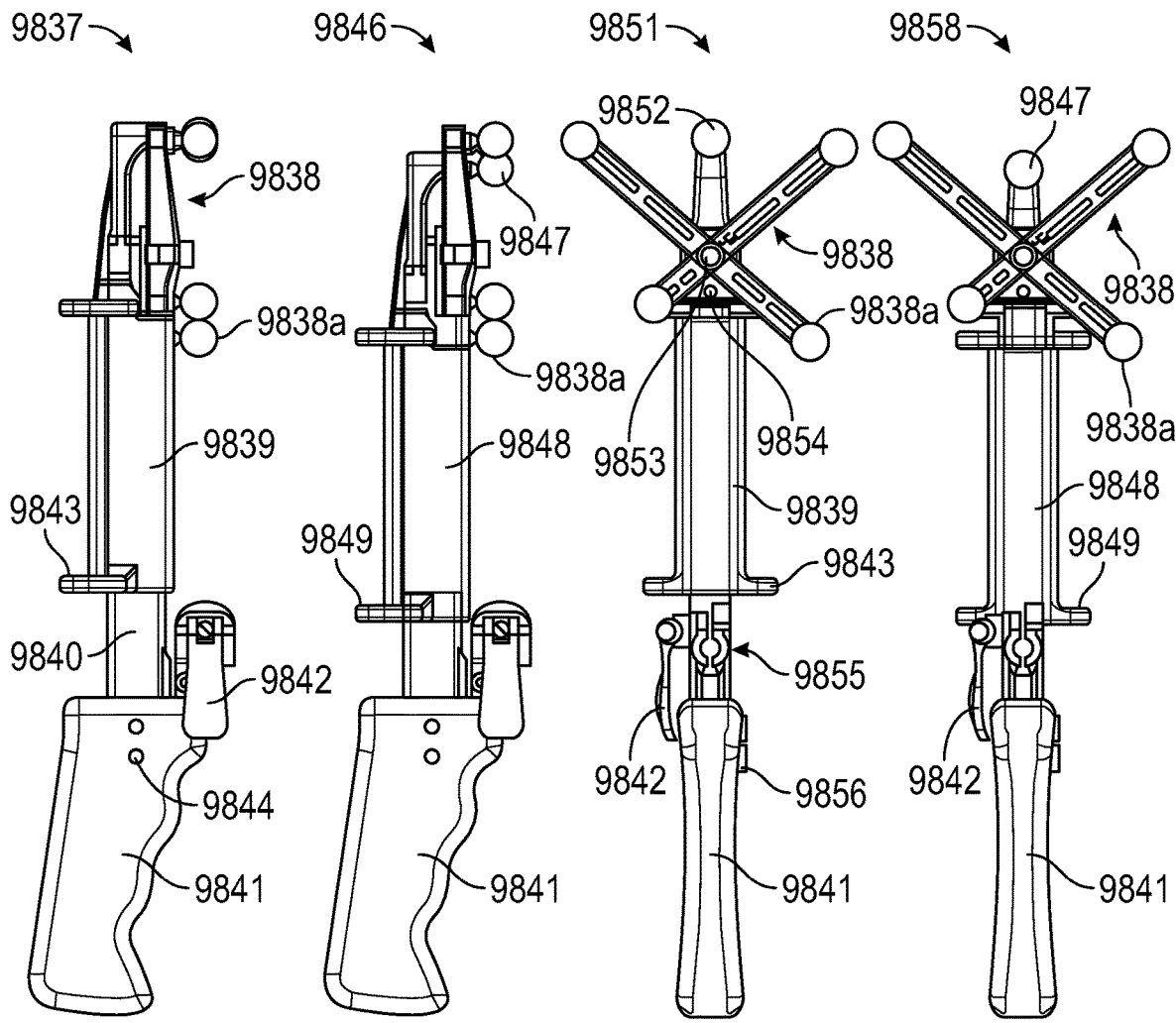

FIG. 98H illustrates a side view of a coordinate reference tool in an inactive triggered state as described previously in relation to FIGS. 98A-98G in accordance with some embodiments of the invention.

FIG. 98I illustrates a side view of a coordinate reference tool in an active triggered state as described previously in relation to FIGS. 98A-98H in accordance with some embodiments of the invention.

FIG. 98J illustrates a front view of a coordinate reference tool in an inactive triggered state as described previously in relation to FIGS. 98A-98I in accordance with some embodiments of the invention.

FIG. 98K illustrates a front view of a coordinate reference tool in an active triggered state as described previously in relation to FIGS. 98A-98J in accordance with some embodiments of the invention.

Figures 98L, 98M, 98N:
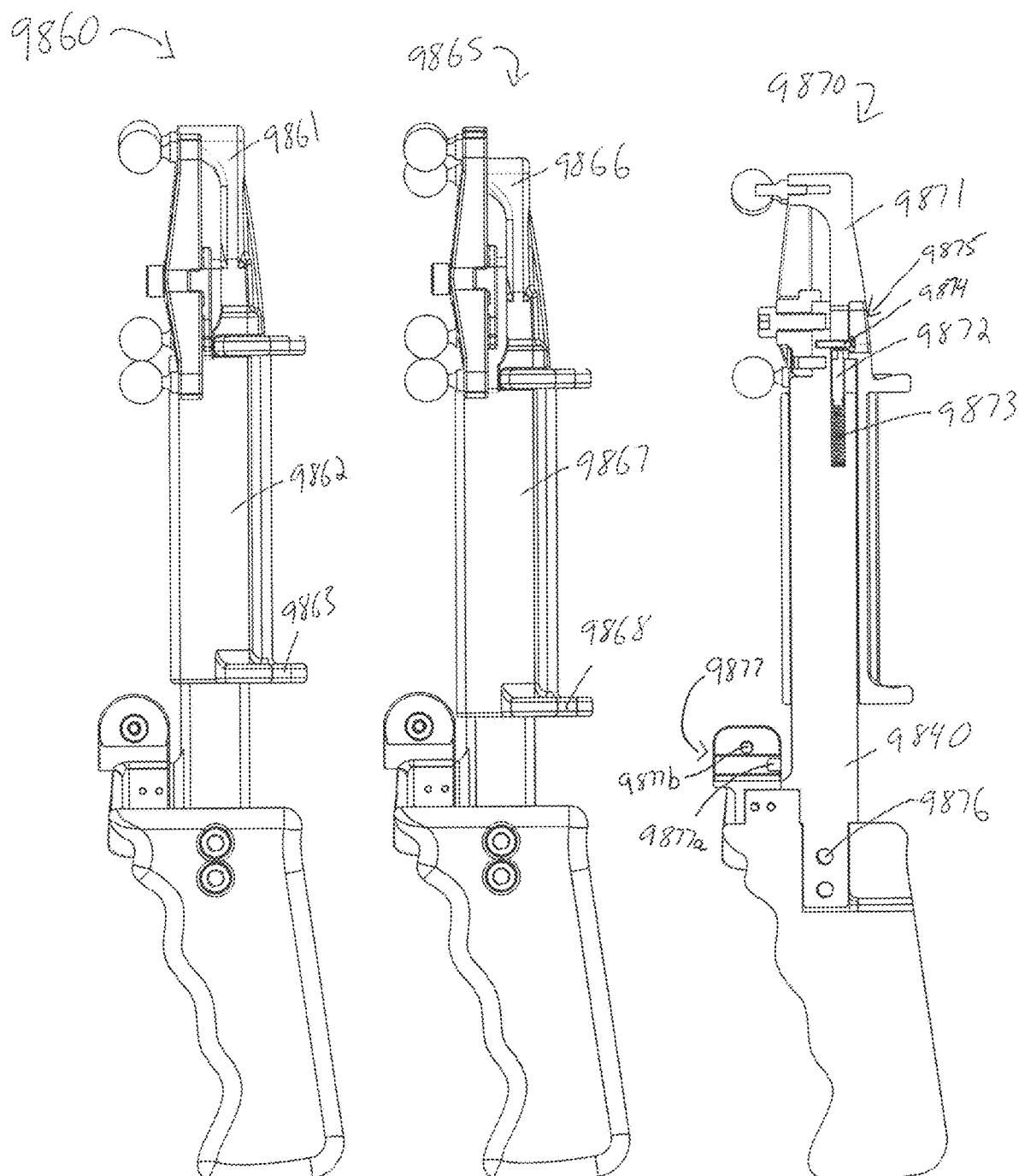

FIG. 98L illustrates a side view of a coordinate reference tool in an inactive triggered state as described previously in relation to FIGS. 98A-98K in accordance with some embodiments of the invention.

FIG. 98M illustrates a side view of a coordinate reference tool in an active triggered state as described previously in relation to FIGS. 98A-98L in accordance with some embodiments of the invention.

FIG. 98N illustrates a cross-sectional view of a coordinate reference tool in an inactive triggered state as described previously in relation to FIGS. 98A-98M in accordance with some embodiments of the invention.

FIGS. 98O-98S illustrate perspective views of a rod attached to a coordinate reference tool and a rod contour registration tool engaged with the rod as described previously in relation to FIGS. 98A-98N in accordance with some embodiments of the invention.

Figure 98O:
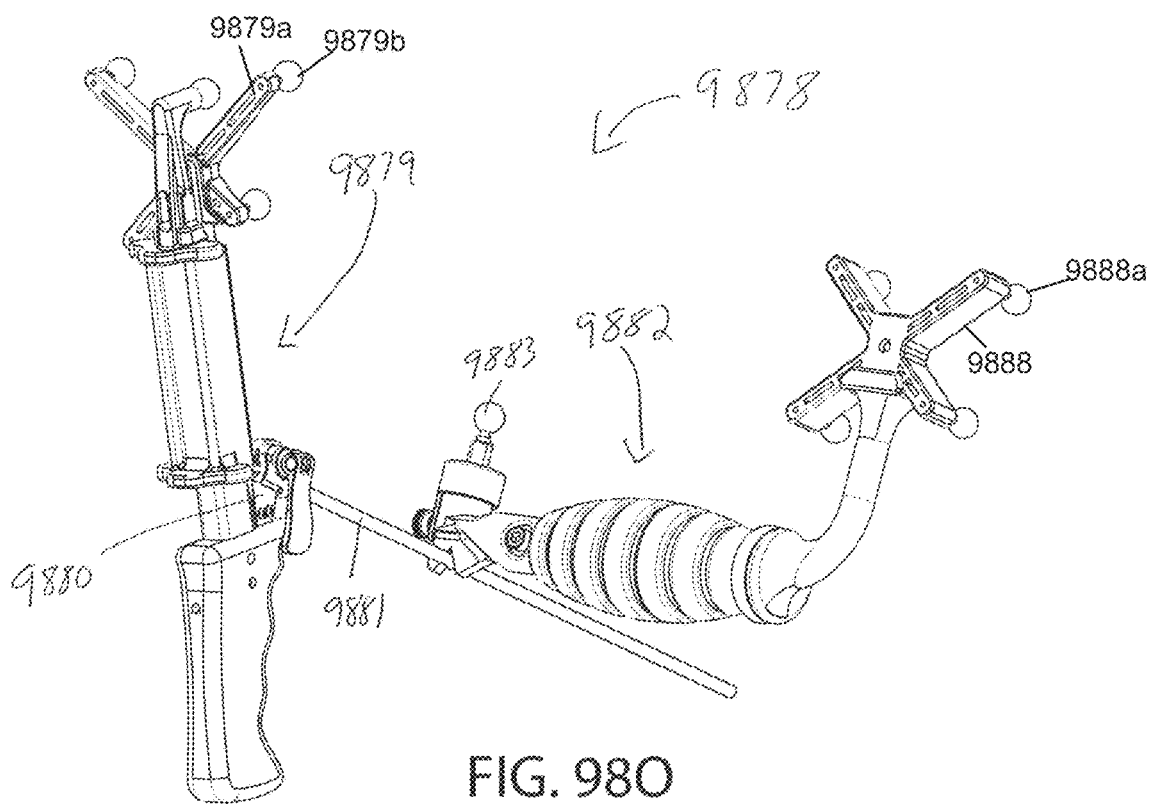
Figure 98P:
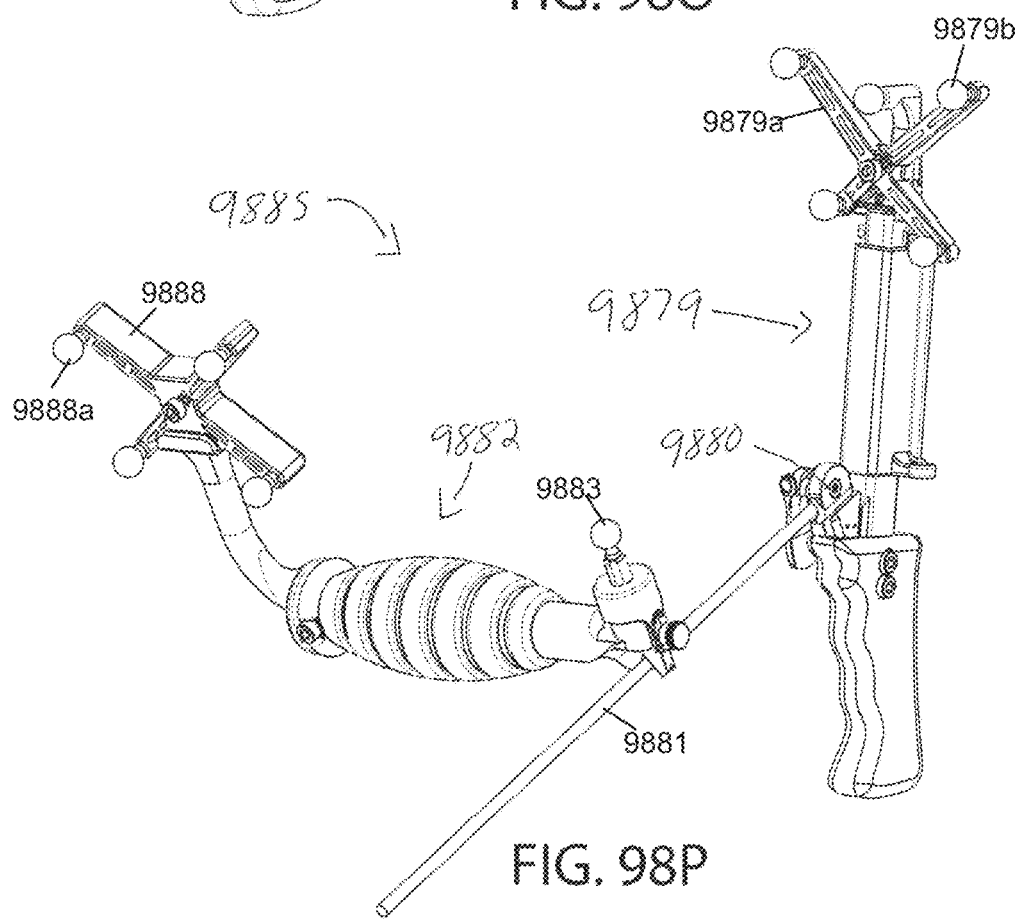
Figure 98Q:
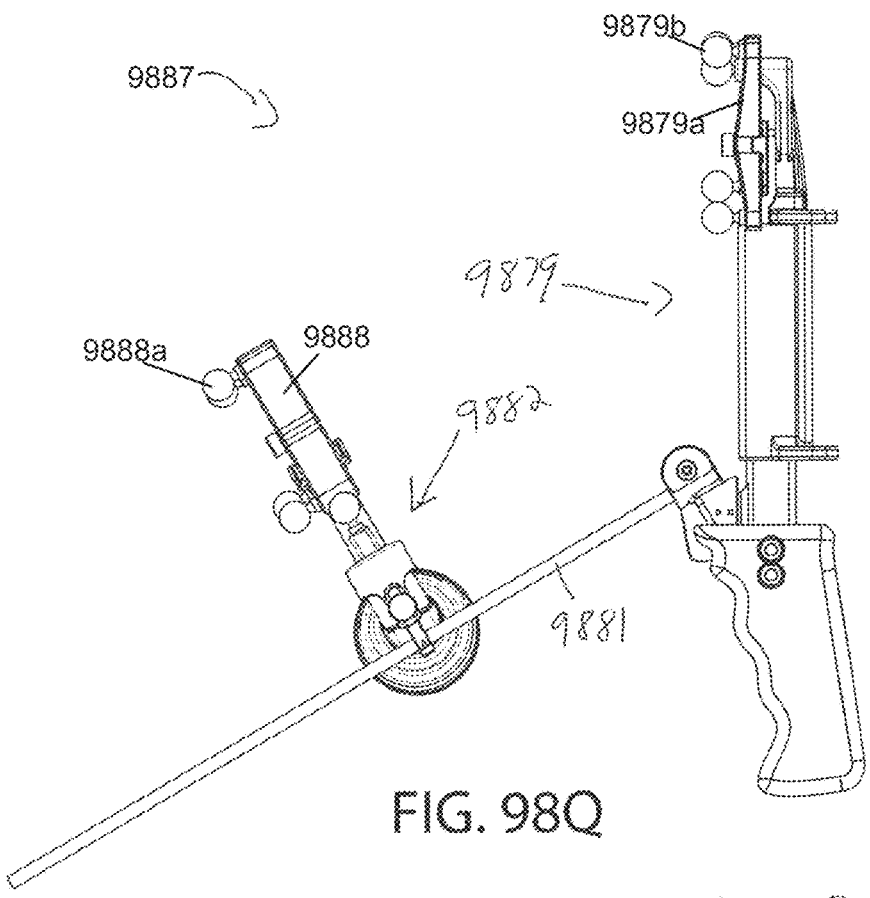
Figure 98R:
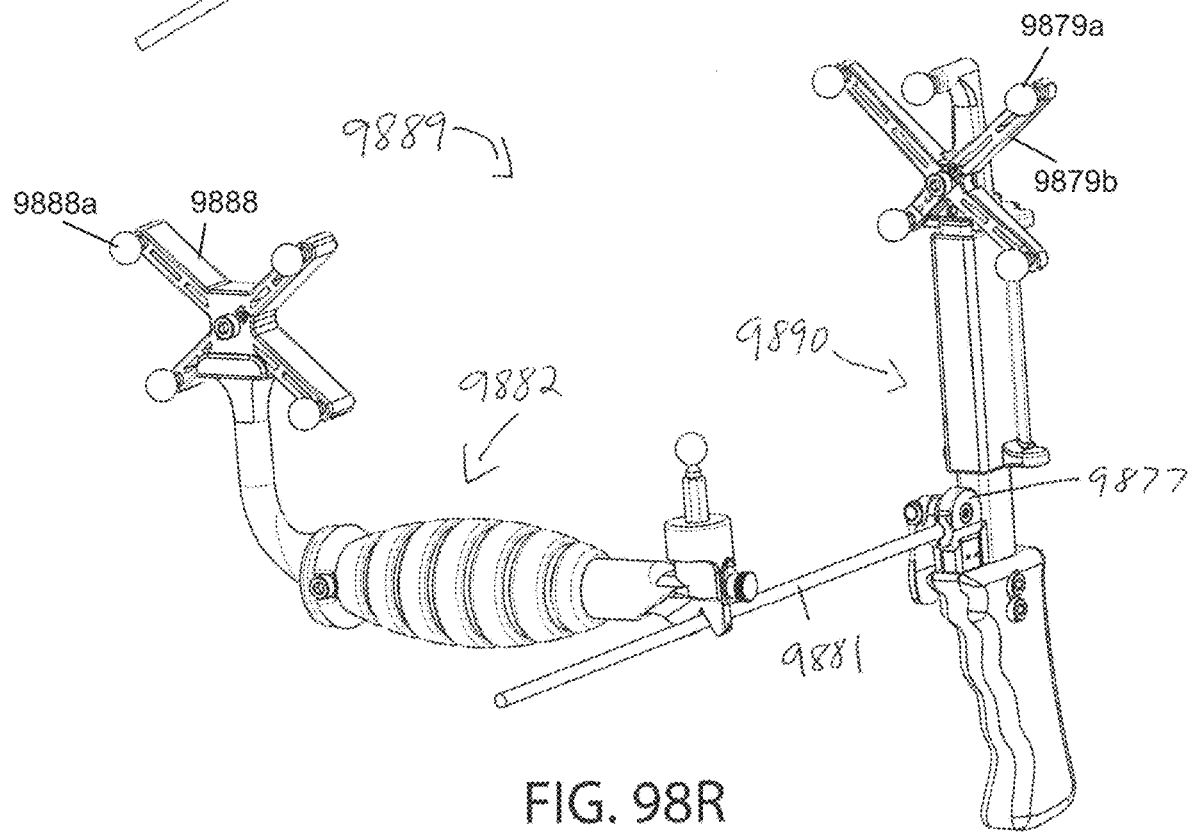
Figure 98S:
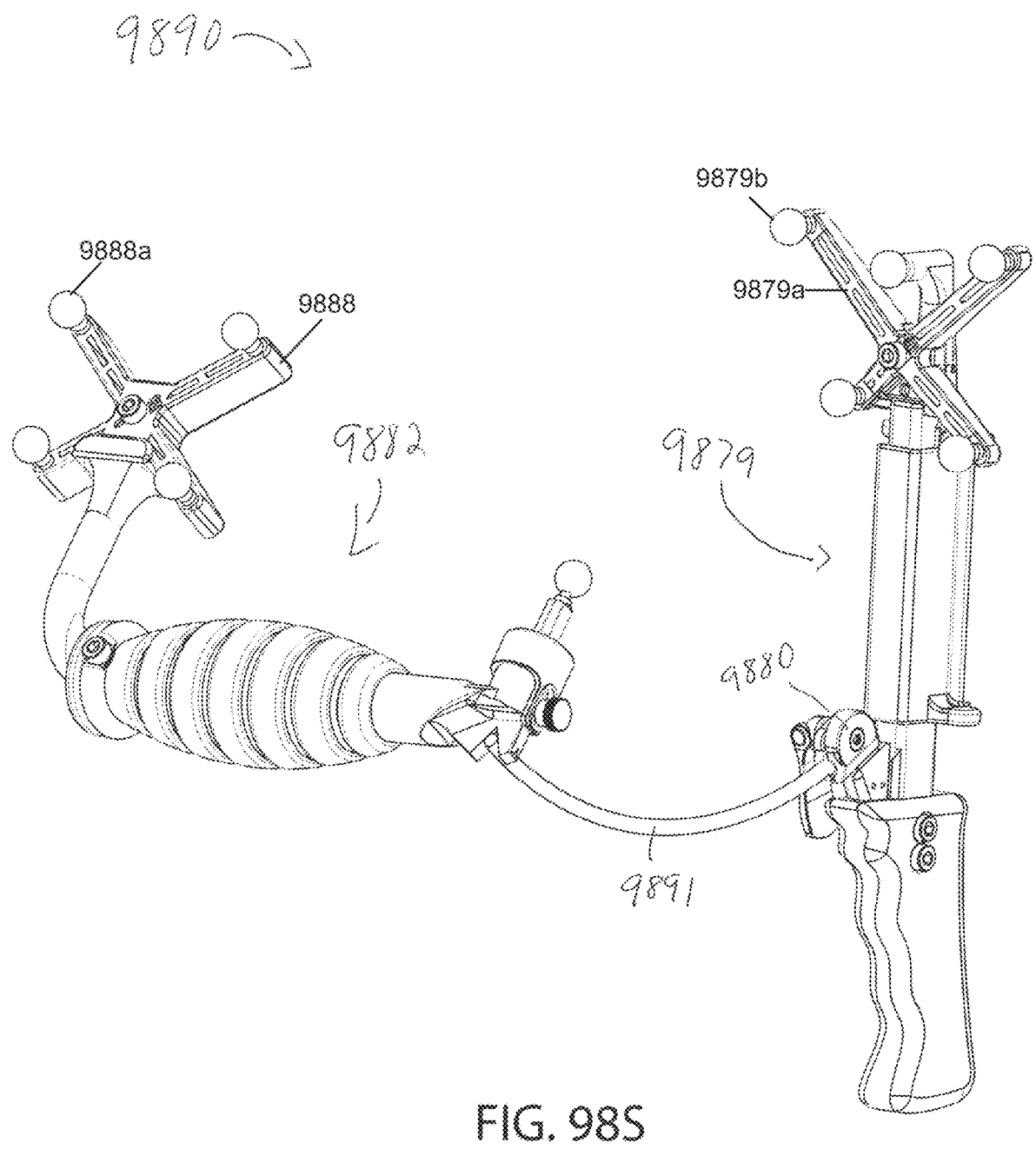
Figure 98T:
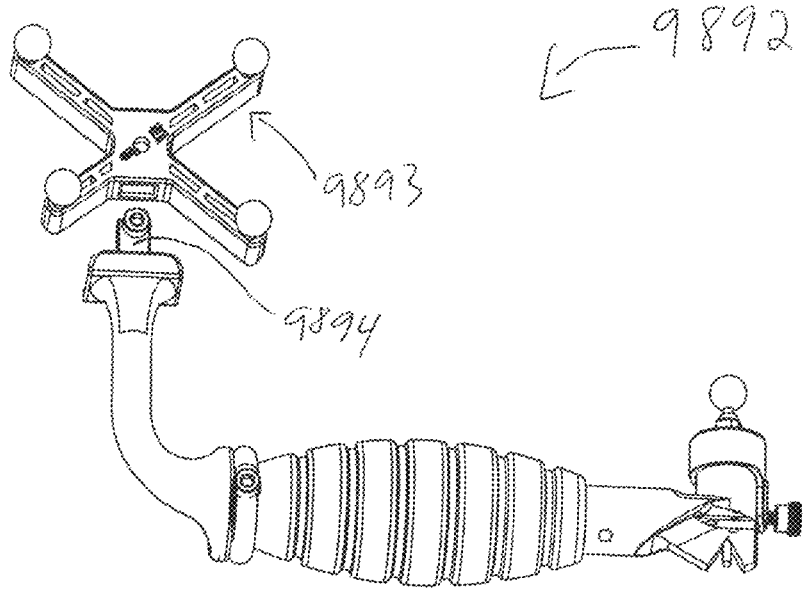
Figure 98U:
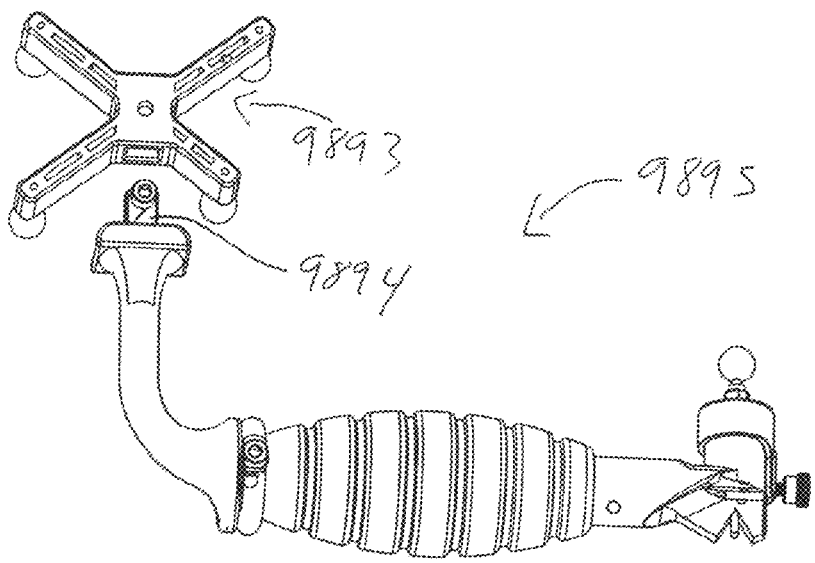
Figure 98V:
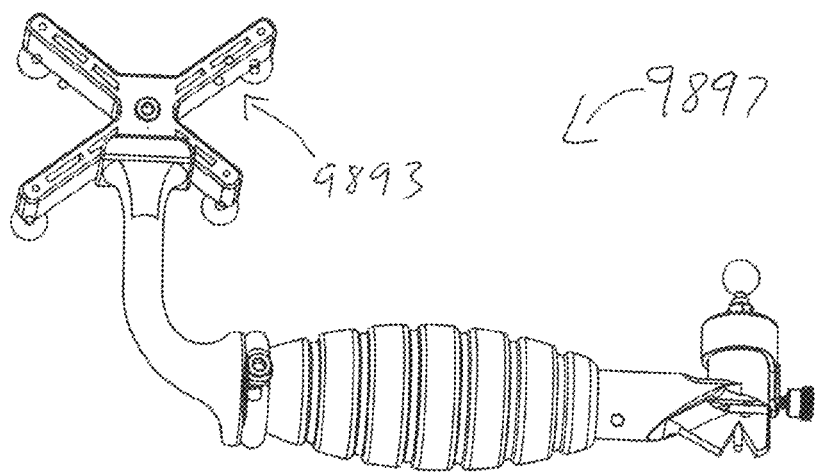

FIGS. 98T-98V illustrate perspective views of a rod contour registration tool with a reversible DRF-mounting mechanism as described previously in relation to FIGS. 98A-98S in accordance with some embodiments of the invention.

FIG. 99A illustrates a front view of a rod contour registration tool attachment in an inactive triggering state in accordance with some embodiments of the invention.

FIG. 99B illustrates a front view of a rod contour registration tool attachment in an active triggering state as described previously in relation to FIG. 99A in accordance with some embodiments of the invention.

FIG. 99C illustrates a perspective view of a rod contour registration tool attachment in an inactive triggering state as described previously in relation to FIGS. 99A-99B in accordance with some embodiments of the invention.

FIG. 99D illustrates a side view of a rod contour registration tool attachment as described previously in relation to FIGS. 99A-99C in accordance with some embodiments of the invention.

Figure 99E:
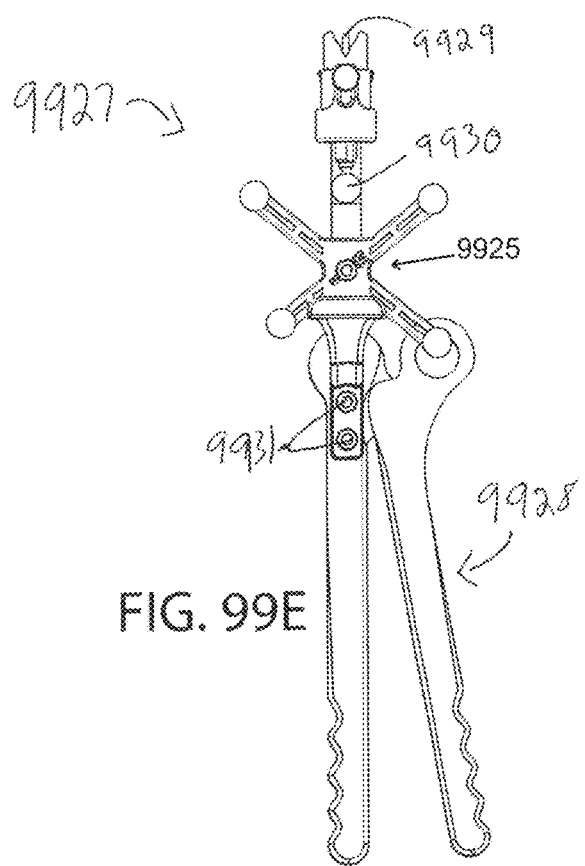
Figure 99F:
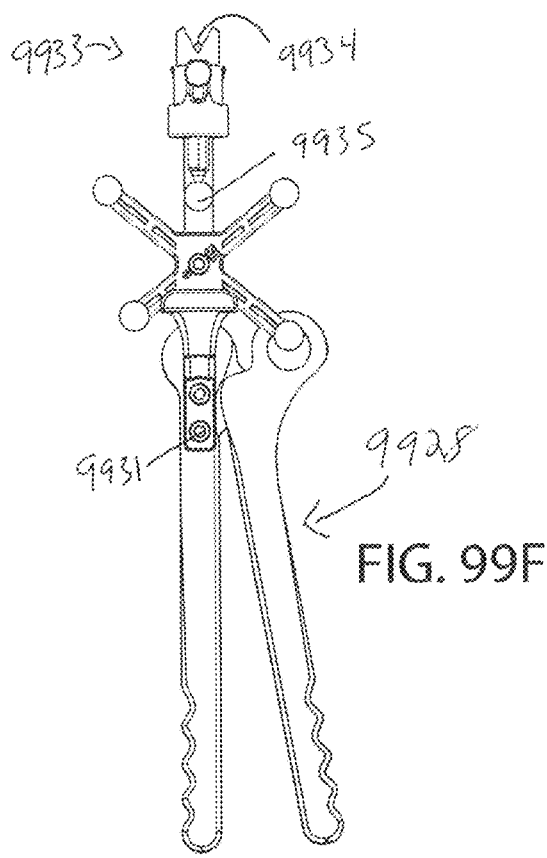

FIGS. 99E-99F illustrate rear views of a rod bender with a rod contour registration tool attachment mounted onto the rod bender as described previously in relation to FIGS. 99A-99D in accordance with some embodiments of the invention.

Figure 99G:
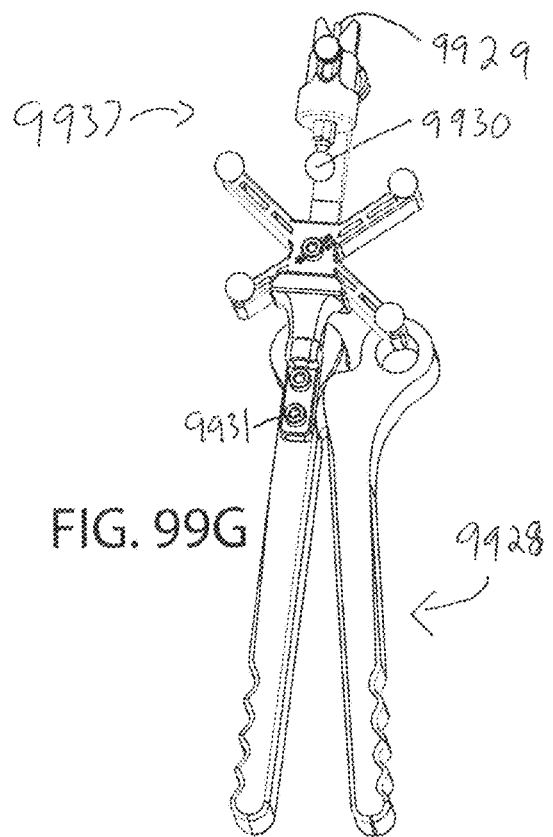
Figure 99H:
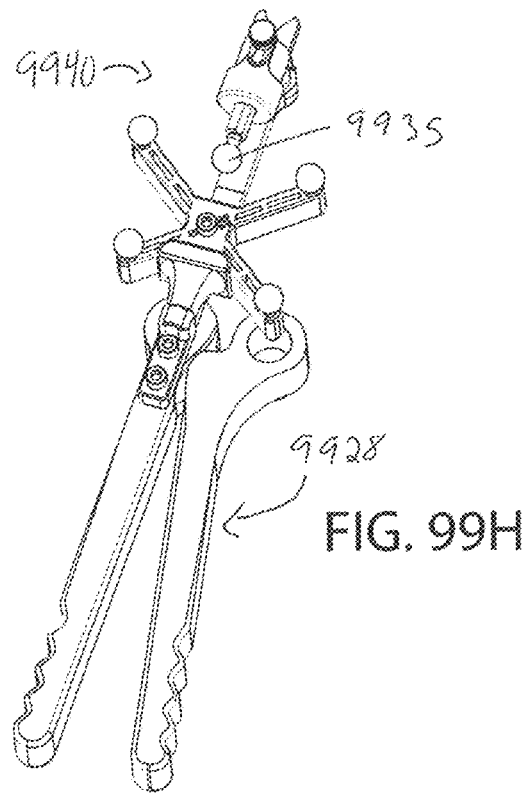

FIGS. 99G-99H illustrate back perspective views of a rod bender with a rod contour registration tool attachment mounted onto the rod bender as described previously in relation to FIGS. 99A-99F in accordance with some embodiments of the invention.

Figure 99I:
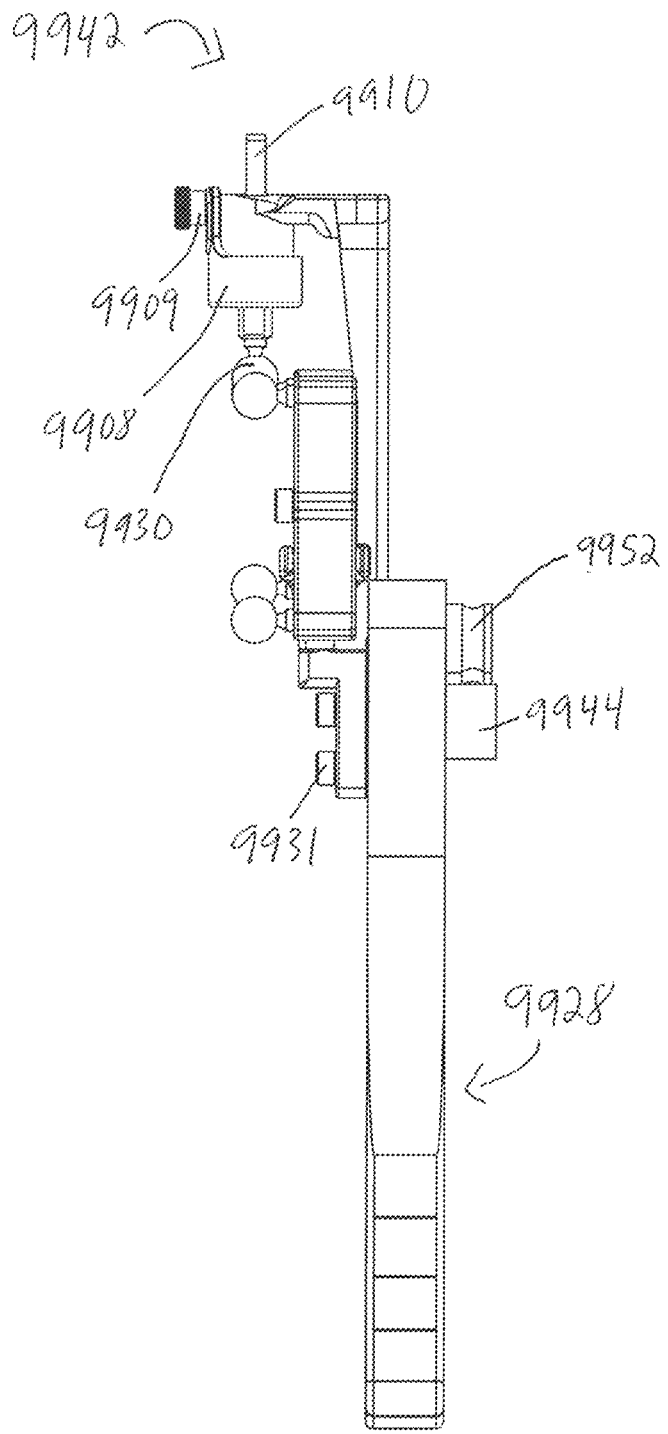
Figure 99J:
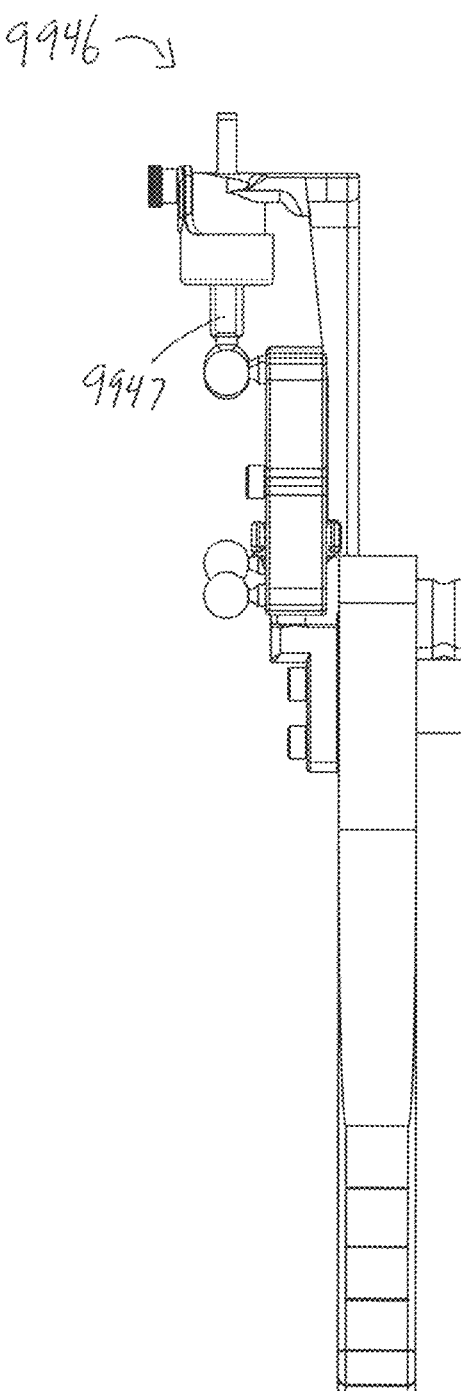

FIGS. 99I-99J illustrate side views of a rod bender with a rod contour registration tool attachment mounted onto the rod bender, with the trigger in an active and inactive state as described previously in relation to FIGS. 99A-99H in accordance with some embodiments of the invention.

Figure 99K:
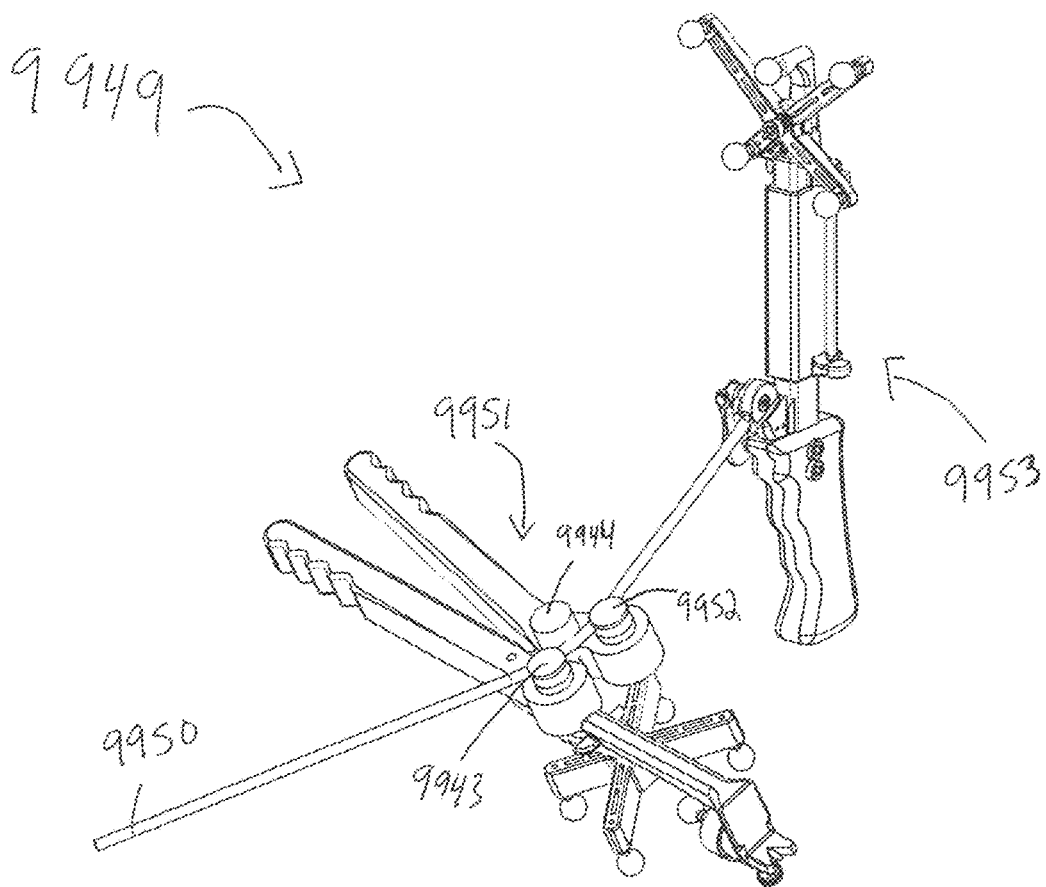
Figure 99L:
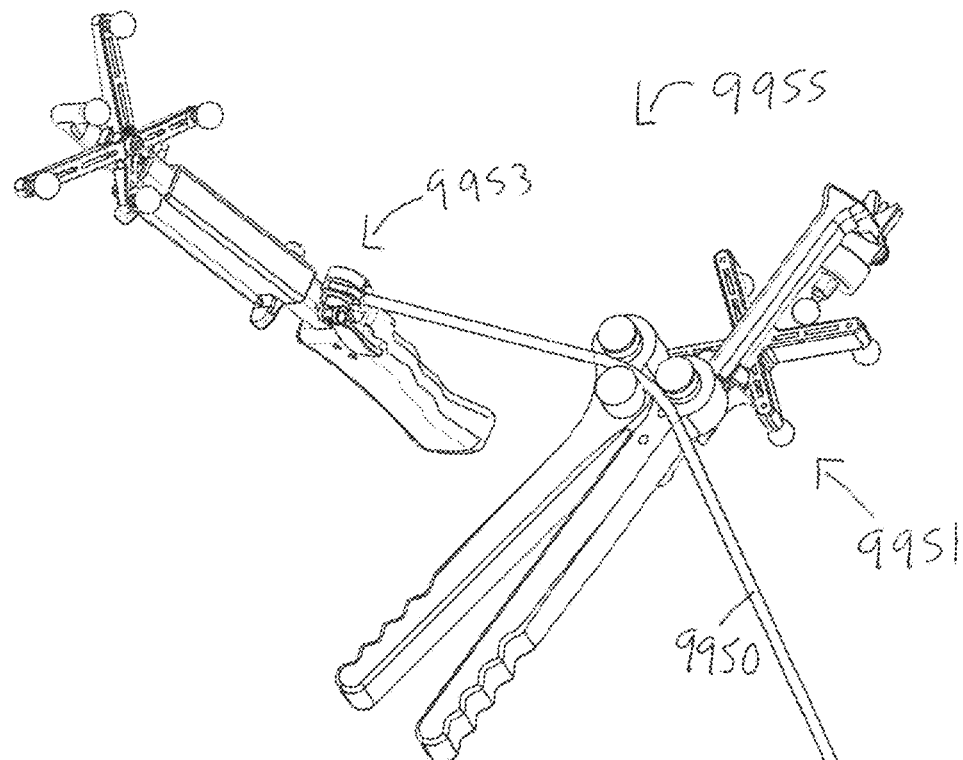

FIGS. 99K-99L illustrate perspective views of a rod bender with a rod contour registration tool attachment mounted onto the rod bender, with the rod bender actively contouring a rod mounted to a coordinate reference tool, as described previously in relation to FIGS. 99A-99J in accordance with some embodiments of the invention.

Figure 99M:
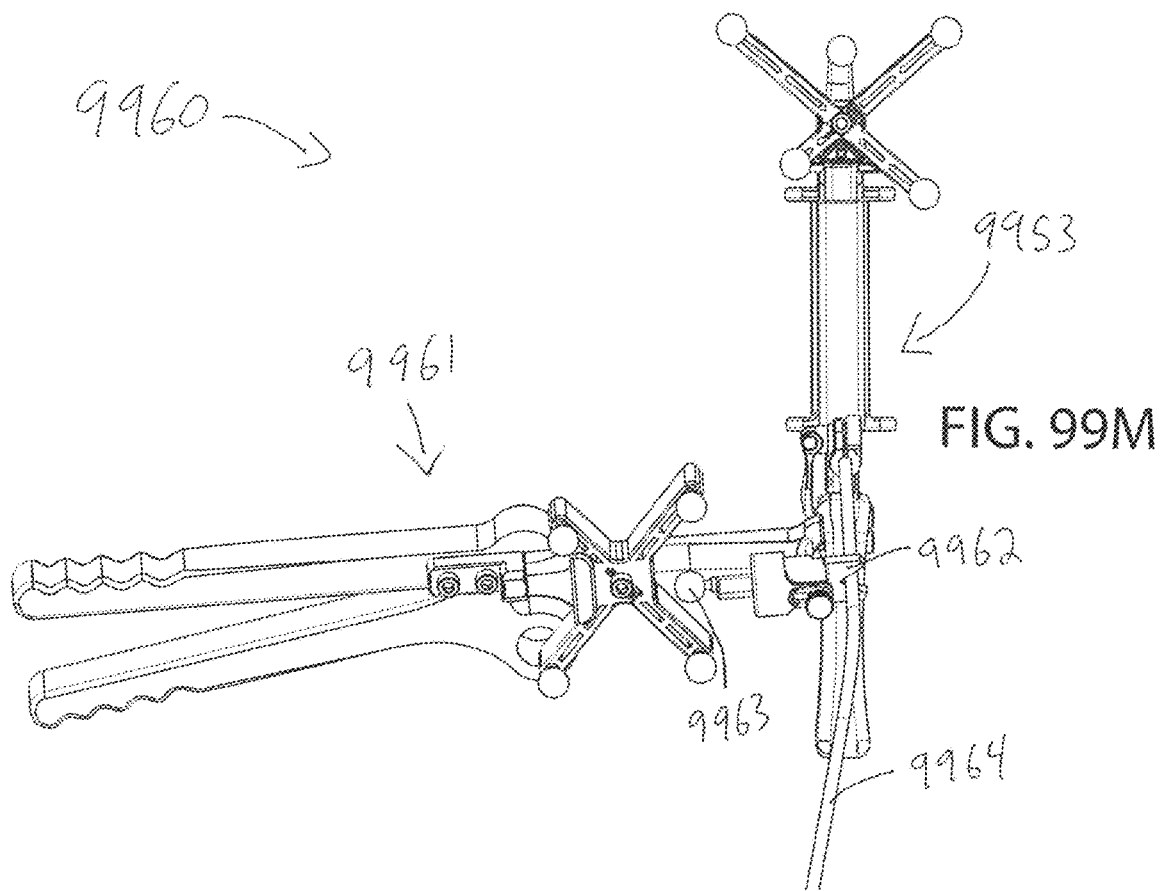
Figure 99N:
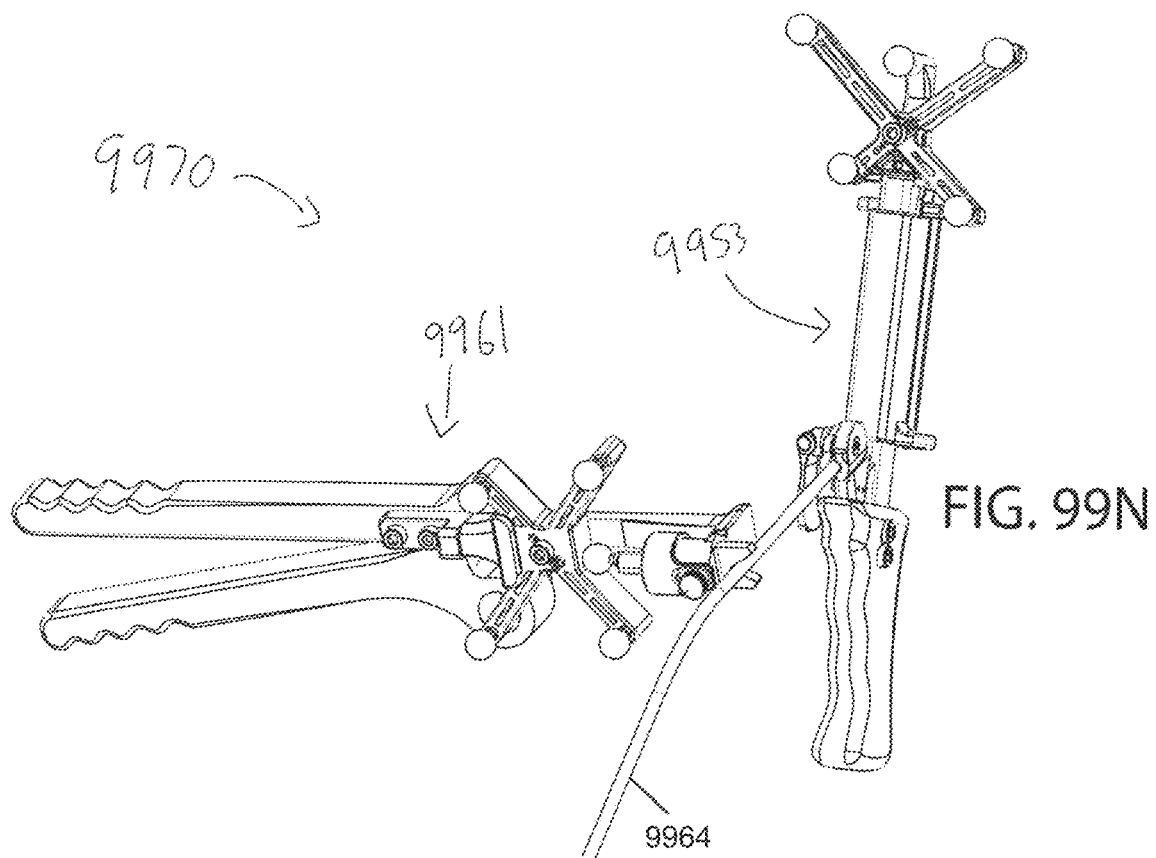

FIGS. 99M-99N illustrate perspective views of a rod bender with a rod contour registration tool attachment mounted onto the rod bender, with the rod bender attachment actively tracing the contour of a rod mounted to a coordinate reference tool, as described previously in relation to FIGS. 99A-99L in accordance with some embodiments of the invention.

Figure 99O:
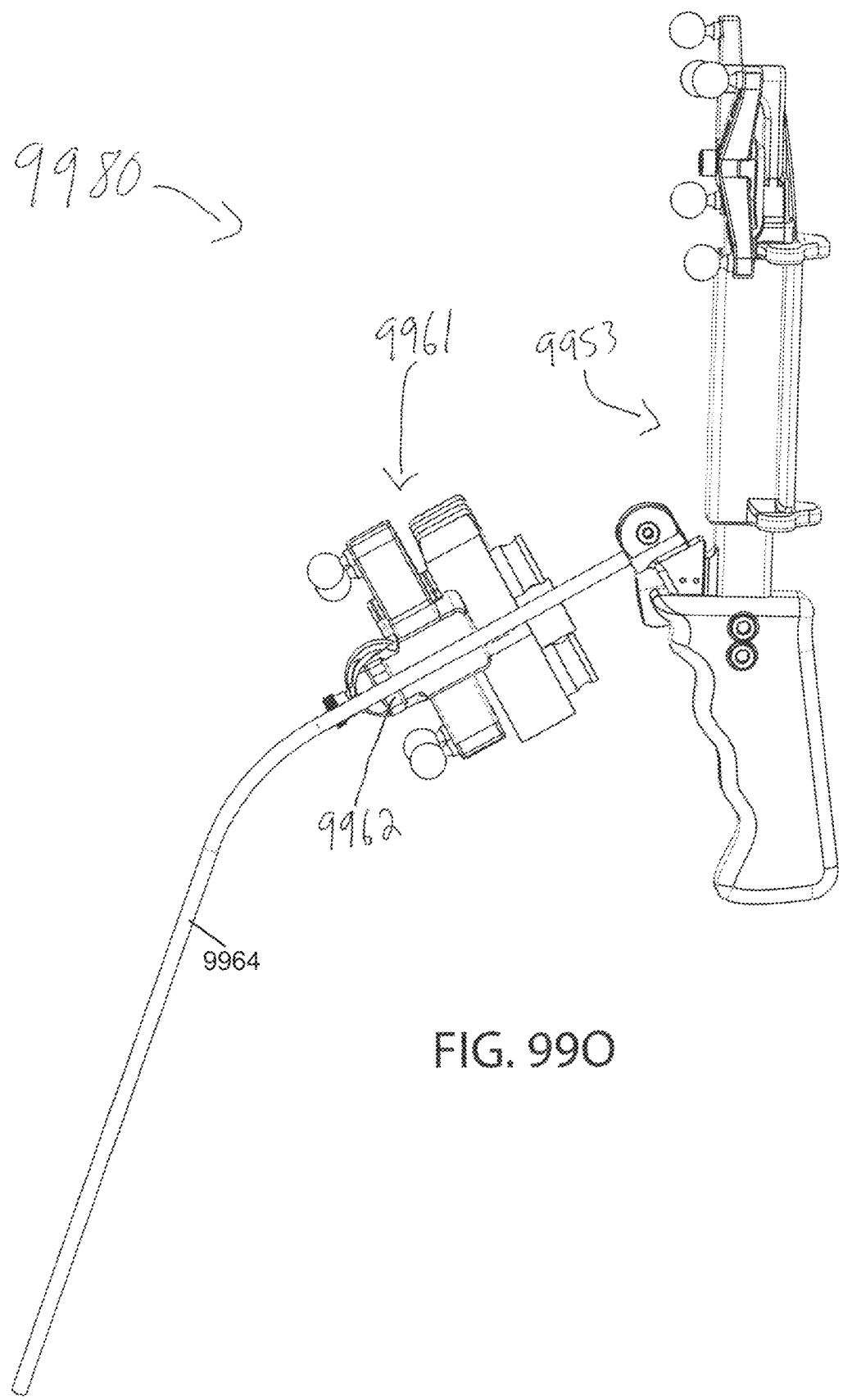

FIG. 99O illustrates a side view of a rod bender with a rod contour registration tool attachment mounted onto the rod bender, with the rod bender attachment actively tracing the contour of a rod mounted to a coordinate reference tool, as described previously in relation to FIGS. 99A-99N in accordance with some embodiments of the invention.

Figure 100A:
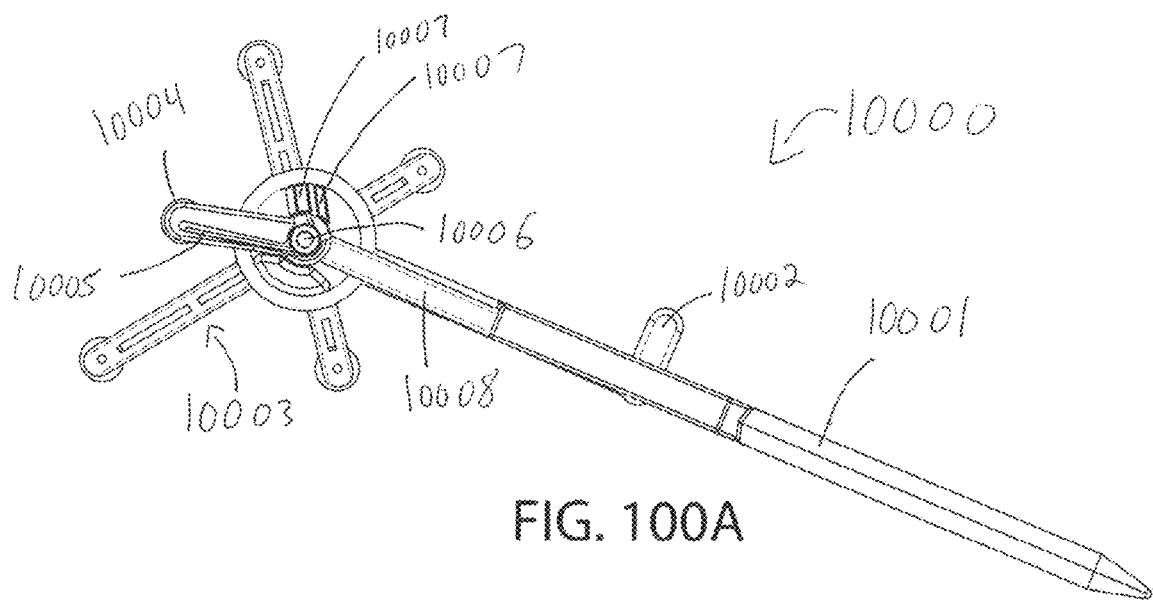

FIG. 100A illustrates a rear view of a 3D-tracked tool with a rotational triggering mechanism and the tool in an inactive state in accordance with some embodiments of the invention.

Figure 100B:
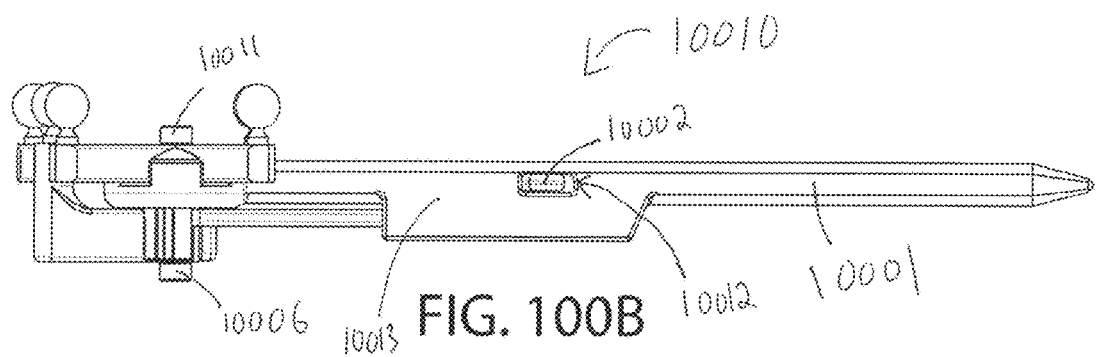

FIG. 100B illustrates a side view of a 3D-tracked tool with a rotational triggering mechanism and the tool in an inactive state, as described previously in relation to FIG. 100A in accordance with some embodiments of the invention.

Figure 100C:
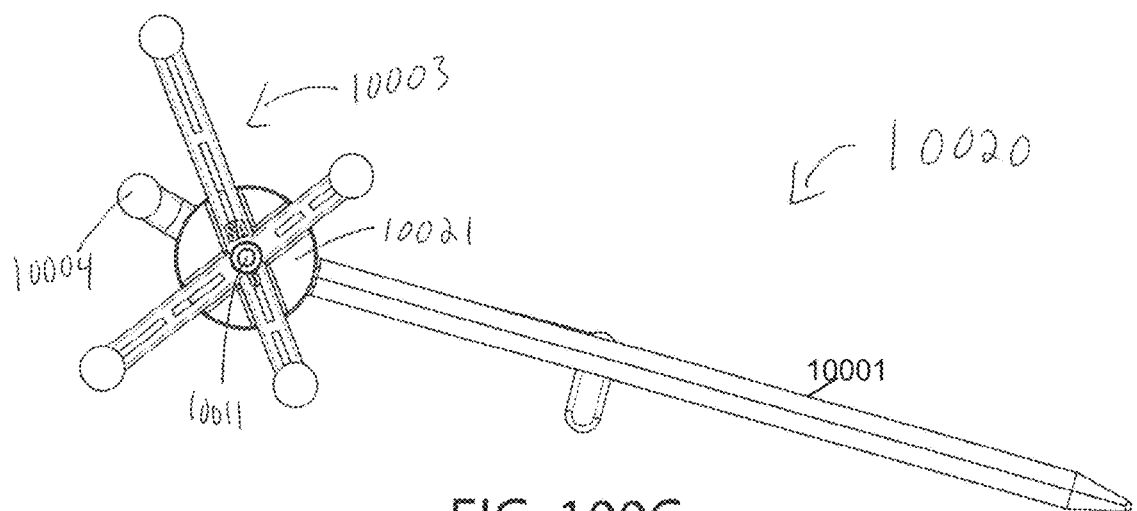

FIG. 100C illustrates a front view of a 3D-tracked tool with a rotational triggering mechanism and the tool in an inactive state, as described previously in relation to FIGS. 100A-100B in accordance with some embodiments of the invention.

Figure 100D:
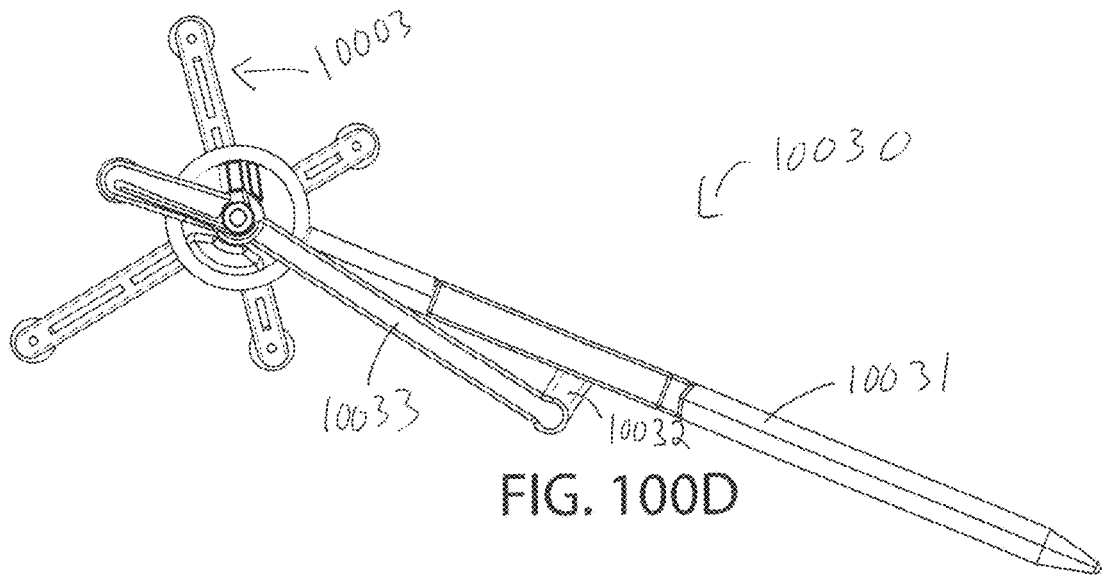

FIG. 100D illustrates a rear view of a 3D-tracked tool with a rotational triggering mechanism and the tool in an active state, as described previously in relation to FIGS. 100A-100C in accordance with some embodiments of the invention.

Figure 100E:
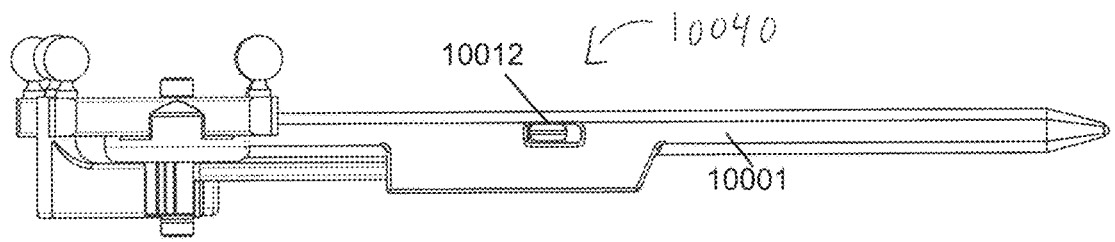

FIG. 100E illustrates a side view of a 3D-tracked tool with a rotational triggering mechanism and the tool in an active state, as described previously in relation to FIGS. 100A-100D in accordance with some embodiments of the invention.

Figure 100F:
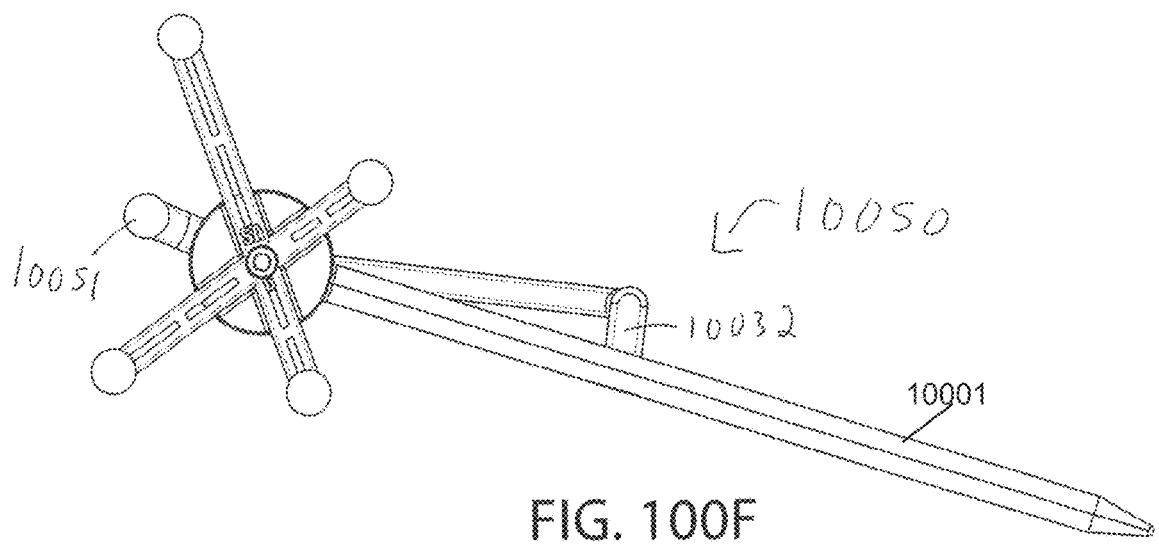

FIG. 100F illustrates a front view of a 3D-tracked tool with a rotational triggering mechanism and the tool in an active state, as described previously in relation to FIGS. 100A-100E in accordance with some embodiments of the invention.

Figure 101A:
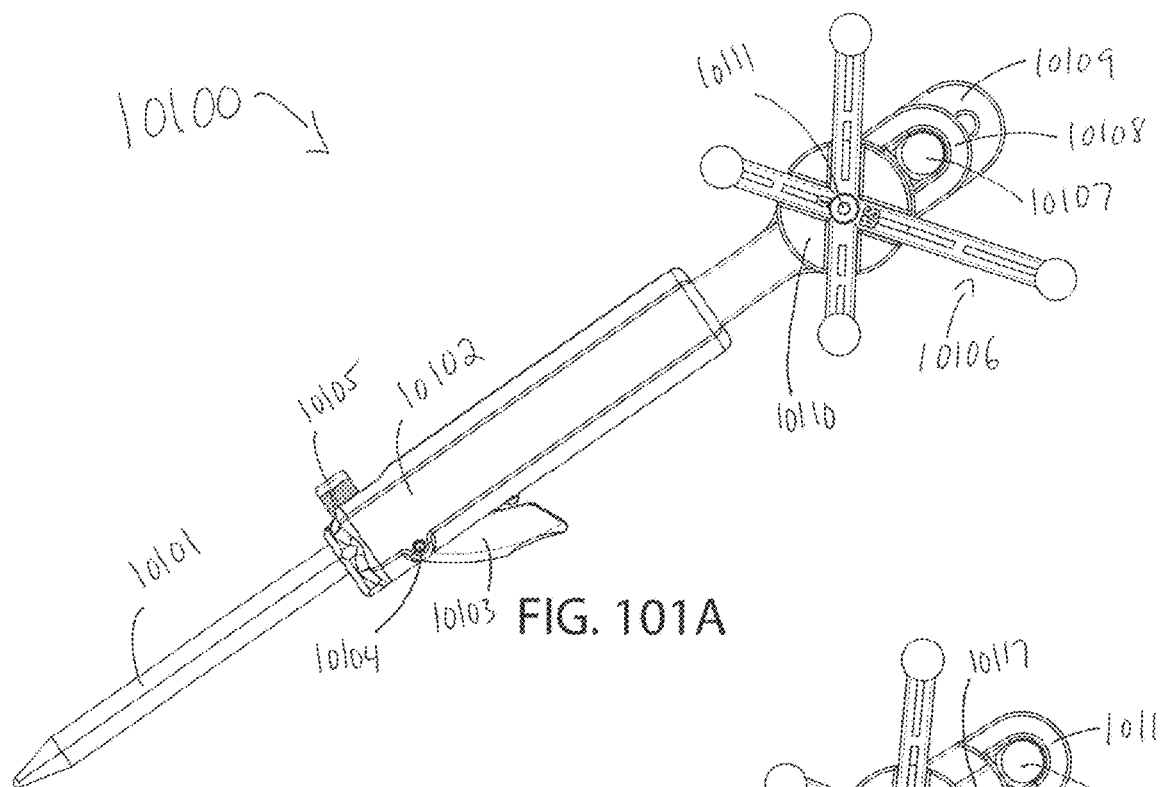

FIG. 101A illustrates a front view of a 3D-tracked tool with a linear triggering mechanism and the tool in an inactive state in accordance with some embodiments of the invention.

Figure 101B:
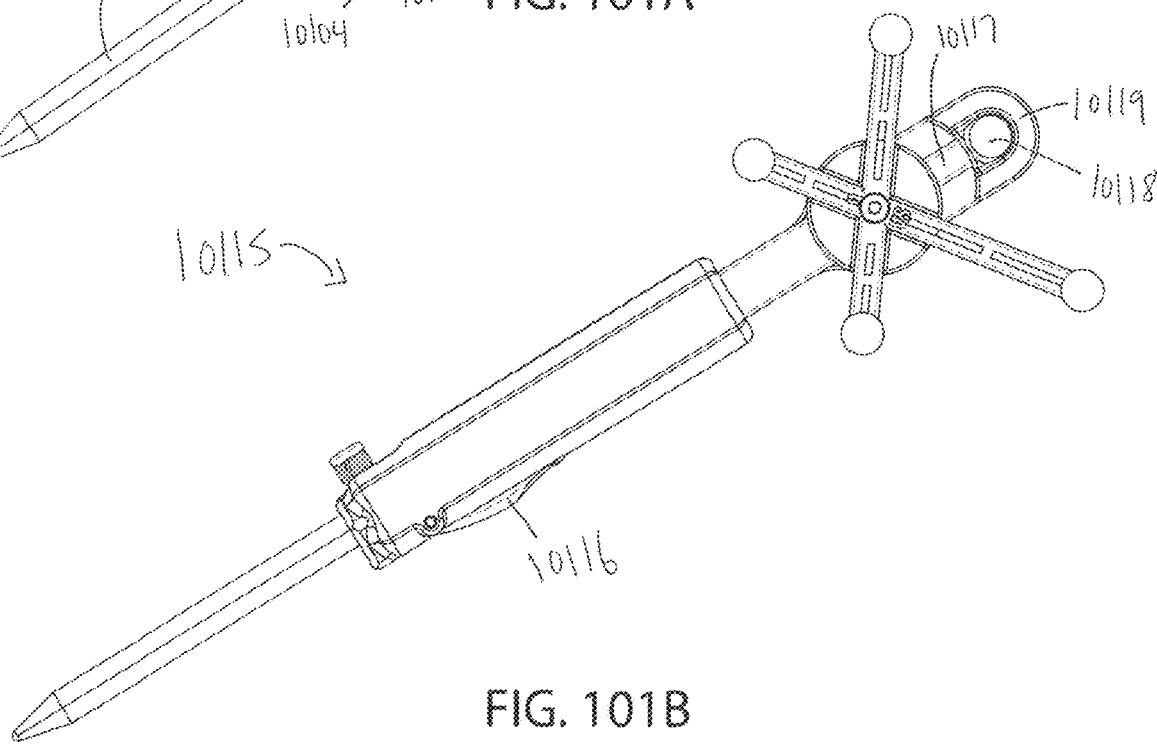

FIG. 101B illustrates a front view of a 3D-tracked tool with a linear triggering mechanism and the tool in an active state, as described previously in relation to FIG. 101A in accordance with some embodiments of the invention.

Figure 101C:
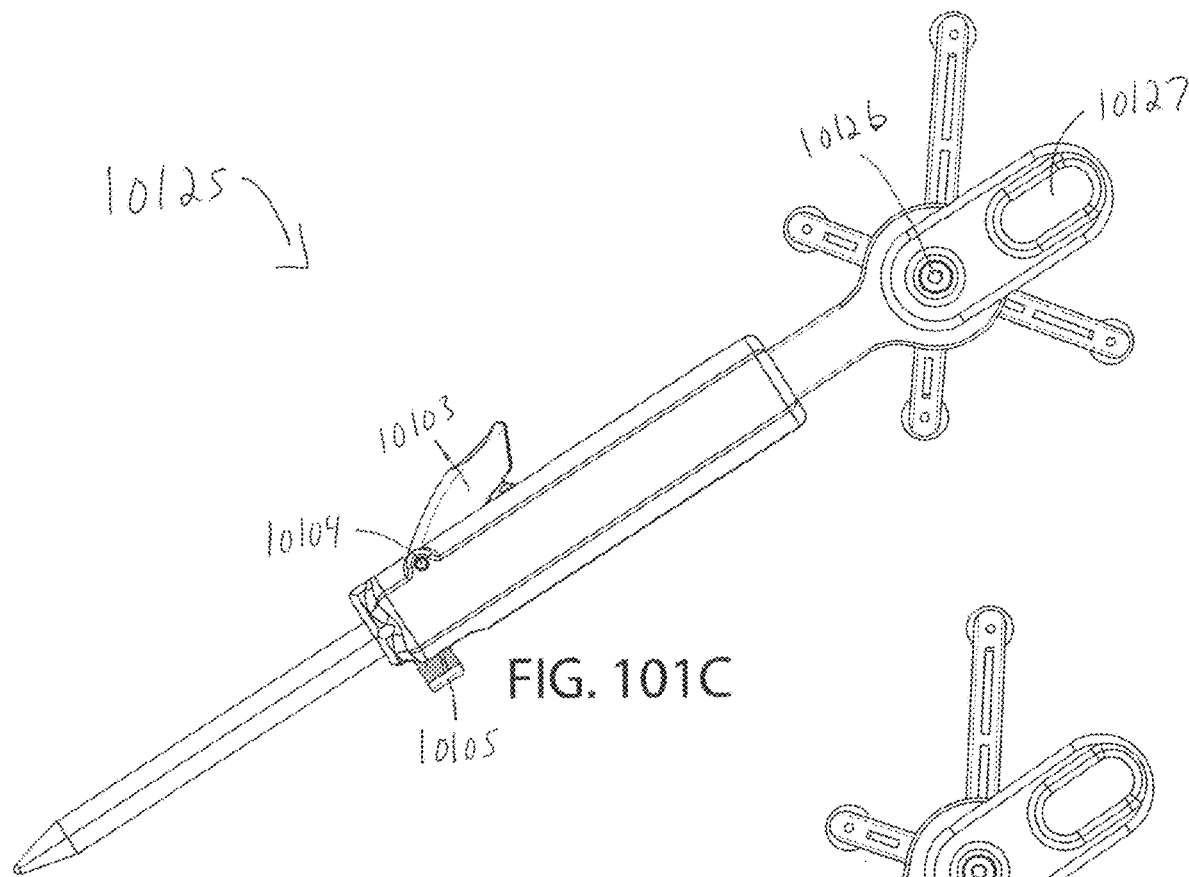

FIG. 101C illustrates a rear view of a 3D-tracked tool with a linear triggering mechanism and the tool in an inactive state, as described previously in relation to FIGS. 101A-101B in accordance with some embodiments of the invention.

Figure 101D:
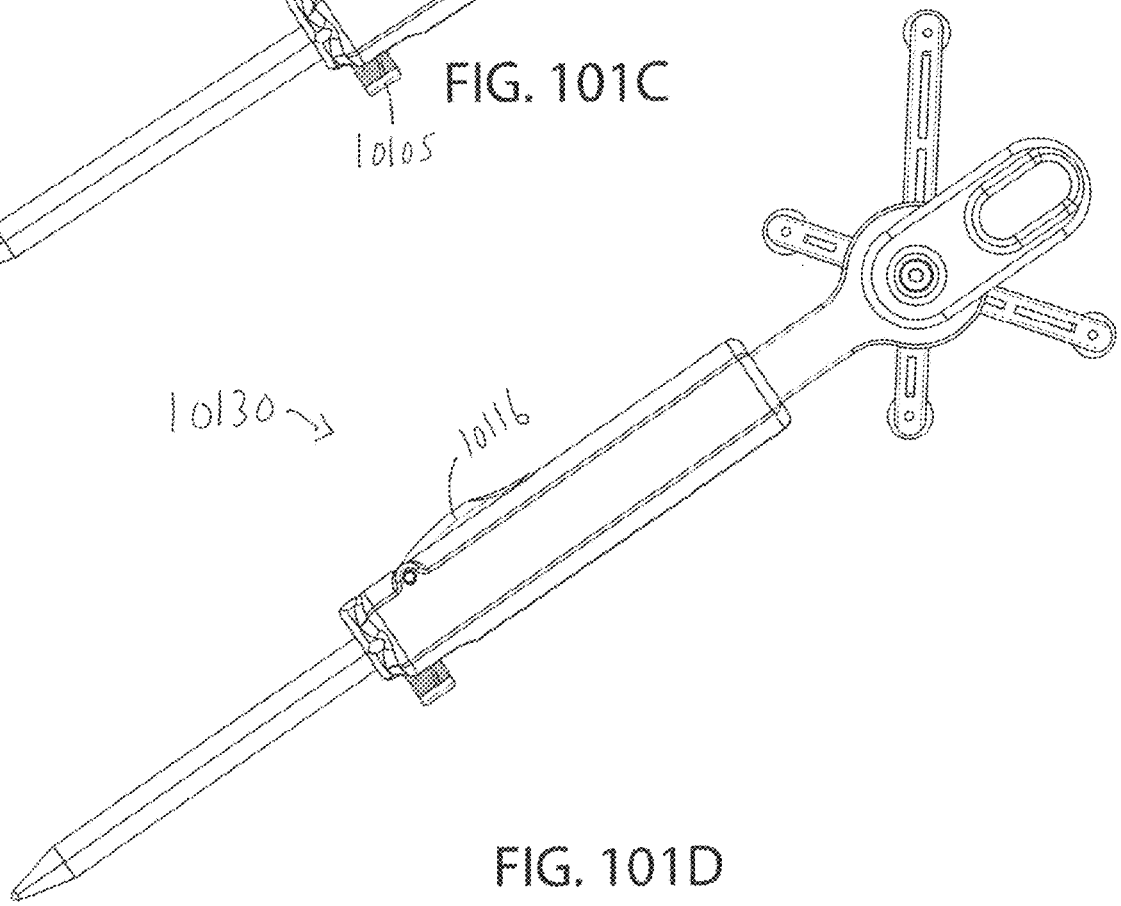

FIG. 101D illustrates a rear view of a 3D-tracked tool with a linear triggering mechanism and the tool in an active state, as described previously in relation to FIGS. 101A-101C in accordance with some embodiments of the invention.

Figure 101E:
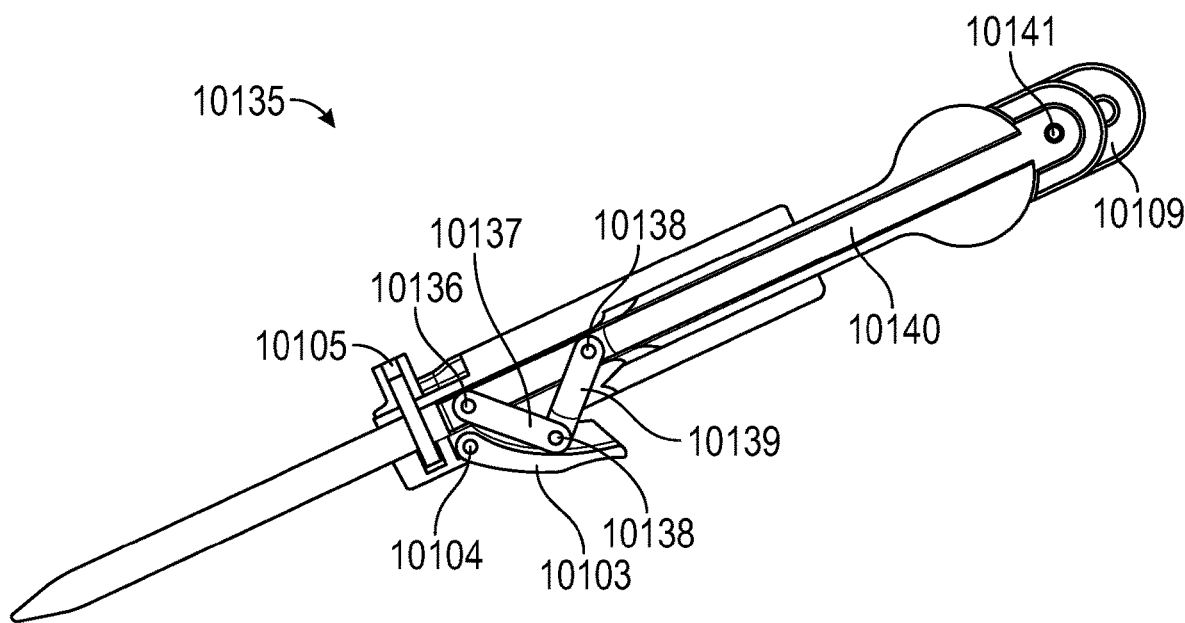

FIG. 101E illustrates a cross-sectional view of a 3D-tracked tool with a linear triggering mechanism and the tool in an inactive state, as described previously in relation to FIGS. 101A-101D in accordance with some embodiments of the invention.

Figure 101F:
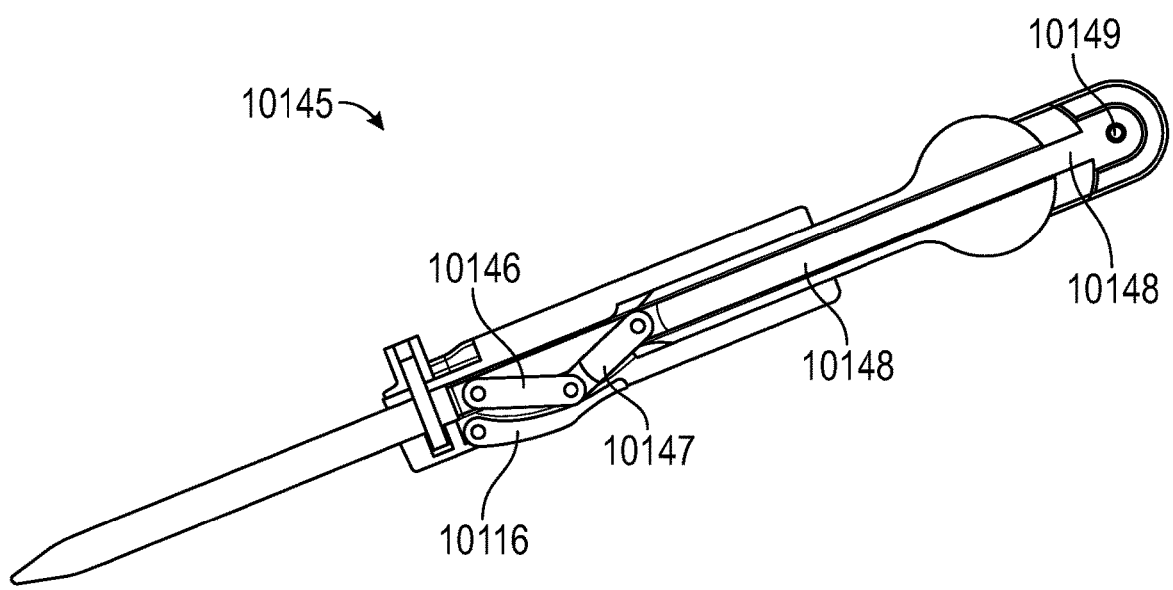

FIG. 101F illustrates a cross-sectional view of a 3D-tracked tool with a linear triggering mechanism and the tool in an active state, as described previously in relation to FIGS. 101A-101E in accordance with some embodiments of the invention.

Figure 101G:
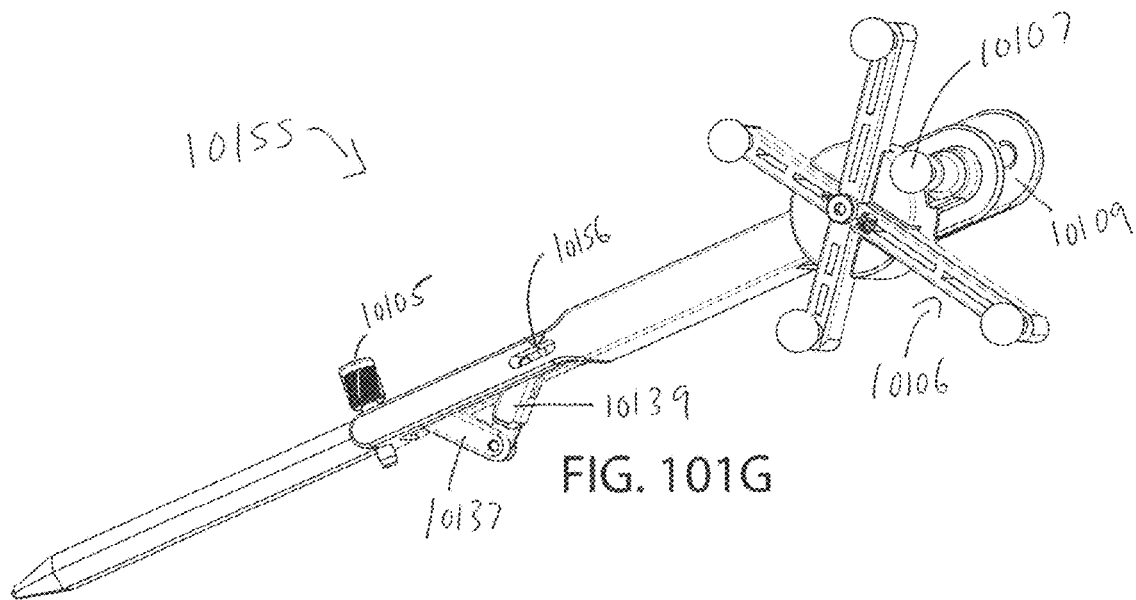

FIG. 101G illustrates a front view of a 3D-tracked tool without a trigger sleeve and with a linear triggering mechanism (oriented for a left-hand-dominant user) and the tool in an inactive state, as described previously in relation to FIGS. 101A-101F in accordance with some embodiments of the invention.

Figure 101H:
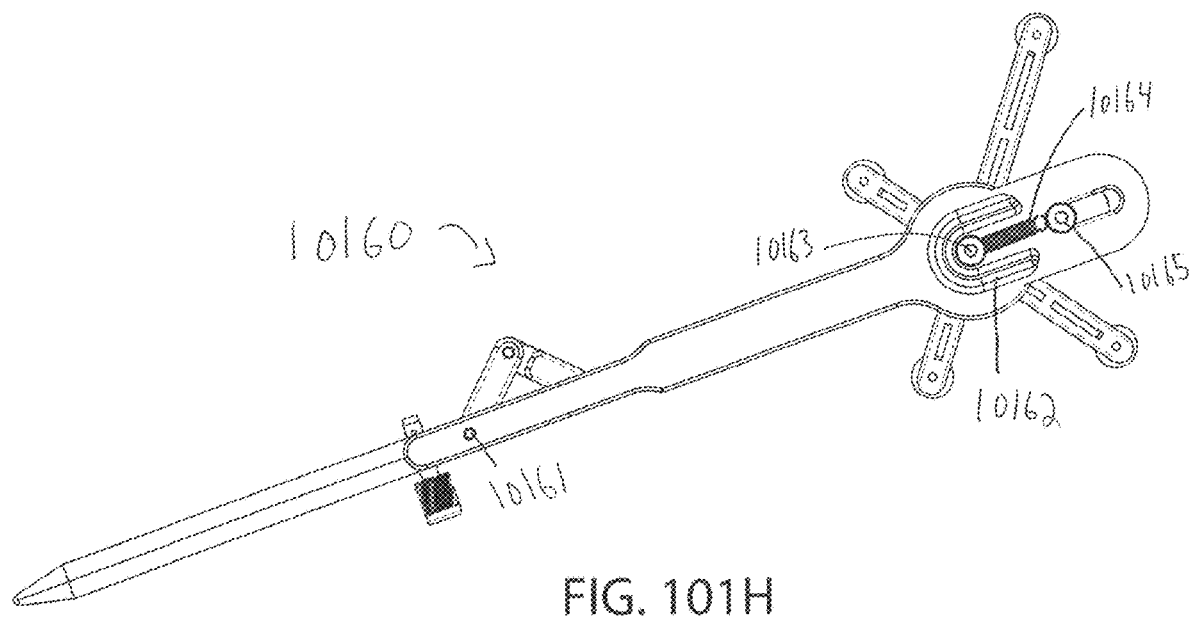

FIG. 101H illustrates a rear view of a 3D-tracked tool without a trigger sleeve and with a linear triggering mechanism (oriented for a left-hand-dominant user) and the tool in an inactive state, as described previously in relation to FIGS. 101A-101G in accordance with some embodiments of the invention.

Figure 101I:
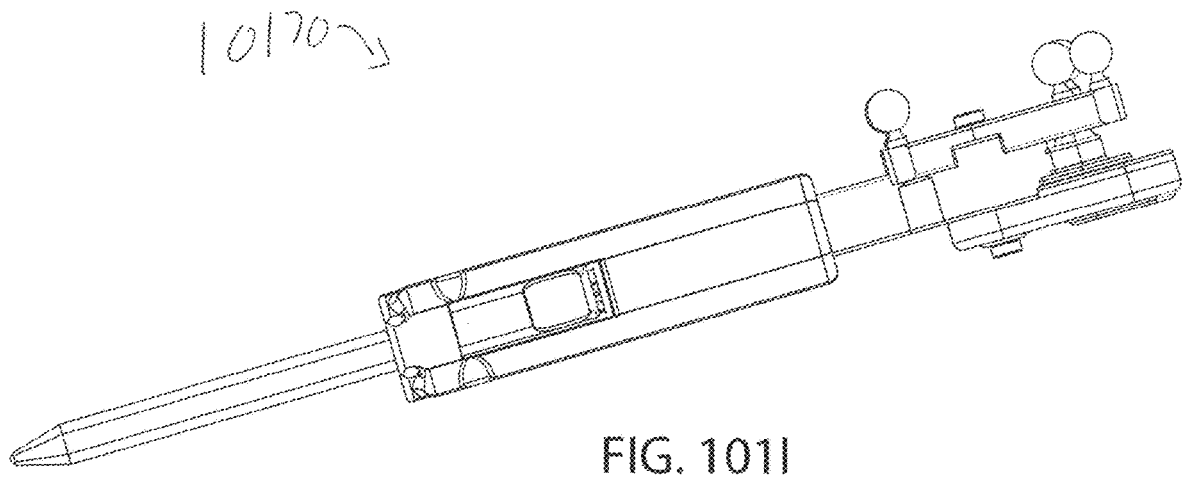

FIG. 101I illustrates a side view of a 3D-tracked tool with a linear triggering mechanism and the tool in an inactive state, as described previously in relation to FIGS. 101A-101H in accordance with some embodiments of the invention.

Figure 101J:
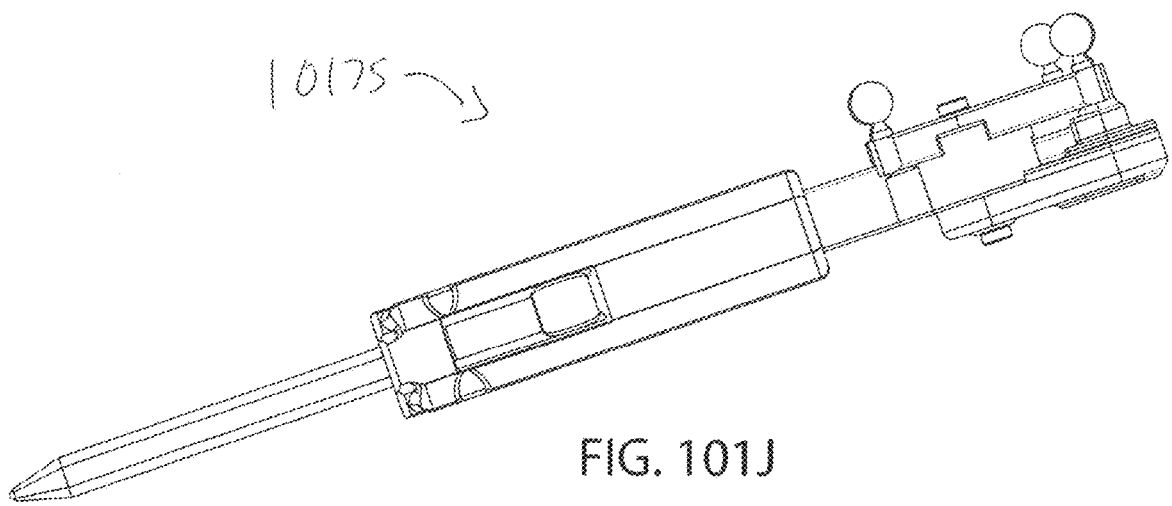

FIG. 101J illustrates a side view of a 3D-tracked tool with a linear triggering mechanism and the tool in an active state, as described previously in relation to FIGS. 101A-101I in accordance with some embodiments of the invention.

Figure 101K:
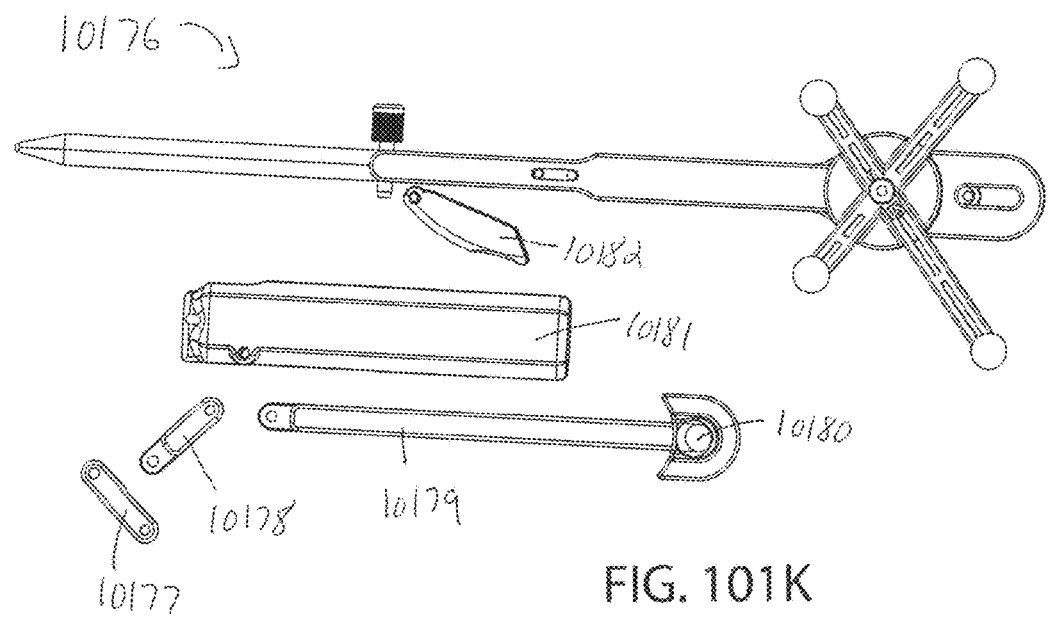

FIG. 101K illustrates an assembly view of a 3D-tracked tool with a linear triggering mechanism as described previously in relation to FIGS. 101A-101J in accordance with some embodiments of the invention.

FIGS. 101L-101O illustrate perspective views of a trigger sleeve of a 3D-tracked tool with a linear triggering mechanism as described previously in relation to FIGS. 101A-101K in accordance with some embodiments of the invention.

Figures 101L, 101M, 101N, 101O:
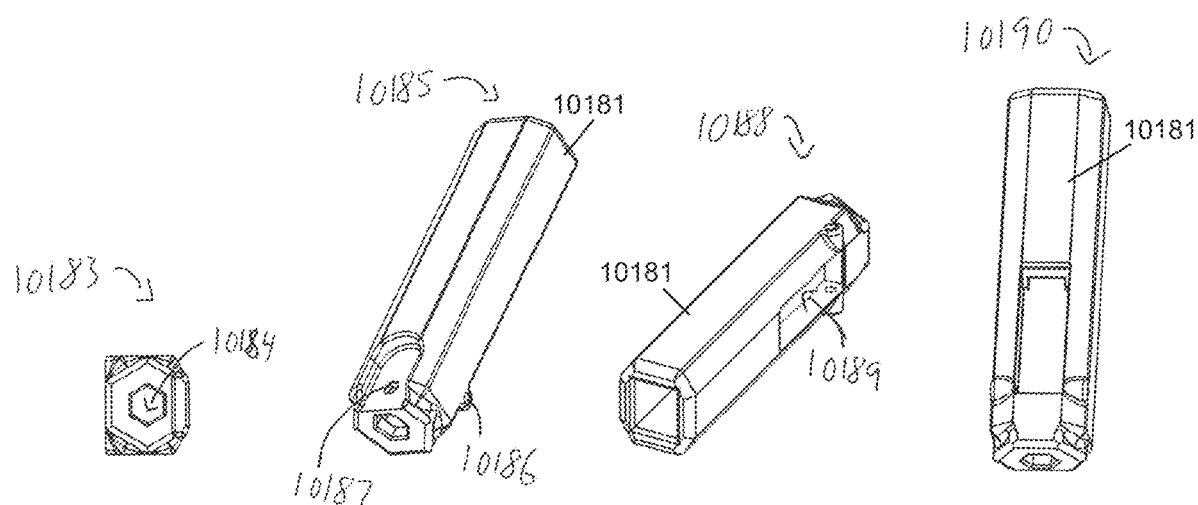
Figure 101P:
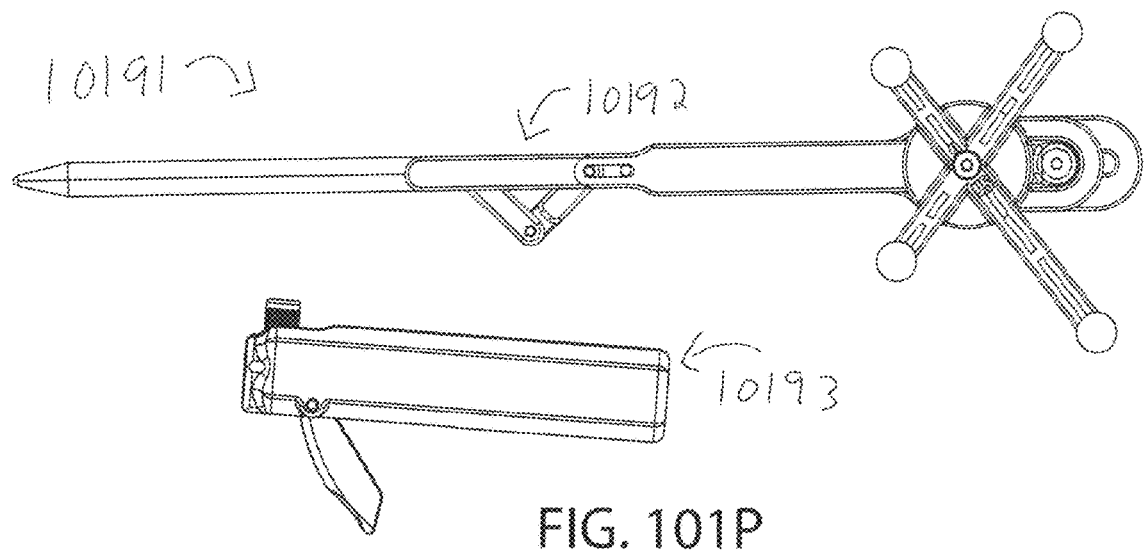

FIG. 101P illustrates an assembly view of a 3D-tracked tool with a linear triggering mechanism, with the trigger sleeve oriented for a left-hand-dominant user, as described previously in relation to FIGS. 101A-101O in accordance with some embodiments of the invention.

Figure 101Q:
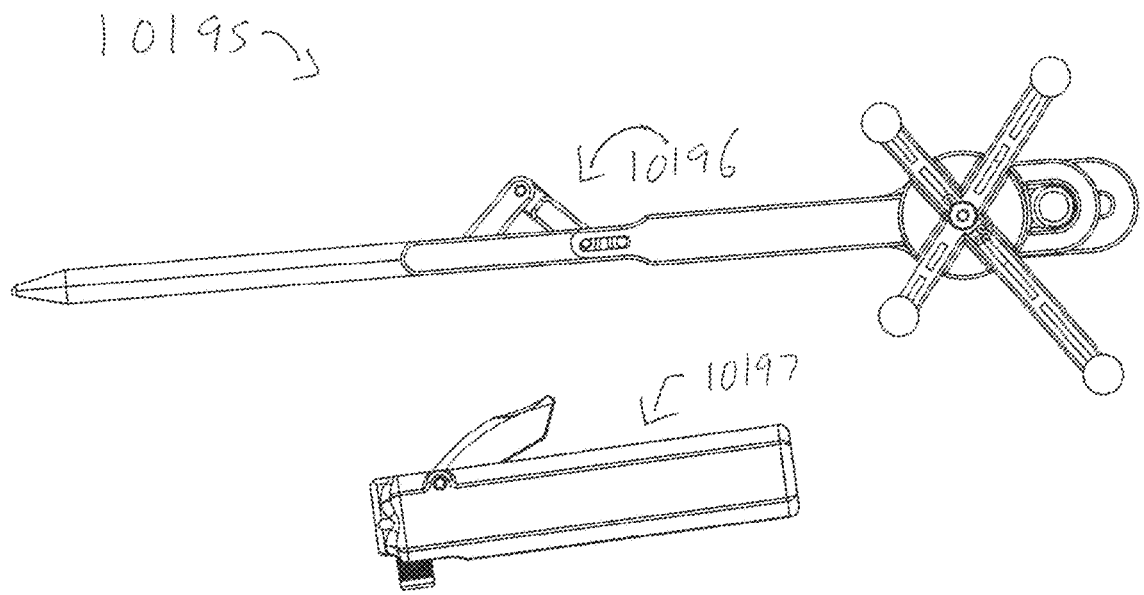

FIG. 101Q illustrates an assembly view of a 3D-tracked tool with a linear triggering mechanism, with the trigger sleeve oriented for a right-hand-dominant user, as described previously in relation to FIGS. 101A-101P in accordance with some embodiments of the invention.

Figure 102A:
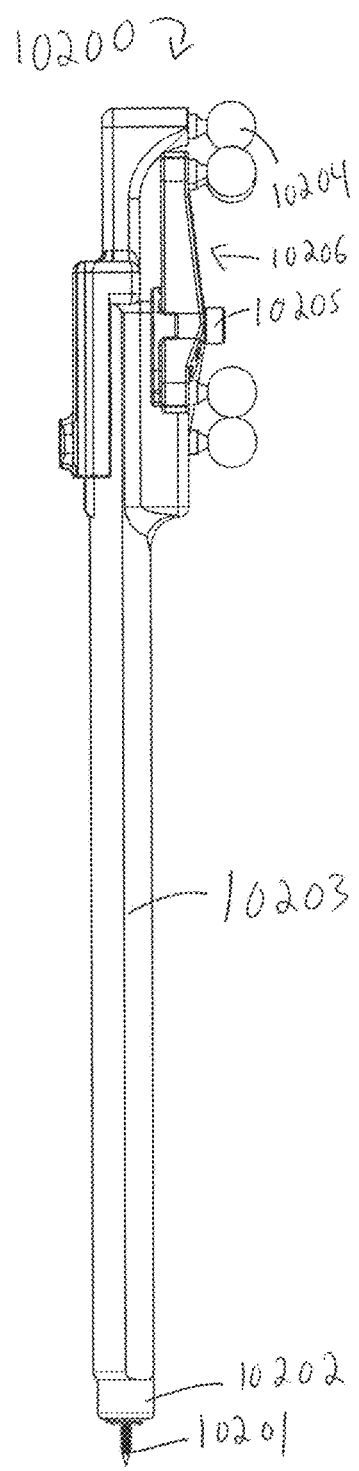

FIG. 102A illustrates a side view of a 3D-tracked tool engaged with an external-mating bone-mounted fiducial in accordance with some embodiments of the invention.

Figure 102B:
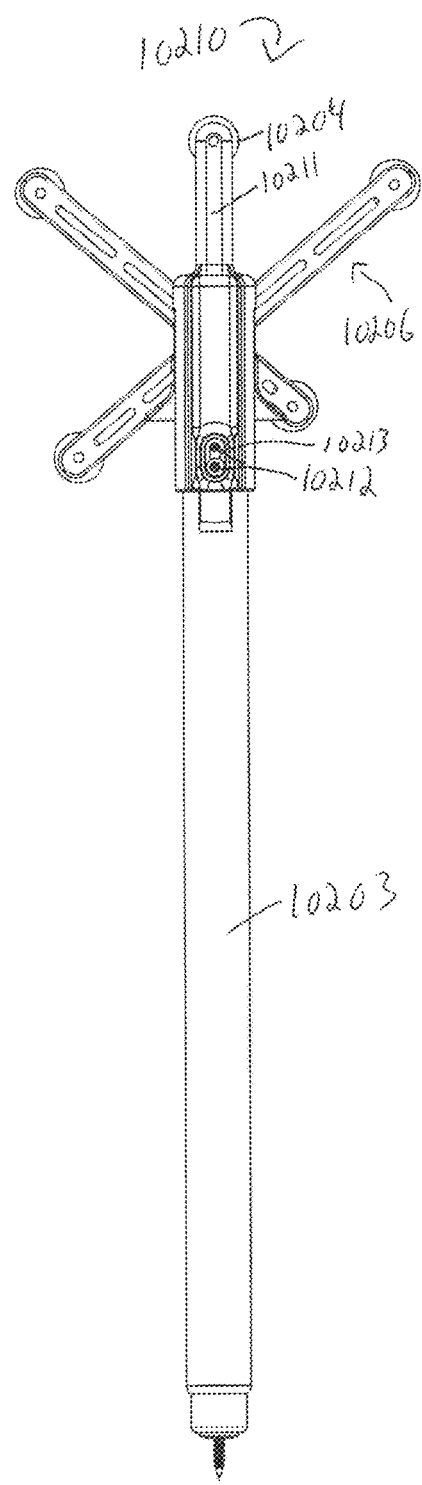

FIG. 102B illustrates a rear view of a 3D-tracked tool engaged with an external-mating bone-mounted fiducial as described previously in relation to FIG. 102A in accordance with some embodiments of the invention.

Figure 102C:
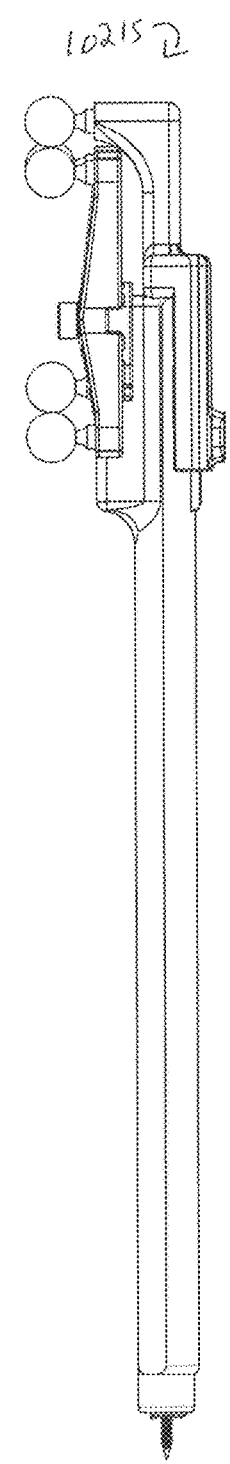

FIG. 102C illustrates a side view of a 3D-tracked tool engaged with an external-mating bone-mounted fiducial as described previously in relation to FIGS. 102A-102B in accordance with some embodiments of the invention.

FIG. 102D illustrates a perspective assembly view of a 3D-tracked tool that is not engaged with an external-mating bone-mounted fiducial as described previously in relation to FIGS. 102A-102C in accordance with some embodiments of the invention.

FIG. 102E illustrates a side assembly view of a 3D-tracked tool that is not engaged with an external-mating bone-mounted fiducial as described previously in relation to FIGS. 102A-102D in accordance with some embodiments of the invention.

FIG. 102F illustrates a front assembly view of a 3D-tracked tool that is not engaged with an external-mating bone-mounted fiducial as described previously in relation to FIGS. 102A-102E in accordance with some embodiments of the invention.

Figure 102G:
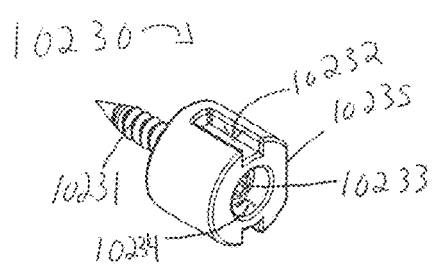

FIG. 102G illustrates a perspective view of an external-mating bone-mounted fiducial as described previously in relation to FIGS. 102A-102F in accordance with some embodiments of the invention.

Figure 102H:
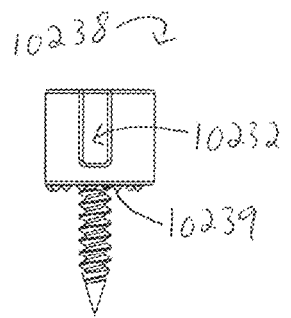

FIG. 102H illustrates a side view of an external-mating bone-mounted fiducial as described previously in relation to FIGS. 102A-102G in accordance with some embodiments of the invention.

Figure 102I:
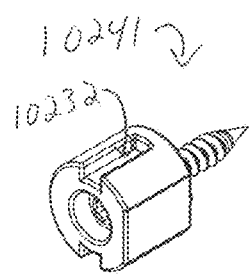

FIG. 102I illustrates a perspective view of an external-mating bone-mounted fiducial as described previously in relation to FIGS. 102A-102H in accordance with some embodiments of the invention.

Figure 102J:
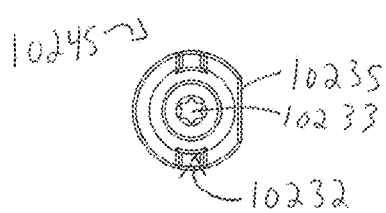

FIG. 102J illustrates a top view of an external-mating bone-mounted fiducial as described previously in relation to FIGS. 102A-102I in accordance with some embodiments of the invention.

Figure 102K:
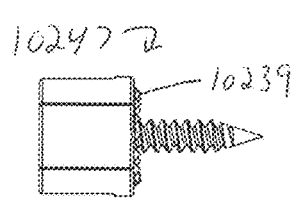

FIG. 102K illustrates a side view of an external-mating bone-mounted fiducial as described previously in relation to FIGS. 102A-102J in accordance with some embodiments of the invention.

Figure 102L:

FIG. 102L illustrates a perspective view of an external-mating bone-mounted fiducial as described previously in relation to FIGS. 102A-102K in accordance with some embodiments of the invention.

Figure 102M:
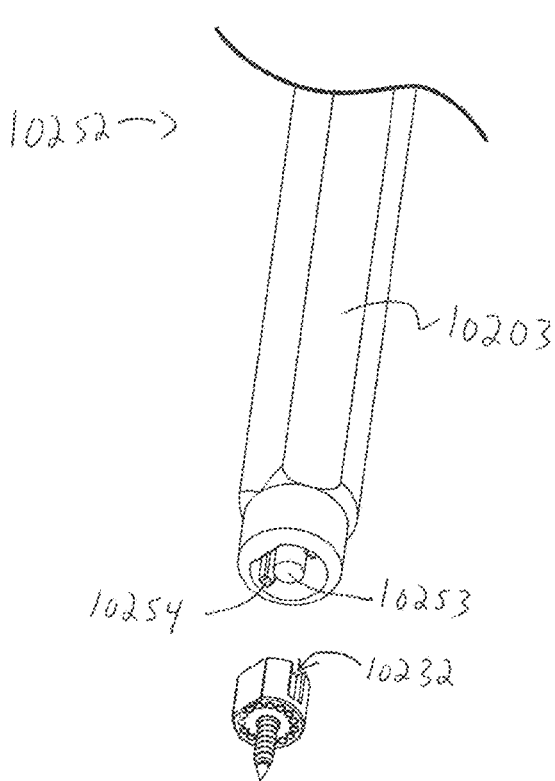

FIG. 102M illustrates a perspective view of a 3D-tracked tool that is not engaged with an external-mating bone-mounted fiducial, as described previously in relation to FIGS. 102A-102L in accordance with some embodiments of the invention.

Figure 102N:
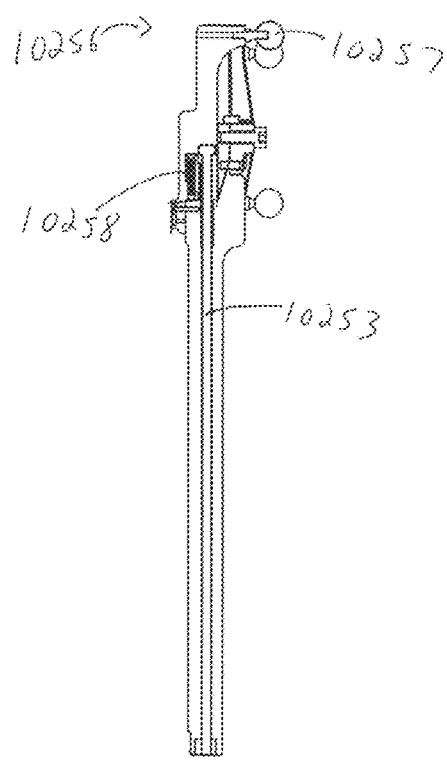

FIG. 102N illustrates a cross-sectional view of a 3D-tracked tool's triggering mechanism for engaging with an external-mating bone-mounted fiducial, as described previously in relation to FIGS. 102A-102M in accordance with some embodiments of the invention.

Figure 102O:
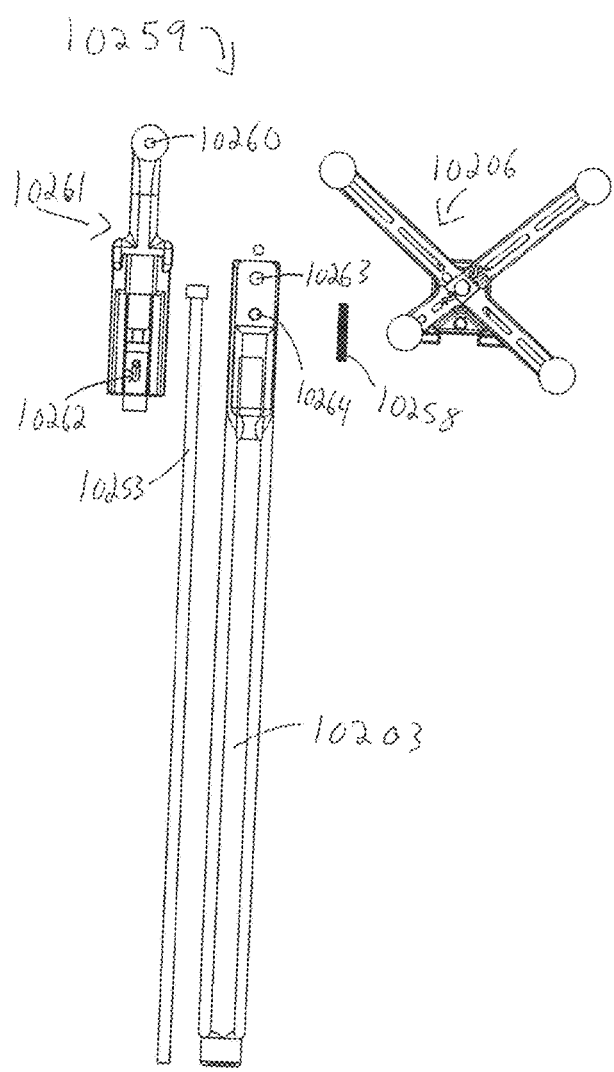
Figure 102P:
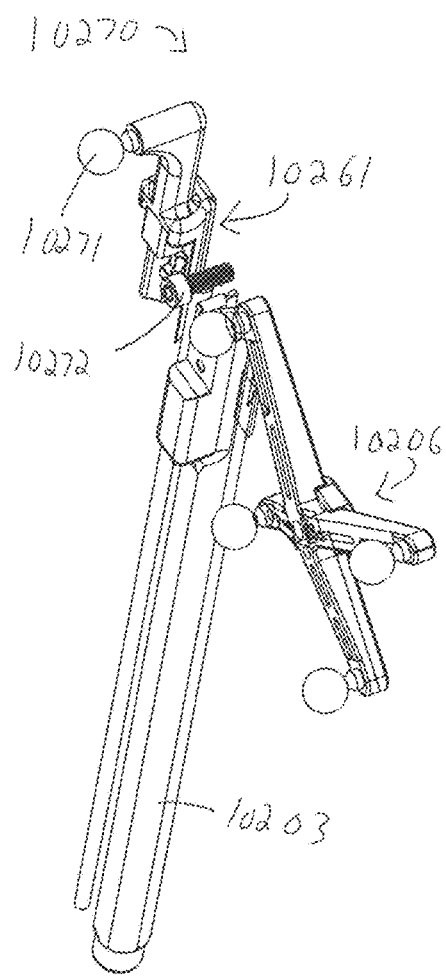

FIGS. 102O-102P illustrate assembly views of a 3D-tracked tool that mates with an external-mating bone-mounted fiducial, as described previously in relation to FIGS. 102A-102N in accordance with some embodiments of the invention.

Figures 103A, 103B, 103C:
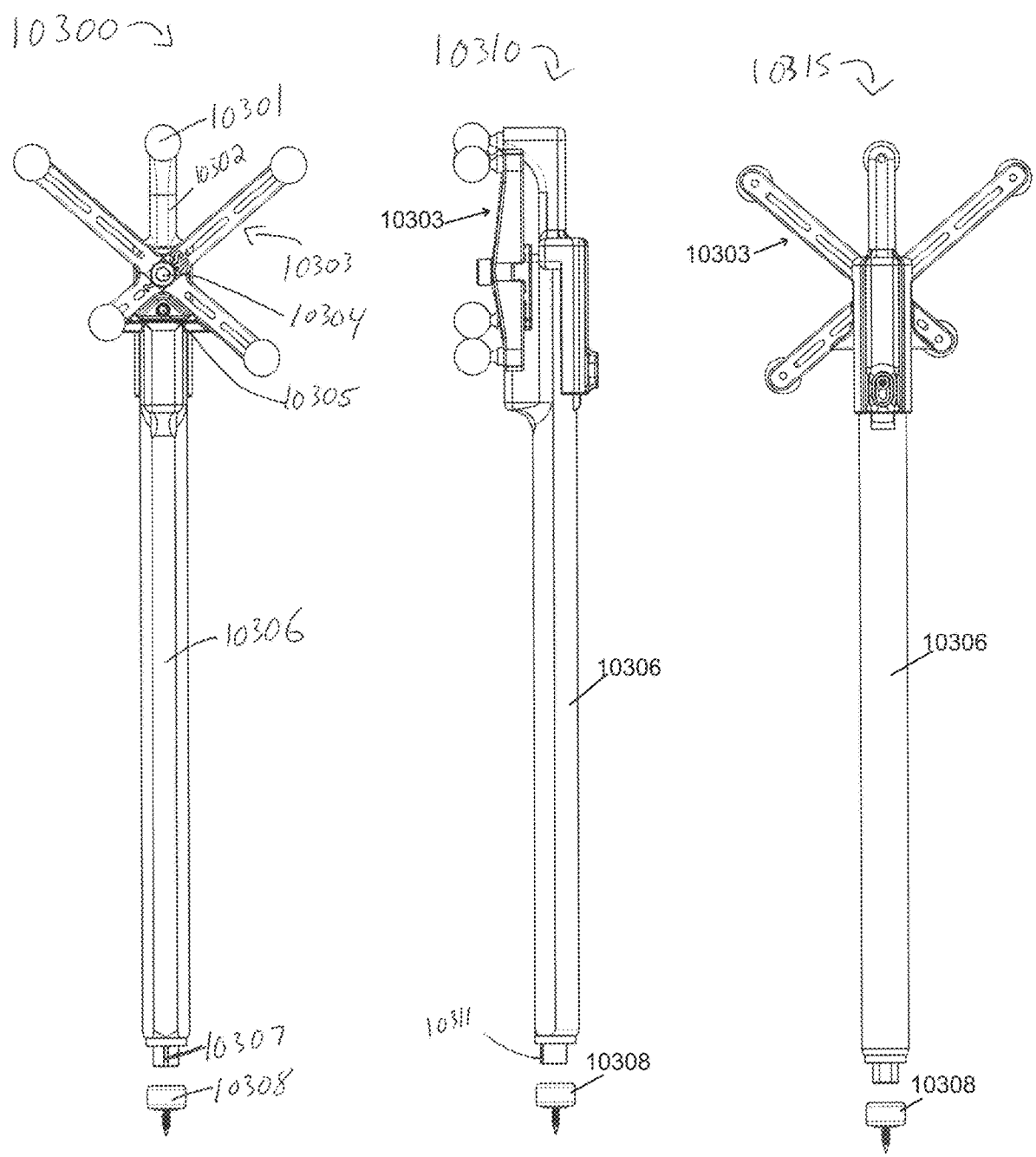

FIG. 103A illustrates a front view of a 3D-tracked tool that mates with an internal-mating bone-mounted fiducial in accordance with some embodiments of the invention.

FIG. 103B illustrates a side view of a 3D-tracked tool that mates with an internal-mating bone-mounted fiducial, as described previously in relation to FIG. 103A in accordance with some embodiments of the invention.

FIG. 103C illustrates a rear view of a 3D-tracked tool that mates with an internal-mating bone-mounted fiducial, as described previously in relation to FIGS. 103A-103B in accordance with some embodiments of the invention.

FIGS. 103D-103F illustrate perspective views of a 3D-tracked tool that mates with an internal-mating bone-mounted fiducial, as shown in its various mating trigger states, as described previously in relation to FIGS. 103A-103C in accordance with some embodiments of the invention.

Figure 103G:
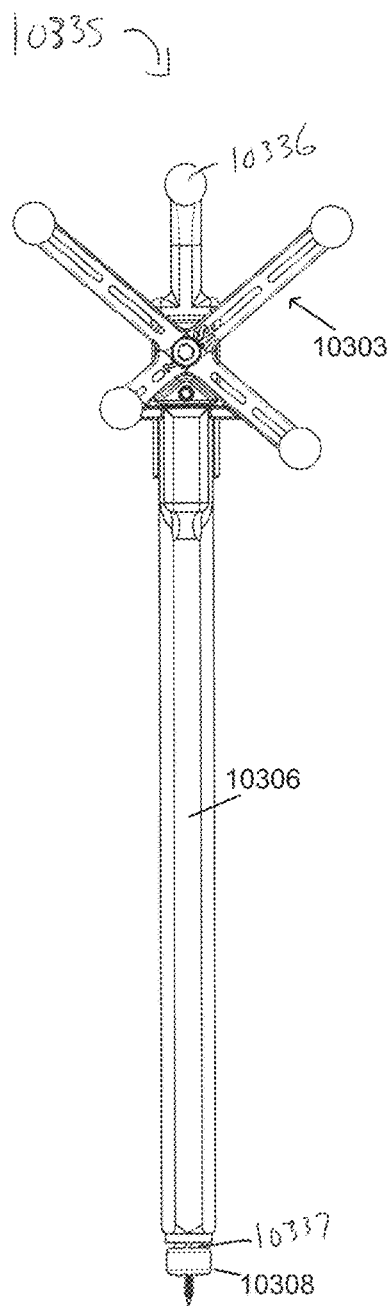

FIG. 103G illustrates a front view of a 3D-tracked tool that mates with an internal-mating bone-mounted fiducial, as shown with both devices fully mated, as described previously in relation to FIGS. 103A-103F in accordance with some embodiments of the invention.

Figure 103H:
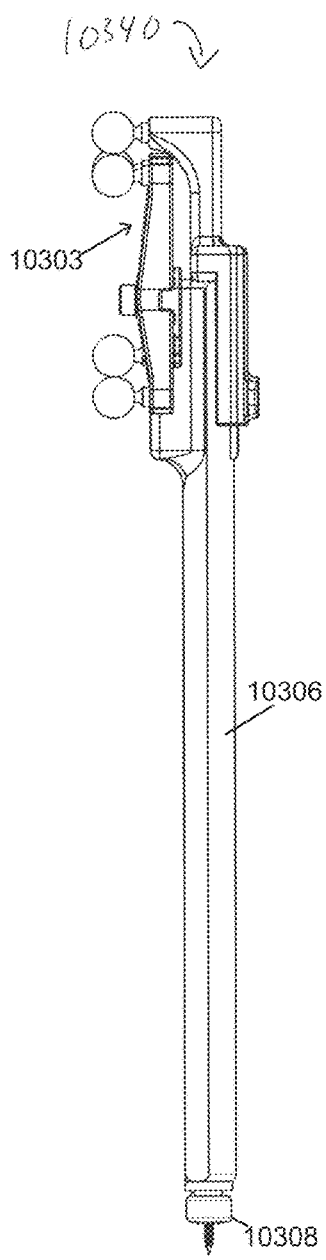

FIG. 103H illustrates a side view of a 3D-tracked tool that mates with an internal-mating bone-mounted fiducial, as shown with both devices fully mated, as described previously in relation to FIGS. 103A-103G in accordance with some embodiments of the invention.

Figure 103I:
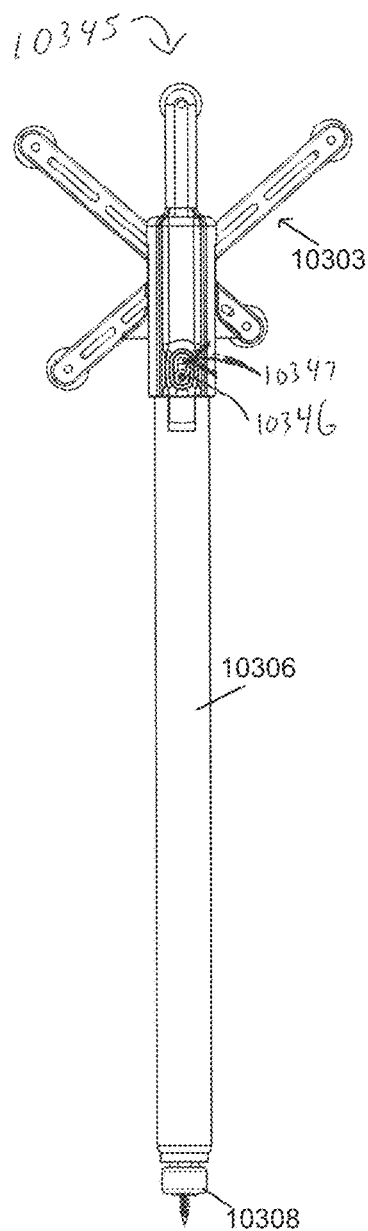

FIG. 103I illustrates a rear view of a 3D-tracked tool that mates with an internal-mating bone-mounted fiducial, as shown with both devices fully mated, as described previously in relation to FIGS. 103A-103H in accordance with some embodiments of the invention.

Figure 103J:
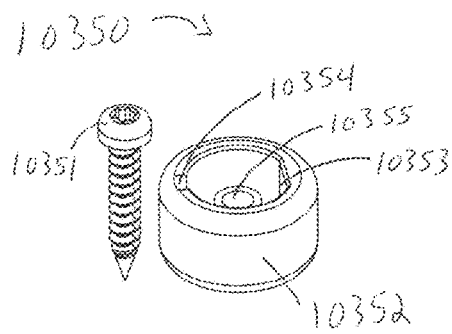

FIG. 103J illustrates a perspective view of an internal-mating bone-mounted fiducial's assembly components as described previously in relation to FIGS. 103A-103I in accordance with some embodiments of the invention.

Figure 103K:
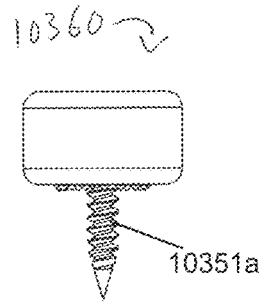
Figure 103L:
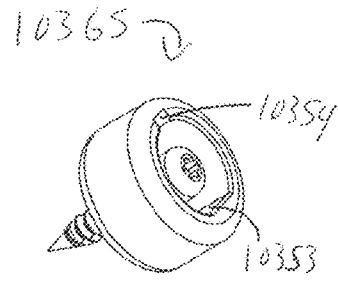
Figure 103M:
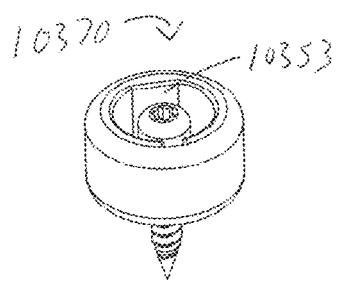
Figure 103N:
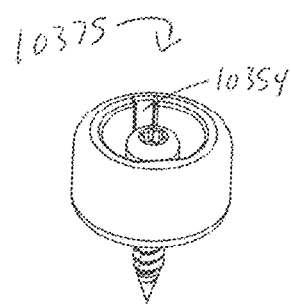

FIG. 103K illustrates a side view of an internal-mating bone-mounted fiducial, as described previously in relation to FIGS. 103A-103J in accordance with some embodiments of the invention.

FIGS. 103L-103O illustrate perspective views of an internal-mating bone-mounted fiducial, as described previously in relation to FIGS. 103A-103K in accordance with some embodiments of the invention.

Figure 103O:
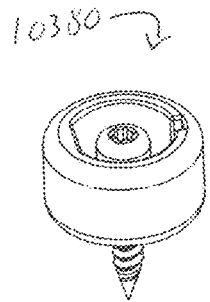
Figure 103P:
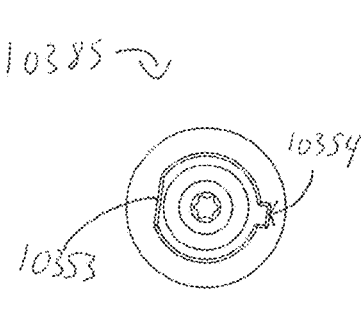

FIG. 103P illustrates a bottom view of a 3D-tracked tool that mates with an internal-mating bone-mounted fiducial, as described previously in relation to FIGS. 103A-103O in accordance with some embodiments of the invention.

Figure 103Q:
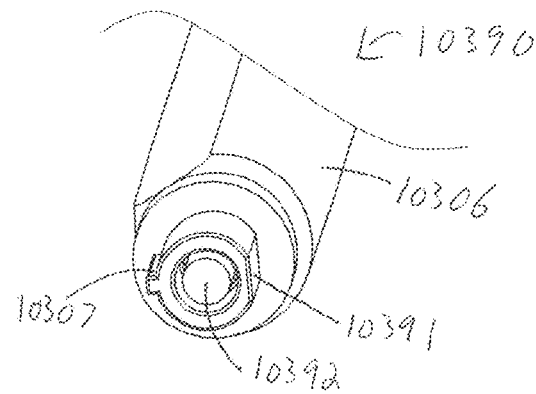

FIG. 103Q illustrates a perspective view of a 3D-tracked tool that mates with an internal-mating bone-mounted fiducial, as described previously in relation to FIGS. 103A-103P in accordance with some embodiments of the invention.

Figures 104A, 104B, 104C:
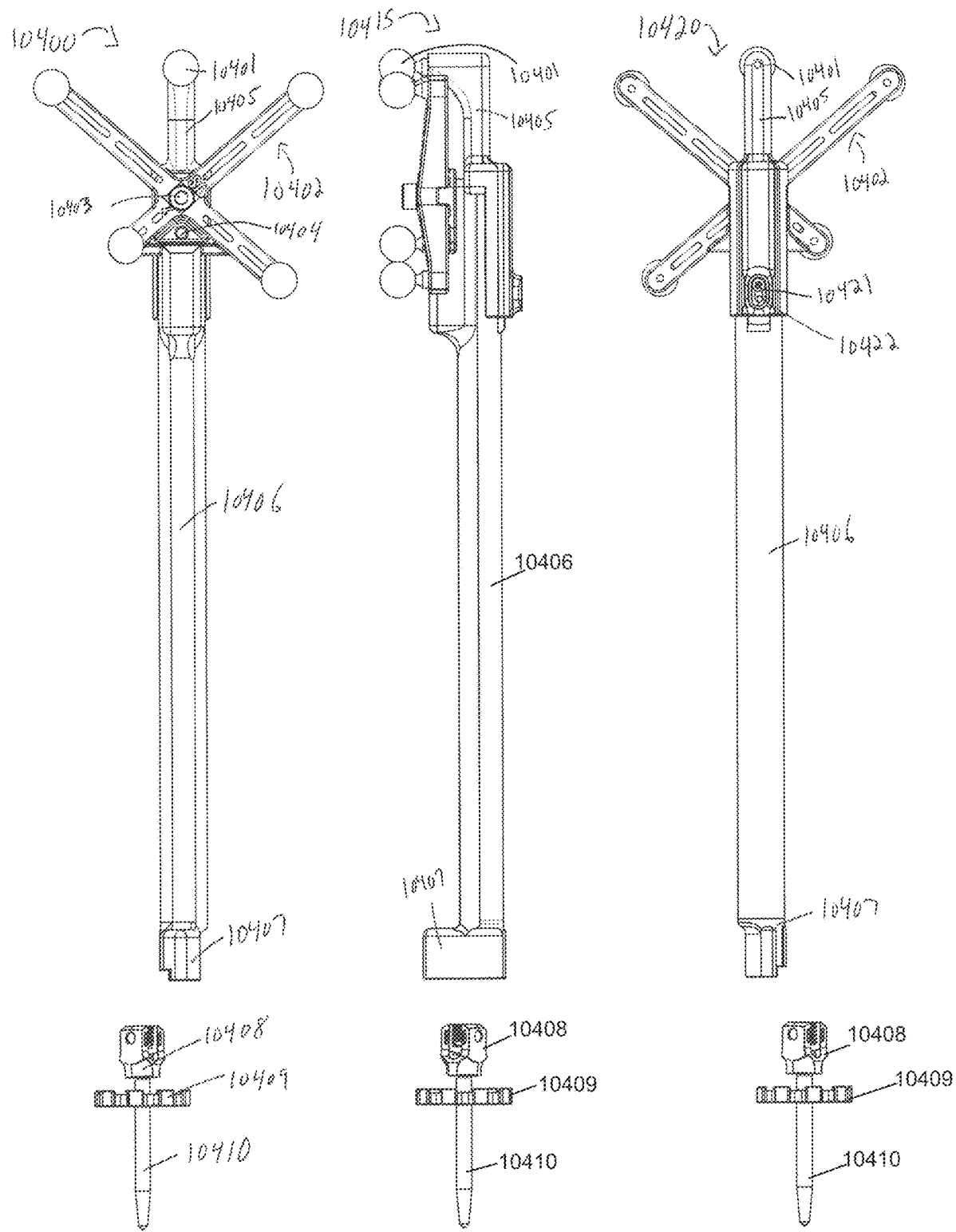

FIG. 104A illustrates a front view of a 3D-tracked tool that mates with a fastener with a depth-stop interface, with the devices not mated as shown, in accordance with some embodiments of the invention.

FIG. 104B illustrates a side view of a 3D-tracked tool that mates with a fastener with a depth-stop interface, with the devices not mated as shown, as described previously in relation to FIG. 104A in accordance with some embodiments of the invention.

FIG. 104C illustrates a rear view of a 3D-tracked tool that mates with a fastener with a depth-stop interface, with the devices not mated as shown, as described previously in relation to FIGS. 104A-104B in accordance with some embodiments of the invention.

FIG. 104D illustrates a front view of a 3D-tracked tool that mates with a fastener with a depth-stop interface, with the devices mated as shown, as described previously in relation to FIGS. 104A-104C in accordance with some embodiments of the invention.

FIG. 104E illustrates a side view of a 3D-tracked tool that mates with a fastener with a depth-stop interface, with the devices mated as shown, as described previously in relation to FIGS. 104A-104D in accordance with some embodiments of the invention.

FIG. 104F illustrates a rear view of a 3D-tracked tool that mates with a fastener with a depth-stop interface, with the devices mated as shown, as described previously in relation to FIGS. 104A-104E in accordance with some embodiments of the invention.

Figures 104G, 104H, 104I:
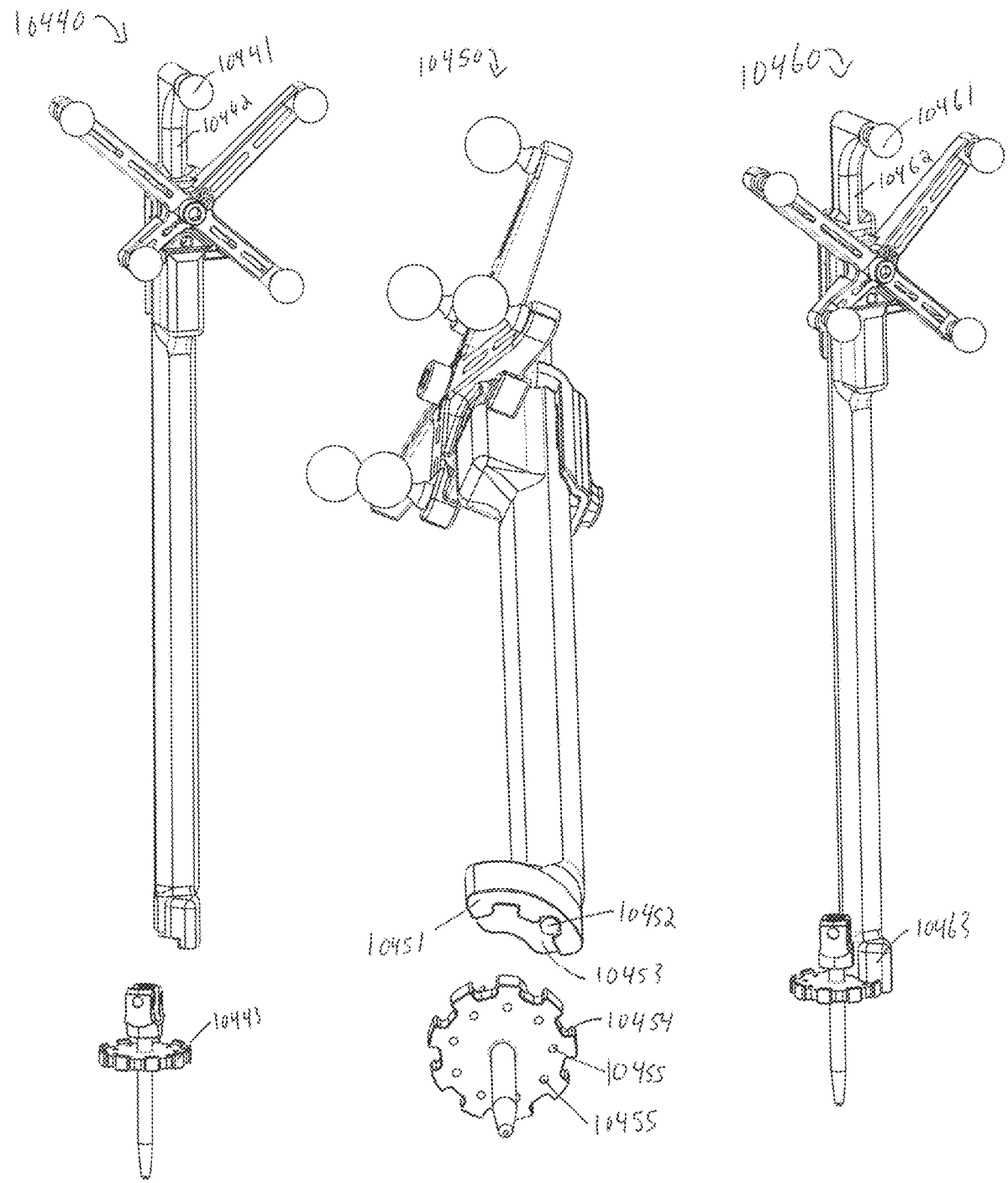

FIG. 104G illustrates a perspective view of a 3D-tracked tool that mates with a fastener with a depth-stop interface, with the devices not mated as shown, as described previously in relation to FIGS. 104A-104F in accordance with some embodiments of the invention.

FIG. 104H illustrates a perspective view of a mating interfaces between a 3D-tracked tool and a fastener with a depth-stop interface, with the devices not mated as shown, as described previously in relation to FIGS. 104A-104G in accordance with some embodiments of the invention.

FIG. 104I illustrates a perspective view of a 3D-tracked tool that mates with a fastener with a depth-stop interface, with the devices mated as shown, as described previously in relation to FIGS. 104A-104H in accordance with some embodiments of the invention.

Figure 104J:
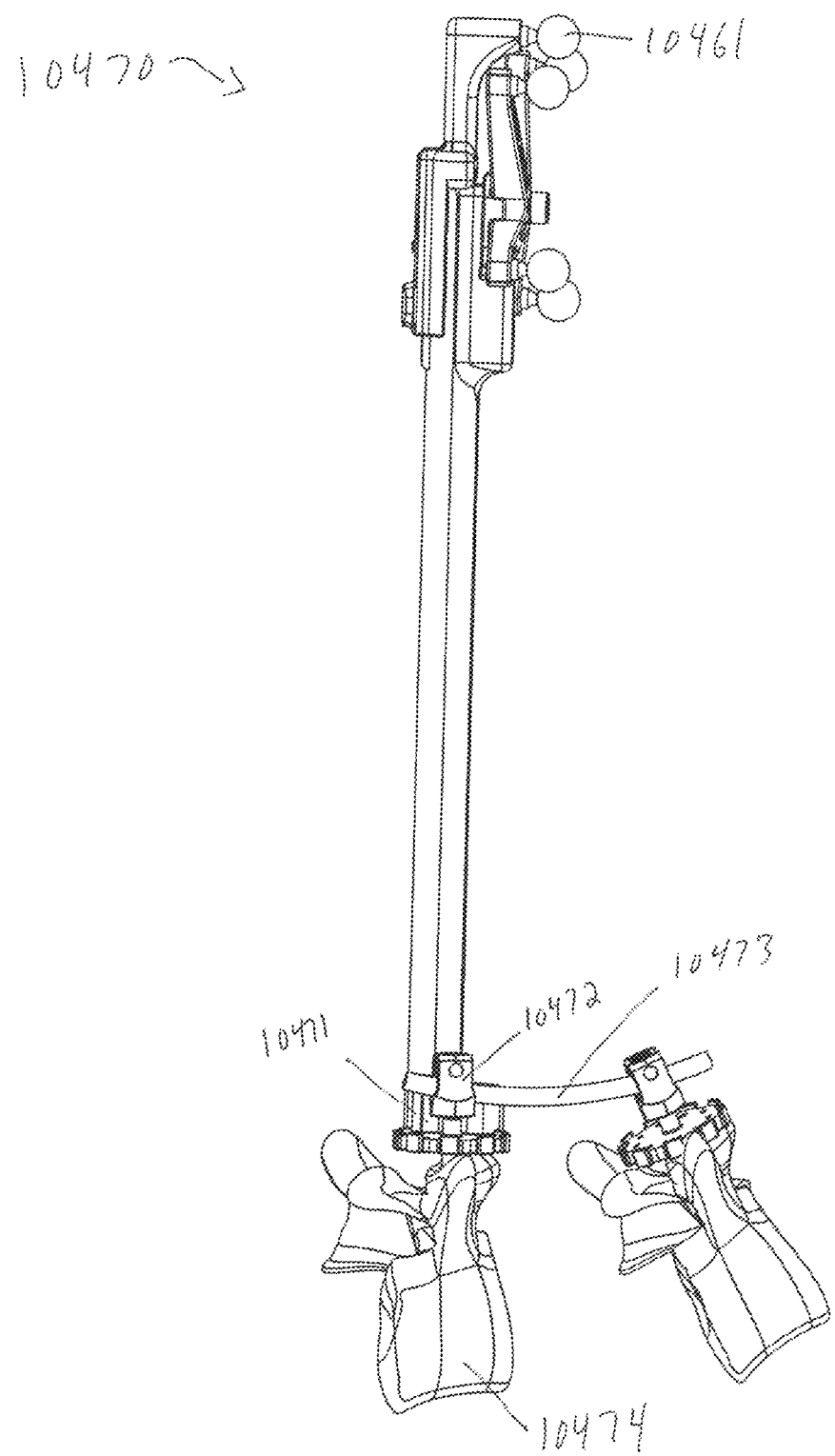

FIG. 104J illustrates a side view of a 3D-tracked tool that mates with a fastener with a depth-stop interface, with the devices mated and engaged to a vertebra with an implanted rod as shown, as described previously in relation to FIGS. 104A-104I in accordance with some embodiments of the invention.

Figure 105A:
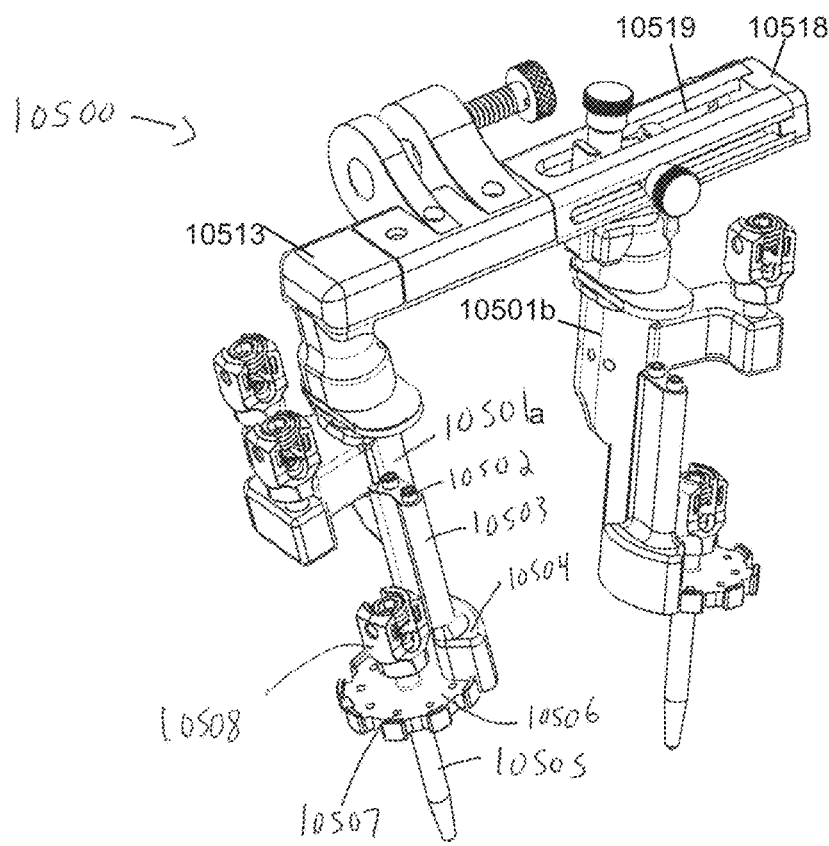

FIG. 105A illustrates a perspective view of an adjustable pedicle screw interface base, with one fixed side arm and one side arm with height and angle adjustments, and with the device mated with a fastener with depth-stop mating interfaces, of a flexibility assessment device in accordance with some embodiments of the invention.

Figure 105B:
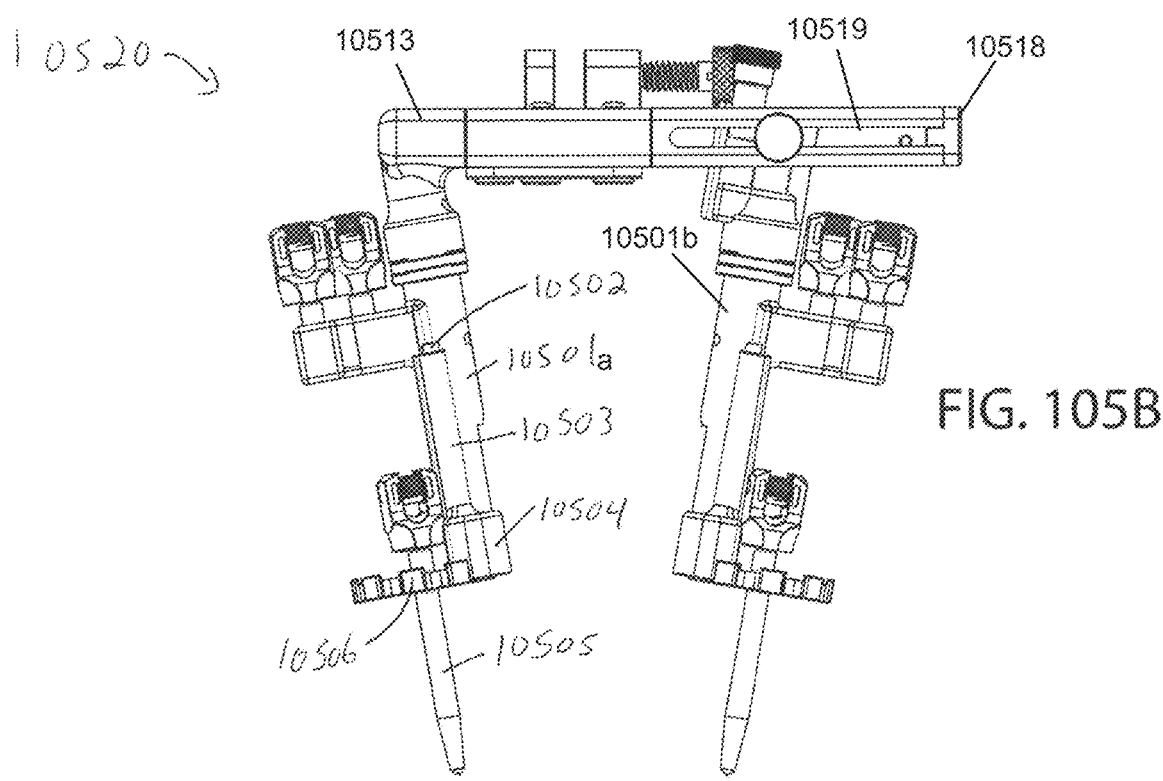

FIG. 105B illustrates a front view of an adjustable pedicle screw interface base, with one fixed side arm and one side arm with height and angle adjustments, and with the device mated with a fastener with depth-stop mating interfaces, of a flexibility assessment device as described previously in relation to FIG. 105A in accordance with some embodiments of the invention.

Figure 105C:
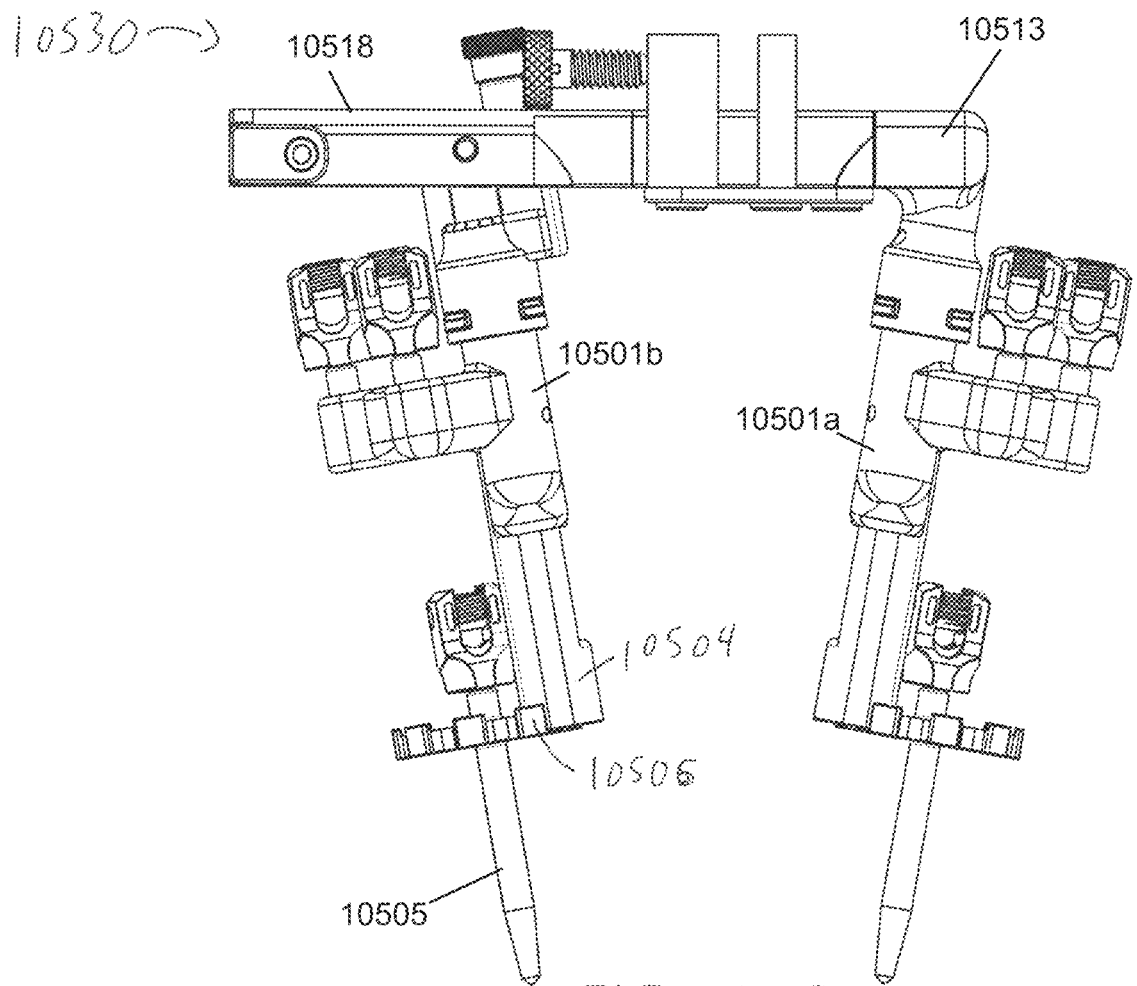

FIG. 105C illustrates a rear view of an adjustable pedicle screw interface base, with one fixed side arm and one side arm with height and angle adjustments, and with the device mated with a fastener with depth-stop mating interfaces, of a flexibility assessment device as described previously in relation to FIGS. 105A-105B in accordance with some embodiments of the invention.

Figure 105D:
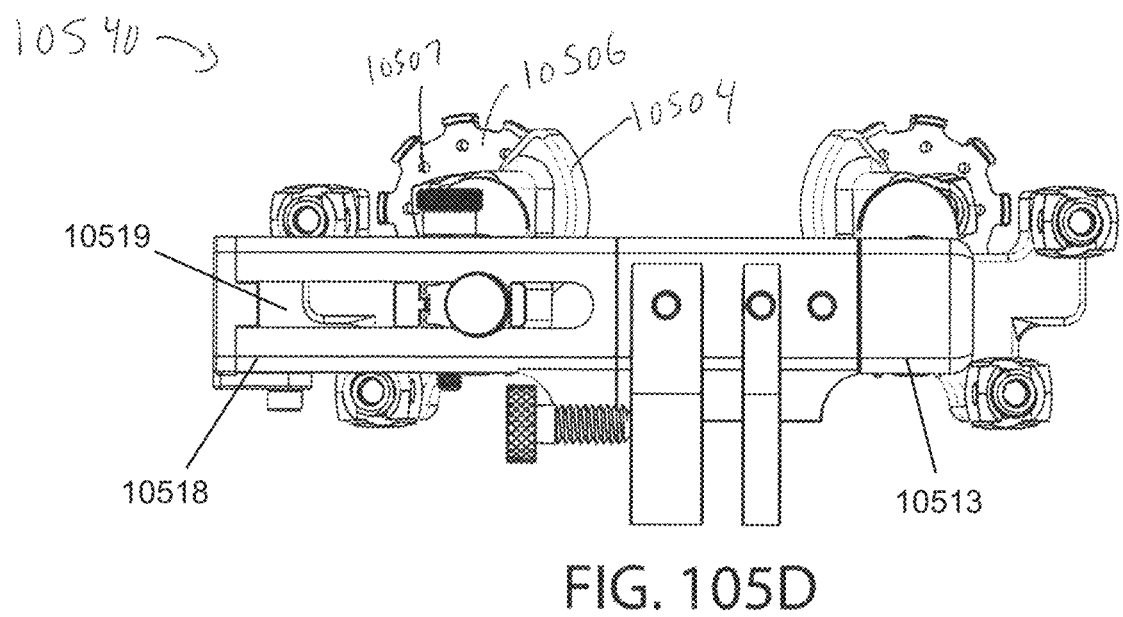

FIG. 105D illustrates a top view of an adjustable pedicle screw interface base, with one fixed side arm and one side arm with height and angle adjustments, and with the device mated with a fastener with depth-stop mating interfaces, of a flexibility assessment device as described previously in relation to FIGS. 105A-105C in accordance with some embodiments of the invention.

Figure 105E:
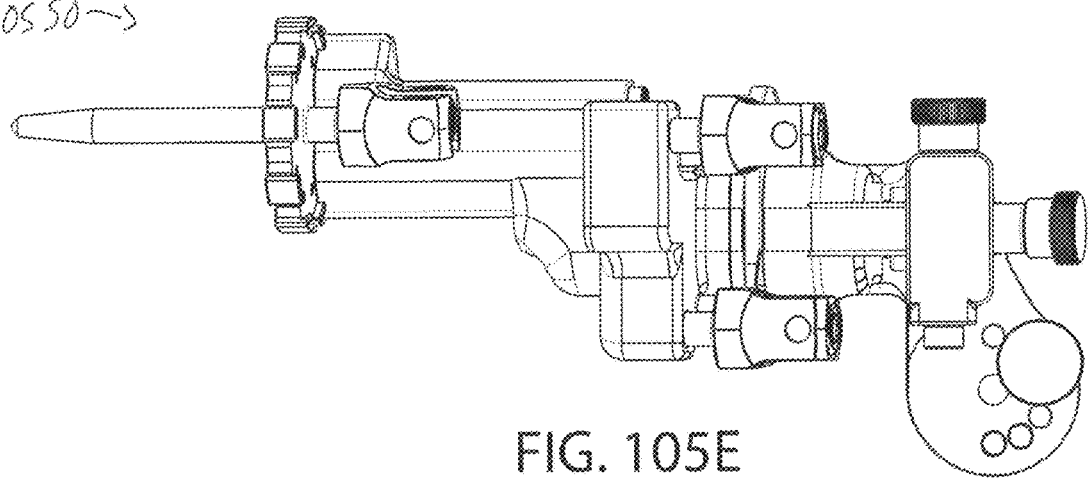

FIG. 105E illustrates a side view of an adjustable pedicle screw interface base, with one fixed side arm and one side arm with height and angle adjustments, and with the device mated with a fastener with depth-stop mating interfaces, of a flexibility assessment device as described previously in relation to FIGS. 105A-105D in accordance with some embodiments of the invention.

Figure 105F:
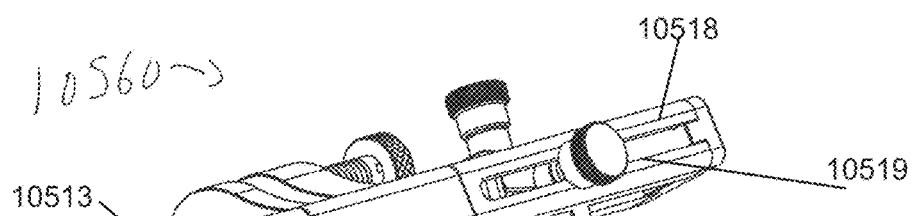

FIG. 105F illustrates a perspective view of an adjustable pedicle screw interface base, with one fixed side arm and one side arm with height and angle adjustments, and with the device mated with one of the displayed fasteners with depth-stop mating interfaces, of a flexibility assessment device as described previously in relation to FIGS. 105A-105E in accordance with some embodiments of the invention.

Figure 105G:
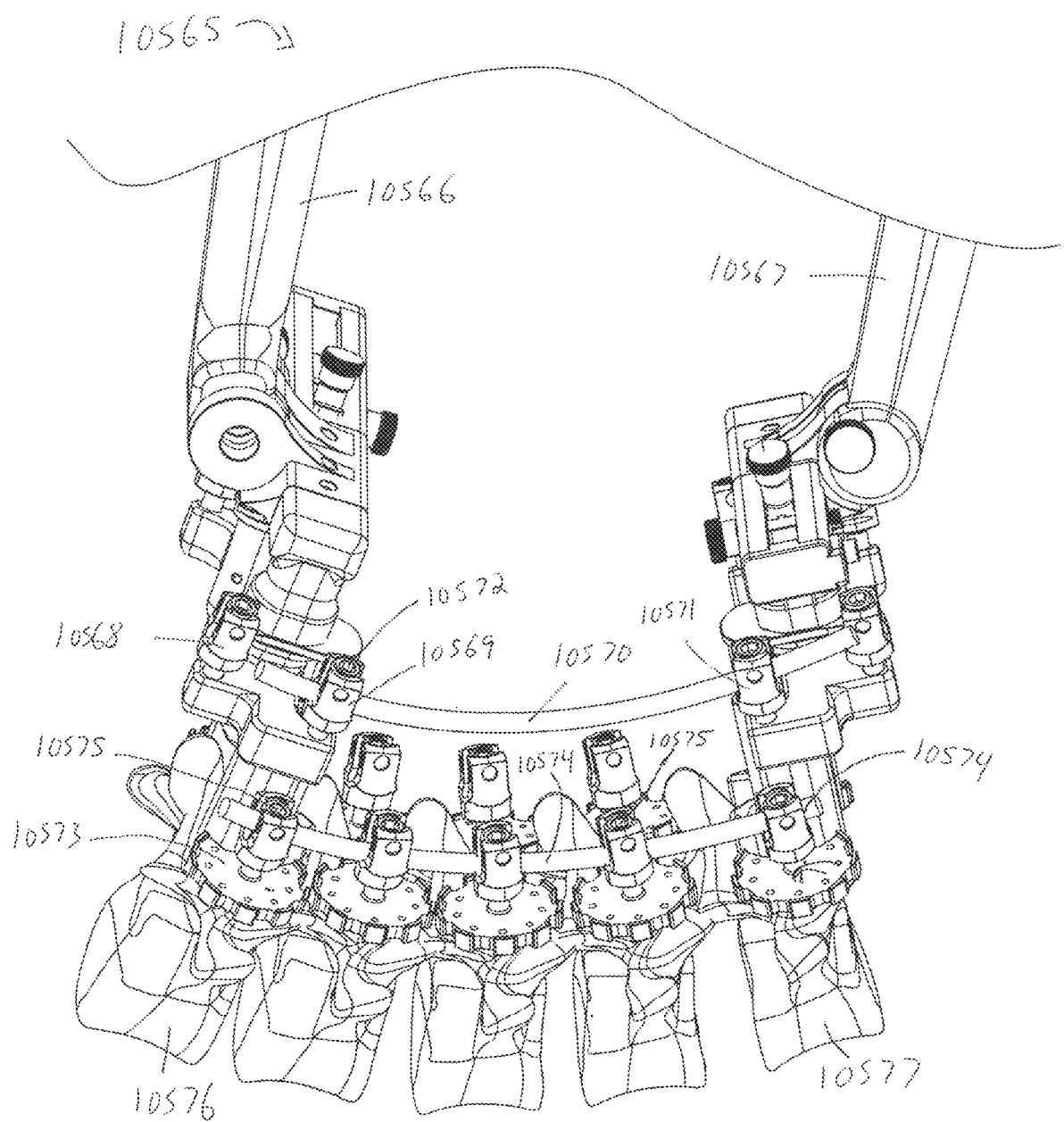

FIG. 105G illustrates a perspective view of flexibility assessment devices with adjustable pedicle screw interface bases, with the devices mated with fasteners with depth-stop mating interfaces, the engaged vertebrae substantially rigidly linked via an implanted rod, and the devices substantially rigidly linked via an accessory rod between the screw interface bases, as described previously in relation to FIGS. 105A-105F in accordance with some embodiments of the invention.

FIG. 106A illustrates a perspective view of a coordinate reference end cap device with a lockable trigger tab in accordance with some embodiments of the invention.

FIG. 106B illustrates a rear view of a coordinate reference end cap device with a lockable trigger tab, as described previously in relation to FIG. 106A in accordance with some embodiments of the invention.

FIG. 106C illustrates a top view of a coordinate reference end cap device with a lockable trigger tab, as described previously in relation to FIGS. 106A-106B in accordance with some embodiments of the invention.

Figure 106D:
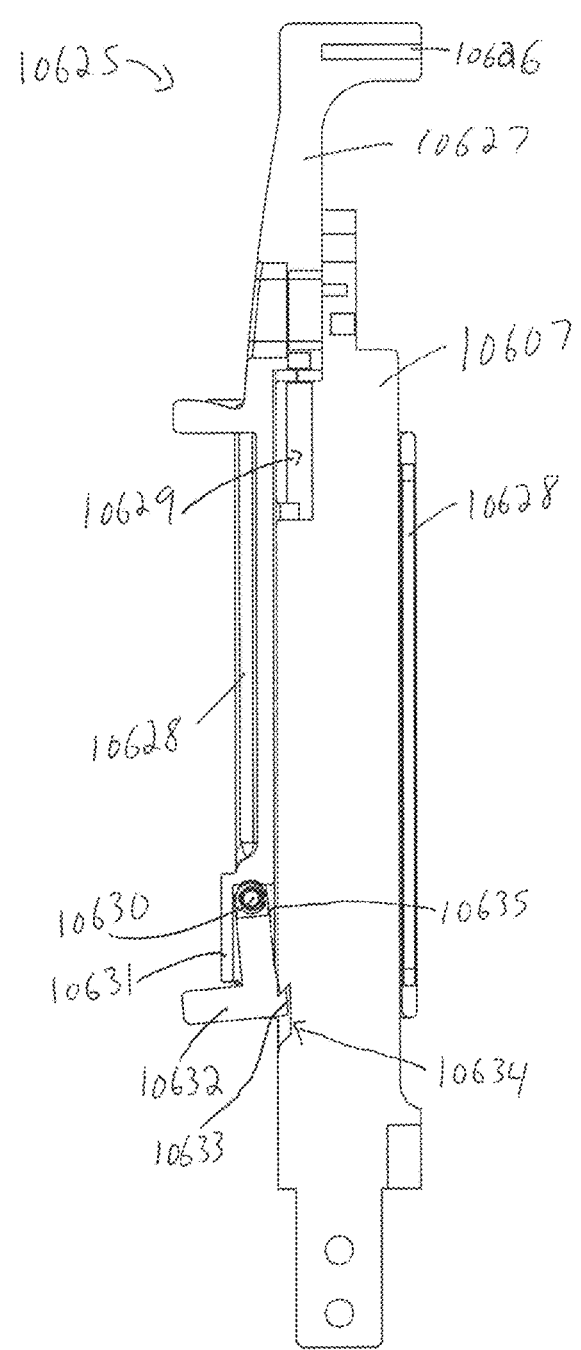

FIG. 106D illustrates a side cross-sectional view of a coordinate reference end cap device with a lockable trigger tab in its active locking state, as described previously in relation to FIGS. 106A-106C in accordance with some embodiments of the invention.

Figure 106E:
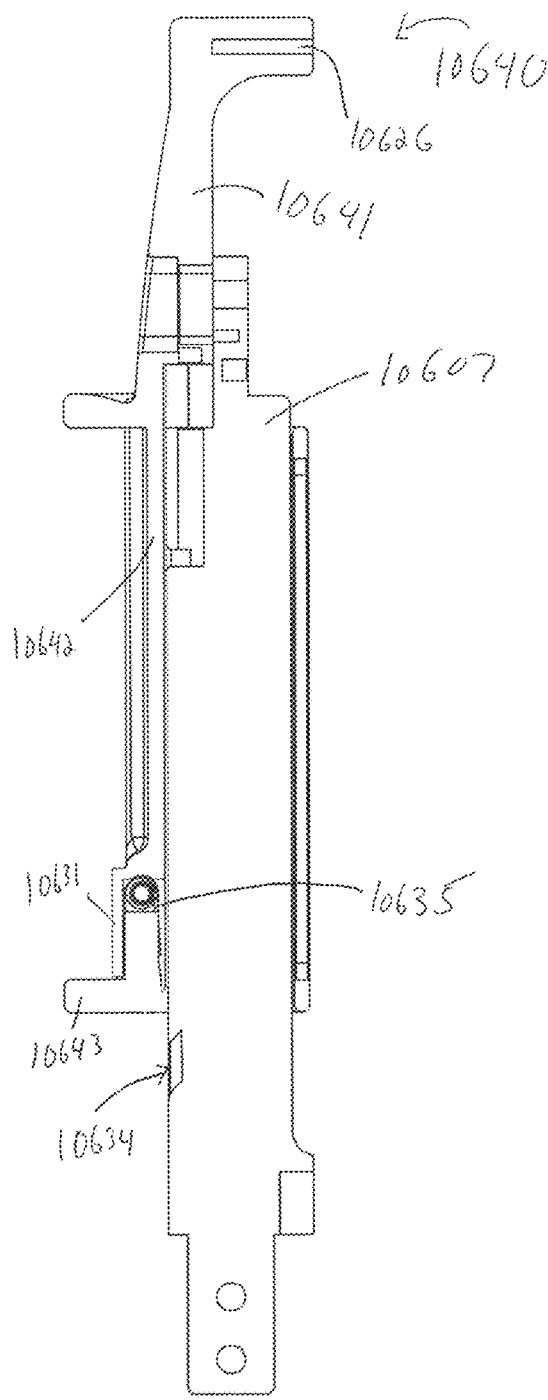

FIG. 106E illustrates a side cross-sectional view of a coordinate reference end cap device with a lockable trigger tab in its inactive locking state, as described previously in relation to FIGS. 106A-106D in accordance with some embodiments of the invention.

Figure 106F:
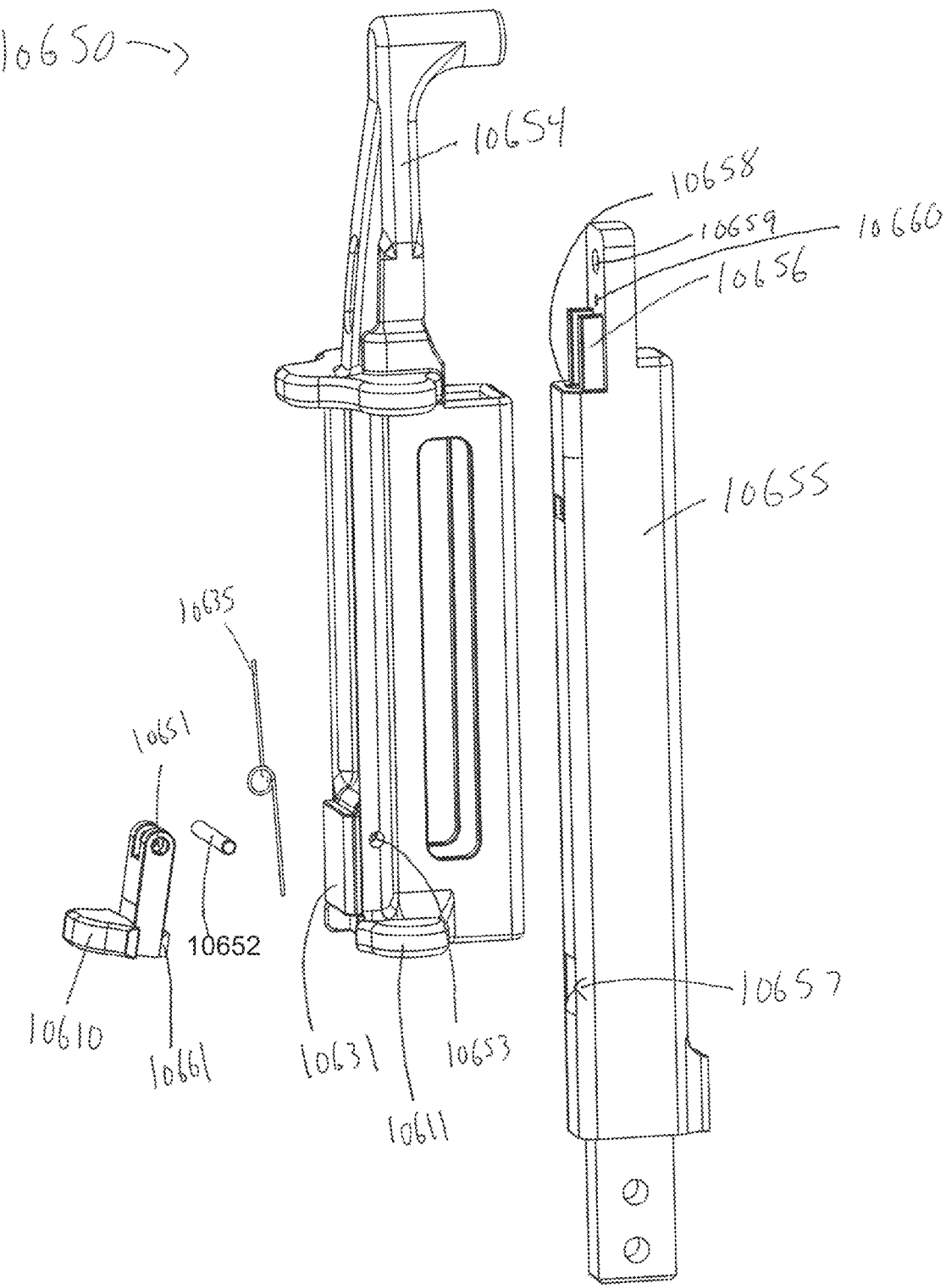

FIG. 106F illustrates an assembly view of a coordinate reference end cap device with a lockable trigger tab, as described previously in relation to FIGS. 106A-106E in accordance with some embodiments of the invention.

Figure 107A:
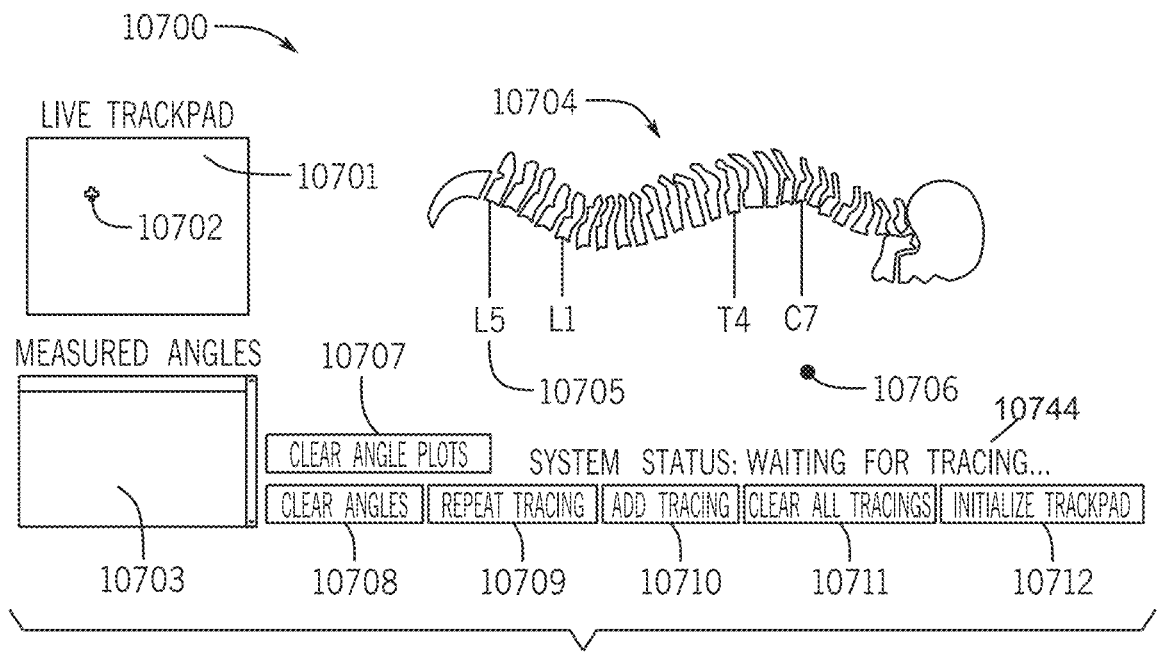

FIG. 107A illustrates a display interface for analyzing the contour of patient and illustrating spinal alignment parameters from landmarks of interest, as well as a trackpad display-controlling interface in its active state, in accordance with some embodiments of the invention.

Figure 107B:
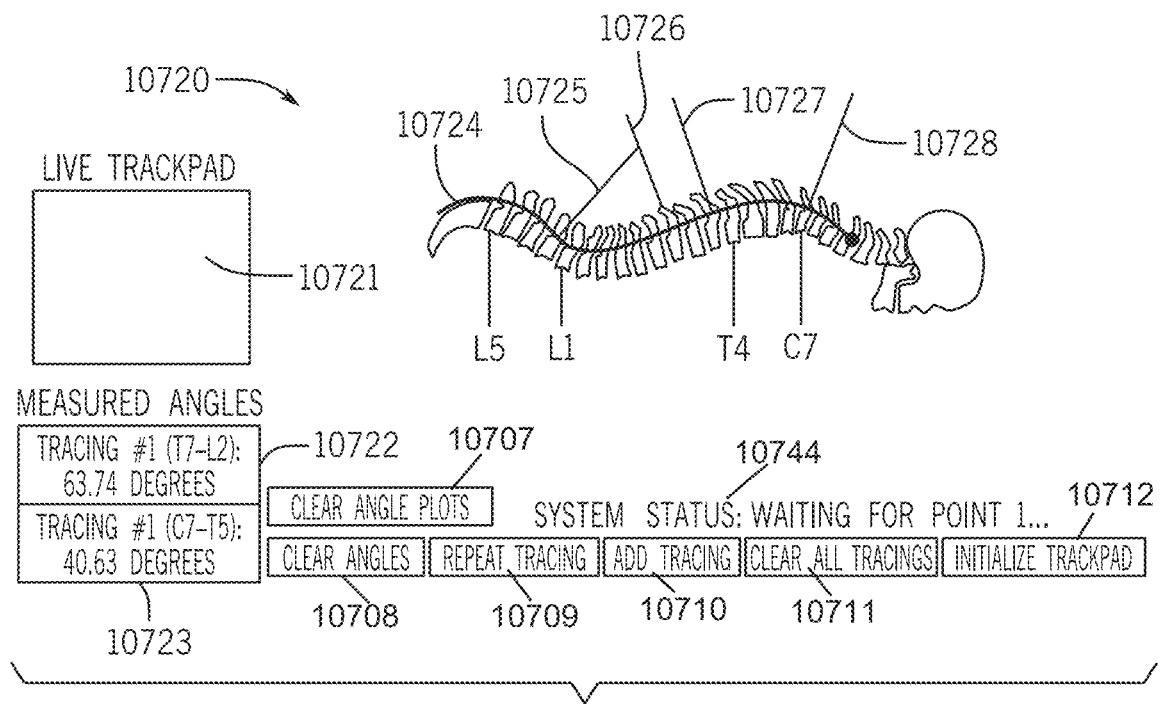

FIG. 107B illustrates a display interface for analyzing the contour of patient and illustrating spinal alignment parameters from landmarks of interest, as well as a trackpad display-controlling interface in its inactive state, as described previously in relation to FIG. 107A in accordance with some embodiments of the invention.

Figure 107C:
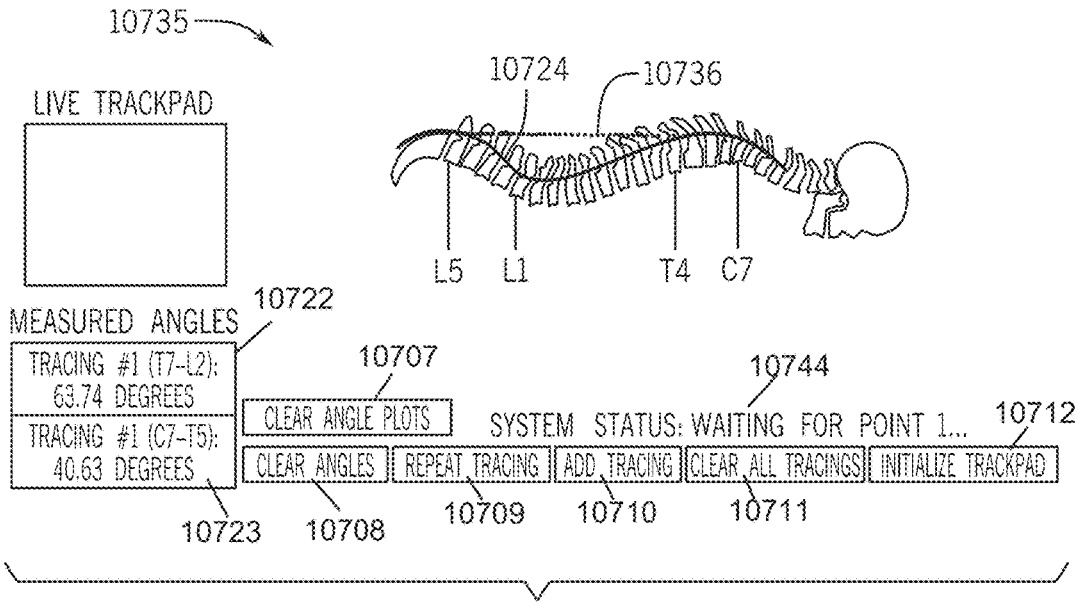

FIG. 107C illustrates a display interface for analyzing the contour of patient and illustrating spinal alignment parameters from landmarks of interest, as well as a trackpad display-controlling interface and overlays of several contour acquisitions, as described previously in relation to FIGS. 107A-107B in accordance with some embodiments of the invention.

Figure 107D:
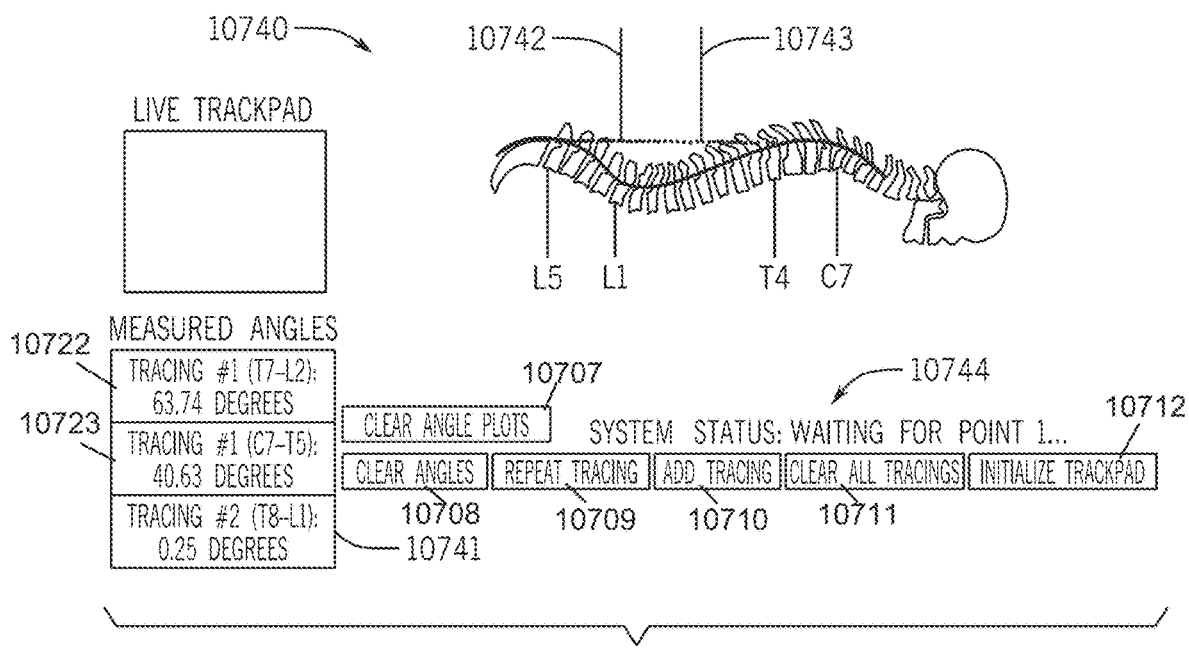

FIG. 107D illustrates a display interface for analyzing the contour of patient and illustrating spinal alignment parameters from landmarks of interest, as well as a trackpad display-controlling interface, overlays of several contour acquisitions, and the latest contour's measurements, as described previously in relation to FIGS. 107A-107C in accordance with some embodiments of the invention.

Figure 108A:
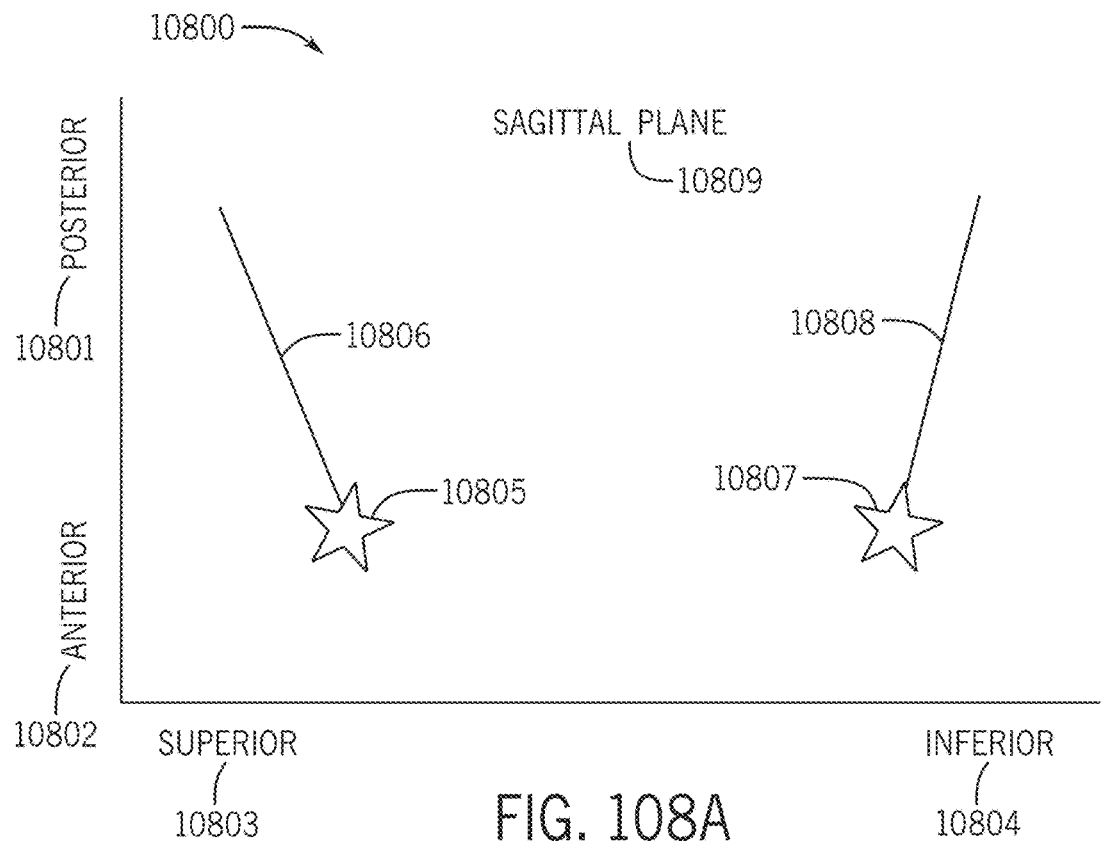

FIG. 108A illustrates a display interface for analyzing the position and orientation of flexibility assessment devices in accordance with some embodiments of the invention.

Figure 108B:
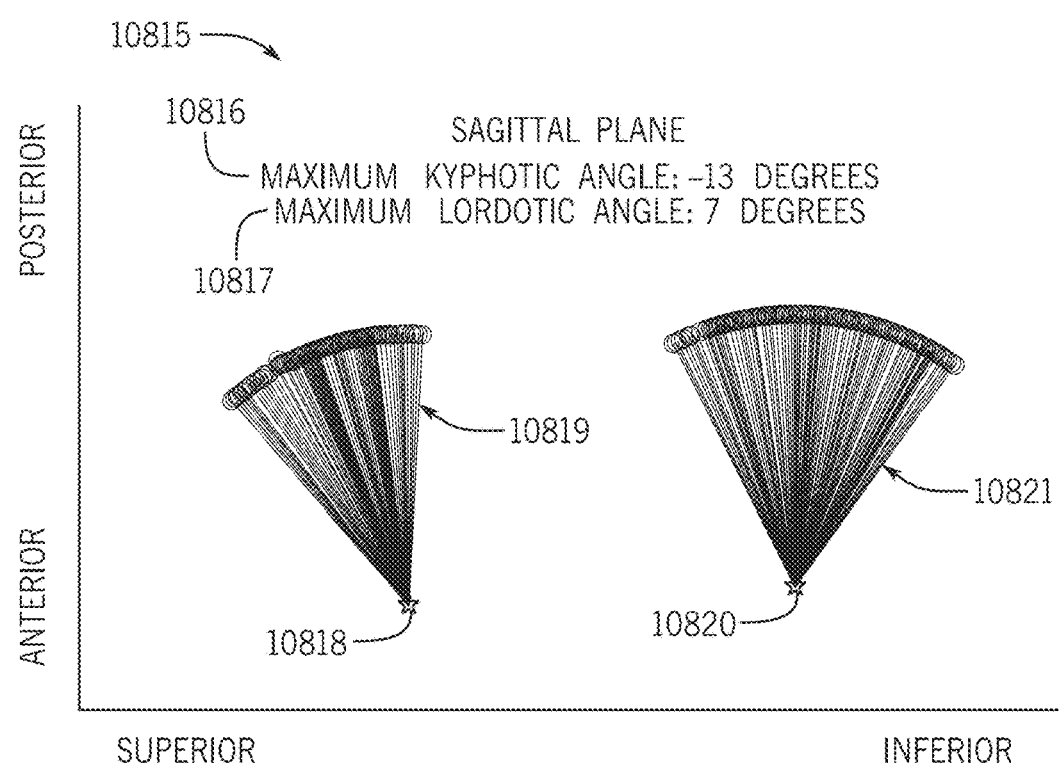
Figure 108C:
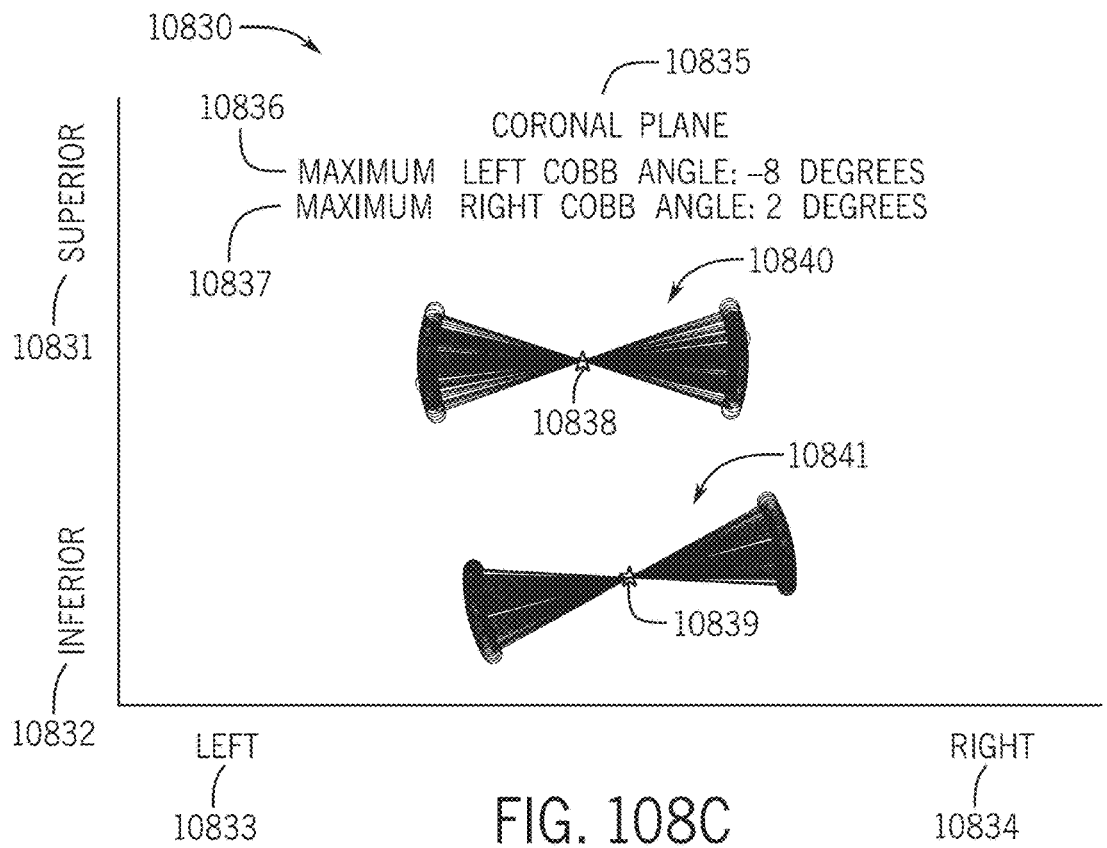
Figure 108D:
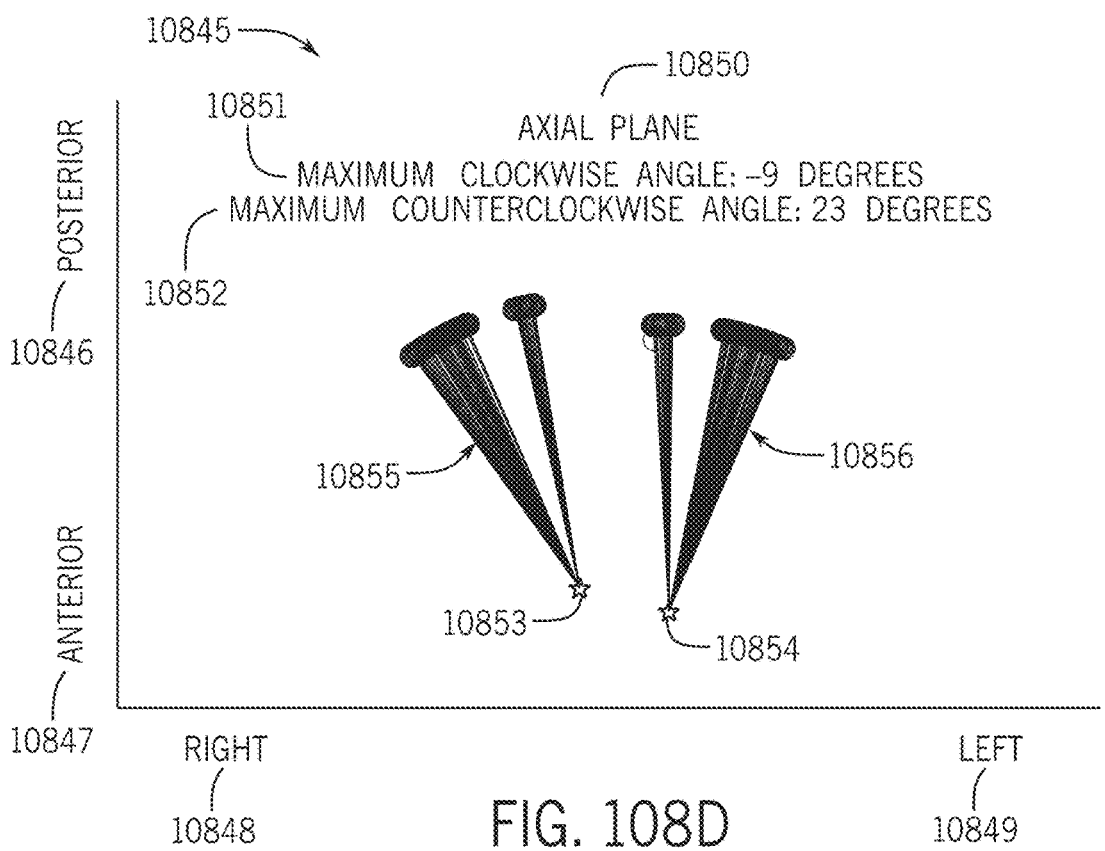

FIGS. 108B-108D illustrate a display interface for analyzing the position and orientation of flexibility assessment devices, with the devices in their active triggering state and displaying the range of the motion of engaged vertebrae across all anatomical planes, as described previously in relation to FIG. 108A in accordance with some embodiments of the invention.

Figure 108E:
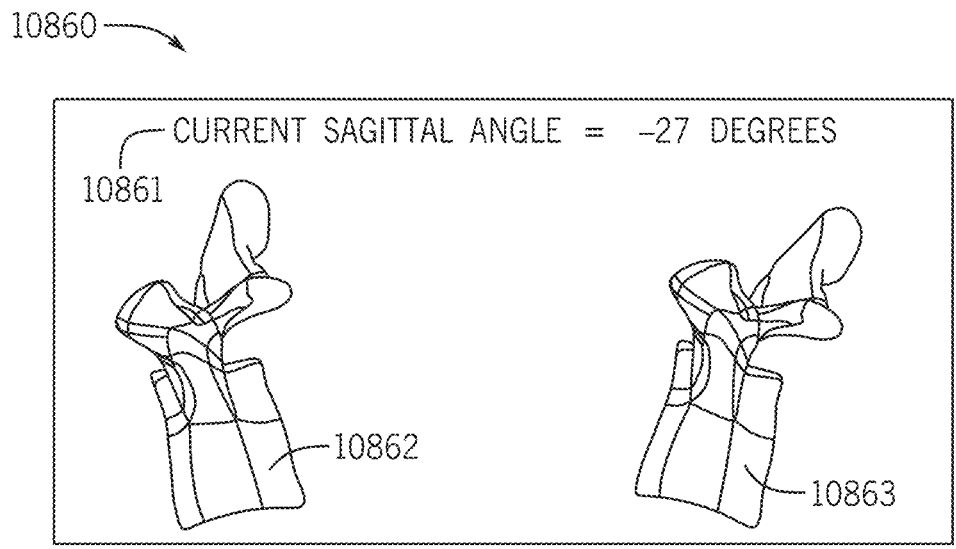

FIG. 108E illustrates a display interface for analyzing the position and orientation of flexibility assessment devices, with the devices in their active triggering state and displaying a rendered view of each engaged vertebra, as described previously in relation to FIGS. 108A-108D in accordance with some embodiments of the invention.

Figure 108F:
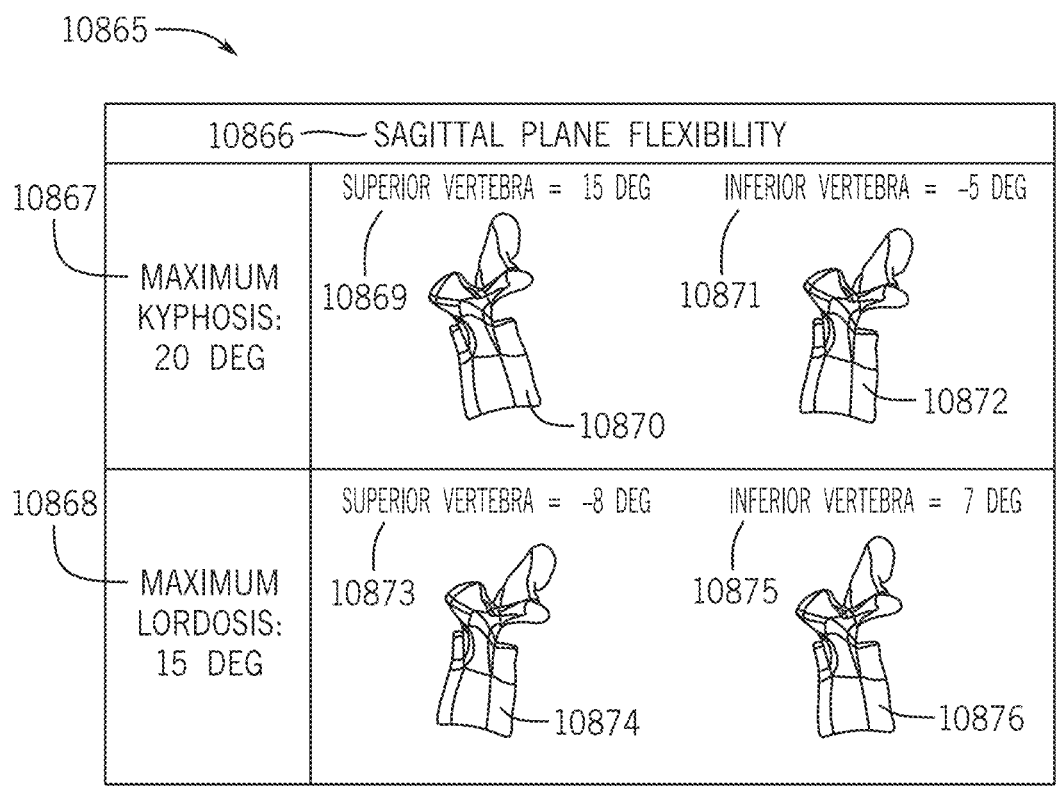
Figure 108G:
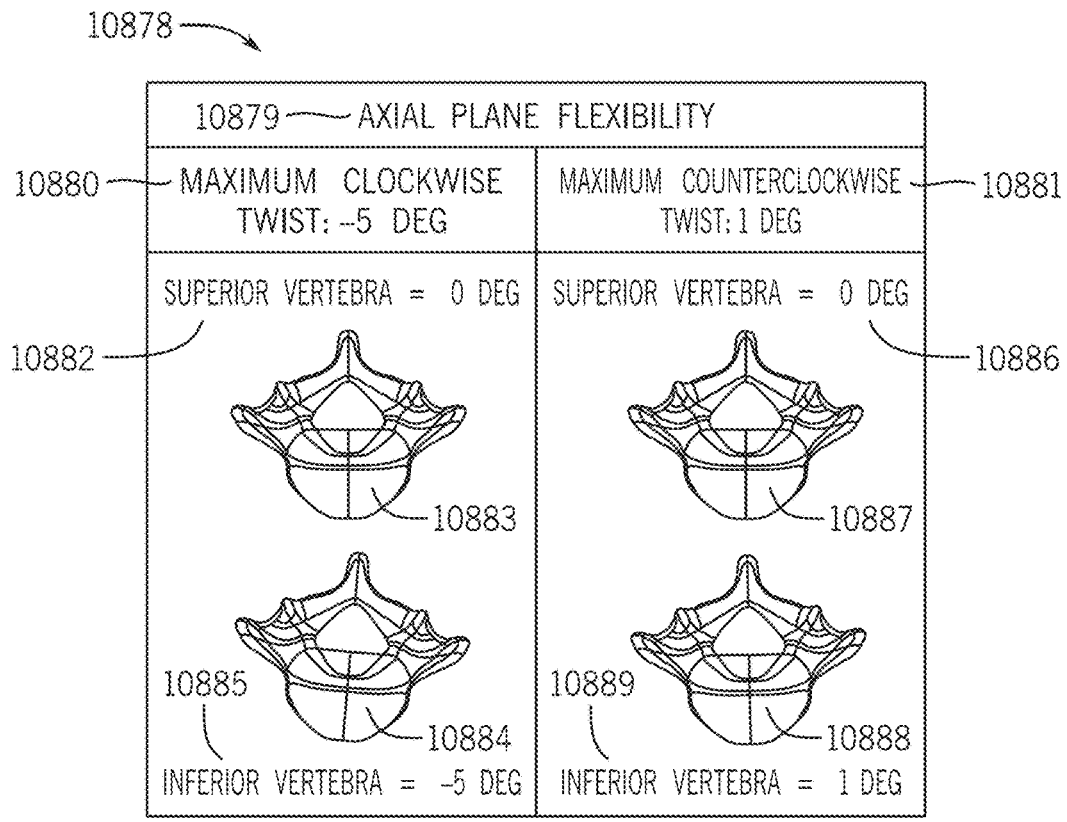
Figure 108H:
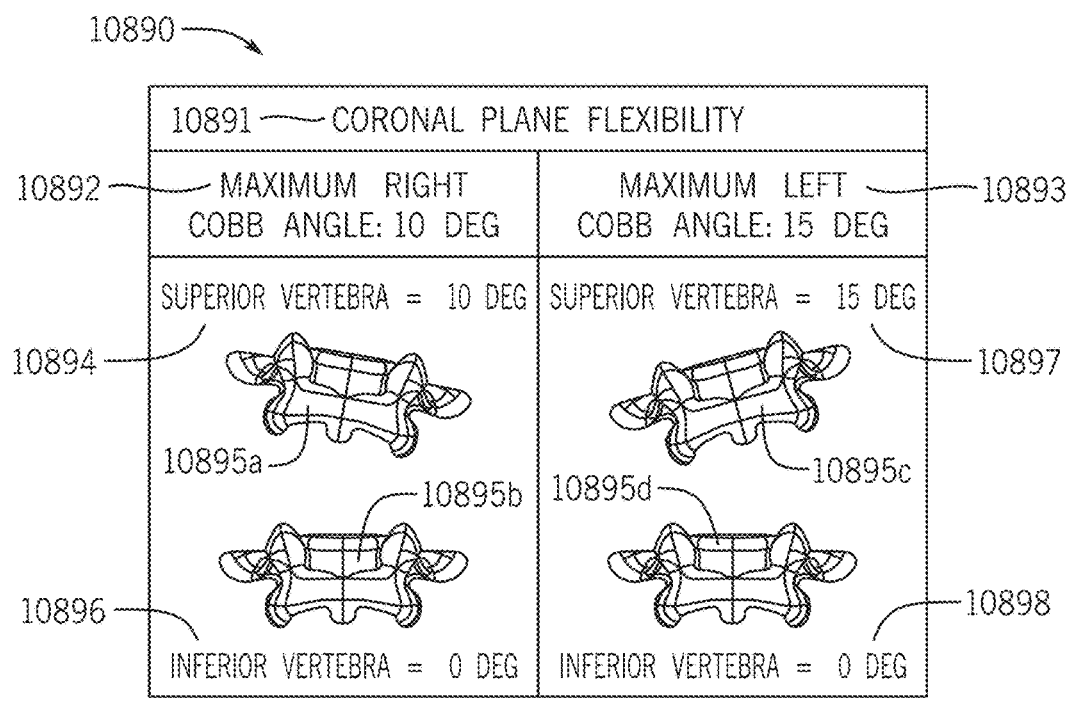

FIGS. 108F-108H illustrate a display interface for analyzing the position and orientation of flexibility assessment devices, displaying a summary view across all anatomical planes of the exhibited range of motion of engaged vertebrae during an assessment, as described previously in relation to FIGS. 108A-108E in accordance with some embodiments of the invention.

Figure 109A:
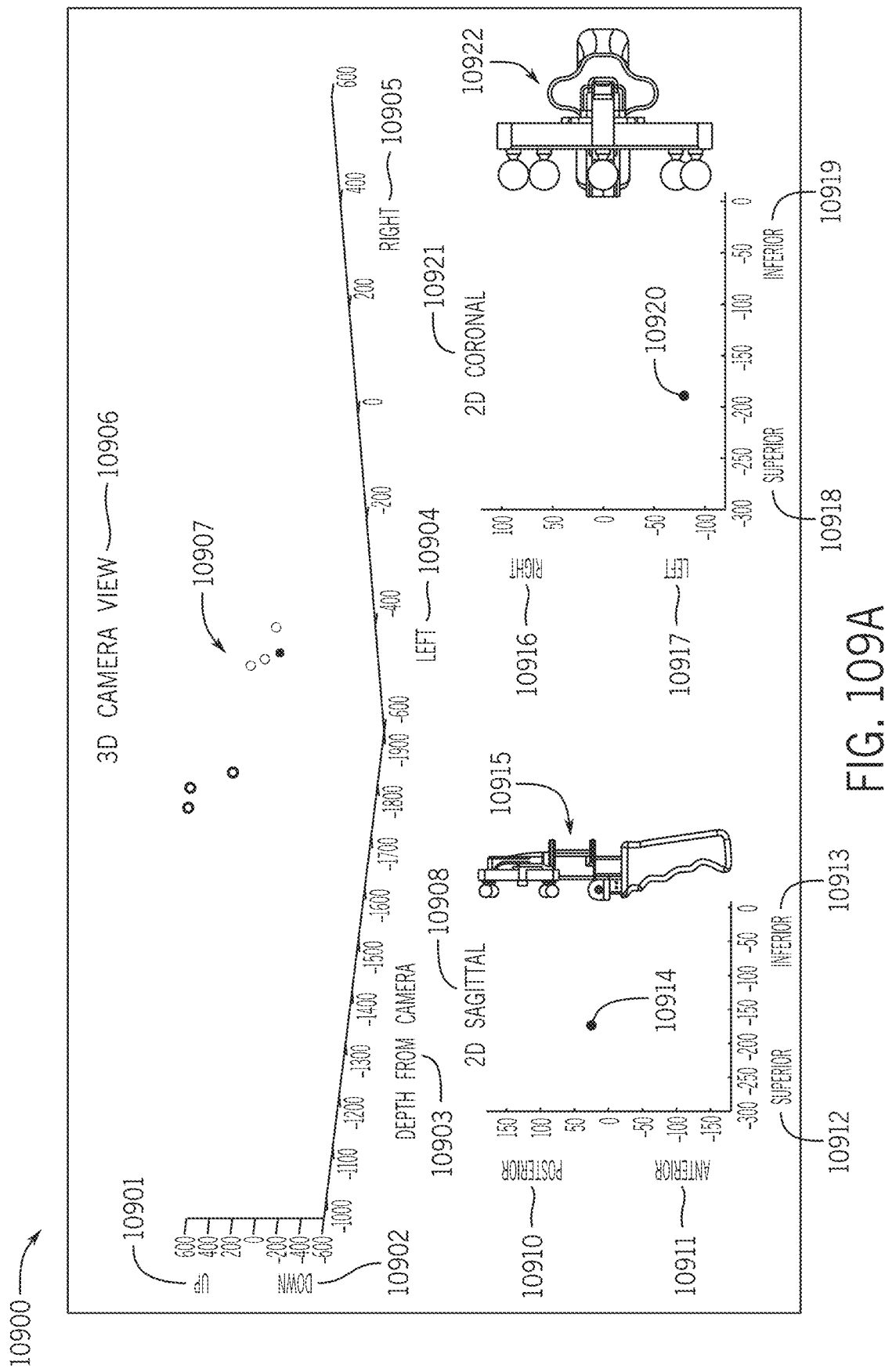

FIG. 109A illustrates a display interface for displaying the live location of devices used for the registration of a rod contour in accordance with some embodiments of the invention.

Figure 109B:
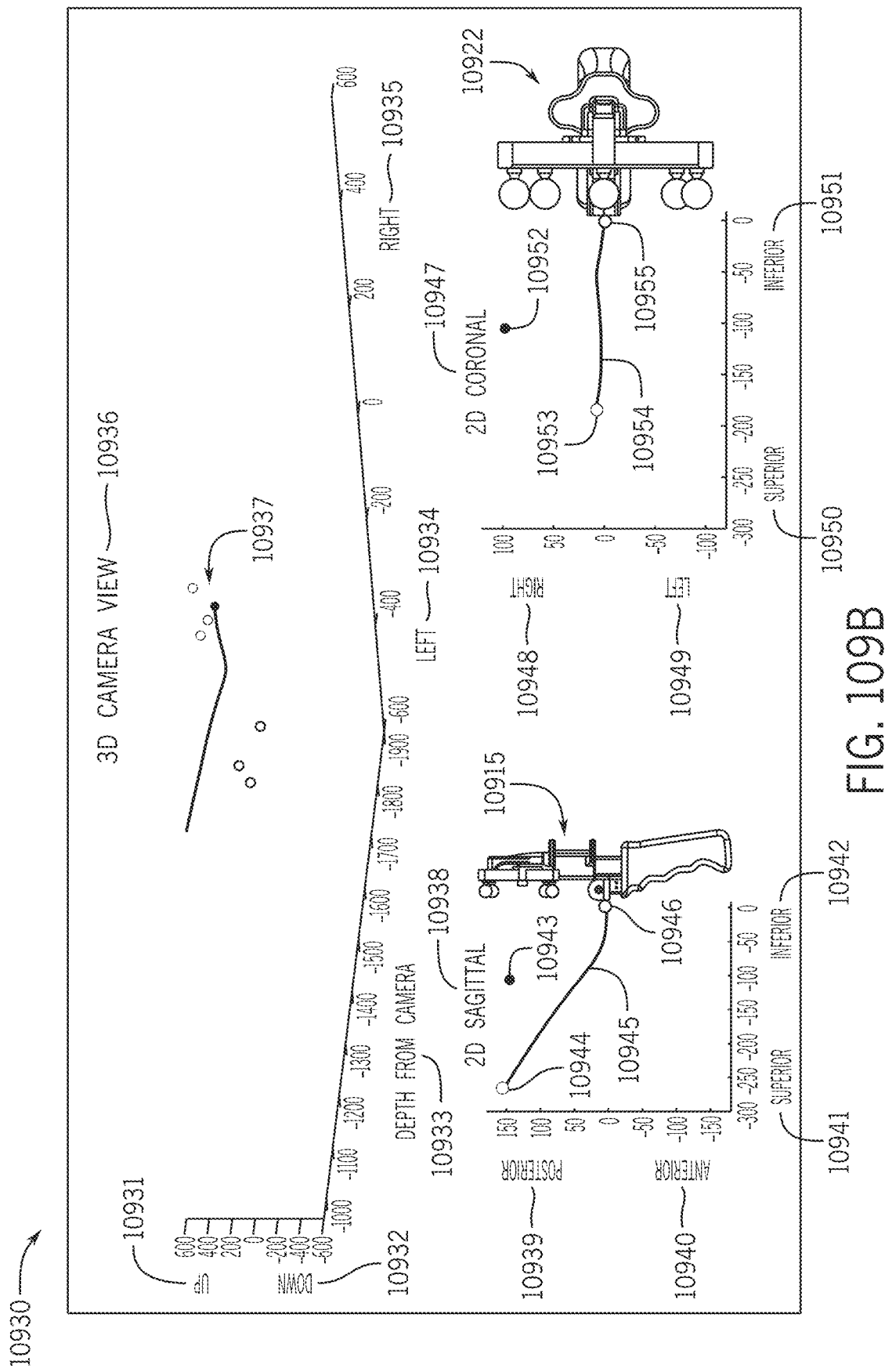

FIG. 109B illustrates a display interface for displaying the live location of devices used for the registration of a rod contour and a completed tracing of the rod's contour as described previously in relation to FIG. 109A in accordance with some embodiments of the invention.

Figure 109C:
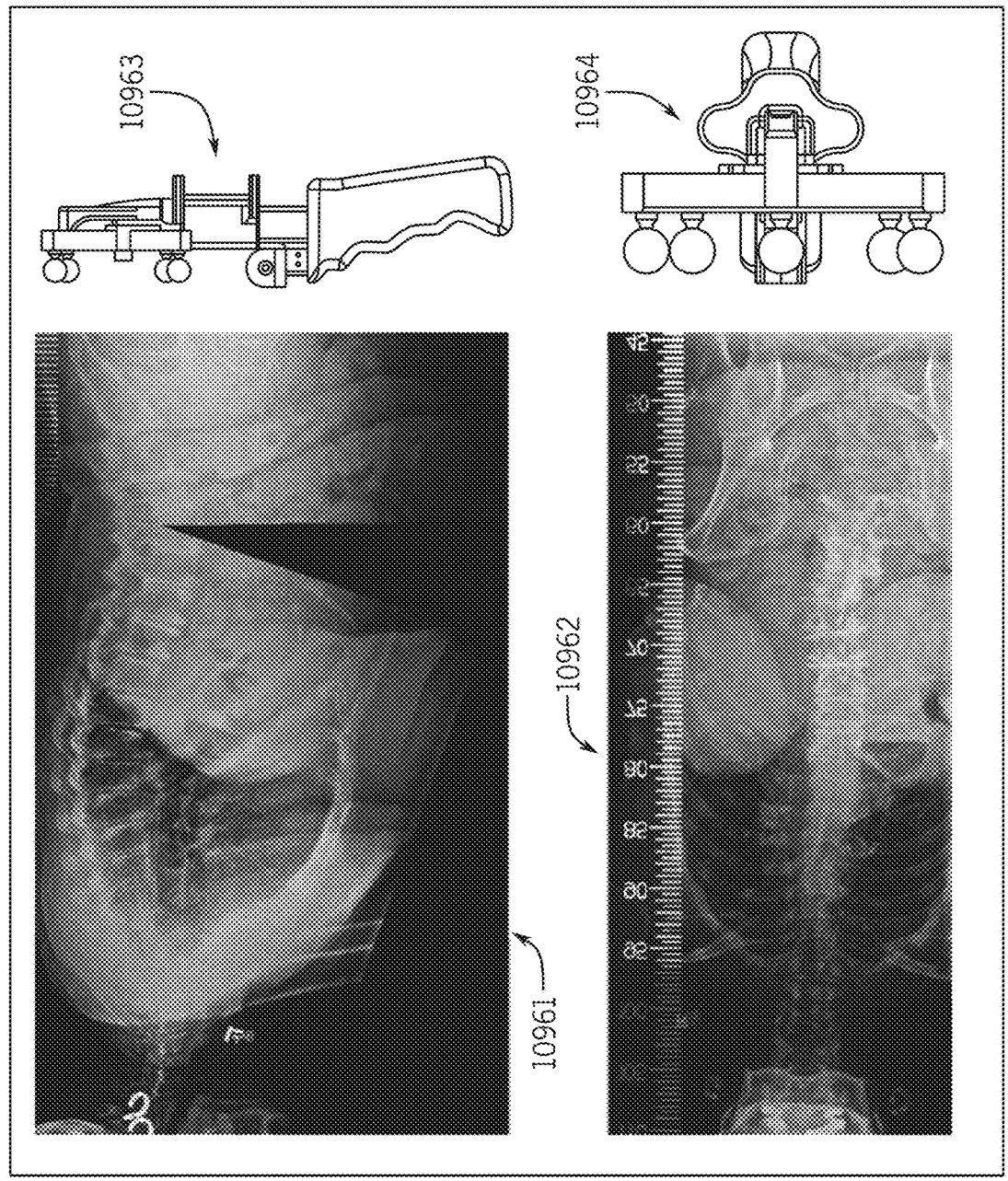
Figure 109D:
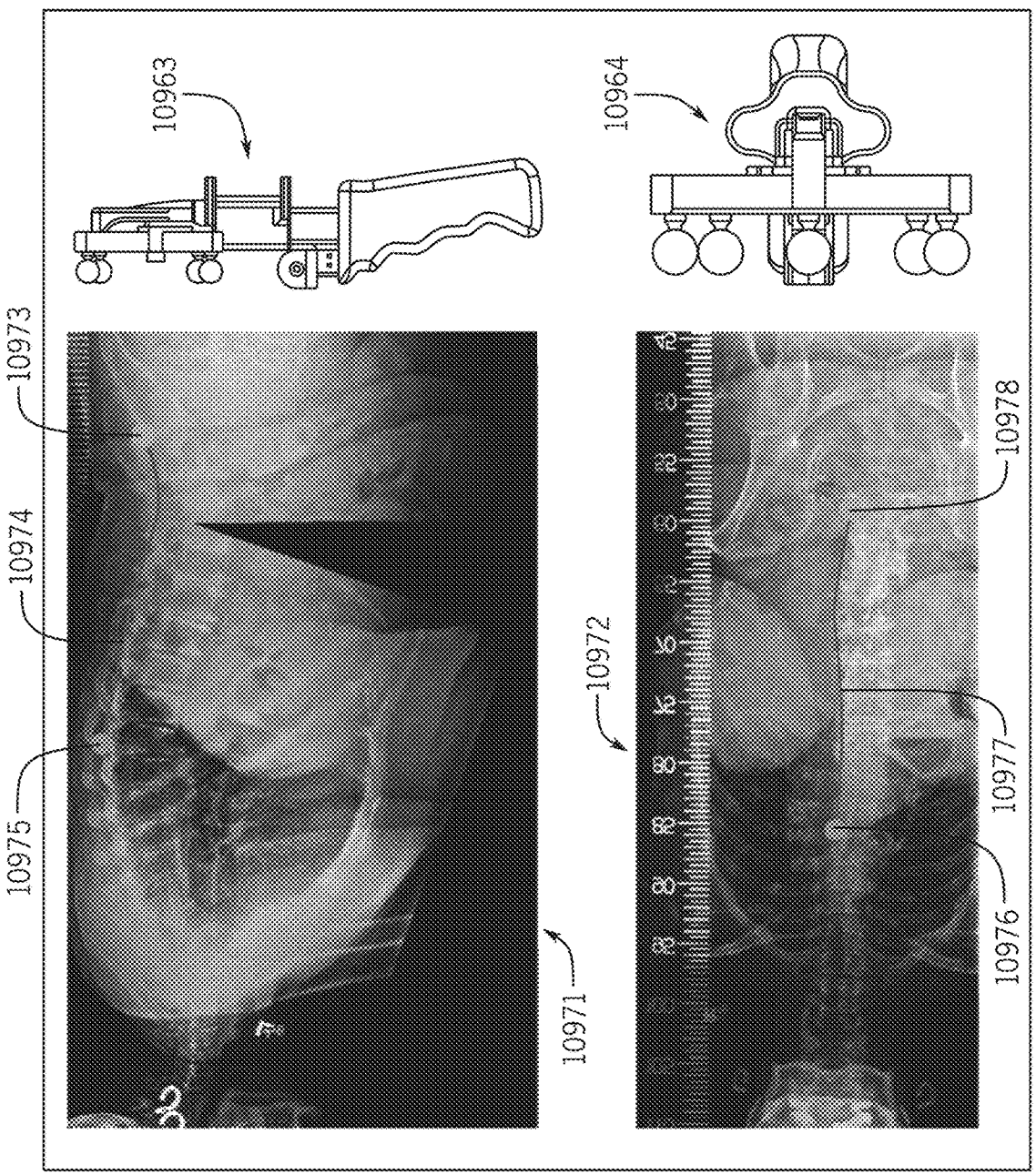

FIGS. 109C-109D illustrate a display interface with patient images and the overlay of a registered rod contour that has been adjusted to match the user's goal for the patient's contour, as described previously in relation to FIGS. 109A-109B in accordance with some embodiments of the invention.

Figure 110A:
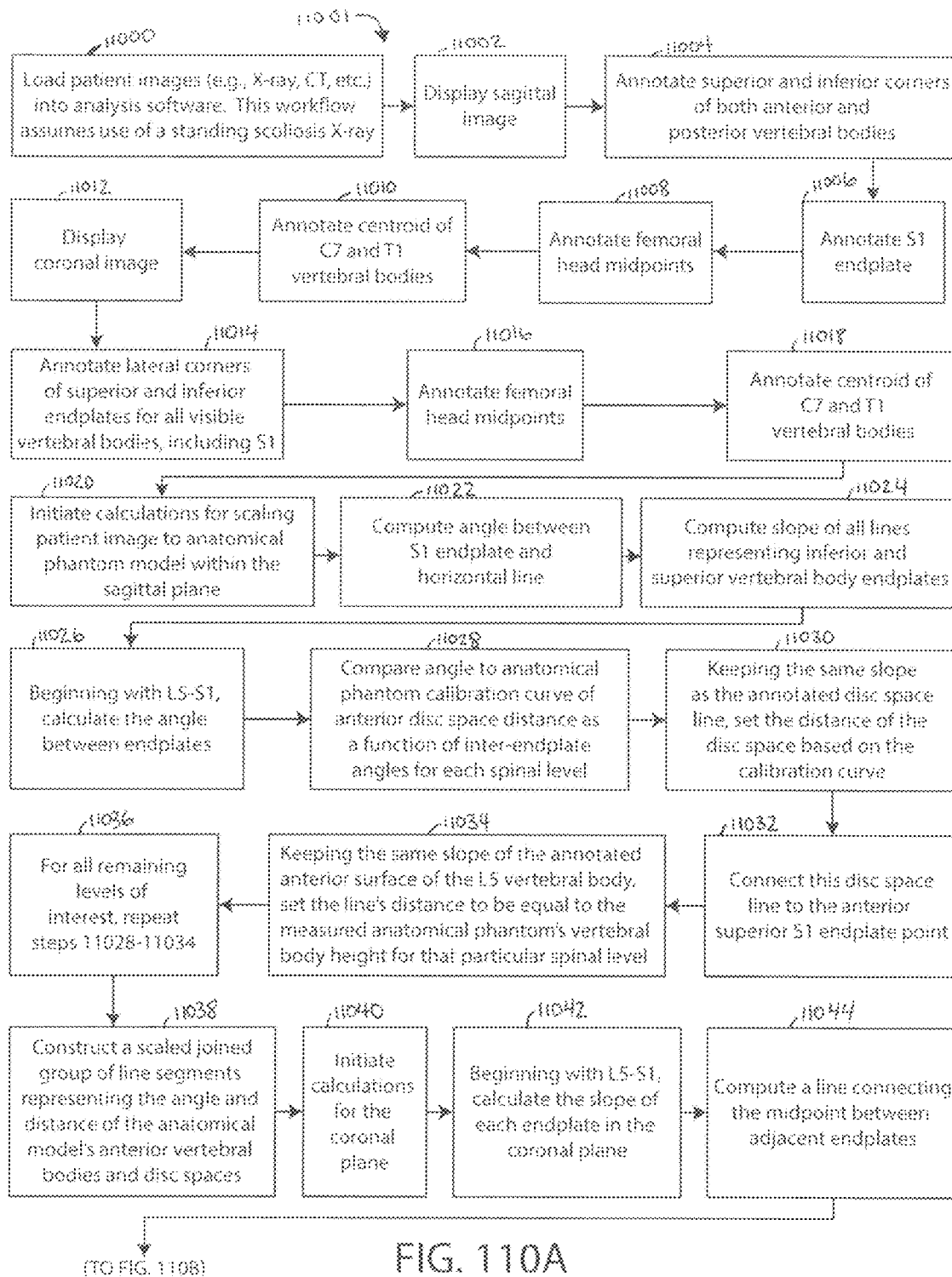
Figure 110B:
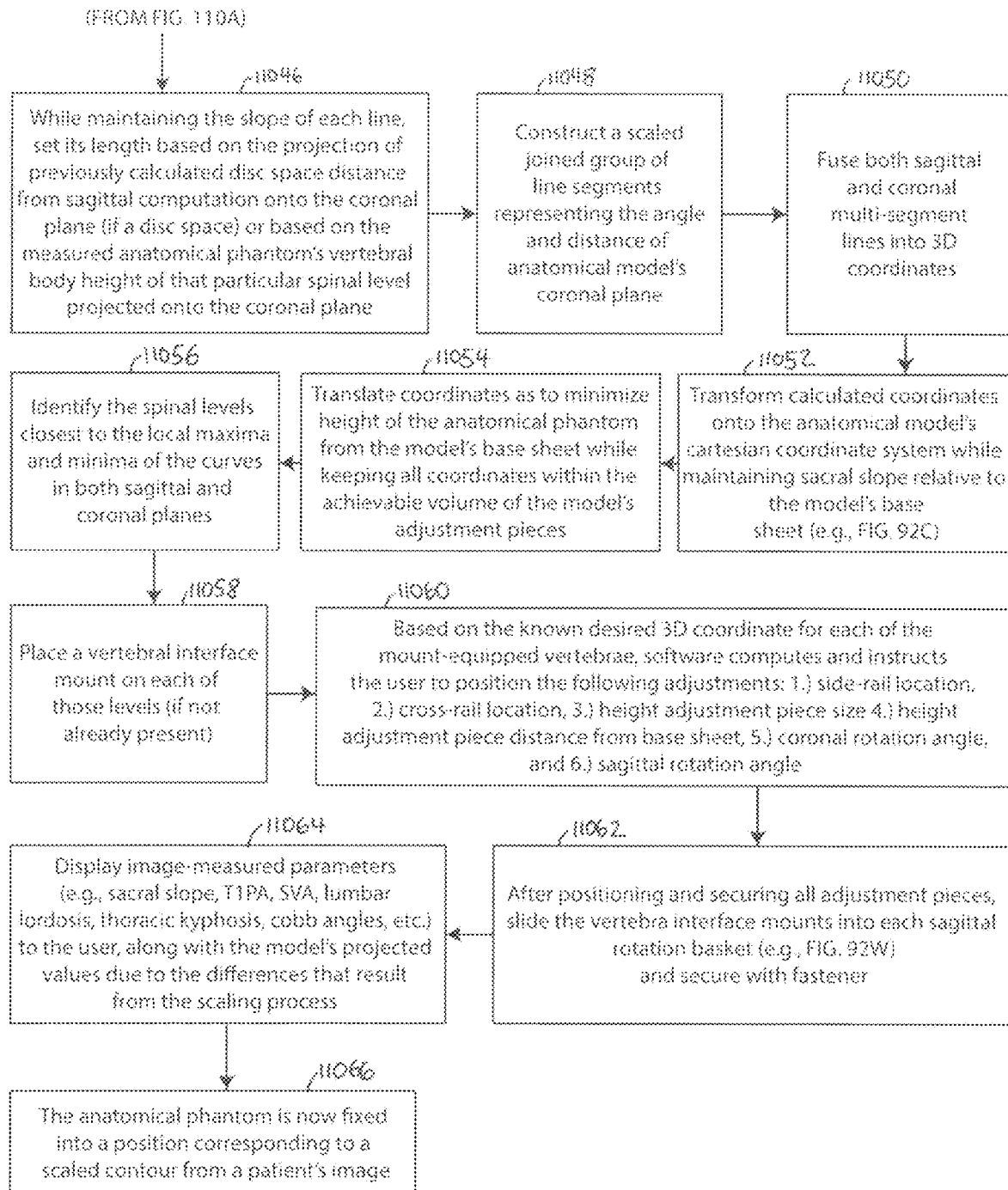

FIGS. 110A-110B illustrate a workflow for adjusting the positions of vertebral holders for an adjustable model holder with inputs from patient imaging in accordance with some embodiments of the invention.

Figure 111A:
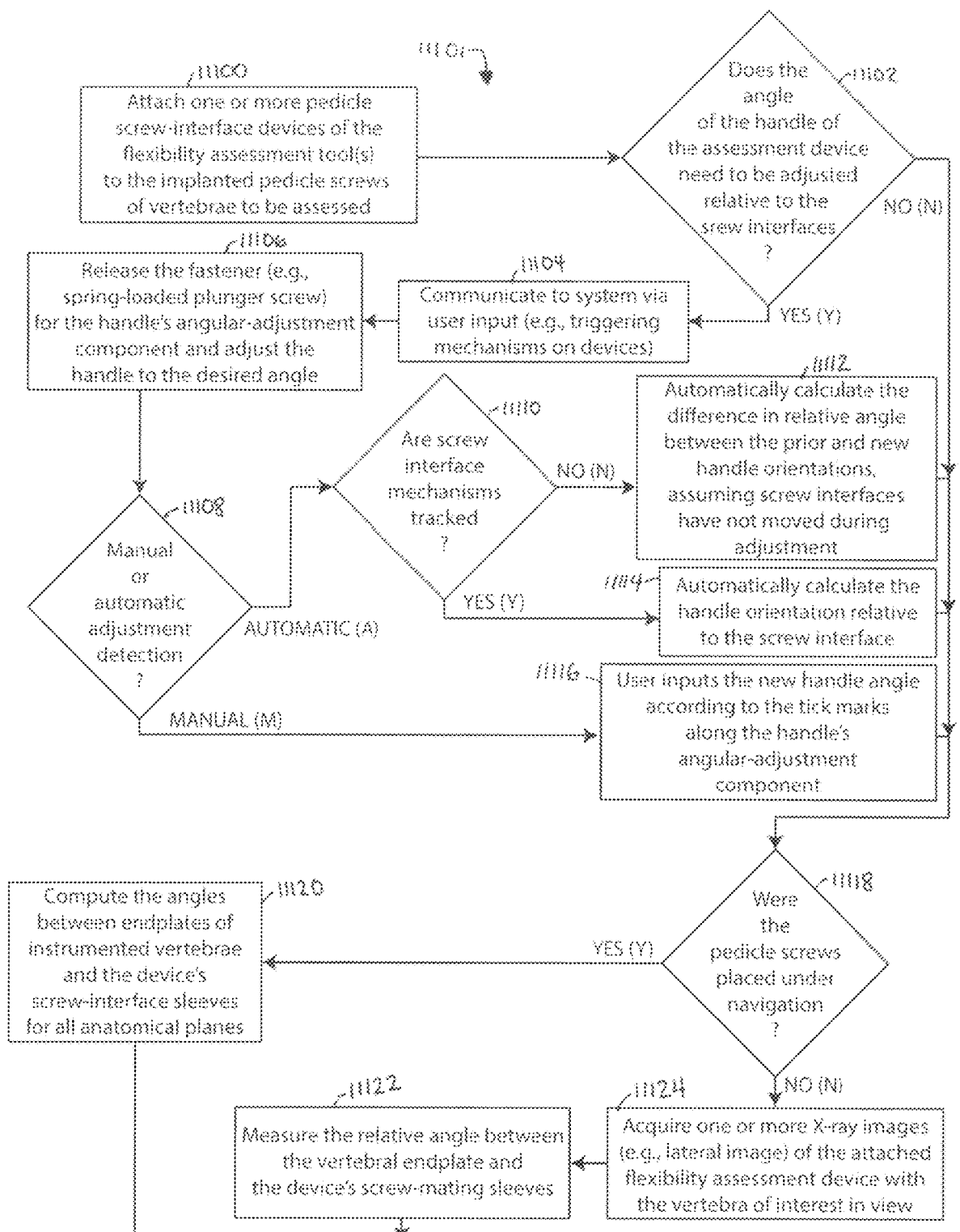
Figure 111B:
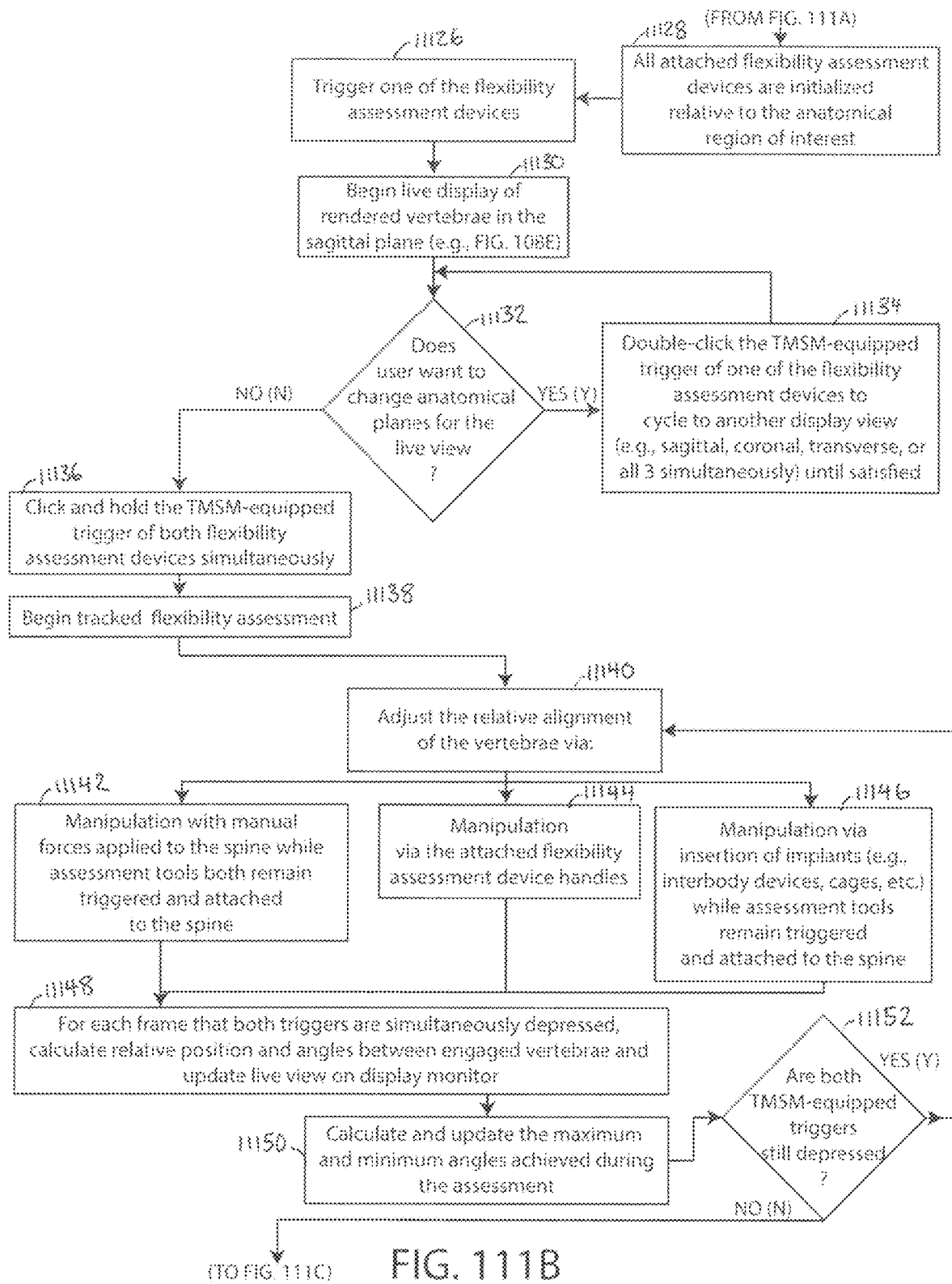
Figure 111C:
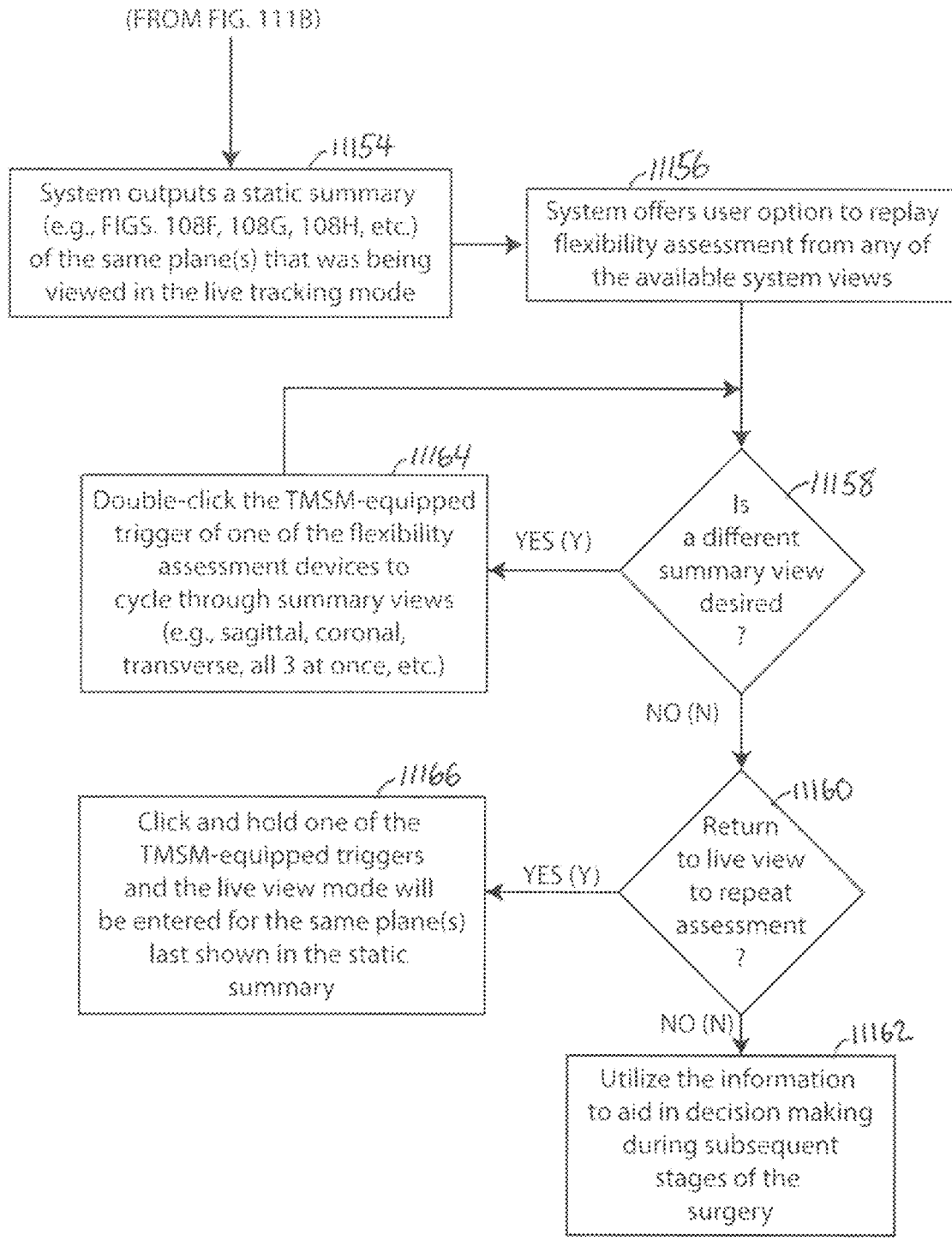

FIGS. 111A-111C illustrate a workflow for analyzing and outputting the range of motion results of engaged vertebrae during and after a flexibility assessment in accordance with some embodiments of the invention.

Figure 112A:
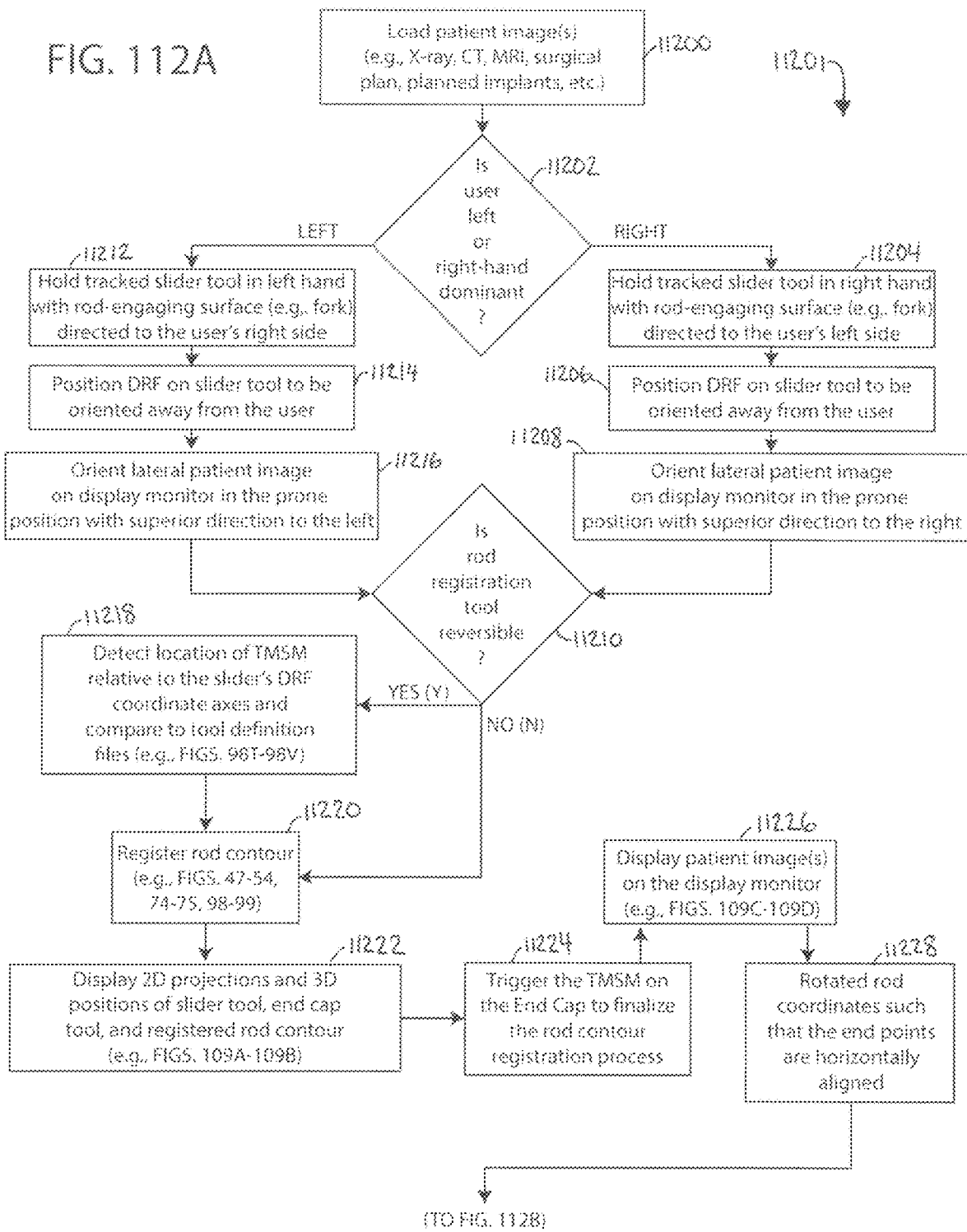

FIGS. 112A-112C illustrate a workflow for registering and overlaying the contour of a rod and subsequent contours of adjusted rods in accordance with some embodiments of the invention.

Figure 113:
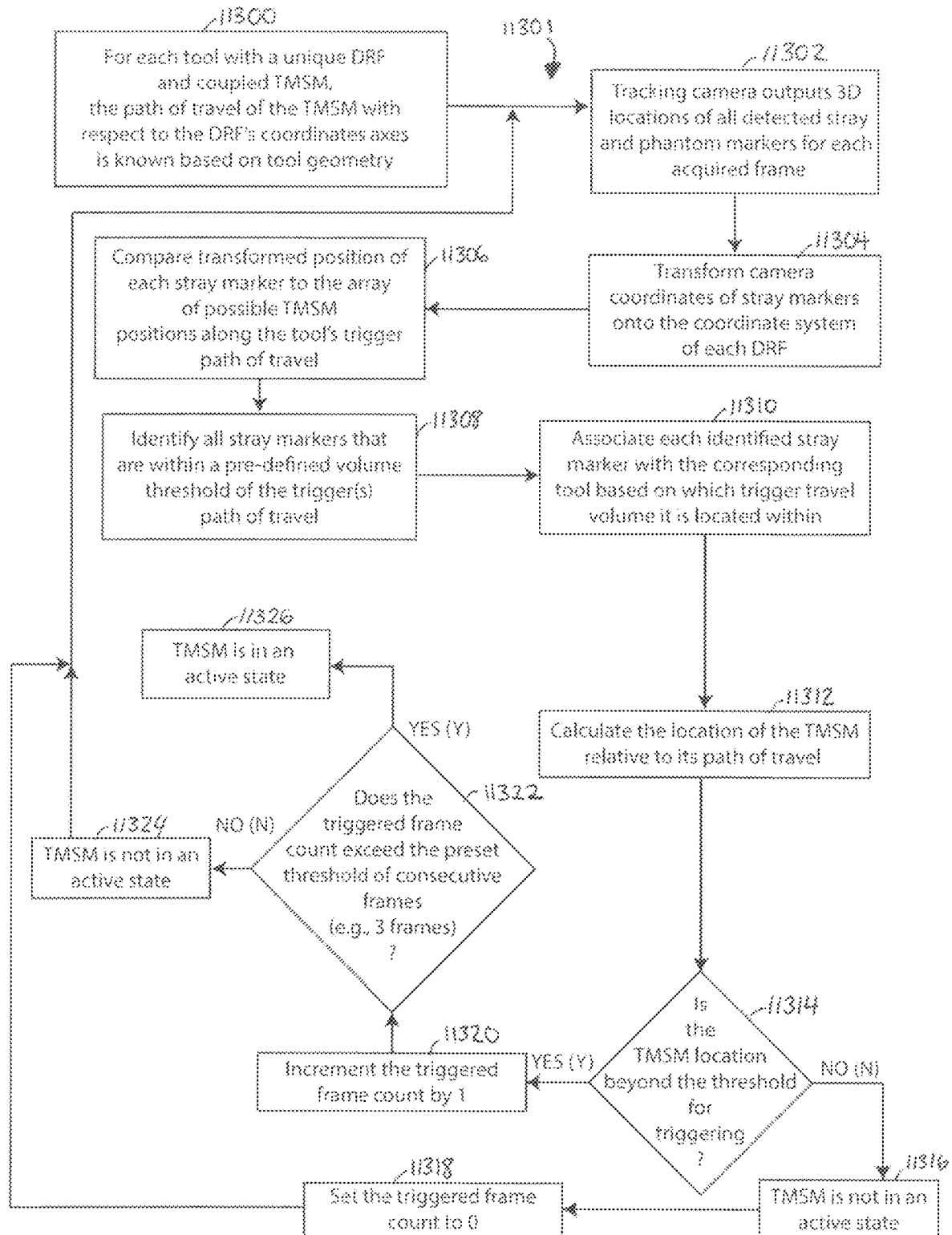
Figure 114A:
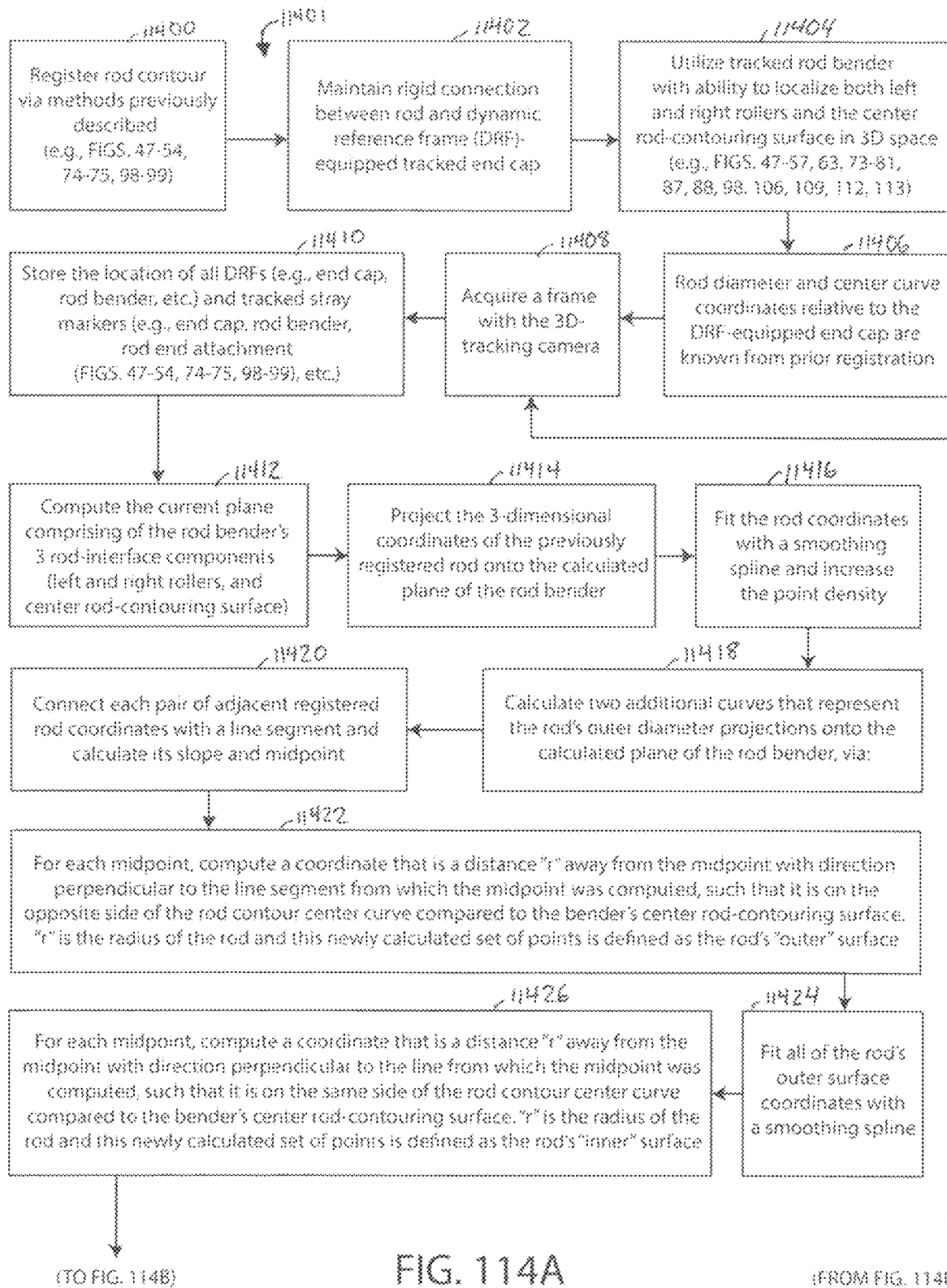
Figure 114B:
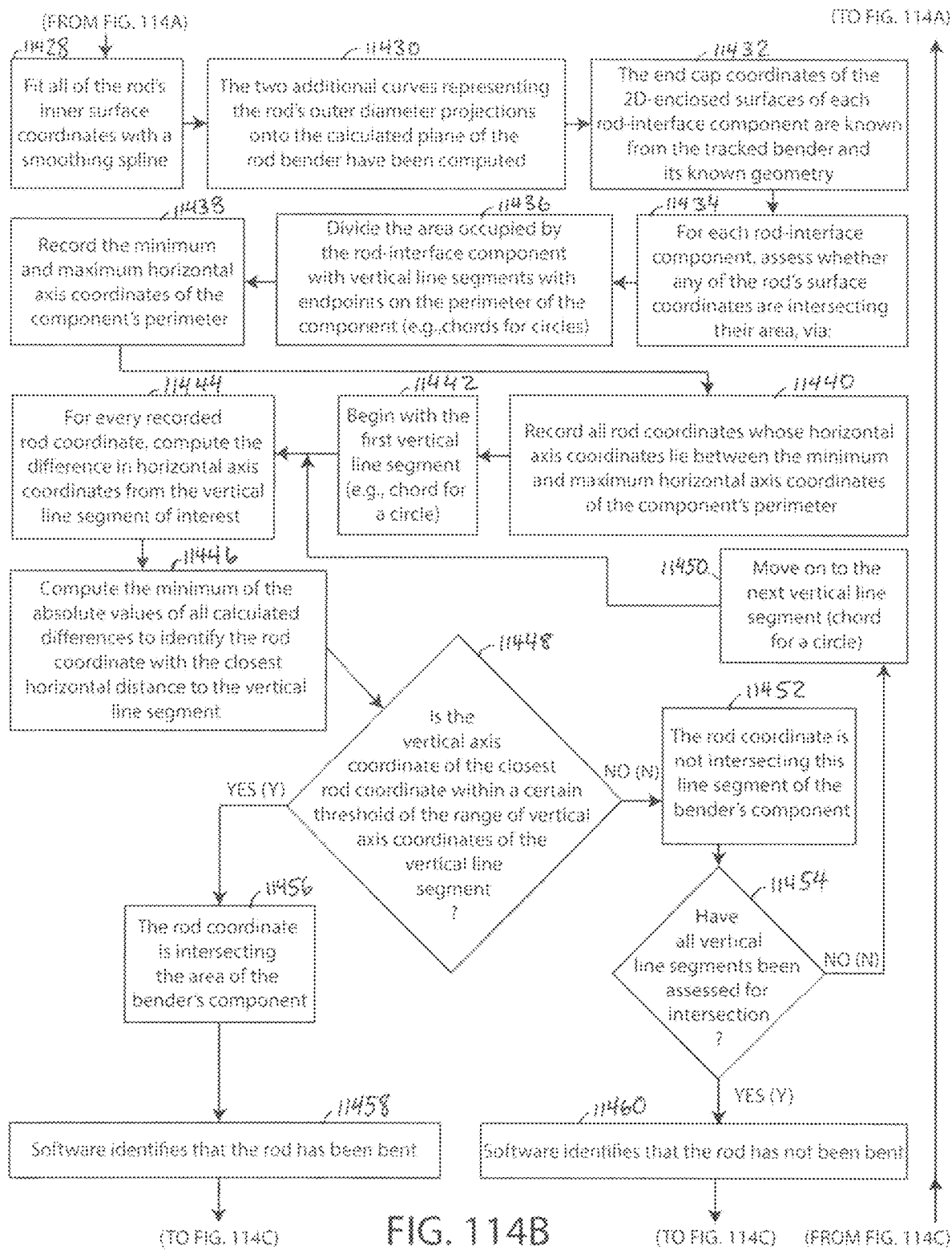
Figure 114D:
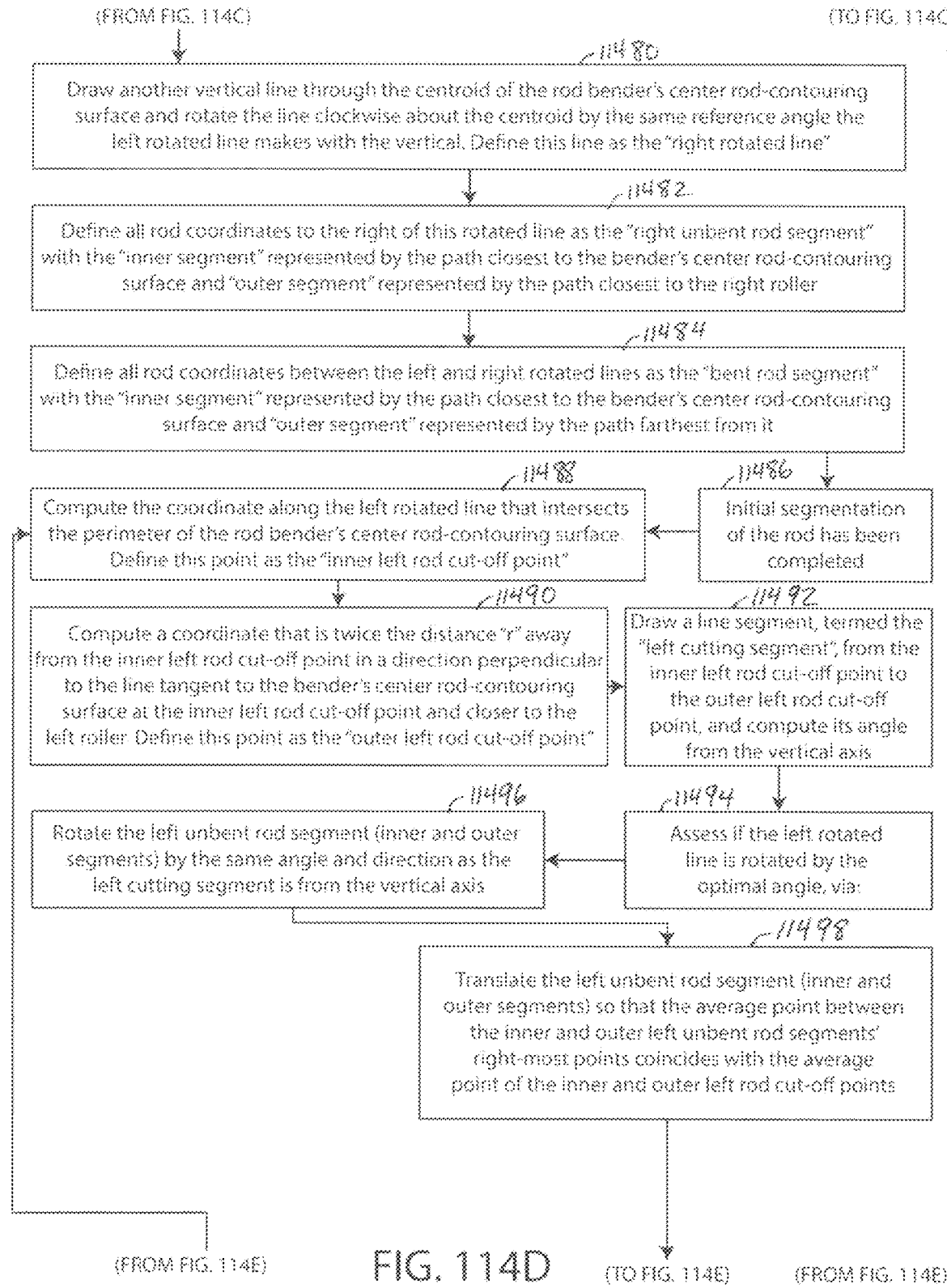
Figure 114E:
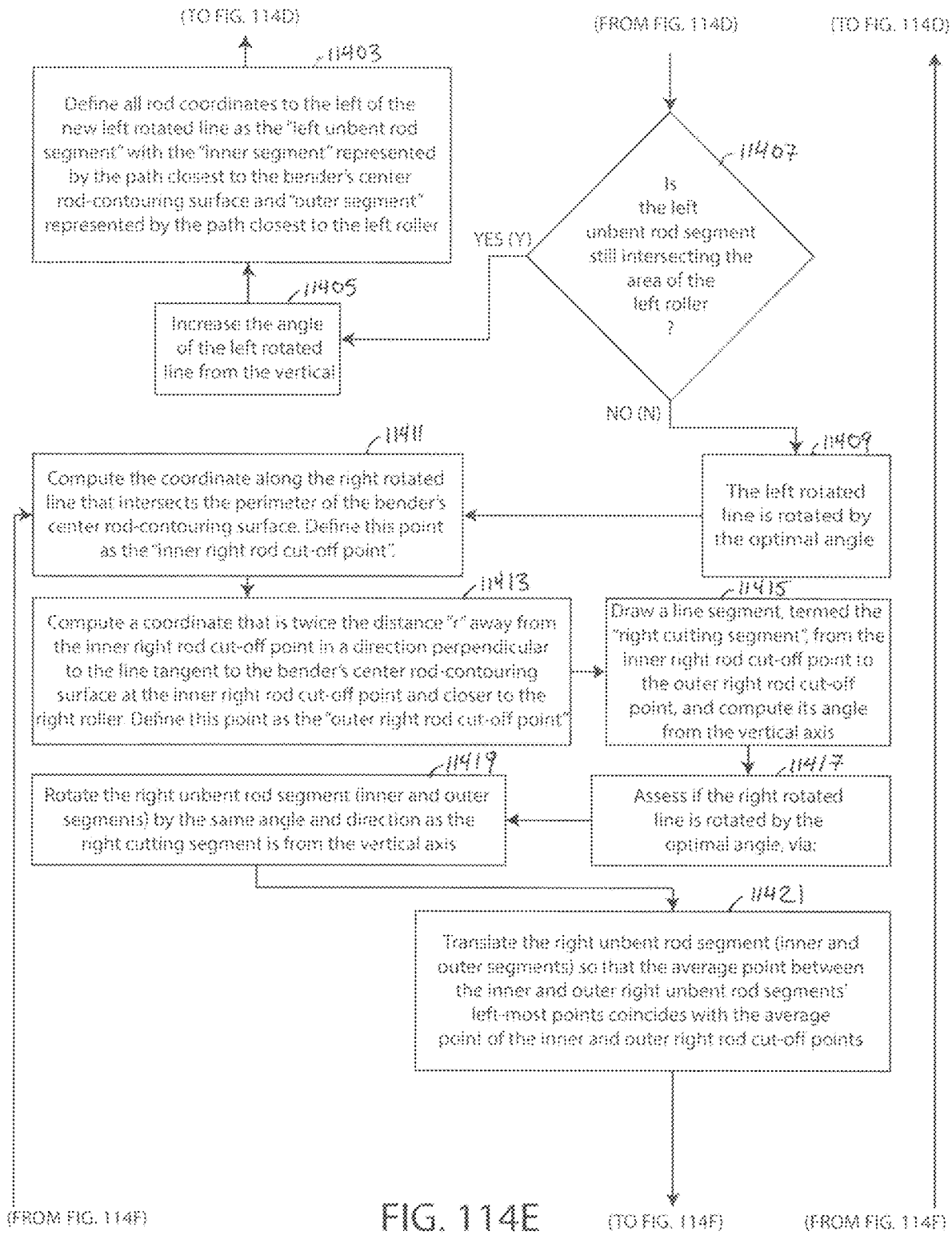
Figure 114F:
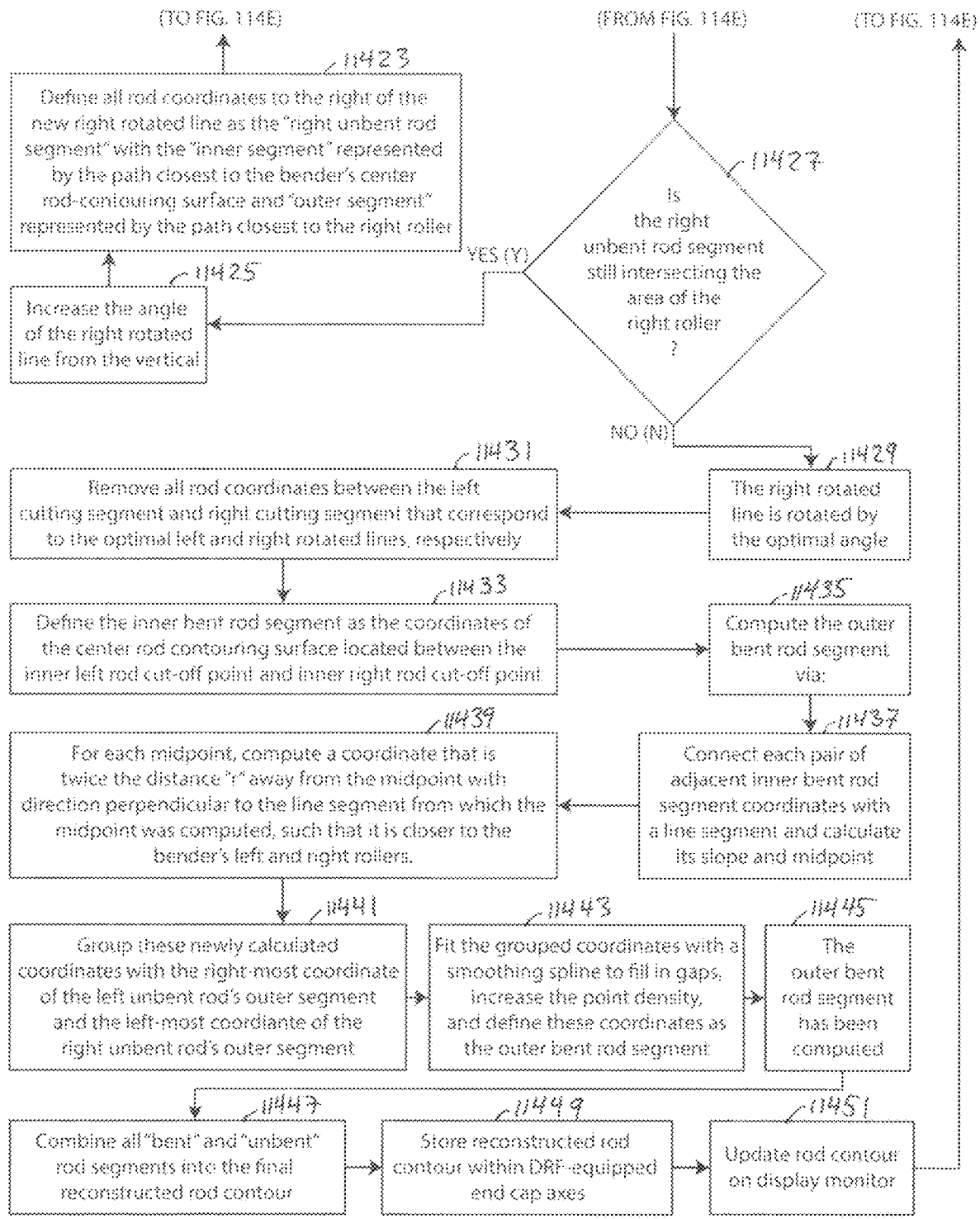

FIG. 113 illustrates a workflow for filtering stray markers outputted by a 3D-tracking camera, identifying the TMSM(s) of DRF-equipped tools with triggering mechanisms, and analyzing if the TMSMs are in an active triggering state, in accordance with some embodiments of the invention.

FIGS. 114A-114F illustrate a workflow for estimating the contour of a rod during and after it is bent in accordance with some embodiments of the invention.

Figure 115A:
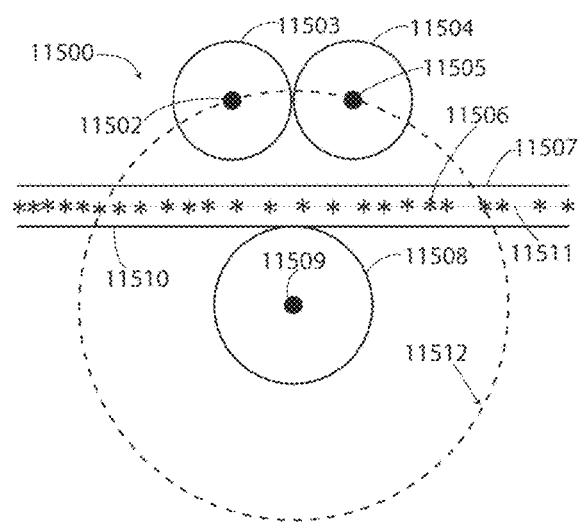

FIG. 115A illustrates a front view of a rod contour and roller surfaces of a rod bender in accordance with some embodiments of the invention.

Figure 115B:
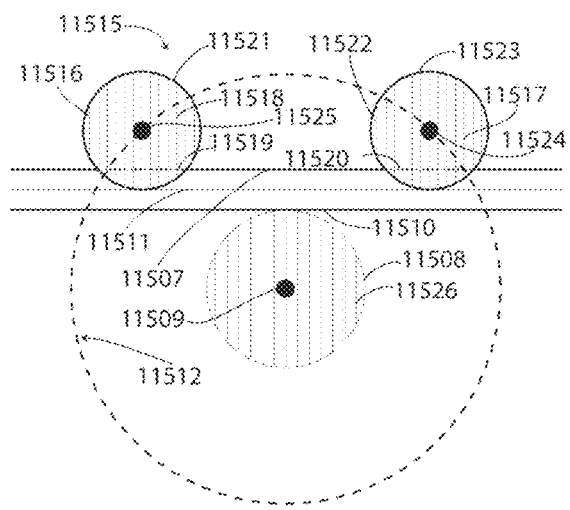
Figure 115C:
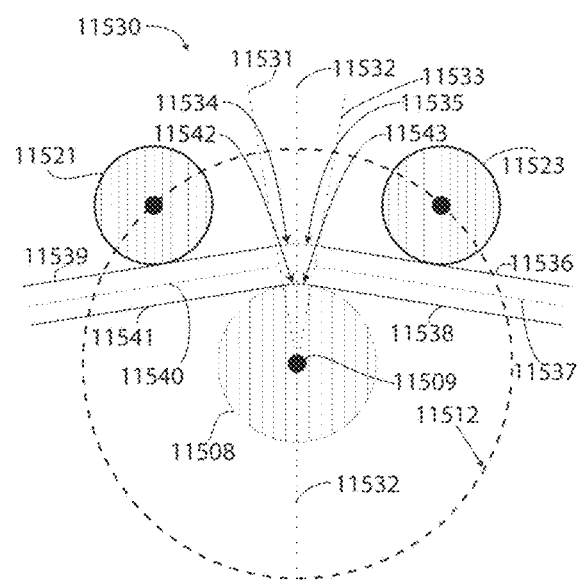

FIGS. 115B-115C illustrate a front view of a rod contour and roller surfaces of a rod bender during the process of contouring an engaged rod, as described previously in relation to FIG. 115A in accordance with some embodiments of the invention.

Figure 115D:
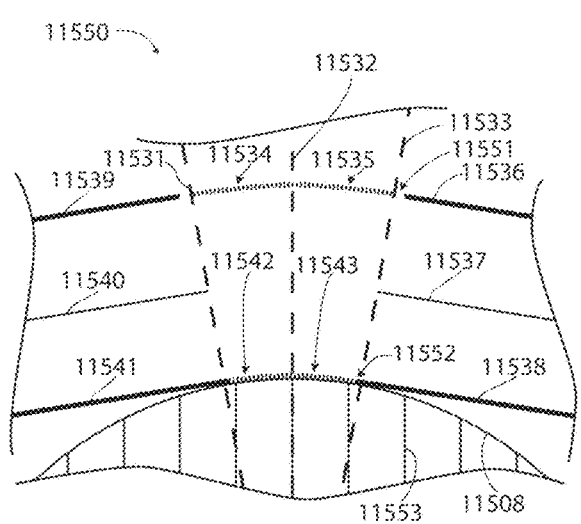

FIG. 115D illustrates a front, close-up view of an adjusted, segmented rod contour against the center rod-contouring surface of a rod bender, as described previously in relation to FIGS. 115A-115C in accordance with some embodiments of the invention.

Figure 115E:
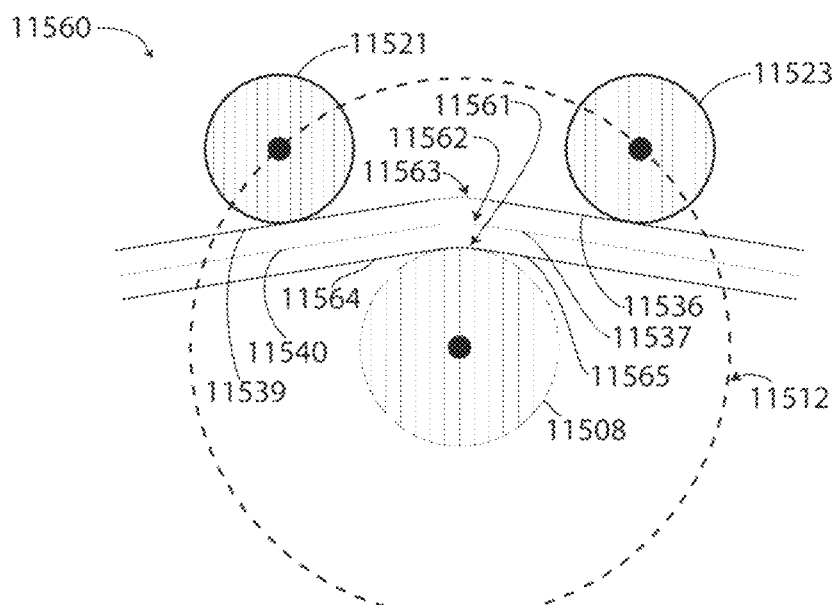

FIG. 115E illustrates a front view of an adjusted rod contour with estimated contour corrections while engaged with the center rod-contouring surface of a rod bender, as described previously in relation to FIGS. 115A-115D in accordance with some embodiments of the invention.

Figure 115F:
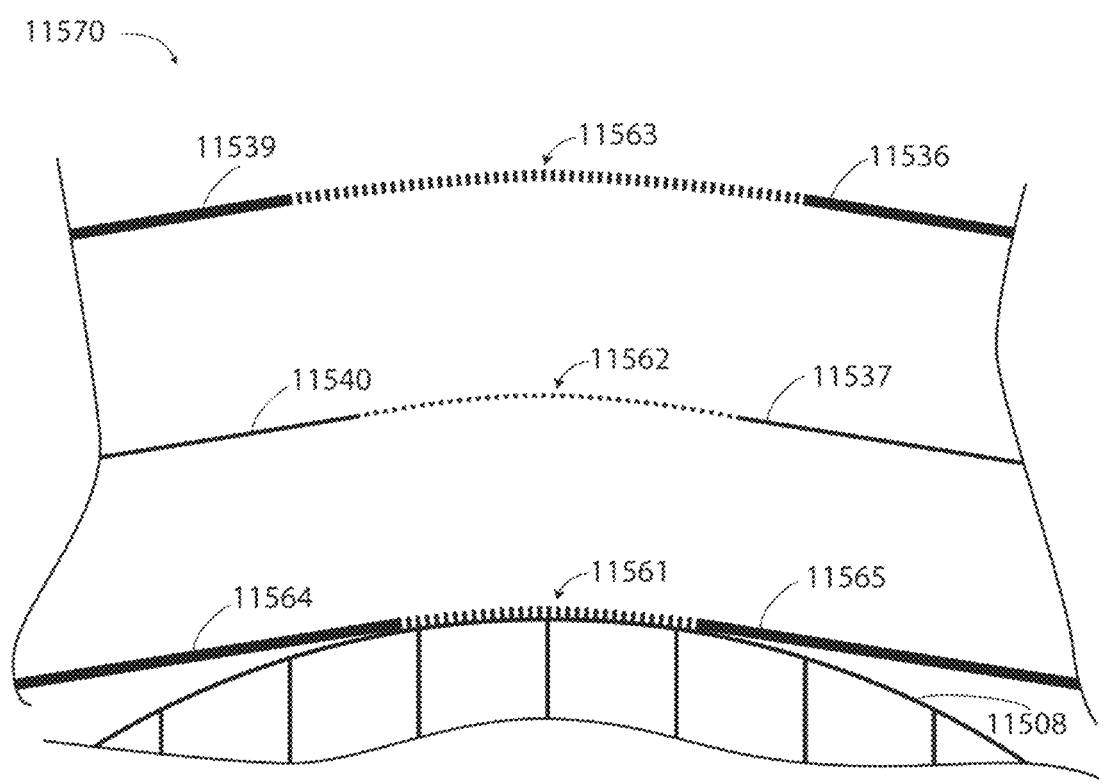

FIG. 115F illustrates a front, close-up view of an adjusted rod contour with estimated contour corrections while engaged with the center rod-contouring surface of a rod bender, as described previously in relation to FIGS. 115A-115E in accordance with some embodiments of the invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

As used herein, "tracked" refers to the ability of a particular object to interface with a tracking device (e.g., such as one or more 3D-tracking optical cameras and/or one or more 3D-tracking electromechanical devices) in at least FIG. 4H, FIG. 5B, FIGS. 7-8, FIGS. 10A-10G, FIGS. 11A-11B, FIGS. 14A-14C, FIGS. 15A-15C, FIG. 16, FIGS. 17A-17B, FIGS. 18A-18B, FIGS. 19A-19E, FIGS. 20, and 20A-20E, FIGS. 21A-21B, FIG. 22, FIGS. 23A-23C, FIGS. 24-26, FIGS. 27A-27D, FIGS. 28A-28B, FIGS. 29A-29D, FIG. 30B, FIG. 31, FIG. 38, FIGS. 38A-38G, FIGS. 39A-39F, FIGS. 40A-40C, FIGS. 41A-41D, FIGS. 42A-42K, FIGS. 43A-43F, FIGS. 44A-44D, FIGS. 44A-44B, FIGS. 46A-46G, FIGS. 47A-47B, FIGS. 48A-48C, FIGS. 49A-49D, FIGS. 50A-50E, FIGS. 51A-51I, FIGS. 52A-52D, FIGS. 53A-53F, FIGS. 54A-54D, FIGS. 55A-55I, FIGS. 56A-56F, FIGS. 57A-57D, FIGS. 64A-64B, FIGS. 73A-

73B, FIGS. 77A-77C, FIGS. 79A-79G, FIGS. 82A-82B, FIGS. 87A-87K, FIGS. 88A-88F, etc., that tracks the 3D coordinates of the tracked object relative to the tracking system's coordinate system. One example of an object that is "tracked" is when it possesses a substantially rigidly-attached dynamic reference frame that is tracked in 3D space.

As used herein, a dynamic reference frame (hereinafter "DRF") refers to three or more points (markers) that are positioned in a uniquely identifiable configuration such that their discrete locations are associated with an object identity. These uniquely-arranged markers allow for the calculation of both the 3D location and pose of a DRF, and also define a coordinate system relative to the DRF. Further, as used herein, a stray marker refers to a 3D-tracked object, typically either light-reflective or light-emitting, that can be visualized by a 3D-tracking camera and is not one of the markers that define a DRF. A stray marker can be associated with a DRF as well as have its location, pose, and behavior computed relative to one or more DRFs.

As used herein, a tracked mobile stray marker (TMSM) refers to a stray marker that is designed to move relative to either other stray markers or to nearby DRFs. The computation of a TMSM's position and/or motion relative to those other entities can be interpreted to communicate information and/or commands to a computer acquisition system.

As used herein, a probe refers and/or defines a device that is tracked in such a way that its location, orientation, and identity are known in 3D space. With that information, the system can extrapolate the location and orientation of other points and/or markers on and/or near the tracked object (e.g., the tip, shaft, unique features, etc.) even if they aren't directly tracked independently.

As used herein, a fiducial is an object that is used primarily as a reference to another point in space, in that when a fiducial is placed nearby to an object/region of interest, the relative position of the fiducial to the object of interest can be initialized. When the location and orientation of the fiducial is referenced in the future after initialization, the precise location of the initialized object/region of interest can then be calculated. Fiducials can have unique surface patterns in the form of indentations to be tapped, grooves to be traced, and/or mating features to be coupled, such that when interacted with by a 3D-tracked probe or end effector, the fiducial's 3D location and orientation, as well as identity, can be calculated by the acquisition system. In addition, a fiducial is most commonly an object with embedded radiopaque markers that enable for the fiducial's visualization and registration by radiographic imaging. If "fiducial marker" is ever used, that is an equivalent term to "fiducial", unless referring specifically to the embedded "radiopaque markers" within the fiducial structure that can be visualized on X-rays.

As used herein, the term "3D rigid transform" describes the mathematical operation that involves the computational application of a matrix containing both rotation and translation transformations. The 3D rigid transform is utilized when the system needs to transform the relations of an object from one coordinate axes to another, without deformation of the object. For example, instead of having a 3D-tracked tool's location coordinates and orientation values to be in reference to a 3D-tracking, acquisition system, the 3D-tracked tool can be substantially rigidly transformed to be in reference to the coordinates and orientation of another 3D-tracked tool or DRF within the scene. Another term that is used herein is "rigid body transform", a synonym.

As used herein, a pedicle screw is a screw that is inserted into the anatomical structure of a spinal vertebra called a pedicle. Whenever this screw is referenced, it is assumed that the system can also be compatible with any other screw, fastener, and/or other surgical implants (e.g., cages, rods, etc.).

As used herein, a tulip head is an object that attaches to a screw head and can be polyaxial or uniaxial in its range of motion. The tulip head typically has internal threads that enable a fastener to engage substantially rigidly with the structure. The tulip head can also have mating features on the external wall/surface that enable a device to substantially rigidly attach to the tulip head. Typically, tulip heads are designed to accept the insertion of a rod implant.

As used herein, a rod can be any object with a cross-section similar to a circle, but also other shapes (e.g., keyhole, semi-circle, etc.). A rod can be of any length and curvature. A rod can be coupled to tracked and non-tracked tools. A rod is typically inserted into the cavity of a tulip head and then substantially rigidly fixed in-place via a cap screw that is fastened via threads on the interior wall of a tulip head.

As used herein, "register" or a "registration" refers to any time a 3D-tracked tool or object signals information to the computer system regarding an object's state, 3D location, 3D orientation, unique identity, relative position to other objects, or other relevant information for the system's algorithms. For example, "a 3D-tracked probe can register the position and identity of a fiducial" means that the 3D-tracked probe is able to communicate to the computer system that a particular fiducial has a specific position and orientation in 3D space relative to the 3D-tracking, acquisition system.

As used herein, "sagittal" is an anatomical plane that refers the side view of a patient in which the superior portion of the patient (e.g., the head) is on the right or left side and the inferior portion of the patient (e.g., feet) is on the opposite end, depending on which side of the patient the perspective is from, left or right half. The posterior aspect of the patient will be visible on either the top or bottom of the view, depending on whether the patient is supine or prone.

As used herein, "coronal" is an anatomical plane that refer to the top view of a patient in which the superior portion of the patient (e.g., the head) is on the top or bottom and the inferior portion of the patient (e.g., feet) is on the opposite end, depending on which side of the patient the perspective is from, below or above, as well as which side the left or side of the patient appears in view, right or left.

As used herein, "axial" is an anatomical plane that refer to the cross-sectional view of a patient in which the posterior portion of the patient is on the top or bottom and the anterior portion of the patient is on the opposite end, depending on which side of the patient the perspective is from, prone or supine. The patient view can also change depending on whether the view is pointed towards the inferior or superior aspect of the patient. If "tranverse" is ever used, that is an equivalent term to "axial".

As used herein, "depressible sliding shaft" or "plunger" refers to a depressible, sometimes spring-loaded, sliding shaft that actuates via pressing against a surface, a spring-loaded button, or other mechanical means of actuation. A plunger typically has a mechanically-linked TMSM that is able to communicate its position along the plunger relative to the position of a nearby DRF or other tracked stray markers. This shaft is typically coaxial with a 3D-tracked tool. The shaft does not necessarily have to be protruding out of an object, as it can also be engaged within an object.

As used herein, an electromechanical, 3D-tracking system refers to the invention described throughout in which the 3D location and orientation of a probe is tracked in space via mechanical linkage to extensible cords that are independently tracked in 3D space. This system includes rotary encoders for measuring the length of extensible cords as well as sensors for detecting spherical rotation angles of the cord's trajectory traveling through ball-and-socket interfaces.

As used herein, spinal alignment parameters of an assessment of the segmental and/or full-length spinal alignment is produced with values for each relevant radiographic alignment parameter (e.g., Cobb angle, lumbar lordosis (LL), thoracic kyphosis (TK), C2-C7 sagittal vertical axis (SVA), C7-S1 SVA, C2-S1 SVA, central sacral vertical line (CSVL), T1 pelvic angle (T1PA), pelvic tilt (PT), pelvic incidence (PI), chin-brow to vertical angle (CBVA), T1 slope, sacral slope (SS), C1-2 lordosis, C2-C7 lordosis, C0-C2 lordosis, C1-C2 lordosis, PI-LL mismatch, C2-pelvic tilt (CPT), C2-T3 angle, spino-pelvic inclination from T1 (T1SPi) and T9 (T9SPi), C0 slope, mismatch between T-1 slope and cervical lordosis (T1S-CL), and/or global sagittal angle (GSA)). Any time alignment assessments or calculation of alignment parameters are mentioned in this document, it can be assumed that any of the above parameters, and others not mentioned but commonly known, can be calculated in that portion of the description.

Figure 5A:
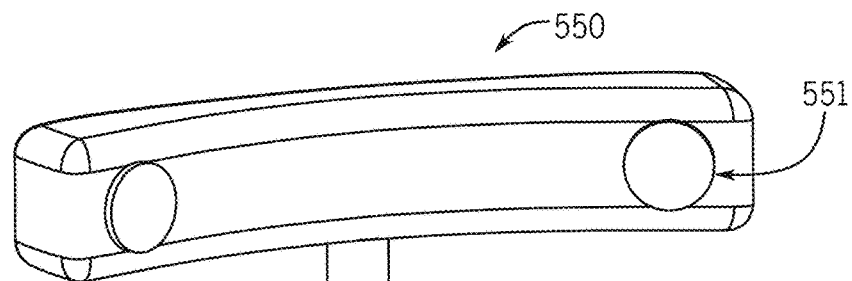
FIG. 5A illustrates an optical tracking system in accordance with some embodiments of the invention.

As used herein, a 3D-tracking acquisition system refers broadly to the use of a 3D-tracking system to acquire points in 3D space and register particular commands via 3D-tracked tools. Primary examples of this term are: 1) an optical-tracking system such as that is used in surgical navigation (e.g., NDI Polaris Spectra stereoscopic camera system, as depicted in FIG. 5A, which tracks tools or objects, as depicted in FIG. 12, FIGS. 15A-15C, etc.), and 2) an electromechanical tracking system described in at least FIG. 16, FIGS. 17A-17B, FIGS. 18A-18B, FIGS. 19A-19E, FIG. 20, FIGS. 20A-20E, FIGS. 21A-21B, FIG. 22, FIGS. 23A-23C, FIGS. 24-26, FIGS. 27A-27D, FIGS. 28A-28B, etc.

As used herein, a 3D-tracked probe is a tool that can be handheld or robot-held, and can be tracked in 3D physical space by any 3D-tracking acquisition system, such as an optical surgical navigation system (e.g., NDI Polaris stereoscopic camera in FIG. 5A) or electromechanical, 3D-tracking systems (e.g., a tracking system described in FIG. 16, FIGS. 17A-17B, FIGS. 18A-18B, FIGS. 19A-19E, FIG. 20, FIGS. 20A-20E, FIGS. 21A-21B, FIG. 22, FIGS. 23A-23C, FIGS. 24-26, FIGS. 27A-27D, FIGS. 28A-28B, etc.). One embodiment, relying on an optical surgical navigation system, includes a probe with a substantially rigidly-attached, 3D-tracked DRF. Some embodiments also involve the inclusion of a mechanically-linked, 3D-tracked mobile stray marker (TMSM) that is mounted on, or coupled with, a depressible, spring-loaded, and/or user-actuated shaft that is able to actuate the motion of the TMSM either linearly or rotationally (e.g., about a hinge pivot on the probe).

As used herein, an optical, 3D-tracking system refers broadly to any optical system that can provide a 3D mapping or image of a scene or calculate the location, orientation, and identity of a tracking-compatible object. One example of the optical, 3D-tracking system, as depicted in FIG. 5A, is a surgical navigation system (e.g., an NDI Polaris Spectra® stereoscopic camera system, from NDI International, 103 Randall Drive, Waterloo, Ontario, Canada N2V 1C5.) However, similar information can be gathered from almost any 3D-tracking, optical-based system.

As used herein, a skin-mounted fiducial is specifically able to be mounted directly on the skin surface of a patient, or within the skin in a percutaneous manner. As used herein, an over-the-drape-mating fiducial is specifically able to mate with another fiducial that is beneath a surgical drape, or any other obstructing material.

As used herein, a tracked stray marker ("TSM") refers to an optically-3D-tracked stray marker, which is defined as an independent light-reflective or light-emitting marker that is not registered as part of a DRF. This particular stray marker does not exhibit direct movement relative to the dynamic reference marker, however, it can be used as a toggle to signal various, unique commands to the acquisition unit.

As used herein, a display monitor refers to any display embodiment that is able to visually depict the output of the system, its feedback systems and instructions, its calculations, and other relevant information or settings that are available.

As used herein, a "tracked end cap" refers to a 3D-tracked object that contains a substantially rigidly-attached, 3D-tracked DRF and can be substantially rigidly attached to a rod or rod-like object. The end cap provides a reference frame of the rod in a manner of establishing a dynamic coordinate system for the implant while its contour is traced, structurally manipulated/contoured, or any other assessment. This term is also being used in the form "tracked DRF-equipped end cap", a synonym.

As used herein, a tracked slider refers to a 3D-tracked object that contains a substantially rigidly-attached, 3D-tracked DRF and is able to register the contour of a rod via mechanically engaging with its surface and tracing along the length of the rod. The slider tool is typically transformed to output 3D coordinates and orientation values relative to a 3D-tracked end cap tool. This term is also being used in the form "slider tool equipped with a DRF"; typically used for assessing a rod contour.

As used herein, an acquisition system is synonymous with the 3D-tracking acquisition system term described above. Typically, this system is a 3D-tracking camera (e.g., NDI Polaris Spectra® stereoscopic camera) and the computer system with which it is communicating.

As used herein, an end effector refers to any component of an object that interfaces with another surface or object in a manner that enables the registration or communication of information including, but not limited to: 3D location, 3D orientation, unique identity, physical or identity-based relations to other objects in a scene, forces applied to an object or forces experienced by an end effector, etc. One example, is the 3D-tracked distal tip of a robotic arm.

As used herein, a tracing refers to the method of acquiring discrete or continuous points along a surface via a 3D-traced probe or object.

As used herein, an endplate refers to the surface of a spinal vertebra that interfaces with the intervertebral disc and the nearby vertebra coupled on the other side of the intervertebral disc. The endplate is a common anatomical landmark used for measuring the spinal alignment parameters of a patient (e.g., Cobb angles), mainly due to the way that an endplate surface X-ray can be utilized to represent an anatomical line segment or vector, from which two or more endplates can be used to calculate relative angles between two or more vertebrae (e.g., L1 and S1 endplate measurements can be used to calculate the lumbar lordosis angle of the patient's lumbar spine).

As used herein, pose refers to the orientation of an object with respect to another object or 3D-tracking acquisition system. The pose of an object can be redundant from multiple perspectives or it can be unique and identifiable in a way that it distinguishes itself from other objects. The pose of an object is typically outputted via 3D orientation values (e.g., quaternions, Euler angles, rotation matrices, series of vectors, etc.).

As used herein, the term "unique" in this document typically refers to the distinct identity of an object, or its distinguishable configuration, position, or orientation. The phrase "unique pattern" used in the document refers typically to either the 1) embedded pattern surface on the ball component in the electromechanical, 3D-tracking system (depicted in FIGS. 19A-19E, FIGS. 23A-23C, FIGS. 25-26, FIGS. 27A-27D, FIG. 28A), or 2) an asymmetric or identifiable arrangement of objects that can be registered in a manner that the group of objects can be identified uniquely compared to another group of tracked/registered objects.

As used herein, "level" refers to a specific spinal vertebra within the span of the vertebrae of the spinal column. A level can refer to any of the vertebrae (e.g., L5, T10, C1, S3, etc.). The abbreviations of the sections of the spinal vertebrae are as follows: lumbar (L), thoracic (T), cervical (C), and sacral (S) vertebrae.

As used herein, "fully engaged" is used to describe two or more objects that are completely linked, mated, coupled, adhered, joined, fastened, or aligned. Often when two or more objects are fully engaged, the computer system can record an event, collect information, acquire 3D locations or orientations, determine the identity of one or more objects, receive a command, or output information regarding the engagement. Fully engaged objects will typically trigger a communication to the computer system of a particular command or acquisition to store.

As used herein, a "trigger" is used to describe either a button or a moment of communication that signals to the computer or acquisition system to store data, output calculations or other relevant information, interpret a command, or register an object's identity.

Some embodiments of the invention include a system that allows a surgeon to make intraoperative assessments and adjustments of the patient's alignment and biomechanical abilities. Embodiments of the disclosed system register the patient's local and/or full-length spinal curvature and flexibility. The system also registers the instruments and/or implants used to assess and/or manipulate the conformation of the spine. The system uses various calculations and algorithms to produce a quantitative assessment of the patient's spinal biomechanical qualities and the customized implants used to enhance these qualities. These quantitative assessments include, but are not limited to, calculated values for various radiographic parameters related to both global and segmental alignment of the spine (e.g., lumbar lordosis, central sacral vertical line, T1 pelvic angle, thoracic kyphosis, Cobb angle, etc.).

Some key features of one or more of the embodiments described herein can include anatomical landmark(s) of interest (e.g., C7, S1, etc.) that are initialized relative to the 3D-tracking acquisition system. In some embodiments, a continuous or discrete 3D-tracked acquisition is made along the surface (e.g., posterior, anterior, or lateral) of the spine, both within and beyond the surgical site (e.g., skin surface). In some embodiments, a series of algorithms filter continuous or discrete 3D-tracked probe data to identify a relationship between the acquired points and anatomical regions of interest (e.g., centroids of the vertebral bodies). In some embodiments, an assessment of the segmental and/or full-length spinal alignment is produced with values for each relevant radiographic parameter (e.g., Cobb angle, lumbar lordosis, thoracic kyphosis, C2-C7 lordosis, C7-S1 sagittal vertical axis, central sacral vertical line, T1 pelvic angle, pelvic incidence, pelvic-incidence-lumbar-lordosis mismatch, etc.). In some embodiments, an assessment of the contour, position, and/or alignment of instrumented hardware, such as screws, rods, or cages, can be produced.

Some embodiments include a visual display and quantitative feedback system for assessing and adjusting implants that are or will be implanted into/onto the anatomy, including 3D, dynamic renderings of registered anatomical landmark(s) of interest. In some embodiments, an assessment of segmental, regional, or full-length flexibility and range of motion can be produced between a selected range of vertebral segments. In some embodiments, the display outputs the information about the spine's curvature and alignment, quantitative radiographic alignment parameter values, instrumented hardware analysis, flexibility or range of motion of the spine, and also various ways to acquire or analyze radiographic images. In some embodiments, the display enables interactive feedback and interfaces for the user to signal particular commands to the system for computing, beginning operations for, or outputting the quantitative or visual analysis of a system or anatomical region(s) of interest.

Figure 1:
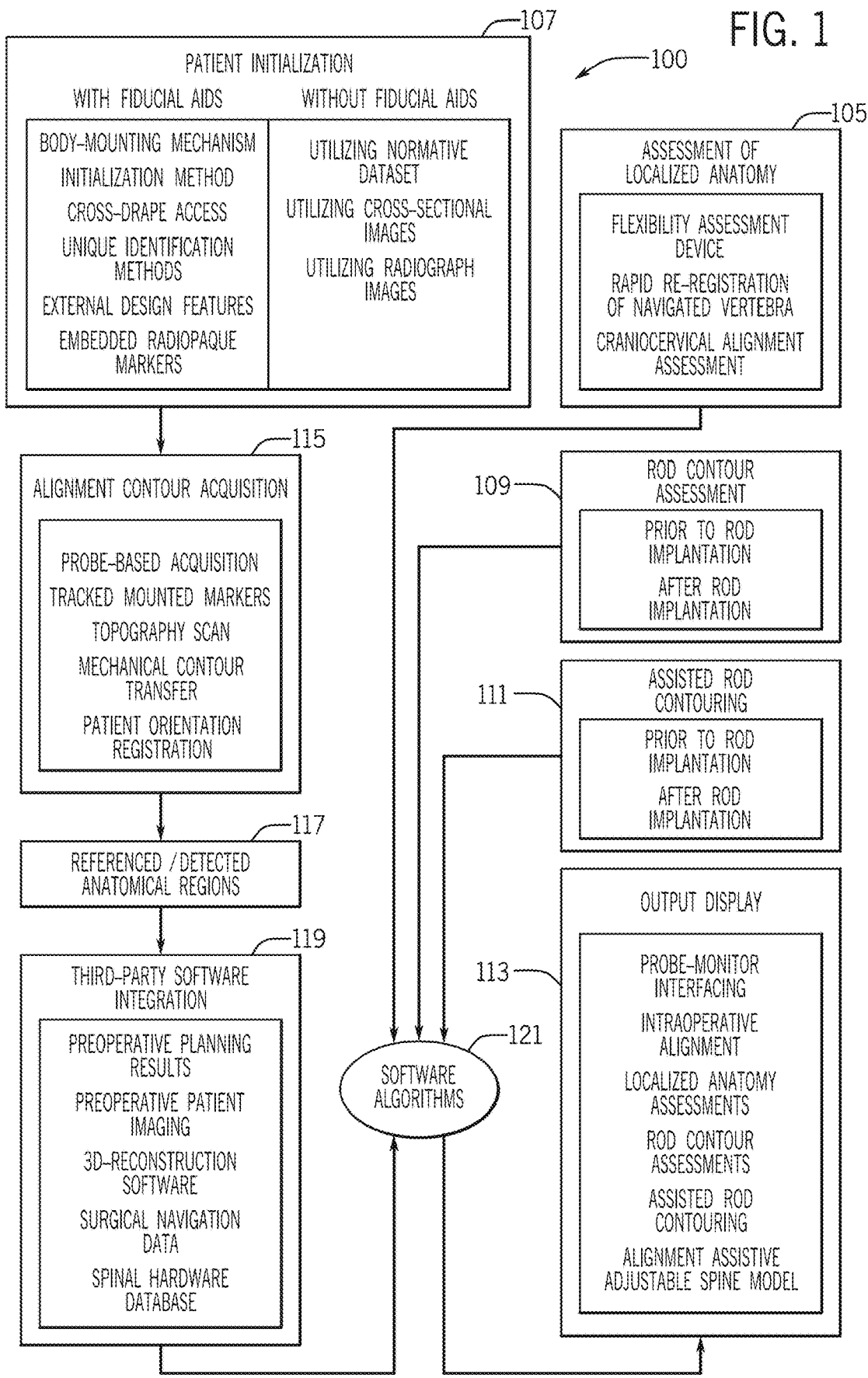
FIG. 1 illustrates a system for assessing spinal alignment, local anatomy biomechanics, rod contours, and active contouring of a rod, as well as initialization of fiducials and interactive displays of various outputs in accordance with some embodiments of the invention.

Any of the proposed embodiments can be independent inventions and do not have to be precluded by other inventions or categorical system workflows (e.g., patient initialization, alignment contour acquisition, etc.), as illustrated in FIG. 1. For example, some embodiments of the invention described herein include devices, assemblies, systems, and methods to assess the intraoperative alignment of the spine, extract information as to the contour or alignment of instrumented hardware, and evaluate some of the biomechanical qualities of the patient's spine. Some embodiments of the overall system are illustrated in FIG. 1, where a central software system can receive inputs from discrete and/or continuous location data (e.g., inside and/or outside of the surgical site), where the data is gathered by non-radiographic or radiographic embodiments, algorithmic calculations, or manual user-based interactions, to generate visual and quantitative outputs relating to the intersegmental or full-length alignment, curvature, position, range-of-motion, and biomechanical flexibility of the patient's spine. Any of the embodiments described herein can be independent embodiments and do not have to be within the categorical series of systematic steps (e.g., 3D trace, local anatomy, landmarks, etc.) shown in FIG. 1, illustrating a system for assessing spinal alignment, local anatomy biomechanics, rod contours, and active contouring of a rod, as well as initialization of fiducials and interactive displays of various outputs in accordance with some embodiments of the invention. The overall system 100 of FIG. 1 can include devices, assemblies, systems, and/or methods described in the following description in reference to one or more of the figures, including processes that utilize one or more software modules 121 of one or more computer-implemented methods. In some embodiments, the system 100 can comprise devices, assemblies, systems, and methods for patient initialization 107, alignment contour acquisition 115, referenced/detected anatomical regions 117, third-party software integration 119, assessment of localized anatomy 105, rod contour assessment 109, assisted rod contouring 111, and output display 113.

Figure 2A:
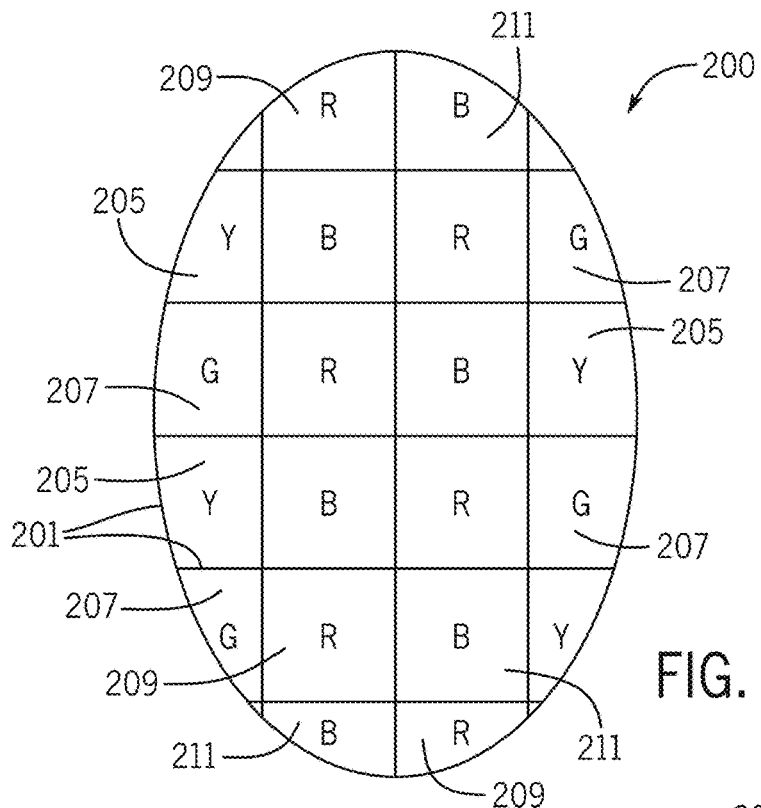
FIG. 2A shows a representation of a body-surface-mountable fiducial patch in accordance with some embodiments of the invention.

Some embodiments of the invention relate to systems and methods for precise placement of skin surface markers or percutaneous access devices that provide the relative position of underlying bony anatomy to a visible surface grid. In some embodiments, the systems and methods described herein can reduce the number of X-rays needed to be taken to verify location of overlying or percutaneous devices relative to bony anatomy. Some embodiments can include a skin-mounted patch that has visible markings with colors in the visible spectrum for a user to see. Further, in some embodiments, the patch can include corresponding radiopaque patterns (e.g., grid lines, letters, numbers, symbols, icons, etc.) embedded in the patch such that when an X-ray is taken, the patch provides a large area of landmarks that can aid a user with percutaneous device placement, the placement of one or more additional surface marker fiducials, and/or with localizing surgical incision sites relative to underlying anatomy. For example, FIG. 2A shows a representation of a body-surface-mountable fiducial patch 200 in accordance with some embodiments of the invention, where radiopaque grid lines can be visualized on the X-ray image. Other relevant figures and discussions herein can include those related to skin-fiducial marker examples to apply onto a patch such as FIGS. 6B, 9A-9B, and FIGS. 11A-11B. As shown in FIG. 2A, some embodiments include a body-surface-mountable fiducial patch 200 that can comprise an array of radiopaque markers with visible and/or radiopaque grid lines 201. In some embodiments, the shapes or markers defined by the grid lines 201 can be colored and/or marked with an identifier, including, but not limited to, a red-colored grid surface with a radiopaque "R" (label 209), a blue-colored grid surface with a radiopaque "B" (label 211), a yellow-colored grid surface with a radiopaque "Y" (label 205), and/or a green-colored grid surface with radiopaque "G" (label 207). In some embodiments, the grid lines can be further apart or closer than shown. In some embodiments, the markers can be larger or smaller, as well as fewer or greater in number, than shown in this non-limiting embodiment. In some embodiments, the body-surface-mounted fiducial patch 200 can enable precise placement of surface-mounted objects or percutaneous devices that require recognition or understanding of the relative location of underlying bony or soft-tissue structures.

It should be noted that the visible surface of the patch 200 need not be a distribution of colors, but can also consist of any recognizable pattern that is also displayed in a meaningful way on X-ray imaging. In some embodiments, the patch can be adhered to surface anatomy via an adhesive (not shown) or other methods. In some embodiments, one side of the patch 200 can include adhesive (e.g., such as the skin-mounted side). In some embodiments, the size and density of unique identifiable grid sections on the patch can be varied based on a particular application. In some embodiments of the invention, a radiopaque lining can be included that at least partially matches one or more overlying visible markings. In this instance, the patch 200 can facilitate a user understanding where each visible marking is and how it corresponds with an underlying anatomical region or element. This can facilitate a user making incisions in known or identified regions of a patient.

Figure 2B:
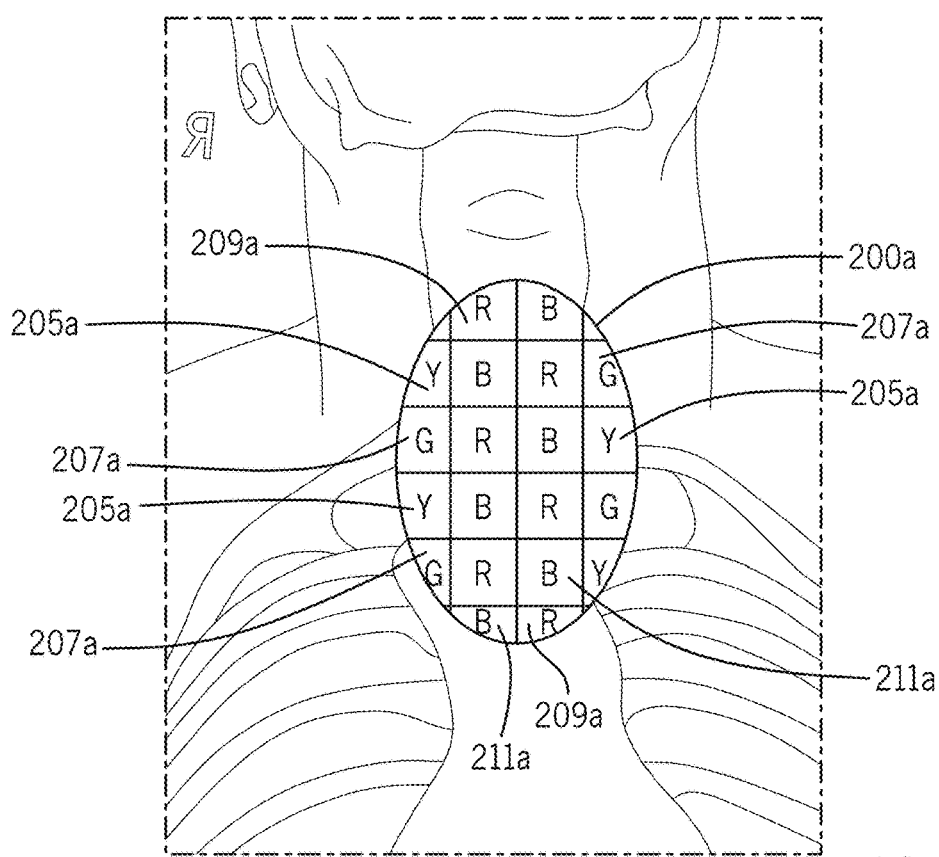
FIG. 2B displays the radiopaque elements of the fiducial patch of FIG. 2A as would be visible on an X-ray image of a patient with the patch applied in accordance with some embodiments of the invention.

FIG. 2B displays the radiopaque elements of the fiducial patch of FIG. 2A as would be visible on an X-ray image of a patient with the patch applied in accordance with some embodiments of the invention. For example, X-ray patient image 225 is shown with radiopaque fiducial grid patch 200a displayed on the image 225. The image displays the radiopaque elements of the fiducial patch 200 as would be visible on an X-ray image 225 of a patient with the patch 200 applied. In some embodiments, after taking an X-ray of the patch 200 applied to the patient, users can place surface fiducials or direct percutaneous access devices towards the bony anatomy of interest based on the corresponding grid location on the patch that represents the underlying anatomy of interest. In this non-limiting example embodiments, the red-colored grid surface with radiopaque "R" (label 209) is shown as 209a, the blue-colored grid surface with radiopaque "B" (label 211) is shown as 211a. Further, the yellow-colored grid surface with radiopaque "Y" (label 205) is shown as 205a, and the green-colored grid surface with radiopaque "G" (label 207) is shown as 207a in the X-ray image 225. In some embodiments, when used in this way, the patch 200 of FIG. 2A and imaging of FIG. 2B can aid with the precise selection of correct surgical site access points, ensuring that incisions overlay the desired bony anatomy on which will be operated. Additionally, in some embodiments, this patch 200 can be used to precisely place secondary skin-mounted fiducials such that they superimpose underlying bony anatomy of interest. Some example embodiments of fiducials that can be applied onto the imaged patch include FIG. 6B, FIGS. 9A-9B, FIGS. 11A-11B. In some embodiments, the patch 200 can be applied to a patient's skin using adhesive or other conventional methods. In some embodiments, the type of identifiable surface marker can be different than the non-limiting embodiment shown.

Figure 3A:
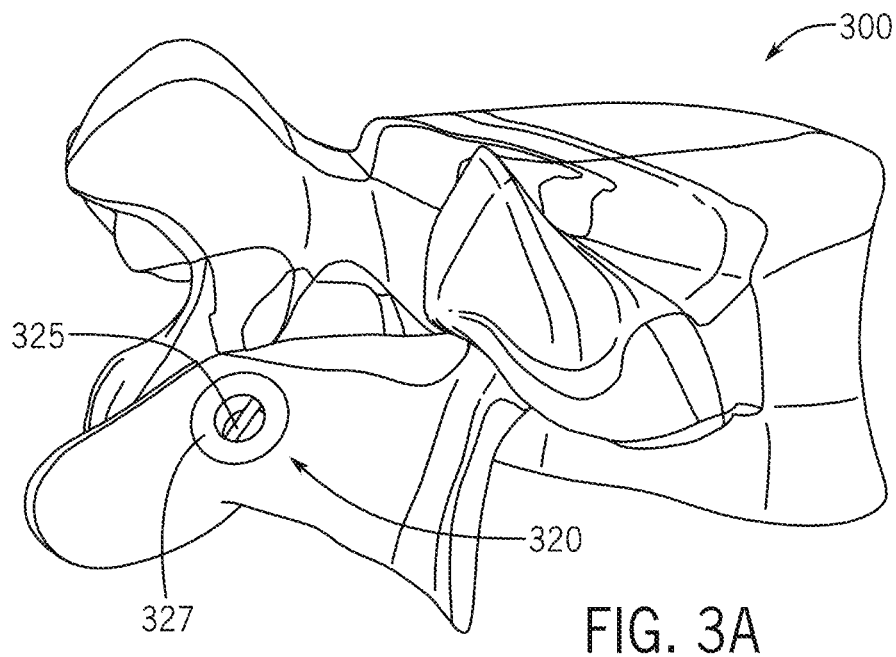
FIG. 3A displays a vertebra with a bone-mounted fiducial fastened to the bone in accordance with some embodiments of the invention.
Figure 3B:
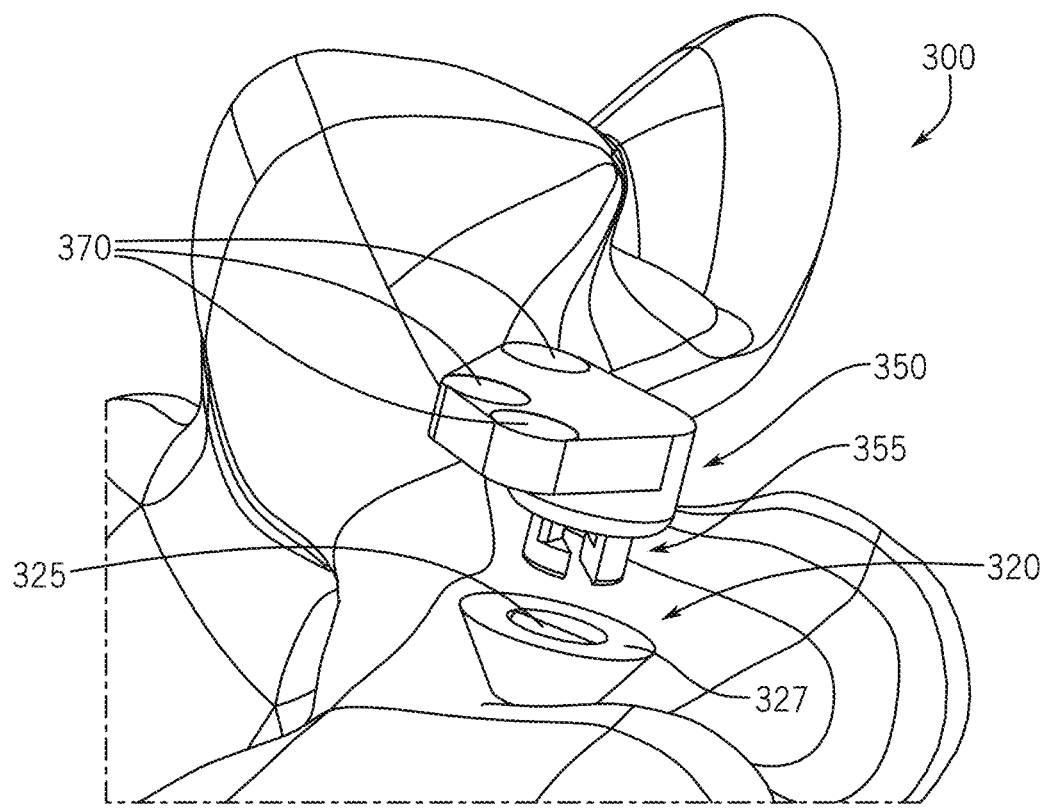
FIG. 3B shows an assembly view of a vertebra with a bone-mounted fiducial and top fiducial for coupling to the bone-mounted fiducial in accordance with some embodiments of the invention.
Figure 3C:
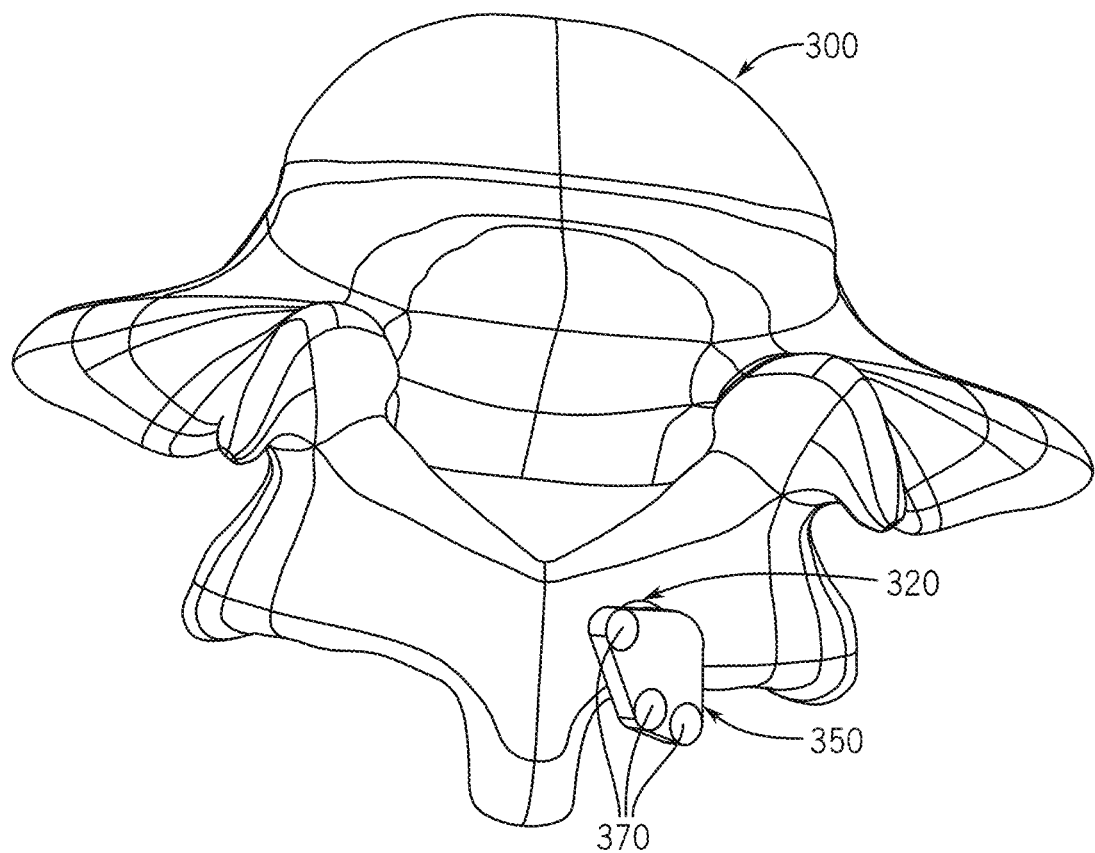
FIG. 3C shows a vertebra with a bone-mounted fiducial coupled with a top fiducial in accordance with some embodiments of the invention.

FIGS. 3A-3C illustrate a bone-mounted fiducial device that is designed with a crossbar to interface with one or more mating devices that can either help to register the fiducial's location and pose in 3D space (e.g., via tracing, tapping discrete locations, being tracked directly), help initialize the fiducial relative to anatomical structures of interest registered with X-ray images or 3D-tracking acquisition systems, or directly manipulate the fiducial and attached bony anatomy after they are coupled. In some embodiments, after imaging a fiducial mounted to bony anatomy, the fiducial's relative location in space to an anatomical landmark of interest can be registered, such that when the fiducial is located and registered by 3D-tracked tools in the future, the corresponding bony anatomy elements are also localizable and/or identifiable. The vertebra 300 is shown with a bone-mounted fiducial 320 fastened to the bone. In some embodiments, the fiducial 320 can be fastened to the medial border of the right spinal lamina, but because of its small size and profile, it can be mounted anywhere on the bony anatomy. In some embodiments, the bone-mounted fiducial 320 can contain a threaded or smooth bone-piercing component (not shown) so that it can be substantially rigidly fastened to the anatomy of interest (e.g., the vertebra 300). In some embodiments, the bone-piercing component can be significantly miniaturized such that it does not pierce through the opposite side of the bony anatomy, or otherwise harm any sensitive anatomical structures.

In some embodiments, the fiducial 320 can contain one or more rigid crossbars 325 that travel across the fiducial 320. In some embodiments, the crossbars 325 can be positioned such that there is an open space underlying it to allow for a mating interface of a coupled fiducial accessory 350 to directly engage with it. In this instance, the fiducial 320 can be substantially rigidly fixed to the accessory fiducial 350 (see FIG. 3B below) so as to interpret the pose and location of the fiducial 320 in space when accessed by a 3D-tracked device.

In addition, some embodiments involve a patterned perimeter surface (FIG. 3B), including but not limited to groove 327 (not shown) and other identifiable patterns, that can be traced or discrete registered by a 3D-tracked probe. FIG. 3B shows an assembly view of a vertebra 300 with a bone-mounted fiducial 320 and accessory fiducial 350 for coupling to the bone-mounted fiducial 320, illustrating the mating capability of the bone-mounted fiducial 320 such that it can mechanically couple with an accessory fiducial 350 via a variety of mechanisms. For example, one non-limiting mechanism includes a quarter-turn interlocking mechanism 355 such that the accessory fiducial 350 is tightly pulled into the crossbars 325 of the base bone-fiducial 320 when the accessory fiducial 350 is rotated 90 degrees into the interlocking design of the mechanism 355. In some embodiments, the structure of the accessory fiducial 350 is such that it can contain surface features, including, but not limited to, asymmetric pattern of three or more identifiable indentations 370. In some embodiments, the identifiable indentations 370 can enable the registration of the unique position and pose of the fiducial 320 in 3D space by interfacing with 3D-trackable devices, as further described in more detail below in reference to FIG. 3C, and FIGS. 44A-44D. In some other embodiments, other conventional mating mechanisms with the fiducial include, but are not limited to, a quarter-turn, half-turn, internal threads, a clamping device, and/or a spring-loaded snap-in device.

Some embodiments of the uniquely identifiable surface structure of the accessory fiducial 350 that can be used for registration of the orientation of the fiducial 320 in 3D space when interacting with a 3D-tracked probe, can include, but not be limited to, 1.) three or more uniquely spaced indentations, 2.) a uniquely identifiable groove in which a 3D-tracked probe can trace in order to identify the location and pose of the fiducial 320, 3.) an insert that contains a set of three or more tracked markers whose location in 3D space are able to be tracked by a 3D-tracking camera, 4.) a tracked DRF, 5.) a larger embodiment with radiopaque features to enable its unique pose and location to be identifiable with X-ray imaging, and 6.) interfacing with a tracked probe that can substantially rigidly couple to the fiducial 320 in such a way that it can interpret the location and pose of the fiducial 320 in 3D space, as described below in reference to FIGS. 44A-44D. For example, FIG. 3C shows a vertebra 300 with a bone-mounted fiducial 320 coupled with a top fiducial (fiducial 350) in accordance with some embodiments of the invention. The bone-mounted fiducial 320 includes an accessory fiducial 350 substantially rigidly attached and demonstrates one embodiment of a uniquely identifiable surface pattern 370 (surface indentations) that can be registered with a 3D-tracked probe. In some embodiments, the three or more discrete indentations that make up the surface pattern 370 can couple with at least a portion of a 3D-tracked probe that can couple with the surface pattern 370. Consequently, one or more computer systems can then be used to compute the location and unique pose of the fiducial 320 in 3D space.

FIG. 4A illustrates an assembly or operation process 450 for a skin-surface-mounted fiducial 400 being applied to a patient 425 in accordance with some embodiments of the invention. The skin-surface-mounted fiducial 400 is applied to the patient's posterior skin as they are positioned prone on an operative table 435. In some embodiments, this fiducial 400 can be adhered to the patient's skin via attached adhesive compound, staples, suture, or overlying adhesive draping.

FIG. 4B illustrates a sample lateral radiograph of the radiopaque markers 444 embedded within a skin-based fiducial 442 applied to an anatomical model 443, adhered to its skin surface 446, in accordance with some embodiments of the invention. In some embodiments, the radiopaque elements of the fiducial markers 444 allow the fiducial 442 to be clearly visualized and identified on radiograph images. Additionally, the known sizing of the radiopaque markers 444 allow for reference scaling within the X-ray image 441. Furthermore, the nearby anatomical structures that are also within the field of view of the X-ray image 441 can then be initialized such that a displacement vector can be drawn within the plane of the X-ray image 441 as described below in FIG. 4C and FIG. 4F. In some embodiments, the arrangement of the radiopaque fiducial markers 444 can be designed in an asymmetric pattern to enable an X-ray image of the fiducial from any perspective to visualize a unique pose of the pattern and to subsequently enable the system to automatically estimate the 3D orientation of the fiducial 442. For example, FIG. 4C illustrates the sample lateral radiograph 440 of FIG. 4B with annotated vectors in accordance with some embodiments of the invention. FIG. 4C displays one aspect of the initialization process for fiducials located nearby anatomical elements whose position is desired to be known relative to that of the fiducial 442. In some embodiments, manual or automated software annotation can enable the identification of the radiopaque markers within the fiducial (shown as vectors 465 and 460 extending between radiopaque markers 444).

Given the relative sizing of the fiducial markers 444 to one another as well as their relative orientations to one another, the pose of the fiducial 442 relative to the plane of the X-ray image 440 can be calculated. In some embodiments, the user interfaces with the system to select one or more additional anatomical points to which the displacement vector 470 from the fiducial 442 will be calculated. In this example, the central region of a particular vertebral body was selected, indicated by a large circle (e.g., shown as 427), and the software calculated the pixel distance between each radiopaque marker 444 and the annotated region 427 on the display monitor. Based on the known size of the radiopaque markers 444 that are in or on the fiducial 442, the image can be scaled such that length measured in pixels can be converted to length measured in distance units (e.g., mm, cm, etc.). In other embodiments, the software can also calculate displacement vectors from the fiducial to any anatomical landmarks of interest, even across several vertebrae.

Figure 4D:
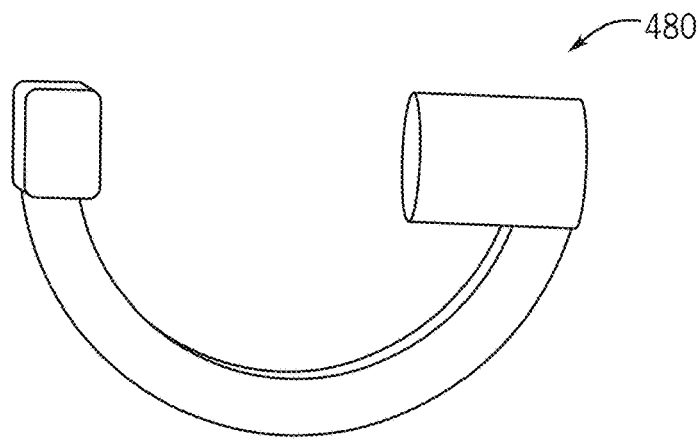
FIG. 4D illustrates a C-arm based mount a type of an X-ray imaging system that can be utilized for image acquisition and subsequent initialization of fiducial markers in accordance with some embodiments of the invention.

FIG. 4D illustrates a C-arm X-ray imaging system 480 that can be utilized for image acquisition and subsequent initialization of fiducial markers 442 in accordance with some embodiments of the invention. In some embodiments, following the first X-ray image that was taken, the relative angle between the patient-fiducial complex and the X-ray emitter is rotated by either a known or unknown amount to take a subsequent image. The second image allows for added information outside of the plane of the first X-ray image to construct the 3D displacement vector between the fiducial and the bony anatomy of interest. This X-ray system needs not be a C-arm-based device 480, but can also consist of other image acquisition systems including but not limited to the O-arm, flat-plate X-rays, CT scan, MM, and wall or bed-mounted acquisition systems.

Figure 4E:
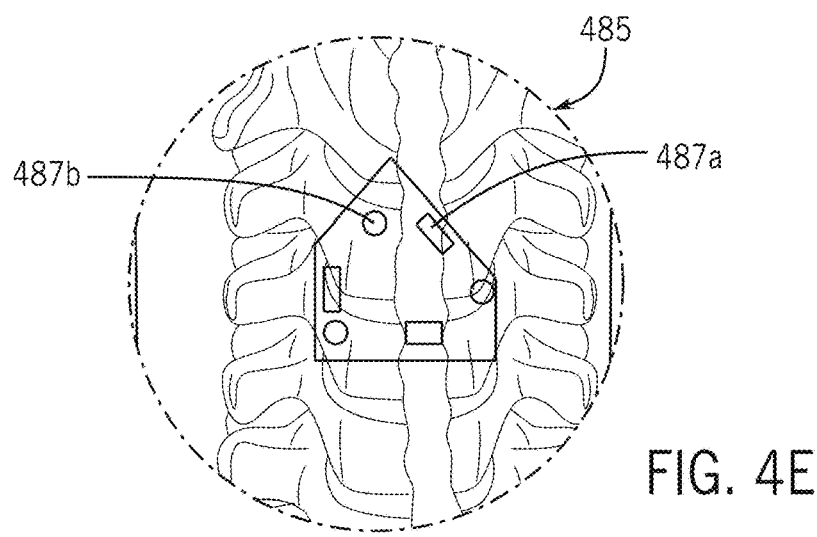
FIG. 4E illustrates a sample X-ray image of a spine-fiducial pair from a different imaging angle from that of FIGS. 4A and 4B in accordance with some embodiments of the invention.

FIG. 4E illustrates a sample X-ray image 485 of a spine-fiducial pair from a different imaging angle from that of FIGS. 4A and 4B in accordance with some embodiments of the invention, and illustrates the fiducial radiopaque markers (shown as 487*a*, 487*b*) as one embodiment of an arrangement of radiopaque markers in or on the fiducial distributed to enable image scaling and localization to nearby anatomical areas of interest.

Figure 4F:
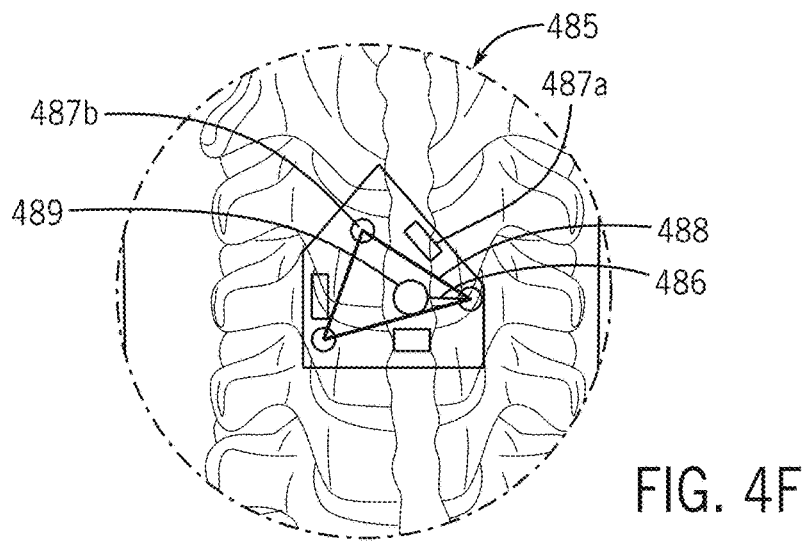
FIG. 4F illustrates the sample X-ray image of FIG. 4E including annotated vectors in accordance with some embodiments of the invention.

FIG. 4F illustrates the sample X-ray image 485 of FIG. 4E, including annotated vectors in accordance with some embodiments of the invention. FIG. 4F displays the X-ray image initialization process for the fiducial-body pair that was imaged and described above in FIG. 4E. The annotated vectors 488 are used to reference the relative position of each of the radiopaque markers (487*a*, 487*b*) within the fiducial 442 (FIGS. 4B-4C) as well as calculate the displacement vector 486 to the user-indicated nearby anatomical region of interest (shown as 489), for which the fiducial 442 can serve as a reference point upon future localization of that fiducial. In some embodiments, the arrangement of the radiopaque fiducial markers can be designed in an asymmetric pattern, as seen by the example unique triangular pattern of vectors between the radiopaque markers 487*a*, 487*b*, to enable an X-ray image of the fiducial from any perspective to visualize a unique pose of the pattern that can enable the system to automatically estimate the 3D orientation of the fiducial. In this respect, the estimation of the fiducial's orientation enables the system to calculate the 3D vector with respect to the fiducial axes.

Figure 4G:
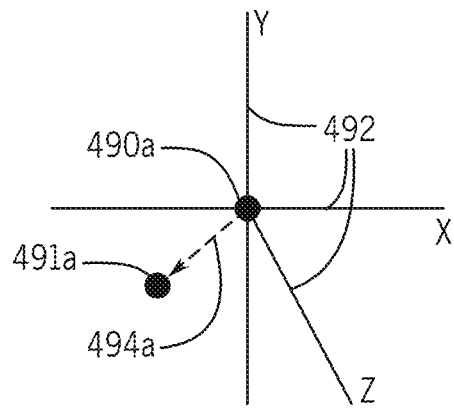
FIG. 4G illustrates 3D axes relative to the fiducial origin point onto which displacement vectors drawn over each of the 2D X-rays are able to be added based on input or calculated angle between each X-ray image plane in accordance with some embodiments of the invention.

FIG. 4G displays the 3D axes of a fiducial device 442 in coordinates of the X-ray imaging system, in which the unique location and pose of the fiducial 442 was registered in accordance with some embodiments of the invention. In this non-limiting embodiment, the X-ray imaging system coordinate axes 492 are shown with a 3D-displacement vector 494*a* that indicates the relative 3D offset initialized between the fiducial origin 490*a* and the triangulated position of the anatomical landmark of interest 491*a*, which was annotated previously (annotations 427 and 489). Displacement vectors drawn over each of the 2D X-rays are able to be combined based on an input or calculated angle between each X-ray image plane in accordance with some embodiments of the invention. This input enables the calculation of a rigid body transform between the coordinate axes of the two or more X-ray images of the fiducial 442, and thus enable for the calculation of a 3D-displacement vector that combines displacement vector inputs from two or more X-ray images. It must be noted that the series of X-ray images of a fiducial device 442 relative to the anatomical regions of interest, such as 427 or 489, may not always differ by a purely rotational transformation, and may include a translational transformation, especially if the fiducial 442 is not isocentrically aligned with the volume of the C-arm field-of-view, as it is rotated by its boom (as seen in FIG. 4D). This non-circularity of the C-arm's field of view may be caused by the center of the imaging cone not aligning with the center of the C-arm's axis of rotation.

Figure 4H:
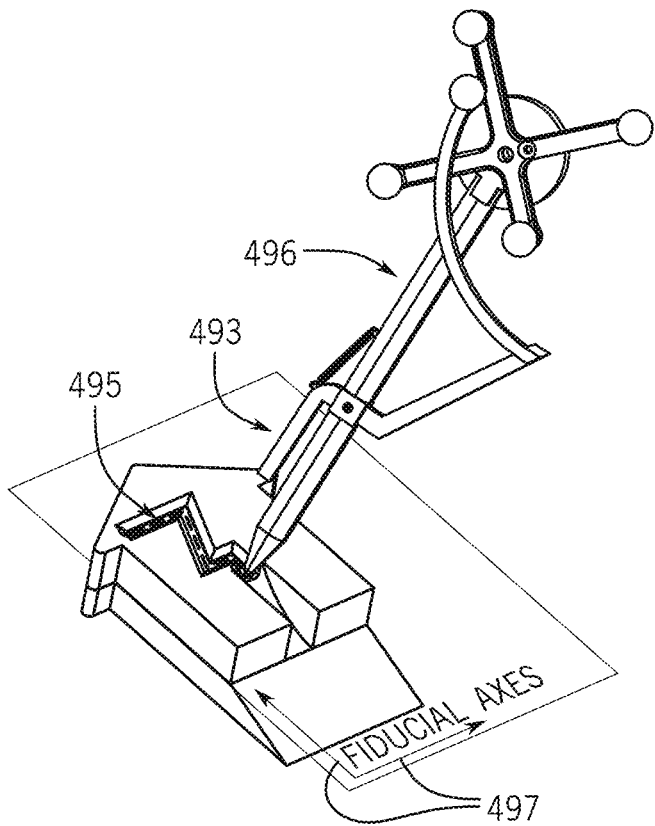
FIG. 4H illustrates a system and method of localizing the fiducial in 3D tracking camera coordinates in accordance with some embodiments of the invention.

FIG. 4H illustrates a system and method of localizing the fiducial in 3D-tracking camera coordinates in accordance with some embodiments of the invention. Shown in the non-limiting embodiment are an identifiable tracing pattern 495, a tracked probe with triggering capability 496 (shown with the probe in an active tracing state 493), and fiducial coordinate axes 497, relative to the 3D-tracking acquisition system. FIG. 4H displays one method of localizing the fiducial in 3D-tracking camera coordinates as a non-limiting embodiment. As shown, the fiducial is equipped with a unique groove pattern 495 into which a tracked probe 496 can trace the fiducial's signature pattern. As described above in relation to FIG. 4A, the recognizable features of the fiducial are not limited to a uniquely traceable pattern, but also discrete points to tap, mount locations for tracked markers, and substantially rigidly coupling with a tracked probe in a way such that the probe's pose can be used to interpret the fiducial's position and pose. By tracing the unique surface pattern 495 on the fiducial with a tracked probe 496, the fiducial's axes 497 and origin are able to then be interpreted with respect to the 3D-tracking acquisition system's coordinate system. In some embodiments, the acquisition system will subsequently be able to interpret the location of the initialized nearby anatomical region (such as 427 and 489) as described below in FIG. 4I.

Figure 4I:
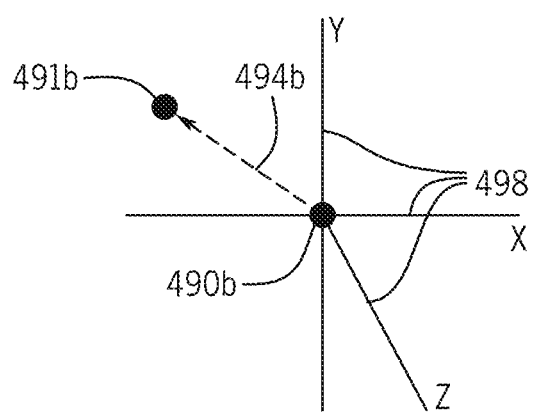
FIG. 4I displays the axes of a 3D-acquisition system with which the unique location and pose of the fiducial was registered as of FIG. 4H in accordance with some embodiments of the invention.

FIG. 4I illustrates the 3D coordinate axes of the fiducial device 498 relative to the 3D-tracking acquisition system. This non-limiting embodiment includes the fiducial coordinate axes 498 relative to that of the 3D-tracking acquisition system and the 3D-displacement vector 494*b* between the fiducial 442 and the anatomical regions of interest (427 and 489). The 3D-displacement vector 494*b*, between the fiducial origin 490*b* and the anatomical region of interest 491*b* relative to the coordinates of the 3D-tracking acquisition system, represents the vector 494*a* (shown in FIG. 4G) after it has undergone a 3D rigid transform, utilizing the calculated transform between the fiducial location and orientation in both the X-ray imaging and 3D-tracking acquisition systems, as depicted in FIGS. 4C, 4F, and 4H. This resultant 3D-displacement vector enables for the calculation of the location of the anatomical region of interest 491*b* (depicted in FIGS. 4C-4G as labels 427 and 489 relative to the X-ray imaging system coordinates) with respect to the fiducial's origin and coordinate axes relative to the coordinate system of the 3D-tracking acquisition system. In some embodiments, this enables localization of the bony anatomy regions of interest by interpreting the location and pose of the fiducial within other 3D-tracking acquisition system axes, as depicted in FIG. 4H.

Figure 5B:
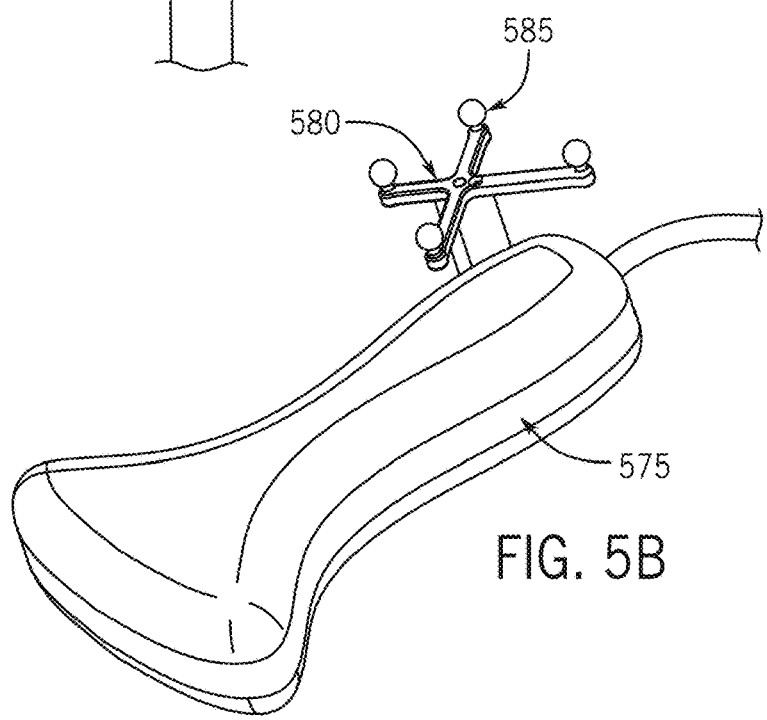
FIG. 5B illustrates an ultrasound probe equipped with a tracked dynamic reference frame in accordance with some embodiments of the invention.
Figure 5C:
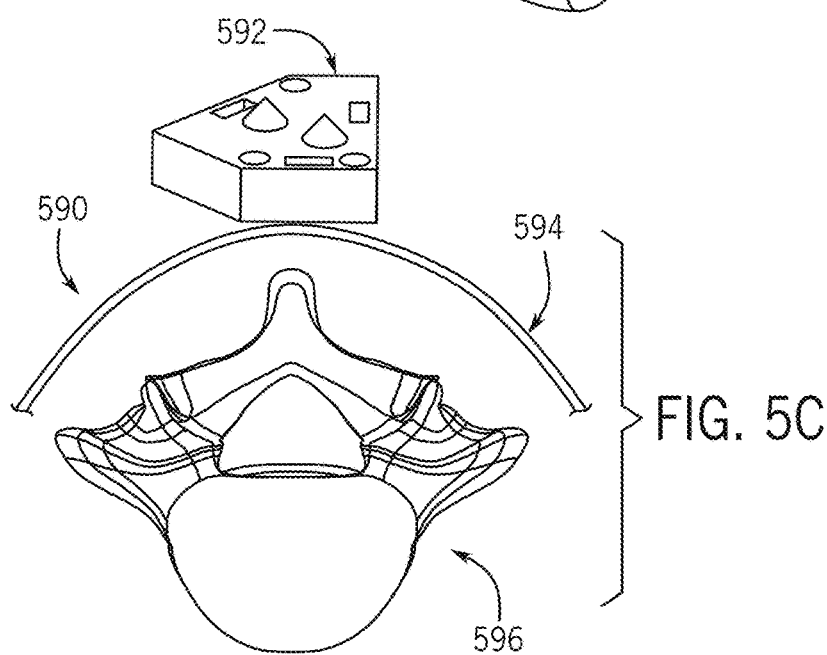
FIG. 5C illustrates an assembly or process view of a patient's skin surface overlying a cross-sectional view of a vertebra as a representation of a particular region of bony anatomy that could be registered to a skin-mounted fiducial in accordance with some embodiments of the invention.

FIGS. 5A-5C display components, systems and methods of initializing a fiducial to serve as a reference point for underlying anatomical regions of interest, as described above in reference to FIGS. 4A-4I. However, instead of utilizing X-ray images, the methods can utilize an ultrasound-based probe 575 equipped with a tracked DRF 580 so that its location and pose are able to be computed when visualized by a 3D-tracking camera. For example, FIG. 5A illustrates an optical 3D-tracking system 550 in accordance with some embodiments of the invention, and FIG. 5B illustrates an ultrasound probe 575 equipped with a tracked DRF 580 in accordance with some embodiments of the invention. Further, FIG. 5C illustrates an assembly or process view 590 of a patient's skin surface 594 overlying a cross-sectional view of a vertebra 596 as a representation of a particular region of bony anatomy that could be registered to a skin-mounted fiducial 592 in accordance with some embodiments of the invention. In some embodiments of the invention, the optical 3D-tracking camera 550 of FIG. 5A can be utilized for the 3D-tracking acquisition system referenced throughout this document. This system utilizes stereoscopic cameras 551 to detect the location of tracked markers that reflect or emit infrared light. This is one example of a tracking system that can be used for acquisition of 3D coordinates throughout this document, but this can also be achieved by other methods including but not limited to light-emitting markers, electronic communication, etc. Further, in some embodiments, the ultrasound probe 575 of FIG. 5B is equipped with a tracked DRF 580 that enables the probe's location and pose to be tracked in 3D space using passive, light-reflective markers 585. In some embodiments, tracking the precise location of the probe allows for recording the relative angles between each cross-sectional imaging plane of an acquisition that can be used for creating the 3D-displacement vector to the anatomical point of interest via the computation of 3D rigid transformations of the relative location and pose of the ultrasound probe 575 between acquisitions of the ultrasound cross-sectional images.

FIGS. 6A-D includes depictions of devices, systems and processes of applying a skin-mounted fiducial along with its top-mating component that enables mating across surgical drapes so that the fiducial can be both visualized and referenced during procedures during which a drape is obstructing the surface overlying bony anatomy for which the location is desired to be known.

Figure 6A:
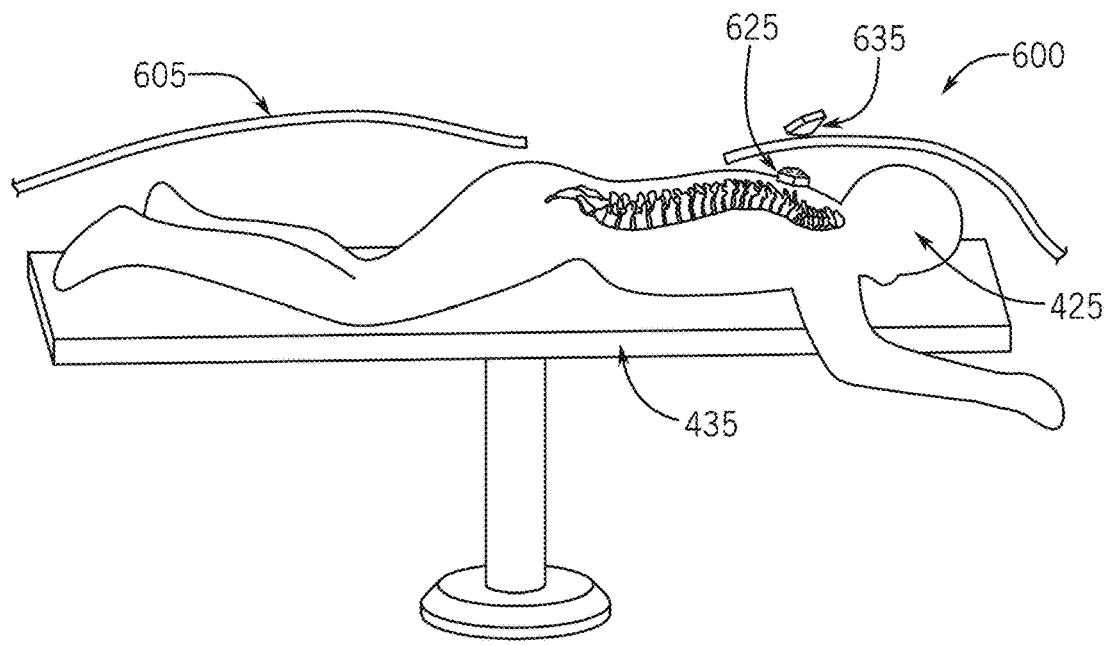
FIG. 6A illustrates an assembly or process view for applying a skin-mounted fiducial and its associated over-the-drape fiducial in accordance with some embodiments of the invention.
Figure 6B:
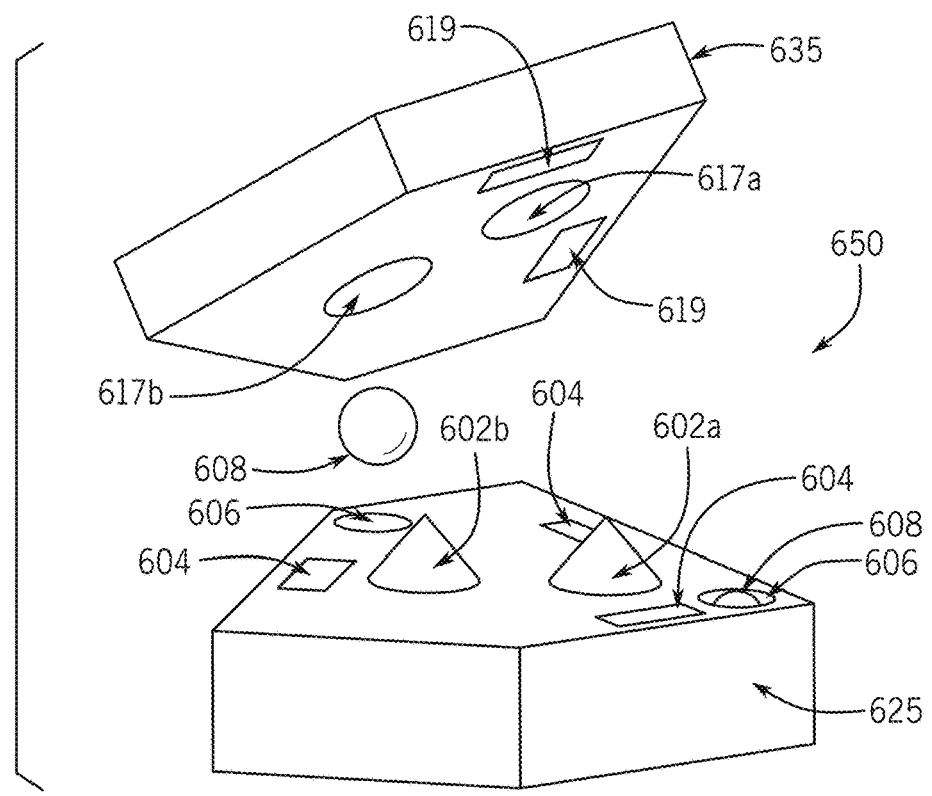
FIG. 6B illustrates an assembly view of a skin-mounted fiducial and its associated over-the-drape mating fiducial in accordance with some embodiments of the invention.

FIG. 6A portrays a sample scenario for which applying a skin-mounted fiducial 625 and its associated over-the-drape-mating fiducial 635 could be used. With the patient positioned prone on the operative table, skin-mounted fiducials can be applied over regions that will not be surgically exposed but under which contain bony anatomy for which a location is desired to be known relative to other anatomical regions. After the surgical drape 605 is applied over the skin-mounted fiducial, the over-the-drape-mating fiducial can then be used to interpret the position of the underlying skin-mounted fiducial, described in more detail below in FIGS. 6B-D. For example, FIG. 6A illustrates an assembly or process view 600 for applying a skin-mounted fiducial 625 and its associated over-the drape fiducial 635 in accordance with some embodiments of the invention, and FIG. 6B illustrates an assembly view 650 of a skin-mounted fiducial 625 and its associated over-the-drape mating fiducial 635 in accordance with some embodiments of the invention. In some embodiments, the fiducial 625 can comprise the fiducial 400 and the fiducial 635 can comprise the fiducial 635.

In reference to FIG. 6B, detailed components of one embodiment depict a skin-mounted fiducial 625 and its associated over-the-drape-mating fiducial 635. In some embodiments, the skin-mounted fiducial 625 can include a method of adhering to the skin surface (not shown), including but not limited to adhesive material, looped regions to be sutured or stapled to the skin, percutaneous or bone-piercing screws, pins, wires, or other common fasteners, and/or attached bands to be tightly wrapped around body surfaces. In some embodiments, contained within or on either of the fiducials can be one or more radiopaque markers 608 that are readily visualized on X-ray images of the fiducials. Furthermore, in some embodiments, these radiopaque markers 608 can be positioned relative to one another via shape-specific cutouts 606 and the fiducial body itself in such a way that the markers can be used to identify the pose of the fiducial on 2D X-ray images, as described above in FIG. 4. In some embodiments, the fiducials can contain magnets (e.g., shown as magnet 604 in the fiducial 625, and 619 in the fiducial 635 embedded in or on the fiducial surfaces in such a way that it helps to securely fasten the two fiducials when separated by a surgical drape (shown as 605 in FIG. 6A). In some embodiments, the magnets can have varying geometry. For example, some embodiments include spherical magnets that can be used to serve both functions of a radiopaque marker as well as feature to help join mating fiducials across drapes. In some embodiments, the skin-mounted fiducial can also be equipped with protrusions to serve as mechanical alignment mates (shown as 602a and 602b). In some embodiments, the mates can protrude from one fiducial (e.g., 625 as shown and/or alternatively from both fiducial 625 and fiducial 635) and have complementary mating cutouts, such as 617a, 617b, within the opposite fiducial to help ensure both fiducials are properly aligned relative to one another. The protrusions are conical in shape in the non-limiting embodiment of FIG. 6B, but can also be created with other tapered or non-tapered geometry in other embodiments.

Figure 6C:
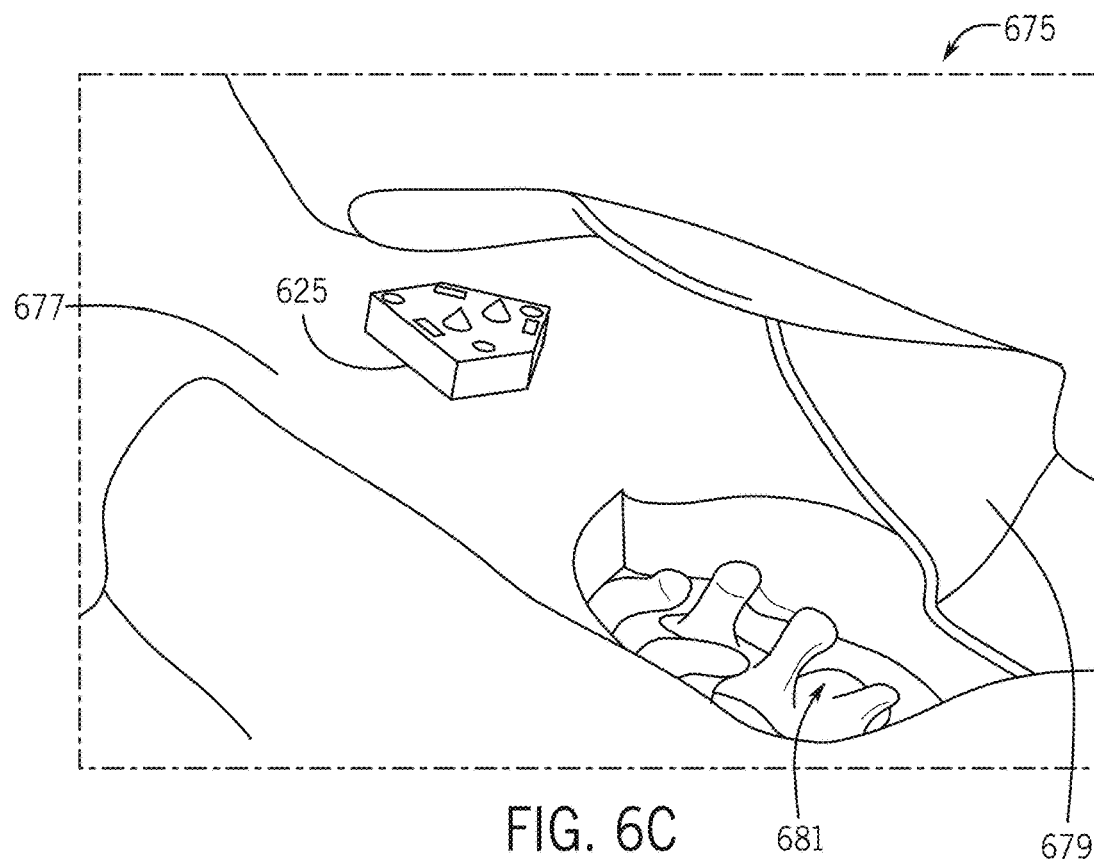
FIG. 6C illustrates one embodiment of a skin-mounted fiducial applied to an anatomical phantom in a region that is outside the surgical site but located over regions of underlying anatomy for which their location within 3D-tracking coordinates is desired to be known in accordance with some embodiments of the invention.
Figure 6D:
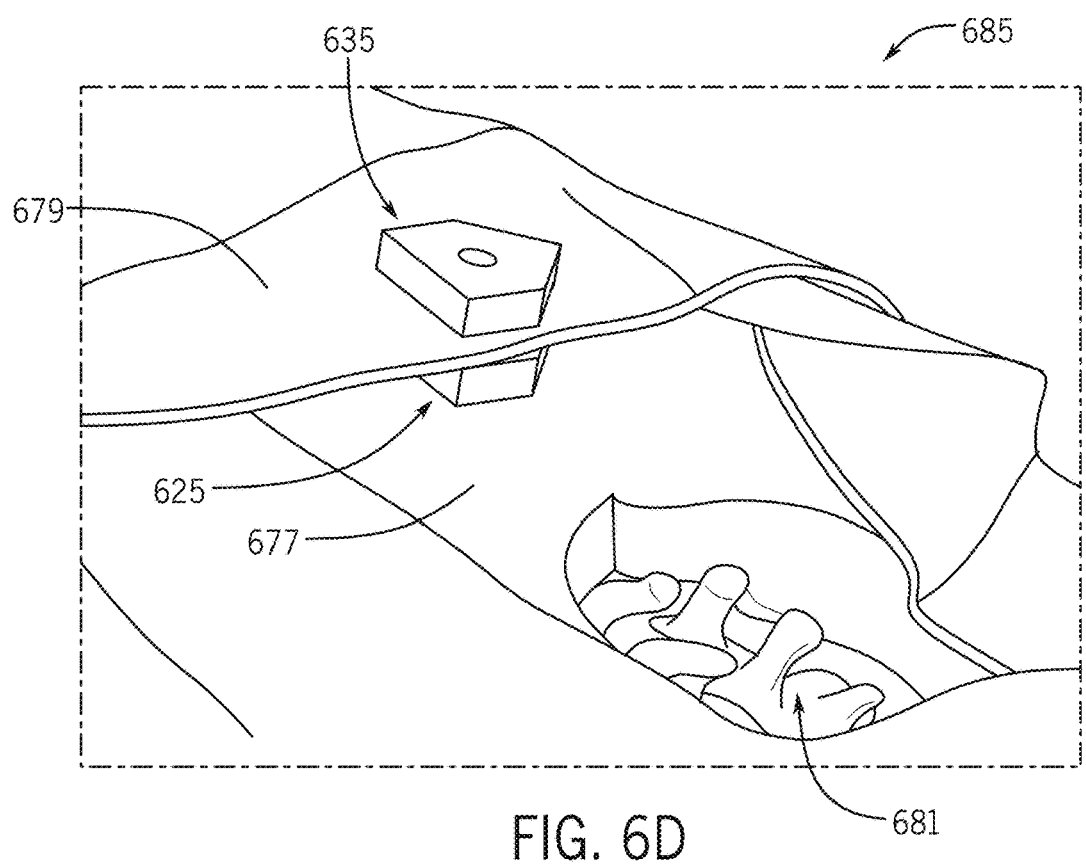
FIG. 6D illustrates an embodiment of a skin-mounted fiducial mating with its over-the-drape fiducial across a surgical drape/towel in accordance with some embodiments of the invention.

FIG. 6C illustrates one embodiment of a skin-mounted fiducial applied to an anatomical phantom in a region that is outside the surgical site but located over regions of underlying anatomy for which their location within coordinates of the 3D-tracking acquisition system is desired to be known in accordance with some embodiments of the invention. Further, FIG. 6D illustrates an embodiment of a skin-mounted fiducial mating with its over-the-drape fiducial across a surgical drape/towel in accordance with some embodiments of the invention. In reference to FIG. 6C, in some embodiments, the skin-mounted fiducial 625 can be applied to an anatomical phantom 677 in a region that is outside the surgical site 681. For example, FIG. 6D illustrates an embodiment of a skin-mounted fiducial mating 625 with its over-the-drape fiducial 635 across a surgical drape/towel 679 in accordance with some embodiments of the invention. In some embodiments, because the over-the-drape-mating fiducial 635 is mechanically mated in a predictable fashion with the skin-surface fiducial 625, the location and pose of the over-the-drape-mating fiducial 635 can be used to compute the location and pose of the underlying skin-mounted fiducial 625. Furthermore, if the skin-mounted fiducial 625 had been previously initialized to nearby anatomical structures, as described above in relation to FIGS. 4A-4I, the location and pose of the over-the-drape-mating fiducial 635 can then be used as a surrogate reference point for the underlying anatomy of interest 681.

Figure 7:
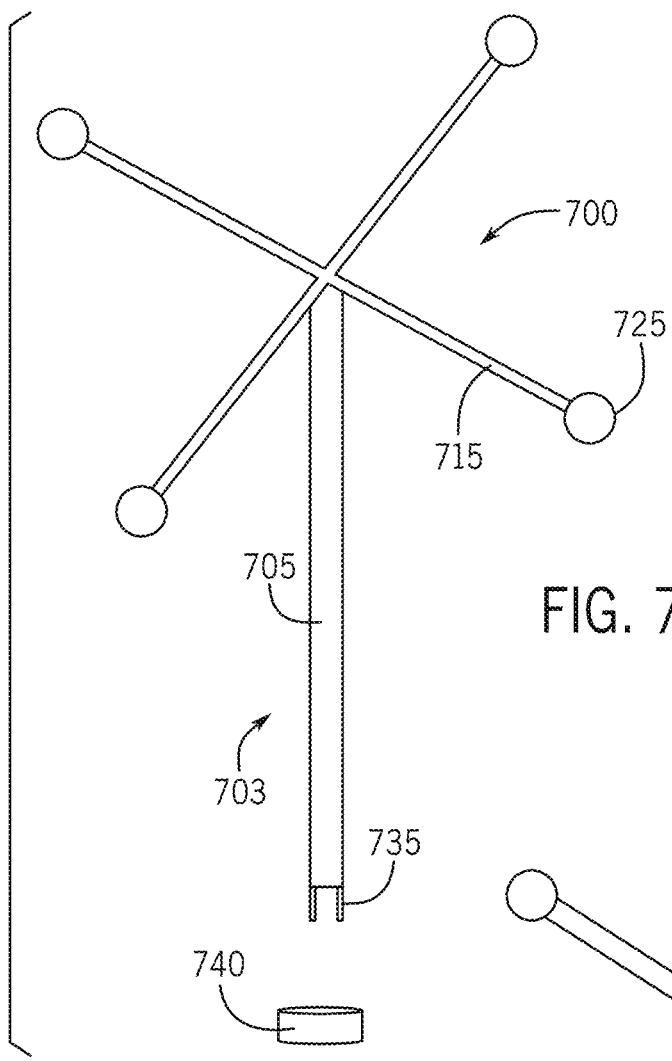
FIG. 7 illustrates an assembly view of a fiducial in accordance with some embodiments of the invention.

FIG. 7 illustrates an assembly view 700 of a fiducial 740 in accordance with some embodiments of the invention and portrays an embodiment that enables unique identification of one fiducial to another. In some embodiments, this can be applied to scenarios when more than one fiducial is used, and the identity of the fiducial is required. In this embodiment, an interfacing probe 703 is shown designed with electrodes 735 to mate with the fiducial 740. In some embodiments, the electrodes can be coupled to or inserted into the fiducial 740, and based on the circuit characteristics built into the fiducial material (e.g., electrical resistance, capacitance, etc.), the fiducial's unique identity can be made known by the mating probe. As shown, in some embodiments, the probe 703 can include a probe shaft 705 coupled to a tracked DRF 715 with 3D-trackable markers 725. Further, in some embodiments, the fiducial 740 can include two electrodes built-in, and can possess identifying circuit components (e.g., resistors, capacitors, etc.) embedded between electrodes. In this way, a probe 703 equipped with a tracked DRF 715 can be designed such that it has mating electrodes 735 that can interface with the fiducial 740, measuring the unique electrical characteristics of the fiducial 740, while simultaneously identifying the location and pose of the fiducial 740 in 3D space. Thus, the embodiments described above can enable identification of unique fiducials, which can be useful when multiple fiducials are being deployed.

Figure 8:
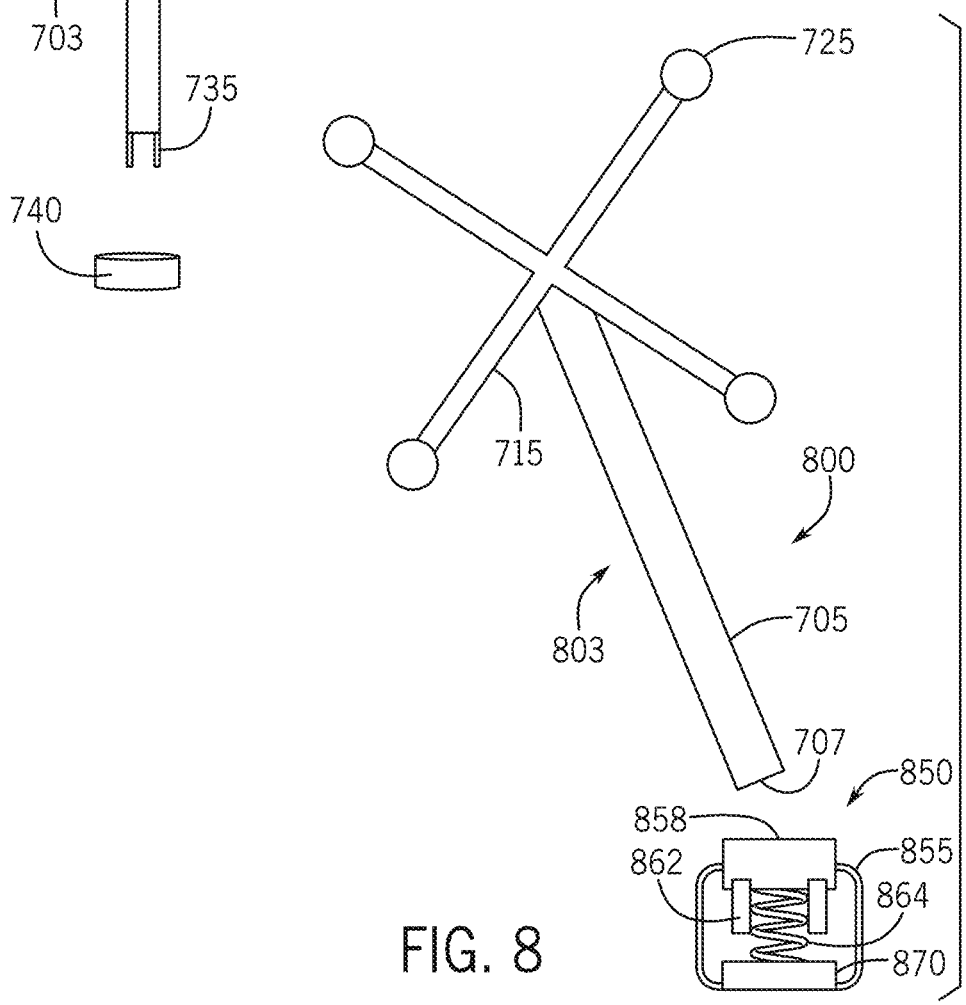
FIG. 8 illustrates an assembly view of a fiducial in accordance with some embodiments of the invention.

FIG. 8 illustrates an assembly view 800 of a fiducial in accordance with some embodiments of the invention, and enables unique identification of one fiducial compared to another. This can be applied to scenarios when there is more than one fiducial used, and the unique identity of the fiducial is desired to be known. In this design, a probe equipped with an RFID-reading circuit interfaces with a spring-embedded RFID-tag circuit within the fiducial. In this way, the probe 803 is able to simultaneously communicate that the fiducial has been accessed by a depressed spring-loaded momentary push button, and can also acquire information as to which fiducial has been referenced. As shown, the probe 803 can comprise a tracked DRF 715 with trackable markers 725 configured to be coupled to an embedded RFID reader 850 including a spring-loaded button 855. In some embodiments, the tip 707 of the shaft 705 can couple with the surface 858 of the button 855, compressing the spring 864, and eventually enabling contact of the terminals 862 with the RFID tag 870. In some embodiments, if accessed by a probe 803 equipped with an RFID reader 850 in addition to a tracked DRF 715, a probe 803 that depresses the spring 864 can simultaneously perform three tasks 1.) trigger that it has approximated the fiducial, 2.) interpret the location of the fiducial surface, and 3.) interpret the unique identity of the fiducial based on its embedded RFID tag.

Figure 9A:
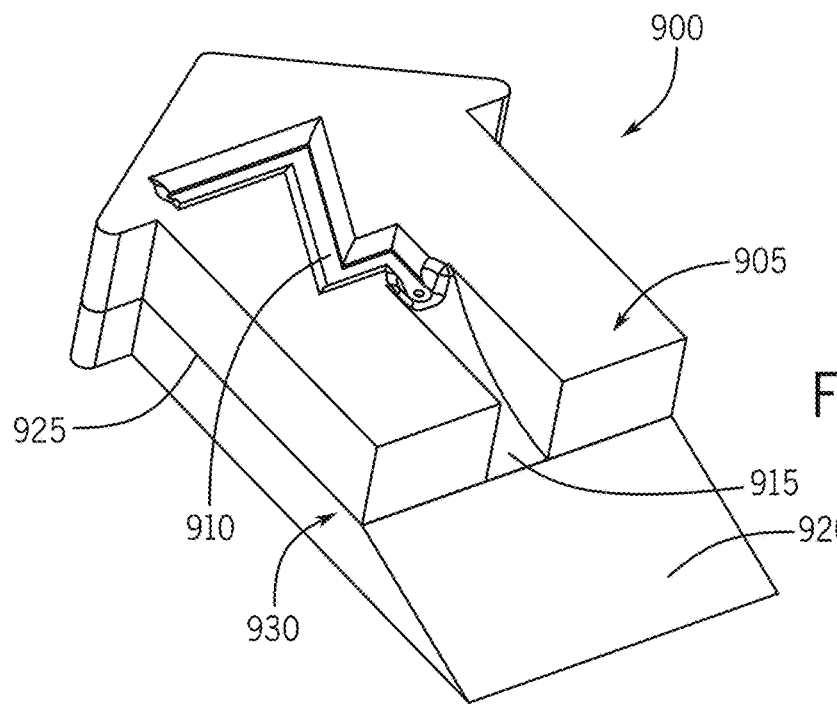
FIG. 9A illustrates an assembled skin-surface fiducial with mating top surface fiducial in accordance with some embodiments of the invention.

FIG. 9A displays another embodiment of a skin-surface fiducial described previously in relation to FIGS. 6A-6B. In this instance, the assembled skin-surface fiducial 900 includes a mating top-surface fiducial 905 coupled to a skin-mountable fiducial. For example, FIG. 9A displays an assembled skin-surface fiducial 930 with its over-the-drape-mating fiducial 905. The bottom surface fiducial 930 is equipped with a mechanism (not shown) of adhering to the skin surface. The fiducial pair 905, 930 joins together at an interface 925 designed to accommodate surgical drapes or towels, while maintaining a predictable mating configuration. One embodiment of the top fiducial contains a groove (tracing pattern 910) in a unique geometry (e.g., "z" geometry shown here) such that a 3D-tracked probe (e.g., any of the 3D-tracked probes described herein) can trace the pattern, as depicted previously in relation to FIG. 4H, and from that information interpret the unique identity of the fiducial, as well as interpret its location and pose in space, enabling the identification of a fiducial-based axes as described previously in relation to FIGS. 4A-4I.

The external design of the fiducial 900 is configured to communicate information to the user as embedded instructions. One embodiment of the fiducial possesses an external arrow appearance (FIG. 9A depicts an example of fiducial 900 assembled as an arrow) that can be used to indicate how the user should place the fiducial (e.g., position the fiducial on the skin such that the arrow points away from the surgical site). In some embodiments, a sloped decline 920 of known geometry on the bottom fiducial, as well as a curved decline 915 on the top fiducial, can be implemented to facilitate a user tracing a probe from the groove surface 910 of the top-half fiducial 905 down to the bottom surface of the bottom-half fiducial 930, which transitions to skin or drape-covered skin, onto which the top-half fiducial 905 is placed. In some embodiments, the framed structure of the fiducial 900 can allow for more predictable tracing over the transition from the fiducial groove 910 to the underlying surface. Additionally, in some embodiments, it allows for the ability to calculate the location of the underlying body surface given the known geometry of the fiducial slope design.

Figure 9B:
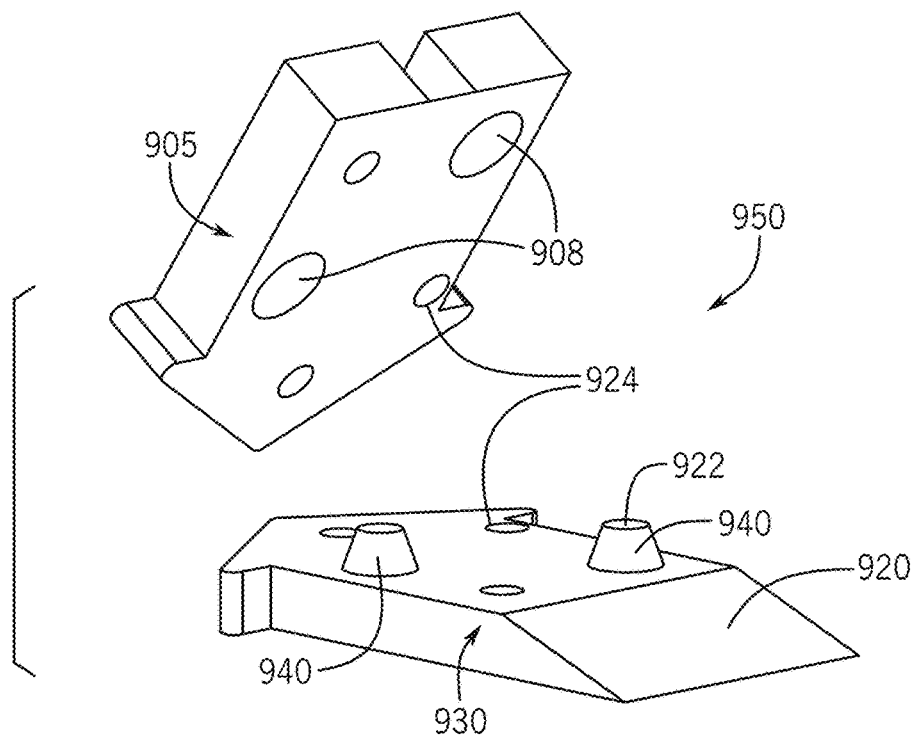
FIG. 9B illustrates an assembly view of the fiducial of FIG. 9A in accordance with some embodiments of the invention.

FIG. 9B illustrates an assembly view of the fiducial 900 of FIG. 9A in accordance with some embodiments of the invention. In this non-limiting embodiment, the skin-mounted fiducial 930 contains male alignment-aiding protrusions 940, similar to those described previously in relation to FIG. 6B. Further, the protrusions have a flattened top 922 to accommodate added volume of an overlying material, as in the case of a surgical drape. In this way, the structure allows for close approximation of the two fiducial mates in the presence of a sandwiched drape by avoiding tenting of the drape in between the two fiducial halves. In some embodiments, the fiducials 905, 930 are equipped with cutouts 924 to accommodate both radiopaque markers and/or magnets, which can also act as radiopaque markers, as described previously in relation to FIG. 6B. One embodiment of the cutouts 924 involves an asymmetric geometric pattern that substantially rigidly embeds the radiopaque markers in a relative configuration that enable unique pose estimations at any radiographic viewing angle. Instead of magnets used to help approximate the two fiducials, other embodiments can include protrusions with a quarter-turn or twisting mechanism that allows for tight mechanical linking across surgical drapes. In some embodiments, the over-the-drape-mating fiducial 905 is equipped with female alignment-aiding cutouts 908 configured to mate with the location of the protrusions 940, 922 on the skin-mounted fiducial 930. It should be noted that the location, size, and geometry of these protrusions and mating cutouts can vary and that this is just one embodiment. Furthermore, it is not necessary for the protrusions to only be located on the skin-mounted fiducial, and the cutouts on the over-the-drape-mating fiducial can include varying combinations of shapes and size.

In place of magnets, some embodiments can include a "clamp-over-drape" feature (e.g., tabs on the top fiducial to clamp down over the lower fiducial sides, while grabbing the drape in between). Other embodiments of this invention include two or more clamping arms equipped on the over-the-drape fiducial designed to snap onto corresponding regions of the lower fiducial for ensuring proper alignment when separated by a surgical drape.

In some embodiments, the fiducial 905 can be equipped with other components mentioned throughout the document, such as the depth-stop-based fiducial and probe combination described later in reference to FIGS. 10A-10G. Other embodiments of the fiducial that enable it to be uniquely identifiable include detents of discrete depths designed to mate with a probe equipped with depth-sensing technology, as described below in reference to FIGS. 10A-10G, such that the fiducial and unique location of the detent relative to the fiducial can be determined based on the distribution of measured detent depths.

In some embodiments, the bottom fiducial 930 can have a flexible component to enable it to successfully adhere and/or conform to the uneven surface contour of patient's skin.

Figures 10D, 10E:
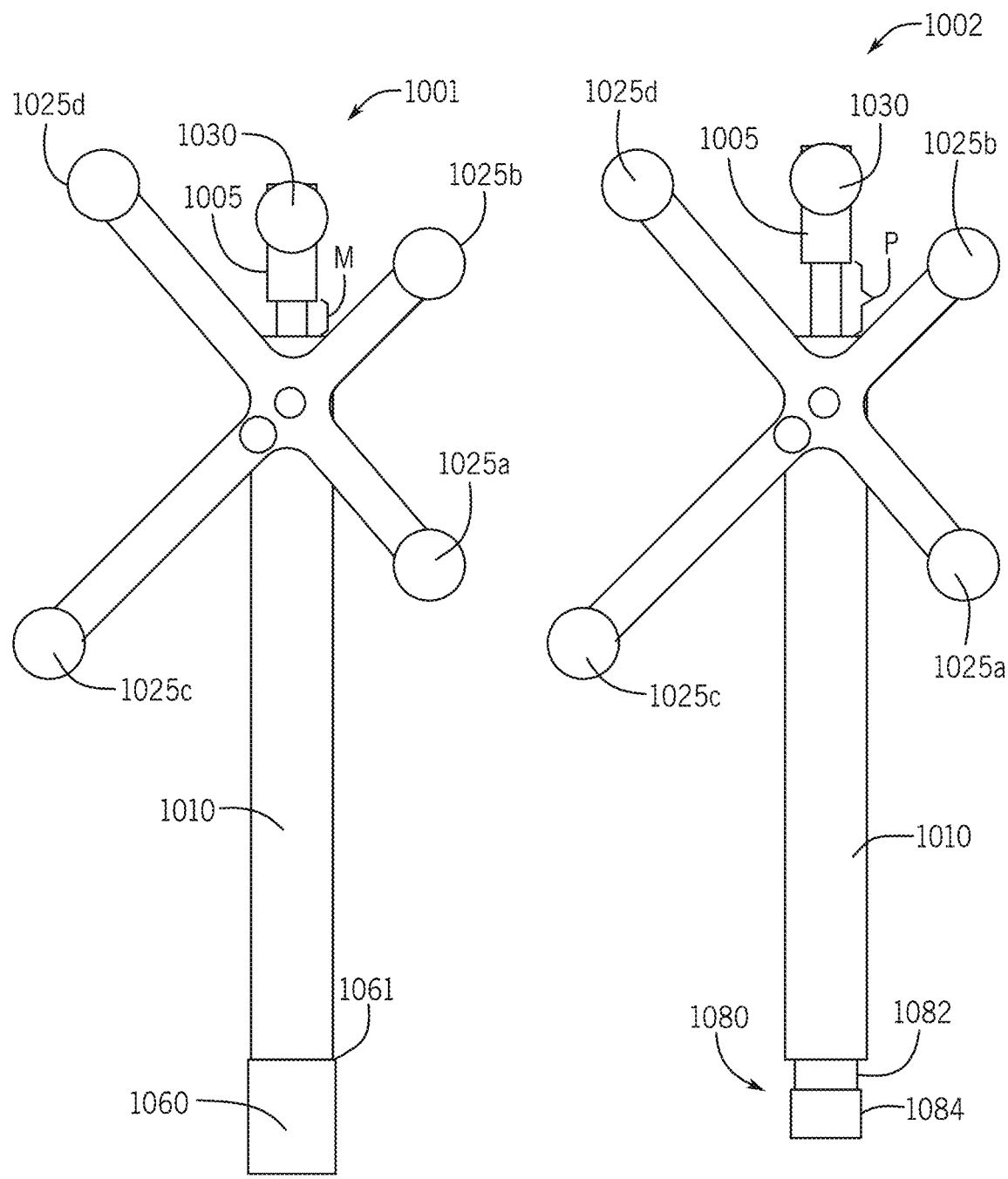
FIG. 10D illustrates the probe of FIG. 10A mated with a particular receptacle of FIG. 10C in accordance with some embodiments of the invention.
FIG. 10E illustrates the probe of FIG. 10A mated with a receptacle designed to mate with a different height selector of the probe than shown in FIG. 10D in accordance with some embodiments of the invention.

Some embodiments of the invention described in FIGS. 10A-10G include a 3D-tracked probe coupled with an actuating TMSM that indicates the depth of depression of a spring-loaded sliding shaft, as well as an embodiment of complementary mating fiducials that are designed to interface with and deflect the shaft by discrete amounts. The purpose of this design is multifactorial. For example, FIG. 10A illustrates a 3D-trackable probe 1000 equipped with a substantially rigidly-attached, 3D tracked DRF 1020 in accordance with some embodiments of the invention. In some embodiments, the actuated TMSM 1030 on the tracked probe 1000 allows for analog communication between the probe 1000 and an acquisition system, as will be described below in reference to at least FIGS. 15A-15C and 63. In some embodiments, the actuated TMSM 1030 conveys information about the depth of deflection of the shaft 1049 at the tip 1049b of the probe 1000. Further, when coupled with mating fiducials that are designed to deflect the shaft tip 1049b by set heights when fully-engaged, the probe 1000 can convey the following three things: 1.) when it is fully engaged with a mating fiducial, 2.) the location and pose of the mating fiducial, and 3.) the unique identity of the mating fiducial based on the designed depression depth that the fiducial will deflect the sliding shaft 1049. As shown, the tracked DRF 1020 includes fixed 3D-tracked markers 1025a, 1025b, 1025c, 1025d. Some or all of the markers 1025a, 1025b, 1025c, 1025d shown in the DRF frame 1020 can be used in any of the DRFs described herein. In some embodiments, any of the DRFs described herein can use these markers, or may use fewer markers. In some embodiments, any of the DRFs described herein may use more markers similar or identical to any of the markers 1025*a*, 1025*b*, 1025*c*, and/or 1025*d*. In some embodiments, any of the probes or DRFs described herein can include any of the markers 1025*a*, 1025*b*, 1025*c*, and/or 1025*d* but with different geometries and/or shapes (e.g., the markers can be smaller or larger than shown, or can be placed at different distances from the probe shaft).

One embodiment of the invention includes a 3D-tracked probe equipped with a substantially rigidly-attached 3D-tracked DRF 1020. In addition, a TMSM 1030 is substantially rigidly attached to a spring-loaded shaft 1049 that is coaxial with the probe 1000 and actuates within a through-hole down the length of the probe shaft 1010 of the probe 1000. In some embodiments, the sliding shaft 1049 can be actuated via a depressible tip 1049*b* that translates the shaft along with a mount 1005 for the TMSM 1030. This embodiment of the probe also contains a series of concentrically-oriented, varying-diameter, protrusions 1040 near the probe tip 1049*b*. These varying diameter protrusions 1040 can serve as variable-depth-stop selections (1041, 1045, 1047) when mating with depth-stop fiducials, as described below in reference to FIG. 10C, designed with varying inner diameters for mating with specific depth-stops 1040 on the probe 1000. For example, FIG. 10B displays a more detailed perspective of the probe 1000 with actuating tip and variable depth-stops as described previously in FIG. 10A. The tracked probe shaft 1010 includes coaxial cylindrical extrusions 1040 of various heights that act as a depth-stops to the actuation of the depressible sliding shaft tip 1049*b*, and its associated TMSM 1030, to different heights (1041, 1045, 1047) for unique trigger signals that are communicated to the computer system.

FIG. 10C displays one embodiment of depth-stop fiducials designed to mate with the probe previously described above in relation to FIGS. 10A-10B. These depth-stop fiducials (1050, 1052) have variable inner diameters and/or heights such that they can couple with varying depth-stops on the probe. In addition to having variable inner diameters to mate with defined depth-stops on the probe (e.g., such as probe 1000), which can lead to identifiable deflections of the TMSM 1030 relative to the DRF 1020. Further, other embodiments of these depth-stop fiducials also contain variable floor depths, such that the sliding probe tip 1049*b* can be actuating by varying amounts despite mating with depth-stop fiducials with matching inner diameters. In this way, these depth-stop fiducials (1050, 1052) can be distinguished from one another and their mating inner diameters and/or depth-stops provide for additional, unique identifiers. These depth-stop fiducials can therefore be coupled as probe-interface components coupled to fiducials previously described in relation to FIGS. 3A-3B, 6A-6D, and 9A-9B.

FIG. 10D displays the probe 1000, previously described in relation to FIGS. 10A-10B, mated with a particular depth-stop fiducial 1050, previously described in relation to FIG. 10C. With these two components coupled in this way, the TMSM 1030 can be actuated coaxially with the probe shaft 1010 and based on the known geometry of both the probe and its mating depth-stop fiducial, the deflection can be measured relative to the tracked DRF and compared to what deflection amounts are anticipated based on particular mates to the probe's depth-stop heights 1061 (previously shown as 1041 in FIG. 10A). In this way, the measured deflection ("M") of the sliding tip and attached TMSM 1030 to the sliding shaft is able to serve as a unique identifier of when the probe (e.g., 1000 and/or 1001) is fully engaged with a specific depth-stop fiducial 1060 (previously shown as 1050 in FIG. 10C).

FIG. 10E displays a probe 1002, as previously described in relation to FIG. 10A, mated with a depth-stop fiducial 1084 (previously shown as 1052 in FIG. 10C) designed to mate with a unique depth-stop 1082 (previously shown as 1045 in FIG. 10A) of the probe 1000 than was shown previously in relation to FIG. 10D. As compared to FIG. 10D, this figure displays the different region of mating 1080 on the probe's unique depth-stop 1082 along with the associated difference in deflection height ("P") of the TMSM 1030, indicating the different depression depth of the sliding probe tip (compare "P" in FIG. 10E with "M" in FIG. 10D).

Figure 10F:
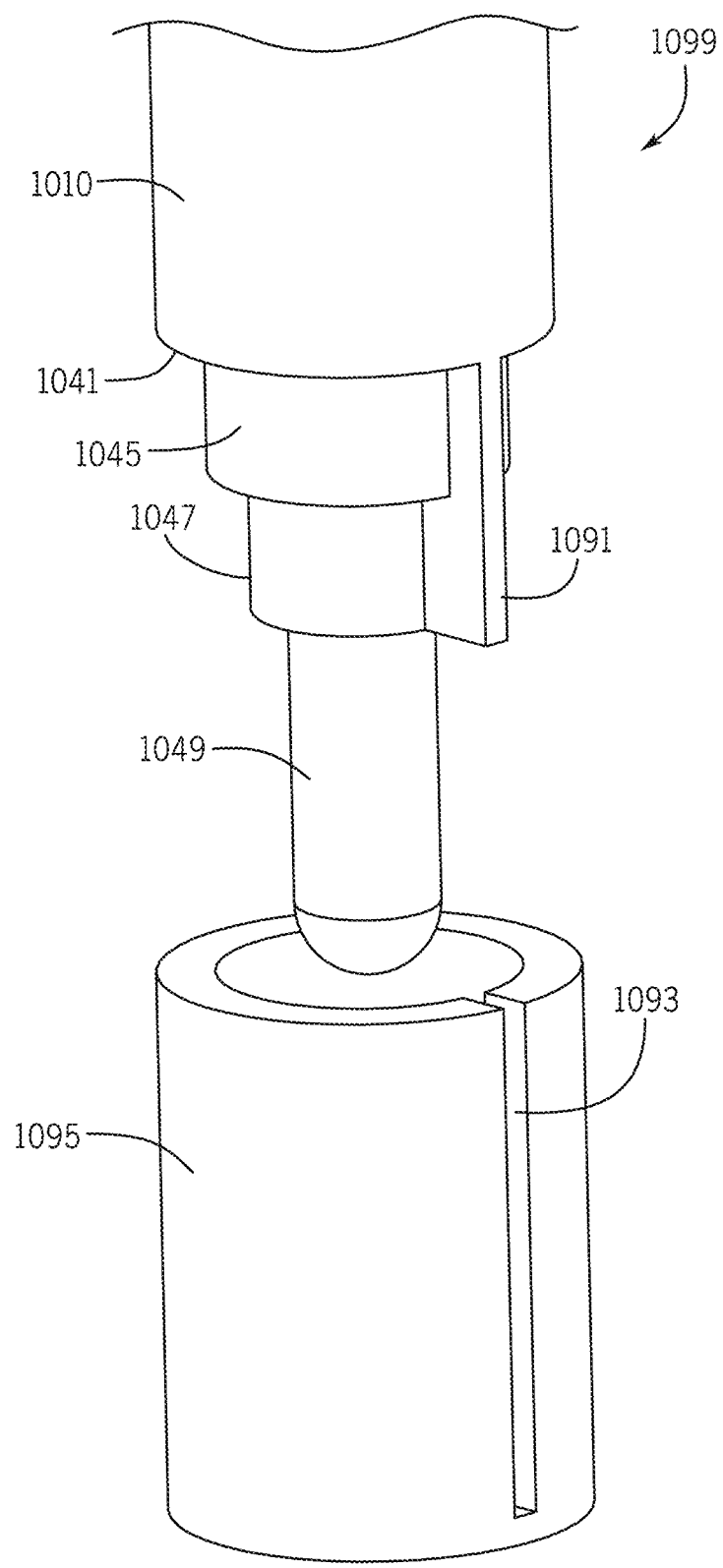
FIG. 10F illustrates an assembly view of a portion of a probe in accordance with some embodiments of the invention.
Figure 10G:
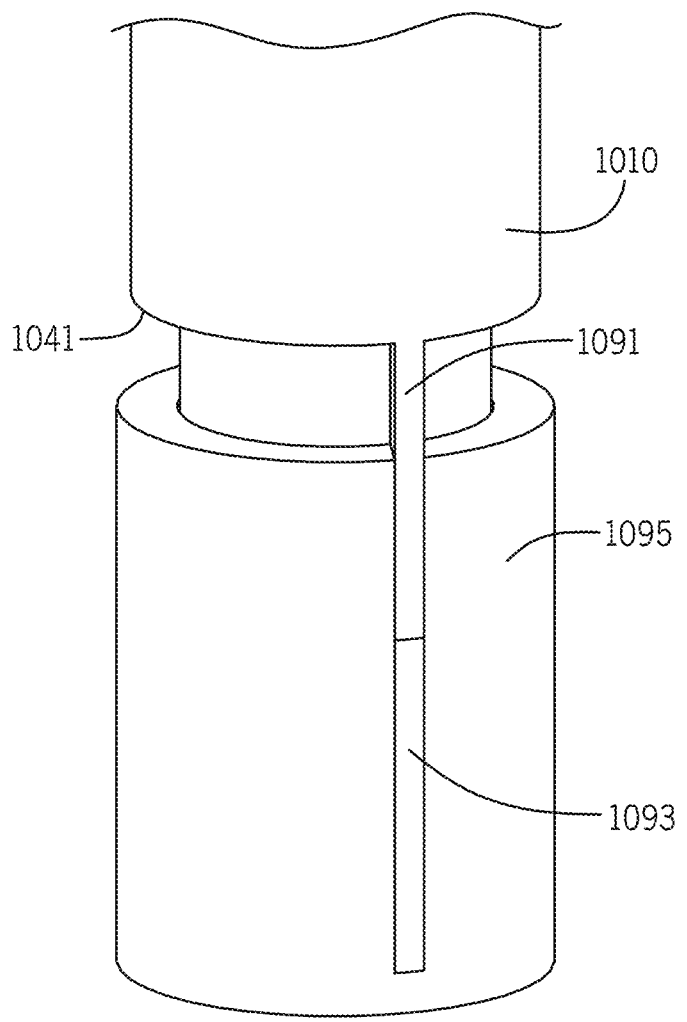
FIG. 10G illustrates a partially assembled view of the probe of FIG. 10F in accordance with some embodiments of the invention.

FIG. 10F illustrates an assembly view 1099 of a portion of an embodiments of the probe 1000 in accordance with some embodiments of the invention. In one embodiment, the 3D-tracked probe 1000, as described previously in relation to FIG. 10A, contains an asymmetric, protruding extrusion 1091 that can engage with any of the depth-stop fiducials, as described previously in relation to FIG. 10C, where a corresponding slot 1093 of a depth-stop fiducial mates with the probe's extrusion 1091. The probe can only mate in one orientation with the depth-stop fiducial due to the asymmetrical design of the slot cutout 1093. This asymmetric alignment enables the probe 1099 to register the unique orientation of the coordinate axes of the fiducial 1095, and thus detect how the fiducial 1095 rotates and translates in 3D space between registrations. FIG. 10G illustrates a perspective view of the depth-stop fiducial 1095 partially engaged with the depth-stop-equipped, 3D-tracking probe 1000, both previously depicted in relation to FIG. 10F.

Figure 11A:
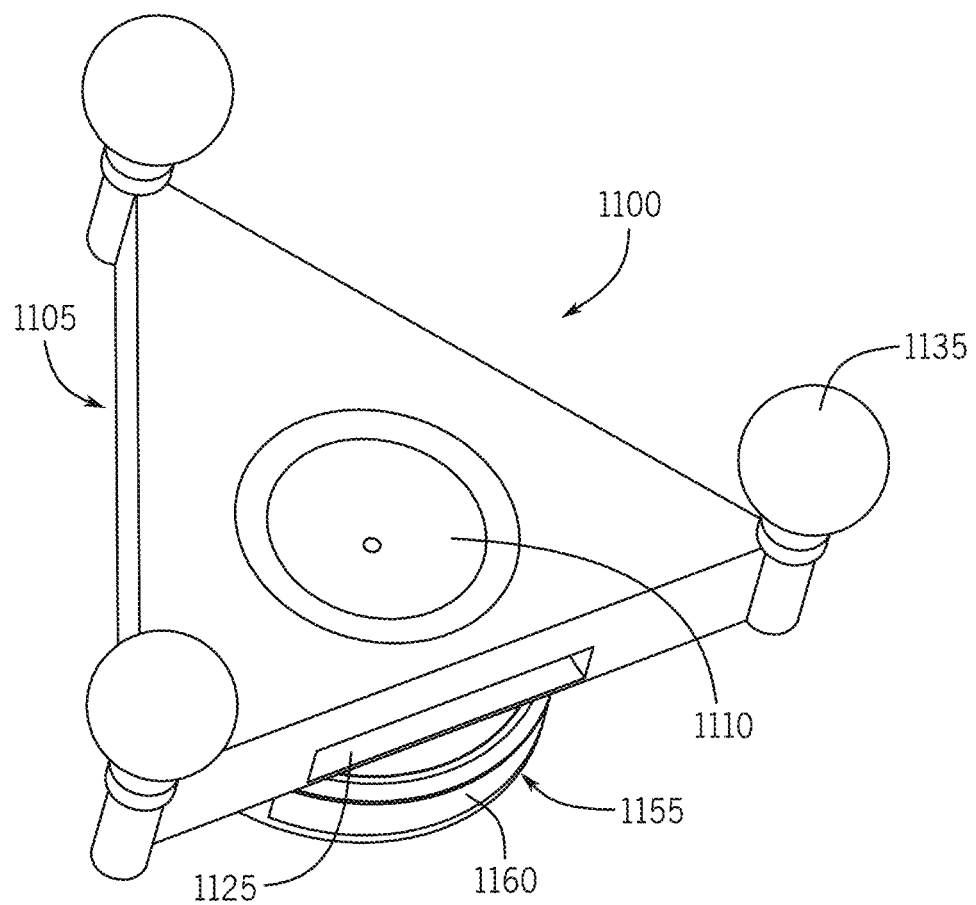
FIG. 11A illustrates a top perspective assembly view of a skin surface fiducial mated with an over-the-drape fiducial that contains three or more tracked markers in accordance with some embodiments of the invention.
Figure 11B:
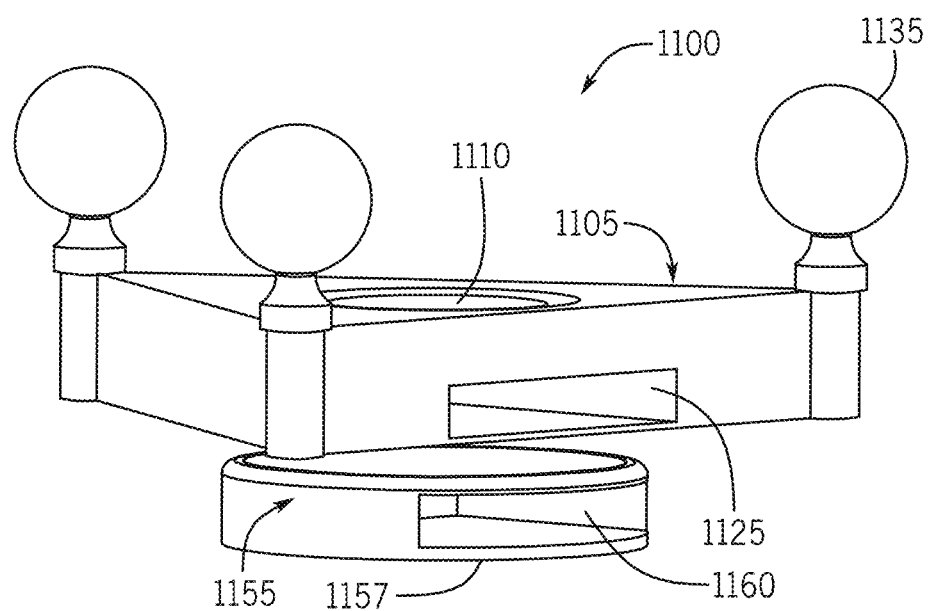
FIG. 11B illustrates a side perspective assembly view of the fiducial of FIG. 11A accordance with some embodiments of the invention.

FIGS. 11A-11B displays an embodiment of skin-surface and mating fiducial design as previously described in FIGS. 6A-6B and FIGS. 9A-9B. The primary difference in this design is that there are tracked markers mounted to the top fiducial such that its location, pose, and identity are all able to be registered by a 3D-tracking acquisition system without the need for the fiducial to interface with a tracked probe. In this way, the fiducial's information is constantly being registered provided it is in line of sight of the 3D-tracking camera system. The assembled fiducial can serve the same purpose as previously described in that once initialized, it serves as a surface reference point for the 3D location in space of underlying anatomical structures. For example, FIG. 11A displays a top view assembly view 1100 of a skin-surface fiducial 1155 mated with an over-the-drape-mating fiducial 1105 that contains three or more tracked markers 1135. These markers 1135 are arranged in a predetermined configuration to form a DRF object, such that a camera acquisition system can recognize them as a unique entity related to the fiducial. These tracked markers 1135 allow for the constant registration of the fiducial's location and pose in 3D space provided that they are within line of sight of the camera. In the event that these tracked markers 1135 are not within line of sight of the camera, the top fiducial component 1105 also contains a surface contour 1110 that can be accessed and traced and/or tapped by a 3D-tracked probe. In this way, the fiducial assembly (1105, 1155) is designed with redundancy to ensure it can be registered in 3D space, regardless of whether the line of sight of the tracked markers is obstructed or not.

In some embodiments, the markers mounted on the fiducial can be placed in a way to enable unique identification of the fiducial. Other embodiments include three or more 3D-tracked markers that are arranged in a unique, identifiable pattern (e.g., asymmetric triangle).

Figure 27A:
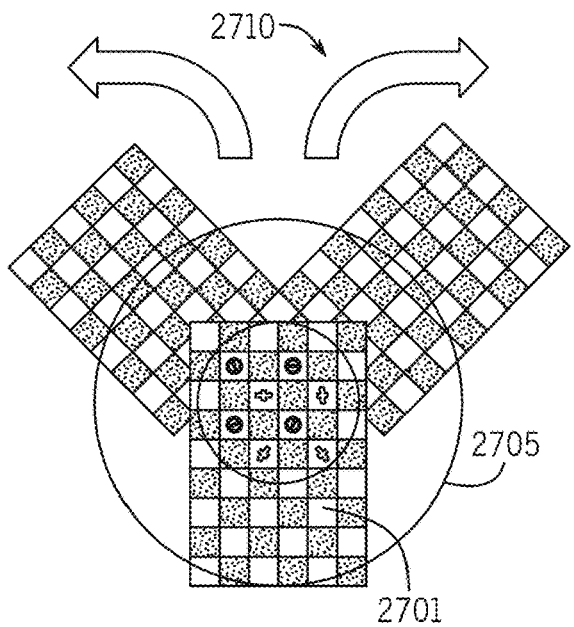
FIGS. 27A-27D includes representations of 3D tracking methods in accordance with some embodiments of the invention.
Figure 27B:
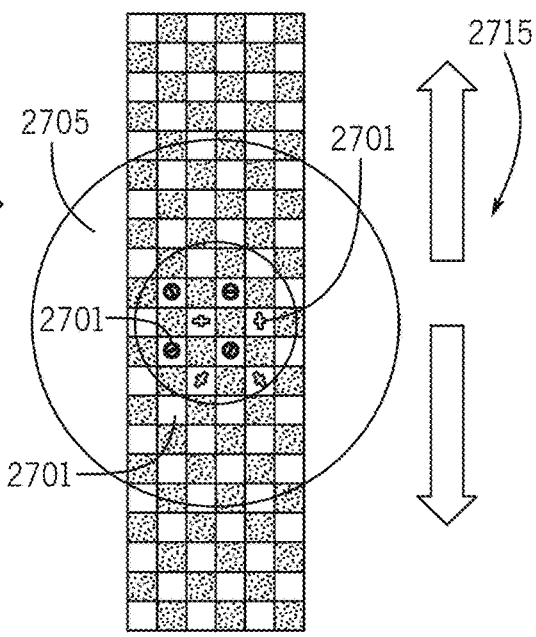

Some embodiments include embedding the unique pattern, depicted in FIGS. 27A-27B, on a fiducial, example embodiment depicted in FIGS. 6A-6D, 9A-9B, 11A-11B, in order to enable enhanced X-ray imaging fusion with optical systems to provide localization features across two coordinate systems. In some embodiments, a unique pattern (e.g., CALTag/ARtag) can be applied to a fiducial patch or a skin-based fiducial. This design involves a radiopaque, unique-pattern surface (e.g., CALTag) that can be easily visualized in both 3D-tracking camera space and 2D or 3D X-ray imaging space. Some embodiments involve using the absolute location of the C-arm relative to the unique-pattern surface to calculate the relative location and pose between separate X-ray images and enable a robust stitching algorithm to understand their spatial relationships and overlaps. This invention could be used with a corresponding optical sensor that is mounted to the X-ray imaging device, and the system knows the relative geometric relationship between the camera and X-ray imaging device's emitter or detector. This system can enable stitching, unique 3D pose detection, absolute location relations, and should be robust with X-ray images that are acquired with a rotated/oblique X-ray imaging system. The unique-pattern surface visualized in the X-ray image could enable automated scaling of the image into physical units (e.g., millimeters), as well as automatically detect the pose of the fiducial relative to anatomical landmark of interest, and relative to the X-ray imaging device.

FIG. 11B displays another view of a fiducial embodiment equipped with tracked markers on the over-the-drape-mating fiducial 1105 coupled with a skin-mounted fiducial 1155 that is mounted to the patient skin via an adhesive backing 1157. This embodiment can also contain insert slots for inserted radiopaque magnets and/or electronics 1125, 1160. It should be noted that although not shown in FIGS. 11A-11B, this fiducial 1100 can also be equipped with protrusions and mating cutouts for alignment as previously described in relation to FIGS. 6A-6D and FIGS. 9A-9B.

Figure 12:
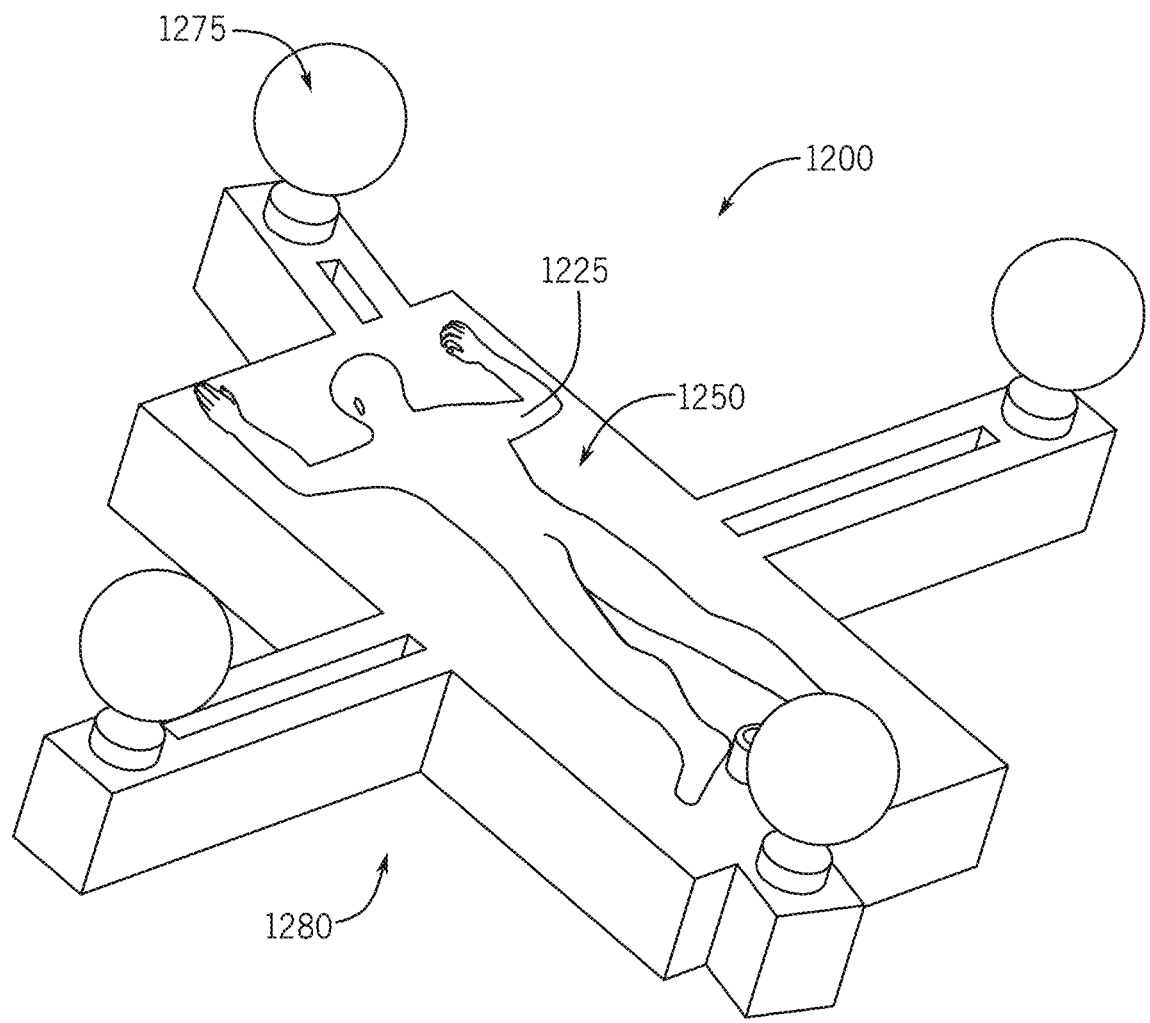
FIG. 12 illustrates a representation of a tracked dynamic reference frame in accordance with some embodiments of the invention.

Some embodiments of the invention depicted in FIG. 12 include a tracked DRF that is equipped with indications of the relative anatomical reference planes. In this instance, the functional aspects reside in the external indication methods to inform the user how to best orient a tracked DRF for it to indicate to the acquisition system how to interpret camera coordinates relative to anatomical axes coordinates. For example, FIG. 12 displays a representation 1200 of a tracked DRF 1250 with built-in indication for communicating relative referenced anatomical axes. This design includes four 3D-tracked markers 1275 that define a DRF, but also an overlying body outline reference 1225 to help instruct the user how to appropriately position the DRF nearby the patient. Attached to this device is an adjustable mounting surface (marked as 1280 as being under the frame 1250) that allows the user to rotate the device until it is aligned with the patient's orientation and then lock it into place via any common fastening mechanism. This device allows the acquisition system to register not only a DRF, but also define anatomical reference planes relative to the known geometry of the dynamic reference plane. By utilizing this device, it allows for the acquisition system to display data to the user onto anatomical reference planes (e.g., sagittal, coronal, axial) rather than camera coordinates which often appear skewed and challenging to interpret by a user depending on the camera's orientation relative to the subject. It should be noted that the methods of indicating anatomical reference axes on this device are not limited to the human body overlay as shown in this figure. Other methods include but are not limited to written text displaying the associated anatomical axes, images of discrete body parts to represent anatomical orientations, and alphanumeric or unique pattern labels for regions that should be aligned with particular anatomical axes so that software interfaces can walk the user through orienting the DRF relative to the patient appropriately. Of note is that the reference frame can be mounted almost anywhere and does not need to have an adjustable mount, and could be rigid/orthogonal relative to the patient or surgical table. For example, other embodiments involve the reference frame being mounted substantially rigidly in one orientation to the surgical table, or any rigid surface, or substantially rigidly mounted directly to the patient anatomy (e.g., spinous process of the spine).

Figure 13:
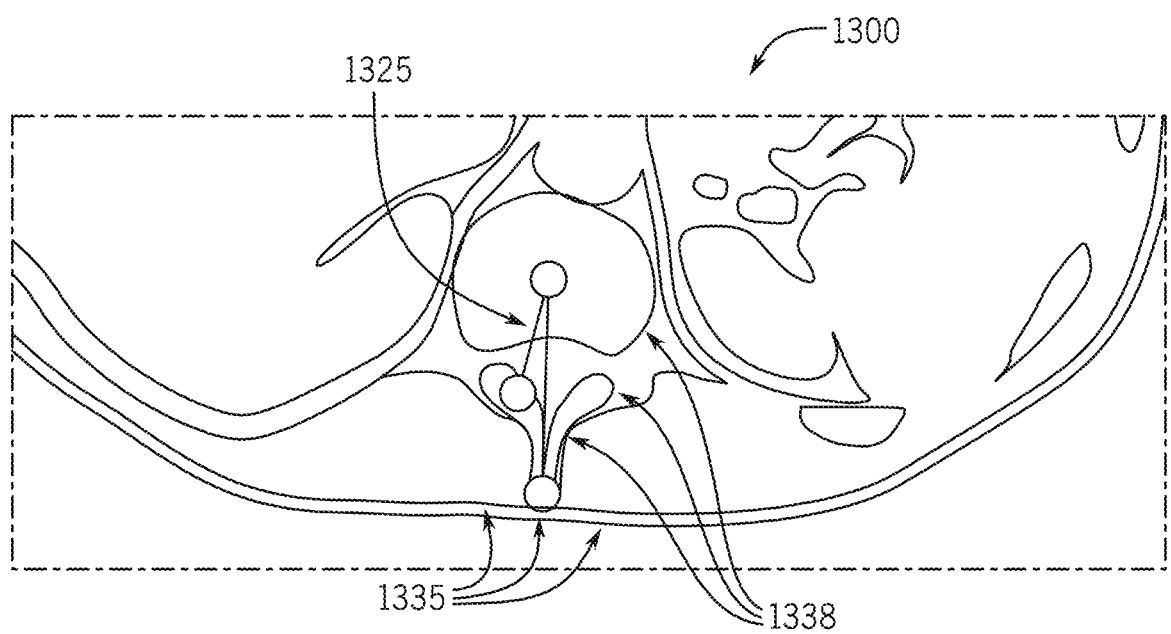
FIG. 13 illustrates a sample cross-sectional CT scan view of a spine in accordance with some embodiments of the invention.

Some embodiments of the invention include a cross-sectional CT scan view of a spine and highlights a few anatomical regions of interest that may be used to initialize patient data prior to performing assessments of the contour of the spine via tracing methods that will be described in more detail below in reference to FIGS. 65A-65E and FIGS. 66A-65B. In some embodiments, this can be used to interpret the cross-sectional displacement vectors between certain regions (e.g., the skin surface, lamina, transverse process) and other regions of interest (e.g., centroid of the vertebral body, anterior segment of the vertebral body, etc.). Using a CT scan to initialize a patient prior to intraoperative assessments of spinal alignment enables software to better interpret localization of exposed regions (e.g., lamina) as a surrogate for the location of other regions (e.g., vertebral body centroid). In doing this, intraoperative interpretation of acquired data can be performed with or without the use of fiducial landmarks as described previously in relation to FIGS. 3A-3B, 4A-4I, 6A-6B, 9A-9B, and 11A-11B. For example, FIG. 13 displays a sample cross-sectional CT image 1300 of a patient in which particular anatomical regions are visible including posterior skin surface 1335, and cross-sectional view of the vertebral landmarks 1338 and many of its bony elements. From CT image sets, it is possible to initialize a patient's anatomy by calculating displacement vectors 1325 from particular regions of interest to another (e.g., skin midpoint to vertebral body centroid, and lamina to vertebral body centroid). After initialization, it is possible for software to interpret the location of one region in terms of its relative location to other initialized regions of interest. For example, although the location of the centroid of the vertebral body may be most advantageous for interpreting spinal alignment parameters, if the skin or lamina is all that is exposed during surgery, the coordinates of the exposed elements can be gathered and then interpreted, based on pre-operative and/or intraoperative initialization data, to represent the location of unexposed regions (e.g., vertebral body centroid).

Some embodiments of the invention include an assembly with an arrangement of 3D-tracked markers that can be utilized for discrete signaling to an acquisition system. In some embodiments, four tracked markers that make up a dynamic reference frame (DRF), and two tracked stray markers (TSMs) are included in the assembly. In this embodiment, the center of the assembly can include a rotating shield that can be positioned to cover select TSMs, or none at all. With the tools geometry known, the acquisition system software can interpret which TSMs are exposed, and based on pre-programmed combinations, the tool is able to communicate discrete messages with the acquisition system. For example, if a first TSM is covered, this can indicate the system is in a particular state as opposed to if a second TSM is covered, which would indicate another state. Because the tool contains a DRF, its location and pose can be interpreted by a 3D-tracking camera, and the arrangement of covered and uncovered stray markers can then be used for communication particular commands or device states.

Figure 14A:
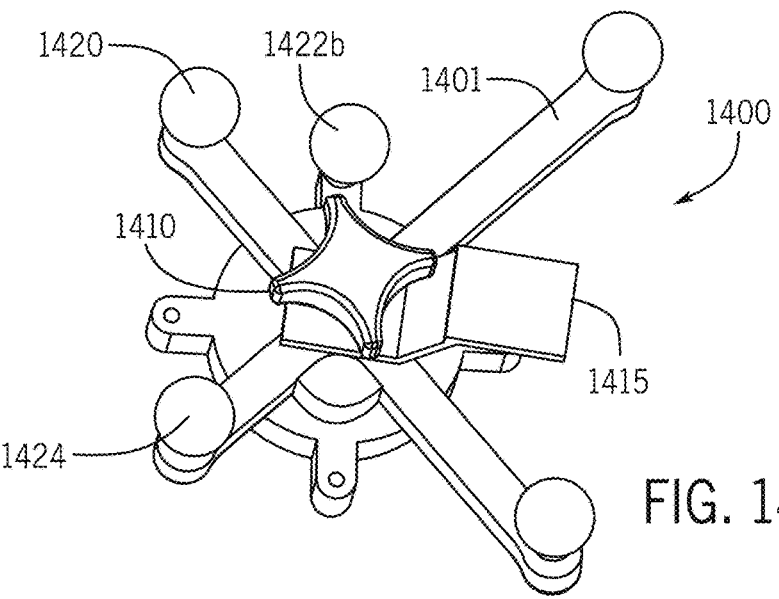
FIG. 14A illustrates a tool equipped with a tracked dynamic reference frame in accordance with some embodiments of the invention.
Figure 14B:
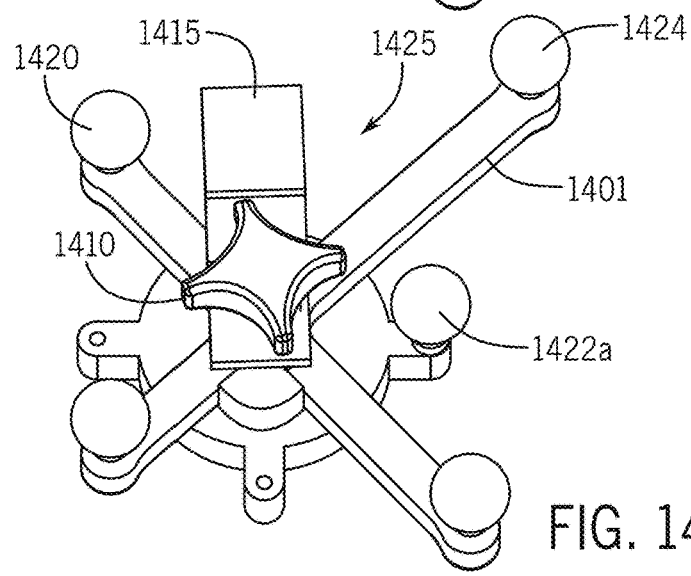
FIGS. 14B-14C illustrate the tool of FIG. 14A in different arrangements in accordance with some embodiments of the invention.
Figure 14C:
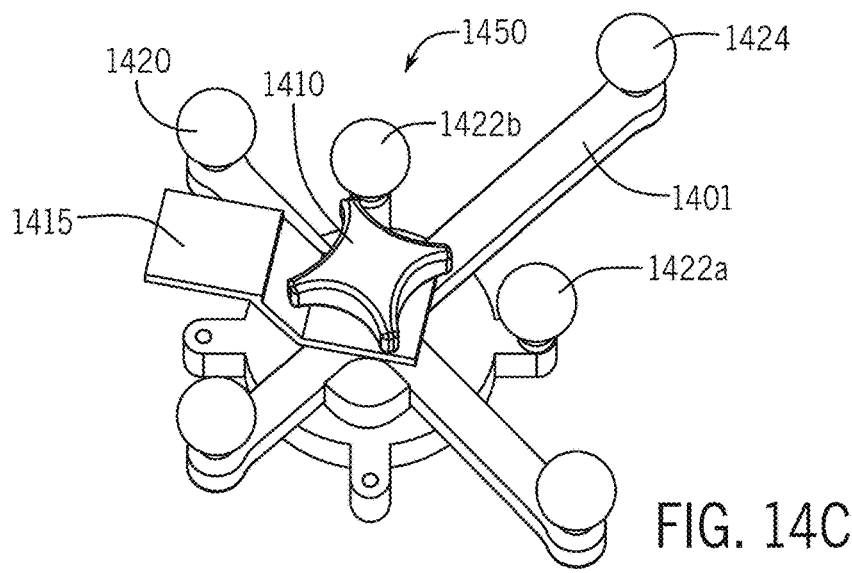

FIG. 14A displays a tool equipped with a tracked DRF 1401 with markers (1420, 1424), two TSMs identified as 1422*a* (not visible) and 1422*b*. The tool is also equipped with a rotating shield 1415 that is currently positioned to cover visibility of a TSM 1422*a*. Because it is equipped with a DRF, a 3D-tracking camera is able to locate the location and pose of tool 1400 in 3D space, as well as distinguish between the four markers serving as a DRF and those serving as TSMs. The tool can be programmed to communicate with the acquisition system via having varying combinations of the TSMs visible or invisible. For example, when the 1422*a* is covered, the system indicates that it is in a certain state, that is different than if 1422*b* is covered, as is shown in FIG. 14B, which is also different from the state communicated by neither of the TSMs being covered, as is shown in FIG. 14C. It should be noted that there can be any combination of one or more TSMs associated with this tool, and there can also be any permutation of covering or uncovering individual or combinations of TSMs to communicate various states to the acquisition system. The static, known location of the TSMs relative to the registered DRF enable the computer system to robustly filter out any phantom markers or additional stray markers not associated with this tool as the computer algorithms can determine which stray markers visible to the camera possess locations relative to the tool (1400, 1425, 1450) that match the pre-set locations of the TSMs via the design of the tool base mount. The rotating shield shown in this figure is only one embodiment of how to block the 3D-tracking camera's visualization of the TSMs. Other embodiments of blocking visualization include but are not limited to spring-loaded rotational wipers, linear-motion sliders, actuating the TSMs such that they move from covered to uncovered positions, and rotating shields with multiple panels such that varying combinations of TSMs can be covered or uncovered. It should be noted that this technology of signaling through covering and uncovering TSMs can also be combined with actuating TSMs as was previously described in reference to FIGS. 10A-10G and as will be described in more detail below in relation to FIGS. 15A-15C, 63, and 64A-64B.

FIGS. 14B-14C illustrate the tool of FIG. 14A in different arrangements in accordance with some embodiments of the invention. For example, FIG. 14B displays one embodiment of a tool previously discussed in relation to FIG. 14A, but in this arrangement, the rotating shield 1415 is covering visualization of the TSM 1422*b*, and the TSM 1422*a* is uncovered. This combination can be used to communicate its unique state to the acquisition system software. Further, FIG. 14C displays one embodiment of a tool previously discussed in relation to FIG. 14A, but in this arrangement, the rotating shield 1415 is positioned such that both TSMs 1422*a* and 1422*b* are visible, which is used to communicate a unique state to the acquisition system software.

Figure 15A:
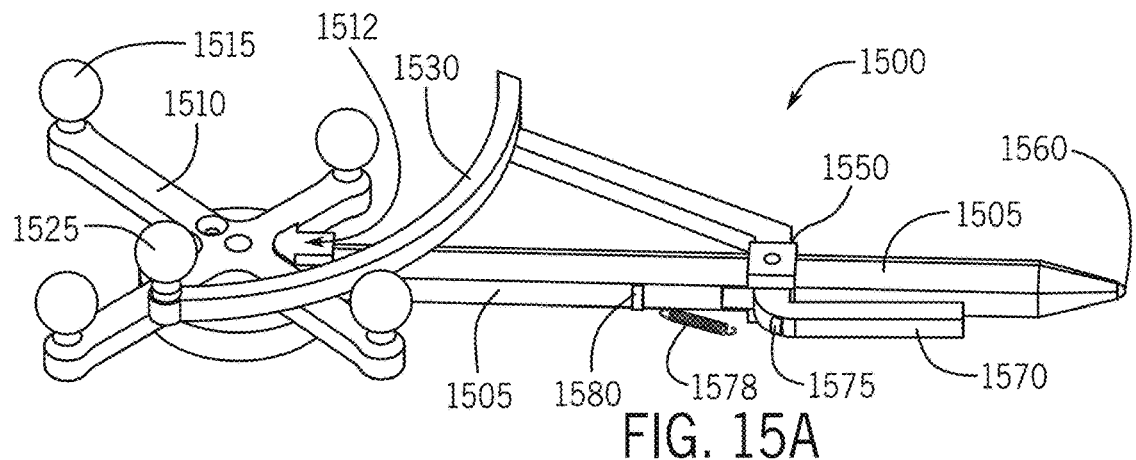
FIGS. 15A-15C shows a probe equipped with a tracked dynamic reference frame (DRF) in various configurations in accordance with some embodiments of the invention.
Figure 15B:
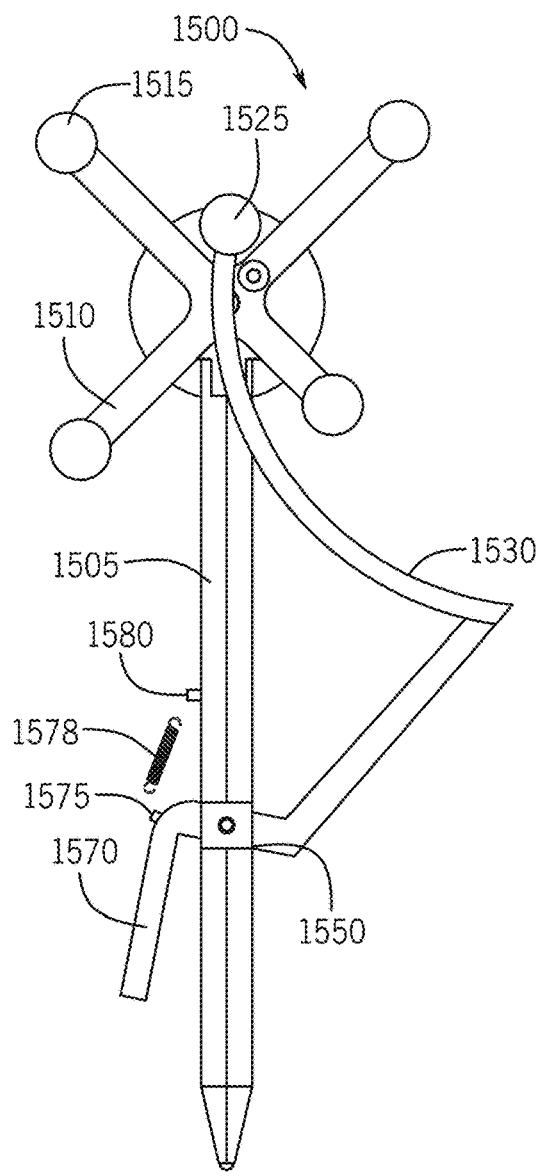
Figure 15C:
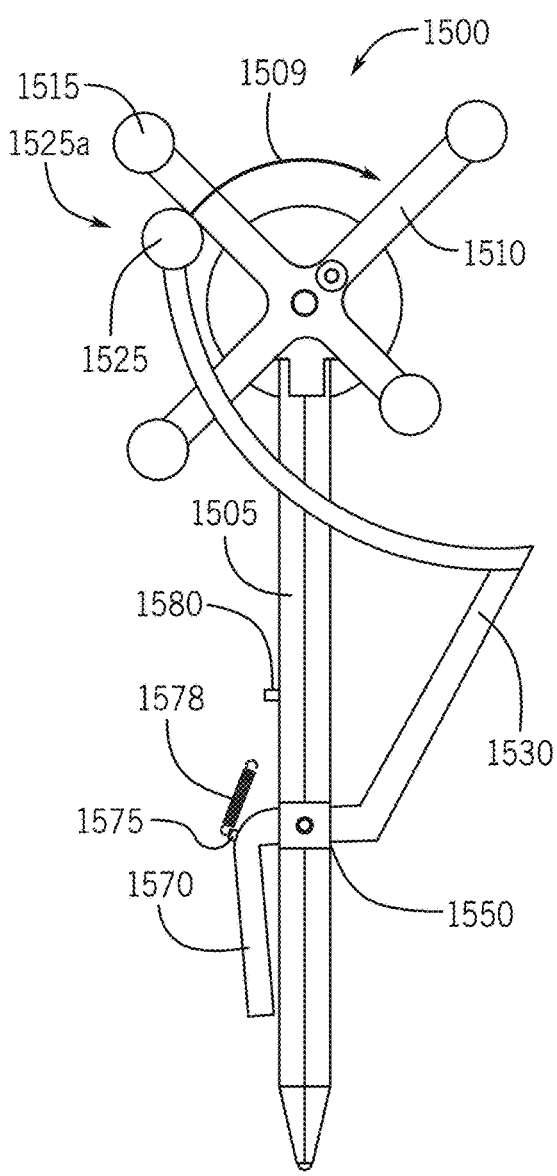

Some embodiments of the invention include a 3D-tracked probe, equipped with a tracked DRF and a tracked mobile stray marker (TMSM) that can be actuated by a user and utilized to indicate analog and/or binary information to the acquisition system software. For example, FIGS. 15A-15C shows a probe equipped with a tracked dynamic reference frame (DRF) in various configurations in accordance with some embodiments of the invention. By the user actuating a tracked mobile stray marker that rotates about a pivot point in the probe shaft, the location of the tracked mobile stray marker can be computed relative to the DRF, and when visualized in certain positions, can be used to communicate varying messages to the acquisition system's software. In reference to FIG. 15A, one embodiment of a probe 1500 can be equipped with a tracked DRF 1510, which is coupled to a mount 1512 that provides structural integrity to the DRF's attachment to the probe 1505, a TMSM 1525 coupled to an arm 1530 that rotates about a pivot hinge 1550 on a hexagonal extruded probe shaft 1505. The arm 1530 is spring-loaded (via spring 1578) via spanning external spring mounts 1580, 1575 that allow for a depressible tab 1570 to be actuated by a user depressing it inward towards the coaxial probe shaft. The embodiment of the probe 1500 shown has a blunt semi-spherical tip 1560 to avoid damaging sensitive anatomical structures, and also has a hexagonal extruded probe shaft 1505 for added grip by the user. This probe 1500 is designed to have the TMSM 1525 rotate about the pivot hinge 1550 when a user depresses or releases the depressible tab 1570. The location and relative angle of the TMSM 1525 to the DRF 1510 is computed by the acquisition software of any of the disclosed systems, and can be used for both binary or analog communication with the system, as will be described in more detail in relation to FIGS. 63 and 64A-64B.

It should be noted that with regards to the type of motion of components of the TMSM 1525, the TMSM 1525 can move linearly, as described previously in relation to FIGS. 10A-10E, rotationally, as will be described in more detail in relation to FIGS. 63 and 64A-64B, or a combination of the two types of motion. With regards to the actuation method, one embodiment is a user-depressible tab 1570 as shown here but it can also consist of user sliding buttons, rotating buttons, and depressible sliding shafts as described previously in relation to FIG. 10A-10B. With regards to the spring location, an external compression spring 1578 is shown but is only one embodiment which can also include but is not limited to torsion springs, internal compression springs, deformable materials with shape memory. With regards to the probe shaft 1505, the hexagonal extrusion shape as shown is only one embodiment and other embodiments include, but are not limited to, circular, triangular, rectangular, pentagonal extrusions and non-uniform revolved profiles for both user grip and probe placement within limited-access environments. The probe shaft 1505 need not be linear or symmetric. With regards to the depressible tab 1570, the location of the tab 1570 can also be positioned anywhere on the body of the tool 1500. With regards to the probe tip 1560, the blunted semi-spherical design is only one embodiment as it can also comprise varying shapes and degrees of sharpness of point at the tip 1560. Other embodiments can include motion type, linear/rotational, and include other actuation methods. Some embodiments include a user button, slider, or depressible sliding shaft (shown before in FIGS. 10A-10B). Other embodiments include a different spring location, internal or external placement, a torsion spring, a compressible spring or a non-compressible spring. Other embodiments include alternative tip shape and size, blunt or sharp. Some further embodiments include a mating tip as shown in other fastening devices such as FIGS. 33D-33F and 44B-44D.

Referring to FIG. 15B, the tracked probe 1500 with a rotating TMSM 1525 can be used for analog and/or binary communication previously described in relation to FIG. 15A. This embodiment displays the location of the TMSM 1525 when the depressible tab 1570 is in its undepressed location and the spring 1578 in its most compressed state. The location and angle of the TMSM 1525 relative to the DRF 1510 can be calculated as will be described in more detail in relation to FIG. 63 and FIGS. 64A-64B.

FIG. 15C displays one embodiment of a tracked probe 1500 with a rotating TMSM 1525 used for analog communication previously described in relation to FIG. 15A. This embodiment displays the location of the TMSM 1525 when the depressible tab 1570 is in its depressed location 1525*a*, and the spring 1578 in its most extended state. The arc that is traveled by the tracked mobile stray marker (marked as 1509) can be visualized and computed by the computer system by comparing the location of the TMSM 1525 relative to the tracked DRF 1510 as it is actuated via the depressible tab 1570, with examples depicted in FIGS. 15A-15C. The location and angle of the tracked mobile stray marker 1525 relative to the DRF 1510 can be calculated as will be described in more detail in relation to FIGS. 63 and 64A-64B.

Figure 23A:
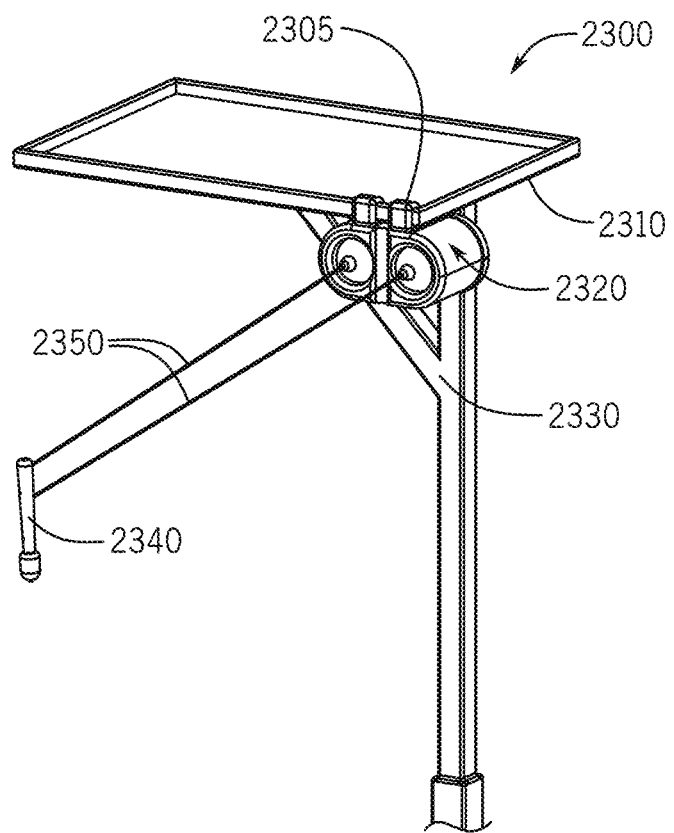
FIG. 23A illustrates an example 3D tracking system in accordance with some embodiments of the invention.
Figure 23B:
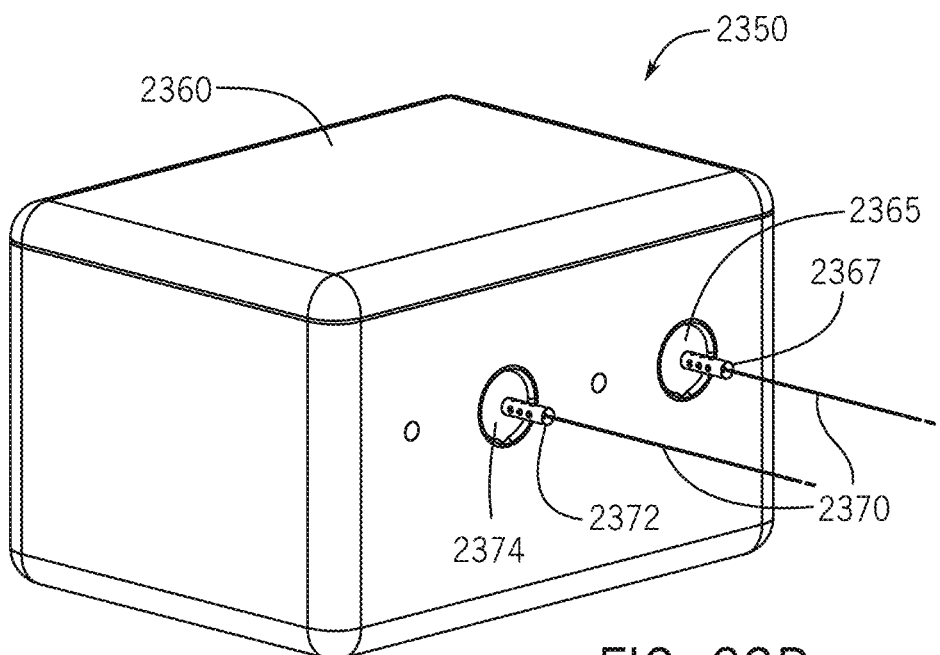
FIG. 23B illustrates 3D tracking system in enclosure in accordance with some embodiments of the invention.
Figure 23C:
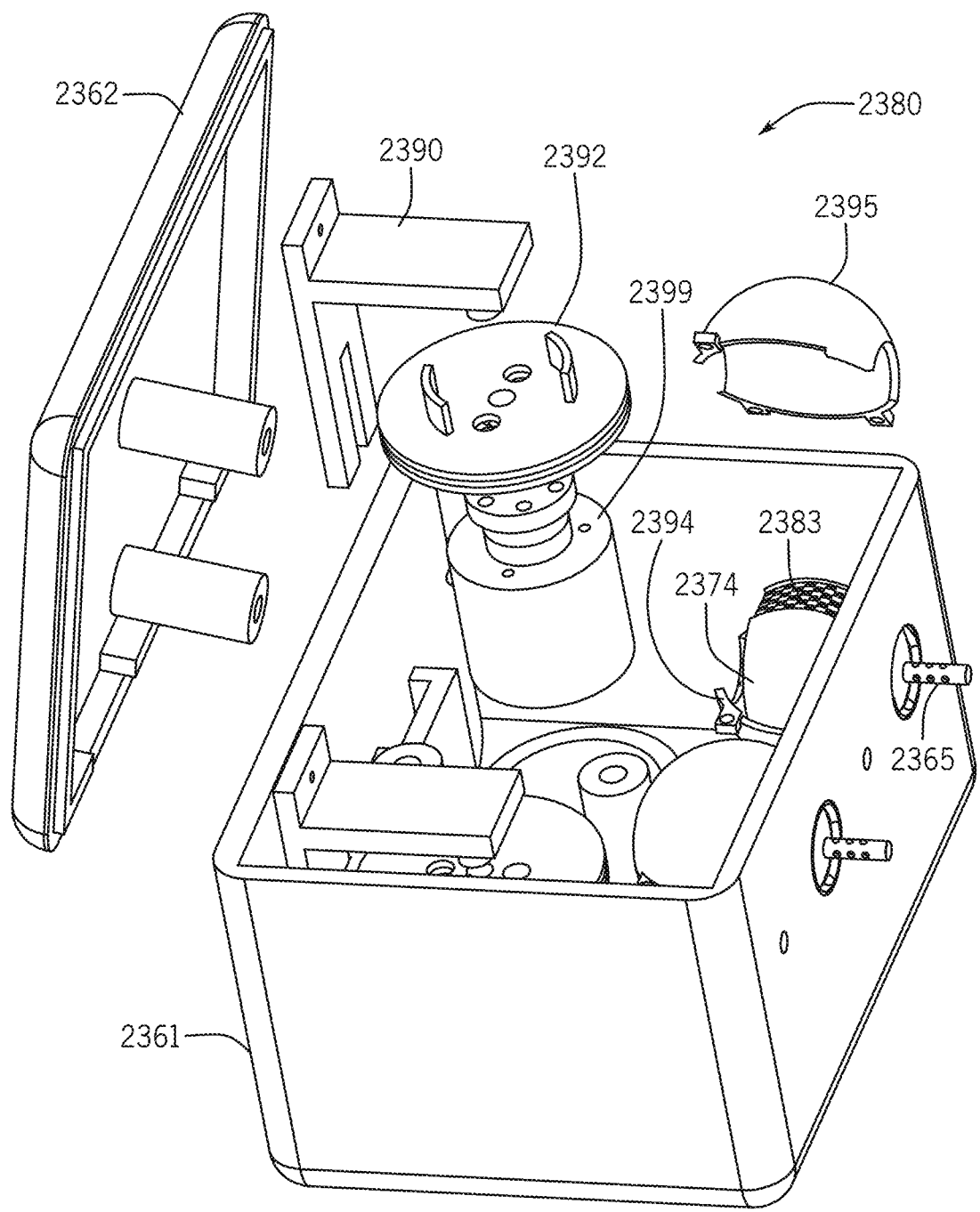
FIG. 23C shows an exploded assembly view of the 3D tracking system of FIG. 23B in accordance with some embodiments of the invention.

Some embodiments of the invention utilize rotary encoders that are used to measure the precise length of an extensible cord that is retracted outside of the electromechanical, 3D-tracking system (e.g., such as the system depicted in FIGS. 23A-23C). This length calculation is accomplished by the encoder measuring the amount of rotation a mechanically-linked cord causes due to retraction. The rotary encoder is mechanically linked either directly with the traversing cord or linked with a spool that stores several revolutions of the cord. This component of the electromechanical tracking system provides accurate length measurements of the extensible cord between the acquisition unit and the probe. The rotation measurement system of the electromechanical tracking system consists of a system that is capable of measuring the degree of rotation, and any supporting mechanical systems to enable or enhance the rotation measurement process. The rotation measurement system interfaces mechanically with an extensible cord and/or a retracting spool/tension system to measure the linear distance of extensible cord that has interfaced with the encoder. For example, one embodiment of the rotation measurement system is a rotary encoder 1600 shown in FIG. 16. A rotary encoder is an electromechanical device, which converts the position or motion of a shaft 1630 about the body 1610 to an electrical signal. In some embodiments, the electrical interface 1650 of the rotary encoder is dependent on the type of rotary encoder and the manufacturer. Internal circuitry inside the rotary encoder 1600 can automatically calculate the amount of shaft rotation, the direction of shaft rotation, or communicate the measurement data over a digital or analog interface. The method and interface over which the rotation measurement data is communicated is of no significance to the encoder system. Only the degree and direction of shaft 1630 rotation is of importance to the calculation of linear distance. In other embodiments, potentiometers can also be used to measure rotation, specifically absolute rotation, which can eliminate the need for length calibrations in order to measure the length of the extensible cord that is actively being retracted outside the electromechanical, 3D-tracking system.

FIG. 17A illustrates a pulley-gear system 1701 for use with the encoder 1600 of FIG. 16 in accordance with some embodiments of the invention, and FIG. 17B illustrates a gear 1710 of the pulley-gear system 1701 of FIG. 17A in accordance with some embodiments of the invention. This component of the electromechanical, 3D-tracking system depicted in FIGS. 23A-23B enables for the increased accuracy of length measurements of the extensible cord that transverses through the enclosure and extends beyond the system to the probe 2000 illustrated in FIG. 20. The pulley-gear embodiment 1701 enables for a gear-based actuation of the encoder shaft 1630, depicted in FIG. 16, in a manner that multiplies the sensitivity of rotational measurements made by the encoder by a factor nearly equal to the gear-ratio between the set of gears that are mechanically arranged between the cord-interfacing pulley 1710 and the encoder-shaft gear 1715.

Some embodiments involve a pulley-gear system that is installed between the encoder shaft, the retracting spool/tension system, and/or the extensible cord to increase the accuracy of the rotation measurement system depicted in FIG. 16. One embodiment of the pulley-gear system is shown in FIG. 17A. Linear movement of the extensible cord 1705 is coupled to the pulley-gear 1710 using surface friction between the extensible cord 1705, passive pulleys 1707 that help wrap the cord 1705 around the pulley-gear 1710 to maximize friction and avoid cord slippage, and the high-friction O-ring 1748 that surrounds the internal diameter of the pulley. The pulley-gear 1710 (shown in detail in FIG. 17B) mechanically interfaces with a rotary encoder shaft gear 1715, and during linear movement of the extensible cord 1705, any rotation of the pulley-gear 1710 corresponds to a greater degree of rotation of the rotary encoder shaft gear 1715, with the relationship of the corresponding rotations being determined by the gear ratio between 1710 and 1715. The resolution of the rotary encoder 1720 can been increased by a fixed quantity using the described pulley-gear system 1701, and leads to an increase in the measurement accuracy of the extensible cord length. In some embodiments, the described pulley-gear 1710 can be designed with a notch 1745 to allow for the simple removal of the O-ring, and a cutout 1740 placed at the center of the pulley-gear 1710 is designed to allow for the insertion of a bearing that enables for the minimally-frictional rotation of the pulley-gear 1710 about its center axis, which can have a significant effect on the ease-of-use of the system for the user to retract the probe in a responsive manner.

Some embodiments of the surface of the pulley-gear 1710 that interface mechanically with the extensible cord 1705 can involve specific geometric cross-sectional contours that enhance the friction between the extensible cord 1705 and the pulley-gear 1710 surface. One example embodiment includes a v-shaped groove that the pinches on the surface of the cord 1705, and this design forms a tight-tolerance fit between the cord and the pulley-gear 1710 when the overall system is placed under tension. Other embodiments can include the linkage of the pulley-gear system directly with a tensioned spool system, (described in more detail below in reference to FIG. 18A-18B), that stores multiple revolutions of the extensible cord.

Figure 18A:
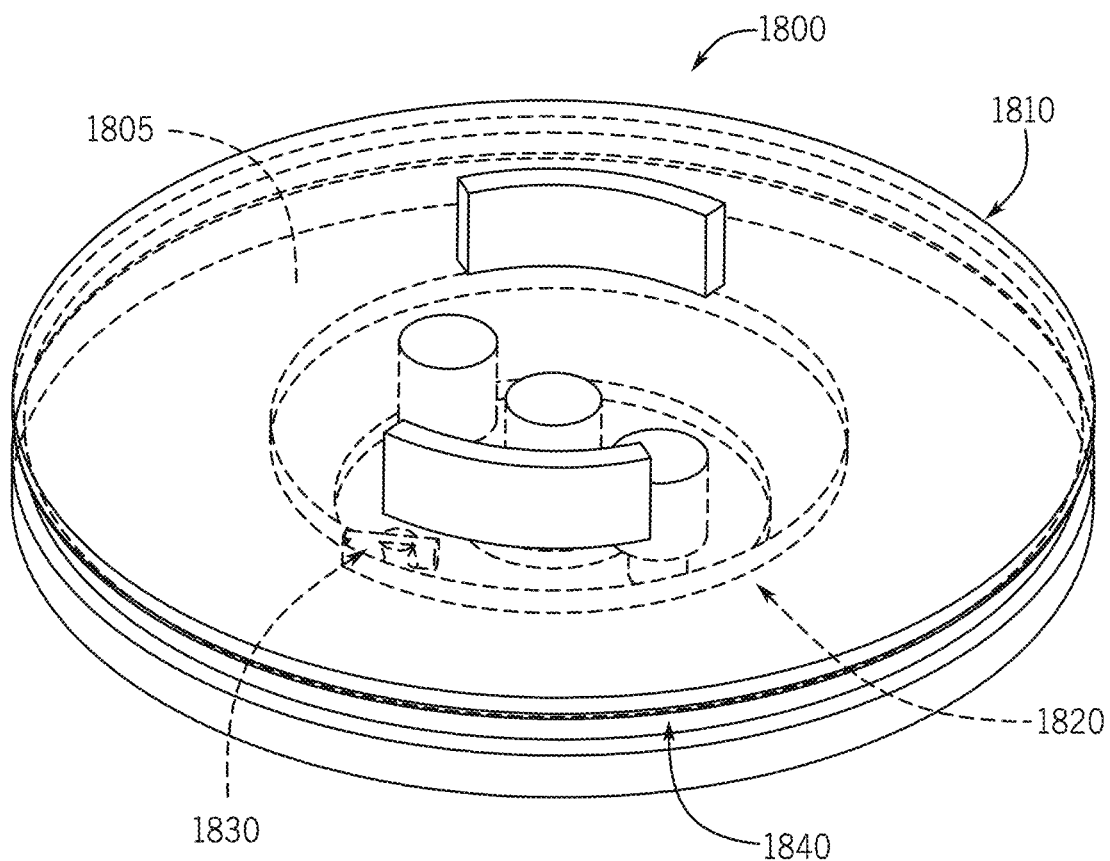
FIG. 18A illustrates a perspective view of a cord spool for use in the pulley-gear system of FIG. 17 in accordance with some embodiments of the invention.
Figure 18B:
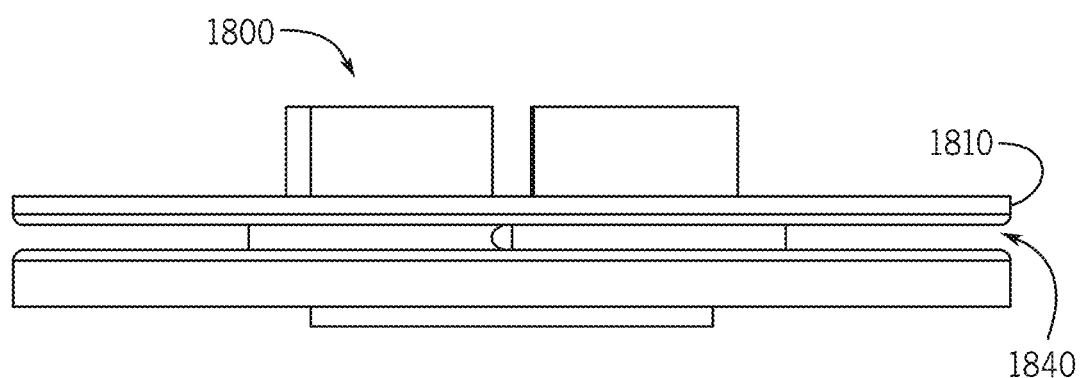
FIG. 18B illustrates a side view of the cord spool for use in the pulley-gear system of FIG. 17 in accordance with some embodiments of the invention.

FIG. 18A shows a perspective view of a cord spool for use in the pulley-gear system of FIG. 17 in accordance with some embodiments of the invention, and FIG. 18B shows a side view. This component of the electromechanical, 3D-tracking system, depicted in FIG. 23C, involves the spiral storage of extensible cord to be exchanged in and out of the spool at pre-defined cord lengths/circumferences per revolution. Some embodiments involve the spool directly interfacing mechanically with a rotary encoder, depicted in FIG. 16, in a coaxial manner between the spool and encoder shaft, to measure the number of revolutions of cord that are extended away from the enclosure at any time.

One embodiment of the spool system involves a linkage with a tension system that provides an opposing force to the extensible cord 1705 to maximize coupling in the pulley-gear system depicted in FIG. 17A and/or the rotary encoder 1600 depicted in FIG. 16. In some embodiments, the tension system can be pre-loaded with cord and tuned in tension to ensure that there is no slack along the extensible cord. If slack develops on the cord, accurate measurement of the degree of rotation about the encoder system is less optimal. One embodiment of the retracting spool/tensioning system is a spring-based system that provides tension to the extensible cord. One embodiment of the retracting spool/tensioning system can include a sub-system to allow variable degrees of tension of the extensible cord to a user's specification. One embodiment of the retracting spool/tensioning system can include a mechanism that slows and/or stops the motion of the spool to prevent the extensible cord from traveling at dangerously high speeds, in the event that the pre-tensioned extensible cord is suddenly released.

The retracting spool provides a system by which the extensible cord can be contained within. For example, one embodiment of a cord spool 1800, illustrated in FIGS. 18A-18B, is composed of a cylindrical disc 1805 with a cord entry slot 1840 removed from the side such that the cord 1705 can be rotated about center of the spool in set revolution increments. The embodiment may have the cord entry slot 1840 with a thickness much larger than the diameter of the cord. The embodiment can have the cord entry slot 1840 be the approximate diameter of the cord, such that the cord is forced to spiral outward from the spool's center in a single-revolution-thick spiral stack. The embodiment can have the inner cord spool radius 1820 be a fixed value. The embodiment may have the inner cord spool radius 1820 may be represented by an equation. In one embodiment, the radial distance of the Archimedean spiral is equal to the diameter of the cord such that the extensible cord spools continuously around itself as described by an Archimedes spiral, which simplifies the calculation of the distance between the center of the spool and the center of the cord, in addition to the calculation of the linear cord distance.

One embodiment involves the cord beginning its fixation to the spool at a known radius set by the designed mount point 1830 of the spool 1805. One embodiment involves the cord wrapping around inner cord spool surface (defined by inner radius 1820) until the cord length is completely contained within the spool 1800 or when the cord reaches the outer spool edge (defined by outer radius 1810). The larger the outer spool edge, the more torque that can be applied by the movement of the cord and the less resistance the user will feel when engaging the retraction of the cord tensioning system. However, the large inner radius surface leads to a less accurate measurement by increasing the length of cord contained with a single resolution step of the encoder's rotational sensitivity.

In the rotational measurement system described herein, the extensible cord 1705 provides a mechanical connection between the retracting spool and the rotation measurement sensor. The extensible cord 1705 provides a mechanical connection between the probe (FIGS. 20A-20E) and the encoder system 1600 (FIG. 16), allowing for the three-dimensional measurement of the probe tip location as the probe moves through space. The generic embodiment of the extensible cord 1705 is a thin-diameter, low-stretch cord. One embodiment of the extensible cord is a metal cable, with some embodiments containing special coatings, such as a nylon coating. Another embodiment of the extensible cord is a Kevlar cable.

FIGS. 19A-19C illustrates a ball assembly 1900 of a 3D-tracking system of FIG. 23A in accordance with some embodiments of the invention. This component of the electromechanical, 3D-tracking system depicted in FIGS. 23B-23C, involves a ball-and-socket interface that is manipulated via the traversing motion of an extensible cord 1705 that passes through the center of the ball. In some embodiments, an extensible cord (e.g., such as cord 1705 shown in FIG. 17A, cord 2120 shown in FIG. 21A, or cord 2150 shown in FIG. 21B) can traverse through the ball-and-socket system via entry to the cord insertion point (cord entry passage 1903) through the central barrel. The entry point for the cord is designed to intersect with the center of the spherical structure, and subsequently aligned with the sphere's center of rotation. This alignment of the cord entry point 1903 enables the movement of the cord to be mathematically separated into two sections, the straight line between the cord storage system (e.g., spool depicted in FIGS. 18A-18B) and the center of the ball 1903, as well as the straight line between the center of the ball 1903 and the mounting posts on a probe (e.g., probe depicted in FIG. 20). In some embodiments, the barrel is supported by mechanical structures added to minimize undesired forces and torques imposed by the cord, which can deflect the barrel during movement of the cord. In some embodiments, the ball assembly can include barrel support structures 1940 of ball (or sphere) 1901. As the barrel exits the front of the ball, the barrel is supported internally by a reinforced wall 1902. To minimize barrel deflection at the cord entry location, support bars 1940 provide mechanical rigidity to the barrel to minimize deflection created during cord movement.

In some embodiments, the sphere includes a cylindrical groove 1950 extruded out of the top of the spherical surface, which allows for the installation of an image, or any unique pattern, without any spherical distortion of the pattern surface. An imaging sensor can thus be used to visualize and measure the ball's rotation in the spherical coordinates, theta and phi, by examining how the pattern on the cylindrical groove 1950 rotates and translates relative to an imaging sensor. In order to maintain the cylindrical groove's alignment with the center of the ball 1901 and imaging sensor, the ball 1901 includes an orthogonal extrusion (roll-prevention rod 1920) relative to the cylindrical window, that prevents the rotation of the ball about the barrel structure when inserted into a complementary mating slot that limits the movement of the roll-prevention rod to a linear arc that is orthogonal to the cylindrical groove 1950.

In some embodiments, as shown in FIGS. 19B and 19D, the ball 1901 contains a cylindrical barrel 1930, which begins inside the ball 1901 and extends radially to a fixed distance in front of the ball 1901. The cord (e.g., such as cord 1705) can pass through the extrusion in the back of the ball, enters the barrel at the cord insertion point (shown as 1903), passing through and exiting the barrel in front of the ball (through barrel 1930). The barrel 1930 contains a plethora of holes (barrel fenestrations 1922) to reduce the surface contact area between the inside of the barrel 1931 and the outside of the cord, which helps to ensure smooth cord movement through the barrel 1930. The barrel design provides the encoder (e.g., such as encoder 1600) with a fixed exit point that is required to calculate of linear cord distance. As the barrel 1930 extends from the front of the ball 1901, the barrel 1930 is supported externally by a reinforced wall by the barrel shaft base fillet (barrel tip fillet 1924). Further, in some embodiments, the cylindrical groove 1950 provides a cross-sectionally-flat surface from which an imaging sensor can calculate the degree of spherical ball rotation without requiring additional transformations caused by distortion (e.g., barrel distortion) of the pattern. In reference to FIG. 19C, a cylindrical groove (groove 1950) is extruded out of the top of the spherical surface, and allows for the installation of an image, or any unique pattern, without any spherical distortion of the pattern surface. In some embodiments, the support structures illustrated to reinforce the rigidity of the barrel are not required in the final manufactured product, and can include components for prototypes created via 3D printing with fragile materials.

FIGS. 19D-19E illustrate a ball and socket assembly of the 3D-tracking system of FIG. 23A accordance with some embodiments of the invention. The socket enclosure 1950 for the ball 1901 provides a joint surface to rotate within due to traversing motions and trajectory changes in the extensible cord. The socket embodiment contains a window cutout 1980 that restricts the movement of the barrel 1930 to within a defined range-of-motion (in window 1932). The window's boundaries can help maintain the optimal tracking volume for the electromechanical, 3D-tracking system without having multiple ball-and-socket systems allowing for cord to intersect or obstruct each other. The system also contains a complementary roll-prevention channel 1976 that allows for the restricted movement of a rod extrusion 1920 from the ball to travel along a path that prevents the rotation of the ball 1901 about its barrel 1930. The roll-restriction feature (1920, 1976) of the system provides assurance that the cylindrical window is in constant view within the sensor's preview window 1999, such that any movement of the pattern will always be visible to an imaging sensor. Multiple socket regions 1998 are removed from the top and bottom of the socket structure to minimize surface friction between the outside of the ball and the inside of the socket. As noted multiple times, the need to minimize friction between the socket, ball, and cord is paramount to the functionality of three-dimensional tracking system. The proposed method represents one embodiment of the ball and socket structure. One embodiment may include a layer of ball bearings installed between the ball and the socket surfaces. One embodiment may include some form of lubricant placed in between the ball and the socket surfaces. One embodiment may include some form of lubricant placed in between the barrel and the cord surfaces. A high-strength and high-durability material is required to maintain the structural integrity of the ball and socket. Other embodiments of the ball-and-socket system may be comprised of metals, polymers, and/or plastics.

Figure 20A:
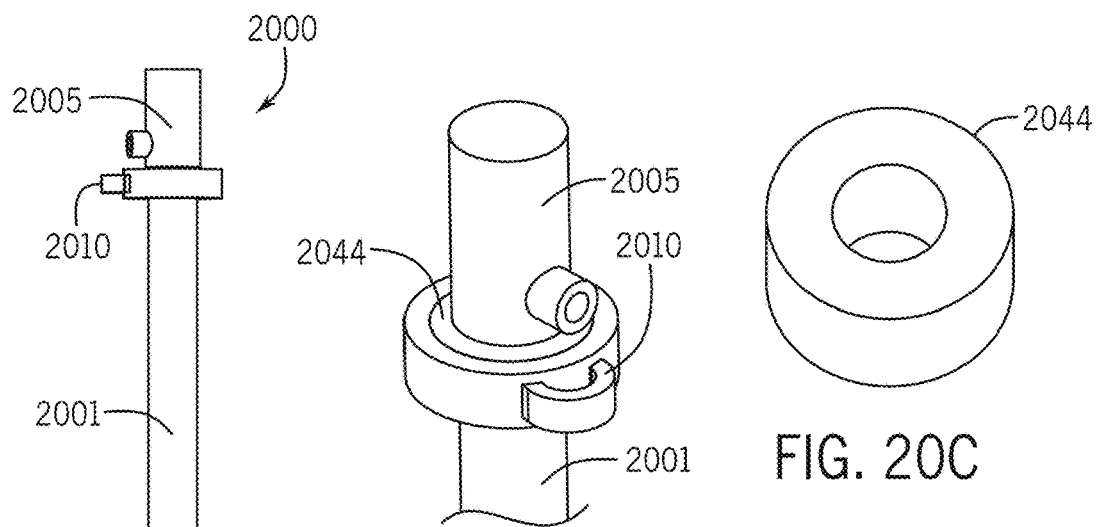
FIGS. 20A-20E show views of components of the probe of FIG. 20 in accordance with some embodiments of the invention.
Figure 20C:
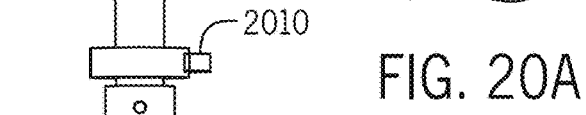
Figure 20D:
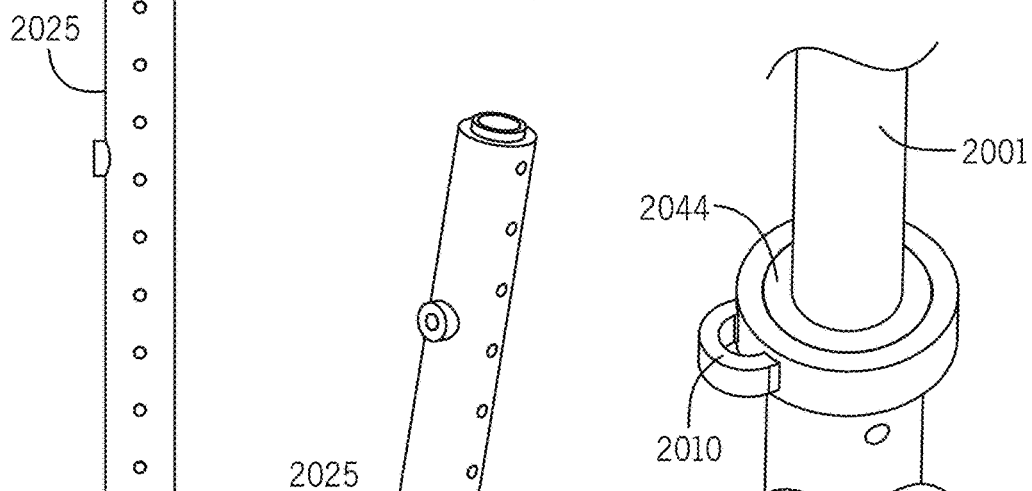
Figure 20:
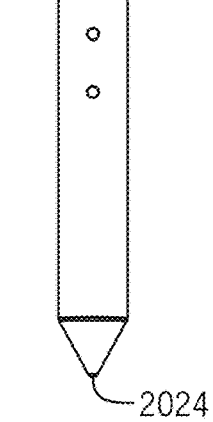
FIG. 20 illustrates a probe of a 3D tracking system in accordance with some embodiments of the invention.
Figure 20B:
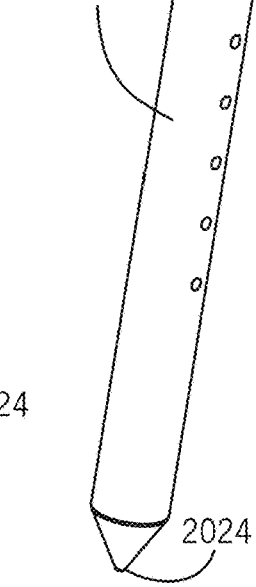
Figure 20E:
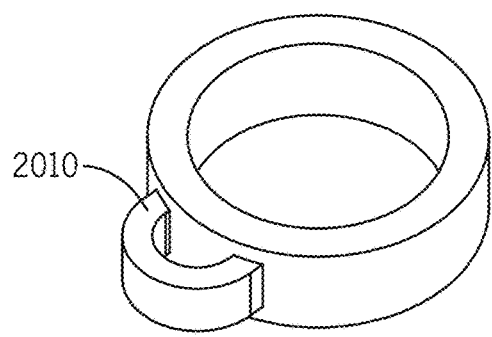

FIG. 20 illustrates a probe 2000 of a 3D-tracking, electromechanical system in accordance with some embodiments of the invention. FIGS. 20A-20E show views of components of the probe 2000 of FIG. 20 in accordance with some embodiments of the invention. This component of the electromechanical, 3D-tracking system, depicted in FIGS. 23B-23C, involves a probe that is used to register 3D points in space while the tracking system dynamically registers the probe's 3D location and orientation with respect to the tracking system's coordinate system. The probe 2000 contains two freely-rotating fixation points 2010 where extensible cord (e.g., 1705) distal ends that are tracked in 3D space mount at a fixed distance apart. In some embodiments, the probe 2000 can comprise a probe shaft 2025. The probe 2000 provides various functions to the electromechanical, 3D-tracking system. First, the probe 2000 enables the user to trace along a 3D-surface. Second, the probe provides a fixed mechanical interface to each encoder's extensible cord. The 3D pose of the probe 2000 can be derived from the calculated linear cord distances from each encoder, the rotational values (spherical coordinates) of the previously described ball 1901 within its ball-and-socket joint, the fixed distance between each cord connection point, and trigonometric identities. With the pose of the probe 2000 and the linear cord distances, the exact location of the probe tip 2024 can be extrapolated in 3D-space. Third, the probe 2000 has the ability to identify interactions with multiple materials through electrical, mechanical, optical, and/or electro-mechanical interfaces. Fourth, the probe 2000 has a grip area 2025 that allows the user to hold the probe 2000 and trace a three-dimensional surface without interfering with the cords or any additional measurement system.

One embodiment of a probe 2000 is shown in FIG. 20, has mount points 2010 for two cords. The cords from an encoder (such as described earlier in FIG. 16) can couple to the cord fixation mounts 2010, each of which is mechanically coupled to individual bearings 2044 that are separated by a cord-mount spacer 2001 coupled to the probe shaft 2025, with each bearing's internal surface linked substantially rigidly to an internal rod structure (not shown) coaxial within the probe enclosure. The spacer 2001 and bearings 2044 are coaxial with an internal rod that is fixed to the probe half 2025 that the user can grip (e.g., see bearing 2044). In some embodiments, the internal rod structure is maintained within the probe enclosure via a rigid cap 2005. However, it should be noted that several components, including, but not limited to, the probe cap 2005, are not required for the device's function. The cord mount and bearing system allows the probe 2000 to move freely in any direction without affecting the accuracy of the measurement system of the encoder embodiment. The probe grip area (on shaft 2025) provides spacing for the user to trace in three-dimensions.

Figure 21A:
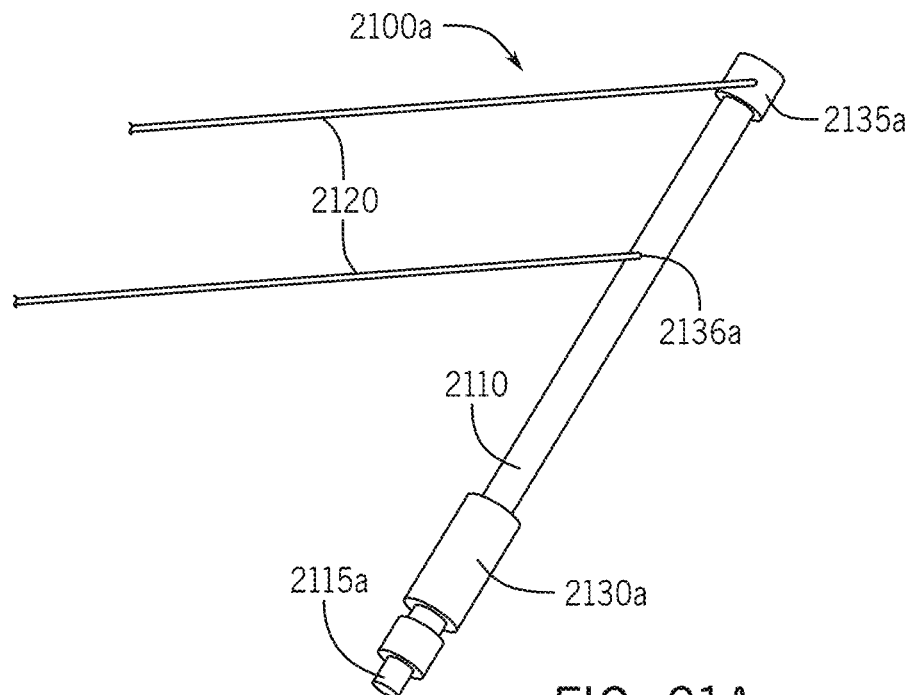
FIGS. 21A-21B illustrate assemblies of a 3D tracking system including a probe coupled to cord fixation points in accordance with some embodiments of the invention.
Figure 21B:
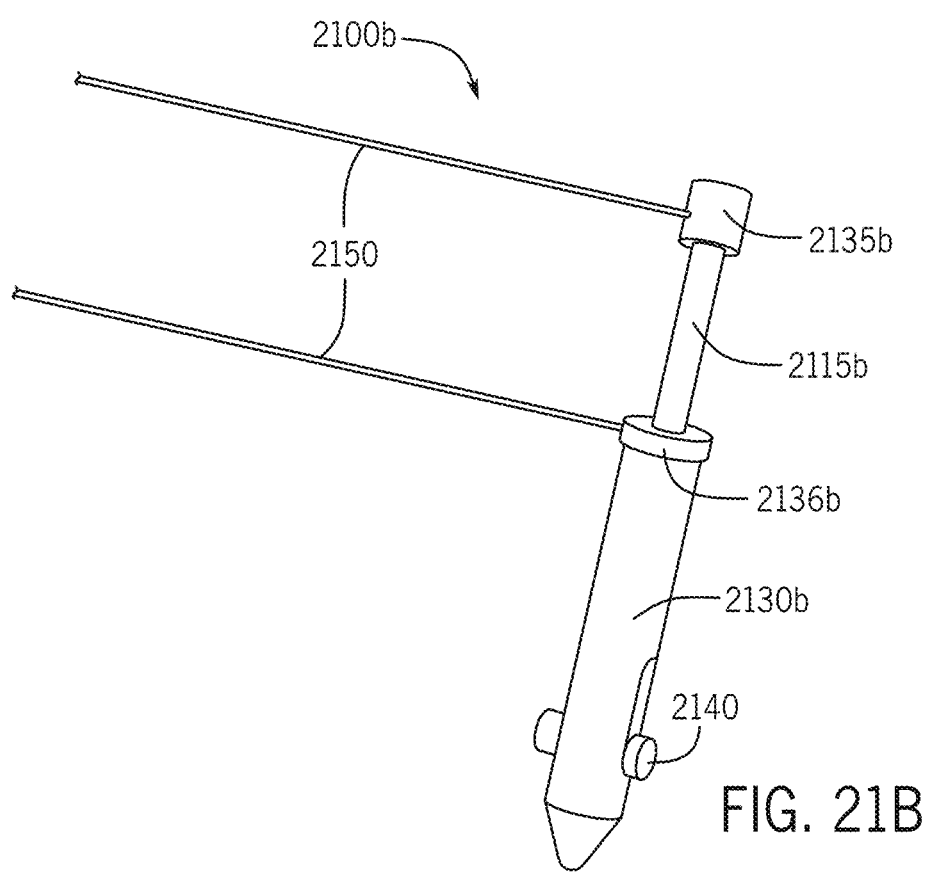

Some embodiments include a component of the electromechanical, 3D-tracking system, depicted in FIGS. 23A-23C, that involves a probe that is mechanically linked to two 3D-tracked cord fixation points that are spaced by adjustable distance via mechanical actuation between the two fixation points. For example, FIGS. 21A-21B illustrate assemblies of a 3D tracking system including probes 2100a and 2100b coupled to cord fixation points (see extensible cord 2120, 2150 extending from the probes 2100a, 2100b). In some embodiments, the probes comprise probe handle 2130a, 2130b with depressible sliding shaft 2115a, 2115b, and spring-loaded trigger 2140 (of probe 2100b). Each 3D-tracked probe 2100a, 2100b includes an embedded mechanical system such that the distance between the extensible cord fixation mounts is selectively changed when the depressible shaft (spring-loaded; spring not shown) 2115a linked to the probe 2100a is pressed against a surface, or manually actuated by the user via a spring-loaded button 2140 on the shaft 2130b of the probe 2100b, which increases distance between the dynamic cord-fixation mount (2135a for probe 2100a; 2135b for probe 2100b) and the static cord-fixation mount (2136a for probe 2100a; 2136b for probe 2100b). The extensible cords 2120, 2150 are mechanically linked to the electromechanical, 3D-tracking system (sample embodiments shown in FIG. 23A-23C).

In some embodiments, a processing algorithm detects the changes in the relative distance between cord mounts and signals to the electromechanical, 3D-tracking system that it should actively register points at the probe tip, or interpret a specific command that designates what type of measurement the probe is performing, or the object identity the probe is interacting with. The distance between the two dynamic cord fixation mounts can be calculated with respect to the axes of the probe by substantially rigidly transforming the 3D cord fixation mount coordinates with respect to the probe tip coordinates and pose. In this way, the 3D distance between the cord fixation mounts can be calculated without variability in calculations caused by the changing relationship between a cord fixation mount and its relative distance to the electromechanical, 3D-tracking system, in comparison with that of the other cord fixation mount.

Figure 22:
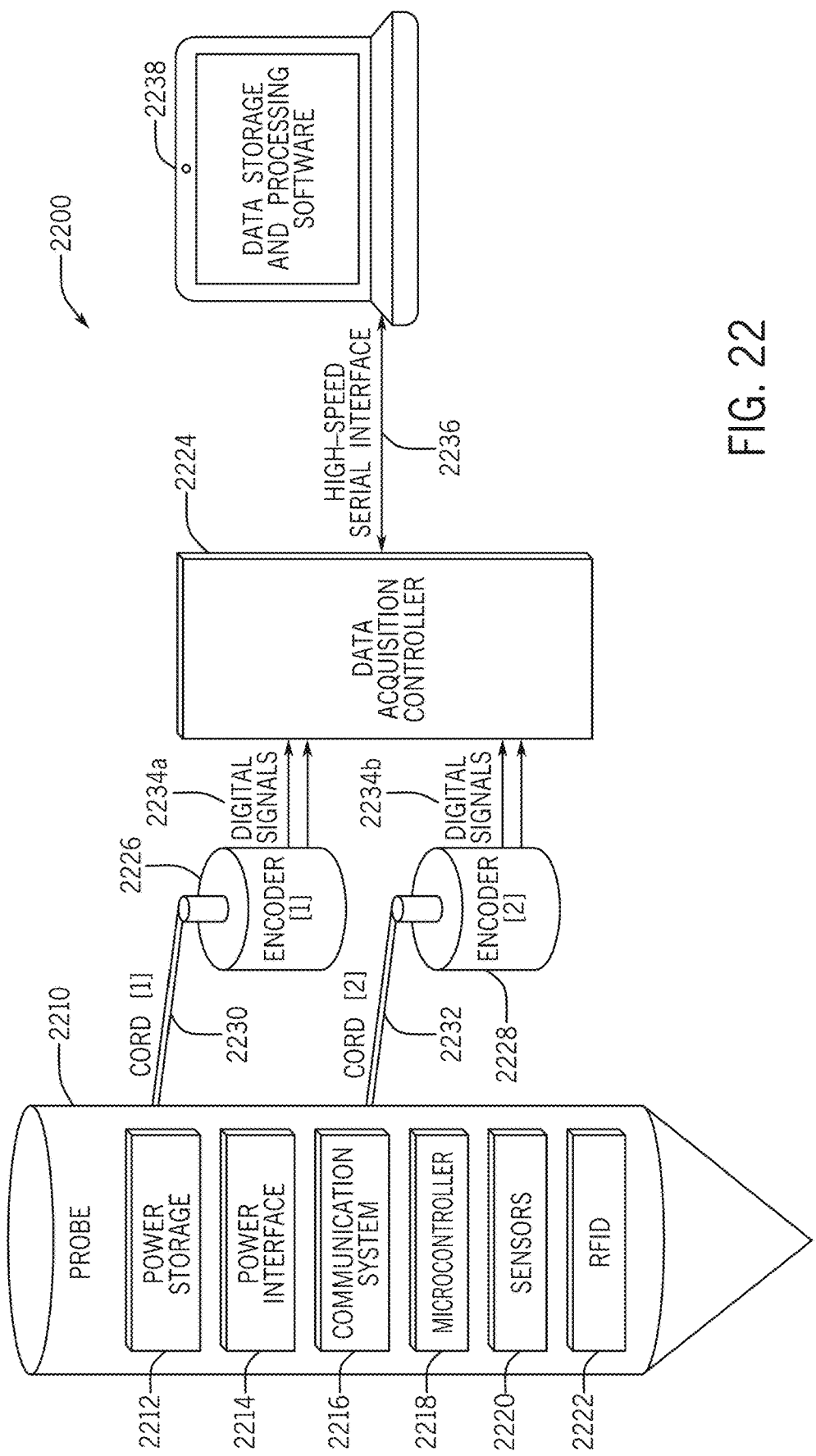
FIG. 22 illustrates an example system enabling 3D tracking of a probe in accordance with some embodiments of the invention.

FIG. 22 illustrates an example system enabling 3D tracking of a probe in accordance with some embodiments of the invention. This component of the electromechanical, 3D-tracking system depicted in FIGS. 23A-23C, involves a system of active and passive components that communicate to enable the 3D tracking of the probe's location and orientation. A number of embodiments exist for the probe linked to the electromechanical, 3D-tracking system, with FIG. 22 depicting the interface between a system of components that communicate with each other to enable the 3D tracking of a probe. Some embodiments include a probe with no electrical or mechanical feedback systems for which the encoder embodiment and processing software to detect during tracing, as described in the above embodiment. In some embodiments, a probe with embedded electrical subsystems (FIG. 22) can contain a plethora of user-controlled toggle switches that allow the user to control the registration of points and active tracking of the probe (FIGS. 21A-21B). Some embodiments include a method of communication to a microcontroller or a computer processing system that can be transmitted through a wireless electromagnetic radiation (RF), light-emitting devices. In some embodiments, cords can be mechanically linked to the docked tracking system. Some embodiments include a method of delivering power to the probe through a voltage applied across two cords that are mechanically linked to the probe for positional tracking. A battery system or equivalent energy source, such as a capacitor, that is capable of being recharged can be included. In some embodiments, an electrical connection that exists between the probe and the enclosure to provide energy during non-use when the probe is located on the enclosure. In some embodiments, a plurality of sensors of a sensing system can be a plurality of inertial measurement unit, accelerometers, and/or gyroscopes to measure the motion and/or pose of the probe. This embodiment may negate the necessity for mechanical linkages with an encoder or extensible cord. One embodiment can be a tilt sensor. One embodiment can be a sensor to measure the rotation of the cord mounts on the probe. One embodiment can be a system to measure mechanical force applied to the probe and/or the probe tip. In some embodiments, a radio-frequency identification (RFID) tag and/or reader placed at a fixed location on the probe can include an RFID is an RFID reader placed in the probe that reads an RFID tag to begin or halt the registration of points and active tracking of the probe tip in 3D. One embodiment of RFID is an RFID reader placed in the probe that reads an RFID tag placed at specific locations to identify the locations with specific identities during use of the probe. For example, see power storage 2212, power interface 2214, communication system 2216, microcontroller 2218, sensors 2220, and RFID 2222 of the probe 2210, cord 2230 coupled to encoder 2226, cord 2232 coupled to encoder 2228, digital signals 2234*a* (from encoder 2226) and digital signals 2234*b* (from encoder 2228). Further, see data acquisition controller 2224 coupled to a data storage and processing software in computer system 2238 coupled through interface 2236.

Some embodiments of the invention include an enclosure of the electromechanical, 3D-tracking system that houses all of the components of the tracking system in a compact form that can be mounted onto a multitude of various surfaces. For example, FIG. 23A illustrates an example 3D-tracking system 2300 in accordance with some embodiments of the invention, including extensible cords 2350 extending from ball-in-socket structures 2320 (e.g., such as those described earlier in related to FIGS. 19A-19E), a coupled probe 2340, and a rigid surface mount 2305 coupled to structures 2310, 2330. As shown, one embodiment contains an interface for fastening mounting mechanisms enabling it to be utilized in a variety of settings. Fastening mounting mechanisms 2305 may include, but are not limited to, a suction cup mount or fastener holes for mating to rigid structures (e.g., such as 2310, 2330). Some embodiments of the mounting mechanism 2305 include hooks and clamps to interface with surgical tables, beds, anesthesia poles, a removable instrument tray on a movable stand that is configured to be positioned over or adjacent to a surgical site of a patient (e.g., a Mayo stand), the patient's anatomy, and/or any other rigid structure. Some embodiments involve extensible cords (shown as 2350) retracted out by the user via the use of a probe 2340 to collected discrete and continuous tracing registrations.

In some embodiments, the components of the electromechanical, 3D-tracking system can be compiled into a compact design and surrounded by an enclosure device 2350. For example, FIG. 23B illustrates a 3D-tracking system in an enclosure 2360 in accordance with some embodiments of the invention. In some embodiments, the enclosure 2360 is shown with extensible cords 2370 extending from barrel 2367, 2372 of spheres 2374, 2365 (with the cord coupling to a probe, such as probe 2000 of FIG. 20). In some embodiments, the enclosure 2360 can shield internal components from debris, trauma, bodily fluids, and light exposure. Further, the enclosure 2360 can contains an external probe mounting system to substantially rigidly fix the probe (e.g., such as the probe 2000 shown in FIG. 20) to the enclosure 2360 for when the extensible probe system is not in use. In some embodiments, the enclosure also houses the spool system (as shown previously in FIGS. 17A-17B, 18A-18B) which outputs two extensible cords to attach to the probe, and each cord 2370 passes through the barrel structure 2367, 2372 of each sphere 2365, 2374 to enable the electromechanical triangulation of the probe (e.g., the probe 2000 shown in FIG. 20).

Some embodiments include internal light sources to prevent variability in lighting for the camera system. Some embodiments include an electrical interface over which power and/or data can be transmitted to and/or received from the probe when it is docked. One embodiment of the electrical interface can be metal contacts extending from the probe mounting system to couple to electrical contacts on the probe.

FIG. 23C shows an exploded assembly view of the 3D-tracking, electromechanical system of FIG. 23B in accordance with some embodiments of the invention. For example, some embodiments include enclosure 2361 housing a rotary encoder 2399, a fixed spring-tensioner arm 2390 for spool spring (not shown), a spool 2392, a bottom half of a socket 2394, a top half of a socket 2395 (reference FIGS. 19D-19E), an embedded, unique pattern 2383, a ball 2374 (reference FIGS. 19A-19C), a barrel of ball 2365, and enclosure lid 2362 with embedded optical sensors (not shown). FIG. 23C illustrates the compilation of components from one embodiment of the electromechanical, 3D-tracking system. Each of the two rotary encoders 2399 measure the length of an extensible cord coupled to the probe (not shown). Each extensible cord (not shown) is stored and retracted from the spool 2392 that is being tensioned via a spring (not shown) that is fixed at one end by a spring tensioning arm 2390, which is mounted to the rigid enclosure 2361. Each extensible cord passes through a ball 2374, that can rotate within a socket (2394, 2395) with viewing windows (not shown; as seen in FIGS. 19D-19E), via a barrel 2365 that originates at the center of the ball 2374 to enable controlled movement of the cord during rotation of the ball. The rotation of the ball is measured via an embedded pattern 2383 on the ball surface 2374 that is aligned above the center of the ball and able to mirror the phi and theta rotation of the ball in spherical coordinates for visualization via an above imaging sensor. The enclosure includes a lid 2362 that couples with the bottom-component of the enclosure 2361 can help to create a protected environment while also housing the optical sensors (not shown), lights (not shown), and microcontrollers (not shown), for recording and analyzing the visual and electrical outputs from the embedded optical sensors and rotary encoders. In other embodiments, wireless communication components (not shown) are also included within the enclosure.

Figure 24:
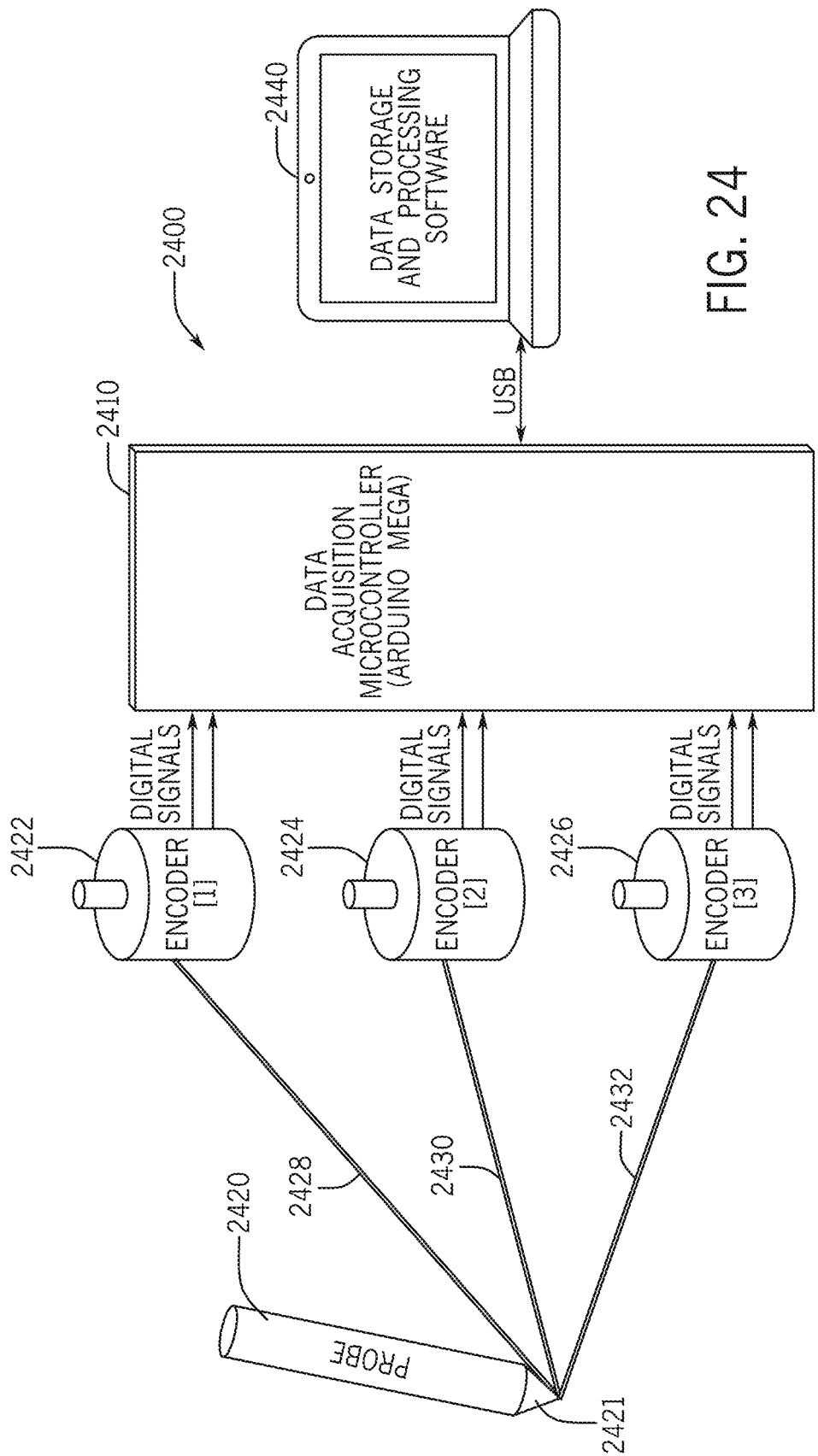
FIGS. 24-26 illustrate systems enabling 3D tracking of a probe in accordance with some embodiments of the invention.

FIG. 24 illustrates a system enabling 3D tracking of a probe in accordance with some embodiments of the invention. This embodiment depicts a system of components that enable for the electromechanical localization of a 3D point at the tip of a probe (e.g., such as any of the probes described herein). Three extensible cords (2428, 2430, 2432) mechanically link to the probe tip 2421 of probe 2420 via connections extending from three separate rotary encoders 2422, 2424, 2426 that measure the length of each cord, from which the software system calculates the 3D point of the probe tip via triangulation geometric equations. The embodiment of an encoder (such as those of the encoders 2422, 2424, 2426) is represented by a spool wound with an extensible cord (e.g., 2428, 2430, 2432), a spring-loaded retractor system (not shown), which can be represented by any system that provides a tensioning force, and a rotary encoder, which can be represented by other sensors used to detect the degree of rotation. The three encoder embodiments are placed at fixed distances relative to each other. The probe 2420 contains a single cord mount connection at the probe tip 2421, through which all cords 2428, 2430, 2432 interface to the probe 2420. As the probe 2420 is moved in 3D space, the individual, distinct cord lengths are measured via rotary encoders 2422, 2424, 2426 (e.g., as illustrated in FIG. 16), however other sensors can be used to detect the length of the extended cord. With the known distance between each encoder 2422, 2424, 2426, the measured cord lengths to the probe tip 2421, the system's triangulation algorithm can process the data through a geometric relationship to calculate the 3D location of the probe tip 2421. The three-cord encoder system requires at least three encoder embodiments to calculate the 3D position of the probe 2420.

Figure 25:
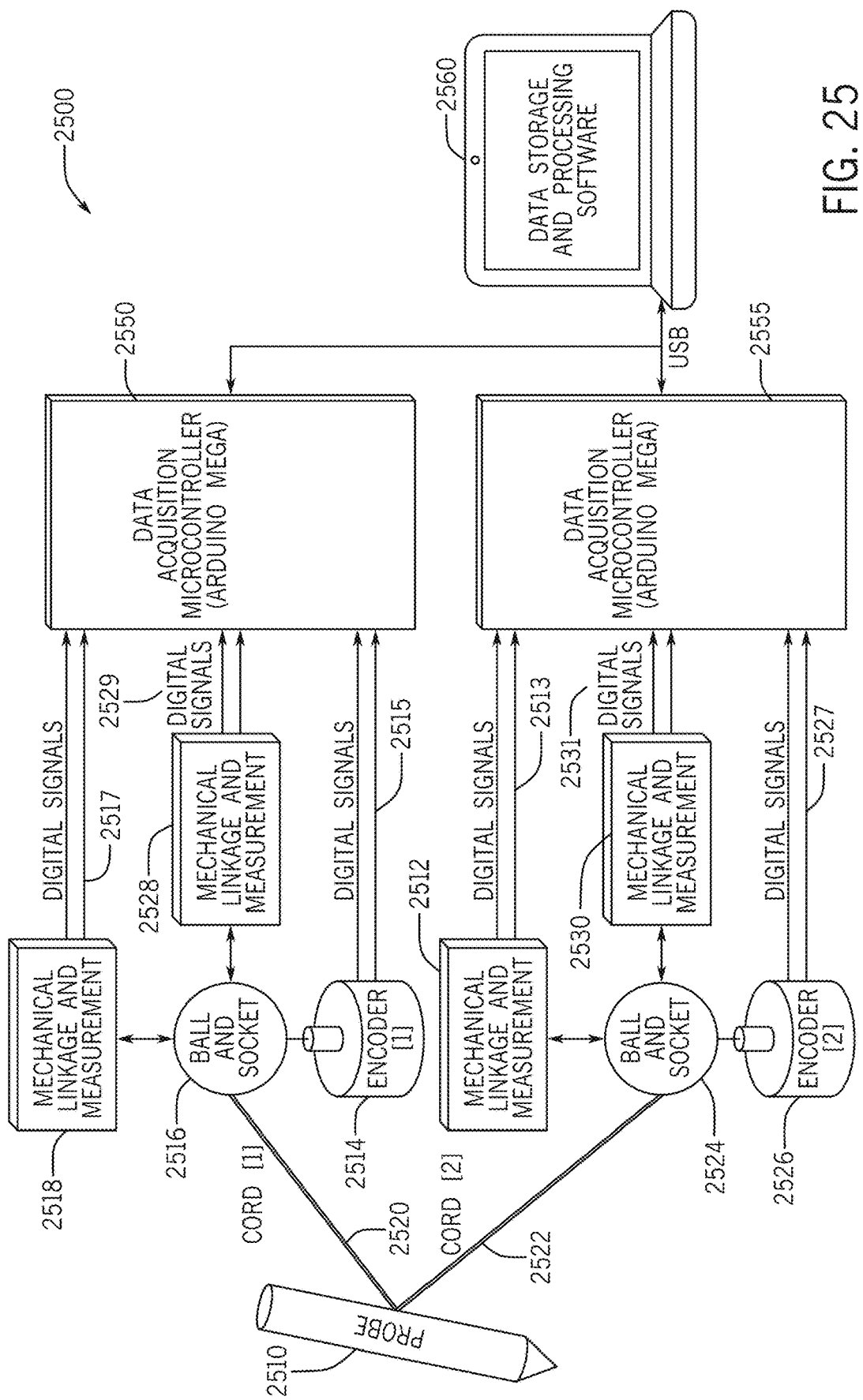

Another embodiment of the electromechanical, 3D-tracking system, illustrated in FIG. 23B-23C, can contain in the system of components shown in FIG. 25, where the ball-and-socket movement is sensed by mechanically-linked rotary encoders that measure the phi and theta movement of the ball in spherical coordinates (e.g., using two encoders per ball and socket system or assembly). The encoder-based 3D-tracking system embodiment shown in FIG. 25 includes probe 2510, cords 2520, 2522, encoders 2514, 2526, mechanical linkage and measurement 2518, 2512, 2528, 2530, ball and socket 2516, 2524, digital signals from encoders 2515, 2527, digital signals from mechanical linkage and measurement 2517, 2529, 2513, 2531, data acquisition controllers 2550, 2555, and computer 2560. Each ball-and-socket 2516, 2524 is mechanically linked to two encoders 2514, 2526. An extensible cord 2520, 2522 passes radially through the barrel located at the center of the ball and connects to a probe 2510, allowing the barrel to follow the location of the extensible cord. Since the barrel is fixed at the center of the ball and the ball's axis of rotation is fixed by a rod seated in a slot on the socket, the ball is unable to rotate radially about the barrel's axis and the barrel can track the location of the probe. Measurement of the ball's rotation in the socket allows for the calculation of the angular takeoff of the barrel in spherical coordinates as the probe is moved through 3D space. The cord length is measured via rotary encoders 2514, 2526 as described in relation to FIG. 16, however other sensors can be used to detect the length of the extended cord. The measurement of cord length and angular takeoff provide sufficient data to calculate the 3D location of the probe in the spherical coordinate system.

One embodiment of the measurement system used to calculate the angular takeoff is a mechanical linkage between the surface of the ball and a rotary encoder, however other sensors can be used to detect the degree of rotation. As the ball rotates in the theta and phi directions due to probe translation, a mechanical linkage (2512, 2518, 2528, 2530) rotates the shaft of a rotary encoder (2514, 2526), and the degree of a ball's rotation in each spherical coordinate plane can be calculated.

One possible mechanical linkage is a spherically or cylindrically-shaped coupling object fixed radially to a rotation measurement system as described in FIG. 16. One embodiment of a rotation measurement device could be a rotary encoder. The position of the rotary encoder is fixed such that the cylindrically shaped object makes physical contact with the ball and is mechanically secured to the rotary encoder shaft. Any movement of the probe results in rotation of the ball, rotation of the cylindrically-shaped object, and thus rotation of the rotary encoder shaft. Two embodiments of the described mechanical linkage (2512, 2518, 2528, 2530), oriented orthogonal to each other, are required to calculate the rotation of the ball's barrel in theta and phi directions.

In some embodiments, algorithms calculate the degree of ball rotation in theta and phi from the radius of the cylindrically shaped object, the rotation measured by the rotary encoder, and the radius of the ball. After calculating phi and theta of the barrel, the system then uses spherical coordinate formulas to calculate a vector from the center of the ball to the location of the first cord as it mates with the probe. The same process is repeated for the second ball-and-socket pair, also using a mechanical linkage to sense the spherical rotation of the ball. The second ball-and-socket system calculates a 3D vector from the center of the ball to the end location of the second cord as it mates with the probe.

The pose of the probe is then calculated from the vector subtraction of two calculated cord vectors. The three-dimensional position and orientation of the probe tip can be extrapolated given the known dimensions of the probe and the distance between the cord fixation points on the probe.

Figure 26:
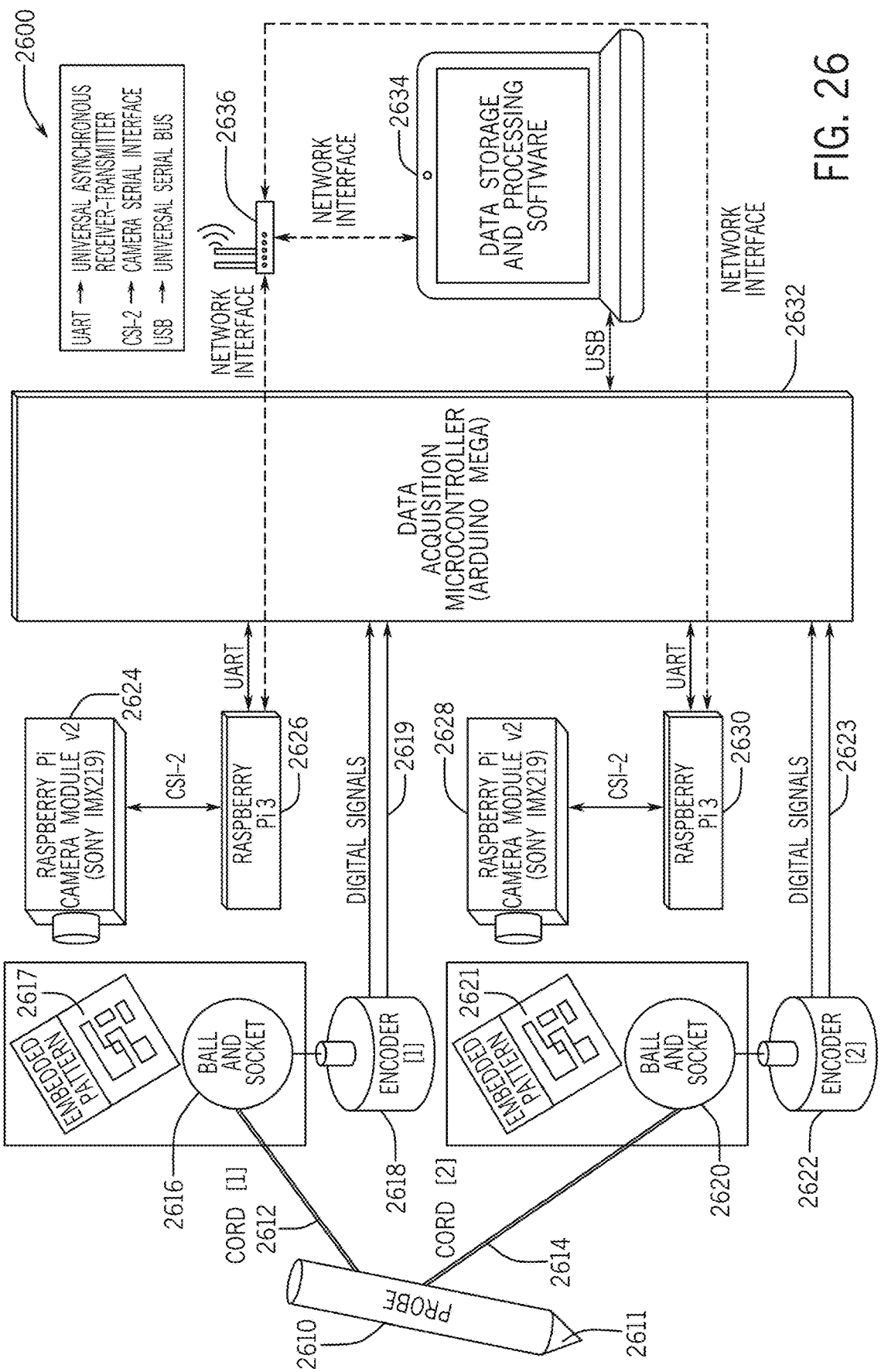

Another embodiment of the electromechanical, 3D-tracking system, illustrated in FIGS. 23A-23C, can contain the system of components shown in FIG. 26, where the ball-and-socket movement is sensed by optical sensors that interpret the rotation and relative location of the ball-mounted pattern with respect to the image sensor. This system measures the phi and theta movement of the ball in spherical coordinates. The combined mechanical, electrical, electro-mechanical, and optical components of the system 2600 shown in FIG. 26 that enable for the 3D-tracking of a probe's location and pose include a probe 2610, coupled cords 2612, 2614, coupled ball and socket 2616, 2620, embedded, unique patterns 2617, 2621 on the ball surfaces, encoders 2618, 2622, cameras 2624, 2628 processor or controller 2626, 2630, data acquisition 2632, computer 2634, and modem 2636. Two encoders are able to measure length of the cord, and the two ball-and-socket assemblies enable measurements of cord trajectory for cord that is past the center of the ball (see FIGS. 19A-19E). One optical-sensing and unique pattern embodiment per ball-and-socket embodiment for measuring the spherical rotation of the ball (depicted in FIGS. 27A-27D). One probe embodiment to link the 3D-tracked, extensible cords in 3D space and provide the user a medium for acquiring 3D points (as depicted in FIG. 20).

In one embodiment, an extensible cord passes through the center of rotation of a sphere and exits via a radial barrel that follows the location of the extensible cord end that is mounted to the probe. The location of the center of the sphere is fixed by the sphere being constrained by a socket with a slot to allow for the free movement of the barrel to track the exiting cord. The socket ensures that the sphere cannot rotate about its barrel shaft via a radial slot in the socket that receives a complementary rod tip that is mounted to the sphere and is concentric with the center of the sphere.

The cord length is measured via rotary encoders, however other sensors can be used to detect the change in length of the cord during use (e.g., potentiometers). Since the portion of the extensible cord that has exceeded the center of the sphere is no longer always coaxial with the starting portion of the extensible cord near the encoder, a measurement must be made of the angular takeoff of the sphere's barrel, through which the cord passes, to produce the spherical coordinates needed calculate the 3D location of the cord end that is mounted to the probe.

One embodiment to calculate the angular takeoff of the sphere's barrel is to embed a pattern on the sphere's cylindrical window such that while the sphere moves due to the translation of the cord in space, the pattern rotates about the center of the sphere in a manner that mimics the phi and theta angles produced by the barrel relative to the coordinate system of the center of the sphere.

One possible pattern is a checkerboard that has a unique black-and-white tag pattern (as shown by labels 2617, 2621 in FIG. 26), similar to that used in augmented reality registration markers, in each square of the board. The unique checkerboard has an established x-y coordinate system, such that one corner of the checkerboard is the origin and each square represents one unit of known size.

An optical sensor embedded in the socket, with the sensor located concentrically to both the center of the sphere and the preview window of the socket, records the viewable portion of the overall pattern that can be seen through the preview window of the socket. The optical sensor transmits image frames to the processing software to utilize computer vision algorithms to detect all visible corners of checkerboard pattern, identify the signature of each visible square, and reference each square's known location within the overall pattern. The pixels in the image frame are converted into millimeters, or any other physical unit, by calculating the ratio between pixels and millimeters for a known side length of one of the visible squares of the pattern surface. The center of the image frame represents the center of the sphere.

The algorithms then calculate the absolute location of the center of the image along the unique pattern, identifying the exact location in the units of the physical pattern. The vertical location of the image center is used to calculate the theta of the barrel by identifying the arc length between the current image center in the active image frame and the location on the pattern surface that aligns with the image center when the barrel is concentric with the side window of the socket, producing a theta of zero. This arc length input is combined with the known radius of the pattern surface relative to the center of the sphere, and then theta is calculated using the arc length formula that extrapolates the angle of the arc section. The theta angle of the barrel represents the up and down motion of the barrel.

In addition, a vector is calculated between the checkerboard corner closest to the image center and a corner nearest that first corner that is vertically in-line with respect to each other in the coordinate system of the pattern. A second vector is calculated along the vertical axis of the image, passing through the image center. The algorithms calculate the relative angle between these two vectors by calculating the inverse cosine of the cross product of the two vectors; this calculation can also be done several different ways using known geometry formulas. The angle between these vectors represents the phi angle of the barrel, which indicates the left and right motion of the barrel. After calculating phi and theta of the barrel via the location of the image center on the unique pattern and the pose of the pattern relative to the optical sensor, the system then uses spherical coordinate formulas to calculate the end location of the cord end that mates with the probe tip, given the input length of the cord that exists past the center of the sphere. Given two cord fixation points with known, calculated 3D locations on the probe shaft, the system can calculate the 3D vector between the two fixation mounts, and then extrapolates the 3D location of the probe tip, given the known dimensions of the probe, and calculating the offset between the probe tip and the 3D line.

The same process is repeated for the second ball-and-socket pair, which also have an embedded pattern and optical sensor combination, to calculate the 3D location of the second extensible cord end that mounts to the probe. One embodiment of the electromechanical, 3D-tracking system involves using an optical sensor to measure the spherical rotation of a ball in correspondence with the movement of an extensible cord that transverses through the center of the ball's rotation. As the barrel translates left and right in the phi plane of the spherical coordinate system of the ball, the embedded pattern also rotates by the same angle, since the pattern viewable to the camera is aligned to be above the center of the ball. The system thus measures the angle of the pattern with respect to the optical sensor to calculate the phi angle 2710 of the barrel in spherical coordinates. Some embodiments of the electromechanical, 3D-tracking system, illustrated in FIGS. 23A-23C, can involve the use of unique patterns embedded on the ball surface, as shown in FIGS. 27A-27D (and discussed earlier with respect to 2383 of FIG. 23C), where the ball-and-socket movement is sensed by optical sensors that interpret the rotation and relative location of the ball-mounted pattern 2701 with respect to the image sensor. The unique pattern enables for the computer vision algorithms of the system to calculate the absolute position of the center of the image sensor with respect to coordinate system of the grid-based pattern. This system measures the phi 2710 and theta 2715 movement of the ball 2705 in spherical coordinates. Unlike a typical optical sensor used in a computer mouse, this system does not lose its sense of position with respect to the pattern if image frames are lost or not able to be calculated for any reason, since the pattern provides the system an ability to calculate absolute position on its surface. As shown, barrel phi rotation 2710, ball 2705, and pattern 2701.

In reference to FIG. 27B, and barrel theta rotation 2715, one embodiment of the electromechanical, 3D-tracking system involves using an optical sensor to measure the spherical rotation of a ball in correspondence with the movement of an extensible cord that transverses through the center of the ball's rotation. As the barrel translates up and down vertically in the theta plane of the spherical coordinate system of the ball, the embedded pattern translates away from the center of the image sensor as the ball rotates about the y-axis. Subsequently, the system measures the location of the image center with respect to the grid coordinate system to calculate the translation along the vertical portion of the grid, and then using the known radius between the ball center and pattern surface, the system calculates the theta angle 2715 of the barrel in spherical coordinates.

Figure 27C:
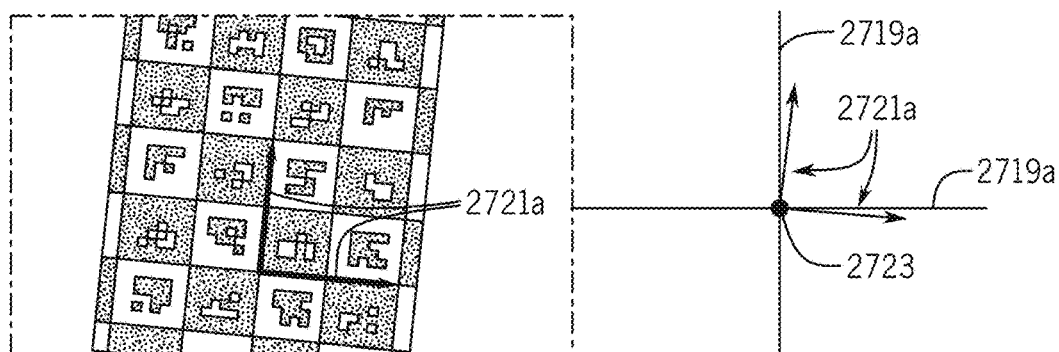
Figure 27D:
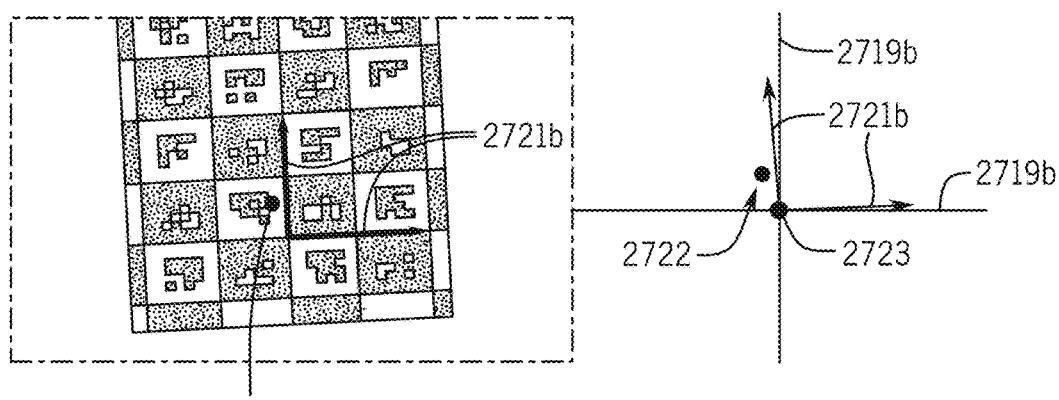

In reference to FIGS. 27C-27D, a vector is calculated between the checkerboard corner closest to the image center and a corner nearest that first corner that is vertically in-line with respect to each other in the coordinate system of the pattern. A second vector is calculated along the vertical axis of the image, passing through the image center. The algorithms calculate the relative angle between these two vectors, by calculating the inverse cosine of the cross product of the two vectors; this calculation can also be done several different ways using known geometry formulas. The angle is calculated using one vector from each of the grid axes 2721*a* and camera axes 2719*a*, selecting the two vectors with the closest angles to the zero-phi angle. The angle between these vectors represents the phi angle of the barrel, which indicates the left and right motion of the barrel. After calculating phi and theta of the barrel via the location of the image center on the unique pattern and the pose of the pattern relative to the optical sensor, the system then uses spherical coordinate formulas to calculate the end location of the cord end that mates with the probe tip, given the input length of the cord that exists past the center of the sphere. The theta angle of the barrel represents the up and down motion of the barrel. The system algorithms calculate the absolute location of the center of the image along the unique pattern, identifying the exact location in the units of the physical pattern. First, the grid axes 2721*b* rotation is identified and then the image center 2722 relative to the camera axes 2719*b*. Next, the projected length of the vector between the grid axes origin 2723 and the image sensor center 2722 is calculated. This arc length input is combined with the known radius of the pattern surface relative to the center of the sphere, and then theta is calculated using the arc length formula that extrapolates the angle of the arc section.

Figure 28A:
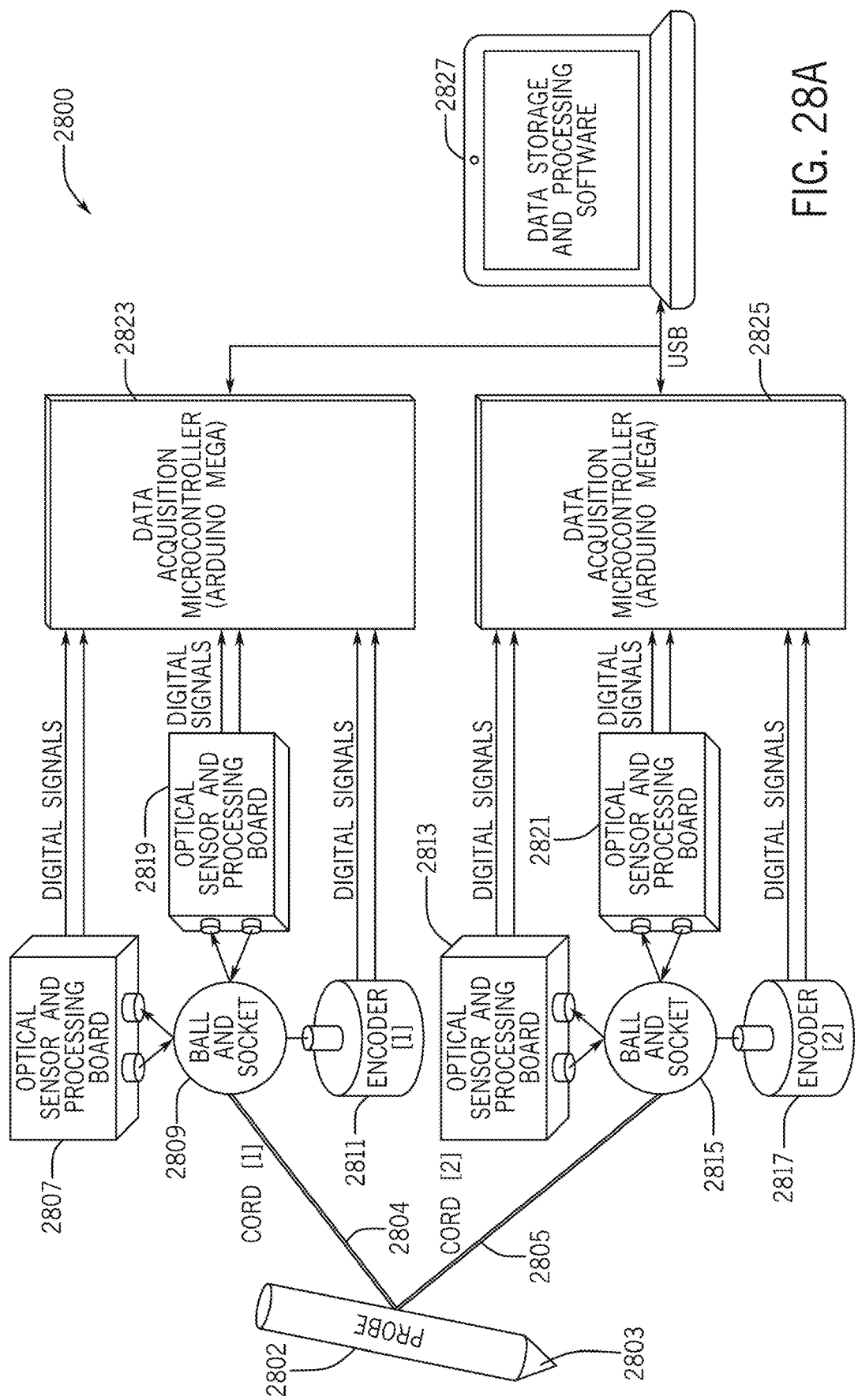
FIG. 28A illustrates an example 3D tracking system in accordance with some embodiments of the invention.

Another embodiment of the electromechanical, 3D-tracking system, illustrated in FIGS. 23A-23C, can contain the system of components shown in FIG. 28A, where the ball-and-socket movement is sensed by optical sensors that interpret the relative translation of the ball surface with respect to the image sensor as the ball rotates due movement of the barrel. This system measures the phi and theta movement of the ball in spherical coordinates. The system 2800 can include encoder embodiments to measure length of the cord, two ball-and-socket assemblies to enable measurements of cord trajectory for cord that is past the center of the ball, two optical sensors per ball-and-socket assembly for measuring the translation of the ball surface with respect to the image sensor to calculate the spherical rotation of the ball, and one probe assembly to link the 3D-tracked, extensible cords in space and provide the user a medium for acquiring 3D points. For example, the system 2800 can include couple components comprising probe 2802 with probe tip 2803, cords 2804, 2805, ball and sockets 2809, 2815, optically-coupled sensor and processing boards 2807, 2813, 2819, and 2821, coupled encoders 2811, 2817, data acquisition microcontrollers 2823, 2825, and computer system 2827 with data storage and processing software.

For each ball-and-socket embodiment there is one encoder embodiment and two optical sensor embodiments. An extensible cord passes radially through the barrel located at the center of the ball and connects to a probe, allowing the barrel to follow the location of the extensible cord. Since the barrel is fixed at the center of the ball and the ball's axis of rotation is fixed by a rod seated in a slot on the socket, the ball is unable to rotate radially about the barrel's axis and the barrel can track the location of the probe. Measurement of the ball's rotation in the socket allows for the calculation of the angular takeoff of the barrel as the probe is moved through three-dimensional space. The cord length is measured via rotary encoders as described in FIG. 16, however other sensors can be used to detect the length of the extended cord. The measurement of cord length and angular takeoff provide sufficient data to calculate the 3D location of the probe in the spherical coordinate system.

One embodiment of the measurement system used to calculate the angular takeoff is a pair of optical sensors oriented normal to the ball and socket and orthogonal to each other, each one aligned with the theta and phi spherical coordinate planes of the ball system.

In one embodiment, a light-emitting device emits light in a finite spectrum that is reflected off the surface of the ball and is converted to electrical signals via a photodetector array. The converted data is then processed using an algorithm to transform the photodetector array data into translational changes of the ball surface with respect to the camera. A data acquisition and computing system converts the translational data from cartesian to spherical coordinates, and subsequently calculates the theta and phi rotation of the sphere, based on the known radius of the ball that is being sensed. One embodiment of the system may include a laser diode and photodiode array, light-emitting diode and photodiode array, and/or an imaging sensor. A pattern or image installed on the cylindrical window of the ball to increase the contrast, reflectivity, or sensitivity of the optical signal, as well as to produce higher signal-to-noise ratios, and increase the accuracy of theta and phi spherical coordinate calculations. The pattern or image may contain repeating variations of patterned and/or colors, and may be manufactured with a reflective surface, which maximizes the optical coupling between the light-emitting device and the photodetector array.

Another embodiment involves a surface pattern that is etched on the ball surface during the manufacturing process, and the surface pattern enhances the sensitivity of optical signals to change at the slightest of translational changes of the ball surface with respect to the image sensor.

Some embodiments can involve additional lighting sources that provide lighting on the ball surface at any possible finite spectrum of light, from which certain light source frequencies provide an optimal sensitivity for the system to have a high-resolution sensing of rotational changes, but not erroneously estimating movement that is not actually occurring, but rather just artifacts of optical noise.

Figure 28B:
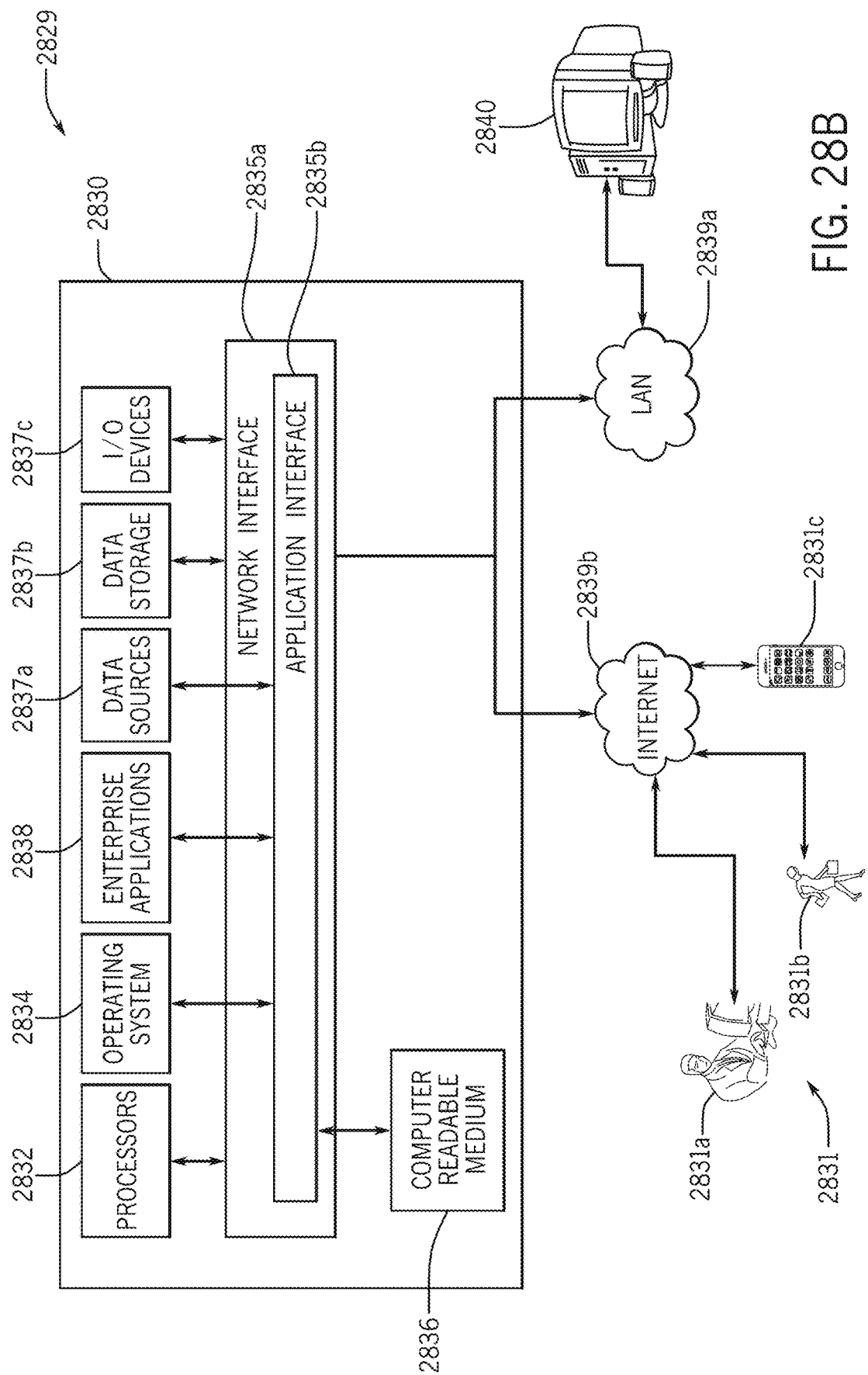
FIG. 28B illustrates a computer system configured for operating and processing components of the system in accordance with some embodiments of the invention.

FIG. 28B illustrates a computer system 2829 configured for operating and processing components of the any of the systems disclosed herein. For example, in some embodiments, the computer system 2829 can operate and/or process computer-executable code of one or more software modules of any of the systems shown in one or more of the figures herein, including, but not limited to FIGS. 24-26, and 28A. In some embodiments, the system 2829 can comprise at least one computing device including at least one processor 2832. In some embodiments, at least one processor 2832 can include a processor residing in, or coupled to, one or more server platforms. In some embodiments, the system 2829 can include a network interface 2835a and an application interface 2835b coupled to the least one processor 2832 capable of processing at least one operating system 2834. Further, in some embodiments, the interfaces 2835a, 2835b coupled to at least one processor 2832 can be configured to process one or more of the software modules 2838 (e.g., such as enterprise applications). In some embodiments, the software modules 2838 can include server-based software and/or can operate to host at least one user account and/or at least one client account, and operating to transfer data between one or more of these accounts using the at least one processor 2832.

With the above embodiments in mind, it should be understood that the invention can employ various computer-implemented operations involving data stored in computer systems. Moreover, the above-described databases and models throughout the system 2829 can store analytical models and other data on computer-readable storage media within the system 2829 and on computer-readable storage media coupled to the system 2829. In addition, the above-described applications of the 2829 system can be stored on computer-readable storage media within the system 2829 and on computer-readable storage media coupled to the system 2829. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated. In some embodiments of the invention, the system 2829 can comprise at least one computer readable medium 2836 coupled to at least one data source 2837a, and/or at least one data storage device 2837b, and/or at least one input/output device 2837c. In some embodiments, the invention can be embodied as computer readable code on a computer readable medium 2836. In some embodiments, the computer readable medium 2836 can be any data storage device that can store data, which can thereafter be read by a computer system (such as the system 2829). In some embodiments, the computer readable medium 2836 can be any physical or material medium that can be used to tangibly store the desired information or data or instructions and which can be accessed by a computer or processor 2832. In some embodiments, the computer readable medium 2836 can include hard drives, network attached storage (NAS), read-only memory, random-access memory, FLASH based memory, CD-ROMs, CD-Rs, CD-RWs, DVDs, magnetic tapes, other optical and non-optical data storage devices. In some embodiments, various other forms of computer-readable media 2836 can transmit or carry instructions to a computer 2840 and/or at least one user 2831, including a router, private or public network, or other transmission device or channel, both wired and wireless. In some embodiments, the software modules 2838 can be configured to send and receive data from a database (e.g., from a computer readable medium 2836 including data sources 2837a and data storage 2837b that can comprise a database), and data can be received by the software modules 2838 from at least one other source. In some embodiments, at least one of the software modules 2838 can be configured within the system to output data to at least one user 2831 via at least one graphical user interface rendered on at least one digital display.

In some embodiments of the invention, the computer readable medium 2836 can be distributed over a conventional computer network via the network interface 2835a where the 2829 system embodied by the computer readable code can be stored and executed in a distributed fashion. For example, in some embodiments, one or more components of the system 2829 can be coupled to send and/or receive data through a local area network ("LAN") 2839a and/or an internet coupled network 2839b (e.g., such as a wireless internet). In some further embodiments, the networks 2839a, 2839b can include wide area networks ("WAN"), direct connections (e.g., through a universal serial bus port), or other forms of computer-readable media 2836, or any combination thereof.

In some embodiments, components of the networks 2839a, 2839b can include any number of user devices such as personal computers including for example desktop computers, and/or laptop computers, or any fixed, generally non-mobile internet appliances coupled through the LAN 2839a. For example, some embodiments include personal computers 2840 coupled through the LAN 2839a that can be configured for any type of user including an administrator. Other embodiments can include personal computers coupled through network 2839b. In some further embodiments, one or more components of the system 2829 can be coupled to send or receive data through an internet network (e.g., such as network 2839b). For example, some embodiments include at least one user 2831 coupled wirelessly and accessing one or more software modules of the system including at least one enterprise application 2838 via an input and output ("I/O") device 2837c. In some other embodiments, the system 2829 can enable at least one user 2831 to be coupled to access enterprise applications 2838 via an I/O device 2837c through LAN 2839a. In some embodiments, the user 2831 can comprise a user 2831a coupled to the system 2829 using a desktop computer, and/or laptop computers, or any fixed, generally non-mobile internet appliances coupled through the internet 2839b. In some further embodiments, the user 2831 can comprise a mobile user 2831b coupled to the system 2829. In some embodiments, the user 2831b can use any mobile computing device 2831c to wireless coupled to the system 2829, including, but not limited to, personal digital assistants, and/or cellular phones 2831c, mobile phones, or smart phones, and/or pagers, and/or digital tablets, and/or fixed or mobile internet appliances.

In some embodiments of the invention, the system 2829 can enable one or more users 2831 coupled to receive, analyze, input, modify, create and send data to and from the system 2829, including to and from one or more enterprise applications 2838 running on the system 2829. In some embodiments, at least one software application 2838 running on one or more processors 2832 can be configured to be coupled for communication over networks 2839a, 2839b through the internet 2839b. In some embodiments, one or more wired or wirelessly coupled components of the network 2839a, 2839b can include one or more resources for data storage. For example, in some embodiments, this can include any other form of computer readable media in addition to the computer readable media 2836 for storing information, and can include any form of computer readable media for communicating information from one electronic device to another electronic device.

FIGS. 29A-29B illustrates a screw-head-registering screwdriver 2900 equipped with a tracked dynamic reference frame in accordance with some embodiments of the invention. FIG. 29C illustrates a close-up perspective view of a screwdriver head and depressible tip 2957 of the screwdriver of FIGS. 29A-29B in accordance with some embodiments of the invention. Further, FIG. 29D illustrates a cross-sectional view of the screwdriver-screw interface in accordance with some embodiments of the invention. FIG. 29A-29B displays a tool that serves three functions: 1.) it registers the 3D position and pose of the screw shaft, 2.) fully engages in the screw head interface, and 3.) signals when it is fully engaged via a depressible sliding shaft 2957 that extends from the probe shaft 2910 of the tool 2900 and is coupled to a tracked mobile stray marker that is actuated when the tool is fully engaged with the mating screw. The overall purpose of this invention is to identify the location and pose of a screw via a coupling mechanism with the screw head, and to have a triggering system via the TMSM 2945 to indicate to the acquisition system when the tool is fully engaged with the screw. This tool 2900 and other embodiments can be applied when there is not a rod seated in the screw obstructing the tool's interface with the screw head. As shown in FIG. 29A, the tool can comprise tracked DRF 2929 (with markers 2930), a probe shaft 2910, a TMSM (undepressed) 2945, handle 2940, screwdriver head 2950, depressible sliding shaft (undepressed) 2957, pedicle screw shaft 2960, pedicle screw tulip head 2955, and coupling mechanism 2905.

This tool (screwdriver) 2900 is designed to interface with a pedicle screw shaft 2960 in such a way that it can engage with the head of the screw to both tighten and loosen the screw, but furthermore, that when the tool 2900 is fully engaged in the screw head 2955, its 2910 is fixed in one orientation relative to the screw shaft 2960. In this way, this tool 2900 can be used to quickly register both the location and pose of the screw shaft 2960 by only accessing the screw head 2955 of the screw shaft 2960. As shown in FIG. 29A, the TMSM 2945 is in the position corresponding with an undepressed, and therefore unengaged, screwdriver depressible shaft 2957. This embodiment possesses a similar design of actuating a TMSM 2945 via a depressible tip 2957 as described previously in relation to FIG. 10A-10G. It should be noted that the depressible tip 2957 and the screw head interface component 2950 of the tool 2900 can have many different embodiments.

In some embodiments, the sliding shaft (tip 2957) can be structured such that it always remains within the shaft of the tool or screwdriver, and the screw head 2960 is designed with a center protrusion to deflect the inner sliding shaft of the screwdriver. In this way, the tip 2957 of the sliding shaft is unable to be actuated by any object that cannot fit inside the shaft 2950. When the tracked mobile stray marker 2945 is actuated, the acquisition system's software detects its motion (shown as linear) and is able to distinguish when it is fully or partially engaged with a screw head by the known geometry of the tool and interfacing screw as described in more detail below in reference to FIG. 63. It should be noted that the motion of the TMSM 2945 can be linear, rotational, or any combination thereof. Further, the mechanism of detecting the motion of the TMSMs can also consist of covering and uncovering a particular stray marker with actuation of the sliding shaft as described previously in relation to FIG. 14. Additionally, the design of the screwdriver head 2950 can be such that it also has components that allow for ensuring it will mechanically couple with the screw shaft 2960 such that it can only achieve one unique orientation when fully engaged. In some embodiments, structures to help with engaging in a unique configuration include, but are not limited to, expanding screwdriver heads, a depth-stop flange to help the screwdriver head align with the screw head, and screws designed with screw heads of increased depth to ensure the screwdriver shaft firmly engages in one orientation when fully seated into the head. In addition, since the depicted location of the tracked DRF 2929 is not the only manner to substantially rigidly attached the DRF, it must be noted that the DRF 2929 can be placed anywhere on the surgical tool screwdriver 2900 as long as it can be substantially rigidly attached, even on adjustable joints.

FIG. 29B displays another embodiment of the tool shown previously in reference to FIG. 29A, except in this image, the tool 2900 is fully engaged with the screw head 2960, highlighting the new position of the TMSM 2945 to indicate to the acquisition software system that the screwdriver head 2950 and depressible shaft 2957 is fully seated and the location and pose of the screw shaft 2960 can subsequently be calculated from that position.

FIG. 29C illustrates a close-up perspective view of a screwdriver head 2950 and depressible tip 2957 of the screwdriver 2900 of FIGS. 29A-29B in accordance with some embodiments of the invention, and shows the aforementioned depressible sliding shaft 2957 in an undepressed position. FIG. 29C shows a more detailed perspective of the screwdriver head 2950 and the depressible tip 2957 of the screwdriver tool 2900 previously described in relation to FIG. 29A-29B, and its interface 2905 with a pedicle screw head 2960. In this view it is possible to see the interface of the screwdriver head 2950 and the top of the screw head 2960, as well as the depressible tip 2957, shown undepressed. Other embodiments involve a depressible sliding shaft that is contained within the screwdriver head. This spring-loaded, depressible shaft can only be engaged when a male protrusion in the screw head engages the screwhead coaxially, and then the depressible shaft 2957 is pushed up, actuating the TMSM 2945 attached to the depressible shaft 2957, to signal that the 3D-tracked tool 2900 and the screw shaft 2960 are fully engaged and coaxial, and thus ready to be registered in 3D space.

FIG. 29D illustrates a cross-sectional view of the screwdriver-screw interface 2905 in accordance with some embodiments of the invention, and shows the depressible sliding shaft tip (partially depressed) 2965. As shown in figure FIG. 29D, the screwdriver tool 2900 would not signal to the acquisition system that it is fully engaged with the screw head 2960, as the partially-depressed depressible shaft 2965 and its mechanically-linked TMSM 2945 would not be fully-actuated relative to the tracked DRF 2929.

In some embodiments, the tracked DRF does not have to be substantially rigidly attached to the tool's shaft, but can be allowed to rotate about the tool shaft (e.g., linked with a bearing) and adjust its relative position to the tool (still able to be substantially rigidly locked when desired). As it shown in the simplified drawings FIG. 29A-29B, it makes it very challenging for users to use the tool as a screwdriver if the DRF 2929 gets in the way. It should be noted that in other embodiments of the design, the tracked DRF 2929 is both located and attached to the screwdriver in different ways that better facilitates the user interface of the handle while maintaining visualization of the DRF 2929.

For instance, in some embodiments, the tracked DRF 2929 is coupled to the screwdriver shaft 2910 via a bearing (which can be coupled with or without a lockable ratcheting mechanism), such that it is allowed to rotate about the long-axis of the screw driver shaft. In other embodiments it is positioned above the handle with or without bearings to enable it to rotate about the screwdriver shaft axis.

Figure 30A:
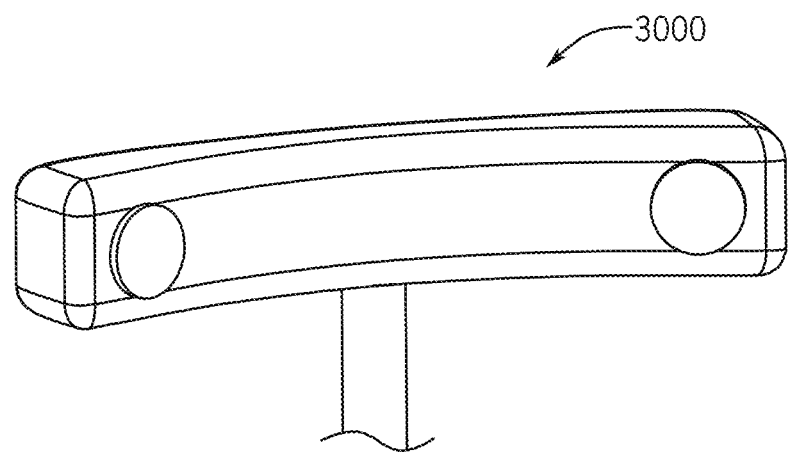
FIG. 30A illustrates a 3D-tracking camera system in accordance with some embodiments of the invention.
Figure 30B:
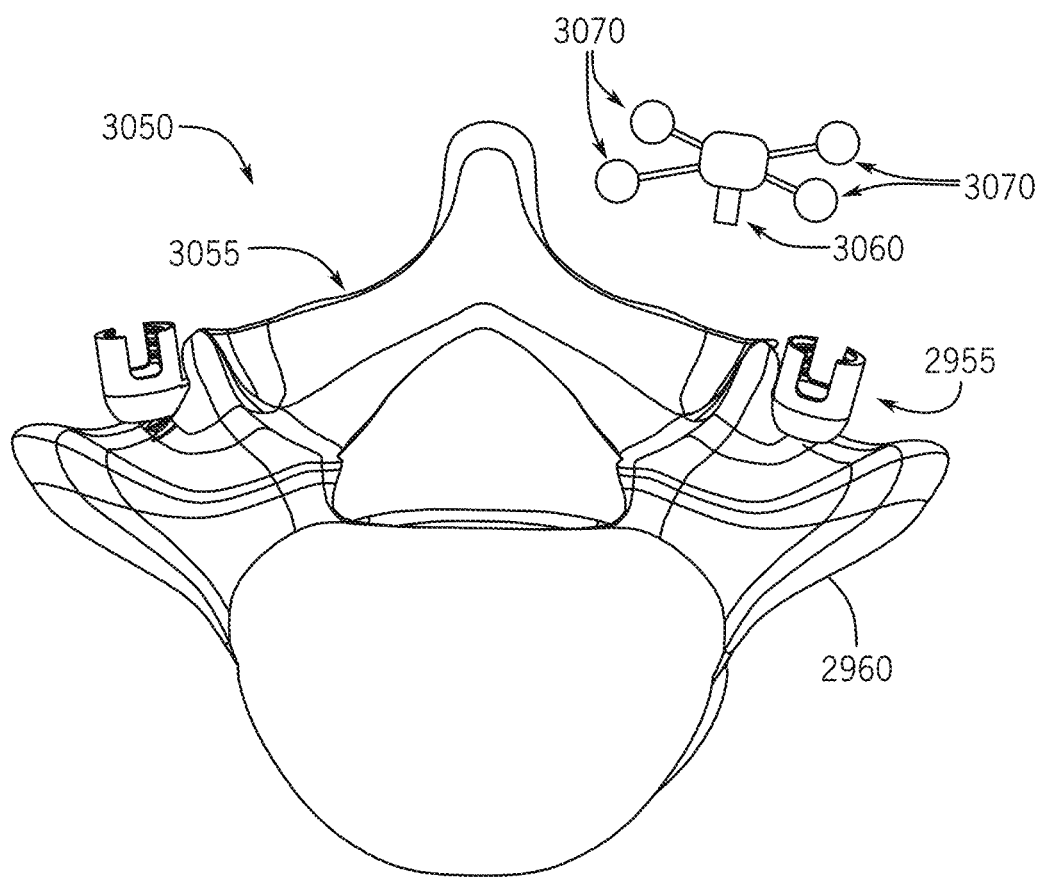
FIG. 30B comprises an image of a tracked reference frame accordance with some embodiments of the invention.

In some embodiments of the invention, as seen in FIG. 30A-30C, a pedicle screw insert cap 3060 with an attached series of 3D-tracked markers 3070, which form a DRF, couples to the tulip head 2955 of a pedicle screw. In this way, the tulip head can be tracked in 3D space whenever the markers 3070 are within line of sight of the camera 3000, and do not require a probe to interface with them to register their position in space. FIG. 30A displays an optical, 3D-tracking system 3000 that can be used as the acquisition device for these and any other tracked markers throughout this document. FIG. 30B displays a tracked DRF with 3D-tracked markers 3070 on a cap device equipped with a mating mechanism 3060 to substantially rigidly mount to the tulip head 2955 of a pedicle screw 2960 (not visible; instrumented into spinal vertebrae 3055 in FIG. 30B). With this tracked reference frame of markers 3070 coupled to the screw 2960, the location of the pedicle screw 2960 can be tracked in 3D space, provided it is in line of sight of the 3D-tracking camera 3000. The interface 3060 between the DRF markers 3070 and the tulip head 2955 can consist of an array of mechanisms, described in more detail below in reference to FIGS. 34A-34F, 35A-35E, 36A-36I, and 37A-37G.

Figure 31:
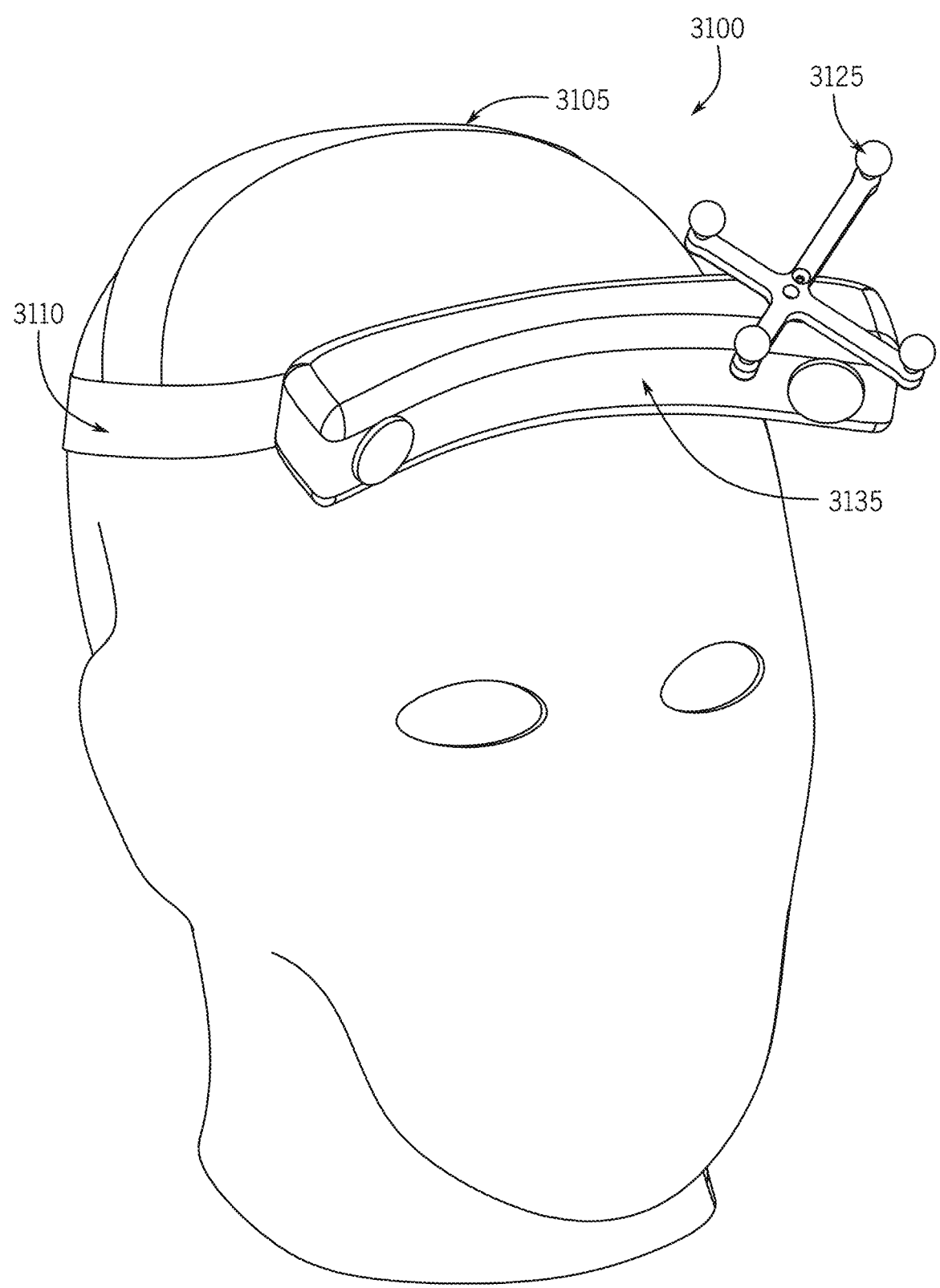
FIG. 31 illustrates a body-mounted 3D-tracking camera in accordance with some embodiments of the invention.

FIG. 31 illustrates a body-mounted 3D-tracking camera in accordance with some embodiments of the invention, and operates in a way to avoid line of sight obstruction between a 3D-tracking camera and a surgical site, or any other area of visualization interest. This design involves a user equipped with a body-mounted tracked DRF 3125 substantially rigidly fixed to a body-mounted 3D-tracking camera 3135 such that information can be fused between the user's field of view and the external 3D-tracking camera (not shown) because the location and pose of the body-mounted camera 3135 will typically be visible and known to the larger field-of-view 3D-tracking camera (not shown). FIG. 31 displays the body-mounted 3D-tracking sensor 3135 equipped with a tracked DRF 3125. One embodiment for the mounting mechanism of the 3D-tracking sensor 3135 to the body is via a head-mounted fastener with adjustable components 3110, 3105. In this embodiment, surgical areas that are typically obstructed from the line of sight of a large field-of-view camera can be visualized via the body-mounted, 3D-tracking optical sensor 3135. Since the body-mounted, optical sensor 3135 is equipped with a substantially rigidly-mounted tracked DRF 3125, the larger-field-of-view camera (not shown) can register the body-mounted, optical sensor's location and pose in 3D space, and with that information, interpret the scene visualized by the headset-mounted, 3D-tracking optical sensor 3135 to create a dynamic, 3D stitched mapping of the global coordinate system relative to the large field-of-view camera coordinate system. The fusion of the coordinate systems of the body-mounted camera 3135 and the larger field-of-view camera (not shown) will be computed via a 3D rigid transform, which will be applied to 3D data collected by the body-mounted camera 3135 for all frames of its acquisition. Thus, this embodiment enables for the computation of 3D positions and poses of objects of interest (e.g., 3D-trackable tools, DRFs, anatomical landmarks, fiducials, surgical accessories, other optical or electromagnetic sensors, etc.) within the field of view of the body-mounted camera 3135, which is being tracked by the larger field-of-view camera (not shown).

Figure 32:
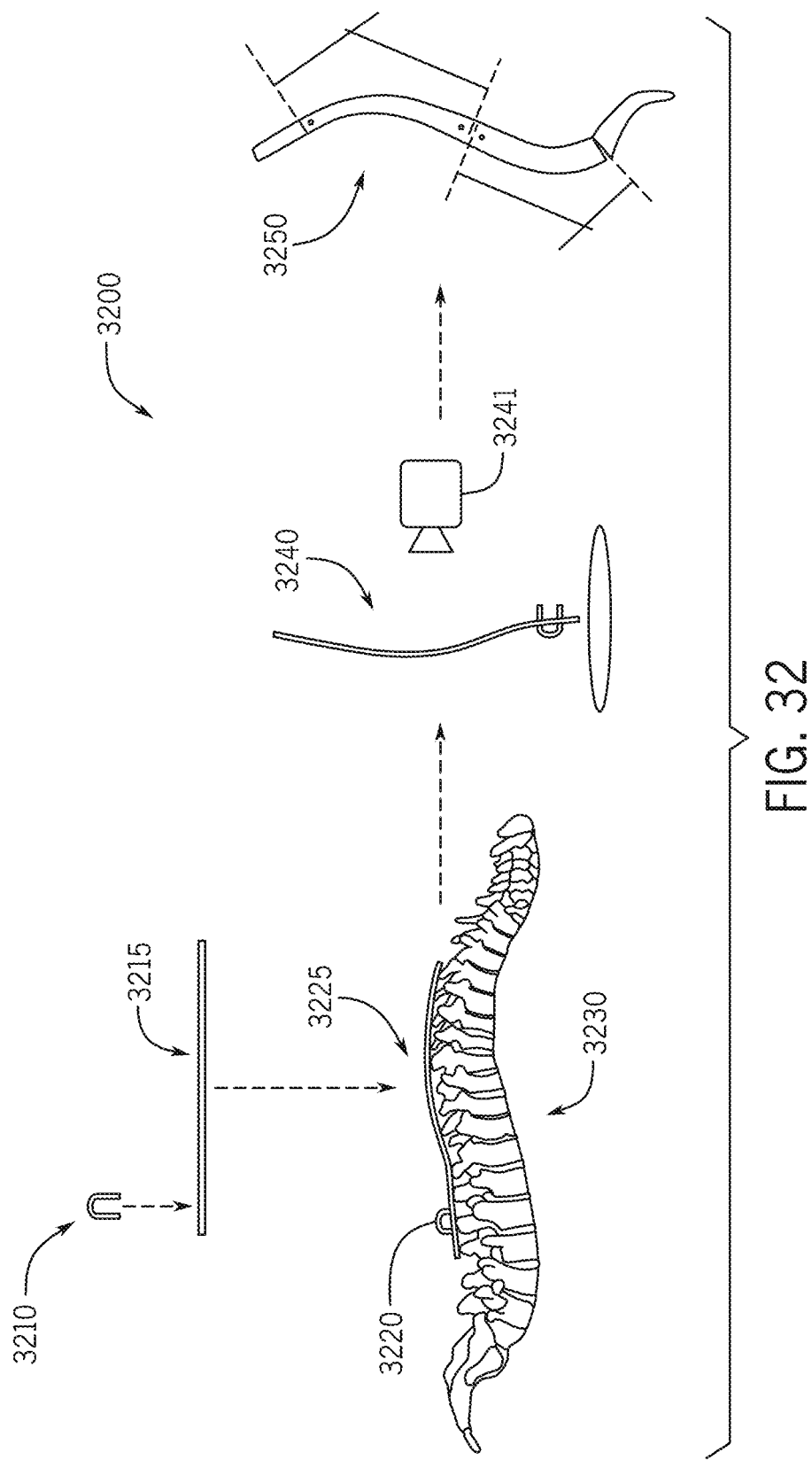
FIG. 32 displays a method of interpreting the contour of the posterior elements of the spine in accordance with some embodiments of the invention.

FIG. 32 displays a method of interpreting the contour of the posterior elements of the spine by placing a malleable object over the surgically-exposed bony elements such that it matches the contour of the exposed spine, and then the malleable object is removed and its contour registered with optical systems, including stereoscopic cameras, and from that information about the surface contour of the malleable object which now serves as a surrogate for the contour of the posterior elements of the spine, the spinal alignment parameters of the contour-matched spine can be calculated. Other relevant other figures (relating to the calculation of spinal alignment parameters and the location of other anatomical landmarks of interest processed by software algorithms) include FIGS. 65A-65E, 66A-66B, and 68. FIG. 32 displays the system 3200 where a malleable rod 3215 that is placed over the surgically exposed elements of the spine 3230 with an adjustable clip 3210 to register a particular spinal level for software interpretation. After the rod 3215 is inserted into the surgical site, the malleable rod 3215 is conformed to match the contour 3225 of the exposed spinal elements, and one or more mounted clips 3220 are aligned along the rod 3215 with nearby anatomical landmarks of interest. This malleable rod 3215 then undergoes topological registration 3240 by one or more imaging sensors 3241 to interpret the 3D contour of the rod 3215 that matches the contour 3225 of the spinal column 3230. The 3D contour of the malleable rod 3215 is then processed by software algorithms described in detail below in reference to FIGS. 65A-E, 66A-B, and 68. The optical registration system 3241 can be any optical system to register 3D surface contours including, but not limited to, one or more depth sensors, stereoscopic vision cameras, and structured light systems, with the rod fixed onto a stationary or movable platform base. Based on some embodiments for registering the 3D contour of the malleable rod 3215 using optical methods, and the associated clip 3210 that indicates spinal levels, the system can calculate the spinal alignment parameters 3250 of each anatomical plane of the rod 3215 an interpret the relative alignment and contour of the spine 3230.

Some embodiments of the invention seen in FIGS. 33A-33I, include a screw and screwdriver combination that allows for the ability to mechanically couple both devices such that the screwdriver becomes coaxial with the screw shaft, and also has the ability to then substantially rigidly manipulate the screw shaft, which if fixed in bone has the ability to then manipulate the associated bony structures. For example, FIG. 33A illustrates a pedicle screw design in accordance with some embodiments of the invention, and FIG. 33B illustrates a pedicle screw in accordance with another embodiment of the invention. Further, FIG. 33C illustrates a pedicle screw mated with a polyaxial tulip head in accordance with some embodiments of the invention, and FIG. 33D illustrates a tool designed to interface with the pedicle screw of FIG. 33B in accordance with some embodiments of the invention. FIG. 33E illustrates a visualization of a couple between the tool of FIG. 33D, and the screw of FIG. 33C in accordance with some embodiments of the invention. Further, FIG. 33F illustrates the coupling tool, depicted in FIG. 33D, coupled to a pedicle screw, as seen in FIG. 33C, in accordance with some embodiments of the invention, FIG. 33G illustrates a top view of the screw of FIG. 33A in accordance with some embodiments of the invention, and FIG. 33H illustrates a top view of the screw of FIG. 33B in accordance with some embodiments of the invention. As shown, some embodiments include an Allen key inset 3325, rigid single crossbar 3320, coupled threaded shaft 3305, and a curved screw head 3315. FIG. 33A and FIG. 33I displays one embodiment of a screw that consists of an Allen key inset 3325, a rigid crossbar 3320 that spans across the sidewalls of the screw head 3315 but allows for a gap above the inset, a threaded shaft 3305 and a curved screw head 3315 to accommodate mating with a tulip head (seen in FIG. 33C as label 3365). FIG. 33B displays another embodiment of the screw described in detail above in relation to FIG. 33A. The embodiment displays the screw head 3345 with two intersecting crossbars 3350, to enable interfacing with a different tool, an example embodiment depicted in FIG. 33D. It should be noted that the examples of screws portrayed in these figures only represent some embodiments of the invention. The crossbars 3350 can be of varying contour, number, and relative arrangement for each screw head. FIG. 33C displays an embodiment of the screw described previously in relation to FIG. 33B mated with a polyaxial tulip head 3365 with a cutout 3375 to interface with a rod, and a thread 3370 to receive a tightening cap.

FIG. 33D displays one embodiment of a tool designed to interface with the screw previously described in detail in relation to FIG. 33B. This tool consists of four mechanically-coupling extensions 3390 designed to engage with the screw head cross-bars via a quarter-turn mechanism. After performing a quarter-turn, the tool becomes substantially rigidly fixed to a screw head and shaft, as depicted in FIG. 33B. The end of the center shaft of the screw has a depressible sliding shaft 3393 that can be coupled to a TMSM (not shown) to indicate full engagement of the tool 3390 and screw, as depicted in FIG. 33B, in a communication method previously described in detail in relation to FIGS. 10A-10E and FIGS. 29A-29C. It should be noted that the center of the tip 3393 of this tool can also consist of a threaded shaft that is tightened down at the top segment (not shown) of the tool 3390 to push a sliding rod against the rigid cross bars of the screw head. In this way, the tool has increased fixation strength at the screw head interface. This threaded middle shaft can also be attached to a TMSM (not shown) to indicate its position relative to a tracked DRF (not shown) mounted to the screwdriver. Further, FIG. 33E displays a transparency view of the interface between the screw head, its crossbars, and the screwdriver coupling end effector, previously discussed in relation to FIGS. 33A-33I. From this view, the threaded screw shaft 3391, curved screw head walls 3318, and the mechanically-coupling extensions 3390 of the tool are visible as the two tools engage with one another. Further, unlike FIG. 33E, FIG. 33F displays a different perspective of the screwdriver (3392) and crossbar-equipped screw 3395 interfacing with one another. From this perspective, the coaxial alignment of the screwdriver shaft with the screw shaft is appreciable. FIG. 33G displays an underside view of the cross-bar-equipped screw previously described in relation to FIG. 33B and this view highlights the circular cutout 3380 of the tulip head interfacing with the curved walls of the screw head (3318, 3345; not shown).

Some embodiments include a tool or assembly to interface directly with the tulip heads of pedicle screws, in such a way that it substantially rigidly fixes the rotating tulip head relative to the pedicle screw shaft, to then enable measurement and manipulation devices to act on the coupled spinal elements to aid with alignment measurements and fixation as will be described in more detail below in reference to FIGS. 39A-39F, and 42A-42K.

FIG. 34 illustrates a tool for interfacing with a pedicle screw accordance with some embodiments of the invention. FIG. 34A displays a cross-sectional view interfacing directly with the threaded inserts of the tulip heads of pedicle screws. This figure displays a pedicle screw shaft 3410 (threading not shown), its associated tulip head 3420, the interfacing device's thread-tightening knob 3440, its sleeve body 3425, device body connection 3430, protruding tip 3423 to substantially rigidly push towards the screw head, and inner shaft threading 3422 of the device. Tightening of the device through the thread-tightening knob 3440 leads the inner shaft threading 3422 to interface directly with the tulip head threads to cause the protruding tip 3423 to push against the screw head. Tightening in this way provides a rigid connection between the device, tulip head, and pedicle screw, such that the motion of the polyaxial tulip head has been restricted and all three parts coupled to one another. The device body connection 3430 displayed in this figure is designed to interface with a larger tool that will be described in more detail below in reference to FIGS. 39A-39D, 40A-40C, 41C, 42A42-F. It should be noted that the protruding tip displayed in this figure is only one embodiment of the device and other embodiments include but are not limited to cylindrical extrusion, spherical tip, and a non-rigid cylindrical extrusion coaxial or perpendicular to the inner shaft and coupled via rivet or other mechanism that enables its rotation about the axis of the inner shaft.

FIGS. 34B-34C display a non-cross-sectional, side view of the device described in relation to FIG. 34 interfacing with a pedicle screw. Visible are side-tab extensions 3421 that extend over the tulip head cutouts. These side tabs extensions provide additional rigid interfacing between the device and the tulip head of the screw, further helping to substantially rigidly fix the device, tulip head, and screw to one another.

FIG. 34D displays a cross-sectional view of the device described in relation to FIG. 34A interfacing with a pedicle screw. FIG. 34E displays a non-cross-sectional, rendered side view of the device described in relation to FIG. 34A interfacing with a pedicle screw. FIG. 34F displays a non-cross-sectional, rendered front view of the device described in relation to FIG. 34A interfacing with a pedicle screw.

FIGS. 35A-35F display an assembly or tool 3500 designed to interface directly with the tulip heads of pedicle screws, in such a way that it substantially rigidly fixes the rotating tulip head relative to the pedicle screw shaft, to then enable measurement and manipulation devices to act on the spinal elements to aid with alignment measurements and fixation as will be described in more detail below in reference to FIGS. 39A-39F, and 42A-42K. This is an alternative embodiment from that previously described in detail in relation to FIGS. 34A-34F. As shown, the tool 3500 comprises pedicle screw shaft 3510, tulip head 3503, drafted shaft advancement knob 3540, sleeve body 3525, device body connection 3530, protruding tip 3504, outer shaft threading 3535, protruding-tip advancement knob 3545, drafted pin 3546, retaining ring 3502, and expanding teeth 3527. In operations, after interfacing directly with the tulip head 3503, the drafted pin advancement knob 3540 leads the outer shaft threading 3535 to drive the expansion of the expanding teeth 3527 to interface directly with the tulip head threads. The retaining ring 3502 limits expansion of the device to prevent over stress, and the protruding tip advancement knob 3545 can then be tightened to increase the tension on the expanded teeth with the tulip head threads and thereby substantially rigidly fix the device, tulip head, and screw shaft together. The device body connection 3530 displayed in this figure is designed to interface with a larger tool that will be described in more detail below in reference to FIGS. 39A-39F, and 42A-42K.

FIG. 35B displays a non-cross-sectional, front view of the device described in relation to FIG. 35A interfacing with a pedicle screw. Visible in this figure are side-tab extensions 3529 that extend over the tulip head cutouts. These side tabs provide additional rigid interfacing between the device and the tulip head of the screw, further helping to substantially rigidly fix the device, tulip head, and screw to one another. FIG. 35C displays a non-cross-sectional, perspective view of the device described in relation to FIG. 35A interfacing with a pedicle screw. FIG. 35D displays a cross-sectional, rendered view of the device described in relation to FIG. 35A interfacing with a pedicle screw. FIG. 35E displays a non-cross-sectional, rendered front view of the device described in relation to FIG. 35A interfacing with a pedicle screw. FIG. 35F illustrates a close-up perspective view of the tool of FIGS. 35A-35E without a coupled pedicle screw or tulip head in accordance with some embodiments of the invention. FIG. 35F displays a non-cross-sectional, rendered front view of the device described in relation to FIG. 35A without the interfacing pedicle screw and tulip head. In this view, the expanding teeth and side tab extensions are more clearly visual.

Some further embodiments of the invention include a tool or assembly able to interface directly with the tulip heads of pedicle screws via a quarter-turn mechanism, in such a way that it substantially rigidly fixes the rotating tulip head relative to the pedicle screw shaft, to then enable measurement and manipulation devices to act on the spinal elements to aid with alignment measurements and fixation as will be described in more detail below in reference to FIGS. 39A-39F, and 42A-42K. This is an alternative embodiment from that previously described in detail in relation to FIGS. 34A-34F, and 35A-35F. For example, FIG. 36A displays a cross-sectional view of one embodiment of an invention for interfacing directly with the threaded inserts of the tulip heads of pedicle screws via a quarter-turn mechanism. This figure displays a pedicle screw shaft 3610 (threading not shown), its associated tulip head 3620, the quarter-turn knob 3635, its sleeve body 3640, device body connection 3645, protruding tip 3650 to substantially rigidly push towards the screw head, protruding tip advancement knob 3637, side-tab extensions 3695, and quarter-turn retainer 3699. After inserting the device into the tulip head such that the threads are not engaged, the quarter-turn knob is rotated 90 degrees to engage the quarter-turn threads with the threads of the tulip head. After rotating 90 degrees, the quarter-turn retainer prevents excess rotation, to ensure the threading is engaged prior to increasing tension on the threads via tightening the protruding tip advancement knob. By tightening the protruding tip advancement knob, the protruding tip is driven directly against the head of the screw and increasing tension on the quarter-turn threads, thereby removing tolerance from thy polyaxial tulip head. In this way, this device substantially rigidly fixes the tulip head and screw shaft together. The device body connection 3645 displayed in this figure is designed to interface with a larger tool that will be described in more detail below in reference to FIGS. 39A-39F, and 42A-42K.

FIG. 36B displays a non-cross-sectional, front view of the device described in relation to FIG. 36A interfacing with a pedicle screw. More clearly visible in this figure are side-tab extensions 3695, previously described in detail in relation to FIG. 35B. Also, more clearly visualized in this figure is the quarter-turn retainer 3699, previously described in detail in relation to FIG. 36A. Further, FIG. 36C displays a side view of the device described in relation to FIG. 36A interfacing with a pedicle screw, and FIG. 36D displays a non-cross-sectional, perspective view of the device described in relation to FIG. 36A interfacing with a pedicle screw. FIG. 36E displays a non-cross-sectional, perspective view of the device described in relation to FIG. 36A interfacing with a pedicle screw, and FIG. 36F displays a cross-sectional, rendered view of the device described in relation to FIG. 36A interfacing with a pedicle screw. This figure displays the quarter-turn threads engaged with the tulip head threads. FIG. 36G displays a cross-sectional, rendered view of the device described in relation to FIG. 36A interfacing with a pedicle screw. This figure displays the quarter-turn threads disengaged from the tulip head threads. FIG. 36H displays a non-cross-sectional, rendered side view of the device described in relation to FIG. 36A interfacing with a tulip head (pedicle screw shaft not shown). FIG. 36I displays a non-cross-sectional, rendered front view of the device described in relation to FIG. 36A interfacing with a tulip head (pedicle screw shaft not shown).

Some embodiments of the invention include a device for interfacing directly with two implanted pedicle screws in such a way that it substantially rigidly connects to the tulip head and removes tolerance between a polyaxial tulip head and pedicle screw such that the device is mechanically linked to a vertebra or other bony anatomy in which the screw(s) is/are inserted. For clarity, FIGS. 37A-37G do not include a tracked DRF and triggering mechanism, although they can be attached to this device to allow it to provide quantitative data to the user while manipulating or holding the spinal elements, as will be described in more detail in reference to FIGS. 39A-39F, and 42A-42K. Embodiments of the invention comprising the assemblies of FIGS. 37A-37G may include various coupled components including a tightening knob 3740, handle 3705, width-adjustment mechanism 3707, guide rail (×2) 3723, tulip head side rests 3727, spring mechanism 3728 for fastening protrusions, tensioning lever 3732 that presses up against internal spring (not shown) when device is actively clamped, footplate 3710, and/or clamp release lever 3750. For example, FIG. 37A displays a front view of one embodiment of the invention designed to substantially rigidly interface two screws already implanted into the spine or other bony elements. This embodiment is equipped with a tightening knob 3740, handle 3705, width-adjustment mechanism 3707, two guide rails 3723, tulip head rests 3727 to approximate the sidewall of the tulip heads, footplates 3710 to slide under the tulip head, and a clamp release lever 3750. Not shown (for clarity purposes) are tracked DRF, and tracked stray markers that can be applied to the device to make assessments of the tool's position and motion during use, as described in detail below in reference to FIGS. 39A-39F, and 42A-42K. Further, FIG. 37B displays a rear view of one embodiment of the invention previously described in FIG. 37A. Visible from this perspective is the width-adjustment knob 3709, used to adjust the distance between the handle and the tulip head side rests. This viewpoint also provides the front perspective of the width-adjustment mechanism that enables the tulip head side rests to be drawn closer to or farther away from one another. Further, some embodiments include a screw-head interface protrusion 3760, and clamp 3749. For example, FIG. 37C displays a perspective view of one embodiment of the invention previously described in FIG. 37A in the closed position. Visible from this perspective is the screw-head interface protrusions 3760, the clamp 3749 used to securely fasten the device to the pedicle screws, and footplate 3710 to slide underneath the tulip head. This viewpoint displays a better view point of the guide rails 3723, which connects the handle and screw-interfacing arms. Further, FIG. 37E displays a rendered oblique side view of one embodiment of the invention previously described in FIG. 37A in the open position, and FIG. 37D displays a side perspective view of one embodiment of the invention previously described in FIG. 37A in the closed position. Visible from this perspective is the spring 3728 and over center spring structure 3732 in its collapsed position.

Figure 37A:
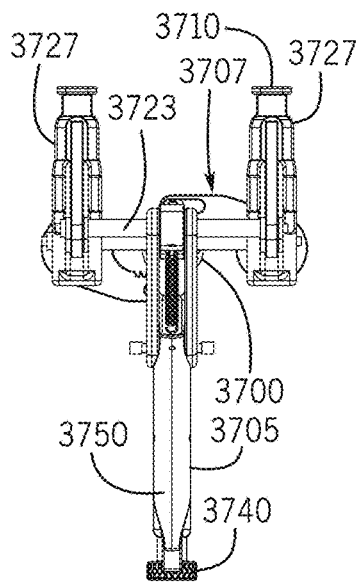
FIGS. 37A-37G illustrate various views of a tool for interfacing directly with two implanted pedicle screws in accordance with some embodiments of the invention.
Figure 37B:
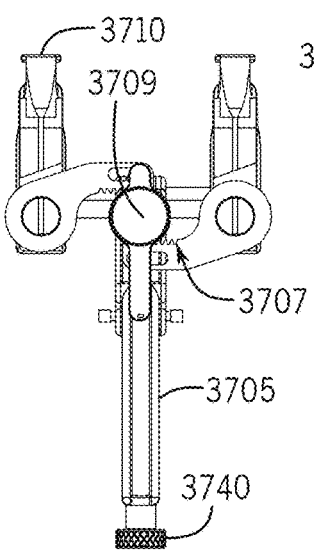
Figure 37C:
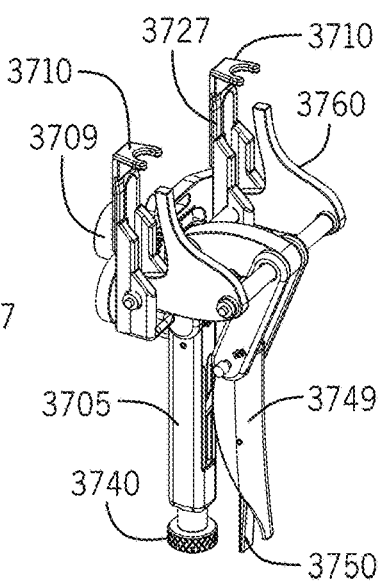
Figure 37D:
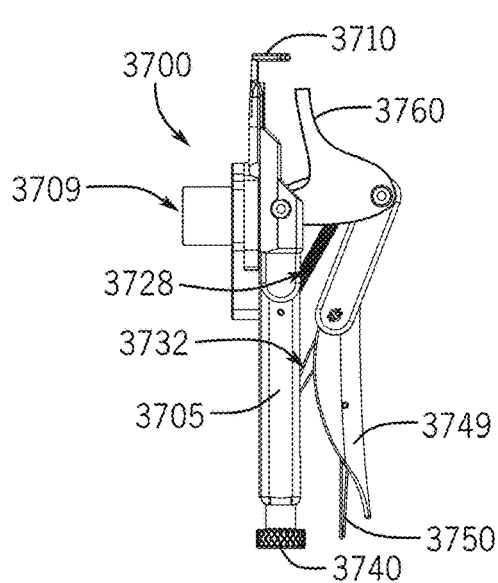
Figure 37E:
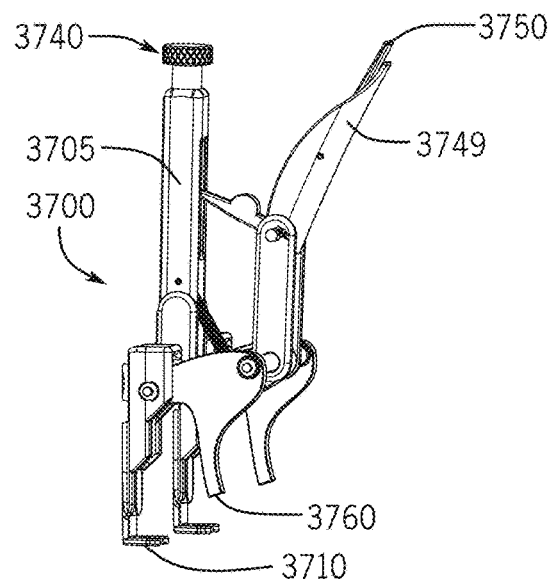
Figure 37F:
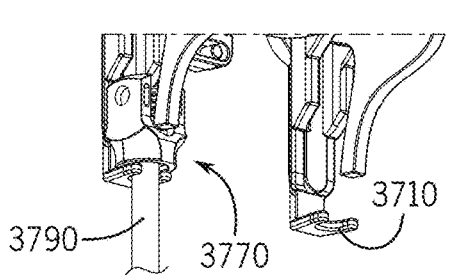

FIG. 37F displays a rendered oblique side view of one embodiment of the invention previously described in FIG. 37A in the closed position with detailed view of the device interfacing on one side with a tulip head 3770 attached to a pedicle screw shaft 3790 (threads not shown). From this perspective, the screw-head interface protrusion is seen engaging with the screw, and by tightly driving the screw head down while the footplate is pulling the tulip head upwards, the tolerance between a polyaxial tulip head and pedicle screw shaft is reduced, resulting in rigid fixation between the three structures. It should be noted that the design and geometry of the screw-head interface protrusion can have a number of embodiments including but not limited to a cylindrical extrusion, spherical head, and a pivoting lever arm.

Figure 37G:
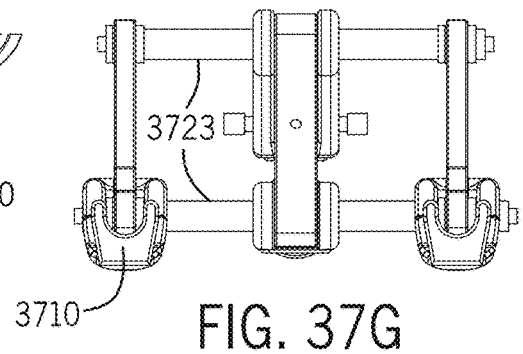

FIG. 37G displays a rendered bottom view of one embodiment of the invention previously described in FIG. 37A. This perspective does not include the width-adjustment mechanism, to aid in visibility of the guide rails, and their cutout groove to enable applying a torque between the tulip head side rests and the screw-head interface protrusion. It should be noted that because the width-adjustment mechanism is not shown in this figure, the handle is not centered between the two screw head interfacing components of the device. In other embodiments of this device previously described, the width-selector mechanism ensures that the handle remains centered between the screw head interfacing components.

In reference to FIG. 38, and FIGS. 38A-38G, some embodiments include FIG. 38 include a pedicle screw shaft (represented without threads) with depth-stop in accordance with some embodiments of the invention. Some embodiments enable assessment of the screw shaft location and pose when equipped with a polyaxial tulip head and with or without the presence of an already-implanted rod seated into the tulip head. The first aspect of the embodiment is a screw designed with a depth-stop ring substantially rigidly attached to the screw shaft at a location beneath the tulip head that still enables full mobility of the attached polyaxial tulip head. In some embodiments, the depth-stop possesses a particular pattern that will interface with the second aspect of the embodiment, a tracked depth-stop assessment tool, in such a way that it allows for the interpretation of the screw shaft location and pose in 3D space, as well as indicate when the assessment tool is fully seated in the depth-stop, to ensure assessment of the screw shaft location is only made when the tool is properly engaged. The indication method shown is via actuation of a TMSM, as previously described in detail in relation to FIGS. 10A-10G, 14A-14C, and 29A-29C, but can also be achieved by other methods including, but not limited to, hand actuation of a TMSM, covering or uncovering of a tracked stray marker, and electronic communication.

FIG. 38A illustrates a top view of the pedicle screw shaft with depth-stop of FIG. 38 in accordance with some embodiments of the invention. For example, some embodiments include a pedicle screw with a shaft 3810 (threads not shown), a depth-stop 3815 substantially rigidly attached to the screw shaft 3805 and designed with a depth-stop mating pattern 3818, depth-stop mating holes 3817, as well as an interface for a polyaxial tulip head (not shown). In some embodiments, the depth-stop distance from the tulip head interface 3820 is designed to stop the screw against bony anatomy such that the polyaxial head maintains full mobility about its ball joint on the screw. In some embodiments, the depth-stop as shown can be circular but can be designed to be of many shapes including interrupted and partial shapes to allow for better fitting within tight anatomical areas. In some embodiments, the mating pattern 3818 and mating holes on the depth-stop 3815 are designed such that an assessment tool, described in detail below in relation to FIGS. 38B-38G, is able to interface with the depth-stop-screw device 3810 and interpret the screw shaft location and pose, irrespective of the position of the tulip head relative to the screw.

FIG. 38B illustrates a screw interface region with coupled handle, with a partial view of an assessment tool designed to mate with the screw previously described in detail in relation to FIG. 38A. The tool consists of a handle 3825, partial-cylinder screw interface region 3827, mating protrusions 3828, and spring-loaded (not shown) mating pins 3829. Further, FIG. 38C illustrates an example assembly view coupling between the screw interface region of FIG. 38B and the pedicle screw shaft with depth-stop of FIGS. 38-38A in accordance with some embodiments of the invention, and FIG. 38C displays the closer perspective of the screw, described previously in relation to FIG. 38A with the assessment tool, described previously in relation to FIG. 38B, aligned and ready to engage with the mating depth-stop. In this image, the tulip head 3804 is visible attached to the top of the screw and an implanted rod 3803 is displayed engaged within the tulip head. In the position displayed, the assessment tool is not engaged with the rigid depth-stop and therefore the mating pins are not depressed. It is not until the assessment device fully is seated into the depth-stop that the spring-loaded mating pins are depressed and an associated tracked mobile stray marker (not shown) can be actuated to communication to the acquisition system.

Some further embodiments involve a combination of staggered heights and shapes of the depth-stop protrusions providing several unique permutations of height changes of TMSM linked to the probe. This could involve two or more TMSMs on the probe. The depth-stop design can be comprised of a radially-repeating pattern of two or more unique depth heights. This unique combination of heights, which is also sensitive to direction/order of height changes will interact with two or more mating pins 3830 of the probe and those will interact with one or more TMSMs 3875 that are subsequently actuated to specific heights along the probe shaft, each height signaling a unique screw identity or anatomical identity. In another embodiment, instead of two TMSMs, the two mating pins that get engaged at different depth-stops can add up their depth differences mechanically against one lever that subsequently actuates a single TMSM to unique, identifiable height along the probe shaft.

FIG. 38D displays a front view of the screw, described previously in relation to FIG. 38A with the assessment tool, described previously in relation to FIG. 38B, aligned and fully engaged with the mating pattern on the depth-stop. From this view it is apparent that the partial-cylinder screw-interface region 3827 allows for engagement of the assessment device with the screw, regardless of the position of the polyaxial tulip head 3804 and/or attached rod 3803. FIG. 38E displays a rear view of the screw, described previously in relation to FIG. 38A with the assessment tool, described previously in relation to FIG. 38B, aligned and fully engaged with the mating pattern on the depth-stop. FIG. 38F displays a side view of the screw, described previously in relation to FIG. 38A with the assessment tool, described previously in relation to FIG. 38B, aligned and fully engaged with the mating pattern on the depth-stop.

FIG. 38G displays a perspective view of the screw, described previously in relation to FIG. 38A with the full assessment tool, described previously in relation to FIG. 38B, aligned but unengaged with the depth-stop of the screw. Visible in this figure is the tracked DRF 3870 attached to the tool handle 3825 for a 3D-tracking camera (not shown) to acquire the 3D location and pose of the assessment tool, a TMSM 3875 and a groove 3885 for the sliding shaft 3880 coupled to the mating pins to slide up and down to actuate the TMSM 3875. One example embodiment for the linear actuation mechanism for the mating pin depressible shaft 3880 coupled to the TMSM 3875 is a slot 3885 for the TMSM 3875 above, below, and/or near the handle 3825. It should be noted that the location of the TMSM can be positioned anywhere on body of the tool and actuation related to the mating pins 3880 can be achieved via linear motion (as shown), rotational motion, or a combination thereof. It should also be noted that other embodiments of the device can contain more than one TMSMs, paired to individual spring-loaded mating pins to indicate tool engagement with the screw or to communicate other states to the acquisition system. In some embodiments, the assessment tool is firmly engaged with the screw depth-stop mating pattern 3815, signaling to the acquisition system to calculate the 3D location and pose of the screw based on the screw's known geometry and the known mating geometry of the tool-screw combination.

Some embodiments of the invention include a device that can be used to assess the intraoperative flexibility of the spine with one or more mountings to substantially rigidly interface with implanted pedicle screws, (as previously described in relation to FIGS. 33A-33H, FIG. 34, FIGS. 35A-35F, and FIGS. 36A-36I). After substantially rigidly fixing two tools, each to individual spinal levels, the spine can be manipulated via directly pushing on body surfaces or indirectly by interacting with the tool's handles to establish a range of motion between the spinal levels onto which the tools are engaged. The range of motion can be displayed to the user on a display monitor via a 3D view or 2D projections onto relevant anatomical planes, as described in more detail below in reference to FIG. 70. Furthermore, after adjusting two or more spinal levels to a desired relative orientation using this tool, another embodiment will be described in which the tools can lock together to temporarily hold the anatomy in that configuration prior to the insertion of a rod, as will be described in more detail in reference to FIGS. 42A-42K.

Figure 39A:
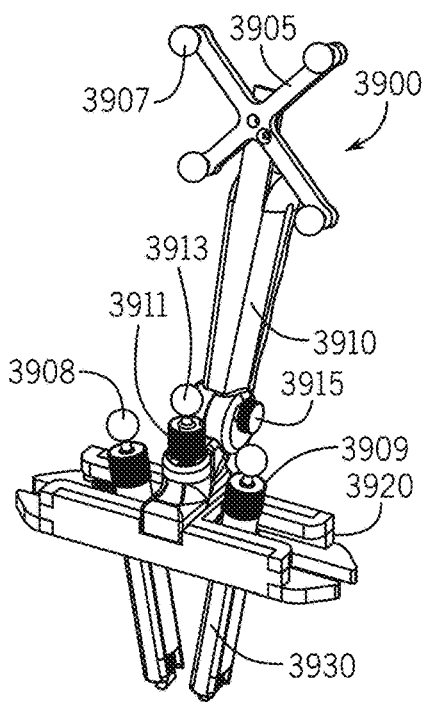
FIG. 39A illustrates a full perspective view of a device used for manipulating bony anatomy and assessing range of motion intraoperatively in accordance with some embodiments of the invention.

FIG. 39A displays a full perspective view of a device 3900 used for manipulating bony anatomy and assessing range of motion intraoperatively. In some embodiments, two devices 3900 can be used at once, such that each securely fasten onto a level of the spine and move each level relative to one another while being tracked in 3D space to assess the achievable ranges of alignment between the two or more spinal segments with coupled devices. One embodiment of the device consists of a tracked DRF 3905 (with markers 3907) for a 3D-tracking camera (not shown) to interpret its location and pose in 3D space, an adjustable handle 3910, width-adjustment knob 3911 equipped with a TSM 3913 to enable the acquisition system software to interpret the angle of the handle relative to the tool end-effectors based on distance between the tracked DRF and this TSM, width-adjustment mechanism 3920, a retractable spring plunger 3915 to allow for the handle to lock into discrete preset angles, sleeve bodies 3930 for housing the screw-interface component of the tool, thread-tightening knobs 3909 for tightly interfacing with tulip heads as described in detail previously in relation to FIGS. 34, 34A-34F, 35A-35E, and 36A-36G, and TSM 3908 for indicating the location and/or pose of the screw interface component 3930 of the device. It should be noted that this is one embodiment of the device and that in other embodiments the angle of the sleeve bodies relative to the width-adjustment mechanism can either be adjustable or fixed at varying angles to accommodate the pedicle screws with which the tool will interface. It should also be noted that the handle of the tool can be outfitted with a spring-loaded trigger to actuate the motion of the TMSM, used to indicate its active state and/or signal a command to the acquisition system, as will be described in more detail in reference to FIG. 39B. It should also be noted that other embodiments of the tool can possess varying numbers of TSMs on and/or near the width-adjustment knob 3911 or screw-interface component 3930 of the tool.

Figure 39B:
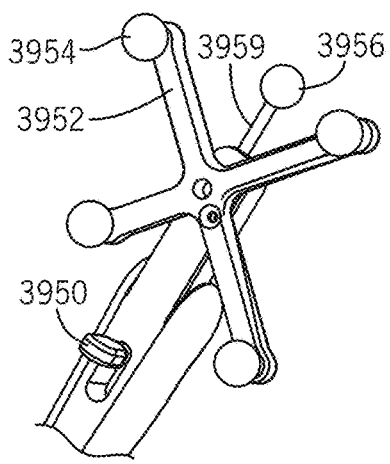
FIG. 39B illustrates another embodiment of the handle of the tool described previously in relation to FIG. 39A in accordance with some embodiments of the invention.

FIG. 39B displays another embodiment of the handle of the tool described previously in relation to FIG. 39A in which it is equipped with a TMSM 3956 coupled to a spring-loaded trigger 3950 via a sliding shaft 3959. With this embodiment, the user is able to communicate to the acquisition system that the probe is in an active state, during which its coordinates can be recorded, by actuating the TMSM relative to the tracked DRF on the tool, as described previously in detail in relation to FIGS. 10A-10G and 29A-29D. Additionally, other embodiments of this tool are designed for it to be used with one or more additional flexibility assessment devices, each equipped with uniquely identifiable tracked DRFs, so that their relative motion can be independently recorded while adjusting patient positioning, as described below in reference to FIGS. 40A-40C, and 42A-42K.

Figure 39C:
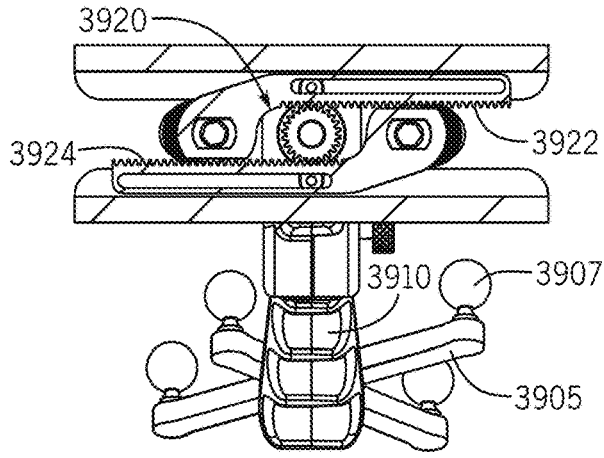
FIG. 39C illustrates a bottom view of the embodiment described above in relation to FIGS. 39A-B in accordance with some embodiments of the invention.
Figure 39D:
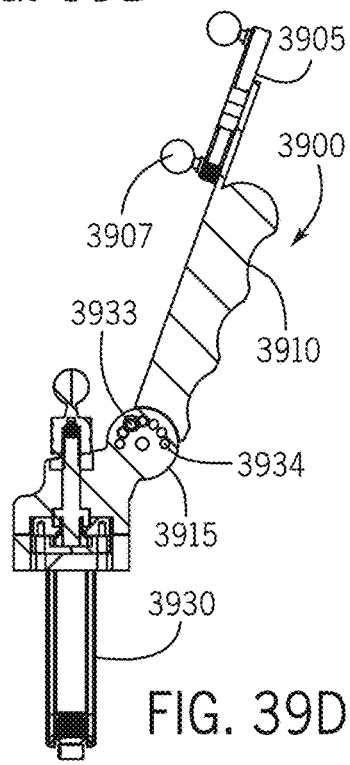
FIG. 39D displays a cross-sectional side view of the tool as described previously in relation to FIGS. 39A-39C in accordance with some embodiments of the invention.

FIG. 39C displays a bottom view of the embodiment described above in relation to FIGS. 39A-39B. From this view, the width-adjustment mechanism 3920 is visualized with linear gears 3922, 3924, which allow for adjustment of the distance between the screw-interface components 3930 of the device to accommodate varying anatomical locations of screws with which it will interface. FIG. 39D displays a cross-sectional side view of the tool describe previously in relation to FIGS. 39A-39C. From this perspective, the retractable spring plunger 3933 is visualized, engaged within one of the detents 3934 at discrete angles, within the central device connection body 3915, for adjusting the angle of the tool's handle 3910. In this way, the tool handle 3910 can be adjusted such that it does not interfere with additional tools placed within the surgical site, as described below in relation to FIGS. 40A-40C and 42A-42K. It should be noted that this is only one embodiment of the handle 3910, in which it is joined at the middle of the width adjustment mechanism. In other embodiments, the tool's handle is joined at an off-center location on the width-selection mechanism, and in other embodiments, the tool's handle projects at non-orthogonal angles to the width-adjustment mechanism to allow for enhanced tracking-camera visibility of the tracked DRF markers (3907, 3954) and TMSM 3956 on each tool.

Figure 39E:
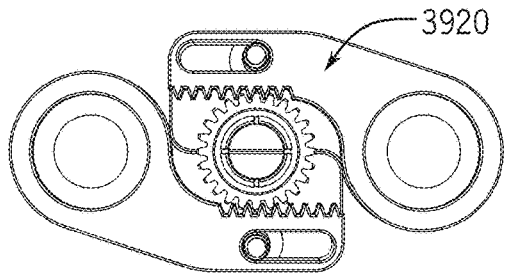
FIG. 39E illustrates a bottom view of a width-adjustment mechanism that allows for variation in the distance between screw-interface locations of the tool in accordance with some embodiments of the invention.
Figure 39F:
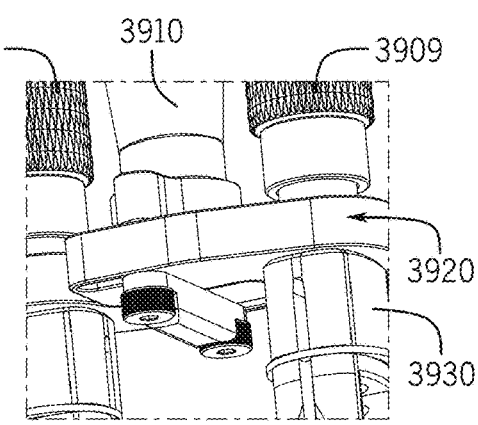
FIG. 39F illustrates a close-up perspective of the width-adjustment mechanism, thread-tightening knobs, and sleeve body of the device as described above in relation to FIGS. 39A-E in accordance with some embodiments of the invention.

FIG. 39E displays a bottom view of the width-adjustment mechanism 3920 that allows for variation in the distance between screw-interface locations of the tool. Further, FIG. 39F illustrates a close-up perspective of the width-adjustment mechanism 3920, thread-tightening knobs 3909, and sleeve body 3930 of the device as described above in relation to FIGS. 39A-39E in accordance with some embodiments of the invention.

Some embodiments can be equipped with the quarter-turn tip as described in relation to FIGS. 36A-36I to mate with the screws described. Other embodiments of the device include variations in the screw interface components such that they are able to mate with crossbar-equipped screws, as previously described. For embodiments interfacing with screws of this design, the screw-interface components are designed with the quarter-turn mechanism previously described in relation to FIGS. 3B, 33D-33F, and 44D.

FIGS. 40A-40C display the application of the flexibility assessment device previously described in detail in relation to FIGS. 39A-39E, as applied to an anatomical model of the spine. The figures show the application of the device as applied across spinal levels L1-S1, an example assessment region. Because the assessment device tools both contain tracked DRFs, their location and pose are tracked during manipulation of the spine such that the maximum and minimum angles as well as positions of the assessment devices can be recorded and the calculations displayed to the user. Furthermore, other embodiments of this device allow for the relative position of two or more of these devices to lock to one another and allow for the insertion of hardware to fix the spine into that conformation, as described below in reference to FIGS. 41A-41C, and 42A-42K.

FIG. 40A illustrates a lateral view of a spine model with a straight curve, and two flexibility assessment tools engaged with the model in accordance with some embodiments of the invention. FIG. 40A displays a straight curve 4010a, and two flexibility assessment tools (4077a, 4077b) engaged with the model and screw-interface components 4015, 4018. In this non-limiting embodiment, the user's hand 4008 interfaces with the handle of each assessment tool 4077a, 4077b and each tool is equipped with a unique tracked DRF (4076a, 4076b) to enable tracking of the device's location and pose in 3D space by a 3D-tracking camera (not shown). In this embodiment, the width and height between the screw-interface components are fixed. Within this configuration, when the assessment devices are activated, their relative 3D angles (4075a, 4075b) can be calculated, and projected onto anatomical reference planes. In FIG. 40A, the angle between handles shown is 10 degrees, which can be displayed to a user as the maximum limit of spine flexion.

FIG. 40B displays one embodiment of two flexibility assessment devices (4077a, 4077b) interfacing with a spine model with a lordotic curve 4010b. 3D-tracking acquisition systems can display relative angles (4075a, 4075b) and positions to a user, as described above in relation to FIG. 40A, and as applied to this embodiment, can display the maximum limit of spine extension to be 45 degrees. Further, FIG. 40C displays an embodiment of the invention from a 3D-tracking camera (not shown) perspective. Both tool's unique tracked DRFs 4076a, 4076b are shown, as well as the mirrored angles of the handles relative to the screw-interface components of the device. Different embodiments of the device position the handles at varying angles to the width adjustment mechanism, and also possess spring-loaded triggers (not shown), to communicate the probe's active state to the acquisition system, as described above in relation to FIG. 39B.

FIGS. 41A-41D displays an embodiment of the flexibility assessment device, described previously in detail in relation to FIGS. 39A-39F and 40A-40C, equipped with detachable components to allow for the removal of the tool handle and body without detaching the screw-interface components. The removal of the handle allows for retaining rigid fixation on the screws while regaining workable space within the surgical site. It also enables utilization with locking the alignment into a certain configuration on one side, removing the handle and body of the device, and then placing a rod to secure the spine in that configuration, as will be described in detail below in FIGS. 42A-42K.

Figure 41A:
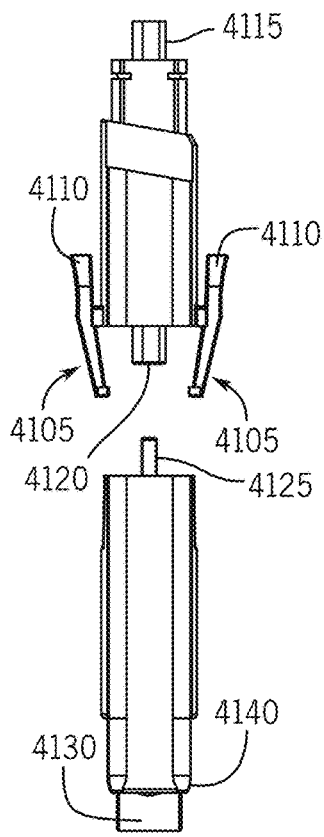
FIG. 41A illustrates a side view of one embodiment of the screw-interface components of the flexibility assessment device described previously in relation to FIGS. 34A-34F, 35A-35E, and 36A-36G, 39A-39F, and 40A-40C in accordance with some embodiments of the invention.

Referring to FIG. 41A, illustrating a side view of one embodiment of the screw-interface components of the flexibility assessment device described previously, where a detachable component of the screw-interface devices mates with the bottom component via spring-loaded snap arms 4105 that can be released by pressing the release tabs 4110. The top component contains a post 4115 for the thread-tightening knob (not shown) previously described in relation to FIGS. 34, 34A-34F, 35A-35F, and 36A-36I. The mating interface of the two components contains a center-alignment post 4120 and peripheral alignment pins 4125 to facilitate alignment and enable rigid mating of the components.

Figure 41B:
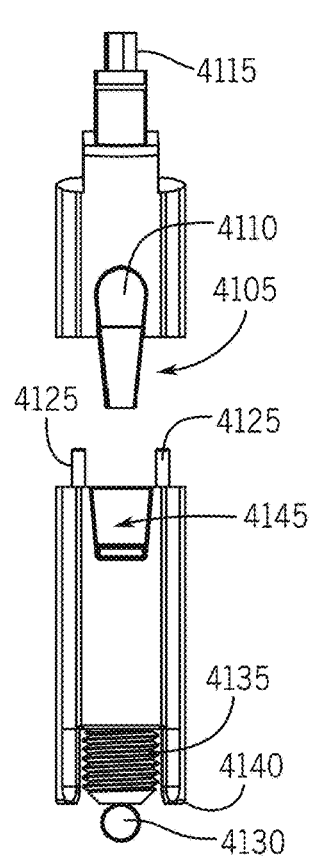
FIG. 41B illustrates a front view of the embodiment described above in relation to FIG. 41A in accordance with some embodiments of the invention.

FIG. 41B displays a front view of the embodiment described above in relation to FIG. 41A. This view of the embodiment displays the screw-interface rod 4130 intended to interface with the top surface of the pedicle screw head while the device threads 4135 interface with the tulip head threads (not shown), side-tab extensions 4140, snap-arm mating detent 4145, and spring-loaded snap arm 4105. Further, FIG. 41C illustrates the device of FIGS. 41A-41B assembled with a flexibility assessment device previously described in relation to FIGS. 39A-39F, and 40A-40C in accordance with some embodiments of the invention. For example, FIG. 41C displays an embodiment of the device in which the detachable screw-interface components previously described in relation to FIGS. 41A-B are assembled with a flexibility assessment device previously described. In this embodiment, one side of the flexibility assessment device is equipped with a detachable screw-interface component, and the other is equipped with a non-detachable component, as described in FIGS. 34, 34A-34F, 35A-35E, and 36A-36I. For example, the screw-interface rod 4130 is visible on the non-detachable screw interface component, as is the thread 4135 to interface tulip heads. The side-tab extension 4140, snap-arm mating detent 4145, and spring-loaded snap arm 4105 are visualized on the detachable screw-interface component. Further, on the flexibility assessment device, previously described in relation to FIGS. 39A-39B and 40A-40C, the tracked DRF 4150, handle 4160, retractable spring plunger 4165, width-adjustment knob 4170, TSM 4175 for width-adjustment knob 4170, thread-tightening knob 4178, TSM 4182 for thread tightening knob 4178, width-adjustment mechanism 4184, and sleeve body 4186 are all displayed. Additionally, the detachable screw interface component is shown interfacing with a tulip head 4192 attached to a pedicle screw (threads not shown) shaft 4188.

Figure 41D:
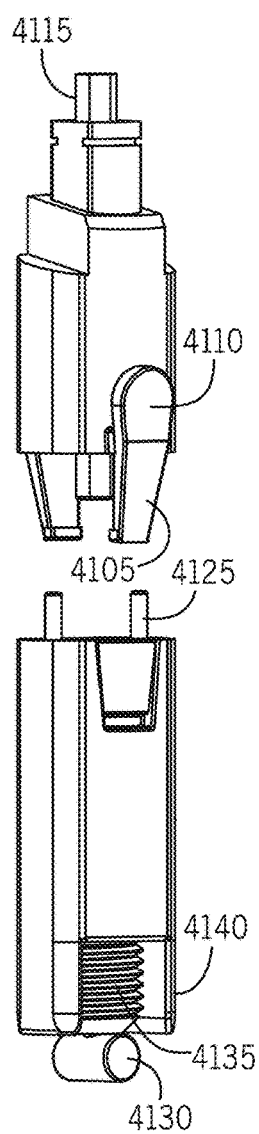
FIG. 41D illustrates a perspective assembly view of a detachable screw-interface component displaying release tabs, center-alignment post, peripheral alignment pins, screw-interface rod, side-tab extensions, and spring-loaded snap arm in accordance with some embodiments of the invention.
Figure 41C:
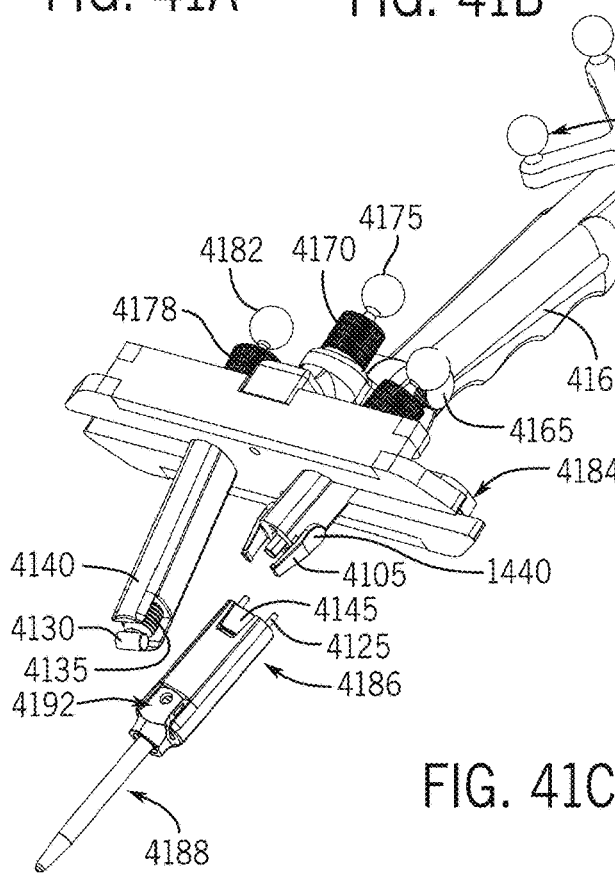
FIG. 41C illustrates the device of FIGS. 41A-41B assembled with a flexibility assessment device previously described in relation to FIGS. 39A-39F, and 40A-40C in accordance with some embodiments of the invention.

FIG. 41D displays a perspective assembly view of one embodiment of the detachable screw-interface component displaying the release tabs 4110, center-alignment post 4120, peripheral alignment pins 4125, screw-interface rod 4130, side-tab extensions 4140, and spring-loaded snap arm 4105.

Some embodiments include an assessment device equipped with detachable screw interface components and adjustable cross-linking devices. For example, in reference to FIGS. 42A-42C, some embodiments include a spinal flexibility assessment device as described above in relation to FIGS. 39A-39F, 40A-40C, and 41A-41D, equipped with a fixation mechanism, described below in reference to FIGS. 43A-43F, that allows for the flexibility assessment devices to be locked in a particular position, and removed from one side to accommodate the placement of a fixation rod on the contralateral side. In this way, the user can position the spine into a desired conformation with feedback from the 3D tracking acquisition system tracking the location of each flexibility assessment device. It should be noted that the feedback displayed to the user can either be relative positioning of the tools, or relative positioning of initialized vertebra, as described in detail below in reference to FIG. 70.

Figure 42A:
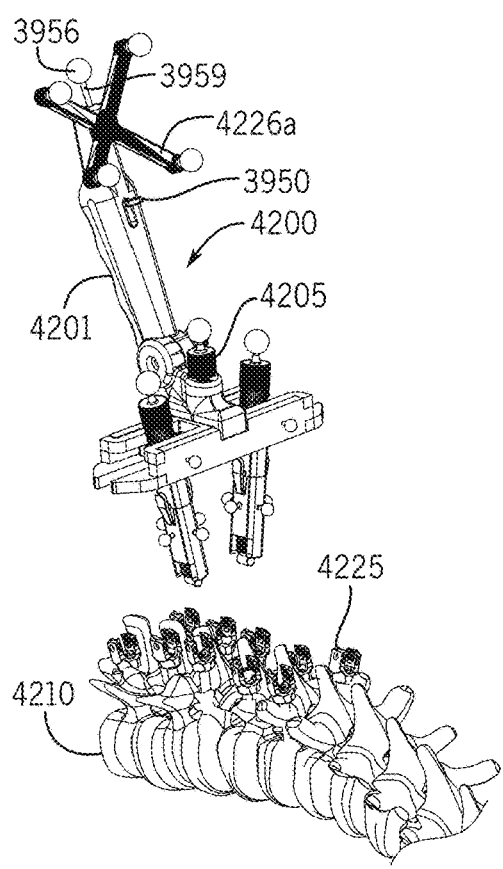
FIG. 42A illustrates the flexibly assessment device of FIGS. 39A-39F, and 40A-40C equipped with detachable screw interface components, previously described in FIG. 41 with adjustable cross-linking devices, described below in reference to FIG. 43A-43F in accordance with some embodiments of the invention.

One non-limiting embodiment is shown in FIG. 42A, and shows the flexibility assessment device 4200, as described previously equipped with detachable screw interface components with adjustable cross-linking devices. This embodiment of the device includes a width-adjustment mechanism 4205 (e.g., 4170 of FIG. 41C) to match the distance between screw-interface components with the distance between implanted pedicle screws and their associated tulip heads 4225. As shown, this embodiment is intended to be used after the pedicle screws have been placed into the spine 4210 during surgery. In other embodiments (not shown), this device can be equipped with a bone-clamping mechanism that enables it to substantially rigidly fix to the spine in the absence of pedicle screw and tulip heads with which to interface.

Figure 42B:
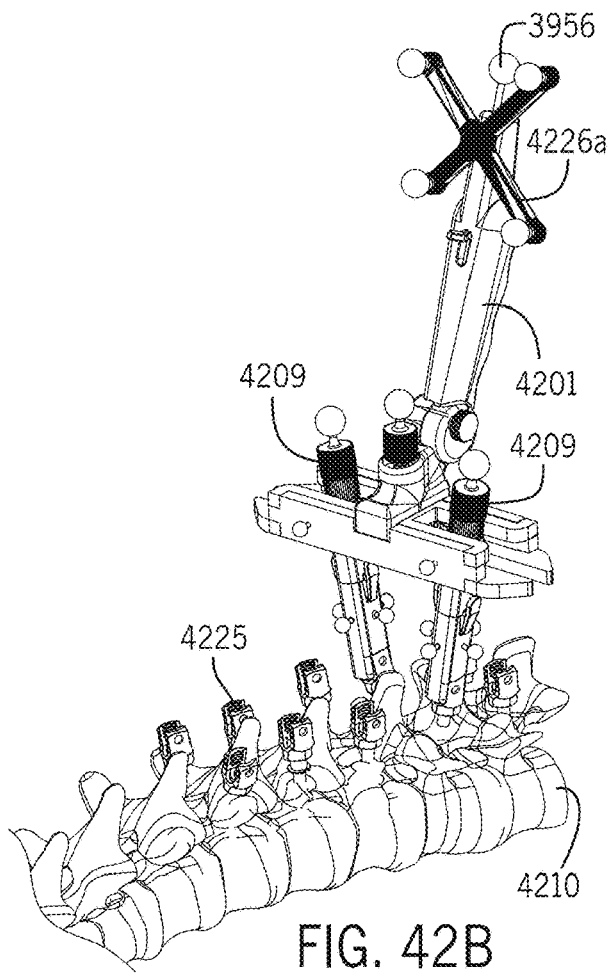
FIG. 42B illustrates the flexibility assessment device described previously in relation to FIG. 42A substantially rigidly coupled to the pedicle screws by interfacing with the tulip heads in accordance with some embodiments of the invention.

Further, FIG. 42B illustrates the flexibility assessment device described previously in relation to FIG. 42A substantially rigidly coupled to the pedicle screws by interfacing with the tulip heads in accordance with some embodiments of the invention, and shows thread-tightening knob 4209. Illustrated is the flexibility assessment device, where the screw interface components can substantially rigidly couple to the tulip heads via the thread-tightening-knobs 4209. When they are tightly coupled to the tulip heads, the tolerance between the pedicle screw shaft and polyaxial tulip head is removed, thus resulting in a substantially rigidly fixed system between the screw shaft, tulip head, and flexibility assessment device.

Figure 42C:
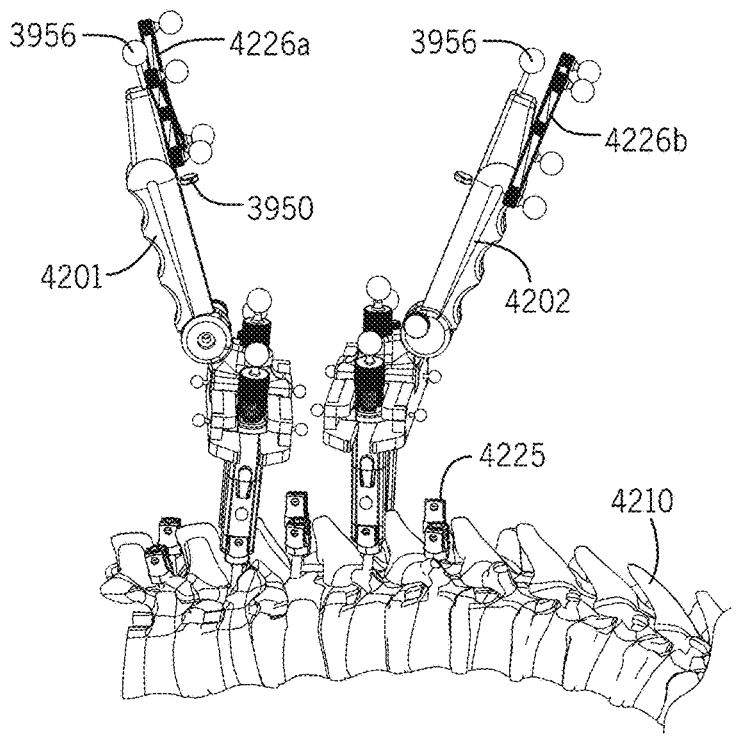
FIG. 42C illustrates a second flexibility assessment device interfacing with a spinal level at a user-defined distance from the already mated device described previously in relation to FIGS. 39A-39F, 41A-41D, and 42A-42B in accordance with some embodiments of the invention.
Figure 42D:
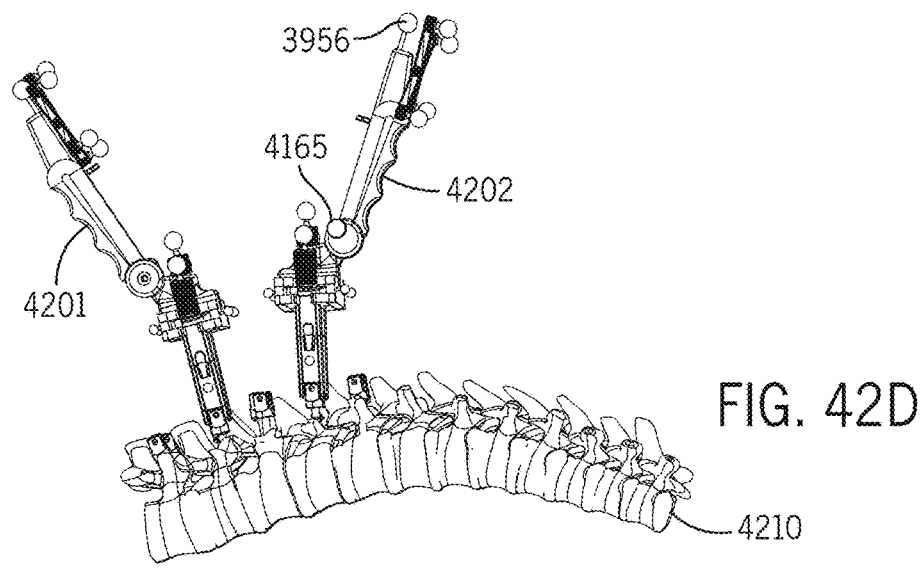
FIG. 42D illustrates two mated flexibility assessment devices, as previously described in relation to FIGS. 39A-39F, 41A-41D, and 42A-42C in accordance with some embodiments of the invention.

Further, FIG. 42C displays a second flexibility assessment device 4202 interfacing with a spinal level at a user-defined distance from the already mated device 4201 described previously. Because both assessment devices possess unique tracked DRFs 4226a, 4226b, the 3D-tracking acquisition system is able to distinguish them from one another. Further FIG. 42D displays the two mated flexibility assessment devices 4201, 4202. After the devices are substantially rigidly attached to the spine, their handles can be adjusted relative to their screw-interface components by releasing and subsequently re-engaging the retractable spring plunger 4165 to enable greater degrees of freedom without the devices obstructing one another. The 3D acquisition system interprets the position of the handle by comparing the individual tool's tracked DRF to the location and/or of the TSMs located over the corresponding tools' width-adjustment mechanism or screw-interface components. Furthermore, in this embodiment, after the assessment devices are substantially rigidly fixed to the spine 4210 through mating with screws 4225, they can be placed in an active state by user-triggering (trigger 3950 as seen previously in relation to FIG. 39B) of a TMSM 3956 coupled to a depressible shaft 3959 within each device handle 4201, 4202, and then manipulate the contour of the spine until the user is satisfied with the software-displayed measurements. The relative contour of the spine between devices can then be held in place by utilization of adjustable cross-linking devices, described below in reference to FIGS. 42E-42I, and 43A-43D.

Figure 42E:
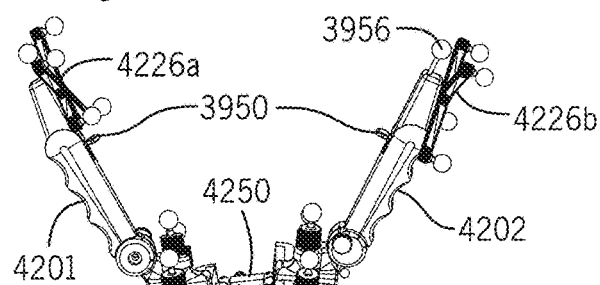
FIG. 42E illustrates two flexibility assessment devices substantially rigidly attached to the spine as described previously in relation to FIGS. 39A-39F, 41A-41D, and 42A-42D in accordance with some embodiments of the invention.
Figure 42F:
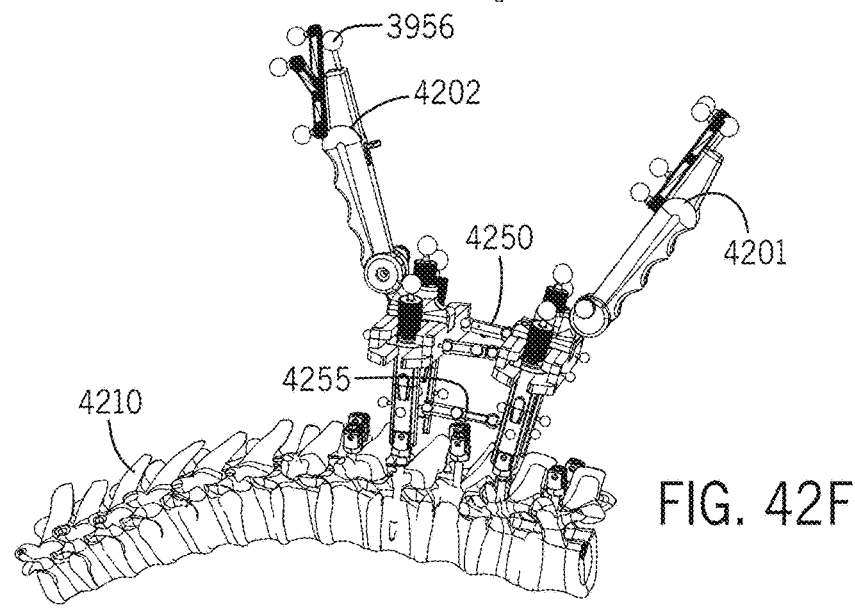
FIG. 42F illustrates two flexibility assessment devices substantially rigidly attached to the spine as described previously in relation to FIGS. 39A-39F, 41A-41D, and 42A-42F in accordance with some embodiments of the invention.
Figure 42G:
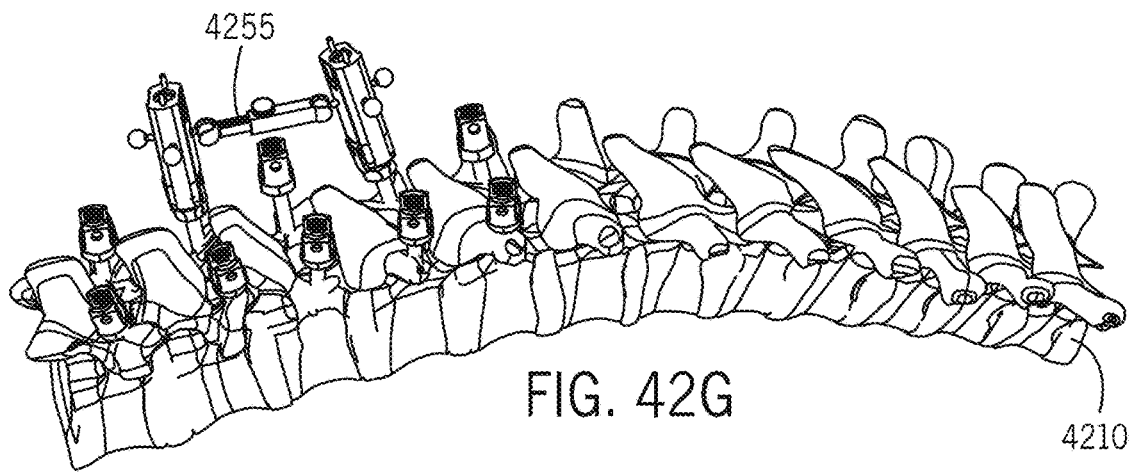
FIG. 42G illustrates an instrumented spine previously described in relation to FIGS. 42A-42F in accordance with some embodiments of the invention.

FIG. 42E displays two flexibility assessment devices substantially rigidly attached to the spine as described previously in relation to FIGS. 39A-39F, 41A-41D, and 42A-42D. When the devices are positioned in a way such that the spine 4210 is held in a desirable contour, they can be locked together utilizing adjustable cross-linking devices 4250 attached to the width-adjustment devices 4201, 4202. Further, FIG. 42F illustrates two flexibility assessment devices 4201, 4202 substantially rigidly attached to the spine 4210, further including an adjustable cross-linking device 4250 for screw-interface device 4255. For example, in addition to substantially rigidly connecting the devices between the width-adjustment mechanisms, the screw-interface components can also be substantially rigidly fixed to one another via the adjustable cross-linking devices 4255. FIG. 42G illustrates an instrumented spine 4210 previously described in relation to FIGS. 42A-F in accordance with some embodiments of the invention, and shows adjustable cross-linking device for screw-interface device 4255 coupled to the spine 4210. In this instance, the detachable screw-interface components, as described enable the body and one screw-interface component of the assessment device to be removed to leave behind two screw-interface components, held in place by the coupled, adjustable cross-linking device 4255.

Figure 42H:
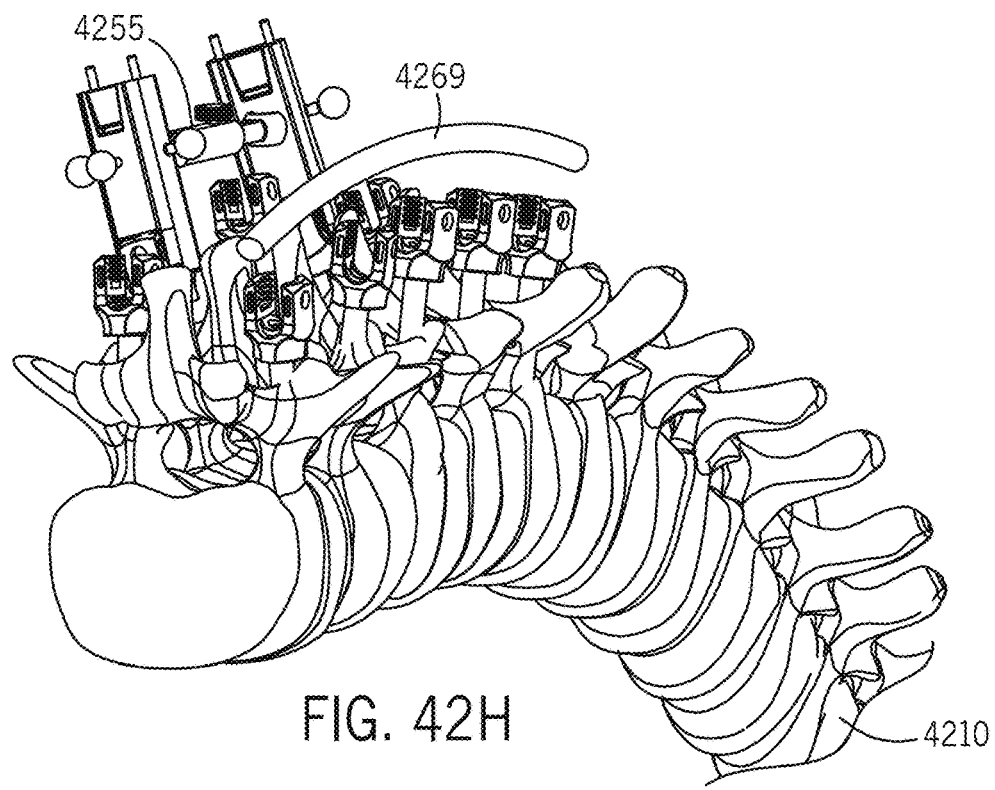
FIG. 42H displays an instrumented spine previously described in relation to FIGS. 42A-42G in accordance with some embodiments of the invention.
Figure 42I:
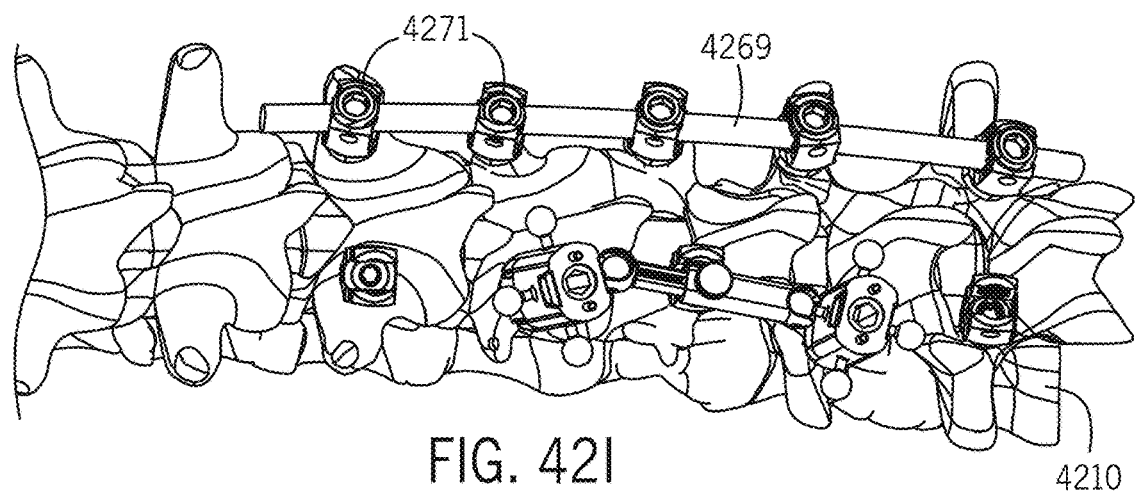
FIG. 42I illustrates an instrumented spine previously described in relation to FIGS. 42A-42H in accordance with some embodiments of the invention.
Figure 42J:
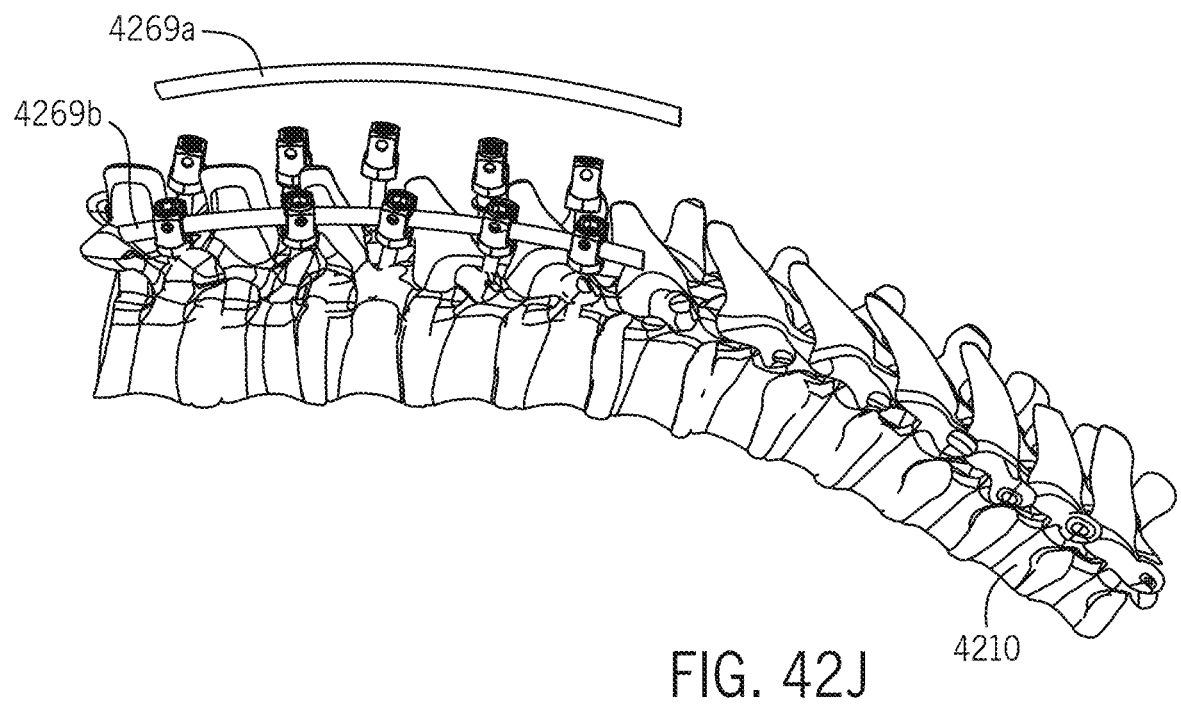
FIG. 42J illustrates an instrumented spine previously described in relation to FIGS. 42A-42I in accordance with some embodiments of the invention.
Figure 42K:
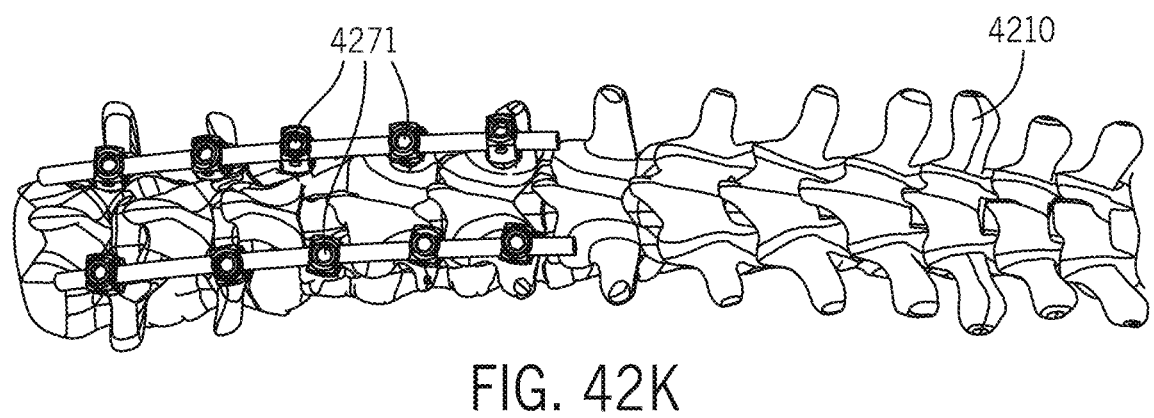
FIG. 42K illustrates an instrumented spine previously described in relation to FIGS. 42A-42J in accordance with some embodiments of the invention.

FIG. 42H displays an instrumented spine 4210 previously described in relation to FIGS. 42A-42G. With the spine 4210 held in a fixed contour, the removed components of the flexibility assessment devices allow for the placement of a rod 4269 within the exposed set of contralateral screws. Further, FIG. 42I illustrates an instrumented spine previously described in relation to FIGS. 42A-42H in accordance with some embodiments of the invention. The rod 4269 placed within the exposed set of pedicle screws is secured in place with cap screws 4271. With the rod 4269 holding the spine 4210 in the desired contour, the remaining screw-interface components are now able to be removed. Further, FIG. 42J displays an instrumented spine 4210 previously described in relation to FIGS. 42A-42I. With the contour of the spine held in place with the already-secured rod 4269b, the remaining components of the flexibility assessment device shown in FIG. 42I are removed, enabling placement of a second rod 4269a within the screws. Further, FIG. 42K displays an instrumented spine previously described in relation to FIGS. 42A-42J. This figure displays the final step of securing the adjusted alignment of the spine achieved with the lockable pair of flexibility assessment devices. During this step, the second rod is secured with cap screws 4271.

Figure 43A:
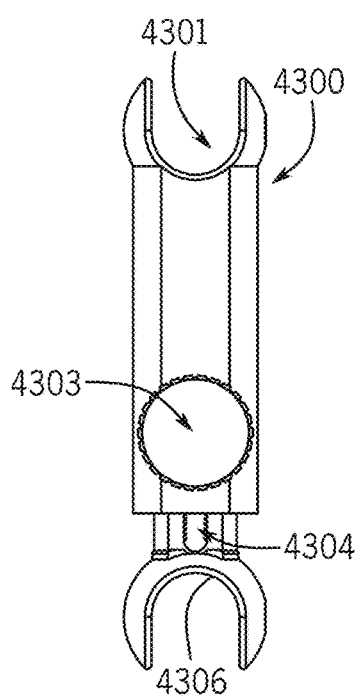
FIGS. 43A-43D includes views of an adjustable cross-linking device in accordance with some embodiments of the invention.

FIG. 43A displays a top view of one embodiment of the device 4300 which is an adjustable cross-linking device, as described above in relation to FIGS. 42A-42K, mates with components of the flexibility assessment device, as described previously in relation to FIGS. 39A-39F, 40A-40C, 41A-41D, and 42A-42K. This embodiment consists of an outer-slider ball socket 4301 designed to mate with protruding balls on components of the flexibility assessment device including the width-adjustment mechanism, as described previously in relation to FIGS. 39A-39F, 40A-40C, 41A-41D, and 42A-42K, and the screw-interface components of the device, as described previously in relation to FIGS. 34-36, 41A-41D. This embodiment also contains a retractable spring plunger 4303 with teeth that engages with an internal rack with teeth 4304. Additionally, there is an inner-slider ball socket 4306 designed to mate with a secondary flexibility assessment device component, as described previously in FIGS. 42A-42K.

Figure 43B:
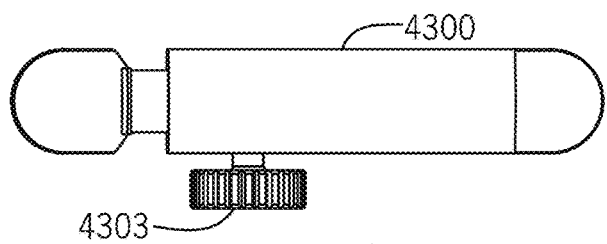
Figure 43C:
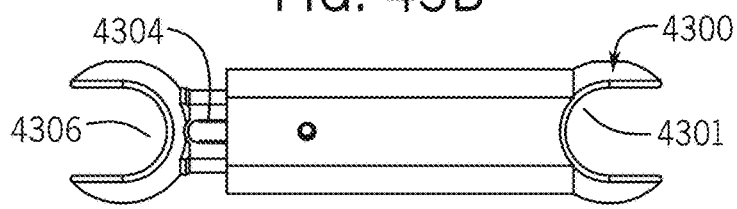
Figure 43D:
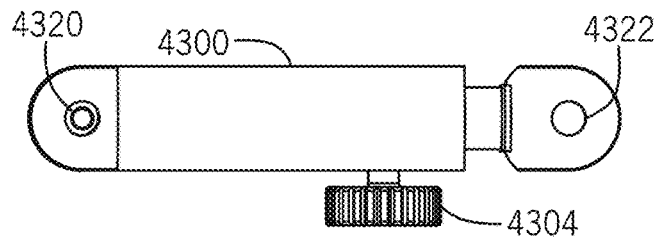

FIG. 43B displays a bottom view of one embodiment of the device 4300, shown previously in FIG. 43A, which is an adjustable cross-linking device, a described above in relation to FIGS. 42A-42K. From this perspective, the outer-slider ball socket 4301, internal rack with teeth 4304 and inner-slider ball socket 4306 are all visible. In order to adjust the length of the adjustable cross-linking device, a user depresses the retractable spring plunger with teeth such that it disengages from the internal rack with teeth. When the length is as desired, the user releases the retractable spring plunger with teeth such that it re-engages with the internal rack with teeth 4304. FIG. 43D illustrates a retractable spring plunger 4303 with teeth 4304, outer-slider set screw 4320, and inner-slider set screw 4322.

Figure 43E:
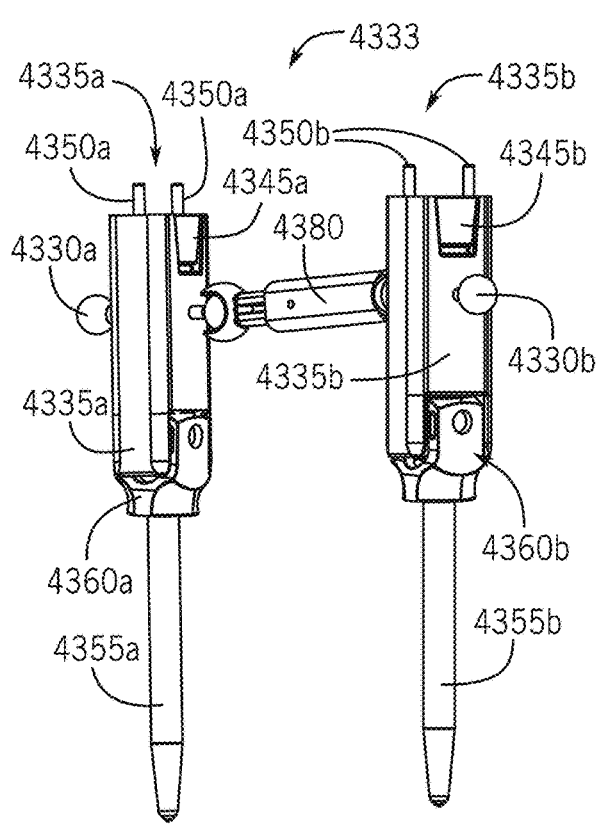
FIGS. 43E-43F illustrate views of an adjustable cross-linking device in accordance with some embodiments of the invention.
Figure 43F:
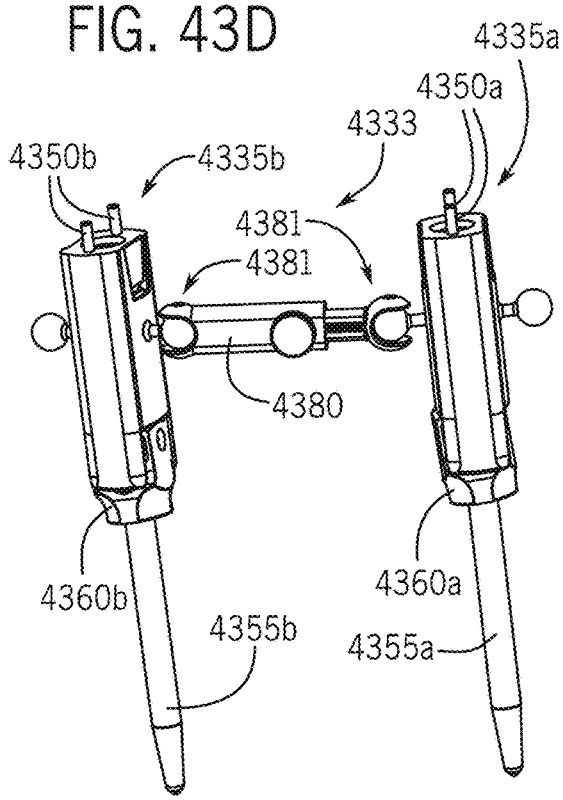

FIGS. 43E and 43F shows an adjustable cross-linking device 4333, described previously in relation to FIGS. 42A-43K, 43A-43D, engaged with detachable screw-interface components (shown here as 4335a, 4335b, and adjustably coupled through coupler 4380, with rotation balls or joints 4381) of the flexibility device previously described in relation to FIGS. 41A-41C. As shown, coupled components can include fixation ball 4330a, 4330b, snap-arm mating location 4345a, 4345b (e.g., shown previously in relation to FIG. 41B as snap-arm mating detent 4145), peripheral alignment pin(s) 4350a, 4350b, pedicle screw shaft 4355a, 4355b, and tulip heads 4360a, 4360b. In this embodiment, the detachable screw-interface devices 4335a, 4335b possess a fixation ball 4330a, 4330b to interface with the inner and outer-slider ball sockets, a snap-arm mating locations 4345a, 4345b, and peripheral alignment pins 4350a, 4350b. Further, screw-interface components are engaged with the tulip heads 4360a, 4360b of pedicle screw (threads not shown) shafts 4355a, 4355b.

Figure 44A:
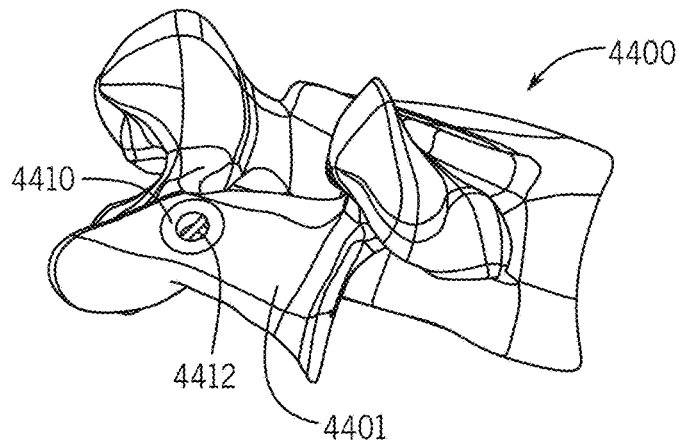
FIG. 44A illustrates a bone-implanted fiducial equipped with a crossbar and substantially rigidly fixed to the lamina of a vertebra as previously described in relation to FIGS. 3A-3C in accordance with some embodiments of the invention.
Figure 44B:
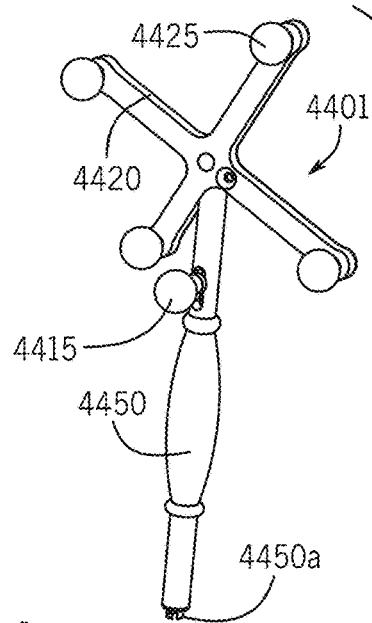
FIG. 44B illustrates a process view of a pre-engagement of a bone-implanted fiducial and bone-fiducial mating screwdriver equipped with a tracked DRF and a TMSM coupled to a depressible sliding shaft at the end of the screwdriver in accordance with some embodiments of the invention.
Figure 44C:
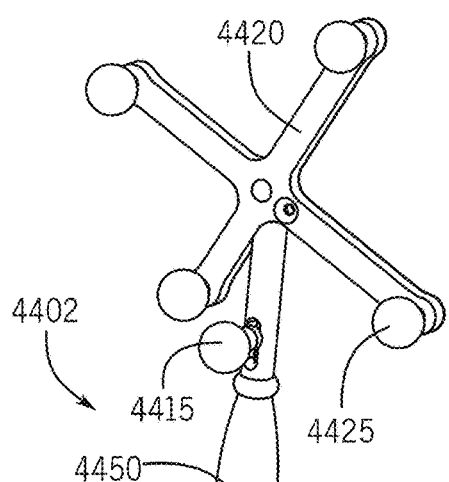
FIG. 44C illustrates an engagement of a bone-implanted fiducial and bone-fiducial mating screwdriver equipped with a tracked DRF and a TMSM coupled to a depressible sliding shaft at the end of the screwdriver in accordance with some embodiments of the invention.
Figure 44D:
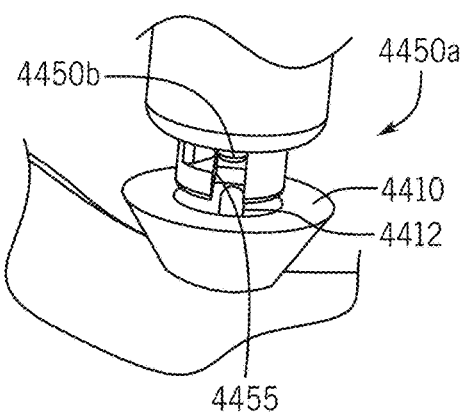
FIG. 44D illustrates a bone-implanted fiducia with crossbar and overlying bone-fiducial-mating screwdriver in accordance with some embodiments of the invention.

Some embodiments of the invention include a bone-implanted fiducial equipped with a rigid crossbar that substantially rigidly mates with a tracked probe equipped with a TMSM to indicate to the acquisition system when it is fully engaged. Because the probe is only able to mate with the fiducial in one conformation, when the tracked probe fully engages with the fiducial, the location and pose of the fiducial can be interpreted. If the fiducial has been previously initialized to the vertebra, reassessing the location and pose of the fiducial enables re-registration of the location and pose of the vertebra. Furthermore, if the fiducial is placed under surgical navigation, interfacing the probe with the fiducial enables rapid re-registration of bony anatomy for surgical navigation cases, providing value when anatomy moves relative to a reference DRF or when the anatomy changes conformation from when its imaging was last registered for surgical navigation. In this way, the bone fiducial serves as another method of rapid re-registration of anatomy, as similarly described in FIGS. 38, and 38A-38G. For example, FIG. 44A illustrates a bone-implanted fiducial equipped with a crossbar and substantially rigidly fixed to the lamina of a vertebra as previously described in relation to FIGS. 3A-3C in accordance with some embodiments of the invention. The bone-implanted fiducial 4410 is equipped with a rigid crossbar 4412 and substantially rigidly fixed to the lamina 4401 of a vertebra 4400 as previously described. Further, FIG. 44B illustrates a process view of a pre-engagement of a bone-implanted fiducial 4410 and bone-fiducial mating screwdriver 4450 equipped with a tracked DRF 4420 (composed of 3D-tracked markers 4425) and a TMSM 4415 coupled to a depressible sliding shaft (shown later as 4450b) at the end of the screwdriver in accordance with some embodiments of the invention. This embodiment is an alternative to other embodiments used to interpret the location and pose of a vertebra in space, as previously described in FIGS. 3A-3C, 29A-29C, 33A-33H, and 38, 38A-38G. In this embodiment, the probe tip 4450a is equipped with a quarter-turn mechanism to tightly engage with the bone-implanted fiducial. By fully engaging with the crossbar 4412 on the fiducial, the depressible sliding shaft is mechanically actuated to move the linked TMSM 4415 and thereby signal to the 3D-tracking acquisition system to record the coordinates of the screwdriver, and calculate the location and pose of the implanted-bone fiducial, and associated vertebra if it has been initialized. For example, FIG. 44C illustrates an engagement of a bone-implanted fiducial and bone-fiducial mating screwdriver equipped with a tracked DRF 4420 and a TMSM 4415 coupled to a depressible sliding shaft 4450b at the end of the screwdriver 4450, and FIG. 44C displays the bone-fiducial mating screwdriver 4450 engaged with the bone-implanted fiducial 4410. When fully engaged, as shown, the bone-fiducial mating screwdriver 4450 is aligned coaxially with the bone-implanted fiducial 4410, and the TMSM 4415 is actuated, indicating to the acquisition system that the screwdriver tip 4450b is fully engaged with the bone-implanted fiducial. Further, FIG. 44D illustrates a bone-implanted fiducial with crossbar and overlying bone-fiducial-mating screwdriver in accordance with some embodiments of the invention. In some embodiments, a quarter-turn mating tip 4455 and depressible sliding shaft 4450b. In some embodiments, the quarter-turn mating tip 4455 is shown as is the depressible sliding shaft 4450b which is depressed upon complete engagement between the screwdriver 4450 and fiducial 4410 (engaging around crossbar 4412). It should be noted that in other embodiments, the acquisition system can be triggered to calculate the location of the fiducial, based on user-input to the software, hand-triggering a TMSM or electronic communication system, and can be used for rapid re-registration of a vertebra's location within camera coordinates prior to rod implantation, as described below in FIGS. 45A-45B and 72.

Some embodiments of the invention include rapid re-registration with depth-stop-screws and depth-stop-engaging screw-assessment tool. For example, some embodiments include a system and method to enable rapid re-registration and 3D-rendering of a vertebra's relative location in space by utilizing a depth-stop equipped pedicle screw and depth-stop engaging assessment tool, as previously described in relation to FIGS. 38, and 38A-38G. In this embodiment, the depth-stop attached to the screw can be accessed by the depth-stop engaging assessment tool, with or without an implanted rod present, to accurately calculate the location and pose of the screw in 3D-tracking camera coordinates. If screws were initially placed under image guidance, the acquisition system has already stored and recorded the relative position of each screw to the vertebra in which they are implanted. With this information, after re-registering the new location of both screws in space, the acquisition software is able to reconstruct the location of the vertebra in which they are inserted. In this way, if a surgical navigation system becomes decoupled from the patient's anatomy, either through movement of the tracked DRF serving as a patient reference or through change in contour of the spine from the time the image was acquired, the system can be rapidly re-registered to the patient's current position in space.

FIG. 45A displays one embodiment of the invention in which two vertebra 4525a, 4525b are instrumented with depth-stop-equipped pedicle screws 4540, described previously in relation to FIGS. 38, 38A-38G, which can be registered in 3D space by having the depth-stop-engaging 3D-tracked tool 4505 interfaces with each screw on each vertebra. One embodiment of the 3D-tracked tool 4505 for registering the position and orientation of the screws comprises of a handle 4510, a depressible sliding shaft that mates with the screw depth-stop interface that actuates a TMSM 4511 to change the triggering state of the tool to active, and a 3D-trackable DRF 4515 of 3D-tracked markers in a unique configuration. If the screws were initially placed under surgical navigation, and the position of the screw shafts relative to the vertebrae are known, then assessment of screw shafts' location and pose for each vertebra, is able to yield a 3D rendering of each vertebra (shown as representations 4561, 4562) in space relative to one another. It should be noted that utilizing depth-stop-equipped pedicle screws and their associated assessment tool, is only one embodiment of obtaining the information needed for the software to make this assessment. Other embodiments include mating directly with screw heads coaxially to interpret their location and pose, as previously described in FIGS. 29A-29C, and FIGS. 33A-33H. In cases when an assessment of the screw, and thereby vertebrae locations, are desired after implantation of a rod, the depth-stop-equipped pedicle screws preserve access to the screw shaft with the depicted assessment tool. Further, FIG. 45B shows one embodiment of the invention previously described in FIG. 45A, in which case the position of vertebra #1 4525c has changed relative to that of vertebra #2 4525b. By engaging the depth-stop-equipped tracked assessment tool, into both depth-stop-equipped pedicle screws 4540 in vertebra 4525c and vertebra 4525b, the acquisition system's software can then reconstruct an updated rendering 4563 on the display monitor of each vertebra in their relative 3D position and orientation to one another.

In some embodiments, the probe depicted in FIG. 38, used to update 3D renderings of a vertebra via re-registration of screws can also be updated via mating with a bone fiducial, depicted in FIGS. 3A-3C and 44A-44D. Other embodiments include mating directly with bone-mounted, percutaneous, or skin-mounted fiducials that are initialized to anatomical landmark(s) of interest for 3D renderings.

Some embodiments of the invention can enable significantly reduced X-ray and radiation exposure during minimally invasive, as well as open, surgeries and procedures. In some embodiments, tracked surgical tools are able to be placed in the field of view of previously-acquired X-ray images, such that their projected outline can be displayed over anatomy visualized in a previously-acquired X-ray image. The acquisition software interprets the location of the tool surface relative to the X-ray emitter/detector and using that information is able to accurately display a real-time overlay of the tools' position on the previously acquired X-ray image, accounting for the appropriate size scaling of the tool's outline, as described below in reference to FIG. 71.

FIGS. 46A-46B illustrate a 3D tracking tool in accordance with some embodiments of the invention. In these embodiments, a 3D-tracked tool 4600 includes a handle 4610, tracked DRF 4605 (with markers 4607) and tool tip 4620 (which is often a coupled implant). It should be noted that in other embodiments of this invention, each mobile component of the surgical tool that is used, requires 3D-tracking relative to each of the other components within said tool. FIG. 46C displays one embodiment of the invention in which an X-ray emitter 4684 is equipped with a tracked DRF 4686 positioned in a known location relative to the emitter, and the X-ray detector 4682 can also be equipped with a tracked DRF 4699 positioned in a known location relative to the detector. With the X-ray system imaging a spine 4691 resting on an operative table 4683, the X-ray emitter produces a conical volume of its X-ray beam 4695. All objects within this conical volume are then projected onto the X-ray detector 4682. With known geometry of the X-ray system 4680, the location and pose of this conical volume 4695 is known relative to either of the tracked DRFs (4686, 4699) mounted to the X-ray system. With a 3D-tracking camera having recorded the location of the emitter, and thereby the conical imaging volume, when an X-ray is taken, the acquisition system can determine when any component of the tracked surgical tool enters within the volume. When the surgical tool 4689 is positioned within the volume, its virtual projection can be overlaid on the previously-acquired x-ray image, as shown in FIG. 46D. The proximity of the tracked tool's surface to the emitter, enables the acquisition software to determine its relative size scaling in the overlay image, as described below in reference to FIG. 71.

FIG. 46D illustrates a virtual overlay of a tracked surgical tool positioned close to the X-ray detector on top of an X-ray image of the spine in accordance with some embodiments of the invention. As shown, the X-ray image of spine 4601 includes an overlay image of surgical tool close to detector 4615a. This virtual overlay is updated in real-time as the tool moves relative to the previously acquired X-ray's conical volume as described below in reference to FIG. 71. FIG. 46E displays an embodiment of the invention previously described in FIG. 46C, with the tracked surgical tool 4689 positioned closer to the X-ray emitter. Further, FIG. 46F displays a virtual overlay of a tracked surgical tool in the X-ray image 4602, with the tool 4620a positioned close to the emitter, as shown in FIG. 46E. Because the tool's surface is located closer to the X-ray emitter, its virtual projection is scaled to be larger to match the case of if a real X-ray image was acquired of the tool in that position. The software interpretation of the tool's relative scaling size is described below in reference to FIG. 71. Further, FIG. 46G displays an X-ray image 4603 with a virtual overlay of a tracked surgical tool 4620b close to the emitter, turned 90 degrees, from the tool position previously described in FIGS. 46E-46F. In this way, the tool's real-time location in space relative to the previously acquired X-ray volume, can be displayed via an overlay onto the previously acquired X-ray image. In other embodiments, the virtually-overlaid tool 4689 can also be simultaneously overlaid or interfaced with other 3D-tracked surgical tools that are within, or outside of, the field of view of the X-ray volume 4695. In some embodiments, if 3D-tracked DRFs are mounted onto anatomical landmarks of interest that are also in the X-ray image, the 3D-tracked location and pose of the surgical tool 4689 can be overlaid while the anatomical structures in image also become virtually adjusted to reflect their movements relative to the C-arm DRFs (4699, 4684) and the main surgical tool 4689 (e.g., when the surgical tool 4689 with a coupled implant, such as a cage) is inserted between two vertebrae, with mechanically-linked DRFs, and the corresponding X-ray image virtual overlay adapts the position and orientation of the imaged vertebrae to reflect their approximate real-world positions and orientations relative to one another.

Some embodiments of the invention include components that make up the two-part system for a handheld mechanism of assessing the contour of the rod prior to implantation. For example, FIG. 47A displays components of an embodiment of a tracked end cap, used to substantially rigidly hold a rod, define anatomical reference planes relative to the 3D-tracking camera, and establish the coordinate system within which all coordinates of the rod's location will be recorded. Further, FIG. 47B displays components of an embodiment of a tracked slider tool, used in combination with the tracked end cap, to slide along the surface of a rod and interpret its coordinates within the coordinate system established by the tracked end cap, as described in detail below in reference to FIG. 74. As shown, some embodiments include an end cap handle 4720, mount 4722 for interfacing with the mount-mate 4714 containing anatomical axes reference arrow labels consisting of, but not limited to inferior 4718 and posterior 4719. This embodiment also consists of a rod mount hole 4712 to insert a rod and a threaded hole 4716 for a set screw to secure the rod in place relative to the end cap, a mounting platform 4710 for a tracked DRF, a tracked DRF 4730, and fasteners 4740. Some embodiments utilize a separate, tracked DRF, but in other embodiments, the DRF-based markers mount directly into the tool surface itself, as described below in reference to FIGS. 52A-52B, and 53A-53F. Furthermore, other assembled embodiments of this invention are shown below in reference to FIGS. 48A-48B, 49D, 50E, 51A-51C, 51H-51I, and 56A-56F.

Figure 47A:
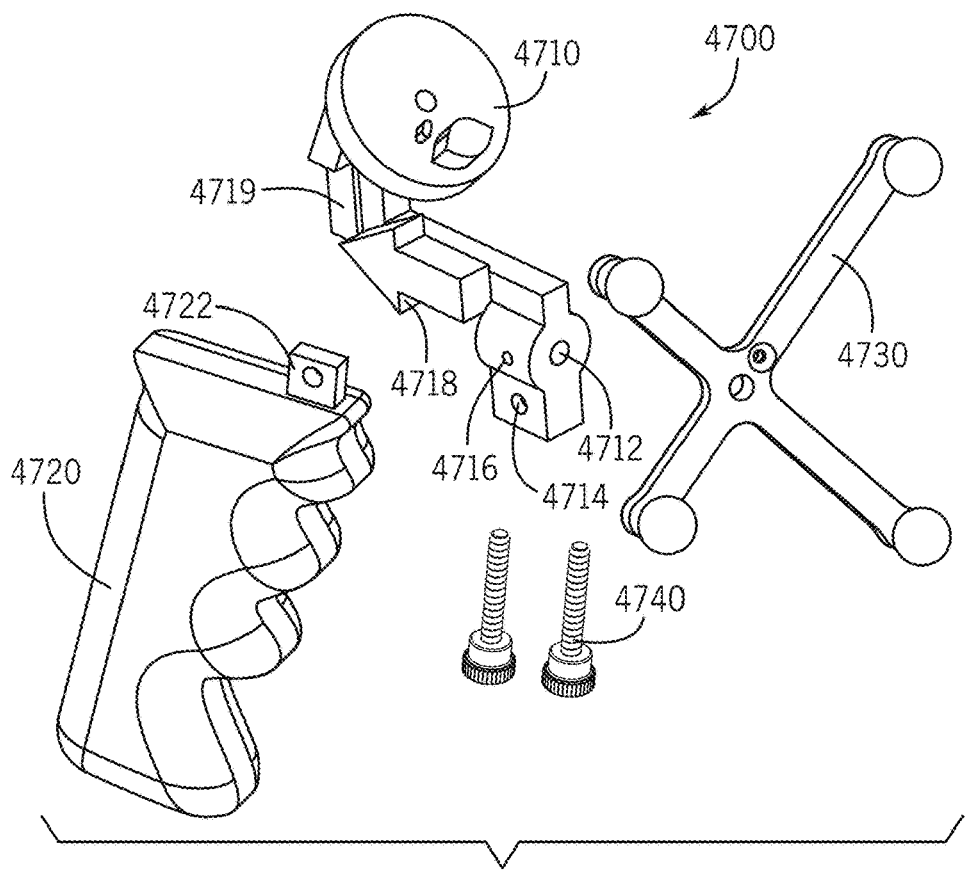
Figure 47B:
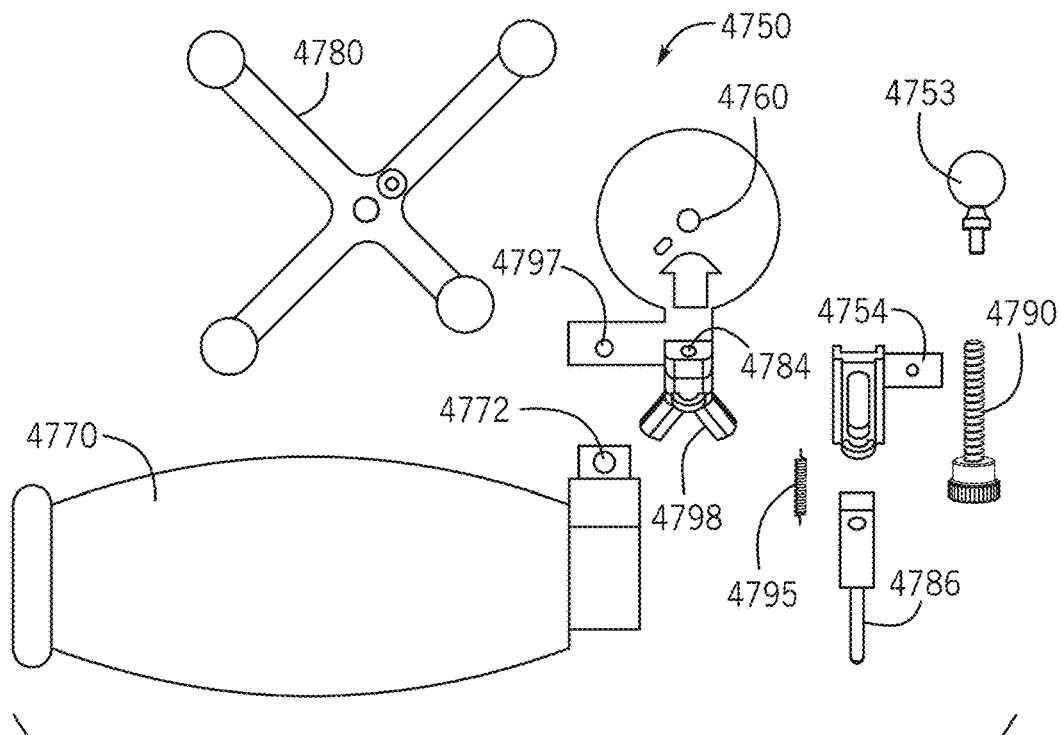

FIG. 47B displays the components of one embodiment of a tracked slider, designed to interface with a rod fixed to a tracked end cap, described previously in relation to FIG. 47A. This embodiment of the slider consists of a handle 4770, mount 4772 for joining with the mount-mate 4797, a rod-centering fork 4798 designed to straddle and center the rod during acquisition of the rod's contour, a through hole 4784 for receiving a depressible sliding shaft 4786 that mates with a TMSM mount 4754 via a fastener 4790 and is spring-loaded 4795. This embodiment also consists of a DRF mount 4760 to receive a tracked DRF 4780 and a TMSM 4753 attached to its corresponding mount. Other embodiments of this device are described below in reference to FIGS. 51D-51I. It should be noted that other embodiments of the rod-centering fork component, meant to interface with the rod, are ring-shaped designs meant to accommodate specific rod diameters, adjustable diameter rings, U-shaped designs, and polygonal-shaped designs including but not limited to triangular, rectangular, pentagonal, etc.

Figure 48A:
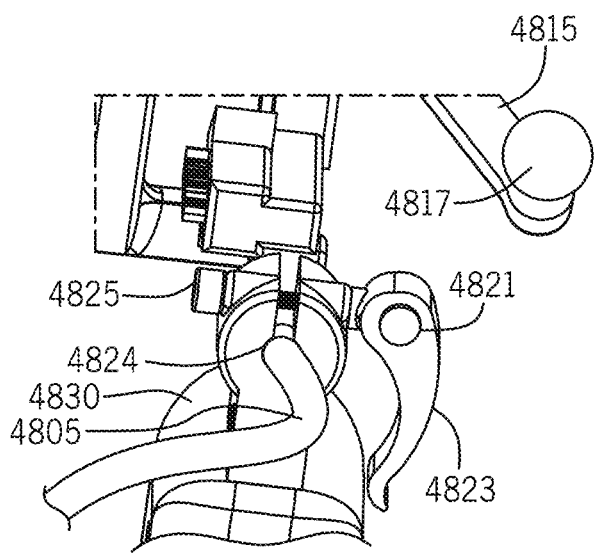
Figure 48B:
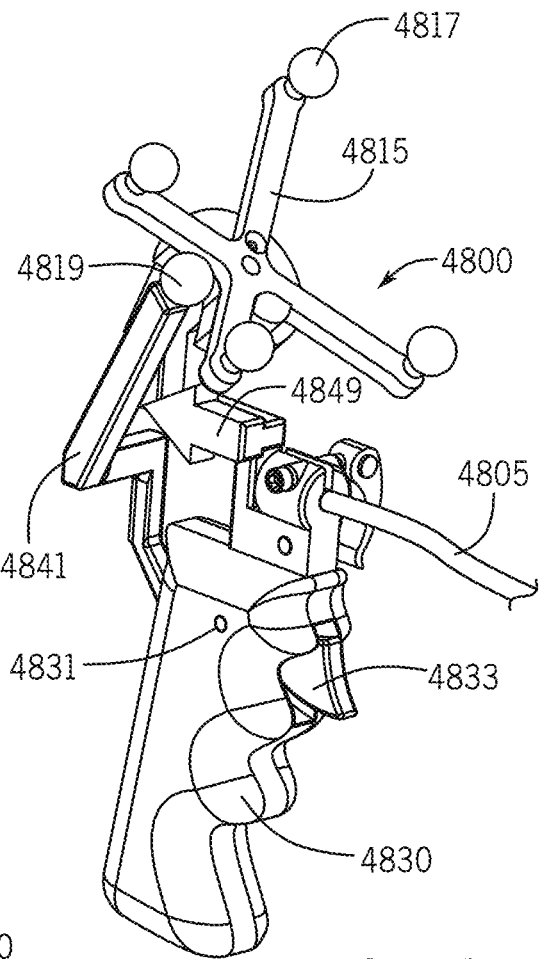
Figure 48C:
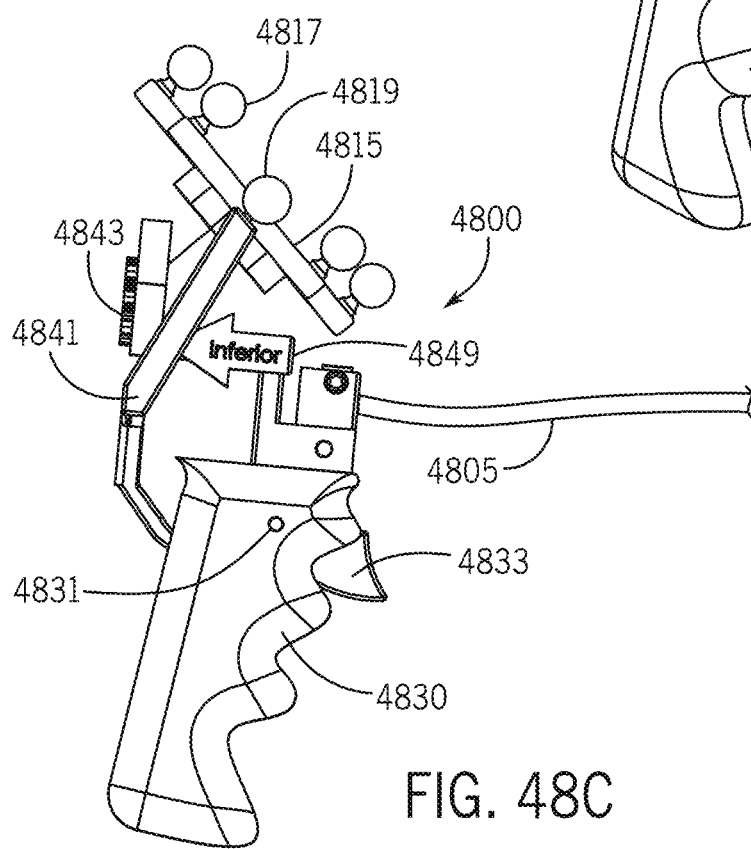

FIGS. 48A-48C relate to the tracked end cap previously described in relation to FIG. 47A. This embodiment is equipped with a spring-loaded TMSM actuated by a trigger on the handle used to communicate with the 3D-tracking acquisition system. Additionally, it contains an alternative method of fixing the rod than a set screw which was previously described in FIG. 47A. In this embodiment, the rod mount hole is split and tightened by the combination of a cam lever and threaded fastener for more rapid exchange and fixation of rods with the end cap, as well as maintaining the center alignment of the rod after fixation. For example, FIG. 48A illustrates a close-up view of a portion of an end cap in accordance with some embodiments of the invention, showing an assembly comprising a rod mount hole 4824, rod 4805, end cap handle 4830, cam lever 4823, hinge pin 4821, and threaded fastener 4825. The rod 4805 is inserted into the rod mount hole 4824 and secured in place by a cam lever 4823 rotating about a hinge pin 4821 to tighten against a threaded fastener 4825.

FIG. 48B illustrates a perspective view of an end cap 4800 assembled from components of FIG. 47A in accordance with some embodiments of the invention, and shows a rod 4805, trigger 4833, spring-loaded hinge 4831, trigger arm (4832, 4841), TMSM 4819, and end cap tracked DRF 4815 (with 3D-tracked markers 4817). The perspective shows the end cap previously shown in FIG. 47A, in which a rod 4805 is fixed. This embodiment also contains a hand-actuated trigger 4833 that rotates about a spring-loaded hinge 4831 inside the handle 4830, to actuate a trigger arm 4841 with a coupled TMSM 4819. This embodiment also contains a tracked DRF 4815 used to interpret the location of the end cap and its attached rod via a 3D-tracking camera (not shown). The location of the TMSM actuated by the trigger on this embodiment is compared to the location of the tracked DRF by the acquisition software, to determine if the user is triggering the device, as described in more detail below in reference to FIGS. 64A-64B and 65A-65E. It should be noted that in other embodiments of this device, the trigger can be actuated via other mechanisms such as covering or uncovering a tracked marker, as described previously in relation to FIG. 14, using linear motion rather than rotational, as described previously in relation to FIGS. 10A-10G, 29A-29D, 38, 38A-38G, 39A-39F, 42A-42K, 44A-44D, and 45A-45B, using electronic communication, or via direct user-input to a display monitor interface. Further, FIG. 48C illustrates a side view of the end cap 4800 of FIG. 48B in accordance with some embodiments of the invention. This perspective shows a rod 4805 fixed inside the end cap handle 4830, equipped with a trigger 4833 rotating on a spring-loaded hinge 4831 and mounting a TMSM 4819 on the trigger arm 4841. This figure also displays the tracked DRF 4815 used for interpreting the end caps location and pose in 3D space, and two relative anatomical axes indicators with inferior 4849 and posterior 4843 shown. This embodiment can be applied to any application mentioned below with regards to a tracked DRF-equipped end cap, in reference to FIGS. 49D, 50E, 51H-51I, 56, and 87A.

Some embodiments of the invention can be used to assess the contour of a rod prior to implantation via coupling an embodiment of a tracked end cap, previously described in FIGS. 47A and 48A-48C, with a fixed-base, single-ring assessment device. Rather than utilizing two handheld tools to assess the rod contour, as previously described, this device enables rod contour assessments via mounting the rod to one handheld end cap and passing the rod through a substantially rigidly-fixed ring device. Because the diameter of the ring is designed or adjusted to be closely matching the diameter of the rod, this embodiment forces the portion of the rod engaged with the ring to be nearly concentric with the ring. To compute the contour of the rod from this embodiment, the acquisition system interprets the path traveled by the end cap, rather than the path traveled by the slider relative to the end cap, as previously described. The software interpretation of this invention is described in detail below in reference to FIG. 75.

FIG. 49A displays assembly 4900 used to assess the contour of the rod prior to implantation, applied to when a rod is attached to a tracked end cap. This embodiment consists of a fixed base 4905 with a coupled post 4915 holding a rod-receiving ring 4910 designed for a rod of set diameter to pass through. Attached to the ring is a TSM 4903 as well as a hinge 4907 about which a hinged flap 4909, shown in the closed position, rotates. A TMSM 4920 is attached to the hinged flap and used to signal to the acquisition system when a rod is engaged with the ring 4910 via the TMSM 4920 attached to the hinged flap 4909 moving relative to the TSM 4903 attached to the ring. The software interpretation of this motion is completed by simply comparing the distances between the TSM 4903 and the TMSM 4920 when the hinge 4907 is closed versus opened. In this embodiment, the hinged flap 4909 stays closed in the absence of a rod through the force of gravity acting on the TMSM 4920 attached to the hinged flap 4909. In other embodiments, the hinged flap can also be spring loaded. It should be noted that in other embodiments of this design, the fixed base 4905 can be resting on a surface, or mounted to a rigid surface including a component of a robot.

FIG. 49B displays an embodiment of the invention described previously in FIG. 49A, except with the hinged flap 4909 and its attached TMSM 4920 in the open position, analogous to its position when a rod 4960 is inserted into the ring 4910 and pushing up on the hinged flap 4909. FIG. 49C displays a different view of the embodiment of the invention described previously in FIGS. 49A-B, with the hinged flap 4909 and its attached TMSM 4920 in the open position, and direct visualization of the rod-receiving ring 4910, held up from the base 4905 by a rigid post 4915. FIG. 49D illustrates the assembly of FIGS. 49A-49C coupled with a rod and tracked end cap previously described in relation to FIGS. 47A, and 48A-48B in accordance with some embodiments of the invention.

FIG. 49D displays an embodiment of the fixed-base, single-ring rod assessment device as previously described in FIGS. 49A-C, coupled with a rod 4960 and tracked end cap 4990, previously described in FIGS. 47A and 48. This embodiment shows the rod 4960 pushing the hinged flap 4909 out of the way and by doing so, actuating the TMSM 4920 attached to the hinged flap 4909. When the software acquisition system detects the distance between the TSM 4903 and the TMSM 4920 closer than that when the hinged flap is closed, it is triggered to record the coordinates of the end cap. The recorded coordinates of the end cap's path can then be used to calculate the contour of the rod, as described in detail in FIG. 75. It should be noted that in other embodiments, the user can trigger the acquisition via other triggering methods described previously in relation to FIG. 48B. Following registration of the contour of a rod attached to a tracked end cap, the tracked end cap can be used for the user to directly interface with the display monitor portraying the rod contour, as described in detail below in reference to FIG. 78.

FIGS. 50A-50D illustrates embodiments of a fixed-base, variable-ring, mobile rod assessment device in accordance with some embodiments of the invention. In some embodiments, the device assembly is described in FIGS. 49A-49D, in which it is able to accommodate the contour assessment of a series of rod diameters via a variable-ring-size selector component. After the user rotates the appropriate diameter ring in front of the hinged flap by using the retractable spring plunger, a rod of corresponding diameter attached to a tracked end cap can then be passed through the ring and have its contour interpreted by the same method previously described in relation to FIGS. 49A-49D.

Referring initially, FIG. 50A, illustrating a front view of an embodiment 5000, fixed base 5001 coupled to post 5005 is shown to which a revolving rod-width selector 5007 containing multiple rod-receiving rings 5009 of varying diameter is coupled via a fastener 5011 and can be rotated into preset angles via a retractable spring plunger 5013, and a TSM 5017 fixed to the post 5005. The rod-width selector 5007 containing rings of varying diameter is designed to enable this embodiment of the device to accommodate varying diameter rods rather than necessitating multiple devices.

FIG. 50B displays an oblique view of an embodiment 5001 of the device shown in FIG. 50A with the rotating rod-width selector 5007, retractable spring plunger 5013, and fastener removed. Discrete-angle detents 5015 receive the retractable spring plunger 5013 at set angles. A hinge 5019 interfaces with a hinged flap 5021, shown in the closed position, and with an attached TMSM 5023, as previously described in relation to FIGS. 49A-49D. FIG. 50C displays a rear view an embodiment 5002 of the invention shown in FIG. 50B. FIG. 50D displays an embodiment 5003 of the invention as described previously in relation to FIGS. 50A-C, interfacing with a rod 4960 passing through one of the fixed rings and pushing the hinged flap 5021 and its attached TMSM 5023 to the open position.

FIG. 50E illustrates the fixed-base, variable-ring, mobile rod assessment device of FIGS. 50A-50D engaged with a rod 4960 coupled to an end cap 5095 in accordance with some embodiments of the invention. As described previously in FIG. 49D, the end cap 5095 is used to track the path of the end of the rod 4960 as its length is passed through the fixed ring. The software to calculate the rod's contour from this interaction is described below in reference to FIG. 75. It should be noted that the hinged flap 5021 shown in this figure is only one embodiment of the invention. Other embodiments include a linearly-actuated TMSM 5023 that is moved when the rod 4960 is passed through the fixed ring. Following registration of the contour of a rod attached to a tracked end cap, the tracked end cap can be used for the user to directly interface with the display monitor portraying the rod contour, as described in detail below in reference to FIG. 78.

Some embodiments of the invention include a handheld, mobile rod contour assessment device. In reference to FIGS. 51A-51I, some embodiments include a method of using two handheld tracked devices to assess the contour of a rod prior to implantation. To utilize these embodiments to register the contour of a rod, the rod is substantially rigidly fixed within the tracked end cap, as previously described in FIGS. 48A-C, 49D and 50E, and then the tracked slider, previously described in FIG. 47B, is slid over the surface of the rod one or more times. For example, FIG. 51A displays a side view of one embodiment 5100 of the invention which is a tracked end cap, previously described in FIGS. 47A, 48, 49D, and 50E. It consists of a handle 5101, rod mount hole 5103, anatomical axes reference labels (5105, 5107), a tracked DRF 5189 (made of 3D-trackable markers 5188 in a unique configuration), a set screw 5108 to fasten the DRF mount to the handle 5101, and a set screw 5109 for substantially rigidly fixing the rod in place. When inserted and fixed within this device, the rod is interpreted by the acquisition software relative to the anatomical labels contained on the device. FIG. 51B displays a front view of one embodiment of the invention, a tracked end cap, shown previously in FIG. 51A. FIG. 51C displays a rear view of one embodiment of the invention, a tracked end cap, shown previously in FIGS. 51A-51B.

FIG. 51D displays an assembled view of one embodiment of the invention, a tracked slider, described previously in relation to FIG. 47B, consisting of a handle 5129, rod-centering fork 5130, tracked DRF 5136 (made of 3D-trackable markers 3135), spring-loaded depressible shaft 5140, and shaft-mounted TMSM 5145. When used with a rod fixed to the tracked end cap previously described in relation to FIGS. 51A-51C, this embodiment is able to register the coordinates of the rod by sliding along its surface. When it is fully engaged with the surface of the rod, the sliding shaft and attached TMSM are actuated, and the acquisition system is triggered to record the coordinates corresponding to the center of the rod. The software to calculate the coordinates of the rod is described below in reference to FIGS. 73A-73B, and 74. It should be noted that the rod-centering fork attached to the slider is only one embodiment of the device. Other embodiments include a coupled ring as previously described in reference to FIGS. 49A-49D, and 50A-50E. Additionally, linearly actuating a TMSM is only one method of triggering to the acquisition system that the slider is fully engaged with the rod. Other embodiments include, but are not limited to, rotational motion of a TMSM, handheld triggering on the tracked slider or tracked end cap, electronic communication from embedded electronics on the tracked end cap or tracked slider, or direct user input via software interface.

FIG. 51E displays a rear view of the embodiment shown previously in FIG. 51D displaying the depressible shaft 5140, rod-centering fork 5130, and tracked DRF 5136. FIG. 51F displays a closeup view of the embodiment shown previously in FIGS. 51D-51E in which the tracked DRF 5136, spring 5150 and spring-loaded depressible shaft tip 5140, and its attached TMSM 5145 are visible. In this configuration of the embodiment, the sliding shaft 5140 and its mounted TMSM are in the extended position, indicating that the tracked slider is not engaged with a rod.

FIG. 51G displays a closeup view of the embodiment shown previously in FIGS. 51D-F in which the engaged depressible shaft 5155 and its mounted TMSM 5160 are in the depressed location, which if at a preset height corresponding to the rod diameter being used, would indicate to the acquisition software that the tracked slider is firmly engaged with a rod and its coordinates should be recorded. Further, FIG. 51H displays one embodiment of the invention which is a mechanism of registering the contour of a rod prior to implantation by substantially rigidly fixing a rod 5170 in a tracked end cap and sliding the tracked slider over the rod one or more times. Following registration of the contour of a rod attached to a tracked end cap, the tracked end cap can be used for the user to directly interface with the display monitor portraying the rod contour, as described in detail below in reference to FIG. 78. FIG. 51I displays another view of an embodiment of the invention previously shown in FIG. 51H.

Some embodiments of the invention include a TMSM-based, implanted rod contour assessment device. Some embodiments are used to assess the contour of a rod after it has been implanted into a patient. This embodiment utilizes the rod-centering fork design with a sliding shaft and spring-loaded TMSM, previously described in FIGS. 47A and 51D-51I on the end of a tracked probe, such that it can fit into the surgical site and trace over the implanted rod. The probe is able to skip over any obstructing hardware without its coordinates being recorded because the acquisition system is only triggered to record when the TMSM is in the position corresponding to the sliding shaft being depressed by a rod of a preset diameter. The software for calculating and interpreting the rod contour is described below in relation to FIGS. 76, and 77A-77C.

FIG. 52A illustrates a component of a TMSM-based, implanted rod contour assessment device 5200 in accordance with some embodiments of the invention. In some embodiments, the device 5200 comprises a probe shaft 5210, rod-centering fork 5230, 5235 for interfacing with a rod, mounts 5215 for tracked DRF markers (not shown) to be inserted, mounts 5225 for spring(s), a depth-stop for a sliding shaft 5220 and sliding shaft guides 5205 to prevent the inserted shaft (not shown) from rotating. This embodiment is intended to be coupled with the embodiment described below in reference to FIG. 52B.

FIG. 52B illustrates a depressible sliding shaft for coupling to the component of FIG. 52A comprising a depressible sliding shaft 5250 with rounded tip 5264, mounts 5260 for springs, threaded hole 5268 for adjustable depth-stop, mount 5209 for a TMSM, and a guide-fitting profile 5252 to prevent rotation when inserted within its complementary probe described above in relation to FIG. 52A.

FIG. 52C illustrates a top view of the component of FIG. 52A in accordance with some embodiments of the invention, and shows spring mount 5225, and sliding shaft through-hole 5229, able to accommodate the sliding shaft 5250 in relation to FIG. 52B. FIG. 52D displays another view of the embodiment shown previously in FIG. 52B, enabling closer visualization of the depressible sliding shaft 5250, spring mounts 5260, threaded hole 5268 for an adjustable depth-stop, mount 5209 for a TMSM, and a guide-fitting profile 5252.

FIG. 53A displays one embodiment of a device 5300 configured to assess the contour of a rod after it has been implanted within the surgical site. The embodiment described in this figure comprises an assembly of the components described previously in relation to FIGS. 52A-52D. In some embodiments, the device 5300 comprises a tracked probe 5310 with a rod-centering fork 5315, through-hole (not shown) to accommodate a depressible sliding shaft 5335, with a coupled TMSM 5325, and tracked DRF 5320 (made of several 3D-trackable markers 5330). This embodiment is used to engage with an implanted rod (not shown) such that the rod depresses the depressible sliding shaft 5335, thereby moving the attached TMSM 5325 relative to the attached tracked DRF 5320. When the TMSM 5325 moves relative to the tracked DRF 5320 by a preset amount based on the rod diameter, the acquisition system is triggered to record the coordinates corresponding to the center of the rod, as described below in reference to FIGS. 76-77. Further, FIG. 53B illustrates a close-up rear view of a portion 5301 of the assembly of FIG. 53A in accordance with some embodiments of the invention. Further, FIG. 53B displays a rear view of the embodiment of the invention shown previously in 53A, visualizing the depressible sliding shaft 5335, its attached TMSM 5325, the tracked DRF 5320, springs 5354, depth-stop 5356 for sliding shaft, and depth-stop set screw 5352 used to adjust the maximum protrusion length of the sliding shaft tip beyond the bifurcation of the fork. It should be noted that the adjustable depth-stop design is just one embodiment of this invention. Other embodiments do not possess a mechanism of adjusting the maximum protrusion length of the sliding shaft. Additionally, the external springs referenced in this embodiment can consist of internal compressible springs, torsion springs, and memory-embedded materials within other embodiments. This figure displays how the sliding shaft guides prevent rotation of the sliding shaft, restricting the TMSM 5325 to linear motion relative to the tracked DRF 5320.

FIG. 53C displays a closer view of the rod-interface region of the embodiment shown previously in FIGS. 53A-53B. In this embodiment, the spring-loaded depressible sliding shaft 5335a is in its extended position. In this position the acquisition system is not triggered to record the coordinates of the probe, as it is not indicating that it is interfacing with a rod to be measured. Further, FIG. 53D displays a view of the embodiment described previously in FIGS. 53A-53C interfacing with a rod 5367 within the rod-centering fork 5315 and depressing the sliding shaft 5335b into the depressed position causing the attached TMSM (not shown) to move relative to the probe's attached DRF (not shown), indicating for the acquisition system to record 3D coordinates corresponding to the center of the rod's cross-section.

FIG. 53E displays a closer view of the tracked DRF portion of the device embodiment described previously in relation to FIGS. 53A-53D. The location of the TMSM 5325a relative to the tracked DRF 5320 as shown, corresponds to the depressible shaft being in the extended position, as shown in FIG. 53C. In this configuration, the acquisition software is not triggered to record the probe's coordinates. FIG. 53F displays a closer view of the tracked DRF 5320 portion of the device embodiment described previously in relation to FIGS. 53A-E showing sliding shaft guide 5329. The location of the TMSM 5325*b* relative to the tracked DRF 5320 as shown, corresponds to the depressible shaft 5335 being in the depressed position, as shown in FIG. 53D. In this configuration, the acquisition software is triggered to record the location of the probe, from which the rod's coordinates can be calculated as described below in reference to FIGS. 76-77.

Some embodiments of the invention include a conductivity-based, implanted rod contour assessment device. Some embodiments are intended to assess the contour of a rod after it has been implanted within the surgical site. This embodiment differs from those previously described in relation to FIGS. 52A-52D, and 53A-53F, in that it possesses electrical contact terminals on the inside walls of the rod-centering fork. These electrically-isolated terminals are used then to sense conductivity between them. In the absence of a rod touching both terminals, no current flows between them. When a rod is fully engaged within the fork however, current flows from one contact to another, indicating that the device is fully engaged with the rod, and the contour assessment device electrically communicates, either wirelessly or through a wire, with the 3D-tracking acquisition system that it should record the coordinates of the device. Therefore, embedded in the probe is a small power supply via battery or capacitor, and circuit components to communicate with the acquisition system. For example, FIG. 54A displays one embodiment of the invention (assembly 5400) which includes a probe shaft 5410 equipped with a rod-centering fork 5425 on one end and a tracked DRF 5415 on the other. This embodiment of the invention can be applied to an already-implanted spinal rod and used to assess its 3D contour by sliding the internal sides of the fork 5425 along the exposed surfaces of the rod 5440. This device fork possesses electrical contact terminals, described below in reference to FIG. 54B, on the inside surfaces of the rod-centering fork 5425, and internal electronics within the rod (not shown) that detect when current flows between them. When current flows between the terminals, the contour assessment tool signals for the acquisition system to record its location in space. Other embodiments of the probe's communication method with the acquisition system include but are not limited to wireless radiofrequency transmission, optical signaling via infrared or visible light illumination of elements on the probe that are detected by the system, and wired signal transmission. The process of interpreting the rod's location and contour relative to the probe is described below in reference to FIGS. 76, and 77A-77C.

FIG. 54B illustrates a rod-centering fork and electrical contact pads of the device of FIG. 54A in accordance with some embodiments of the invention. FIG. 54B provides better visualization of the rod-centering fork 5425 and electrical contact pads 5427*a*, 5427*b* located on the inner surface of each arm of the fork. With this embodiment, the probe is unable to signal that it is active, unless an electrical conductor connects both contact terminals. It should be noted that the shape of the contact terminals can be different in other embodiments, including but not limited to cylindrical, semi-cylindrical, flat, and curved surfaces with variation in their distance of protrusion from the inside surface of the fork.

FIG. 54C displays the embodiment previously described in relation to FIGS. 54A-54B interacting with a rod 5440 that is not fully seated within the fork. In this configuration, the rod 5440 is not approximating both electrical contact plates, and therefore the assessment device is in the inactive, non-tracking state. Further, FIG. 54D displays the embodiment previously described in relation to FIGS. 54A-54C interacting with a rod 5440 that is fully engaged within the fork. In this configuration, the metal rod is approximating both electrical contact pads (5427*a*, 5427*b* of FIG. 54B) of the fork and therefore conducting a current across it. When current is being conducted, the probe then signals to the 3D-tracking acquisition system that it is in the active state and its coordinates are recorded to be used for computing the rod contour as described below in reference to FIGS. 76, and 77A-77C.

Some embodiments include a 3D-tracked, manual mobile rod bender. Some embodiments can be utilized with an already-registered rod attached to a tracked end cap, to both bend and re-register the updated contour of the rod during bending. This embodiment also allows for visualization of the precise position of the tracked handheld rod bender relative to a previously registered rod on a display monitor. Additionally, this system also allows for software-assisted and software-directed bending, instructing the user where to place and how to maneuver a tracked, handheld rod bender, to contour the rod to a pre-determined shape. The capabilities of this embodiment and its variations are described in more detail below in reference to FIGS. 56A-56F, 79A-79G, and 81.

Figure 55A:
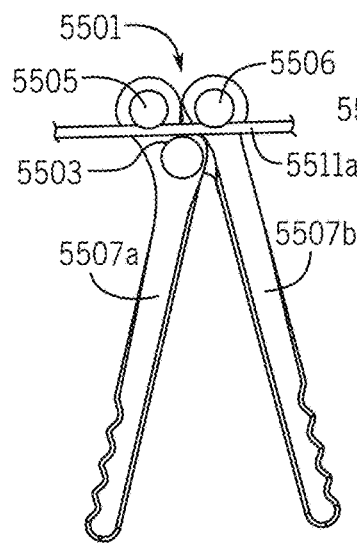

FIG. 55A displays one embodiment of the invention, which is a handheld rod bender 5501 consisting of two handles with handle #1 5507*a*, containing the center rod contouring surface 5503, and left outer roller 5505 and handle #2 5507*b* containing the right outer roller 5506. The embodiment shown is interfacing with a straight rod 5511*a* approximating both rollers and center bend surface, as the bender handles (5507*a*, 5507*b*) are positioned at an open angle to one another. Further, FIG. 55B displays the embodiment of the invention described in relation to FIG. 55A, with the rod bender's handles approximated, resulting in a bent rod 5511*b* contour. FIG. 55C displays a closer view of the rod-interface points of the bender 5501, shown previously in FIG. 55B interfacing with a bent rod 5511*b*.

Figure 55B:
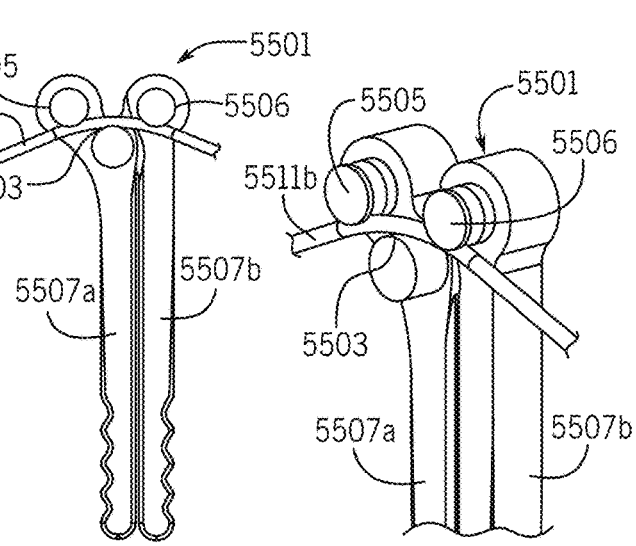
Figure 55C:
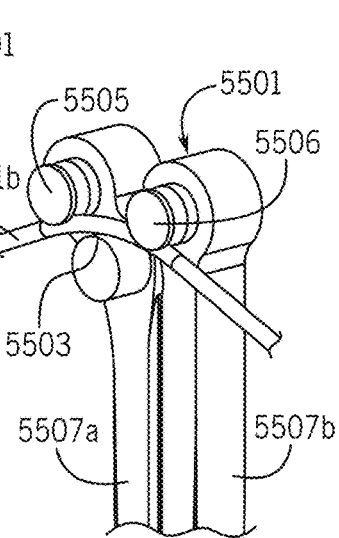
Figure 55D:
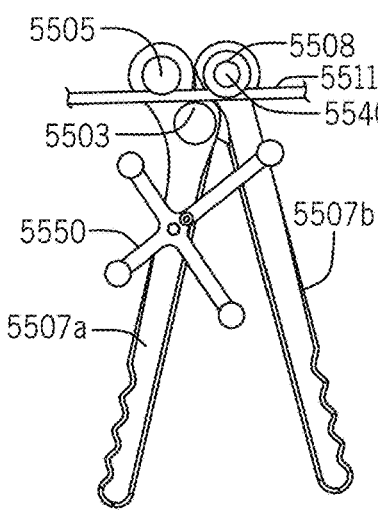

FIG. 55D displays one embodiment of the invention which consists of a handheld rod bender coupled to rod 5511*a*, previously described in relation to FIGS. 55A-55C, equipped with a tracked DRF 5550 fixed to handle #1 5507*a*, a roller mount 5508 on outer roller 5506 and a TMSM 5540 fixed to the roller mount 5508. As displayed, the rod bender 5501 is interfacing with a straight rod 5511*a*, necessitating that the bender's handles 5507*a*, 5507*b* are positioned at a wide angle from one another to accommodate the straight rod. With the tracked DRF 5550 mounted to handle #1 5507*a*, the 3D-tracking acquisition system can register the location and pose of both the center rod contouring surface and the left outer roller. With the TMSM 5540 attached to the right outer-roller 5506, it enables the acquisition system to then register the location of the right outer roller relative to the two-other rod-interface points of the bender. With the ability to locate all three rod-interface points on the bender in 3D space, the acquisition system can interpret the relative angle between the bend handles, and with known rod diameter, the degree of bending induced into a rod. When this embodiment of the invention is coupled to a previously registered rod, fixed to a tracked end cap, as described previously in relation to FIGS. 49D, 50E, 51H-51I, the acquisition system is able to interpret when the three rod-interface points on the tracked bender are engaged with the previously registered rod. When that is the case, the software system is able to provide live tracking of the bender relative to the rod, real-time updates of the rod contour during bending, and software-assisted bending instructions, as described below in reference to FIGS. 56A-56F, 79A-79G, 80-81, 87A-87K, and 88A-88F. Further, FIG. 55E displays one embodiment of the device 5501 as previously described in FIG. 55D, except with the rod bender handles 5507a, 5507b coupled, resulting in a bent rod 5511b. Further, FIG. 55F displays another view of the embodiment shown in FIG. 55E and described previously in relation to FIG. 55D. This perspective enables visualization of the mounting post 5551 for the tracked DRF 5550 attached to handle #1 5507a. It should be noted that in other embodiments, the tracked DRF 5550 is coupled to varying locations on handle #1 5507a and at varying angles and offset heights from the handle. This figure displays only one embodiment of the relative positioning of the tracked DRF 5550 to the rod bender handle. The same variation applies for the relative positioning of the TMSM 5508 (as marked in FIG. 55D) to handle #2 5507b. Although in the embodiment shown, it is located directly over the right outer roller 5506, it can be positioned anywhere on handle #2 5507b to provide the input information the software needs to calculate the aforementioned embodiments of the invention.

Some embodiments include a spring-loaded TMSM attached to the center rod contouring surface of the rod bender such that it moves the stray marker only when the rod is fully pressed up against the surface of the center rod contouring surface, and thereby serving as an indicator of when the rod is fully engaged with the bender (i.e., only when the rod is "being bent" or "engaged"). For example, other embodiments include a spring-loaded (not shown) TMSM (not shown), coupled to the center rod-contouring surface 5503 in such a way that it is fully deflected only when the rod is fully approximated against the center rod-contouring surface 5503 of the rod bender. In this way, the acquisition system has an additional method of indicating when the contour of the rod is actively being bent.

In reference to FIGS. 55A-55I, and 56A-56F, in some embodiments, the tracked bender can be a universal adapter design such that it can be applied to other user-operating rod benders, especially table-top benders that are used in the operating room. Further, it is also essential to note that rod cutters can also be equipped with tracking accessories in a similar manner in order to see where the digital overlay of the rod will be cut. It should be noted that these embodiments can also be applied to other user-operating rod benders that involve two or more contact points with a rod to induce curvature. In other embodiments, these principles are applied to instruments used for rod cutting, such that the location of the cutter relative to a previously registered rod can be visualized.

Figure 55E:
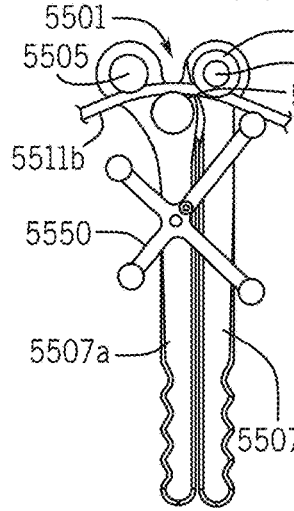
Figure 55F:
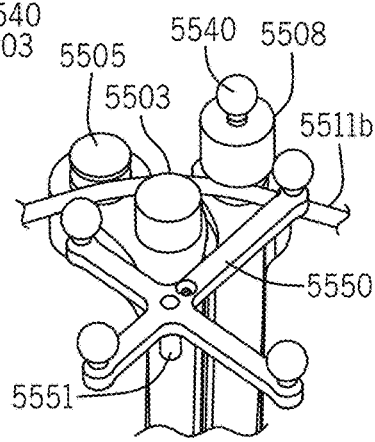
Figure 55G:
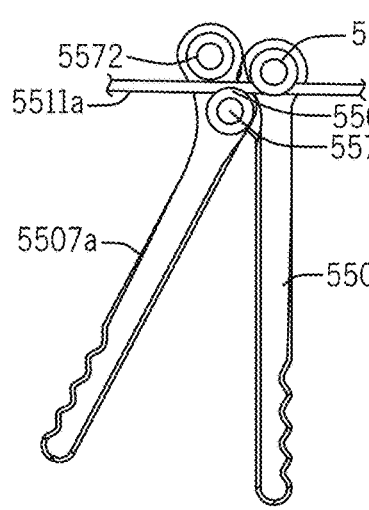

FIG. 55G displays an alternative bender embodiment of the invention from that described previously in relation to FIGS. 55D-55F, in which the rod bender is equipped with two TMSMs on handle #1 5507a (shown as 5571, 5572), and one TMSM 5573 on handle #2 5507b. The three TMSMs 5571, 5572, 5573 are utilized to localize the position of each rod-interface point on the bender. Because the three TMSM mounting points shown are directly over the three rod-interface points of the rod bender, the acquisition software can localize the plane of the rod bender defined by the three markers 5571, 5572, 5573, and then offset it by a known amount based on the known offset between the TMSMs and the rod-interface points on the bender. The acquisition system is able to reliably interpret the direction of offset from the plane defined by the three TMSMs, based on the viewing angle restrictions of a single optical 3D-tracking system, which defines the normal vector the TMSM plane as that which is less than 90 degrees from the vector drawn from the center of the three markers to the 3D-tracking camera. In this configuration, the tracked bender is able to achieve the same functionality as described previously in relation to FIG. 55D. It should be noted that three TMSMs attached to the rod bender is only one embodiment of the invention, and other embodiments include attaching more than three TMSMs to the bender, as well as placing the TMSMs in alternative locations than directly over the rod-interface components of the rod bender. As shown in this figure, the tracked bender is interfacing with a straight rod 5511a, necessitating that the angle between the bender handles be positioned at a wide angle relative to one another. In this configuration, because the distance from the center bend surface to each of the outer rollers is the same, the angle between bender handles, and thereby the degree of bending, can be calculated based on the angle between the two equally-spaced TMSMs 5572, 5573 from the center TMSM 5571.

Figure 55H:
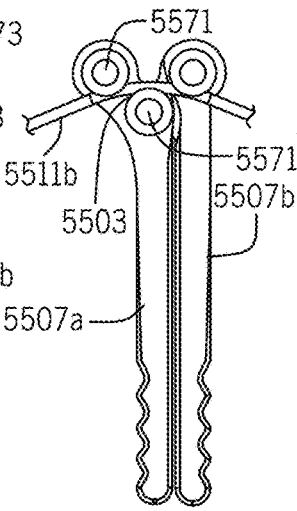
Figure 55I:
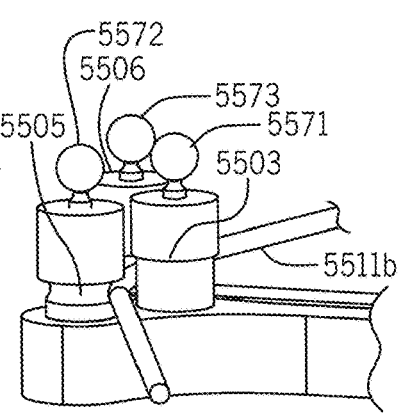

FIG. 55H displays one embodiment of the invention as previously described in FIG. 55G, except with the rod bender handles approximated, resulting in a bent rod 5511b. FIG. 55I displays another view of the embodiment shown in FIG. 55H and described previously in relation to FIG. 55G FIGS. 56A-56F further describe an embodiment of the invention previously described in relation to FIGS. 55A-55I. Depicted are the necessary components of the invention to track bending in real-time, as well as utilize software-assisted instructed bending are all displayed. Furthermore, an additional embodiment of the device is introduced within this figure, that enables the ability to account for shape memory that rod material may experience during and after bending when computing the real-time tracking of bending and computing the re-registered rod. For example, FIG. 56A displays one embodiment of the device 5600 previously described in relation to FIGS. 55G-55I, in which a pre-registered rod 5610 is fixed within a tracked DRF-equipped end cap 5605, and a tracked rod bender 5501b is equipped with three TMSMs interfaces with the rod. In this configuration, the acquisition software can interpret the location of the tracked rod bender relative to the previously-registered rod 5610 within the tracked end cap's relative coordinate system. With this configuration, the acquisition system can provide live tracking of the bender relative to the rod, real-time updates of the rod contour during bending, and software-assisted bending instructions, as described below in reference to FIGS. 79A-79G, 81, 87A-87G, and 88A-88F.

Figure 56A:
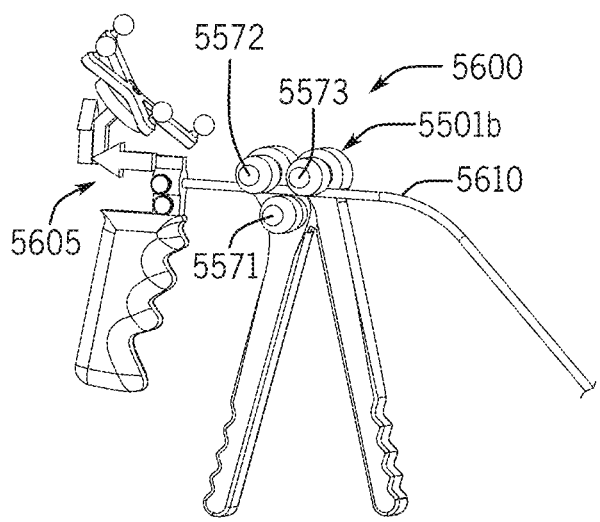
Figure 56B:
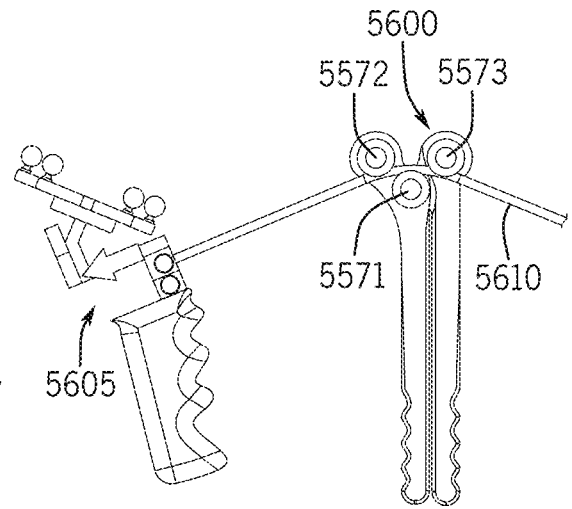

FIG. 56B shows another configuration of the embodiment previously described in relation to FIG. 56A, in which the tracked rod bender 5600 is engaged with an alternative location of the rod that is bent, displaying how the angle between the handles and associated TMSMs changes from when the bender is interfacing with a straight portion of the rod, as shown in FIG. 56A.

Figure 56C:
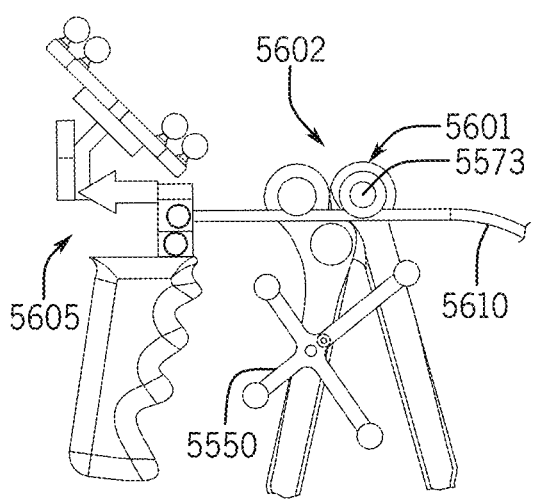

FIG. 56C displays one embodiment of the device (assembly 5602) previously described in relation to FIGS. 55D-55F, in which a pre-registered rod 5610 is fixed within a tracked-DRF-equipped end cap 5605 and a tracked rod bender (assembly 5602 with end cap 5605 and rod bender 5601) is equipped with a tracked DRF 5550 on one handle and a TMSM 5573 on the other. With this configuration, the acquisition system is able to provide live tracking of the bender relative to the rod, real-time updates of the rod 5610 contour during bending, and software-assisted bending instructions, as described below in reference to FIGS. 79A-79G, 81, 87A-87K, and 88A-88F.

Figure 56D:
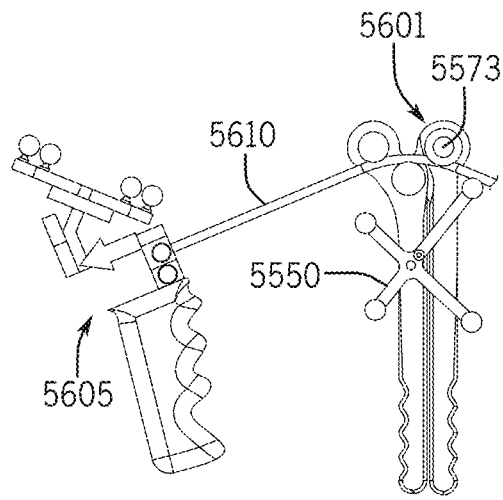

FIG. 56D shows another configuration of the embodiment 5602 previously described in relation to FIG. 56C, in which the tracked rod bender 5601 is engaged with an alternative location of the rod that is bent 5610, displaying how the angle between the handles and associated TMSM 5573 relative to the tracked DRF 5550 changes from when the bender is interfacing with a straight portion of the rod 5610, as shown in FIG. 56C.

Figure 56E:
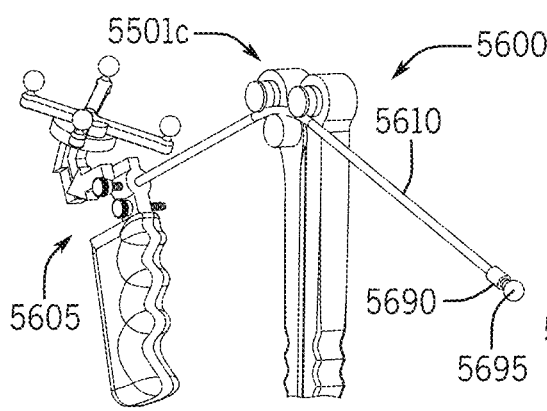

FIG. 56E displays a further embodiment of the invention 5600, which consists of a tracked DRF-equipped end cap 5605, fixed to a pre-registered rod 5610, non-tracked manual bender 5501c, and a rod cap 5690 with a TMSM 5695 mounted to it. This embodiment represents an alternative mechanism and method of updating the previously-registered contour of a rod while it is being bent with a handheld bender. In this embodiment, because the bender is not tracked, the location of the TMSM is detected relative to the tracked end cap to which the rod is fixed. Whenever the system detects relative motion between the TMSM 5695 and the tracked DRF on the end cap 5605, the acquisition system records the path traveled by the TMSM 5695 relative to the end cap 5605. With known geometry of the rod bender's center bend surface, the path of the TMSM is used to calculate the location and curvature of each bend, as described below in reference to FIG. 80.

Figure 56F:
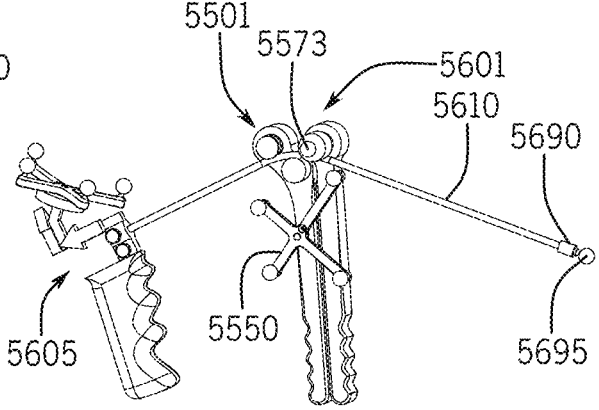

FIG. 56F displays an embodiment of 5601 comprising a tracked DRF-equipped end cap 5605, fixed to a pre-registered rod 5610, tracked manual bender 5501 equipped with a tracked DRF 5550 and one TMSM, and rod cap 5690 with a TMSM 5695 mounted to it. In this embodiment, the contour of the previously-registered rod is updated during bending by the combination of tracking both the rod bender's conformation at interfacing regions of the rod, as described previously in relation to FIGS. 55D-55F, as well as the motion of the TMSM-equipped rod cap relative to the tracked end cap to which the rod is fixed. In this configuration, the acquisition system is able to account for shape memory within the rod material, that previously described embodiments without the TMSM-mounted rod cap were not. Because the end of the rod opposite to the DRF-equipped end cap is tracked in this embodiment, after the rod bender achieves its minimum angle between handles when interfacing with a particular region of the rod, if the rod material retains some of its shape memory and recoils, the TMSM-equipped rod cap will move relative to the DRF-equipped end cap, and the acquisition system software can now account for this memory when recomputing the rod's contour as described in more detail in relation to FIG. 80. As with other embodiments described in FIGS. 56A-56E, this configuration also enables software-assisted bending and interfacing with display monitor, as described below in reference to FIGS. 79A-79G, 80-81, 87A-87G, and 88A-88F.

Some embodiments of the invention include a 3D-tracked, manual implanted rod bending system which enables the ability to track the bending of a rod that has already been implanted within the surgical site. In this embodiment, the user interfaces with an implanted rod using DRF-tracked and trigger-equipped in-situ benders after already registering the contour of the implanted rod via mechanisms described previously in relation to FIGS. 52A-52D, 53A-53F, and 54A-54B. For example, some embodiments include DRF-tracked and trigger-equipped in-situ benders coupled to a rod in accordance with some embodiments of the invention. In some embodiments, two tracked in-situ benders, each equipped with unique tracked DRFs (5705a, 5705b), can interface with a pre-registered rod to alter its contour after implantation. Because the tracked in-situ benders interface with an already-registered rod 5711, their position relative to the registered rod can be displayed via display monitor. Additionally, because they are equipped with depressible sliding shafts 5735 to serve as triggers indicating when they are fully engaged with the rod, their movement will not result in alteration in the software-recorded-contour of the registered rod unless two or more in-situ benders are triggered simultaneously and moved relative to one another while triggered. For example, FIG. 57A displays one embodiment 5700 of the invention consisting of a tracked in-situ bender with handle 5710a, 5710b, rod interface head 5725a, 5725b equipped with depressible sliding shaft tip (not shown) coupled to pre-registered rod 5711, TMSM 5707a, 5707b mounted to depressible sliding shaft, and tracked DRF 5705a, 5705b. Further, in reference to FIG. 57B, showing embodiments 5701 with a spine 5713 with instrumented pedicle screw shafts 5718, tulip heads 5739, an implanted pre-registered rod 5750, and cap screws 5738, in some embodiments, both triggers on the benders can be depressed, actuating the TMSMs (5707a, 5707b) relative to the associated DRFs (5705a, 5705b), indicating to the acquisition system that they are fully engaged with the rods.

FIG. 57C illustrates a close-up view of the rod (marked as 5711) of FIG. 57A in accordance with some embodiments of the invention, and FIG. 57C displays another view of the embodiment shown in FIG. 57A engaging with a pre-registered rod 5711. FIG. 57D illustrates a close-up view of a rod-interface head 5725 of the bender show in FIG. 57A including a view of a depressible sliding shaft 5735 with depressible sliding shaft tip 5735a in an extended position towards the surface 5730 that can accept the rod 5711 in this assembly view. In some embodiments, at least a portion of the surface 5730 can comprise a curved or concave surface 5730a that can complement and/or maximize engagement and/or surface contact with a curved surface of a rod (e.g., such as rod 5711).

Some embodiments of the invention enable the use of skin-mounted fiducial markers to serve as surrogate markers from which the location of the underlying anatomical landmarks can be calculated. For example, FIG. 58 illustrates a workflow 5800 to initialize skin-mounted, or percutaneous, fiducials with two or more X-ray images intraoperatively in accordance with some embodiments of the invention. This figure describes the process of the user and acquisition system interfacing to initialize and calculate the 3D-displacement vector between a fiducial marker and the anatomical region of interest. Some figures relevant to the process include X-ray initialization of 3D-displacement vector with multi-planar X-rays (FIGS. 4A-4G, FIG. 13), feedback on fiducial placement on or in a patient's skin surface (FIGS. 2A-2B), a trans-drape, two-halves fiducial design (FIGS. 6A-6D, and FIGS. 9A-9B), registration of a fiducial in camera coordinates+determining its unique identity (FIGS. 4H-4I, FIG. 5, and FIGS. 7-8, FIGS. 10A-10D, and FIGS. 11A-11B).

In some embodiments, one or more steps of the workflow 5800 can be utilized for the registration of a 3D-displacement vector between a skin-mounted or percutaneous fiducial marker and the anatomical landmark of interest. Following a step 5802 of positioning a patient on an operative table, step 5804 can include the placement of a fiducial on or inside the soft tissue within the anatomical region of interest. For example, one embodiment involves the user placing the fiducial on or inside the general region of interest. Another embodiment of the invention can involve the user receiving feedback on the placement of a fiducial marker via a radiopaque patch that identifies the optimal location on the surface to place or insert the fiducial device; this was previously depicted and discussed in related to FIGS. 2A and 2B.

Some embodiments involve the mating of a second-half fiducial to the original fiducial marker placed on or inside soft tissue to maintain access to the fiducial after the introduction of surgical drapes and other obstructing materials outside of the surgical site. Example embodiments to accomplish one or more embodiments of this invention are depicted in FIGS. 6A-6D, and FIGS. 9A-9B. In some embodiments, step 5806 can include obtaining a first X-ray image containing fiducial and desired bone anatomy to be identified with the fiducial. Further, step 5808 can include rotation of the X-ray emitter, and step 5810 can include obtaining a second X-ray image containing fiducial and desired bone anatomy to be identified with the fiducial.

Some embodiments further include the process of annotating 2D vectors between the fiducial marker and the anatomical landmark of interest for each image acquired from a unique perspective relative to the fiducial. This displacement vector initialization process is depicted and discussed in reference to FIGS. 4A-4F. The overall goal of the initialization process can be visualized in the cross-sectional view depicted previously in FIG. 13. Further some embodiments include the process of using the relative rotational and translational offset information between two or more X-ray images of the fiducial to calculate the 3D-displacement vector between the fiducial marker and the anatomical landmark of interest using the 2D-displacement vectors for each image as inputs into the calculation. This process of calculating the 3D-displacement vector based on a rigid transformation between multiple 2D-displacement vectors is previously depicted in FIG. 4G. For example, step 5812 can include annotation of X-ray images with desired bony anatomy locations, and step 5814 can include calibration of X-ray image distances by known size of the radiopaque markers on the fiducials. Further, step 5816 can include draw a scaled displacement vector on X-ray images from fiducial origin to indicated bony anatomy of interest, and step 5818 can include input or compute displacement angle between X-ray images. Further, step 5820 can include adding displacement vectors to produce 3D displacement vector from fiducial origin to annotated regions.

Steps 5822-5830 describe the process of using 3D-tracked devices to register the location and orientation of the fiducial marker relative to the coordinate system of the 3D-tracking acquisition unit, and then applying the acquired positional information as a rigid transformation to the X-ray-based 3D-displacement vector to convert the vector from imaging units into units of the 3D-tracked acquisition system. This process can be depicted in FIGS. 4H, 4I, 5, 7-8, 10A-10D, and 11A-11B. In addition, these previous figures depict some of the embodiments for determining the unique identity of a fiducial marker in order for the system to be able to utilize several fiducial markers at once and understanding which fiducial is associated with specific mathematical relationships to a unique anatomical landmark of interest. For example, step 5822 can include interpretation of fiducial origin into camera coordinate, and step 5824 can include tracing or tapping the fiducial with tracked probe in discrete points to indicate fiducial pose. Further, step 5826 can include mechanical mating or coupling of tracked probe with fiducial to obtain fiducial pose, and step 5828 can include directly tracking markers mounted on fiducial, and with step 5830 including access to fiducial which then serves as a reference point to initialized nearby bony points of interest.

In some embodiments, any of the above processes, methods, or procedures related to the workflow 5800 can include or be accomplished with one or more of steps or processes 5802, 5804, 5806, 5808, 5810, 5812, 5814, 5816, 5818, 5820, 5822, 5824, 5826, 5828, and 5830. In some embodiments, the steps of workflow 5800 can proceed in the order as shown. In some embodiments, any of the steps of the workflow 5800 can proceed out of the order as shown. In some embodiments, one or more of the steps of the workflow 5800 can be skipped.

Some embodiments of the invention enable the registration of bone-mounted fiducial markers to represent anatomical landmarks that are located within or nearby the bony anatomy that the marker is substantially rigidly attached to. For example, FIG. 59 illustrates a workflow 5900 to initialize one or more bone-mounted fiducial placed intraoperatively with two or more X-ray images taken before placement of one or more bone-mounted fiducials in accordance with some embodiments of the invention. This figure describes the process of the back-end system to use prior X-ray initialization of a skin-based fiducial and its 3D-displacement vector to the anatomical landmark of interest and transform the bone-mounted fiducial location and pose relative to the camera-based registration coordinates of the prior 3D-displacement vector to describe the relationship between the bone-mounted fiducial marker and the anatomical region of interest. Other relevant figures can include embodiments for bone-mounted fiducial design and coupling to an additional fiducial (see FIGS. 3A-3C), and registration of a fiducial in camera coordinates and determining its unique identity (FIGS. 10A-10D, and FIGS. 44A-44D).

In some embodiments, the steps 5910, 5912 of this process can involve the steps described in the workflow of FIG. 58, which outline the process for registering the 3D-displacement vector for a skin-based or percutaneous fiducial in imaging coordinates as well as units of the 3D-tracking acquisition unit. If the registered fiducial marker has to be removed due to the location of the surgical site requiring access to the that location of the anatomy, then the user can utilize the process to reinstate access to the 3D-displacement vector that provides information about other anatomical landmarks of interest. Step 5914 can include removal of the skin fiducial, and step 5916 can include skin incision and exposure of the surgical site.

In some embodiments, step 5918 and 5920 can involve the user implanting the miniature fiducial marker into the bony anatomy and then registering its location and orientation relative to a 3D-tracking acquisition unit via a 3D-tracked probe. One embodiment of this process is depicted in FIGS. 3A-3B, and FIGS. 4A-4D.

Some embodiments, described in steps 5922, and/or 5924, and/or 5926, and/or 5928 can involve the 3D-tracked probe tracing the fiducial surface or tapping discrete points on the fiducial to register the fiducial's 3D location and orientation with respect to the coordinates of the 3D-tracking acquisition unit. Some of the other embodiments are depicted in FIGS. 10A-10D.

In some embodiments, step 5930 can include comparing the location and orientation of the registered bone-mounted fiducial to that of the registered landmarks initialized via the prior 3D-displacement vector converted into coordinates of the 3D-tracking acquisition system via initialization of the skin-based fiducial before the incision of the surgical site.

Further, in some embodiments, steps 5932 and 5934 can include utilizing the relationship calculated in step 5930 as in input for the rigid transformation applied to the registered anatomical landmarks with coordinates from the 3D-tracking acquisition system.

In some embodiments, any of the above processes, methods, or procedures related to the workflow 5900 can include or be accomplished with one or more of steps or processes 5910, 5912, 5914, 5916, 5918, 5920, 5922, 5924, 5926, 5928, 5930, 5932, and 5934. In some embodiments, the steps of workflow 5900 can proceed in the order as shown. In some embodiments, any of the steps of the workflow 5900 can proceed out of the order as shown. In some embodiments, one or more of the steps of the workflow 5900 can be skipped.

Similar to embodiments depicted in FIGS. 58 and 59, FIG. 60 shows a workflow to initialize bone-mounted fiducials placed intraoperatively with two or more X-ray images taken after placement of bone-mounted fiducials in accordance with some embodiments of the invention. In some embodiments, once the user has created a surgical site and exposed the bony anatomy, the user can implant the miniature fiducial marker into the bony anatomy surface until it is substantially rigidly fixed to the anatomy. Examples of this bone fiducial embodiment are depicted in FIGS. 3A and 3B. Some embodiments involve the use of a larger fiducial marker that mates to the surface of the bone-mounted fiducial marker to enhance its visualization in X-ray images for the purpose of annotating the 3D-displacement vector to the anatomical landmark of interest. An example of this embodiment is depicted in FIG. 3C.

In step 6002, incise skin and expose the surgical site, and step 6004, fasten bone-mounted fiducial to spinal level of interest at accessible location, and further, in step 6006, attach mating device (optional) to bone-mounted fiducial to aid with X-ray initialization. In some embodiments, steps 6012, 6010, 6008, 6014, 6016, 6018, 6020, 6022, and 6024 can include the X-ray-based registration of the fiducial marker as described in FIG. 58 to produce a 3D-displacement vector in imaging coordinates between the bone-mounted fiducial marker and the anatomical landmark of interest. Some embodiments then register the bone-mounted fiducial's 3D-displacement vector to the anatomical landmark of interest in the coordinates of the 3D-tracking acquisition system via acquiring the location and orientation of the fiducial marker with respect to the coordinates of 3D-tracking acquisition system. Examples of this process are depicted in FIGS. 4H-4I, FIGS. 10A-10D, and further in FIGS. 44A-44D.

In some embodiments, once the bone-mounted fiducial is registered in both the X-ray imaging system and the 3D-tracking acquisition system, every time the user returns to register the updated location and orientation, the relative relationship between its current position and that of the prior registration are calculated and applied via a rigid transformation to calculate the most accurate location of the anatomical landmark of interest as they currently exist in relation to the fiducial marker in 3D space. For example, in step 6026, the process can include assess location and pose of initialized fiducial, including, but not limited to step 6028 including trace a unique pattern imprinted over fiducial with tracked probe, step 6030 substantially rigidly couple tracked mating probe to fiducial, step 6032, substantially rigidly coupling tracked markers to fiducial, and step 6034, tap discrete points on fiducial or on fiducial mating attachment with tracked probe.

In some embodiments, any of the above processes, methods, or procedures related to the workflow 6000 can include or be accomplished with one or more of steps or processes 6002, 6004, 6006, 6012, 6010, 6008, 6014, 6016, 6018, 6020, 6022, 6024, 6026, 6028, 6030, 6032, 6034, and 6036. In some embodiments, any of the steps of the workflow 6000 can proceed out of the order as shown. In some embodiments, one or more of the steps of the workflow 6000 can be skipped.

Some embodiments of this invention pertain to the initialization of the patient's anatomical planes in relation to the coordinates of the 3D-tracking acquisition system to enable the measurements made during a procedure to be accurately referenced to the dimensions of the anatomy being assessed. For example, FIG. 61 illustrates methods of registering anatomical reference planes intraoperatively in accordance with some embodiments of the invention. In some embodiments, if a user has already established the coordinates of the measurement system via the initialization process of surgical navigation technologies, then coordinates of the data outputted by the 3D-tracking acquisition system are already referenced in relation to the anatomical planes of the patient. In some embodiments, if the user has not already established the coordinates of the measurement system via the initialization process of surgical navigation technologies, then the user will utilize a few of the embodiments described in FIG. 61 to initialize the 3D-tracking data outputs with respect to the patient's anatomical planes.

Some embodiments include utilizing a tracked DRF (e.g., FIG. 12) and its associated 3D orientation and location in relation to the 3D-tracking acquisition system as inputs to a 3D rigid transformation of the measurements that are outputted by the 3D-tracked devices to reference the anatomical planes of the patient. One example of this process of transforming measurements outputted by 3D-tracked devices to be relative to the patient anatomical planes, via a tracked dynamic reference aligned with the patient anatomical planes, is depicted in FIGS. 62A-62C.

Some of the other embodiments for initializing the patient anatomical planes can involve acquiring two or more data points in space with a 3D-tracked probe to define the direction, location, and orientation of the anatomical planes of the patient relative to the 3D-tracking acquisition system. Some further embodiments can involve holding the probe in particular orientation and location in space and registering that position relative to the 3D-tracking acquisition system as the new coordinates system of all acquired measurements outputted by 3D-tracked devices.

In some embodiments, a decision step 6102 can include a determination of whether patient anatomy/imaging has been registered relative to a 3D tracking camera axis. In some embodiments, for a positive answer, the process can include step 6104 including a tracked DRF that serves as a reference for patient cross-sectional imaging fusion with a navigation camera, step 6106, including where the orientation of anatomical planes is interpreted, and step 6126 that can include camera coordinates interpreted within anatomical axis.

In some embodiments, a negative for step 6102 can lead to step 6108 where the position of anatomical planes is indicated relative to camera axis, including, but not limited to step 6110, including adjusting position of a DRF such that it's reference plane labels align with the patient's anatomical planes. Further, step 6112 including tapping two points in space with a tracked probe to represent each anatomical axis aligned with the patient. Further, step 6114, including temporarily holding a tracked probe in instructed orientation. In some embodiments, step 6116 (reached from step 6110 or decision step 6118 from a positive) can include substantially rigidly transforming camera axis to the DRF-referenced anatomical axes, and to step 6126, where camera coordinates are interpreted with anatomical axes.

In some embodiments, from decision step 6118, including checking if a dedicated DRF is used to indicate patient anatomy, a negative can proceed to step 6120 of substantially rigidly transforming camera axes to referenced anatomical axes and to decision step 6122. From step 6122, a positive can lead to step 6124 including a return to step 6108, and a negative can include moving to step 6126 (described above).

In some embodiments, any of the above processes, methods, or procedures related to the workflow 6200 can include or be accomplished with one or more of steps or processes 6102, 6104, 6106, 6108, 6110, 6112, 6114, 6116, 6118, 6120, 6122, 6124, and 6126. In some embodiments, at least one of the steps can include a decision step (e.g., such as step 6102 or 6122), where one or more following steps depend on a status, decision, state, or other condition. In some embodiments, the steps of workflow 6100 can proceed in the order as shown. In some embodiments, any of the steps of the workflow 6100 can proceed out of the order as shown. In some embodiments, one or more of the steps of the workflow 6100 can be skipped.

Some embodiments of the invention in the acquisition and interpretation of spinal contour via tracing body surfaces with a 3D-tracked probe and interfacing with previously initialized skin fiducial markers as described previously. In this embodiment, the tracing can be performed with a trigger-equipped probe, as described previously in relation to FIGS. 10A-10G, and FIGS. 15A-15C, to indicate the body surface type that is being traced (e.g., skin, lamina, etc.) and to ensure the probe is only in an active state when in contact with body surfaces as described below in reference to FIG. 69. The acquired tracing data obtained from this embodiment can then be used to automatically compute spinal alignment parameters as described below in reference to FIGS. 66A-66B, and 67.

FIG. 62A displays one embodiment of the invention which consists of acquiring information regarding the contour of the spine via tracing over body surfaces using a tracked probe. This embodiment consists of spine bony anatomy 6211, overlying skin 6215 interrupted to represent a surgical site 6220, skin-mounted fiducials 6226, 6228 applied to two regions outside of the surgical site with overlying surgical drapes 6208 and over-the-drape-mating fiducials 6225, 6227. Using a 3D-tracked probe, tracing coordinates are acquired over the skin of the cervicothoracic spine 6202, surgical site anatomy 6204, and skin of the lumbosacral spine 6205. After acquiring this traced data, the acquisition system software can interpret it with the aid of fiducial initialization data, previously described in relation to FIGS. 4A-4I and 58 to represent one complete bony surface contour from which spinal alignment parameters can be calculated, as described below in reference to FIGS. 67, and 69.

FIG. 62B displays on embodiment of the invention which is a display of the acquired body surface contours via tracing with a 3D-tracked probe within the optical 3D-tracking camera's axes, containing the 3D coordinates of the over-the-drape-mating fiducials 6251, cervicothoracic skin tracing 6253, surgical site tracing 6255, and lumbosacral skin tracing 6257. In order to properly interpret this data, the acquisition software has to substantially rigidly transform the data such that it is represented within anatomical reference axes rather than camera axes. The mechanism of establishing anatomical reference axes was previously described in relation to FIGS. 12 and 61 and the transformed data is shown below in reference to FIG. 62C.

FIG. 62C displays one embodiment of the invention which is applying a 3D rigid transform to the acquired tracing data as described previously in relation to FIGS. 62A-62B, to be interpreted and displayed within anatomical reference axes including the coordinates of the over-the-drape-mating fiducials 6261, cervicothoracic skin tracing 6263, surgical site tracing 6265, and lumbosacral skin tracing 6267. Interpreting and displaying the acquired 3D-tracing data in this way enables subsequent manipulation and calculations as described below in relation to FIGS. 62D and 67.

FIG. 62D displays one embodiment of the invention which is the translation of the acquired tracing data previously described in relation to FIGS. 62A-62C. In this embodiment, based on the displacement vector between the initialized skin fiducial and anatomical regions of interest, and based on the displacement vectors between the skin tracing locations most closely approximating the surgical site tracing and the end points of the surgical site tracing, any skin-surface tracing is translated to represent one continuous tracing of bony anatomy. As shown in the figure, this embodiment consists of the translated coordinates for the cervical fiducial 6281, cervicothoracic skin tracing 6283, lumbosacral skin tracing 6285, and lumbosacral fiducial 6287. From the data coupling the translated tracings to the surgical site tracing (if applicable), spinal alignment parameters can then be calculated as described below in reference to FIG. 67. Additionally, if a quantitative assessment of aligning is desired for the surgical site only, that is also achievable with the acquired data in this embodiment, as described in more detail below in reference to FIG. 68.

Some embodiments of this invention include the use of a tracked mobile stray marker (TMSM) to communicate particular commands to the computer system via its tracked dynamic motion relative to the 3D-tracked tool's end effector and/or DRF. For example, FIG. 63 shows a workflow 6300 for analog triggering detection of one or more TMSMs relative to a tracked tool with a DRF in accordance with some embodiments of the invention. In some embodiments, other relevant figures related to linear actuation of the TMSM relative to the probe shaft can include, but not be limited to, FIGS. 10A-10E, FIGS. 29A-29C, FIGS. 38C, 38G, FIGS. 39A-39B, FIGS. 44B-44D, FIGS. 45A-45B, FIGS. 51E-51H, FIGS. 53A, 53C-53D, and FIGS. 57A-57B. In some embodiments, other relevant figures related to rotational actuation of the TMSM on a rigid arm relative to the probe shaft can include, but not be limited to, FIG. 4H, FIGS. 15A-15C, FIGS. 48B-48C, FIGS. 49A-49D, FIGS. 50A-50E, and FIGS. 82A-82B. In some embodiments, some relevant figures related to calculation of angle of TMSM with respect to the probe shaft can include, but not be limited to, FIGS. 64A-64B.

Some embodiments of the invention involve the use of a TMSM that is mechanically linked to a 3D-tracked tool and tracking its dynamic position relative to the coordinates of the 3D-tracked tool, which is defined by a coupled DRF and its associated tool definition file. Some embodiments involve the use of a depressible tip that actuates a rod that is coaxial to the shaft of a 3D-tracked tool. In some embodiments, the TMSM is attached to the depressible rod and subsequently its distance from the tip of the 3D-tracked tool, or any other defined component relative to the DRF of the tool, can dynamically change upon actuation of the depressible tip, following a linear path of motion. Some embodiments of the system use the 3D location of the TMSM and apply to it a 3D rigid transformation of the 3D location and orientation of the 3D-tracked tool relative to the 3D-tracking acquisition unit. The TMSM location data is now transformed to be relative to the coordinate system of the 3D-tracked tool, and thus does not perturb with respect to moving the 3D-tracked tool in space without triggering the depressible tip to change the location of the TMSM relative to the 3D-tracked tool. In some embodiments, the resulting magnitude of the vector between the transformed TMSM and the 3D-tracked tool end effector is the mathematical output that is tracked for the system to detect when an event has occurred to note information or store data produced by the position and/or behavior of the 3D-tracked tool.

In some embodiments, the dynamic change of the magnitude of the vector between transformed TMSM coordinates and the coordinates of the 3D-tracked tool's end effector can be analyzed for detecting specific thresholds of magnitude for a binary system behavior, or also analyzed at various levels of magnitude across the possible range of motion of the TMSM relative to the 3D-tracked tool's end effector, representing a more analog system behavior. Some example embodiments are depicted in FIGS. 10A-10B, 10D, 10E, FIGS. 29A-29C, FIGS. 38C, 38G, FIGS. 39A-39B, FIGS. 44B-44D, FIGS. 45A-45B, FIGS. 51E-51H, FIGS. 53A, 53C-53D, and FIGS. 57A-57B. In addition, some embodiments of the system can calculate the angle between two vectors to communicate when the behavior of the TMSM is used to communicate a specific command (e.g., such as the vector between the 3D-tracked tool's end effector and the rotation axis of the arm), which is mechanically linked to the 3D-tracked tool, that the TMSM is substantially rigidly attached to, and the vector between the TMSM and the rotation axis of the arm, which is mechanically linked to the 3D-tracked tool, that the TMSM is substantially rigidly attached to. In some embodiments, the system calculates the angle between these two vectors during the use of the 3D-tracked tool and constantly analyzes the angle of the vectors that are defined with respect to the coordinates of the 3D-tracked tool. In some embodiments, this dynamic angle calculation, such as the example described in FIG. 64A and FIG. 65B, can also be sensed in a binary or analog manner such as described above to enable various commands to be communicated to the 3D-tracking acquisition unit for a variety of applications. One example embodiment involves the use of a 3D-tracked tool with a rotationally-actuating TMSM to trace the spine at select regions and communicate to the system to only store location and orientation data of the 3D-tracked tool while the TMSM-based angle has reached a certain threshold via the actuation of a button on the 3D-tracked tool. Some example embodiments are depicted in FIG. 4H, FIG. 15A, FIG. 15B, FIG. 15C, FIG. 48B, FIG. 48C, FIG. 49A, FIG. 49B, FIG. 49C, FIG. 49D, FIG. 50A, FIG. 50B, FIG. 50C, FIG. 50D, FIG. 50E, FIG. 82A, and FIG. 82B.

In some embodiments, any of the above processes, methods, or procedures related to the workflow 6300 can include or be accomplished with one or more of steps or processes 6310, 6312, 6314, 6320, 6318, 6316, 6322, 6324, 6326, 6328, 6330, 6332, 6334, 6336, 6338, 6340, 6342, 6344, 6346, 6350, 6354, and 6356. In some embodiments, at least one of the steps can include a decision step (e.g., such as step 6328), where one or more following steps depend on a status, decision, state, or other condition. In some embodiments, the steps of workflow 6300 can proceed in the order as shown. In some embodiments, any of the steps of the workflow 6300 can proceed out of the order as shown. In some embodiments, one or more of the steps of the workflow 6300 can be skipped.

FIG. 64A displays one embodiment of the invention consisting of a probe with a tip 6415, tracked DRF 6405, pivot arm 6430 containing a TMSM 6425 and pivoting about a pivot hinge 6410. In this embodiment, the 3D coordinates of the probe tip, pivot hinge, and TMSM are known relative to the tracked DRF axes and the position of the TMSM relative to the DRF can be calculated in terms of relative angles as described below in reference to FIG. 64B. Further, FIG. 64B displays one embodiment of the invention consisting of the interpretation and calculation of the position of a rotating TMSM 6456 relative to the DRF on a probe as described previously in relation to FIG. 64A. In this software interpretation, a vector V1 6450 is defined from the probe tip 6415 through the pivot hinge 6410 and a vector V2 6444 is defined from the pivot hinge to the TMSM 6456. The angle theta between V1 and V2 is calculated as described previously in relation to FIG. 63 and used as a method of communicating analog or binary signals to the 3D-tracking acquisition system. This embodiment can be applied to any embodiment of the invention that involves a TMSM rotating about a hinge relative to a tracked DRF, as in those previously described in reference to FIGS. 15A-15C, 48A-48C, 55A-55I, 56C-56D, and 56F.

In some embodiments of the invention, based on data acquired from cross-sectional imaging (CT shown), a relative body and bony surfaces can be manually or automatically annotated to then calculate relative displacement vectors from points on each surface to one another (e.g., the displacement vector from the midpoint of the lamina to the vertebral body centroid). The acquisition software can utilize this information as input into the manipulation of data created by tracing body-surfaces with a 3D-tracked probe. For example, FIG. 65A illustrates displays of a discrete body surface or bony surface annotations on cross-sectional images used for initialization of patient-specific interpretation of body and bony surface tracings with a 3D-tracked probe in accordance with some embodiments of the invention. FIG. 65A displays a body surface or bony surface annotations on cross-sectional images (6510, 6512) to be used for initialization of patient-specific interpretation of body and bony surface tracings with a 3D-tracked probe. These annotated regions include but are not limited to skin surface, spinous process, lamina, transverse process, pedicle, vertebral body, and vertebral body centroid.

FIG. 65B illustrates 3D perspective of cross-sectional annotations from the CT scan in accordance with some embodiments of the invention, where based on these annotations, software comparison algorithms have a patient-specific reference to compare 3D-tracked tracing contours over bony surfaces to annotated surfaces from the cross-sectional imaging, and use the comparison to attempt to display a 3D perspective of the spine following a contour assessment tracing. Additionally, in other embodiments this data may be utilized for automatically detecting spinal levels represented by the traced contour within the surgical site.

FIG. 65C illustrates a plot of coronal projected coordinates in accordance with some embodiments of the invention. FIG. 65C displays coronal projected coordinates of annotated transverse processes (6514, 6520), laminae (6516, 6518), vertebral body centroids, skin surface, and spinous processes. This embodiment displays the similarity in coronal contours of annotations over varying bony elements. Additionally, it displays the basis of computing displacement vectors within the coronal plane. Further, FIG. 65D illustrates a plot of sagittal projected coordinates in accordance with some embodiments of the invention, and includes sagittal projected coordinates of annotated transverse processes 6528, laminae 6520, vertebral body centroids 6526, skin surface 6522, and spinous processes 6524. This embodiment displays the similarity in sagittal contours of annotations over laminae, transverse processes, and vertebral body centroids across the length of the spine, which serves as valuable input into the interpretation of 3D-traced data previously described in FIGS. 62A-62D as well as in the automated calculation of spinal alignment parameters from the tracings, as described below in reference to FIG. 67.

FIG. 65E illustrates computed cross-sectional distances between corresponding anatomical landmarks and vertebral body centroids in accordance with some embodiments of the invention. Shown are computed cross-sectional distances between corresponding anatomical landmarks and the vertebral body centroids (e.g., left lamina midpoints 6530, right lamina midpoints 6532, left transverse process midpoints 6534, and right transverse process midpoints 6536 etc.).

In some embodiments of the invention, acquired 3D-tracing data can be interpreted to represent the contour of the vertebral body centroids based on initialization data with or without the aid of fiducials. FIG. 66A illustrates a display of cross-sectional slices of vertebra 6601 in their relative anatomical axes in accordance with some embodiments of the invention, with tracing coordinates 6603 from tracing over surgically exposed left lamina with a 3D-tracked probe, and coordinates from tracing the right lamina (not shown), and the corresponding computed coordinates 6605 representing the vertebral body centroids on cross-sectional imaging.

Some other embodiments include a display of a vertebral body calculated via bilaterally traced coordinates and patient initialization data in accordance with some embodiments of the invention. For example, FIG. 66B displays one embodiment of the invention in which the location of a cross-section image's 6601 vertebral body centroid 6615 is calculated via bilaterally traced coordinates and patient initialization data. This embodiment also consists of left 6607 and right 6609 lamina coordinates as input from a 3D-tracked probe tracing, a line segment 6611 connecting the two laminae coordinates, and an orthogonal line segment 6613 from the midpoint of the laminae-connecting segment and of a distance based on patient initialization information. It should be noted that there are varying embodiments of initialization of patient anatomy in this invention including but not limited to CT imaging annotation, as described in reference to FIGS. 13 and 65A-65E, intraoperative X-ray image annotation, normative patient data sets, fiducial-based initialization as previously described in reference to FIGS. 4A-4I, 6A-6C, 9, 44A-44D, 45A-45B, 58-60, and 62A-62D.

Some embodiments of this invention involve the process of filtering and segmenting a contour tracing produced by a 3D-tracked tool. In some embodiments, calculations can be derived from tracing data that is generated inside and outside of the surgical site, with or without annotations of particular anatomical landmarks of interest. For example, FIG. 67 illustrates a workflow 6700 to calculate spinal alignment parameters based on intraoperative tracing in accordance with some embodiments of the invention. Some relevant other figures can include, but not be limited to, FIGS. 9A-9B, FIGS. 21A-21B, and FIGS. 64A-64B (for initialization of tracing sequence), FIG. 12 (for initialization of patient's anatomical planes), FIG. 86 (for alignment parameter output), FIGS. 62, and 65A-65E, and 66A-66B (for transforming of tracing data via 3D-displacement offset to curves generated by connecting other anatomical landmark locations).

Some embodiments of the invention involve the use of an electromechanical, 3D-tracking system, as depicted in FIG. 23A and FIG. 23B. Other embodiments involve the use of an optical, 3D-tracking system, which is depicted in FIG. 5A. Further, some embodiments involve the initialization of the patient's anatomical planes via coordinate transformation references defined by tracked DRFs (e.g., FIG. 12), or tracings of a unique pattern or a plane that defines the orientation, direction, and location of the anatomical plane references that measurements generated by 3D-tracked tools will be transformed relative to after initialization. Further, some embodiments of the invention involve the classification of tracing data based on its relation to specific anatomical regions of interest (e.g., spinous processes, laminae, skin surface, transverse processes, etc.). Some embodiments of this anatomical classification of the tracing data are a result of software-based user inputs, proximity-based detections near registered fiducial markers or anatomical landmarks that have known associated locations relative to a 3D-tracking acquisition system, registration of a unique pattern with known dimensions, or via user-based, selective toggles actuated with 3D-tracked tools or DRFs, such as triggering of a TMSM attached to the 3D-tracked tool. Some examples of these embodiments include FIG. 9A, FIG. 9B, FIG. 21A, FIG. 21B, FIG. 64A, and FIG. 64B.

In some embodiments, once a continuous or discrete series of points is acquired via the 3D-tracked tool used in 3D coordinates relative to the 3D-tracking acquisition system, algorithms of the system can utilize data (e.g., including, but not limited to, fiducial-based 3D-displacement vector to one or more anatomical landmarks of interest, normative data of a patient population, or preoperative imaging annotations that define a 3D-displacement vector between anatomical regions that are traced and anatomical landmarks of interest), to transform the tracing data to approximate the contours produced by connecting points at key anatomical landmarks (e.g., curve generated by fitting line to several vertebral body centroids) across the region of the tracing. Examples of this described transformation process are depicted in FIG. 62A, FIG. 62D, FIG. 65A, FIG. 65B, FIG. 65C, FIG. 65D, FIG. 65E, FIG. 66A, and FIG. 66B.

Some embodiments involve the use of first and second derivative calculations of filtered tracing contours to identify maxima, minima, and inflection points of the curves. Some embodiments involve using these calculated inflection points as reference lines used in the calculation of endplate-based coronal measurements (e.g., Cobb angles).

Figure 86A:
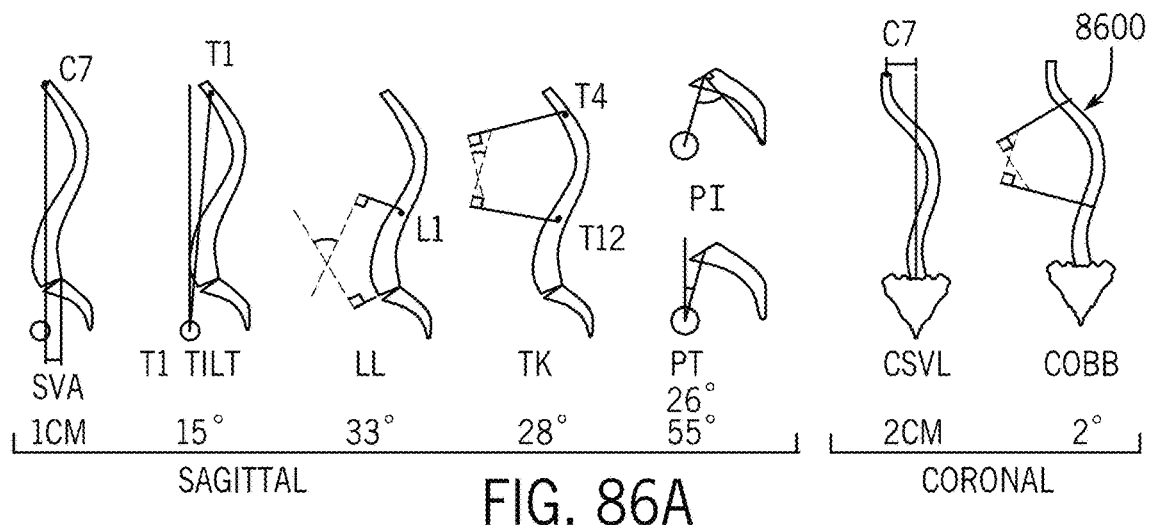
Figures 86B, 86C:
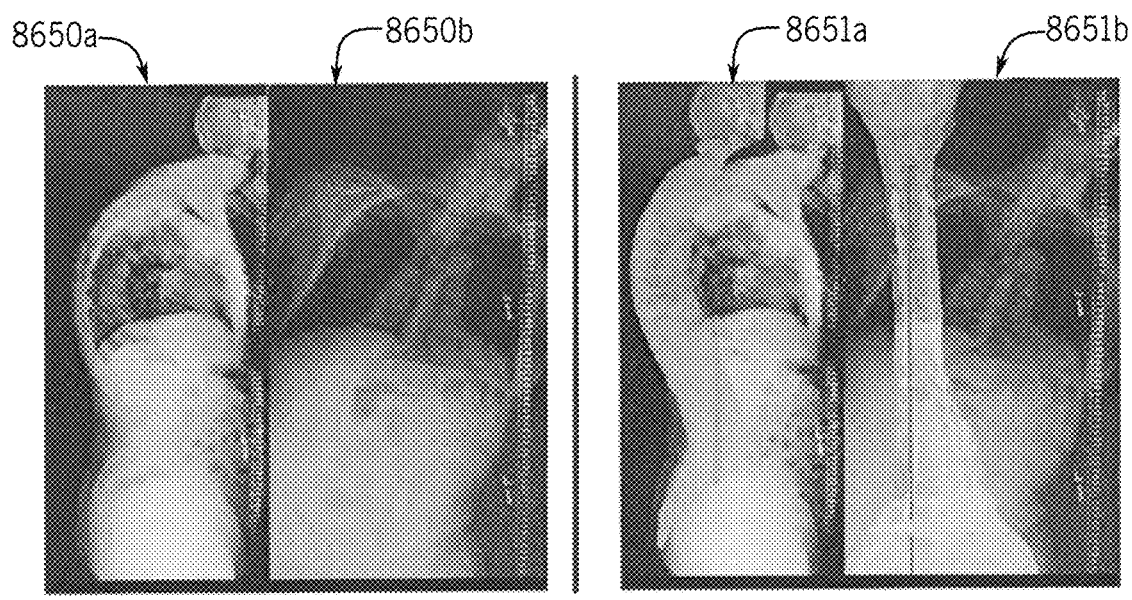

Some embodiments involve the use of annotation of one or more anatomical landmarks of interest as inputs into which segments of the tracing should the algorithm compute perpendicular lines used to make endplate-based measurements of the alignment of vertebral segments in the specific region, defined by one or more annotated anatomical landmarks. Some embodiments of the annotation process involve the registration of anatomical landmarks using 3D-tracked tools, software-based estimations based on registered references to cross-sectional imaging before or during the procedure, or via the location of registered fiducial markers relative to the tracing data. In some embodiments, from these segmented annotations of the tracing data, some embodiments involve the algorithmic calculation of spinal alignment parameters (e.g., Cobb angle, lumbar lordosis (LL), thoracic kyphosis (TK), C2-C7 sagittal vertical axis (SVA), C7-S1 SVA, C2-S1 SVA, central sacral vertical line (CSVL), T1 pelvic angle (T1PA), pelvic tilt (PT), pelvic incidence (PI), chin-brow to vertical angle (CBVA), T1 slope, sacral slope (SS), C1-2 lordosis, C2-C7 lordosis, C0-C2 lordosis, C1-C2 lordosis, PI-LL mismatch, C2-pelvic tilt (CPT), C2-T3 angle, spino-pelvic inclination from T1 (T1SPi) and T9 (T9SPi), C0 slope, mismatch between T-1 slope and cervical lordosis (T1S-CL), and/or global sagittal angle (GSA)). One embodiment of the display of these calculated alignment parameters, along with thresholds predefined in the literature for patient-specific surgical goals, is depicted in FIGS. 86A-86C.

In some embodiments, any of the above processes, methods, or procedures related to the workflow 6700 can include or be accomplished with one or more of steps or processes 6702, 6704, 6706, 6712, 6710, 6708, 6714, 6716, 6718, 6720, 6722, 6724, 6726, 6728, 6730, 6732, 6738, 6740, 6734, 6736, 6742, 6744, 6746, and 6748 as shown. In some embodiments, the steps of workflow 6700 can proceed in the order as shown. In some embodiments, any of the steps of the workflow 6700 can proceed out of the order as shown. In some embodiments, one or more of the steps of the workflow 6700 can be skipped.

Some embodiments of this invention involve the process of filtering and segmenting a contour tracing produced by a 3D-tracked tool only registering points within the surgical site. In some embodiments, calculations are derived from tracing data that is generated inside the surgical site, with or without annotations of a particular anatomical landmark of interest, as well as with or without registration of bone-mounted fiducial markers in the surgical site. For example, FIG. 68 illustrates a workflow to acquire a spinal alignment curve using probe-based tracing within only the surgical site in accordance with some embodiments of the invention. Other relevant figures can include those related to registration of bone-mounted fiducial markers with one or more anatomical landmarks of interest (FIGS. 59 and 60), triggering of tracked mobile stray markers attached to 3D-tracked tool (FIG. 63), calculating spinal alignment parameters based on intraoperative tracing (FIG. 67).

Some embodiments involve the use of bone-mounted fiducial markers that are registered to one or more nearby anatomical landmarks of interest via a 3D-displacement vector, such as the processes depicted in FIGS. 59-60. Some embodiments involve the communication of commands to the 3D-tracking acquisition system that a tracing or registration is occurring, such as the processes depicted in FIG. 63. Some embodiments involve the user annotating particular anatomical landmarks, via processes such as tracing or discrete-point tapping of registered fiducial markers, or also mechanically coupling between the 3D-tracked tool and the fiducial marker. Some embodiments involve the computer system only storing data that is generated by the 3D-tracked tool while it traces or discretely registers the contour of the anatomical region of interest that begins and ends with the registration of or proximity-detection event of a bone-mounted fiducial marker. Some embodiments involve the user identifying the tracing region of interest in relation to the anatomical sections of the patient via manual display monitor inputs that define the landmarks that the tracing will span. Some embodiments involve the calculation of spinal alignment parameters based on registered contour of the tracing data and/or annotation of one or more anatomical landmarks of interest. Some examples of this process were described in FIG. 67.

In some embodiments, any of the above processes, methods, or procedures related to the workflow 6800 can include or be accomplished with one or more of steps or processes such as 6802, 6804, 6806, 6808, 6810, 6812, 6816, 6814, 6816, 6817, 6822, 6818, 6820, 6822, 6824, 6826, 6828, 6830, 6832, 6834, 6836, 6838, 6840, 6842, and 6844. In some embodiments, at least one of the steps can include a decision step (e.g., such as step 6814), where one or more following steps depend on a status, decision, state, or other condition. In some embodiments, the steps of workflow 6800 can proceed in the order as shown. In some embodiments, any of the steps of the workflow 6800 can proceed out of the order as shown. In some embodiments, one or more of the steps of the workflow 6800 can be skipped.

FIG. 69 illustrates a workflow 6900 to acquire a spinal alignment curve using probe-based tracing data spanning beyond the surgical site in accordance with some embodiments of the invention. Some embodiments of the invention involve the process of filtering and segmenting a contour tracing produced by a 3D-tracked tool registering points within and beyond the surgical site. In some embodiments, calculations are derived from tracing data that is generated inside the surgical site, with or without annotations of one or more particular anatomical landmarks of interest, with or without registration of bone-mounted fiducial markers in the surgical site, as well as with or without registration of skin-mounted fiducial markers beyond the surgical site. Some other relevant other figures include FIGS. 59-60 (for registration of bone-mounted fiducial markers with one or more anatomical landmarks of interest), and FIG. 63 (the triggering of tracked mobile stray markers attached to 3D-tracked tool). Others include FIG. 67 (for calculating spinal alignment parameters based on intraoperative tracing), FIG. 68 (outlining a process of calculating alignment using tracings and bone-mounted fiducials, FIGS. 6B, 9A-B, 11A-B (related to skin-based fiducial markers), and FIGS. 62A, 62D, 65A-E, 66A-B (related to calculating the displacement offset between tracing data and anatomical landmarks of interest).

Some embodiments of this invention involve initializing the key anatomical landmarks of interest, such as those that are required for spinal alignment parameter calculations. Some embodiments involve depictions that are shown in FIGS. 6B, 9A-B, 11A-11B, 59, 60, and 68. Some embodiments involve tracing anatomical structures within the surgical site as well as registering landmarks, such as skin-based fiducial markers, beyond the surgical site. Some of these embodiments involve applying offsets based on initialized 3D-displacement vectors, such as the examples depicted in FIGS. 62A, 62D, 65A-65E, and 66A-66B. Further, some embodiments of communicating when to store tracing data and classifying particular tracings as related to an anatomical region involve example embodiments depicted in FIGS. 9A-9B, 62A-62D, 59, and 63.

In some embodiments, any of the above processes, methods, or procedures related to the workflow 6900 can include or be accomplished with one or more of steps or processes such as 6902, 6904, 6906, 6908, 6910, 6912, 6914, 6916, 6918, 6920, 6922, 6924, 6926, 6928, 6930, 6932, and 6934. In some embodiments, at least one of the steps can include a decision step (e.g., such as step 6924), where one or more following steps depend on a status, decision, state, or other condition. In some embodiments, the steps of workflow 6900 can proceed in the order as shown. In some embodiments, any of the steps of the workflow 6900 can proceed out of the order as shown. In some embodiments, one or more of the steps of the workflow 6900 can be skipped.

Some embodiments of this invention involve the process of calculating the flexibility or range of motion of a particular anatomical region of interest. Some embodiments enable the user to mechanically manipulate the conformation of the spine while calculating the quantitative flexibility of a region of the spine. For example, FIG. 70 illustrates a workflow 7000 to assess flexibility of the spine intraoperatively using flexibility assessment device in accordance with some embodiments of the invention. Other relevant figures (e.g., such as in relation to a flexibility assessment device can include FIGS. 34A-34G, FIGS. 35A-35F, FIGS. 36A-36I, FIGS. 37A-37G, FIGS. 39A-39F, and FIGS. 40A-40C). Further, flexibility assessment devices on spine, including during set-and-hold manipulation of adjusting the correction of the spine include FIGS. 42A-42F and FIG. 70.

Some embodiments of this invention involve the rigid fixation of a 3D-tracked tool, which can be arranged in adjustable configurations, with vertebrae in the exposed surgical site via attachment rigid landmarks, such as the pedicle screws. Further, some embodiments of the system involve the ability of the 3D-tracked tool to substantially rigidly attach to more than one pedicle screw on a vertebra at once. Examples of some embodiments in various applications and forms, but not exhaustive to all possible and developed design permutations, include those depicted in at least FIGS. 34A-34G, 35A-35F, 36A-36I, 37A-37G, 39A-39F, and 40A-40C.

Some embodiments involve the X-ray-based registration of the vertebral endplate angle with respect to the 3D-tracked tool side surface. Some embodiments of the system involve the use of one or more of the specified 3D-tracked tools to manipulate multiple regions of the anatomy and store location and orientation information detected by the 3D-tracking acquisition system. Some embodiments of the system involve the calculation of relative angles between two or more 3D-tracked tools substantially rigidly attached to vertebra at the end of the assessment region of interest. In some embodiments, this angle can provide an assessment of the flexibility of the spine, as the system is able to measure the relative angle between two or more 3D-tracked tools during manipulations that explore the full range of motion of the attached vertebrae. Some examples of this manipulation and measurement process are depicted in FIGS. 42A-42F.

In some embodiments, any of the above processes, methods, or procedures related to the workflow 7000 can include or be accomplished with one or more of steps or processes such as 7002, 7004, 7006, 7008, 7010, 7012, 7014, 7016, 7018, 7020, 7022, 7024, 7026, and 7028. In some embodiments, at least one of the steps can include a decision step (e.g., such as step 7014), where one or more following steps depend on a status, decision, state, or other condition. In some embodiments, the steps of workflow 7000 can proceed in the order as shown. In some embodiments, any of the steps of the workflow 7000 can proceed out of the order as shown. In some embodiments, one or more of the steps of the workflow 7000 can be skipped.

Some embodiments of this invention involve the process of overlaying a surgical instrument using 3D-tracking dynamic reference markers to approximate the 2D, projected shape of the instrument on the 2D radiograph of an anatomical region of interest. For example, FIG. 71 illustrates a workflow of producing real-time overlays of surgical instruments over intraoperative X-rays in accordance with some embodiments of the invention. Some other figures, for example as related to a process of overlay illustration using 3D-tracked tool and C-arm X-ray images are described in relation to FIGS. 46A-46G.

Some embodiments of the invention involve utilizing a 3D-tracked tool with a coupled tracked DRF. Some embodiments also involve the use of a DRF substantially rigidly attached to the emitter of an X-ray imaging system, such as a C-arm. Further, some embodiments involve using the relative distance and orientation of the 3D-tracked tool with respect to the X-ray imaging system to calculate the appropriate size and 2D-projected shape of the surgical tool with the attached DRF on the X-ray image.

In some embodiments, the system utilizes the known distance of the 3D-tracked surgical tool away from the X-ray imaging system, the size and dimensions of the surgical tool, the location and orientation of the surgical tool, and the location and orientation of the imaging system, all with respect to the coordinates of the 3D-tracking acquisition system, to produce an accurate 2D projection of the tracked surgical tool with appropriate scaling and pose with respect to the X-ray imaging system. Some embodiments include computing the rigid transformation between the tracked surgical tool and the imaging system to transform the tool's location and orientation to be outputted with respect to the imaging system coordinates. Further, some embodiments of the system enable for the visual overlay of the computed 2D-projection of 3D-tracked surgical tool based on its distance and pose in relation to the volume of the cone beam of the X-ray imaging system.

In some embodiments, any of the above processes, methods, or procedures related to the workflow 7100 can include or be accomplished with one or more of steps or processes such as 7102, 7104, 7106, 7108, 7110, 7112, 7114, 7116, 7118, 7120, 7122, 7124, 7126, 7128, 7130, 7132, 7134, 7136, 7138, 7140, and 7142. In some embodiments, the steps of workflow 7000 can proceed in the order as shown. In some embodiments, any of the steps of the workflow 7000 can proceed out of the order as shown. In some embodiments, one or more of the steps of the workflow 7000 can be skipped.

Some embodiments of this invention involve the process of registering the location and orientation with accessible fiducial markers, surgical implants, or anatomical landmarks, that are registered to the vertebrae and surrounding anatomical landmarks of interest. For example, FIG. 72 shows a workflow 7200 to rapidly re-register a surgical navigation system after a navigated/registered screw insertion in accordance with some embodiments of the invention. The workflow 7200 describes methods for producing 3D renderings of the vertebrae of interest by registering the location and pose of the vertebrae of interest with respect to known landmarks that are registered in 3D-based images acquired of the vertebra (e.g., CT scan). Some other relevant figures include FIGS. 44A-44D (for a method of registering a substantially rigidly-attached landmark of a vertebra), and FIGS. 45A-45B (for a process of re-registering a manipulated vertebra via a known landmark (e.g., pedicle screw shaft)).

Some embodiments of the system involve the use of navigated pedicle screws to register the relationship between the pedicle screw shaft and the vertebral body. Some embodiments of the system involve the use of registered bone-mounted fiducials that are associated with a 3D-displacement vector to anatomical landmarks of interest of the attached vertebra. One example embodiment is depicted in FIGS. 44A-44D.

Some embodiments involve the registration of landmarks of interest of the vertebra with a volumetric 3D reconstruction of the anatomy via modalities such as a CT scan or O-arm scan. Further, some embodiments involve the system registering one or more accessible fiducial markers, surgical implants, or anatomical landmarks as associated components of a 3D reconstruction of the vertebrae. In this way, each time one or more of the described items are registered by a 3D-tracking acquisition system with location and orientation outputs, the system can calculate the updated position and orientation of anatomical objects of interest that have associated 3D reconstructions. One example embodiment is depicted in FIGS. 45A and 45B.

In some embodiments, any of the above processes, methods, or procedures related to the workflow 7200 can include or be accomplished with one or more of steps or processes such as 7202, 7204, 7205, 7206, 7208, 7210, 7212, 7214, 7216, 7218, 7220, 7222, 7224, 7226, 7228, 7230, 7232, 7234, 7236, 7238, 7240, 7242, 7244, 7246, and 7248. In some embodiments, at least one of the steps can include a decision step (e.g., such as step 7212), where one or more following steps depend on a status, decision, state, or other condition. In some embodiments, the steps of workflow 7200 can proceed in the order as shown. In some embodiments, any of the steps of the workflow 7200 can proceed out of the order as shown. In some embodiments, one or more of the steps of the workflow 7200 can be skipped.

FIGS. 73A-73B display one embodiment of the invention which consists of interpretation of the rod contour via interfacing with a rod-centering fork as described previously in relation to FIGS. 47B, 51D-51I, and 53A-53F, and 54A-54D. This acquisition system's calculation is based on the calculated distance from the fork's bifurcation to the rod's cross-sectional center point when a rod of known diameter is fully engaged with the fork of known geometry. For example, FIG. 73A displays one embodiment 7300 of the invention which consists of a rod-centering fork 7315 on the end of a tool shaft 7305 with attached tracked DRF (not shown), bifurcation at point C 7310, and interfacing with a rod 7311. In this configuration, because the fork is not fully engaged with the rod (i.e., the rod is not approximating both side walls of the fork), the tool does not trigger the acquisition system to record the tool's coordinates. This triggering mechanism to indicate the fork is firmly engaged with the rod can be accomplished via a number of varying embodiments including but not limited to a linearly actuated TMSM, rotationally actuated TMSM, electrical conduction through the rod across fork-mounted electrical contact terminals, wireless or wired electronic communication, and optically signaled via visible or infrared lights.

FIG. 73B illustrates the fork of FIG. 73A fully engaged with a rod represented as embodiment 7301 in accordance with some embodiments of the invention. For example, FIG. 73B displays rod-centering fork 7315 on a tool shaft 7305 fully engaged with a rod 7317 such that both inner walls of the fork 7315 are approximating the rod surface. In this embodiment, point C 7310 indicating the bifurcation of the fork is known relative to the tracked DRF (not shown) attached to the tool. Based on the known diameter of the rod and geometry of the fork, a vector V1 7319 is produced to point from C 7310 to the calculated center point of the rod, C' 7318, located along the line that bisects the fork. After interpreting the location of point C' 7318 relative to the tracked DRF attached to the fork-equipped tool, the coordinates of C' 7318 undergo a rigid body transformation to be represented within the coordinates of a DRF-equipped end cap, if applicable. For embodiments that do not involve a coupled end-cap as described previously in relation to FIGS. 52A-52D, 53A-53F, and 54A-54D, the rod coordinates are interpreted relative to the camera coordinates or anatomical reference marker if present.

Some embodiments of this invention involve the process of registering the contour of a rod implant via a combination of 3D-tracked tools. For example, FIG. 74 illustrates a workflow to assess the contour of a rod prior to implantation using two handheld tracked tools in accordance with some embodiments of the invention. Some other relevant other figures (e.g., such as tools used for assessing rod contour include FIGS. 48A-48C, 49D, 50D-50E, 51H-51I, 53C-53D, and 54C-54D). Further, other figures and descriptions for tools using a tracked mobile stray marker as a trigger include FIG. 63.

Some embodiments of this invention involve the use of one or more 3D-tracked tools that have a substantially rigidly attached tracked DRF. Some embodiments of the system involve using a 3D-tracked tool that substantially rigidly attaches to one end of a surgical rod. Some example embodiments are depicted in FIGS. 48A-C, and 49D. Some embodiments involve selecting a rod diameter via various communication signals (e.g., FIGS. 49D, and 50D-50E) using 3D-tracked tools and substantially rigidly attached TMSMs that the computer system can detect as a trigger, as depicted in FIG. 63.

Some embodiments involve using a second 3D-tracked tool with an end-effector that conforms to a rod surface and contains a depressible shaft that is coaxial with the shaft of the 3D-tracked tool. In some embodiments, when the 3D-tracked tool is pressed against the rod surface, the depressible tip actuates up the 3D-tracked tool and translates a TMSM that is substantially rigidly attached to the depressible shaft, which signals to the 3D-tracking acquisition system that the rod is being engaged. Some embodiments of this system involve using this 3D-tracked tool in an active/triggered state to trace the contour of the rod, and simultaneously to apply a rigid transformation to each discrete point of tracing data to reference the 3D-tracked end cap tool that has dynamic location coordinates and orientation with respect to the 3D-tracking acquisition system.

Some embodiments of this system involve the rod, which is attached to the 3D-tracked end cap tool, where inserting the opposite end through a toroid-shaped object can allow for cross-sections of the rod (that are parallel to the toroidal object's entry way) to pass through. In this instance, the dynamic path traveled by the 3D-tracked end cap can be used to calculate the contour of the rod by association of the constraints of the bends causing a travel path for the 3D-tracked end cap. Some example embodiments of this system in various applications and forms are depicted in at least FIGS. 48A-48C, 49D, 50D-50E, 51H-51I, 53C-53D, and 54C-54D.

In some embodiments, any of the above processes, methods, or procedures related to the workflow 7400 can include or be accomplished with one or more of steps or processes such as 7402, 7404, 7406, 7408, 7410, 7412, 7414, 7416, 7418, 7420, 7422, 7424, 7426, 7428, 7430, 7432, 7442, 7443, 7440, 7438, 7434, and 7436. In some embodiments, at least one of the steps can include a decision step (e.g., such as step 7404 and 7422), where one or more following steps depend on a status, decision, state, or other condition. In some embodiments, the steps of workflow 7400 can proceed in the order as shown. In some embodiments, any of the steps of the workflow 7400 can proceed out of the order as shown. In some embodiments, one or more of the steps of the workflow 7400 can be skipped.

Some embodiments of this invention involve the process of registering the contour of a rod implant via a combination of 3D-tracked tools and stationary objects. FIG. 75 illustrates a workflow 7500 to assess the contour of a rod prior to implantation using one handheld tracked tool and one substantially rigidly fixed ring in accordance with some embodiments of the invention. In some embodiments, other relevant figures include tools used for assessing rod contour (FIGS. 48A-48C, 50B-50C), a ring-based tracing tool (FIGS. 49A-49D), and similar tracked end cap-based process of rod contour assessments (e.g., such as FIGS. 74-75).

Some embodiments of this system involve a similar process to that described in FIG. 74, in which a 3D-tracked end cap tool with a substantially rigidly tracked DRF is used to serve as a tracked coordinate system reference for the rod contour. Some embodiments of this system involve inserting the rod's opposite end through a toroid-shaped object that is fixed in space, (and that allows for cross-sections of the rod that are parallel to its entry way) to pass through. In this instance, the dynamic path traveled by the 3D-tracked end cap tool is used to calculate the contour of the rod by association of the constraints of the bends causing a travel path for the 3D-tracked end cap.

Some embodiments involve the use of one or more tracked mobile stray markers (TMSMs) attached to a fixed toroid-shaped object, where one hinge-based TMSM is actuated relative to a fixed TMSM to indicate to the 3D-tracking acquisition system when a rod is being inserted through its passage way. Some example embodiments include FIGS. 49A-49D.

Some embodiments involve applying a rigid transformation to the fixed toroid-shaped object's location and orientation, which is relative to the 3D-tracked acquisition unit, and transforming its position to be relative to the location and orientation of the 3D-tracked end cap tool. Some examples of embodiments in various applications and forms are depicted in FIGS. 48A-48C and 50B-50C.

In some embodiments, any of the above processes, methods, or procedures related to the workflow 7500 can include or be accomplished with one or more of steps or processes such as 7502, 7504, 7506, 7508, 7510, 7512, 7514, 7516, 7518, 7520, 7522, 7524, 7526, 7528, 7530, 7532, 7534, 7536, 7538, 7540, 7542, 7544, 7546, 7548, 7550. In some embodiments, at least one of the steps can include a decision step (e.g., such as step 7504 or 7532), where one or more following steps depend on a status, decision, state, or other condition. In some embodiments, the steps of workflow 7500 can proceed in the order as shown. In some embodiments, any of the steps of the workflow 7500 can proceed out of the order as shown. In some embodiments, one or more of the steps of the workflow 7500 can be skipped.

Some embodiments of this invention involve the process of registering the contour of a rod implant via a combination of 3D-tracked tools after the rod has been implanted into the spinal anatomy. FIG. 76 illustrates a workflow 7600 to assess the contour of a rod after implantation in accordance with some embodiments of the invention. In some embodiments, other relevant figures include those that relate to rod contour triggering of a 3D-tracked tool (FIGS. 53A, and 53C-53D, 54A-54D, and 73A-73B), and rod contour assessment process while rod is implanted (FIGS. 77A-77C).

Some embodiments involve designs with a depressible shaft that is coaxial to the shaft of a 3D-tracked tool, where the depressible shaft is mechanically linked to a TMSM that can signal to the 3D-tracking acquisition system that a rod is being traced when the TMSM is actuated relative to the 3D-tracking tool's end effector. Some examples of embodiments of this process are depicted in FIGS. 53A, and 53C-53D. Other embodiments for sensing when the 3D-tracked tool is pressed against the rod surface are depicted in FIGS. 54A-54D and 73A-73B.

Some embodiments involve using the described rod-sensing, 3D-tracked tool to trace the contour of a rod while it is implanted and collecting the 3D location and pose of the tool during the process. Some embodiments involve the computer system fitting a line between the interruptions in the tracing caused by other surgical implants (e.g., pedicle screw heads) to estimate the full contour of the rod that is implanted. Some examples of embodiments of this system are depicted in FIGS. 77A-77C.

In some embodiments, any of the above processes, methods, or procedures related to the workflow 7600 can include or be accomplished with one or more of steps or processes such as 7602, 7604, 7606, 7608, 7610, 7612, 7614, 7620, 7618, 7616, 7622, and 7624. In some embodiments, any of the steps of the workflow 7600 can proceed out of the order as shown. In some embodiments, one or more of the steps of the workflow 7600 can be skipped.

Some embodiments include interpretation of data generated by the assessment of a rod contour after a rod has been implanted to the tulip heads within the surgical site, including any data from embodiments previously described in relation to FIGS. 52A-52D, 53A-53F, 54A-54D, 73A-73B, and 76.

FIG. 77A displays one embodiment of the invention which involves spinal vertebra 7711 that have been instrumented with pedicle screw shafts 7745 and a rod 7720 implanted into their tulip heads 7722. The contour of this rod can be assessed while implanted within the surgical site in this way via utilization of the embodiments described previously in FIGS. 52-54. FIG. 77B displays one embodiment of the invention which consists of an implanted rod and surrounding elements described previously in relation to FIG. 77A and use of a post-implantation rod contour assessment device 7780, described previously in relation to FIGS. 52A-52D, 53A-53F, and 54A-54D, to interface with and trace the coordinates of the implanted rod such that the coordinates of the activated device 7728 are recorded while the inactive coordinates 7782 (e.g., tracing probe over pedicle screws 7745 that obstruct the path of the implanted rod) are discarded. The contour assessment device is designed in such a way to trigger only when the device is fully engaged with the rod, so when the device is removed from the rod to navigate around path-obstructing hardware, it is not triggering to the acquisition system to record its coordinates. The embodiments describing the acquisition process and interpretation of an implanted rod's coordinates based on the coordinates of the assessment device were previously described in relation to FIGS. 73 and 76. Further, FIG. 77C displays one embodiment of the invention for interpreting the data obtained from an implanted rod's contour assessment with a device as previously described in FIGS. 77A-B consisting of the plotted coordinates representing the rod's contour from actively-triggered assessment device 7790 and the reconstructed rod contour 7792 based on the interpretation of the recorded rod data points. In one embodiment, this reconstructed contour is produced via a spline defined by the inputs of the recorded rod coordinates. Other embodiments of producing this reconstructed rod include but are not limited to variable order polynomial fitting and smoothing filters applied to the recorded rod coordinates.

Some embodiments of this invention involve the process of projecting an overlay of a registered 3D contour of a spinal rod onto patient imaging on a display monitor and allowing the user to interactively place and adjust the position of the rod overlay. For example, FIG. 78 illustrates a workflow 7800 for interactive user placement of a registered rod as an overlay on patient images on a display monitor in accordance with some embodiments of the invention. Some other relevant figures and descriptions include FIGS. 74-76 (for processes for assessing the contour of a rod, pre- and post-implantation), and FIGS. 87F-87G (for interactive overlay of registered rod contour on patient imaging).

Some embodiments of the invention involve maintaining usage of the 3D-tracked end cap tool that is substantially rigidly attached to a previously-registered rod contour. Some embodiments of the invention involve the user confirming the coordinates of the overlay interaction by pointing the 3D-tracked end cap tool with the registered rod at the display monitor and triggering via a TMSM when the orientation of the 3D-tracked end cap tool matches the up/down and left/right motions that map the overlay in an intuitive manner for the user to manipulate on the display monitor.

Some embodiments involve the user manipulating the 2D projections of the registered contour of the rod via the movement of the 3D-tracked end cap tool along the pre-selected orientation of the tool relative to the orientation of the display monitor. Some embodiments involve the patient preoperative or intraoperative imaging being scaled in physical units (e.g., millimeters) and enabling for the accurate scaling of the overlay of the registered rod contour. Some further embodiments involve the user being able to select two or more points on the image that the rod contour overlay should intersect with and manipulate its contour position and orientation to meet those point intersection constraints. Some examples of embodiments of this invention in various applications and form are depicted in FIGS. 74-76, with the interactive overlay of the rod contour on a display monitor with patient imaging depicted in FIGS. 87F-87G.

In some embodiments, any of the above processes, methods, or procedures related to the workflow 7800 can include or be accomplished with one or more of steps or processes such as 7802, 7804, 7806, 7808, 7810, 7812, 7814, 7816, 7822, 7828, 7830, 7832, 7834, 7836, 7838, 7818, 7820, 7826, 7824, 7844, 7840, 7846, 7848, 7842, and 7850. In some embodiments, any of the steps of the workflow 7800 can proceed out of the order as shown. In some embodiments, one or more of the steps of the workflow 7800 can be skipped.

FIGS. 79A-79G relate to an embodiment of the invention which consists of the process of interpreting and calculating a tracked rod bending device, as previously described in relation to FIGS. 55D-55I, 56A-56D, and 56F, interfacing with a rod which has had its contour previously registered via embodiments previously described in relation to FIGS. 49D, 50E, and 51H-51I, and enables the interpretation and calculation of the rod's new contour based on acquisition system input from the tracked rod bender as related to the previously registered rod coordinates relative to the tracked-DRF-equipped end cap to which the rod is secured.

FIG. 79A displays one embodiment of the invention consisting of the coordinates of a previously registered contour of rod 7900 with known diameter, projected onto the 2D plane of the rod bending tool, defined by the middle of the three rod-interface points on the rod bender. FIG. 79B displays one embodiment of the invention consisting of the previously-registered rod contour 7900, described previously in relation to FIG. 79A, and the relative locations of the rod bender's left outer roller 7904, center rod contouring surface 7906, and right outer roller 7905. As shown in this embodiment, the three rod-interface components of the bender are engaged with the rod, indicated by being displayed tangential to the previously registered rod contour.

FIG. 79C displays one embodiment of the invention consisting of the previously registered rod coordinates divided into three segments: the left unengaged rod segment 7901, bender-engaged segment 7903, and right unengaged segment 7902. In addition, this embodiment includes lines connecting the center rod contouring surface to the left outer roller 7920 and right outer roller 7922 from which the angle between them 7924 can be calculated. When the bender is engaged with a straight rod, this angle will be at a minimum, as opposed to when the bender is applying maximum curvature to the rod, this reference angle will be at a maximum.

FIG. 79D displays one embodiment of the invention in which the rod bender's handles are approximated to induce a bend in previously registered rod such that the angle 7952 between inter-roller vectors (7920, 7922) previously described in relation to FIG. 79C is increased. From the known current bend configuration of the tracked bender, the bender's known geometry, and the known rod diameter, the acquisition system software then computes rod contact points (displayed as solid circles) on the left outer roller 7948, center contour surface 7951, and right outer roller 7953 by solving for tangent lines between each rod-interface surface.

FIG. 79E displays one embodiment of the invention which the rod contact points calculated and described previously in relation to FIG. 79D are used as constraints for defining a spline connecting each of them, and producing the newly computed bender-engaged segment of the rod contour 7903a and based on the path length of the spline, (which is longer when the bender is in the bent configuration than straight configuration), updated left 7901b and right 7902b unengaged segments of the rod are interpreted. Further. FIG. 79F displays one embodiment of the invention which involves tangentially re-approximating the left 7971 and right 7972 unengaged segments of the rod contour as previously described in relation to FIG. 79E, by undergoing a rigid body transformation to both translate and rotate to tangentially approximate the spline-produced bender-engaged contour of the rod.

FIG. 79G displays one embodiment of the invention in which the embodiments described previously in relation to FIG. 79A-79F are utilized to produce updated projected coordinates of the rod's contour 7999 after bending with a tracked bender and combined with 3D contour coordinates prior to the bend to compute and update the registered 3D-curvature of the rod. It should be noted that the embodiments described previously in relation to FIGS. 79A-79G can be applied to calculate and update pre-registered rod contours when interfacing with tracked rod benders previously described in FIGS. 55D-55I, 56A-56D, and 56F.

Some embodiments of this invention involve the process of tracking the dynamic contour of a registered rod that is being contoured into a new shape prior to implantation of the rod. For example, FIG. 80 illustrates a workflow for manually bending a rod prior to its implantation with real-time feedback of its dynamic contour in accordance with some embodiments of the invention. Other relevant figures and descriptions can include FIGS. 55A-55I, 56A-56F (devices used to bend registered rod and track changes in its contour), FIGS. 79A-79G (for calculation of rod bending of a registered rod contour), and FIGS. 87A-87G, 88A-88F (for display of rod bending feedback of a registered rod contour), and FIGS. 74-76 (for processes for assessing the contour of a rod, pre- and post-implantation). In some embodiments, the workflow 80 can comprise steps 8002, 8004, 8006, 8008, 8010, 8014, 8016, 8018, 8020, 8022, 8024, 8026, 8028, 8030, 8032, 8034, 8036, 8040, 8044, 8038, 8042, and 8046.

Some embodiments of this invention involve tracking the dynamic changes of a registered rod contour that has maintained rigid fixation to a 3D-tracked end cap tool that has a coupled tracked DRF. Some embodiments of this invention involve processes for previously registering the rod, for which some examples are depicted in FIGS. 74-76.

Some embodiments of this system involve using a mobile, 3D-tracked rod bender and a TMSM substantially rigidly attached to the opposite end of the registered rod to that of the 3D-tracked end cap tool attached to the rod. Some embodiments interpret the angle between the handles of the 3D-tracked rod bender's bending points, the position of the rod bender along the contour of the rod, and the orientation of the rod bender relative to that of the 3D-tracked end cap tool relative to the 3D-tracking acquisition system, to calculate the approximate new contour of the registered rod based on the deflected segments of the rod. One example of this algorithmic calculation process is depicted in FIGS. 79A-79G. Some, but not all, example embodiments and permutations of the system that can assess, manipulate, and update the contour of the registered rod are depicted in FIGS. 55A-55I, 56A-56F. Some embodiments of the system involve an interactive, quantitative-feedback display of the registered rod, an overlay of the 3D-tracked rod bender in its active, relative position and orientation with respect to the 3D-tracked end cap tool. Some examples of these embodiments are depicted in FIGS. 87A-87G, and 88A-88F.

In some embodiments, any of the above processes, methods, or procedures related to the workflow 8000 can include or be accomplished with one or more of steps or processes such as 8002, 8004, 8006, 8008, 8010, 8014, 8016, 8018, 8020, 8022, 8024, 8026, 8028, 8030, 8032, 8034, 8036, 8040, 8044, 8038, 8042, and 8046. In some embodiments, any of the steps of the workflow 8000 can proceed out of the order as shown. In some embodiments, one or more of the steps of the workflow 8000 can be skipped.

Some embodiments of this invention involve the process of tracking the dynamic contour of a registered rod that is being contoured into a new shape prior to implantation of the rod and providing directed software interactive feedback based on surgical planning inputs. For example, FIG. 81 shows a workflow 8100 for manually bending a rod prior to its implantation with directed software input to overlay a projection of the dynamic rod contour onto an intraoperative X-ray image in accordance with some embodiments of the invention. Some other relevant figures include FIG. 80 (e.g., a process for manually bending registered rod contour and outputting adjusted form), and FIGS. 88A-88F (for a display of rod bending feedback of a registered rod contour).

Some embodiments of this system involve directed software feedback that aids the user in determining where along the rod contour a rod bender must be placed, in which orientation with respect to the 3D-tracked end cap tool, and by how much of a bend angle the 3D-tracked rod bender must apply contouring forces and shapes to the registered rod contour. Some embodiments of the system involve a real-time feedback of the rod contouring process of the registered rod and projections of the rod bender in space relative to the position and orientation of the registered rod contour. Some embodiments of the system involve an interactive feedback display that depicts the amount of bending that is occurring, relative to the angle between the handles of the 3D-tracked rod bender, and how much the user should bend the rod contour at that location and orientation to produce the optimal, final new contour of the rod that best matches the surgical planning goals for the procedure.

Some examples of these embodiments in various applications and forms, including the interactive software-based display of the dynamic rod contouring process are depicted in FIGS. 88A-88F.

In some embodiments, any of the above processes, methods, or procedures related to the workflow 8100 can include or be accomplished with one or more of steps or processes such as 8102, 8104, 8106, 8108, 8110, 8112, 8114, 8116, 8118, 8120, 8122, 8124, 8126, 8128, 8130, 8132, 8134, 8136, 8138, 8140, 8142. In some embodiments, any of the steps of the workflow 8100 can proceed out of the order as shown. In some embodiments, one or more of the steps of the workflow 8100 can be skipped.

Some embodiments include a tracked probe with triggering capability, as described previously in relation to FIGS. 10A-10G, and 15A-15C, can be utilized as a user interface device with a non-tracked display monitor via the calibration process described in this figure coupled with the calculations described in detail below in reference to FIG. 83.

FIG. 82A displays one embodiment of the invention in which a non-tracked display monitor 8210 communicates calibration instructions 8205 and displays calibration markers 8230 on the display monitor to guide a user holding a 3D-tracked probe with triggering capability 8240 to calibrate the probe to the screen dimensions and location in space relative to the 3D-tracking camera by sequentially orienting the probe tip and its computed line of trajectory 8245 to each indicated marker on the display monitor (directed to center marker as shown). The workflow of interpreting this calibration process is described in detail below in reference to FIG. 83. It should be noted that utilizing a tracked probe with triggering capability to interface as a laser-pointer analog with a non-tracked display monitor is only one embodiment of the invention. Other embodiments include using a tracked probe with triggering capability to interface as a laser-pointer analog with a tracked monitor as described in detail below in reference to FIGS. 84A-84B, and others involve using a tracked probe with triggering capability to create a user defined trackpad analog to interface with an untracked display monitor as described in detail below in reference to FIG. 85. Further, FIG. 82B displays one embodiment of the invention previously described in relation to FIG. 82A, in which the computed line of trajectory 8247 of the tracked probe is directed toward the top left calibration marker on the display monitor.

Some embodiments of this invention involve the process of using a 3D-tracked tool with attached 3D-tracked triggers to interact with a display monitor and use the tool as a selection cursor. For example, FIG. 83 illustrates a workflow to utilize a trigger-equipped probe to serve as a laser pointer analog for a user-interface system with a non-tracked display in accordance with some embodiments of the invention. Some other relevant figures can include FIGS. 82A-82B (for interactive display of trigger-equipped tool with a display monitor), FIGS. 15A-15C (for a trigger-equipped 3D-tracked tool that can be used for interactive display cursor control), and FIG. 63 (for a process of using tracked mobile stray marker TMSM as a toggling attachment to a 3D-tracked tool).

Some embodiments of this system involve the use of a 3D-tracked tool with a coupled tracked DRF, as well as a mechanically-linked TMSM, that can be used as software-based inputs of location, orientation, and state of tool relative to a 3D-tracking acquisition system. One example of this embodiment is depicted in FIG. 63.

Some embodiments involve the 3D-tracked tool pointing at one or more markers at different locations of a display monitor and signaling a selection at each point once the user is confident that the 3D-tracked tool's shaft is most appropriately aligned for pointing a virtual ray at one or more markers displayed on the screen. Some example embodiments of the 3D-tracked tool in various forms and states of use are depicted in FIGS. 15A-15C. Further, some embodiments involve determining the mapping of the movement, locations, and orientations of the 3D-tracked tool between registered marker points on the display monitor by calculating the lines formed by coupled locations and orientations of the 3D-tracked tool at these registered marker points. Some embodiments also involve using the dimensions and pixel resolution of the display monitor to provide more appropriate mapping of the 3D-tracked tool's motion relative to the display monitor. Further, some embodiments of the system enable the user to be able to use the 3D-tracked tool as a virtual cursor and input-selection tool for the software system visualized by the display monitor. Some examples of these embodiments in various applications and forms are depicted in FIGS. 82A-82B.

In some embodiments, any of the above processes, methods, or procedures related to the workflow 8300 can include or be accomplished with one or more of steps or processes 8302, 8304, 8306, 8308, 8310, 8312, 8314, 8316, 8318, 8320, 8322, 8324, 8326, 8328, 8330, 8334, 8336, 8338. In some embodiments, at least one of the steps can include a decision step (e.g., 8318 or 8328), where one or more following steps depend on a status, decision, state, or other condition. In some embodiments, the steps of workflow 8300 can proceed in the order as shown. In some embodiments, any of the steps of the workflow 8300 can proceed out of the order as shown. In some embodiments, one or more of the steps of the workflow 8300 can be skipped.

Some embodiments of this invention involve the process of using a 3D-tracked tool with attached 3D-tracked triggers to interact with a display monitor and use the tool as a selection cursor, while the display monitor has a coupled 3D-tracked DRF. For example, FIGS. 84A-84B illustrates a workflow to utilize a trigger-equipped probe to serve as a laser pointer analog for a user-interface with a 3D-tracked display monitor in accordance with some embodiments of the invention. Some other relevant figures include FIGS. 82A-82B (interactive display of trigger-equipped tool with a display monitor), FIGS. 15A-15C (for a trigger-equipped 3D-tracked tool that can be used for interactive display cursor control), and FIG. 63 (a process of using TMSM as a toggling attachment to a 3D-tracked tool), and FIG. 83 (a process of using a 3D-tracking tool as an interface display monitor cursor). Some embodiments of this system involve the processes and references made by FIG. 83.

Some embodiments of the system involve substantially rigidly attaching a 3D-tracked DRF to a display monitor that will be used for interactive software purposes. Further, some embodiments of the system involve using the DRF-equipped display monitor as a reference tool in the tracking volume of the 3D-tracking acquisition system. Other embodiments involve processes outlined in FIG. 83, which describe examples of a process for calibrating a display monitor's dimensions according to the movement, location, and orientation of a trigger-equipped 3D-tracked tool. Further, example embodiments of this system are depicted in FIGS. 82A-82B.

In reference specifically to FIG. 84B, some embodiments of this system are dependent on process described in FIG. 84A. Some embodiments of this system utilize processes described in FIGS. 83 and 63. Some embodiments of this system involve substantially rigidly attaching a 3D-tracked DRF to a display monitor that will be used for interactive software purposes. Further, some embodiments of this system involve algorithmic calculations of the relative locations and orientations of the 3D-tracked, trigger-equipped tool (e.g., FIGS. 15A-15C) with respect to the 3D-tracking acquisition system to calculate the appropriate ray intersection of the 3D-tracked tool's probe shaft direction and the orientation of the display monitor. Some embodiments involve using the dimensions and pixel resolution of the display monitor to provide more appropriate mapping of the 3D-tracked tool's motion relative to the display monitor. Some embodiment examples, but not all exhaustive permutations, including the attachment of a DRF to the display monitor, are depicted in FIGS. 82A-82B.

In some embodiments, any of the above processes, methods, or procedures related to the workflow 8400 can include or be accomplished with one or more of steps or processes 8402, 8404, 8406, 8408, 8410, 8412, 8414, 8416, 8418, 8420, 8422, 8424, 8426, 8428, 8430, 8452, 8454, 8456, 8458, 8464, 8466, 8468, 8470, 8462, and 8460. In some embodiments, at least one of the steps can include a decision step (e.g., such as step 8402), where one or more following steps depend on a status, decision, state, or other condition. In some embodiments, the steps of workflow 8400 can proceed in the order as shown. In some embodiments, any of the steps of the workflow 8400 can proceed out of the order as shown. In some embodiments, one or more of the steps of the workflow 8400 can be skipped.

Some embodiments of this invention involve the process of using a 3D-tracked tool with attached 3D-tracked triggers to interact with a display monitor and use the tool as a selection cursor, via the calibration of a non-tracked surface. For example, FIG. 85 illustrates a workflow 8500 to utilize a trigger-equipped probe to serve as an interface device for a non-tracked display via a user-defined trackpad analog in accordance with some embodiments of the invention. Some other relevant figures include FIG. 63 (a process of using tracked mobile stray marker (TMSM) as a toggling attachment to a 3D-tracked tool), FIG. 83 (a process of using a 3D-tracking tool as an interface display monitor cursor), FIGS. 15A-15C (a trigger-equipped, 3D-tracked tool that can be used for interactive display cursor control), and FIGS. 82A-82B (an interactive display of trigger-equipped tool with a display monitor). For example, some embodiments of this system utilize processes described in FIGS. 63 and 83. Some embodiments involve the 3D-tracked tool pointing at one or more markers at different locations of a display monitor and signaling a selection at each point once the user is confident that the 3D-tracked tool's shaft is most appropriately aligned to be pointing a virtual ray at the marker(s) displayed on the screen. Some example embodiments of the 3D-tracked tool in various forms and states of use are depicted in FIGS. 15A-15C.

Some embodiments involve the use of the 3D-tracked tool to either trace the border of a rigid, non-tracked object or register multiple discrete points on the border surface of a rigid, non-tracked object in order to register its border dimensions and the orientation of the frame relative to the 3D-tracking acquisition system. Further, some embodiments involve using the dimensions and pixel resolution of the display monitor to provide more appropriate mapping of the 3D-tracked tool's motion relative to the display monitor.

Some embodiments involve calculating the mapping between the registered rigid, non-tracked object dimensions and orientation and the dimensions of the display monitor. Some embodiments algorithmically calculate the interactive placement of a cursor on the display monitor based on the location of the 3D-tracked tool end effector on the rigid, non-tracked, registered object surface within its border boundaries. Some analogous examples of some of these system embodiments in various applications and forms are depicted in FIGS. 82A-82B and 83.

In some embodiments, any of the above processes, methods, or procedures related to the workflow 8500 can include or be accomplished with one or more of steps or processes 8502, 8504, 8506, 8508, 8510, 8512, 8514, 8516, 8518, 8520, 8522, 8524, 8526, 8528, and 8530. In some embodiments, any of the steps of the workflow 8500 can proceed out of the order as shown. In some embodiments, one or more of the steps of the workflow 8500 can be skipped.

Some embodiments of the system described herein can generate output displays for the alignment assessments performed with embodiments of the invention previously described in relation to at least FIGS. 62A-62D, and 65A-65E, 66A-66B, and 67-69.

FIG. 86A displays one embodiment of the invention consisting of drawings 8600 of computed spinal alignment parameters and their current value displayed beneath each one as calculated from the alignment assessment. Other embodiments include these displays and/or their quantified values changing colors based on proximity to predetermined surgical goals, enabling the user to visualize and focus on parameters that are farthest away from the predetermined ranges. Additional embodiments include the ability of the user to view previously-acquired assessments, and dynamically-responsive spine drawings that change their contour to accurately represent their most recently measured values. It should be noted that this figure displays only one embodiment which does not contain all the spinal alignment parameters for all embodiments. The display as shown and described can be applied to any measurement value between two regions of the spine or between one anatomical region and the spine or pelvis. The data acquisition and interpretation processes to generate these parameters are described previously as described earlier.

FIG. 86B displays one embodiment of the invention which is an output display of a patient image in the sagittal 8650a and coronal 8650b planes with the option to remove any software overlays. Further, FIG. 86C displays one embodiment of the invention which consists of sagittal and coronal patient images with sagittal and coronal overlays (8651a, 8651b respectively) of the patient's spinal anatomy representing their current spinal alignment based on intraoperative assessments. To generate these overlays, manual or automated segmentation of previously-acquired patient images is used to isolate the elements of the spine which is then anchored at a reference point to the prior image, and then both rotated and distorted to provide a qualitative representation of the measured alignment. In other embodiments of the invention, rather than an overlay of a dynamically modified segmented image, an overlay of a line representing the contour of the spine is displayed on the patient image. This curve can be with or without discrete spinal level indications and the user is able to toggle previously acquired tracing contour assessments on and off.

Figure 86D:
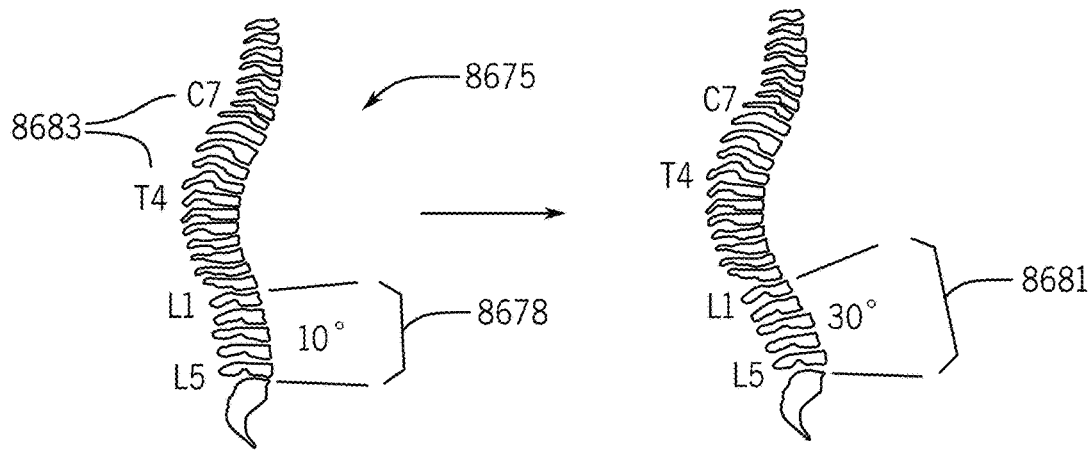

FIG. 86D displays one embodiment of the invention which is an output display 8675 of the measured spinal alignment parameters represented by discrete vertebra that both individually translate and rotate to align tangentially with the measured spinal alignment. In this way, the output can dynamically adjust to localized measurements, such as lumbar lordosis, shown going from 10 degrees 8678 to 30 degrees 8681 which include altering the alignment between the related endplates within the output display. This embodiment also consists of this dynamic display shown in the coronal plane (not shown) and 3D perspective view. Another component of the embodiment is the display of discrete spinal level labels 8683 relative to the output image.

Some embodiments include a rod with previously registered contour fixed to a tracked DRF-equipped end cap and interacting with a tracked rod bender in accordance with some embodiments of the invention. For example, FIG. 87A displays one embodiment of the invention previously described in relation to FIGS. 55D-55I, 56A-D, and 56F, consisting of a rod 8715 with previously registered contour fixed to a tracked DRF-equipped end cap 8710 and interacting with a tracked rod bender 8720.

FIG. 87B displays one embodiment of the invention consisting of a sagittal projection of the registered rod contour 8735, a display indicating the current sagittal location of the tracked rod bender 8755 relative to the registered rod contour as referenced to the end cap DRF axes, and labels 8717 for the anatomical axes for ease of user-interpretation. With this embodiment, the user is able to visualize where the rod bender is located relative to the 2D anatomical projection of the rod, allowing for improved interpretation of complex rod contours as well as interpretation relative to the patient imaging as described below in reference to FIGS. 87F-87G. It should be noted that the rod contour registration process, which takes place prior to utilizing this embodiment of the invention is described above in relation to FIGS. 47A-47B, 51A-51G, and 73A-73B, and 74-75.

FIG. 87C displays one embodiment of the invention consisting of a coronal projection of the registered rod contour 8765, a display indicating the current coronal location of the tracked rod bender 8760 relative to the registered rod contour as referenced to the end cap DRF axes, and labels 8723 for the anatomical axes for ease of user interpretation. In this embodiment, the location of the rod bender is displayed as a projection of the bender onto the displayed plane. As shown, in this figure, the rod bender is located orthogonal to both the segment of the rod with which it is engaged and the coronal plane, as indicated by the narrow rectangle in this projection. When the bender is bending within the displayed plane, it is displayed as it is shown in relation to FIG. 87B.

FIG. 87D displays one embodiment of the invention which displays the location of the bender's center rod contouring surface 8730 relative to a cross-sectional view of the rod 8725 with labels for the anatomical axes 8727. This embodiment allows for interpretation of the location of tracked rod bender's interface components, as rotated about the long axis of each segment of the rod.

FIG. 87E displays one embodiment of the invention which displays a sagittal projection of the registered rod contour 8735, and generates orthogonal lines from the superior rod endpoint 8740, and the inferior rod endpoint 8745, along with the calculated angle between them 8750, in addition to labels 8733 for the anatomical axes. In other embodiments, the user can modify and select discrete locations on the rod between which orthogonal lines will be drawn and angles calculated. In other embodiments of this invention, the rod and corresponding measurements between orthogonal lines can be projected onto the coronal plane. Additionally, in other embodiments these projections and measured angles can be performed after assessing the rod contour both prior to and after implantations, and need not necessitate interfacing with a tracked bender to do so.

FIG. 87F displays a sagittal patient image 8775 with an overlay of a registered rod contour 8777 as well as an overlay display of the location of a tracked rod bender 8779 relative to the previously registered rod. The placement location of the registered rod's contour can be achieved via embodiments described previously in relation to FIG. 78.

FIG. 87G displays a sagittal patient image adjusted for operative planning 8781 with an overlay of a registered rod contour 8783 as well as an overlay display of the location of a tracked rod bender 8785 relative to the previously registered rod. The placement location of the registered rod's contour over this adjusted patient image can be achieved via embodiments described previously in relation to FIG. 78. By overlaying the registered rod contour over the image adjusted to mimic operative goals, the contour of the rod can be adjusted with real-time display feedback to a point where it superimposes over the adjusted patient image in such a way that it is located where it would be on a postoperative image, secured to the tulip heads of implanted pedicle screws.

FIG. 87H displays one embodiment of the invention in which the rod bender's location on the display monitor is represented as an arrow 8786 and the rod is represented as a single colored, solid line 8787.

FIG. 87I displays one embodiment of the invention in which the rod bender's location on the display monitor is represented as an arrow 8786 and the segment of the rod engaged with the rod bender is a different color 8789 than the segments of the rod not engaged with the bender 8788, as described previously in relation to FIG. 79. In other embodiments, rather than a change in color, the engaged segment of rod can be differentiated from the unengaged segment of rod via a change in stroke weight of the line, or changing from dashed to solid lines.

FIG. 87J displays one embodiment of the invention in which the rod bender's location on the display monitor is represented as an outline of the manual rod bender with profile outlines 8795 of the handles and rod interface regions adapting the display based on the current orientation of the handles to one another. In this figure, it is displayed with the handles fully open (i.e., at the largest angle between them) to accommodate interfacing with a straight rod 8793.

Figure 87K:
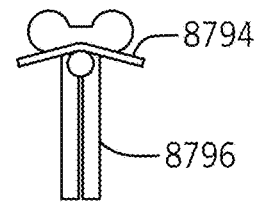

FIG. 87K displays one embodiment of the invention in which the rod bender's location on the display monitor is represented as an outline of the manual rod bender with profile outlines 8796 of the handles and rod interface regions adapting the display based on the current orientation of the handles to one another. In this figure, it is displayed with the handles fully closed (i.e., at the smallest angle between them) and therefore interfacing with a bent region of the rod 8794.

FIG. 87L displays one embodiment of the invention in which the rod bender's location on the display monitor is represented as three filled circles to represent the left outer roller 8789, center rod contouring surface 8790 and right outer roller 8791 engaged with a straight rod 8787. Further, FIG. 87M displays one embodiment of the invention in which the rod bender's location on the display monitor is represented as three filled circles with an outline 8792 to represent the left outer roller 8789, center rod contouring surface 8790 and right outer roller 8791 engaged with a straight rod 8787.

Some embodiments include display monitor interfaces to allow for software-directed bending of a previously registered rod substantially rigidly fixed to a tracked DRF-equipped end cap and interfacing with a tracked rod bender as previously described in relation to FIGS. 87A-87M. These embodiments enable mechanisms of instructing the user where and how to bend the rod with a tracked rod bender in order for the rod's final contour to match preset inputs. It should be noted that these preset inputs are embodied in varying forms and can be based on preoperative imaging, preoperative planning, preset measurement inputs, and intraoperative alignment measures among others. The workflow associated with these embodiments is described previously in reference to FIGS. 80-81.

Some embodiments include a sagittal projection of a registered rod contour, a display of the current location of the rod bender relative to the registered rod contour, a display of the software-instructed location where the user should place the rod-bender, and anatomical axes labels in accordance with some embodiments of the invention.

FIG. 88A displays one embodiment of the invention consisting of a sagittal projection of a registered rod contour 8801, a display of the current location of the rod bender 8803 relative to the registered rod contour, a display of the software-instructed location where the user should place the rod bender 8805, and anatomical axes labels 8825. This embodiment allows for visual display and feedback showing where the rod bender is relative to where the software is instructing the user to place the rod bender on the rod. In other embodiments of this invention, the appearance of the software-instructed location of the bender changes via color, line weight, or shape, to indicate when the user has successfully overlaid the current location of the bender onto the software-instructed location for the bender relative to the registered rod.

FIG. 88B illustrates a display of FIG. 88A as applied to the coronal plane in accordance with some embodiments of the invention, with coronal projection of registered rod contour 8807, coronal display overlay of current bender location relative to rod 8809, software-instructed bending indicator of bender placement location 8811, and anatomical axes labels 8827.

FIG. 88C illustrates a cross-sectional display of the rod, the current location of the rod bender's center contouring surface, the software-instructed location of where the rod bender's center contouring surface should be placed, and anatomical axes labels in accordance with some embodiments of the invention. Shown are the cross-sectional display of rod 8813, current orientation of bender 8815, software-instructed indicator of bender placement location 8817, anatomical axes labels 8829.

FIG. 88D displays one embodiment of the invention consisting of a display representation of the current relative position of the bender's handles 8852, directly related to the degree of bending induced on a rod of known diameter. In this embodiment, the angle between the handles is adaptive and changes based on the detected conformation of the tracked rod bender. Further, FIG. 88E illustrates a display representation of the software-instructed relative position of the bender's handles 8854, directly related to the degree of bending induced on a rod of known diameter in accordance with some embodiments of the invention. The display representation of the software-instructed relative position of the bender's handles 8854, directly related to the degree of bending induced on a rod of known diameter. In this embodiment, the rod bender is displayed in its state of maximum bending (i.e., minimum angle between handles) and any angle within the achievable range of motion of the rod bender's handles can be displayed as the software-instructed degree of bending for the user to match once the bender is placed in the indicated location along the length of the rod, as described in FIGS. 88A-88B, and once the bender is located at the right angle relative to the rod's cross section, as described in FIG. 88C.

FIG. 88F represents one embodiment of the invention consisting of a display representation of an angle gauge 8866 within which the current angle between the tracked rod bender's handles 8862 is shown in addition to the software-instructed indicator 8864 of what angle is necessary at that point of engagement between the previously registered rod and tracked rod bender. With this embodiment, the user is able to watch the current bend angle of the tracked bender changes as the handles are moved closer to or farther from one another. The user adjusts the angle between handles until the current angle indicator is superimposed over the software-instructed angle indicator, at which point the user-interface displays the next location of bending required to achieve the desired rod contour that was input to the system.

In some embodiments, any of the systems and software can be applied with rod cutters to instruct the user where to cut the rod as mentioned above. Other embodiments of the invention also include indications of where a tracked rod-cutting device is relative to a previously registered rod that is still coupled with the tracked DRF-equipped end cap. Both live tracking of the cutter relative to the previously registered rod, as well as software-instructed placement of a cutting device relative to the rod, is included in other embodiments of the invention.

Some embodiments of this invention involve the process of interactively providing instructions of how to manipulate and position an adjustable spine phantom model to approximate orientations and relations available in imaging of the model. For example, FIG. 89 shows a workflow to match the adjustable benchtop spinal model to mimic alignment parameters from patient-specific imaging in accordance with some embodiments of the invention. Other relevant figures include FIGS. 90A-90D (a display and interactive adjustable components of benchtop spine model).

Some embodiments of the system involve the annotation of spinal vertebrae levels of the benchtop spine model based on visualization of the anatomy by imaging technologies (e.g., CT, MRI, 2D X-ray radiograph, ultrasound, etc.) Further, some embodiments of the system involve substantially rigidly attaching an arrangement of adjustable, incrementally-measured levers that both substantially rigidly fix the conformation of the spine model in space, and provide quantitative feedback for the user to interpret the position of each multi-lever, adjustable fixation device. One example embodiment of the multi-lever, adjustable fixation device is depicted in FIG. 90C.

Some embodiments involve the rigid attachment of the multi-lever, adjustable fixation device to each spinal vertebra level. Other embodiments involve attaching select levels of the spine model to substantially rigidly attach to a multi-lever, adjustable fixation device. Some embodiments of the system involve instructing the user to adjust specific segments of the spine via the manipulation of one or more multi-lever, adjustable fixation devices to configure the conformation of the spine model in a manner that matches the configuration of anatomies as visualized in the imaging registration of the spine model. Some further embodiments involve produced transformed 3D CT-based reconstructions or cross-sectional visualization estimates of the spine model anatomy as it is currently positioned on the benchtop, assuming that the user followed software directions correctly to adjust the spine model in a specific conformation.

In some embodiments, any of the above processes, methods, or procedures related to the workflow 8900 can include or be accomplished with one or more of steps or processes 8902, 8904, 8906, 8908, 8910, 8912, 8914, 8916, 8918, 8920, 8922, 8924, 8926, 8928, 8930, 8932, 8934, 8936. In some embodiments, at least one of the steps can include a decision step (e.g., such as step 8918), where one or more following steps depend on a status, decision, state, or other condition. In some embodiments, the steps of workflow 8900 can proceed in the order as shown. In some embodiments, any of the steps of the workflow 8900 can proceed out of the order as shown. In some embodiments, one or more of the steps of the workflow 8900 can be skipped.

Some embodiments relate to patient images that are analyzed to indicate their spinal alignment contour and parameters as well as output instructions of how to position adjustable mounts coupled to an anatomical model of the spine in order to mimic the spinal alignment parameters displayed in the patient images. Other embodiments of this device include inputting desired discrete alignment parameter values (e.g., lumbar lordosis of 30 degrees) to the software which then outputs instructions for how to orient the adjustable mounts to configure the anatomical model to possess the input parameters. Another embodiment of the device consists of a user positioning the anatomical model and then inputting all coordinates of the adjustable mounts into the software for it to then output patient images closely matching the alignment parameters of the anatomical model.

FIG. 90A illustrates sagittal and coronal patient images with overlaid sagittal and coronal contour tracings of the spine, discrete software-instructed placement of adjustable mounts onto the anatomical model, and instructions for the coordinates of each of those adjustable mounts to be positioned on the adjustable benchtop model in accordance with some embodiments of the invention. The sagittal 9001 and coronal 9007 patient images are shown with overlaid sagittal 9003 and coronal 9009 contour tracings of the spine, discrete software-instructed placement of adjustable mounts (9005, 9011) onto the anatomical model, and instructions for the coordinates of each of those adjustable mounts to be positioned on the adjustable benchtop model. The software description for this embodiment is described previously in relation to FIG. 89. Further, FIG. 90B illustrates an anatomical model mounting exploded assembly in accordance with some embodiments of the invention.

FIG. 90B displays one embodiment of the invention consisting of a table top base 9020, side-rail 9022 equipped with distance indicators 9024 and meant to interface with a cross rail 9026 equipped with distance indicators 9028 and designed to interface with a cross-rail sliding piece 9034 within its cross-rail mating slot 9038, which is equipped with a slot 9039 for mating with a height-adjustment slider 9032, which mates with an angular adjustment piece 9030 via a fastener 9036 which interfaces with an individual vertebra on an anatomical spine model (not shown). This embodiment allows for positioning of the coupled anatomical model (not shown) in specific locations anywhere over the table top base.

FIG. 90C displays one embodiment of the invention previously described in relation to FIG. 90B, in its assembled form with the anatomical model interface surface 9040 more easily visualized. In the embodiment shown, this interface is achieved via a through hole for a fastener (not shown) to substantially rigidly couple to the anterior aspect of the anatomical model's vertebral body. In other embodiments, this interface includes a ball joint to allow for the anatomical model to pivot about the interface point. In other embodiments, the fastener to the anatomical model is achieved via a clipping mechanism to pre-installed receptacles on each vertebra of the anatomical model to enable rapid-exchange of interface points.

FIG. 90D displays one embodiment of the invention in which a spine anatomical model 9050 is positioned in a discrete alignment configuration with the adjustable mounts described previously in relation to FIGS. 90B-90C. In this embodiment, each mount is positioned based on software-instructed parameters including: location along the side rail, location along the cross-rail, height from the base piece, angle from the height-adjustment slider, and vertebral level with which it should interface. In other embodiments, the cross rails are cylindrical, allowing for rotation of the base piece about the cross bar. In other embodiments, rather than mating only with select vertebral levels, each vertebra is equipped with an adjustable mount, to allow for matching contours with higher precision.

Some embodiments enable different probe-like extensions to be added or interchanged to a tracked or trackable DRF, while indicating to the acquisition software which extension is currently coupled, and therefore which tool definition file to reference when tracking the associated DRF. For example, some embodiments can enable different probe-like extensions to be added or interchanged to a tracked or trackable DRF (i.e., such as a DRF that can be tracked or is capable of being tracked). Further, in some embodiments, acquisition software of an acquisition system can receive data regarding which extension is currently coupled, and therefore which tool definition file to reference when tracking the associated DRF. For example, FIG. 91A illustrates a non-limiting assembly 9100 with a tracked DRF 9101 with tracked or trackable markers 9101a, and including an engaged, straight probe extension as a selected modular tool tip (shown collectively as probe extension pieces 9105), which includes an associated, unique TMSM 9103 positioned relative to the DRF 9101 when engaged. Some embodiments of this invention are related to devices and systems described earlier in relation to FIGS. 15A-15C, 46A-46G, and 100104, as well as processes described in relation to FIGS. 63, 64A-64B, and 113.

FIG. 91A illustrates one embodiment of the invention that involves a tracked DRF 9101 with a mating extension containing a mating slot in which a spring-loaded TMSM 9103 slides due to protrusions 9111 (see also FIG. 91B) of discrete distances attached to unique probe extension pieces 9105. In some embodiments, when the TMSM 9103 is detected in a preset location relative to the tracked DRF 9101, the acquisition system registers which probe extension tip is coupled and updates a tool definition file for the DRF 9101 accordingly. One embodiment of a process to detect the motion of a TMSM 9103 relative to a DRF 9101 was described previously in relation to FIG. 63 (see workflow 6300 for analog triggering detection of one or more TMSMs relative to a tracked tool with a DRF in accordance with some embodiments of the invention).

FIG. 91B illustrates the embodiment 9110 of the invention previously described in FIG. 91A with the probe extension 9105 unengaged or disengaged from the tracked DRF 9101. In this image, the spring-loaded TMSM 9107 is fastened to a sliding insert 9109 that is not depressed by the unique mating protrusion 9111 of the probe extension, and the mating pin 9113 and associated mating slot 9115 are visible. Further, in this embodiment, the mating pin 9113 can securely fasten to the DRF 9101 within the mating slot 9115 via a spring-loaded plunger (not shown).

FIG. 91C illustrates an embodiment 9120 of the invention previously described in relation to FIGS. 91A-91B, and demonstrates coupling an alternate probe extension 9117 with its own unique mating protrusion 9119. In some embodiments, this structure and arrangement can result in the TMSM 9121 being slid to a different position relative to the 9101 in comparison than when other probe extensions are engaged. As shown, in some embodiments, the probe extension 9117 comprises a curved probe tip 9117a. In some embodiments, when the acquisition system detects the 9107 in this specific position relative to the 9101, it can load the appropriate tool definition file according to the alternate probe extension 9117 with curved probe tip 9117a as shown. Some embodiments of the modular probe extension types can include, but are not limited to: a straight probe, a curved probe, and/or a probe with unique mating features for coupling with a fiducial or another accessory device, a screwdriver head, a rod-centering fork, a ring structure or other closed-loop designs.

Some other embodiments of the invention can include multiple, permanently or semi-permanently coupled probe extensions to one DRF. Further, in some embodiments, one or more TMSM can be moved to discrete positions relative to the DRF to communicate data to the acquisition system, including, but not limited to, data related or associated with which probe extension is being utilized and therefore which tool definition file it should load. Further embodiments include systems compatible with TMSM-equipped systems: It should be noted that other embodiments of this invention are compatible with previously described, TMSM-equipped probes for triggering, in reference to FIGS. 10A-10G, and FIGS. 15A-15C. In these embodiments, the acquisition system can distinguish between the individual stray markers.

Some other embodiments can include one or more TSMs on the extensions: It should be noted that other embodiments of this invention can comprise probe extensions possessing one or more of their own TSMs, such that when the extension engages with the DRF, one or more of the TSMs are in preset locations. This is an alternative embodiment to the sliding TMSM equipped on the DRF itself as discussed above.

In some further embodiments of the invention, the mating mechanism between the modular probe extensions and the DRF can include, but are not limited to: quarter-turn, threaded, spring-loaded snap arms, and retractable spring plunger.

Some embodiments relate to the generation and analysis of patient images, where the patient images are analyzed to indicate their spinal alignment contour and parameters. Further, in some embodiments, the images can be analyzed to output instructions of how to position adjustable mounts coupled to an anatomical model of the spine to mimic the spinal alignment parameters displayed in the patient images. Other embodiments of this device include inputting desired discrete alignment parameter values (e.g., lumbar lordosis of 30 degrees) to the software which then outputs instructions for how to orient the adjustable mounts to configure the anatomical model to possess the input parameters. Another embodiment of the invention includes a user positioning the anatomical model, and then inputting one or more positioning coordinates (e.g., side rail position, cross-rail position, height, coronal angle, sagittal angle, etc.) of the adjustable mounts into the software, where in the system can output patient images closely matching the alignment parameters of the anatomical model. FIGS. 110A-110B provide further detail of one embodiment of a process of using one or more patient images to position the model to match one or more of the patient images. Further, some embodiments of this invention are related to devices and systems described in relation to FIGS. 12 and 90A-90D, as well as processes described in relation to FIGS. 89 and 110A-110B.

FIG. 92A illustrates a lateral view 9200 of an embodiment of the invention, similar to that previously described and shown in relation to FIGS. 90A-90D. In this instance, the lateral view 9200 includes a spine model 9201 and pelvis 9202 positioned into an alignment configuration by a series of adjustable assemblies. In some embodiments, at the level of the spine (9201), there are mounts for each level of spine (9204, 9214, 9215, 9216, 9217), with only a few illustrated in this non-limiting embodiment. In some embodiments, these mounts can be mechanically coupled to the vertebrae via screws 9203. In other embodiments this coupling mechanism can be achieved in various different ways, including, but not limited to, fasteners, and/or adhesive surfaces, and/or direct protrusions built-into each of the vertebrae. The lateral view 9200 of FIG. 92A shows the spine model 9201 resting on underside side rails 9213, a base sheet 9212, top side rails with distance indications 9211, and individual cross-rails 9210 for each of the vertebral and pelvic mounts. In some embodiments, attached to each of the cross-rails 9210 can be a base piece 9209, into which fits a sliding height adjustment piece 9208, and which can be enabled to slide vertically up and down. In some embodiments, multiple sizes of adjustable height adjustment assemblies can be used to achieve varying severities of sagittal curvatures. In some embodiments, a coronal angle indicator 9219 on which the coronal rotation piece 9207 sits can rotate in the coronal plane, and can be attached to the top of the sliding height adjustment piece 9208.

In some embodiments, attached to the top of the coronal rotation piece 9207 can be a sagittal rotation basket 9205 that designed to mate with the individual vertebra interface mounts (e.g., T1 vertebra interface mount 9204, 9214, 9215, 9216, 9217), and further, is able to rotate in the sagittal plane with angles indicated by the sagittal angle indicator 9206. In some embodiments, the model's pelvis can be mounted similarly, except it is supported by a more rigid pelvic coronal angle adjustment piece 9225 and its own unique pelvic interface mount 9218. This non-limiting embodiment also contains a tracked DRF 9220 including an orientation indicator 9222 and/or DRF mount 9221, enabling the model to have a coordinate system established from the 3D tracking camera. In addition, in some embodiments, this DRF 9220 can enable the model to be imaged (e.g., CT, X-ray, etc.) and have its anatomical landmarks fused in camera coordinates. In some embodiments, to enable the model to stand up vertically, one or more base feet 9224 can interface with a corresponding base rotation piece 9223 and interface with the model (shown via the base piece 9209 in this image). In some embodiments, this angular adjustment mechanism can allow for a range of continuous angles for the anatomical phantom to stand vertically to represent and visualize alignment of a standing human.

FIG. 92B displays a lateral view 9230 from the opposite side of the lateral view 9200 of that shown in FIG. 92A and provides an alternate viewing angle of the pelvic interface mount 9218, pelvic coronal angle adjustment piece 9225, and pelvic interface mount 9218. This viewing perspective also enables visualization of the side height indicator 9231 that can allow for discrete height settings of the sliding height adjustment piece 9208, in accordance with some embodiments of the invention.

FIG. 92C displays an alternative perspective view 9235 of the embodiment of FIGS. 92A-92B including the spinal column model 9201, pelvis model 9202, coronal rotation pieces 9207, sliding height adjustment pieces 9208, base pieces 9209, cross-rail 9210, top side rail 9211, model base sheet 9212, coronal angle indicator 9219, and base foot 9224 with interfacing base rotation piece 9223, shown here interfacing with the model base sheet 9212, in accordance with some embodiments of the invention.

FIG. 92D displays an alternative view 9236 of the embodiment of FIGS. 92A-92C, standing upright on the base feet 9224 and/or base rotation pieces 9223. This perspective provides a different viewing angle of the spinal column model 9201, pelvis model 9202, coronal rotation pieces 9207, sliding height adjustment pieces 9208, base pieces 9209, cross-rails 9210, top side rails 9211, model base sheet 9212, underside side rails 9213, a vertebra interface mount (as shown with the L3 spinal level) 9217, pelvic interface mount 9218, DRF 9220, DRF mount 9221, and DRF orientation indicator 9222, in accordance with some embodiments of the invention.

FIG. 92E displays a closer perspective assembly view 9237 of the embodiment's DRF 9220, DRF mount 9221, DRF orientation indicator 9222, and mounting hole 9238 on the DRF mount to allow rigid coupling to the model's base sheet and side rails (not shown). Further, FIG. 92F displays a perspective assembly view illustrating the DRF 9220, DRF mount 9221, and DRF orientation indicator 9222, in accordance with some embodiments of the invention.

FIG. 92G displays a closer assembly view 9240 of the sliding height adjustment piece 9208 and mating base piece 9209. In this non-limiting embodiment, the sliding height adjustment piece 9208 contains a mounting hole 9241 for mating with coronal rotation pieces (not shown), a stop-screw hole 9242, side extensions 9243 to mate around the outside walls of the base piece 9209, a center slot 9244 for sliding around a screw to enable height adjustment, and side screw hole 9245 for height stop selection. In some embodiments, the base piece 9209 contains a side slot 9246 to accommodate height adjustment around a side mounted screw (not shown), and/or a cross-rail-accommodating channel 9247, and/or cross-rail stop-screw holes 9248, and/or front side height indicator markings 9249 to allow visualization of the height set for the mated sliding height adjustment piece 9208, in accordance with some embodiments of the invention.

FIG. 92H displays a different perspective assembly view 9250 from that shown in FIG. 92G, allowing for an alternative view of the sliding height adjustment piece 9208 containing a center slot 9244 for a fastener (not shown), and side height stop hole 9245 for a fastener (not shown). The base piece is also visualized, illustrating its side slot 9246 to accommodate a fastener (not shown) to interface with the side height stop hole 9245 of the sliding height adjustment piece 9208, in accordance with some embodiments of the invention.

FIG. 92I displays a different perspective view 9251 from that shown in FIG. 92H, illustrating the sliding height adjustment piece's mounting hole 9241 for the rotation axis of the coronal rotation piece, and stop-screw hole 9242 for the coronal rotation piece in accordance with some embodiments of the invention.

FIG. 92J displays a closer view 9252 of the side height indicator 9231 that includes height indicator markings 9253. This piece is meant for mating onto the side wall of the base piece (e., base piece 9209 not shown) for reading the discrete height setting of a mated sliding height adjustment piece (e.g., using side slot 9246, not shown). Further, FIG. 92K displays a different perspective view 9254 of the side height indicator 9231 from that shown in FIG. 92J, illustrating the height indicator markings 9253 in accordance with some embodiments.

FIG. 92L displays a closer view 9255 of the coronal angle indicator 9219 (FIG. 92A) containing a mounting hole 9256 and coronal angle indicator markings 9257 to be read relative to a mated coronal rotation piece (not shown). FIG. 92M displays a different perspective view 9258 of the coronal angle indicator 9219 from that shown in FIG. 92L, illustrating the mounting hole 9256 and coronal angle indicator markings 9257 in accordance with some embodiments.

FIG. 92N illustrates a closer view 9259 of the sagittal angle indicator 9206 containing a mounting hole 9260, alignment tab 9261, and sagittal angle indicator markings 9262 in accordance with some embodiments. Further, FIG. 92O displays a different perspective view 9263 of the sagittal angle indicator 9206 from that shown in FIG. 92N, containing the mounting hole 9260 in accordance with some embodiments.

FIG. 92P displays a closer view 9264 of the coronal rotation piece 9207 displaying its arc-shaped slot 9265 that can be used to slide a coronal angle stopping fastener (not shown). Further, a viewing window 9266 is shown that can be used to visualize the angular markings on the underlying coronal angle indicator (not shown) in some embodiments. Further, a mounting hole 9267 is shown that can be used for attaching to the sliding height adjustment piece (not shown) in some embodiments. Further, a support gusset 9268 is shown, and a sagittal angle indicator bar 9269 can be used for reading an angular setting of a mated sagittal rotation basket (not shown) and sagittal angle indicator (not shown) in some embodiments. Further, a sagittal rotation stop-screw hole 9207 and mounting hole 9271 are shown and can be used for attaching a sagittal rotation basket (not shown), in accordance with some embodiments.

FIG. 92Q displays a different perspective view 9272 of the coronal rotation piece from that shown in FIG. 92P, illustrating the coronal angle slot 9265, viewing window 9266 for visualization of the underlying coronal angular markings, sagittal angle indicator bar 9269, sagittal rotation stop-screw hole 9270, a mounting hole 9271, and coronal angle indicator bar 9273. In some embodiments, the coronal angle indicator bar 9273 can be used to provide a reference point relative to the underlying coronal angle indicator as previously described in FIGS. 92M-92N, in accordance with some embodiments.

FIG. 92R displays a closer view 9274 of the pelvic coronal angle adjustment piece, illustrating a mounting hole 9275 for interfacing with the pelvic interface mount (not shown), a sagittal rotation stop-screw hole 9276, and side support bars 9277 in accordance with some embodiments.

FIG. 92S displays a different perspective view 9278 of the pelvic coronal angle adjustment piece from that shown in FIG. 92R, and illustrates the side support bars 9277 and sagittal angle indicator bar 9279 that can be used as a reference point relative to a mated pelvic interface mount (not shown) and sagittal angle indicator (not shown).

FIG. 92T displays a closer view 9279 of the pelvic interface mount 9218 containing extension bars 9280 to flank the model's pubic symphysis (not shown), a slot 9281 for coronal angle indicator, mounting hole 9282 for interfacing with the pelvic coronal angle adjustment piece as previously described in FIGS. 92R and 92S, and slot 9283 for accommodating a sagittal rotation stop-screw (not shown) while adjusting the sagittal angle of the mount. Further, FIG. 92U displays a different perspective view 9284 of the pelvic interface mount 9218 from that shown in FIG. 92T, illustrating the slot 9283 for accommodating a sagittal rotation stop-screw (not shown) while adjusting the sagittal angle of the mount and mounting holes 9285 for coupling to the pelvic model.

FIG. 92V displays a closer view 9286 of the sagittal rotation basket 9205 along with its mounting hole 9287 for mating with the coronal rotation piece previously described in FIGS. 92P-92Q, and slot 9288 for accommodating a sagittal rotation stop-screw (not shown) while adjusting the sagittal angle of the basket, in accordance with some embodiments.

FIG. 92W displays a different perspective view 9289 of the sagittal rotation basket 9205 from that shown in FIG. 92V, illustrating the mounting hole 9290 for interfacing with the coronal rotation piece (not shown) previously described in FIGS. 92P-92Q, in accordance with some embodiments. FIG. 92X displays a different perspective of the sagittal rotation basket 9205 from that shown in FIGS. 92V-92W, illustrating mounting hole 9292 for fastening a vertebra interface mount, in accordance with some embodiments.

FIG. 92Y illustrates a front view 9293 of a vertebral interface component for a vertebral holder of an adjustable phantom spine model holder as described previously in relation to FIGS. 92A-92X in accordance with some embodiments of the invention. As shown, FIG. 92Y displays vertebra interface mount 9214 with mounting extension tab 9294 that is designed to slide into a sagittal rotation basket (not shown) (previously described in FIGS. 92V-92X). Also shown is a mounting hole 9295 as a fastener to secure it to the sagittal rotation basket 9205, in accordance with some embodiments.

FIG. 92Z illustrates a perspective view 9296 of a vertebral interface component and sagittal angle adjustment component for a vertebral holder of an adjustable phantom spine model holder as described previously in relation to FIGS. 92A-92Y in accordance with some embodiments of the invention. The perspective view 9296 provides a closer look of both the sagittal rotation basket 9205 and vertebra interface mount 9214 including its mounting holes 9297 for securing fasteners to the spine model (not shown), in accordance with some embodiments.

FIG. 92AA illustrates a perspective view 9298 of an adjustable vertebral holder substantially rigidly engaged with a phantom spine model holder as described previously in relation to FIGS. 92A-92Z in accordance with some embodiments of the invention. For example, FIG. 92AA displays a closer look of the assembled embodiment as previously described in FIGS. 92A-92D illustrating the spinal column model 9201 substantially rigidly coupled to the vertebra interface mount 9214 that is secured to a sagittal rotation basket 9205 with sagittal angle indicator. In this instance, the assembly is rotated on a coronal rotation piece 9207 resting on a sliding height adjustment piece 9208 with a discrete height setting able to be read from the side height indicator 9231. Further, the assembly is mounted on a base piece 9209 fastened to a cross-rail 9210 that slides along top side rails 9211, and is coupled to the model base sheet 9212. This view demonstrates that in some embodiments, the assembled embodiment of pieces for adjusting a vertebra can be applied to as many individual vertebrae as needed to accommodate the desired end contour of the spinal model.

FIG. 92AB displays a perspective assembly view 9299 of the base rotation piece 9223 and base foot 9224. The base rotation piece 9223 is designed to interface with the model base piece (not shown), in accordance with some embodiments of the invention. Further, FIG. 92AC displays a different perspective (front) assembly view 9299a of the base rotation piece 9223 and base foot 9224 from that shown in FIG. 92AB, in accordance with some embodiments of the invention.

FIG. 92AD illustrates a front assembly view 9299b of a base platform and cross-rails of an adjustable phantom spine model holder as described previously in relation to FIGS. 92A-92AC in accordance with some embodiments of the invention. For example, FIG. 92AD illustrates the cross-rail 9210 with slot 9210a to accommodate fasteners from the base pieces (not shown) and mounting holes 9210b to fasten to the top side rails 9211. In some embodiments, the top side rails 9211 contain a slot 9211a to accommodate sliding movement of the overlying cross-rails, and mounting holes 9211b for fastening to the model base sheet 9212. Further, in some embodiments, the model base sheet 9212 contains slots 9212a to accommodate sliding of the overlying cross-rail fasteners and corner mounting holes 9212b to allow for fastening to the top side rails above and underside side rails 9213 below. Further, in some embodiments, the underside side rails can contain a widened slot 9213a to accommodate both the fasteners for the sliding cross-rails, and also nuts (not shown) for tightening the fasteners. Further, in some embodiments, the underside side rails also contain mounting holes 9213b for fastening to the model base sheet 9212, top side rails 9211, cross-rails 9210, and DRF mount (not shown) previously described in FIGS. 92E-92F.

Some embodiments of the invention include a device that can be used to assess the intraoperative flexibility of the spine with one or more mountings that can substantially rigidly interface with implanted pedicle screws, as previously described in relation to FIGS. 33A-33H, FIG. 34, FIG. 35A-35F, and FIGS. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described previously in relation to FIG. 70. Furthermore, in some embodiments, after adjusting two or more spinal levels to a desired relative orientation using this tool, the tools can lock together to temporarily hold the anatomy in a configuration while a rod is inserted to the spine-instrumented pedicle screws to hold the spine in this contour. Some embodiments of this invention are related to devices and systems described in relation to FIGS. 34, 34A-34F, 35A-35F, 36A-36I, 37A-37G, 39A-39F, 40A-40C, 41A-41D, 42A-42K, 43A-43F, 94A-94H, 95A-95I, 96A-96S, 97A-97L, 105A-105G, and 106A-106F, as well as processes described in relation to FIGS. 63, 70, 108A-108H, 111A-111C, and 113.

FIG. 93A illustrates a rear view 9300 of an adjustable pedicle screw interface base, with one fixed side arm (9309b) and one side arm with height and angle adjustments (shown as adjustable side arm 9309a), of a flexibility assessment device. In some embodiments, the components of 9309a and 9309b can be the same and therefore are shown with the same components. The rear view 9300 shows the lower half of the flexibility assessment device with the handle, its DRF, and associated triggering mechanism removed. As shown, this embodiment comprises handle mount side walls 9303 and a spring-loaded plunger 9301 that can be used to select the relative angle of the handle (not shown). In some embodiments, an assembly (e.g., such as mobile side arm mechanism 9313a) including a height adjustment knob 9302 can be used to alter the extension height of one of the side arms (e.g., adjustable side arm 9309a), and/or can be used to alter a distance between side arms (e.g., by moving the adjustable side arm 9309a towards or away from fixed side arm 9309b in cavity or channel 9327, and/or 9325, and/or 9326). Further, a center mount 9304 body is shown, and a fixed shoulder 9305 that can substantially rigidly hold one of the side arm (fixed side arm 9309b) at a fixed angle relative to the center mount body. Further, in some embodiments, one or more device tulip heads 9307 positioned atop tulip head mounting shafts 9308, (four shown), can allow for substantially rigidly fixing of a rod between two or more devices with cap screws 9306. In some embodiments, the device can interface with pedicle screw tulip heads 9311 with pedicle screw shaft 9310 (threads not shown) that is implanted into bony anatomy. In some embodiments, to enable device assembly, there can be a width adjustment housing mounting bracket 9312 secured with a fastener 9314. In some embodiments, the detachable side arms can couple to the upper part of the device via side arm mounting sleeves 9313. In some embodiments, to accommodate varying locations and angles of contralateral pedicle screws, the relative angle and distance between these side arms can be adjusted via the one mobile side arm (left side in this illustration).

FIG. 93B displays a side view 9315 of the device shown previously in FIG. 93A, including its spring-loaded plunger 9301, angle detents 9316 that can receive the spring-loaded plunger 9301 at discrete handle angles, width adjustment tightening knob 9317, handle mounting hole 9320, width adjustment housing mounting bracket 9312, height adjustment knob 9302, and device tulip heads 9307 on tulip head mounting shafts 9308. The side view 9315 further shows the device coupled to pedicle screw tulip heads 9311 with associated pedicle screw shaft 9310 (threads not shown), and has the front arm of the tulip head mount 9319 shown, in addition to the through hole 9318 for applying the end cap when coupling the device to a pedicle screw. Some embodiments of this device are designed to utilize cap screws that are supplied with the implanted pedicle screws as shown here, but other embodiments contain cap screws that are built-in to the screw-interface regions of the side arms (in reference to FIGS. 94A-94H).

FIG. 93C illustrates a perspective view 9321 of an adjustable pedicle screw interface base, with one fixed side arm and one side arm with height and angle adjustments, of a flexibility assessment device as described previously in relation to FIGS. 93A-93B in accordance with some embodiments of the invention. The perspective view 9321 illustrates the handle mount side walls 9303, the height adjustment knob 9302, and width adjustment tightening knob 9317 that can allow the adjustable side arm to slide in the width adjustment side channel 9325, and width adjustment top channel 9326. Further, a different view of the width adjustment housing mounting bracket 9312 is also shown. This illustration visualizes the sliding retainer clips 9322 which allow for quick coupling or decoupling of the side arms from the upper part of the device. In some embodiments, mounting holes 9323 can connect the device's tulip head attachment pieces are visualized, in addition to the front arm of the tulip head mount 9319 and its built-in screw interface rod 9324. Further, FIG. 93D displays a side view 9328 of the embodiment opposite of that shown in FIG. 93B including the height adjustment knob 9302, width adjustment tightening knob 9317, tulip head mount front arm 9319, tulip head mount back arm 9329, and attached pedicle screw with tulip head 9311 and screw shaft 9310 (threads not shown), in accordance with some embodiments of the invention.

FIG. 93E displays a front view 9330 of the embodiment previously described in FIGS. 93A-93D illustrating a different view of the width adjustment side channel 9325 which allows for the mobile side arm to adjust both its angle and distance from the fixed side arm. Further, also shown is a front view of the sliding retainer clips 9322 that can secure the side arms to the upper part of the device are shown, in addition to the front end of the screw interface rod 9324, in accordance with some embodiments of the invention.

FIG. 93F displays a top view 9332 of the embodiment previously described in FIGS. 93A-93E showing the through hole 9318 that can allow for placement and tightening of the cap screw when securing the device to pedicle screws. The width adjustment top channel 9326 is also shown, which can accommodate the height adjustment knob while the mobile side arm's distance and angle from the fixed side arm is adjusted, in accordance with some embodiments of the invention.

FIG. 93G displays a partially disassembled illustration 9334 of the embodiment previously described in FIGS. 93A-93F showing the sliding retainer clips 9322 which mate with the retainer clip grooves 9336 on the side arms and pass through the retainer clip slots 9335 on the side arm sleeves. In some embodiments, to aid with alignment of the side arms, there are side alignment pins 9337 built-into the side arm, and center alignment pins built-into the side arm mating sleeve, in accordance with some embodiments of the invention.

FIG. 93H displays a view 9339 of the embodiment previously described in FIGS. 93A-93G with one of side arms (9309b) not mated with a pedicle screw. This illustration allows for visualization of the screw interface rod 9324 that is tightened to pedicle screw shafts with an end cap 9340, in accordance with some embodiments of the invention.

FIG. 93I displays a partially disassembled view 9342 of the device from a different view than that shown in FIG. 93G, showing the center alignment pins 9343 attached to the side arm mating sleeves and the side alignment pins 9337 attached to the side arms. The alignment pins in some embodiments are quick release pins that contain a spring-loaded ball bearing.

FIG. 93J displays a cross-sectional view 9345 of one of the side arms mated to a pedicle screw with tulip head 9311 and shaft 9310 (threads not shown). This view allows for visualization of the screw interface rod 9324 securely tightened to the tulip head 9311 with a cap screw 9340. This view also displays the center alignment pin 9343 which aids the rigid coupling between the side arm and the side arm sleeve, in accordance with some embodiments of the invention.

Some embodiments of the invention include a device that can be used to assess the intraoperative flexibility of the spine with one or more mountings to substantially rigidly interface with implanted pedicle screws, as previously described in relation to FIGS. 33A-33H, FIG. 34, FIGS. 35A-35F, and FIGS. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. The range of motion can be displayed to the user on a display monitor via a 3D view or 2D projections onto relevant anatomical planes, as described previously in reference to FIG. 70. Furthermore, in some embodiments, after adjusting two or more spinal levels to a desired relative orientation using this tool, the tools can interlock together to temporarily hold the anatomy in that configuration while a rod is inserted to the spine-instrumented pedicle screws to hold the spine in this contour. Some embodiments of this invention are related to devices and systems described in relation to FIGS. 34, 34A-34F, 35A-35F, 36A-36I, 37A-37G, 39A-39F, 43A-43F, 93A-93J, 95A-95I, 97A-97L, 105A-105G, and 106A-106F, as well as processes described in relation to FIGS. 63, 70, 108A-108H, 111A-111C, and 113.

FIG. 94A displays an embodiment 9400 of the lower half of the device as previously described in FIGS. 93A-93J, except without the mechanism of adjusting the height of the mobile side arm and with a built-in, elongated cap screw 9401. However, in this instance, as in the embodiments of FIGS. 93A-93J, the mobile side arm 9419b can be moved in a cavity or channel 9424 of adjustment housing mounting bracket 9426. In some embodiments, this can be used to secure the device to a pedicle screw's tulip head 9407 and shaft 9410 with a tulip head mount front arm 9409 and back arm 9408 flanking the tulip head 9407, and substantially rigidly securing the screw interface rod (not shown). Further, visualized in this illustration is the width adjustment tightening knob 9402 that firmly locks the angle and location of the mobile side arm in place. Also shown is a spring-loaded plunger 9403 and its associated angle detents 9404 that can be used to adjust the relative angle of the device's handle (not shown), which is mounted with the mounting hole 9405. The device's tulip heads 9406 are also shown, which enable coupling between two or more devices with a rod to hold the devices and anatomy in position while a rod or other hardware is implanted into the surgical site, in accordance with some embodiments of the invention. Further, FIG. 94B displays a top view 9412 of the embodiment 9400 previously described in FIG. 94A containing the spring-loaded plunger 9403, device tulip heads 9406, and cap screws 9413 that can be used to secure the rod(s) connecting devices, handle mount side walls 9414, and width adjustment top channel 9415, in accordance with some embodiments of the invention.

FIG. 94C displays a front view 9417 of the embodiment previously described in FIGS. 94A-94B containing width adjustment tightening knob 9402, center mount 9421, and width adjustment tightening knob 9403. In some embodiments, a fixed shoulder 9420 can be substantially rigidly coupled to the fixed side arm 9419a and secured via a sliding retainer clip 9418. Further, in some embodiments, one side arm can include height and angle adjustments (shown as adjustable side arm 9419b). Similar to the embodiment of FIGS. 93A-93J, in some embodiments, the components of the side arms 9419a and 9419b can be the same and therefore are shown with the same components. Further, as shown, the pedicle screw to which the device is mated are shown including the tulip heads 9407 and screw shafts 9410 (threads not shown), in accordance with some embodiments of the invention.

FIG. 94D displays a different view 9423 of the embodiment previously described in FIGS. 94A-94C containing width adjustment tightening knob 9402, width adjustment mechanism with a top channel 9415, and sliding retainer clips 9418 to secure the detachable side arms 9419a, 9419b, equipped with built-in cap screws 9401 that can allow for mating with the threads of tulip heads on the implanted pedicle screws, in accordance with some embodiments of the invention.

FIG. 94E displays a rear view 9425 of the embodiment previously described in FIGS. 94A-D displaying the width adjustment housing mounting bracket 9426 that enables assembly of the mobile slide arm mechanism 9413*a* including a height adjustment knob 9403 (not shown) that can be used to alter the extension height of the side arm 9419*b*, in accordance with some embodiments of the invention. Further, as discussed earlier, the mobile side arm 9419*b* can be moved in a cavity or channel 9424 of adjustment housing mounting bracket 9426 using the mobile slide arm mechanism 9413*a*, allowing the distance between the side arms 9419*a*, 9419*b* to be increased or decreased by moving mobile side arm 9419*b* in cavity or channel 9424.

Further, FIG. 94F displays a side view 9427 of the embodiment opposite to that shown previously in FIG. 94A displaying the width adjustment tightening knob 9402, mounting hole 9405 for handle (not shown), fixed shoulder 9420 to attach to the fixed side arm, and the tulip head 9407 of the attached pedicle screw, in accordance with some embodiments of the invention.

FIG. 94G displays a front view 9429 of the device previously described in FIGS. 94A-94F. In this illustration, one of the mated pedicle screws has been removed from the fixed side arm 9419*a* to provide improved visualization of the built-in cap screw 9401 and front arm of the tulip head mount (front arm 9409). Further, FIG. 94H displays a different perspective view 9431 of the embodiment from that shown in FIG. 94G illustrating the built-in cap screw 9401 and its threads designed to interface with the tulip head threads of the implanted pedicle screws.

Some embodiments of the invention include a device that can be used to assess the intraoperative flexibility of the spine with one or more mountings to substantially rigidly interface with implanted pedicle screws, as previously described in relation to FIGS. 33A-33H, FIG. 34, FIG. 35A-35F, and FIGS. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described previously in reference to FIG. 70. Some embodiments of this invention are related to devices and systems described in relation to FIGS. 34, 34A-34F, 35A-35F, 36A-36I, 37A-37G, 39A-39F, 40A-40C, 41A-41D, 42A-42K, 43A-43F, 94A-94H, 96A-96S, 97A-97L, 105A-105G, and 106A-106F, as well as processes described in relation to FIGS. 63, 70, 108A-108H, 111A-111C, and 113.

FIG. 95A displays one embodiment 9500 that enables assessment of spinal flexibility via 3D-tracked motion of the device containing an upper portion 9595 comprising a device handle grip 9509 of a handle containing a tracked DRF 9503 secured to a DRF arm with a mounting screw 9504 and alignment pin 9505. In some embodiments, the handle also contains a spring-loaded sliding trigger 9508 with sliding arm 9502 with TMSM 9501 attached such that the TMSM moves linearly up and down, supported by the back wall 9507 for sliding arm, relative to the tracked DRF to communicate with the acquisition system. In this non-limiting embodiment, the TMSM 9501, sliding arm 9502, and trigger 9508 are shown in the undepressed position. Further, the device handle grip 9509 is mounted to a lower portion 9599 comprising a pedicle screw interface tools 9585 of the device, and is able to have its angle adjusted via a spring-loaded plunger 9510 fitting into discrete angle detents (not shown). In some embodiments, the lower portion 9599 of the device can contain a tracked fixed stray marker 9511 mounted to the width adjustment knob 9515 used to adjust the width between the two screw interface tools 9585. The embodiment also contains two screw tightening knobs 9512 used to thread into the tulip heads of the implanted pedicle screws. In some embodiments, tracked fixed stray markers (9511, 9514) can be mounted to these screw tightening knobs in order to compute plane of the device when using the location of all three tracked stray markers 9513, (9514, 9511). The lower part of this device contains a width adjustment guides 9516, and the screw interface tools 9585 can be disconnected from the device via snap arms 9517. The screw interface tools 9585 of the device contain pseudo rods 9518 at their most distant end to be tightened into the saddle of the mating pedicle screws and substantially rigidly fix the position of a polyaxial tulip head (if applicable) to its associated pedicle screw shaft allowing the device to substantially rigidly couple to the bony anatomy into which the pedicle screws are secured.

The embodiment 9520 of FIG. 95B displays the embodiment described previously in FIG. 95A, except with the TMSM 9521, sliding arm 9522, and trigger 9523 in the fully depressed position, in accordance with some embodiments of the invention. Further, FIG. 95C displays a rear view 9525 of the embodiment shown in FIG. 95A including the DRF 9503, handle grip 9509 and back wall 9507 for supporting the sliding arm 9502. The sliding arm 9502 for the TMSM and trigger 9508 are shown in the undepressed position in this non-limiting embodiment. This view allows for visualization of the trigger motion-restricting slot 9426 in the back of the trigger which allows for sliding motion until the slot walls are stopped by the trigger-retaining screw, in accordance with some embodiments of the invention.

FIG. 95D displays a rear view 9529 of the device previously described in FIG. 95C except with the trigger 9523 and sliding arm 9522 for the TMSM in the fully depressed position, in accordance with some embodiments of the invention. Further, FIG. 95E displays a rear view 9531 of the device previously described in FIGS. 95A-D, except it is equipped with a trigger with a unique DRF 9532 on a DRF arm 9533 and sliding arm 9535 with unique geometry (shown as upper portion 9595*a*). In some embodiments, the sliding arm holds a TMSM 9534 and is supported by a back wall 9536, and can signal to the acquisition system by pressing down on the trigger 9537, in accordance with some embodiments of the invention. Further, the embodiment 9539 of FIG. 95F displays the embodiment described in FIG. 95E except with the trigger 9542, sliding arm 9541 and mounted TMSM 9540 in the depressed position, in accordance with some embodiments of the invention.

The embodiment 9544 of FIG. 95G illustrates both devices described previously in FIGS. 95A-F with unique DRFs (9503, 9532), associated sliding TMSMs (9502, 9540) mounted to sliding arms (9502, 9541) with trigger 9542. Shown in this configuration from the 3D-tracking camera's perspective, it can be appreciated that the tracked markers for each tool are facing in the same direction. Additionally, the DRF arms and sliding arms (9541, 9502) are offset away from one another to avoid adjacent tools obstructing the tracking camera's visualization of any of the tracked markers.

FIG. 95H displays a side view 9550 of the embodiment previously described in FIG. 95G, showing flexibility assessment tool #1 9551 and flexibility assessment tool #2 9552 with their pseudo rods 9553 extending to mate with the tulip heads of implanted pedicle screws (lower portion 9599 comprising lower portion 9599a with screw interface tools 9585a), in accordance with some embodiments of the invention.

FIG. 95I displays a cross-sectional view 9560 of the handle of the embodiment previously described in FIGS. 95A-95D containing the sliding trigger 9561, compression spring 9562 to provide the restoring force to the trigger, a dowel pin 9563 to compress the spring and help keep the sliding trigger aligned with its path of motion, and a trigger-retaining screw 9564 which restricts motion of the sliding trigger to the region of the trigger motion-restricting slot. The handle 9566, mounting hole 9567 for the spring-loaded plunger (not shown), and mounting hole 9567 for the handle to coupled with the lower portion of the device (not shown) are also illustrated. The uppermost region of the handle is not visualized due to it curving out of the plane of this cross-sectional image.

Some embodiments of the invention include a device that can be used to assess the intraoperative flexibility of the spine with one or more mountings to substantially rigidly interface with implanted pedicle screws, as previously described in relation to FIG. 33A-33H, FIG. 34, FIG. 35A-35F, and FIG. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described previously in reference to FIG. 70. Furthermore, in some embodiments, after adjusting two or more spinal levels to a desired relative orientation using this tool, the tools can interlock together to temporarily hold the anatomy in that configuration while a rod is inserted to the spine-instrumented pedicle screws to hold the spine in this contour. Some embodiments of this invention are related to devices and systems described in relation to FIGS. 34, 34A-34F, 37A-37G, 39A-39F, 40A-40C, 41A-41C, 42A-42K, 43A-43F, 93A-93J, 95A-95I, 96A-96S, 97A-97L, 105A-105G, and 106A-106F, as well as processes described in relation to FIGS. 63, 70, 108A-108H, 111A-111C, and 113.

FIG. 96A illustrates the flexibility assessment tool top halves consisting of DRFs and sliding triggers previously described in reference to FIG. 95A-95H (e.g., comprising upper portions 9595, 9595a), coupled with the tool bottom halves previously described in reference to FIG. 93A-93J equipped with the built-in cap screw design to mate with pedicle screws (shown as embodiment 9400), previously described in reference to FIG. 94A-94H. This illustration includes a front view of both flexibility assessment tool #1 9602 (which can comprise all or part of upper portion 9595a as described previously) and flexibility assessment tool #2 9601 (which can comprise all or part of upper portion 9595 described previously). Further, FIG. 96B illustrates a rear view of both flexibility assessment tool #1 9602 and flexibility assessment tool #2 9601. FIG. 96C illustrates a different view from that shown in FIGS. 96A-B of flexibility assessment tool #1 9602 and flexibility assessment tool #2 9601. FIG. 96D illustrates a side view of the embodiment shown in FIG. 96C, containing flexibility assessment tool #1 9602 and flexibility assessment tool #2 9601. FIG. 96E illustrates a top view of the embodiment shown in FIG. 96D, containing flexibility assessment tool #1 9602 and flexibility assessment tool #2 9601.

FIG. 96F illustrates an embodiment 9612 of a bottom portion of the embodiments previously described in FIGS. 96A-96E with the handle removed and includes the fixed shoulder 9613, handle mount side walls 9614, spring-loaded plunger 9615 for adjusting the angle of the handle, height adjustment knob 9616 usable to adjust the height of the mobile side arm 9697, width adjustment top channel 9617, width adjustment housing mounting bracket 9618, width adjustment tightening knob 9619, side arm extension 9620 containing device tulip heads 9621 and cap screws 9622. In some embodiment, the built-in cap screws 9623 can be designed to interface with tulip heads 9624 of implantable pedicle screws 9625 (screw threads not shown), and sliding retaining clips 9626 that when removed, enable quick release of the side arms 9627. Further, in some embodiments, the mobile side arm 9697 can be moved within the cavity or channel 9699 as described previously with regard to similar or same structures utilizing a mobile side arm moveably positioned in an adjustment housing mounting bracket (e.g., such as bracket 9618).

FIG. 96G displays a different view 9630 of the embodiment 9612 previously described in reference to FIG. 96F showing the width adjustment housing mounting bracket 9618 among the other previously described components. FIG. 96H displays a different view 9632 of the embodiment 9612 previously described in relation to FIGS. 96F-96G. Further, FIG. 96I displays a different view 9634 of the embodiment previously described in reference to FIGS. 96F-96H, except with the mated pedicle screws removed enabling better visualization of the built-in cap screw 9635. This illustration shows the mobile side arm 9636 positioned at an inward facing angle to the fixed side arm. Further, FIG. 96J displays a view 9637 of the embodiment described previously in relation to FIG. 96J except with the mobile side arm 9638 positioned parallel to the fixed side arm. This illustrates the ability of the mobile side arm to not only translate but also rotate about the axis of the width adjustment tightening knob.

FIG. 96K displays an exploded assembly perspective view 9640 of an embodiment similar to that described in relation to FIGS. 96I-96J, except that it contains a unique screw interface region with pseudo rods 9644 without the front and back walls shown previously in FIGS. 96I-96J. This embodiment also contains previously described components including a fixed shoulder 9641, width adjustment track 9642, width adjustment housing mounting bracket 9618, screws 9643 to fasten the top three components, the width adjustment pivot piece 9645 to which the mobile shoulder 9650 mates, the side alignment pins 9648 and their mating blind holes 9646, and center alignment pins 9649 and their mating blind holes 9647. Further, FIG. 96L displays a front view 9655 of the disassembled embodiment shown from a different view in FIG. 96K containing spring-loaded plunger 9615, width adjustment housing mounting bracket 9618, sliding retainer clips 9626, fixed shoulder 9641, width adjustment track 9642, width adjustment pivot piece 9645, side alignment pins 9648, center alignment pins 9649, mobile shoulder 9650 and center mount 9656.

FIG. 96M displays an assembled view 9660 of the embodiment described previously in relation to FIGS. 96K-96L, including fixed arm portion 9660a and mobile arm portion 9660b. In this view, one of the mating pedicle screws is removed to better visualize the pseudo rod (mating pedicle screw 9660a is shown on pseudo rod 9644 but not on the other). Moreover, this illustration does not include an attached handle with triggering and 3D-tracked tracked components.

FIG. 96N displays a rear view 9670 of the assembled flexibility assessment device #1 9602 as previously described in relation to FIGS. 96A-96E.

FIG. 96O displays a side view 9672 of both flexibility assessment tool #1 9602 and flexibility assessment tool #2 9601 coupled to pedicle screws implanted into a vertebra 9674 and an inter-tool connecting rod 9673 joining the two assessment tools together (e.g., such as 9400). In some embodiments, while using the device, the user can be enabled to adjust each of the tracked assessment devices to position the vertebrae relative to one another as desired, and the inter-tool connecting rod 9673 can be attached to each assessment device to hold the vertebrae in their desired relative positions while a rod connecting pedicle screws is bent and implanted prior to fully removing all components of the assessment devices. Further, FIG. 96P displays a top view of the embodiment described in relation to FIG. 96O, containing flexibility assessment tool #1 9602 and flexibility assessment tool #2 9601, along with the inter-tool connecting rod 9673.

FIG. 96Q displays a side view 9678 of two side arms coupled via an inter-tool connecting rod 9679 and disconnected from the side arm sleeves after being attached to the pedicle screws implanted in vertebrae 9674, and the side alignment pins 9680 shown. This illustration highlights how the assessment devices can be substantially rigidly coupled to one another after positioning the vertebrae in their desired relative orientations, and assessment devices can be disassembled to leave behind unilaterally positioned side arms to expose the contralateral pedicle screws to secure a rod to the implanted pedicle screws, thereby locking the spine segment into the measured and desired relative alignment. In some embodiments, after implanting the rod into the exposed contralateral implanted pedicle screws, the remaining side arms can be removed, with the vertebrae held into the desired contour by the implanted contralateral rod, so then a second rod can be secured to the previously occupied, implanted pedicle screws.

FIG. 96R displays an embodiment 9685 similar to that previously described in relation to FIG. 96Q, except with a rod implanted contralateral to the remaining side arms that are coupled via an inter-tool connecting rod 9679. FIG. 96S displays a top view 9690 of the embodiment described previously in relation to FIG. 96R, including both the inter-tool connecting rod 9679 and the implanted rod 9691 for pedicle screws. In some embodiments, after the cap screws are fully tightened to secure the implanted rod 9691 to the implanted pedicle screws, the remaining side arms are removed from the pedicle screws. In some embodiments, after removing the last side arms, the implanted rod 9691 holds the spine in alignment while the contralateral pedicle screws are now exposed to receive an additional implanted rod.

Some embodiments of the invention include a device that can be used to assess the intraoperative flexibility of the spine with one or more mountings to substantially rigidly interface with implanted pedicle screws, as previously described in relation to FIGS. 33A-33H, 34, 35A-35F, and 36A-36I. In some embodiments, after substantially rigidly fixing two tools, each to individual spinal levels, the spine can be manipulated via direct forces on anatomical structures or indirectly by interacting with the assessment tool's handles to establish a range of motion between the spinal levels onto which the tools are engaged. In some embodiments, the range of motion can be displayed to the user on a display monitor via a 3D view or 2D projections onto relevant anatomical planes, as described previously in reference to FIG. 70. Furthermore, after adjusting two or more spinal levels to a desired relative orientation using this tool, the tools can interlock together to temporarily hold the anatomy in that configuration while a rod is inserted to the spine-instrumented pedicle screws to hold the spine in this contour. FIG. 97 in particular describes example embodiments that enable the system's utility within minimally invasive spine surgery, including both robotically-assisted and non-robotically-assisted cases. Some embodiments of this invention are related to devices and systems described in relation to FIGS. 34, 34A-34F, 35A-35F, 36A-36I, 37A-37G, 39A-39F, 40A-40C, 41A-41D, 42A-42K, 43A-43F, 93A-93J, 95A-95I, 96A96S, 97A-97L, 105A-105G, and 106A-106F, as well as processes described in relation to FIGS. 63, 70, 108, 111, and 113.

FIG. 97A illustrates an elongated side arm embodiment 9700 that can be used as the screw-interface portion of the flexibility assessment devices, enabling it to access pedicle screws implanted through a percutaneous, minimally invasive approach. In some embodiments of the invention, this embodiment mates via a built-in extended screw 9717 with the tulip head 9707 of a pedicle screw shaft 9708 (threads not shown). Further, this embodiment includes a minimally invasive sleeve 9701 that extends from the side arm 9702 that contains a retainer clip groove 9709, side alignment pins 9703, device tulip heads 9704, and cap screws 9705 for coupling two or more of these side arms together across vertebrae. This illustration displays the pedicle screw unmated with the device (pedicle screw shaft 9708), and the side arm is disconnected from flexibility assessment device's side arm sleeves (not shown) and handle (not shown). Further, the view 9710 of FIG. 97B displays the embodiment previously described in relation to FIG. 97A including the side alignment pins 9710, except the device is mated to the pedicle screw (pedicle screw shaft 9708) via tulip head 9707.

FIG. 97C displays a top view 9712 of the embodiment described previously in relation to FIG. 97B, containing the extended screw head 9714 that enables tightening the device to a pedicle screw, side alignment pins 9703 for mating with the side arm sleeve, blind hole 9713 for mating with the center alignment pin, and device tulip head 9704 and cap screw 9705 for coupling 2 or more of these side arms together across vertebrae, in accordance with some embodiments of the invention.

FIG. 97D displays a cross-sectional view 9716 of the embodiment described previously in relation to FIGS. 97B-97C containing the side arm mated to the tulip head 9707 of a pedicle screw shaft 9708 (threads not shown), via extended screw threads 9717 coupled to the extended screw shaft 9714b that passes through the minimally invasive sleeve 9701 and side alignment pins 9703 for mating with the side arm sleeve (not shown). Further, FIG. 97E displays a cross-sectional view 9720 of the embodiment previously described in FIGS. 97B-97D containing an extended screw 9714 that passes through a minimally invasive sleeve 9701, and a side alignment pin 9703 and retainer clip groove 9709 that can be used to aid in attaching the side arm to a side arm sleeve on fixed or mobile shoulder pieces (not shown).

FIG. 97F displays an assembly view 9725 of an embodiment of the device previously described in relation to FIGS. 97B-97E containing two minimally invasive side arm sleeves 9701 with extended screws 9714 and side alignment pins 9703 for mating with the mobile shoulder 9729 on one side and fixed shoulder 9728 on the other. As shown in this non-limiting embodiment, the shoulders contain center alignment pins 9727 that can further aid with alignment when mating the side arms with the upper portion of the device. In some embodiments, the angle and position of the mobile shoulder 9729 can be adjusted using the width adjustment tightening knob 9730 and height adjustment knob 9731. The tracked handle with sliding trigger is disconnected from the upper portion of the device and not shown in view 9725.

FIG. 97G displays a side view 9735 of two fully assembled embodiments of the device previously described in relation to FIGS. 97B-97F including the minimally invasive flexibility assessment tool #1 9736, and the minimally invasive flexibility assessment tool #2 9737, each mated to pedicle screws. Further, FIG. 97H displays a different view 9745 of the two fully assembled embodiments described previously in relation to FIG. 97G including the minimally invasive flexibility assessment tool #1 9736 and the minimally invasive flexibility assessment tool #2 9737, each mated to pedicle screws. FIG. 97I displays a side view 9745 opposite of that shown in FIG. 97G, containing assembled minimally invasive flexibility assessment tool #1 9736 and the assembled minimally invasive flexibility assessment tool #2 9737, each mated to pedicle screws (pedicle screw shaft 9708). FIG. 97J displays a front view 9750 of the embodiments described previously in relation to FIGS. 97G-97I including the minimally invasive flexibility assessment tool #1 9736 and the assembled minimally invasive flexibility assessment tool #2 9737, each mated to pedicle screws, in accordance with some embodiments of the invention.

FIG. 97K displays a top view 9755 of the embodiments described previously in relation to FIGS. 97G-97J including the minimally invasive flexibility assessment tool #1 9736 and the assembled minimally invasive flexibility assessment tool #2 9737. FIG. 97L displays a rear view 9760 of the embodiments described previously in relation to FIGS. 97G-97K including the minimally invasive flexibility assessment tool #1 9736 and the assembled minimally invasive flexibility assessment tool #2 9737, each mated to pedicle screws, in accordance with some embodiments of the invention.

Some embodiments of the invention include a rod contour registration system that can be used to enable a measurement a rod's contour prior to implantation. Some embodiments of this invention are related to devices and systems described in relation to FIGS. 47A-47B, 48A-48C, 49A-49D, 50A-50E, 51A-51I, 52A-52D, 53A-53F, 54A-54D, 55A-55I, 56A-56F, 99A-99O, 106A-106F, 115A-115F, as well as processes described in relation to FIGS. 63, 73A-73B, 74-76, 77A-77C, 78, 109A-109D, 112A-112C, 113, and 114A-114F. For example, FIG. 98A illustrates a front view of a rod contour registration system 9800 in accordance with some embodiment of the invention. In some embodiments, the rod contour registration system 9800 comprises a DRF 9801, mounting screw 9802, DRF aligning wall 9803, mounting screw 9804, handle 9805, TMSM (undepressed plunger) 9806, TMSM sliding post 9807, spring tensioning cap 9808, tensioning screw 9809, rod-engaging fork 9810, and a spring-loaded-plunger (undepressed) 9811. In this embodiment, the spring-loaded plunger 9811 is not depressed, and thus the coupled TMSM 9806 is located at or near its baseline location relative to the DRF 9801. In this instance, the system interprets that the tool is in an inactive state, according to processes that include, but are not limited to, those described in relation to FIGS. 63 and 113. In some embodiments, the plunger 9811 is spring-loaded via an internal spring mechanism (not shown) housed under the spring tensioning cap 9808, which applies a tensioning force on the internal spring(s) (not shown), as indicated via the tensioning screw's 9809 relative position along the slot of the spring tensioning cap 9808. In some embodiments, the rod-engaging fork 9810 can enable the device 9800 to be oriented in-line with the cross-section of the rod during tracing the device 9800 along the rod contour. In this embodiment, the device 9800 can position the DRF 9801 and TMSM 9806 a significant distance apart in order to enable the user to comfortably grip the handle 9805 and not obstruct any of the 3D-tracked markers, either on the DRF 9801 or TMSM 9806. Further, this arrangement also helps to avoid the congregation of markers in a congested volume, which tends to enable a higher yield of phantom and occluded 3D-tracked markers. In some embodiments, the handle 9805 can be attached to the DRF aligning wall 9803 mount via a mounting screw 9804 in a modular fashion, but these components can also be manufactured as one component (e.g., can be coupled and/or integral). In some embodiments, the DRF 9801 is substantially rigidly attached to the DRF aligning wall 9803 via a mounting screw 9802, however, these modular components can also be manufactured as one component in some embodiments of the invention.

FIG. 98B illustrates a front view of a rod contour registration system 9815, similar to the system 9800 previously described in relation to FIG. 98A, in accordance with some embodiment of the invention, showing an assembly comprising a TMSM (depressed plunger) 9816, TMSM sliding post (depressed) 9817, and a spring-loaded plunger (depressed) 9818. In some embodiments, the rod contour registration system 9815 can comprise at least some components or assemblies of the previously described system 9800 shown in FIG. 98A. In this embodiment, the spring-loaded plunger 9818 is fully depressed within the rod-engaging fork 9810 and thus the coupled TMSM 9816 is located at or near its active location, via elevation of the coupled TMSM sliding post 9817, relative to the DRF 9801. In this instance, the system can interpret that the tool is in an active state, according to processes that include, but are not limited to, those described in relation to FIGS. 63 and 113 described earlier.

FIG. 98C illustrates a side view of a rod contour registration system 9820, similar to the systems 9800, 9815 previously described in relation to FIGS. 98A-98B, in accordance with some embodiment of the invention, showing an assembly comprising a DRF 9801, mounting screw 9802, spring tensioning cap 9808, tensioning screw 9809, handle 9805, and TMSM 9821. In this embodiment, an example location of the TMSM 9821 illustrates how the actuation of the TMSM 9821 is in-line with the plane of the DRF 9801 relative to the 3D-tracking camera system, and thus this relative location simplifies the trigger state interpretation, according to processes that include, but are not limited to, those described in relation to FIGS. 63 and 113 described earlier.

FIG. 98D illustrates a perspective view of a rod contour registration system 9823, similar to the systems previously described in relation to FIGS. 98A-98C, in accordance with some embodiment of the invention, showing an assembly comprising a compression spring 9824. In some embodiments, the rod contour registration system 9823 can comprise at least some components or assemblies of the previously described system 9800, 9815 shown in FIGS. 98A-98B.

FIGS. 98E-98F illustrates perspective views of a triggering mechanism of a rod contour registration tool as described previously in relation to FIGS. 98A-98D in accordance with some embodiments of the invention. For example, FIG. 98E illustrates a partial perspective view of a rod contour registration system 9826, similar to the systems previously described in relation to FIGS. 98A-98D, in accordance with some embodiment of the invention, showing an assembly comprising a tensioning screw 9809, rod-engaging fork 9810, TMSM (depressed plunger) 9816, and a compression spring 9824. In this embodiment, the TMSM sliding post 9817 is coupled with three symmetrically-spaced compression springs 9824 that facilitate the spring-loaded triggering mechanism of the plunger 9818 while mitigating uneven spring force along the sides of the TMSM sliding post 9817. In other embodiments, there can be one spring that tensions the TMSM sliding post 9817 and/or other features on/in/near the spring that facilitate the smooth and un-twisting movement of the TMSM sliding post 9817 during actuation of the plunger 9818.

FIG. 98F illustrates a perspective view of a rod contour registration system 9828, similar to the systems previously described in relation to FIGS. 98A-98E, showing an assembly comprising a tensioning screw 9809, compression spring 9824, spring-loaded plunger 9829, and a plunger wall 9830. In this embodiment, the plunger wall 9830 is pressed against the receptacle on the top of the rod-engaging fork 9810 until the plunger 9818 is depressed, which compresses the compression springs 9824, against the preset tension initialized via the tensioning screw 9809, and actuates the coupled TMSM (not shown) 9816 on top of the TMSM sliding post 9817 (FIG. 98E).

FIG. 98G illustrates a side view of a rod contour registration system 9835, similar to the systems previously described in relation to FIGS. 98A-98F, in accordance with some embodiment of the invention, showing an assembly comprising a TMSM (depressed plunger) 9816, compression spring 9824, and a spring-loaded plunger 9829. In this embodiment, as the plunger 9829 is depressed, while the spring tensioning cap 9808 is substantially rigidly fixed to the rod-engaging fork 9810 via the tensioning screw 9809, the coupled TMSM 9816 is elevated relative to the spring tensioning cap 9808 top surface, and thus the TMSM 9816 elevates relative to the position of the DRF, and triggers an active state interpretation by the system via processes that include, but are not limited to, those described in relation to FIGS. 63 and 113.

FIG. 98H illustrates a side view of a rod contour registration reference system 9837, similar to the systems previously described in relation to FIGS. 98A-98G, in accordance with some embodiment of the invention. In some embodiments, the rod contour registration reference system 9837 comprises a DRF 9838, including markers 9839a, sliding trigger body (undepressed) 9839, end cap shaft 9840, end cap handle 9841, cam lock lever 9842, trigger tab (undepressed) 9843, and mounting holes 9844. In this embodiment, the end cap tool 9837 is not in an active state as it's trigger tab 9843 is not depressed, and thus the TMSM 9852 is located at or near its baseline location relative to the DRF 9838. In some embodiments, the handle 9841 is a modular component that can be replaced and installed with the end cap shaft 9840 via mounting holes 9844 that contain fasteners (not shown) for rigid fixation. In this embodiment, the sliding trigger body 9839 wraps around the end cap shaft 9840 to ensure that the trigger mechanism does not actuate out of its primary intended axis and remains only vertical during use. In some embodiments, a rod can be inserted into the device and substantially rigidly fixed to end cap shaft 9840 region via a fastened cam lock lever 9842.

FIG. 98I illustrates a side view of a rod contour registration reference system 9846, similar to the systems previously described in relation to FIGS. 98A-98H, in accordance with some embodiment of the invention, showing an assembly comprising a TMSM (depressed) 9847, sliding trigger body (depressed) 9848, and a trigger tab (depressed) 9849. In this embodiment, the device 9846 is in an active state, since the trigger tab 9849 has been depressed, lowering the position of the substantially rigidly attached TMSM 9847 relative to the DRF 9838, in which the system interprets as an active device state, according to processes that include, but are not limited to, those described in relation to FIGS. 63 and 113.

FIG. 98J illustrates a front view of a rod contour registration reference system 9851, similar to the systems previously described in relation to FIGS. 98A-98I, in accordance with some embodiment of the invention. In some embodiments, the rod contour registration reference system 9851 comprises a DRF 9838, sliding trigger body (undepressed) 9839, end cap handle 9841, cam lock lever 9842, trigger tab (undepressed), TMSM (undepressed) 9852, DRF mounting screw 9853, dowel pin 9854, rod-interface receptacle 9855, and a mounting screw 9856. In this embodiment, the device 9851 is in an inactive state because the trigger tab 9843 is not depressed, and consequently the TMSM 9852 is at or near its baseline location relative to the DRF 9838. In some embodiments, the DRF 9838 is a modular component of the system 9851 and can be removed, replaced, or installed via a DRF-mounting screw 9853 and a dowel pin 9854 through the DRF, and linked to the end cap shaft 9840, that restricts the unwanted rotation of the DRF against its predefined geometry relative to the end cap shaft 9840. In some embodiments, a rod can be inserted into the rod-interface receptacle 9855 and substantially rigidly fixed via a fastened cam lock lever 9842 that compresses the tolerance gap out of the receptacle 9855. In some embodiments, where the handle 9841 is a modular component of the system 9851, the handle 9841 can be substantially rigidly engaged with the end cap shaft 9840 via one or more mounting screws 9856.

FIG. 98K illustrates a front view of a rod contour registration reference system 9858, similar to the systems previously described in relation to FIGS. 98A-98J, in accordance with some embodiment of the invention. In some embodiments, the rod contour registration reference system 9858 comprises a DRF 9838, TMSM (depressed) 9847, sliding trigger body (depressed) 9848, and a trigger tab (depressed) 9849. In this embodiment, the system 9858 is in an active trigger state because the trigger tab 9849 is depressed, and consequently the substantially rigidly coupled TMSM 9847 is lowered relative to the DRF 9838. In this instance, the system interprets this modified relative position as a triggering event, according to processes that include, but are not limited to, those described in relation to FIGS. 63 and 113.

FIG. 98L illustrates a side view of a rod contour registration reference system 9860, similar to the systems previously described in relation to FIGS. 98A-98K, in accordance with some embodiment of the invention. In some embodiments, the rod contour registration reference system 9860 comprises a TMSM trigger mount (in an undepressed state) 9861, sliding trigger body (in an undepressed state) 9862, and a trigger tab (in an undepressed state). This embodiment depicts the opposite side of the system 9860 than that depicted in FIG. 98H, and is also classified to be in an inactive state.

FIG. 98M illustrates a side view of a rod contour registration reference system 9865, similar to the systems previously described in relation to FIGS. 98A-98L, in accordance with some embodiment of the invention, showing an assembly comprising a TMSM trigger mount (depressed) 9866, sliding trigger body (depressed) 9867, and a trigger tab (depressed) 9868. This embodiment depicts the opposite side of the system 9860 than that depicted in FIG. 98I, and is also classified to be in an active state.

FIG. 98N illustrates a side cross-sectional view of a rod contour registration reference system 9870, similar to the systems previously described in relation to FIGS. 98A-98M, in accordance with some embodiment of the invention. In some embodiments, the rod contour registration reference system 9870 comprises an end cap shaft 9840, TMSM trigger mount (depressed) 9871, dowel pin 9872, compression spring 9873, trigger-retaining screw 9874, trigger motion-restricting slot 9875, mounting hole 9876, rod-interface receptacle 9877, cam-lever mounting hole 9877a, and a rod-interface depth-stop 9877b. In this non-limiting embodiment, there is a rod-interface depth-stop 9877a within the rod-interfacing receptacle 9855 that provides a rigid wall for the inserted rod to rest against as the cam lock lever is fastened via threads that are tightened through the cam-lever mounting hole 9877b. Further, in this embodiment, the mating interface of the modular handle 9841 and the end cap shaft 9840 are substantially rigidly coupled via fasteners inserted into the mounting holes 9876. Some further embodiments comprise an embedded compression spring 9873 within the end cap shaft 9840 that is compressed via a dowel pin that is substantially rigidly engaged with the TMSM trigger mount 9871. In this instance, when the trigger body is depressed via the actuation of a trigger tab 9863, the TMSM 9852 is lowered as the spring 9873 is compressed, and provides a restoring force when the triggering is completed.

FIG. 98O illustrates a perspective view of a rod contour registration system 9878, similar to the systems previously described in relation to FIGS. 98A-98N, in accordance with some embodiment of the invention. In some embodiments, the rod contour registration system 9878 comprises a rod-equipped end cap 9879 including coupled DRF 9879a with markers 9879b, 30-degree rod-interface receptacle 9880, straight rod 9881, tracked slider 9882 with DRF 9888 including markers 9888a, and TMSM (depressed) 9883. In this embodiment, a straight rod 9881 is substantially rigidly engaged within a 30-degree (downward facing) receptacle 9880. In this embodiment, the straight rod 9881 is subsequently substantially rigidly engaged with the rod-equipped end cap 9879, which provides the reference 3D coordinate system to which the rod contour will be registered relative to, as was previously described in relation to FIGS. 73A-73B, 74-76, 77A-77C, and 78.

In this embodiment, the tracked slider 9882 is tracing along the exterior surface of the rod 9881 in an active trigger state, as indicated by the elevated TMSM 9883, and subsequently registered the 3D contour of the rod. In some embodiments, angled rod-interfacing receptacles (e.g., receptacles with 10, 15, 30-degree declines, relative to the end cap shaft 9840) facilitate robust visualization of both tools (9879, 9882) and their respective DRFs during a tracing acquisition of the contour of a rod with any shape. Further, FIG. 98P illustrates a perspective view of a rod contour registration system 9885, similar to the systems previously described in relation to FIGS. 98A-98O, in accordance with some embodiment of the invention, showing an assembly comprising a rod-equipped end cap (with 30-degree receptacle) 9879, 30-degree rod-interface receptacle 9880, and a tracked slider 9882. This embodiment depicts a front view of the same system 9878 as that in FIG. 98O. Further, FIG. 98Q illustrates a side view of a rod contour registration system 9887, similar to the systems previously described in relation to FIGS. 98A-98P, in accordance with some embodiment of the invention. In some embodiments, the rod contour registration system 9887 comprises a rod-equipped end cap (with 30-degree receptacle) 9879, straight rod 9881, and a tracked slider 9882. This embodiment depicts a side view of the same system 9878 of FIG. 98O.

FIG. 98R illustrates a perspective view of a rod contour registration system 9889, similar to the systems previously described in relation to FIGS. 98A-98Q, in accordance with some embodiment of the invention. In some embodiments, the rod contour registration system 9889 comprises a rod-interface receptacle 9877, straight rod 9881, tracked slider 9882, and a rod-equipped end cap (with 0-degree receptacle) 9890. In this embodiment, a straight rod 9881, substantially rigidly attached to a tracked end cap 9890 can be traced by a tracked slider tool 9882, similar to process as the system 9878 depicted in FIG. 98O. However, in this embodiment, the rod-interface receptacle 9877 does not have a set slope offset away from the end cap shaft 9840. In this embodiment, it can be appreciated that the horizontally-level rod-interface receptacle 9877 can make it more likely for the tracked slider tool 9882 to occlude the tracked end cap 9890 during a tracing acquisition, and thus presents the receptacle with a slope offset as a potential solution for maintaining visualization of all 3D-tracked markers during tracing acquisition of a rod contour, especially if the rod contour is bent into a lordotic (upward) curve.

FIG. 98S illustrates a perspective view of a rod contour registration system 9890, similar to the systems previously described in relation to FIGS. 98A-98R, in accordance with some embodiment of the invention. In some embodiments, the rod contour registration system 9890 can comprise a rod-equipped end cap (30-degree receptacle) 9879, 30-degree rod-interface receptacle 9880, tracked slider 9882, and a curved rod 9891. In this embodiment, the 30-degree rod-interface receptacle 9880 can improve upon the system 9889 depicted in FIG. 98R in which the curved rod contour 9891 can be robustly traced while maintaining a similar visualization of both tools (9882, 9879) relative to a nearby 3D-tracking camera system, as demonstrated in an example embodiment in FIG. 98R.

FIG. 98T illustrates a rear perspective view of a rod contour registration system 9892, similar to the systems previously described in relation to FIGS. 98A-98S. Some embodiments include a rod contour registration system 9892 comprising a DRF 9893 and a DRF-mounting post 9894 coupled to a handle (e.g., similar to or the same as handle 9805 described earlier). In this embodiment, the modular DRF 9893 can be removed from the DRF-mounting post 9894, and can be re-engaged in the opposing direction, as depicted in an example embodiment in FIG. 98U. In this embodiment, the system 9892 can be used in the user's right hand, while the end cap tool 9879 is held in the left hand. In some embodiments, the system 9892 automatically detects the orientation of the TMSM 9883 relative to the DRF 9893 according to processes that include, but are not limited to, those described in relation to FIGS. 112 and 113.

FIG. 98U illustrates a rear perspective view of a rod contour registration system 9895, similar to the systems previously described in relation to FIGS. 98A-98T. In some embodiments, the rod contour registration system 9895 comprises a DRF 9893 and a DRF-mounting post 9894. In this embodiment, the modular DRF 9893 has been positioned in the opposing direction, as the direction that was depicted previously in an example embodiment in FIG. 98T. Further, FIG. 98V illustrates a rear perspective view of a rod contour registration system 9897, similar to the systems previously described in relation to FIGS. 98A-98U, in accordance with some embodiment of the invention. In some embodiments, the rod contour registration system 9897 comprises a DRF 9893. In this embodiment, the DRF 9893 can be repositioned and re-installed on the DRF-mounting post 9894 (FIG. 98U). In this embodiment, the tracked slider system 9897 can be used in the user's left hand, while the end cap tool 9879 is held in the right hand.

Some embodiments of the invention include a rod contour registration system that is coupled to a rod bending system to enable contouring and/or registration of a rod implant. Some embodiments of this invention are similar to devices and systems described in relation to FIGS. 47-57, 98, 106, and 115, as well as processes described in relation to FIGS. 63, 73A-73B, 74-76, 77A-77C, 78, 79A-79G, 80-81, 87A-87K, 88A-88F, 109A-109D, 112A-112C, 113, and 114A-114F. For example, FIG. 99A illustrates a front view of a rod contour registration system 9900 in accordance with some embodiments of the invention. In some embodiments, the rod contour registration system 9900 comprises one or more mounting screws 9901, and/or DRF aligning wall 9902, and/or DRF 9903, and/or mounting screw 9904, and/or trigger extension arm 9905, and/or TMSM 9906 (shown in an undepressed condition), and/or TMSM sliding post 9907 (shown in an undepressed condition), and/or spring tensioning cap 9908, and/or tensioning screw 9909, and/or rod-engaging fork 9910, and/or a spring-loaded plunger 9911 (shown in an undepressed condition). In this embodiment, the TMSM 9906 is in an inactive state because the spring-loaded plunger 9911 is undepressed, and thus the TMSM 9906 is located at or near its baseline position relative to the DRF 9903. In some embodiments, the DRF 9903 is modular, and can be removed as well as substantially rigidly attached to the rod contour registration device via the DRF aligning wall 9902 mount. In some embodiments, the mounting screws 9901 can substantially rigidly attach the rod contour registration system 9900 to another tool, such as a rod bender. In some embodiments, the TMSM 9906 is spring-loaded using a sub-assembly mechanism similar to those depicted previously in relation to FIGS. 98D-98G.

FIG. 99B illustrates a front view of a rod contour registration system 9915, similar to rod contour registration system 9900 (and using some similar or same components of the system 9900), in accordance with some embodiment of the invention. In some embodiments, the rod contour registration system 9915 can comprise a spring-loaded plunger 9916 (shown in a depressed state), and/or a TMSM sliding post 9917 (shown in a depressed state), and/or a TMSM 9918 (shown in a depressed state). In this embodiment, the system 9915 is in an active state as the spring-loaded plunger 9916 is in a fully depressed state, and the associated TMSM 9918 is actuated into an active position relative to its baseline position, relative to the DRF 9903.

FIG. 99C illustrates a perspective view of a rod contour registration system 9920, similar to the systems previously described in relation to FIGS. 99A-99B, and using some similar or same components, in accordance with some embodiment of the invention. For example, as illustrated, in some embodiments, the rod contour registration system 9920 comprises a mounting screw 9901, and/or a DRF 9903, and/or a mounting screw 9904, and/or a trigger extension arm 9905, and/or a TMSM 9906 (shown in an undepressed condition), and/or a tensioning screw 9909, and/or a rod-engaging fork 9910.

FIG. 99D illustrates a side view of a rod contour registration system 9925, similar to the systems previously described in relation to FIGS. 99A-99C, and using some similar or same components, in accordance with some embodiment of the invention. For example, in some embodiments, the rod contour registration system 9925 comprises a mounting screw 9901, and/or DRF aligning wall 9902, and/or trigger extension arm 9905, and/or spring tensioning cap 9908, and/or tensioning screw 9909, and/or a rod-engaging fork 9910. In this embodiment, the TMSM 9906 is in-line with the DRF 9903, and thus facilitates simplified processing by the system to interpret the trigger state.

FIG. 99E illustrates a front view of a rod contour registration system 9927, similar to the systems previously described in relation to FIGS. 99A-99D, and using some similar or same components, in accordance with some embodiment of the invention. In some embodiments, the rod contour registration system 9927 comprises a tracked-slider-equipped rod bender 9928, and/or a spring-loaded plunger 9929 (shown in an undepressed state), and/or a TMSM 9930 (shown in an undepressed state), and a mounting screw 9931. In this embodiment, the rod contour registration system 9925, as depicted previously in relation to FIG. 99D, is substantially rigidly coupled to a rod bender 9928 via mounting screws 9931. In other embodiments, the rod contour registration system 9925 can be a built-in or integrated with the rod bender 9928, and may not require any attachment processes. In this embodiment, the spring-loaded plunger 9929 is undepressed, and thus the system 9927 is in an inactive tracing state.

FIG. 99F illustrates a front view of a rod contour registration system 9933, similar to the systems previously described in relation to FIGS. 99A-99E, and using some similar or same components, in accordance with some embodiment of the invention. Some embodiments comprise a rod contour registration system 9933 including a tracked-slider-equipped rod bender 9928, and/or a mounting screw 9931, and/or a spring-loaded plunger (shown in a depressed state) 9934, and/or a TMSM 9935 (shown in a depressed state). In this embodiment, the spring-loaded plunger 9934 is depressed, and thus the rod contour registration system 9933 is in an active tracing state, as illustrated by the actuated position of the TMSM 9935 relative to its baseline location (e.g., as further illustrated in FIG. 99E), relative to the DRF 9903.

FIG. 99G illustrates a perspective view of a rod contour registration system 9937, similar to the systems previously described in relation to FIGS. 99A-99F, and using some similar or same components. In some embodiments, the rod contour registration system 9937 includes a tracked-slider-equipped rod bender 9928, and/or spring-loaded plunger 9929 (shown in an undepressed state), and/or TMSM 9930 (shown in an undepressed state), and/or mounting screws 9931. This embodiment also provides an oblique perspective to the system depicted previously in relation to FIG. 99E, which depicts an embodiment of an inactive system.

FIG. 99H illustrates a perspective view of a rod contour registration system 9940, similar to the systems previously described in relation to FIGS. 99A-99G and using some similar or same components, in accordance with some embodiment of the invention. In some embodiments, the rod contour registration system 9940 can comprise a tracked-slider-equipped rod bender 9928, and/or a TMSM 9935 (shown in a depressed state). This embodiment also provides an oblique perspective to the system depicted previously in relation to FIG. 99F, which depicts an embodiment of an active system.

FIG. 99I illustrates a side view of a rod contour registration system 9942, similar to the systems previously described in relation to FIGS. 99A-99H, and using some similar or same components, in accordance with some embodiment of the invention. Some embodiments comprise a rod contour registration system 9942 including a spring tensioning cap 9908, and/or tensioning screw 9909, and/or rod-engaging fork 9910, and/or tracked-slider-equipped rod bender 9928, and/or TMSM (undepressed) 9930, and/or mounting screw 9931, and/or center rod-contouring surface 9944, and/or a left outer roller 9952. This embodiment provides a side perspective of the system depicted previously in relation to FIG. 99E, which depicts an example inactive system. In this embodiment, the tracked slider-equipped rod bender 9928 handles can be grasped by the user and the bending surfaces (9952, 9944) can be fully accessed while still providing the system with the ability to trace the contour of a rod via the slider attachment (e.g., FIG. 99D).

FIG. 99J illustrates a side view of a rod contour registration system 9946, similar to the systems previously described in relation to FIGS. 99A-99I, and using some similar or same components, in accordance with some embodiment of the invention. In some embodiments, the rod contour registration system 9946 can comprise a TMSM sliding post 9947 (shown in a depressed state). This embodiment illustrates a side perspective to the system depicted previously in relation to FIG. 99F, which depicts an example active system.

FIG. 99K illustrates a perspective view of a rod contouring system 9949, similar to the systems previously described in relation to FIGS. 99A-99J, and using some similar or same components, in accordance with some embodiment of the invention. Some embodiments include a rod contouring system 9949 comprising a right outer roller 9943, and/or a center rod-contouring surface 9944, and/or a rod 9950, and/or a tracked-slider-equipped rod bender 9951, and/or a left outer roller 9952, and/or a rod-equipped tracked end cap 9953. In this embodiment, the tracked-slider-equipped rod bender 9951 demonstrates how the contouring surfaces (9943, 9952, 9944) can be fully accessible for contouring a rod while the tracked slider attachment is engaged, and not actively utilized with the bender 9951. In some embodiments, a rod 9950 can be attached into a tracked end cap 9953, and then contoured by the tracked-slider-equipped rod bender 9951 until the user is ready to register the contour of the adjusted rod 9950. In some embodiments, the system (e.g., rod contour registration system 9942 of FIG. 99I) can be oriented to enable the rod-engaging fork of the slider attachment to trace the rod contour with respect to the tracked end cap 9953. An example embodiment of these two primary processes is depicted below in reference to FIG. 99L (rod contouring mode) and FIG. 99M (rod tracing mode).

FIG. 99L illustrates a perspective view of a rod contouring system 9955, similar to the systems previously described in relation to FIGS. 99A-99K, and using some similar or same components, in accordance with some embodiment of the invention. In some embodiments, the rod contouring system 9955 comprises a rod 9950, tracked-slider-equipped rod bender 9951, and a rod-equipped tracked end cap 9953.

FIG. 99M illustrates a perspective view of a rod contour registration system 9960, similar to the systems previously described in relation to FIGS. 99A-99L, and using some similar or same components, in accordance with some embodiment of the invention. Some embodiments comprise a rod contour registration system 9960 including a rod-equipped tracked end cap 9953, tracked-slider-equipped rod bender 9961, rod-engaging fork 9962, TMSM 9963 (shown in a depressed state), and a rod 9964. In this embodiment, the sliding attachment is fully engaged with the rod 9964, and the plunger is fully depressed (i.e., within the rod-engaging fork 9962), which actuates the TMSM 9963 to an active position relative to DRF 9903. In this embodiment, a rod-interfacing receptacle with a slope offset, relative to the end cap shaft, is depicted, as was previously shown in relation to FIGS. 98O-98Q and 98S.

FIG. 99N illustrates a perspective view of a rod contour registration system 9970, similar to the systems previously described in relation to FIGS. 99A-99M, and using some similar or same components, in accordance with some embodiment of the invention. In some embodiments, the rod contour registration system 9970 shows an assembly comprising a rod-equipped tracked end cap 9953 and a tracked-slider-equipped rod bender 9961.

FIG. 99O illustrates a side view of a rod contour registration system 9980, similar to the systems previously described in relation to FIGS. 99A-99N, and using some similar or same components, in accordance with some embodiment of the invention, showing an assembly comprising a rod-equipped tracked end cap 9953, tracked-slider-equipped rod bender 9961, and a rod-engaging fork 9962. In this embodiment, the system 9960 previously depicted in relation to FIG. 99M is shown from a side view perspective to appreciate the robust visualization of both the tracked end cap and the tracked-slider-equipped rod bender tools, and their respective DRFs, with respect to the 3D-tracked camera system during a rod tracing acquisition.

Some embodiments of the invention include a selective-triggering probe system that is able to selectively signal to a 3D-tracking camera system when it is in an "active" and/or "inactive" binary state, and/or analog states in between those two boundaries via a rotational triggering mechanism. Some embodiments of this invention are related to devices and systems described in relation to FIGS. 10A-10G, 14A-14C, 15A-15C, 91A-91C, and 101A-101Q, as well as processes described in relation to FIGS. 24-26, 27A-27D, 28A, 58-61, 62A-62D, 63, 64A-64B, 65A-65E, 66A-66B, 67-69, 82A-82B, 83, 84A-84B, 85, and 113.

FIG. 100A illustrates a rear view of a selective-triggering probe system 10000 in accordance with some embodiment of the invention. In some embodiments, the selective-triggering probe system 10000 comprises a probe shaft 10001, and/or a trigger tab 10002 (shown in an undepressed state), and/or a DRF 10003, and/or a spring-loaded TMSM 10004 (showing an undepressed trigger). Further, in some embodiments, the selective-triggering probe system 10000 further comprises a torsion spring 10005, and/or a mounting screw 10006, and/or a torsion spring side wall 10007, and/or a rotating trigger arm 10008 (shown undepressed). In this non-limiting embodiment, the trigger tab 10002 is undepressed and the probe is thus in an active state due to the spring-loaded TMSM 10004 positioned at or near its baseline location relative to the DRF 10003. In this embodiment, the TMSM 10004 is tensioned via the torsion spring 10005 that is substantially rigidly attached to the TMSM mount and the probe shaft via a mounting screw 10006. Further, in some embodiments, the torsion spring side walls 10007 can restrict the torsion spring probe-engaged arm to remain substantially rigidly fixed as the TMSM moves the opposing spring arm, which creates a restoring spring force as the trigger tab 10002 is depressed. In some embodiments, the dynamic position of the TMSM 10004 is monitored relative to the probe's DRF 10003, and interpreted into a trigger state via processes that include, but are not limited to, those shown and described in FIGS. 63 and 113.

FIG. 100B illustrates a side view of a selective-triggering probe system 10010, similar to the systems previously described in relation to FIG. 100A, and using some similar or same components, in accordance with some embodiment of the invention. In some embodiments, the selective-triggering probe system 10010 comprises a probe shaft 10001, and/or trigger tab 10002 (shown undepressed), and/or mounting screw 10006, and/or mounting screw 10011, and/or slot for trigger tab 10012, and/or a finger rest 10013. In some embodiments, the user can grip the probe 10010 via the finger rest 10013, and actuate the trigger tab 10002 via one of their fingers. In some embodiments, as the trigger tab 10002 is depressed, the TMSM 10004, (which is mounted on an arm that is a rigid extension of the rotating trigger arm 10008), can be actuated in a concentric arc pathway in which the smaller arm extension of the trigger arm 10008 matches the angular displacement of the larger arm via depression of the trigger tab 10002. In this embodiment, the trigger tab 10002 can travel through a slot 10012 through the finger rest 10013. In some embodiments, the DRF 10003 can be substantially rigidly attached to the probe shaft 10001 via the engagement of a mounting screw 10011, while the torsion spring and rotating trigger arm are held in place (i.e., vertical distance from probe shaft 10001) via another mounting screw 10006.

FIG. 100C illustrates a front view of a selective-triggering probe system 10020, similar to the systems previously described in relation to FIGS. 100A-100B, and using some similar or same components, in accordance with some embodiment of the invention. Some embodiments include a selective-triggering probe system 10020 comprising a DRF 10003, and/or spring-loaded TMSM (undepressed trigger) 10004, and/or mounting screw 10011, and/or a DRF-aligning mount 10021. In some embodiments, the DRF 10003 is inserted into the DRF-aligning mount 10021, enabling rigid fixation of the DRF 10003 in a manner that resists its displacement and/or rotation with respect to the probe (probe shaft 10001). In some embodiments, the DRF 10003 can be substantially rigidly attached to the probe shaft 10001 via a mounting screw 10011. In this embodiment, the TMSM 10004 is in an inactive trigger position as the trigger tab 10002 is undepressed.

FIG. 100D illustrates a rear view of a selective-triggering probe system 10030, similar to the systems previously described in relation to FIGS. 100A-C, and using some similar or same components, in accordance with some embodiment of the invention. In some embodiments, the selective-triggering probe system 10030 comprises a DRF 10003, probe shaft 10031, trigger tab (depressed) 10032, and a rotating trigger arm (depressed) 10033. In this embodiment, the TMSM 10004 is in an active trigger position as the trigger tab 10032 is fully depressed, which rotates the trigger arm 10033 to a position that rotates the substantially rigidly coupled TMSM 10004 towards an active position relative to the DRF 10004. In other embodiments, the rotating trigger arm 10033 can also be fully enclosed within a sheath that is substantially rigidly attached to the probe shaft 10031 to enable the trigger arm 10033 to not be obstructed in its actuation by any external forces (e.g., user hand, gloves, bodily tissue and fluids, etc.)

FIG. 100E illustrates a side view of a selective-triggering probe system 10040, similar to the systems previously described in relation to FIGS. 100A-D, and using some similar or same components, in accordance with some embodiment of the invention. In this embodiment, the TMSM 10004 is in an active trigger position as the trigger tab 10032, and is fully depressed and inaccessible for further actuation while inside the slot 10012 inside the probe shaft 10001.

FIG. 100F illustrates a front view of a selective-triggering probe system 10050, similar to the systems previously described in relation to FIGS. 100A-E, and using some similar or same components, in accordance with some embodiment of the invention. Some embodiments include a selective-triggering probe system 10050, and/or a trigger tab 10032 (shown depressed), and/or a TMSM 10051 (shown with depressed trigger). In this embodiment, the TMSM 10051 is in an active trigger position as the trigger tab 10032 is fully depressed, which rotates the trigger arm 10033 to a position that rotates the substantially rigidly coupled TMSM 10051 to the left with respect to the DRF 10004. This rotation comprises an arc pathway defined by the radius of the trigger arm's upper extension coupled to the TMSM 10051.

Some embodiments of the invention include a selective-triggering probe system that is able to selectively signal to a 3D-tracking camera system when it is in an "active" and/or "inactive" binary state, and/or analog states in between those two boundaries via a linear triggering mechanism. In some embodiments, the probe can be configured for a left-hand-dominant or right-hand-dominant user. Some embodiments of this invention are related to devices and systems described in relation to FIGS. 10, 14, 15, 91, and 100, as well as processes described in relation to FIGS. 24-26, 27A-27D, 28A-28B, 58-61, 62A-62D, 63, 64A-64B, 65A-65E, 66A-66B, 67-69, 82A-82B, 83, 84A-84B, 85, and 113.

FIG. 101A illustrates a front view of a selective-triggering probe system 10100 in accordance with some embodiment of the invention, showing an assembly comprising a probe shaft 10101, and/or a trigger sleeve 10102, and/or trigger 10103 (shown in an undepressed state), and/or dowel pin 10104, and/or quick-release pin 10105, and/or DRF 10106, and/or TMSM 10107 (showing undepressed trigger), and/or TMSM sliding mount 10108 (showing undepressed trigger), and/or TMSM sliding mount backing 10109, and/or DRF mount 10110, and/or a mounting screw 10111. In this embodiment, the trigger 10103 is undepressed, and the probe is thus in an inactive state due to the TMSM 10107 positioned at or near its baseline location relative to the DRF 10106. In some embodiments, the boundaries of TMSM sliding mount backing 10109 depict the full possible range of motion of the probe's TMSM 10107. In some embodiments, the trigger sleeve 10102 encloses the internal trigger mechanism (not shown) and enables for the trigger mechanism to bias to one side, depending on the user's dominant hand preference. In some embodiments, the trigger sleeve 10102 can be substantially rigidly engaged with the probe shaft 10101 via quick-release pin 10105 that enters the trigger sleeve 10102 and substantially rigidly fixates to the probe shaft 10101. In this embodiment, when the quick-release pin 10105 is removed, the trigger sleeve 10102 can be removed, reversed in its orientation relative to the probe shaft 10101, and then re-engaged by re-inserting the quick-release pin 10105. In some embodiments, the trigger 10103 rotates about a dowel pin 10104 within the trigger sleeve 10102, and enables for controlled triggering actuations by the user and/or system.

FIG. 101B illustrates a front view of a selective-triggering probe system 10115, similar to the systems previously described in relation to FIG. 101A, and using some similar or same components, in accordance with some embodiment of the invention. Some embodiments include a selective-triggering probe system 10115 comprising a trigger (depressed) 10116, and/or spring-loaded sliding shaft 10117, and/or TMSM 10118 (depressed trigger), and/or a TMSM sliding mount 10119 (depressed trigger). In this embodiment, the trigger 10116 can be fully depressed against the internal trigger mechanism (not shown), which elevates the position of the TMSM 10118 on the TMSM sliding mount backing 10119, and reaches a position relative to the DRF 10106 that signals to the system that the probe is in an active trigger state.

FIG. 101C illustrates a rear view of a selective-triggering probe system 10125, similar to the systems previously described in relation to FIGS. 101A-101B, and using some similar or same components, in accordance with some embodiment of the invention. In some embodiments, the selective-triggering probe system 10125 can comprise a trigger 10103 (undepressed), and/or a dowel pin 10104, and/or a quick-release pin 10105, and/or a back cover mounting screw 10126, and/or a back cover 1027. In some embodiments, the back cover 10127 can house the spring system (not shown) for the probe's internal sliding shaft (not shown). In some embodiments, the back cover mounting screw 10126 can substantially rigidly attach the back cover 10127 to the probe shaft 10101, and can also provide a point of fixation for one end of the spring (not shown), to which the other end is substantially rigidly attached to the TMSM sliding mount backing 10119. Further, FIG. 101D illustrates a rear view of a selective-triggering probe system 10130, similar to the systems previously described in relation to FIGS. 101A-C, and using some similar or same components, in accordance with some embodiment of the invention, showing an assembly comprising a trigger (depressed) 10116.

FIG. 101E illustrates a front cross-sectional view of a selective-triggering probe system 10135, similar to the systems previously described in relation to FIGS. 101A-101D, and using some similar or same components, in accordance with some embodiment of the invention. In some embodiments, the selective-triggering probe system 10135 can comprise a trigger 10103 (shown undepressed), and/or a dowel pin 10104, and/or a quick-release pin 10105, and/or a TMSM sliding mount backing 10109, and/or a dowel pin 10136, and/or a two-link arm (lower link: undepressed trigger) 10137, and/or a dowel pin 10138, and/or a two-link arm (upper link: undepressed trigger) 10139, and/or a spring-loaded sliding shaft (undepressed trigger) 10140, and/or a TMSM mount (undepressed trigger) 10141. In this embodiment, the trigger 10103 is not depressed, and thus the probe is in an inactive trigger state. Further, a non-limiting example embodiment of the internal triggering mechanism is depicted to demonstrate its baseline position against an undepressed trigger 10103. In some embodiments, the two-link arm (lower link: undepressed trigger) 10137 can be fixed at one end relative to the probe shaft 10101 via the lower dowel pin 10136, with the other end of the two-link arm attached to the second two-link arm (upper link: undepressed trigger) 10139 via an intersecting dowel pin 10138. In this embodiment, the upper end of the second two-link arm (upper link: undepressed trigger) 10139 can be linked to the spring-loaded sliding shaft 10140 via an intersecting dowel pin 10138. Further, in this embodiment, the spring-loaded sliding shaft 10140 can be substantially rigidly attached to the TMSM mount 10141, and thus when the trigger 10103 actuates the two-link arm system and elevates the position of the spring-loaded sliding shaft 10140, the TMSM 10107 on the TMSM mount 10141 can be positioned away from the DRF, which signals to the system that the probe is transitioning to an active trigger state.

FIG. 101F illustrates a front cross-sectional view of a selective-triggering probe system 10145, similar to the systems previously described in relation to FIGS. 101A-101E, and using some similar or same components, in accordance with some embodiment of the invention. In some embodiments, the selective-triggering probe system 10145 can comprise a trigger (depressed) 10116, and/or two-link arm (lower link: depressed trigger) 10146, and/or two-link arm (upper link: depressed trigger) 10147, and/or spring-loaded sliding shaft (depressed trigger) 10148, and/or a TMSM mount (depressed trigger) 10149. In this embodiment, the trigger 10116 can be fully depressed against the lower two-link arm 10146, which straightens out to extend the position of the upper two-link arm 10147, and consequently can elevate the position of the spring-loaded sliding shaft 10148, which is substantially rigidly fixed to a TMSM 10118 on a TMSM mount 10149. In some embodiments, this position of the TMSM 10118 relative to the fixed DRF (not shown) is interpreted by the system to signal an "active" state for the probe trigger.

FIG. 101G illustrates a front perspective view of a selective-triggering probe system 10155, similar to the systems previously described in relation to FIGS. 101A-101F, and using some similar or same components, in accordance with some embodiment of the invention. Some embodiments comprise a selective-triggering probe system 10155 comprising a quick-release pin 10105, DRF 10106, TMSM (undepressed trigger) 10107, TMSM sliding mount backing 10109, two-link arm (lower link: undepressed trigger) 10137, two-link arm (upper link: undepressed trigger), and a dowel-loading access slot 10156. In this embodiment, the two-link arms (10137, 1039) are restricted in their vertical range of motion during actuation via a defined dowel-loading access slot 10156, in which the triggering process elevates the position of the dowel 10138 relative to the slot 10156.

FIG. 101H illustrates a rear perspective view of a selective-triggering probe system 10160, similar to the systems previously described in relation to FIGS. 101A-101G, and using some similar or same components, in accordance with some embodiment of the invention. Some embodiments comprise a selective-triggering probe system 10160 including a dowel pin 10161, and/or back cover aligning extrusion 10162, and/or mounting screw 10163, and/or compression spring 10164, and/or a mounting screw for spring 10165. In this embodiment, the dowel pin 10161 (previously 10136) of the lower two-link arm is fixed to the probe shaft 10101, enabling the actuation of the trigger to elevate the spring-loaded sliding shaft away from the probe tip, and against the compression spring, and thus subsequently elevating the position of the TMSM 10107 relative to the DRF 10106. In some embodiments, the enclosed compression spring 10164 is fixed at one end by the mounting screw (previously 10126) and attached to a mobile mounting screw 10165 that is attached to the spring-loaded sliding shaft 10148 via the TMSM mount 10149, allowing the spring 10164 to extend during actuation.

FIG. 101I illustrates a side view of a selective-triggering probe system 10170, similar to the systems previously described in relation to FIGS. 101A-101H, and using some similar or same components, in accordance with some embodiment of the invention. In this embodiment, the trigger is not depressed, and thus the TMSM is not offset from its baseline, inactive position relative to the DRF. Further, FIG. 101J illustrates a side view of a selective-triggering probe system 10175, similar to the systems previously described in relation to FIGS. 101A-101I, and using some similar or same components, in accordance with some embodiment of the invention. In this embodiment, the trigger is depressed, the TMSM is fully offset from its baseline, inactive position relative to the DRF, and the TMSM is thus in an active trigger state.

FIG. 101K illustrates an assembly view of a selective-triggering probe system 10176, similar to the systems previously described in relation to FIGS. 101A-101J, in accordance with some embodiment of the invention, showing an assembly comprising a two-link arm (lower arm) 10177, and/or two-link arm (upper arm) 10178, and/or spring-loaded sliding shaft 10179, and/or TMSM 10180, and/or trigger sleeve 10181, and/or a trigger 10182.

FIGS. 101L-101O illustrate perspective views of a trigger sleeve of a 3D-tracked tool with a linear triggering mechanism as described previously in relation to FIGS. 101A-101K in accordance with some embodiments of the invention. For example, FIG. 101L illustrates an end view of a probe cover system 10183, similar to the systems previously described in relation to FIGS. 101A-101K, in accordance with some embodiment of the invention, showing an assembly comprising a channel for probe shaft 10184. In this embodiment, the channel for the probe shaft 10184 represents a geometric cutout that matches the exterior surface outline of the probe shaft's cross-section. In other embodiments, this channel can embody any shaft that enables the trigger sleeve to be engaged and removed from the probe shaft.

Further, FIG. 101M illustrates a perspective view of a probe cover system 10185, similar to the systems previously described in relation to FIGS. 101A-101L, in accordance with some embodiment of the invention. In some embodiments, the probe cover system 10185 includes a hole for dowel pin 10186 and a hole for quick release 10187. In some embodiments, the quick-release pin 10105 can be inserted through the hole 10187 on the trigger sleeve 10181. In some embodiments, the dowel pin 10104 for the trigger is inserted through another hole 10186 on the trigger sleeve (e.g., such as trigger sleeve 10181.) Further, FIG. 101N illustrates a perspective view of a probe cover system 10188, similar to the systems previously described in relation to FIGS. 101A-101M, in accordance with some embodiment of the invention, showing an assembly comprising a slot for trigger 10189. In some embodiments, the trigger 10182 is inserted in and is restricted within the slot 10189 within the trigger sleeve 10181. Further, FIG. 101O illustrates a perspective view of a probe cover system 10190, similar to the systems previously described in relation to FIGS. 101A-101N.

FIG. 101P illustrates an assembly view of a selective-triggering probe system 10191, similar to the systems previously described in relation to FIGS. 101A-101O, and using some similar or same components, in accordance with some embodiment of the invention. In some embodiments, the selective-triggering probe system 10191 comprises a left-hand dominant probe configuration 10192 and a left-hand dominant trigger configuration 10193. In this embodiment, the trigger sleeve 10193 is oriented for left-hand dominant trigger configuration, in which the accompanying probe configuration 10192 of the internal trigger mechanism is positioned to have a bias in its range of motion towards the probe's left side.

FIG. 101Q illustrates an assembly view of a selective-triggering probe system 10195, similar to the systems previously described in relation to FIGS. 101A-101P, in accordance with some embodiment of the invention. Some embodiments comprise a selective-triggering probe system 10195 comprising a right-hand dominant probe configuration 10196 and a right-hand dominant trigger configuration 10197. In this embodiment, the trigger sleeve 10197 can be oriented for right-hand dominant trigger configuration, in which the accompanying probe configuration 10196 of the internal trigger mechanism is positioned to have a bias in its range of motion towards the probe's right side.

Some embodiments of the invention include a fiducial-registration probe system that can mate with a fiducial that has an outer, embedded depth-stop mating interface and register the position and orientation of the fiducial with respect to a 3D-tracking camera system. In this embodiment, the user can mate the probe with the patterned interface within the fiducial, and when the probe is fully engaged with the fiducial interface, an internal spring-loaded depressible sliding shaft can actuate a TMSM relative to a fixed DRF mounted on the probe to trigger a registration event to the system. In other embodiments, the trigger mechanism of the probe can be actuated by the user, instead of by the successful mating of the probe with the fiducial, via systems that include, but are not limited to, those depicted previously in relation to FIGS. 95A-95I, 98A-98V, etc. Some embodiments of this invention are related to devices and systems described in relation to FIGS. 3A-3C, 10A-10G, 14A-14C, 15A-15C, 29A-29D, 33A-33G, 38A-38G, 44A-44D, 45A-45B, 91A-91C, 101A-101Q, 103A-103Q, 104A-104J, and 106A-106F, as well as processes described in relation to FIGS. 58-60, 62A-62D, 63, 64A-64B, 65A-65E, 66A-66B, 68-69, 72, and 113

FIG. 102A illustrates a front view of a fiducial-registration probe system 10200 in accordance with some embodiment of the invention, showing an assembly comprising a bone fiducial screw threading 10201, and/or probe mating region 10202, and/or probe shaft 10203, and/or TMSM 10204, and/or mounting screw 10205, and/or a DRF 10206. In this embodiment, the probe is fully engaged with the bone fiducial, and thus the TMSM 10204 is elevated to an active triggering state. Further, FIG. 102B illustrates a rear view of a fiducial-registration probe system 10210, similar to the systems previously described in relation to FIG. 102A, and using some similar or same components, in accordance with some embodiment of the invention. In some embodiments, the fiducial-registration probe system 10210a comprises a probe shaft 10203, and/or TMSM 10204, and/or DRF 10206, and/or TMSM sliding post 10211, and/or trigger retaining screw 10212, and/or a trigger motion-restricting slot. In this embodiment, the spring-loaded trigger mechanism (not shown) is housed within the TMSM sliding post 10211. Further, the spring-loaded trigger mechanism is restricted in its range of motion of triggering via a trigger-retaining screw 10212 fastened against the probe shaft 10203 within the trigger motion-restricting slot 10213, which is a component of the TMSM sliding post 10211. Further, FIG. 102C illustrates a side view of a fiducial-registration probe system 10215, similar to the systems previously described in relation to FIGS. 102A-102B, and using some similar or same components, in accordance with some embodiment of the invention.

FIG. 102D illustrates an assembly view of a fiducial-registration probe system 10220, similar to the systems previously described in relation to FIGS. 102A-102C, and using some similar or same components, in accordance with some embodiment of the invention. In some embodiments, the fiducial-registration probe system 10220 comprises assembly comprising a probe shaft 10203, and/or DRF 10206, TMSM 10221 (undepressed), and/or TMSM sliding post 10222, and/or mating groove 10223, and/or a flat mating surface 10224. In this embodiment, the probe is not engaged with the bone fiducial mating features (10223, 10224), and thus the TMSM 10221 is not in an active triggering state.

FIG. 102E illustrates a side assembly view of a fiducial-registration probe system 10225, similar to the systems previously described in relation to FIGS. 102A-102D, and using some similar or same components, in accordance with some embodiment of the invention, showing an assembly comprising a mating groove 10223. FIG. 102F illustrates a front assembly view of a fiducial-registration probe system 10226, similar to the systems previously described in relation to FIGS. 102A-102E, and using some similar or same components, in accordance with some embodiment of the invention. In some embodiments, the fiducial-registration probe system 10226 comprises a DRF 10206, and/or TMSM 10221 (in an undepressed state), and/or a dowel pin 10227. In some embodiments, the DRF 10206 can be restricted from rotational movement via the insertion of a dowel pin 10227 through the DRF 10206 and substantially rigidly fixed to the probe shaft 10203. In other embodiments, the DRF 10206 can be manufactured as one component with the probe shaft 10203, and does not need a rotation-preventing dowel pin 10227.

FIG. 102G illustrates a perspective view of a bone fiducial screw system 10230, similar to the systems previously described in relation to FIGS. 102A-102F, and using some similar or same components, in accordance with some embodiment of the invention. Some embodiments comprise a bone fiducial screw system 10230 comprising a bone fiducial screw threading 10231, and/or mating groove 10232, and/or screw head 10233, and/or access hole for drive 10234, and/or a flat mating surface 10235. In some embodiments, the bone fiducial mating features (10232, 10235) can enable the fiducial to be mated and registered by a probe (e.g., as depicted previously in relation to FIG. 102A) in only one unique orientation. In this instance, the mating features of the probe and fiducial must be aligned and fully engaged for the mating system to actuate the probe's internal depressible spring-loaded plunger (not shown) and trigger the attached TMSM (not shown) towards an active trigger state. In some embodiments, multiple mating grooves 10232 are implemented on the bone fiducial to facilitate a rigid mating interface that mitigates any unnecessary rotations.

FIG. 102H illustrates a side view of a bone fiducial screw system 10238, similar to the systems previously described in relation to FIGS. 102A-102G, and using some similar or same components, in accordance with some embodiment of the invention. Some embodiments include a bone fiducial screw system 10238 comprising a mating groove 10232 and traction spikes 10239. In some embodiments, the bone fiducial screw system 10238, or similar surfaces that interface with the anatomy of interest, can include features such as a series of traction spikes 10239 that can aid in the rigid fixation of the bone fiducial screw system 10238 with the surface of the screw-engaged anatomy. In some embodiments, when the bone fiducial screw is fully engaged with the anatomy of interest, then the mating fiducial attachment and screw head 10233 are pressed against each other and become completely rigid as one component, to which the probe then mates and registers the fiducial's location and orientation.

FIG. 102I illustrates a perspective view of a bone fiducial screw system 10241, similar to the systems previously described in relation to FIGS. 102A-102H, and using some similar or same components, in accordance with some embodiment of the invention, showing an assembly comprising a mating groove 10232. Further, FIG. 102J illustrates a top view of a bone fiducial screw system 10245, similar to the systems previously described in relation to FIGS. 102A-102I, and using some similar or same components, in accordance with some embodiment of the invention, showing an assembly comprising a mating groove 10232, screw head 10233, and a flat mating surface 10235. Further, FIG. 102K illustrates a side view of a bone fiducial screw system 10247, similar to the systems previously described in relation to FIGS. 102A-102J, and using some similar or same components, in accordance with some embodiment of the invention showing an assembly comprising a traction spikes 10239. Further, FIG. 102L illustrates a perspective view of a bone fiducial screw system 10250, similar to the systems previously described in relation to FIGS. 102A-102K, and using some similar or same components, in accordance with some embodiment of the invention.

FIG. 102M illustrates a perspective assembly view of a fiducial-registration probe system 10252, similar to the systems previously described in relation to FIGS. 102A-102L, and using some similar or same components, in accordance with some embodiment of the invention. Some embodiments comprise a fiducial-registration probe system 10252 including a probe shaft 10203, mating groove 10232, spring-loaded plunger 10253, and mating extrusions 10254. In some embodiments, probe's mating extrusions 10254 can engage with the mating groove 10232 of the bone fiducial, and simultaneously can actuate a spring-loaded plunger 10253 that elevates the position of a TMSM 10204 mounted on a TMSM sliding post 10222 towards a position relative to the DRF. This action signals to the system that the probe is in an active trigger state, initiating the registration of the bone fiducial's unique orientation and location.

FIG. 102N illustrates a side cross-sectional view of a fiducial-registration probe system 10256, similar to the systems previously described in relation to FIGS. 102A-102M, and using some similar or same components, in accordance with some embodiment of the invention. Some embodiments comprise a fiducial-registration probe system 10256 including a spring-loaded plunger 10253, and/or TMSM 10257, and/or a compression spring 10258. In some embodiments, the actuation of the spring-loaded plunger 10253, such as via mating with a bone fiducial with complementary mating features, can compress a compression spring 10258 that can elevate the position of a TMSM 10257 located on the TMSM sliding post 10222.

FIG. 102O illustrates a front assembly view of a fiducial-registration probe system 10259, similar to the systems previously described in relation to FIGS. 102A-102N, and using some similar or same components, in accordance with some embodiment of the invention. In some embodiments, the fiducial-registration probe system 10259 comprises a probe shaft 10203, and/or DRF 10206, and/or spring-loaded plunger 10253, and/or compression spring 10258, and/or TMSM mounting hole 10260, and/or TMSM sliding post 10261, and/or trigger motion-restricting slot 10262, and/or mounting hole 10263, and/or a dowel pin hole 10264. In some embodiments, a mounting hole 10263 behind the DRF 10206 serves as a fixation point for a screw (not shown) that substantially rigidly attaches the DRF 10206 to the mounting surface of the probe shaft 10203. In some embodiments, the spring-loaded plunger 10253 directly compresses a spring 10258 housed within the TMSM sliding post 10261, and actuates the attached TMSM 10260 into an active position.

FIG. 102P illustrates a perspective assembly view of a fiducial-registration probe system 10270, similar to the systems previously described in relation to FIGS. 102A-102O, and using some similar or same components, in accordance with some embodiment of the invention. Some embodiments comprise a fiducial-registration probe system 10270 comprising a DRF 10206, spring-loaded plunger, TMSM sliding post 10261, TMSM 10271, probe shaft 10203, and a mounting screw 10272. In some embodiments, a mounting screw 10272 can be inserted through the DRF 10206 and into threads in the mounting hole 10263, enabling for the rigid fixation of the DRF 10206 against the probe shaft 10203.

Some embodiments of the invention include a fiducial-registration probe system that can mate with a fiducial that has an inner, embedded depth-stop mating interface and register the position and orientation of the fiducial with respect to a 3D-tracking camera system. In this embodiment, the user can mate the probe with the patterned interface within the fiducial, and when the probe is fully engaged with the fiducial interface, an internal spring-loaded depressible sliding shaft actuates a TMSM relative to a fixed DRF mounted on the probe to trigger a registration event to the system. In other embodiments, the trigger mechanism of the probe can be actuated by the user, instead of by the successful mating of the probe with the fiducial, via systems that include, but are not limited to, those depicted previously in relation to FIGS. 95, 98, etc. Some embodiments of this invention are related to devices and systems described in relation to FIGS. 3A-3C, 10A-10G, 14A-14C, 15A-15C, 29A-29D, 33A-33G, 38A-38G, 44A-44D, 45A-45B, 91A-91C, 101A-101Q, 102A-102P, 104A-104J, and 106A-106F, as well as processes described in relation to FIGS. 58-60, 62A-62D, 63, 64A-64B, 65A-65E, 66A-66B, 68-69, 72, and 113.

FIG. 103A illustrates a front view of a fiducial-registration probe system 10300 in accordance with some embodiment of the invention, showing an assembly comprising a TMSM 10301 (in an undepressed state), and/or a TMSM sliding post 10302 (in an undepressed state), and/or a DRF 10303, and/or a mounting screw 10304, and/or a dowel pin 10305, and/or a shaft 10306, and/or a probe tip extrusion tab 10307, and/or bone fiducial screw 10308. In this embodiment, the probe is not engaged with the bone fiducial screw 10308, and thus the TMSM 10301 is not in an active triggering state. In some embodiments, the fiducial-registration probe system 10300 can contain a probe tip extrusion tab 10307 that engages with the bone fiducial screw 10308 in one unique orientation to enable registration of the bone fiducial screw's unique pose and location in 3D space.

FIG. 103B illustrates a side view of a fiducial-registration probe system 10310, similar to the systems previously described in relation to FIG. 103A, and using some similar or same components, in accordance with some embodiment of the invention, showing an assembly comprising a probe tip extrusion tab 10311, similar to that depicted previously in relation to FIG. 103A.

FIG. 103C illustrates a rear view of a fiducial-registration probe system 10315, similar to the systems previously described in relation to FIGS. 103A-103B, and using some similar or same components, in accordance with some embodiment of the invention. In this embodiment, the spring-loaded trigger mechanism (not shown) is housed within the TMSM sliding post 10302, and is restricted in its range of motion of triggering via a trigger-retaining screw fastened against the probe shaft 10306 within the trigger motion-restricting slot, which is a component of the TMSM sliding post 10302.

FIG. 103D illustrates a perspective view of a fiducial-registration probe system 10320, similar to the systems previously described in relation to FIGS. 103A-103C, and using some similar or same components, in accordance with some embodiment of the invention, showing an assembly comprising a TMSM 10301 (in an undepressed state). In this embodiment, the fiducial-registration probe system 10320 is not engaged with the bone fiducial screw 10308, and thus the TMSM 10301 is not in an active triggering state. Further, FIG. 103E illustrates a perspective view of a fiducial-registration probe system 10325, similar to the systems previously described in relation to FIGS. 103A-103D, and using some similar or same components, in accordance with some embodiment of the invention. In this embodiment, the probe is fully engaged with the bone fiducial screw 10308, and thus the TMSM 10301 is elevated to an active triggering state. Further, FIG. 103F illustrates a perspective view of a fiducial-registration probe system 10330, similar to the systems previously described in relation to FIGS. 103A-103E, and using some similar or same components, in accordance with some embodiment of the invention showing an assembly comprising a probe tip extrusion tab 10331. In this embodiment, the probe is not engaged with the bone fiducial screw 10308, and thus the TMSM 10301 is not in an active triggering state. Further, FIG. 103G illustrates a perspective view of a fiducial-registration probe system 10335, similar to the systems previously described in relation to FIGS. 103A-103F, and using some similar or same components, in accordance with some embodiment of the invention, showing an assembly comprising a TMSM 10336 (in a depressed state) and probe tip flat mating surface 10337. In this embodiment, the probe is fully engaged with the bone fiducial screw 10308, and thus the TMSM 10336 is elevated to an active triggering state. In some embodiments, the probe tip flat mating surface 10337 aids with the unique alignment of the probe with the bone fiducial screw 10308. Further, FIG. 103H illustrates a side view of a fiducial-registration probe system 10340, similar to the systems previously described in relation to FIGS. 103A-103G, and using some similar or same components, in accordance with some embodiment of the invention. In this embodiment, the probe is fully engaged with the bone fiducial screw 10308, and thus the TMSM 10336 is elevated to an active triggering state.

FIG. 103I illustrates a rear view of a fiducial-registration probe system 10345, similar to the systems previously described in relation to FIGS. 103A-103H, and using some similar or same components, in accordance with some embodiment of the invention. Some embodiments include a fiducial-registration probe system 10300 comprising a trigger-retaining screw 10346 and trigger motion-restricting slot 10347. In this embodiment, the fiducial-registration probe system 10345 is fully engaged with the bone fiducial screw 10308, and thus the TMSM 10336 is elevated to an active triggering state. In some embodiments, the spring-loaded trigger mechanism (not shown) can be housed within the TMSM sliding post 10302, and is restricted in its range of motion of triggering via a trigger-retaining screw 10346 fastened against the probe shaft 10306 within the trigger motion-restricting slot 10347, which is a component of the TMSM sliding post 10302.

FIG. 103J illustrates a perspective view of a bone fiducial screw system 10350, similar to the systems previously described in relation to FIGS. 103A-103I, in accordance with some embodiment of the invention. Some embodiments include a bone fiducial screw system 10350 comprising a screw head 10351, and/or mating fiducial attachment 10352, and/or fiducial flat mating surface 10353, and/or fiducial alignment groove 10354, and/or fiducial screw head offset 10355. In this embodiment, the bone screw with screw head 10351 can be a separate component of the fiducial system, in which the mating fiducial attachment can freely rotate about the screw shaft. In this embodiment, the screw head 10351 interfaces with the fiducial screw head offset 10355, which enhances the triggering mechanism for depressing the sliding shaft (not shown) of the probe. In some embodiments, the mating fiducial attachment 10352 includes, but is not limited to, one or more unique, asymmetric extrusions (e.g., fiducial alignment groove 10354, fiducial flat mating surface 10353, etc.) that enable the probe (e.g., such as probe with probe shaft 10306) to mate with the fiducial attachment 10352 securely and in only one unique orientation, using complementary extrusions such as the probe tip extrusion tab 10311 as depicted in FIG. 103B. In this way, every time the probe mates with the fiducial attachment 10352, the probe can register the unique orientation and location of the bone fiducial screw 10308. In some embodiments, when the bone fiducial screw is fully engaged with the anatomy of interest, then the mating fiducial attachment and screw head are pressed against each other and become completely rigid as one component, to which the probe mates and registers the fiducial's location and orientation.

FIG. 103K illustrates a front view of a bone fiducial screw system 10360, similar to the systems previously described in relation to FIGS. 103A-103J In this embodiment, the screw 10351a is fully inserted into the mating fiducial attachment 10352. In some embodiments, the bottom surface of the mating fiducial attachment 10352, or similar surfaces that interface with the anatomy of interest can include features, such as a series of spikes or hooks, that aid in the rigid fixation of the mating fiducial attachment 10352 with the surface of the screw-engaged anatomy.

FIGS. 103L-103O illustrate several perspective views of a bone fiducial screw system (10365, 10370, 10375, 10380), similar to the systems previously described in relation to FIGS. 103A-103K, in accordance with some embodiment of the invention, showing assemblies comprising a fiducial flat mating surface 10353, and fiducial alignment groove 10354.

FIG. 103P illustrates a top view of a bone fiducial screw system, similar to the systems previously described in relation to FIGS. 103A-103O, in accordance with some embodiment of the invention, showing an assembly comprising a fiducial flat mating surface 10353, and a fiducial alignment groove 10354. In this embodiment, the unique orientation of the fiducial attachment 10352 is apparent and illustrates how the probe registers the unique pose of the fiducial system, regardless of whether the engaged anatomy it is fastened against happens to move.

FIG. 103Q illustrates a perspective view of a fiducial-registration probe system 10390, similar to the systems previously described in relation to FIGS. 103A-103P, in accordance with some embodiment of the invention, showing an assembly comprising a probe shaft 10306, and/or probe tip extrusion tab 10307, and/or probe flat-face mating extension 10391, and/or a spring-loaded plunger 10392. In some embodiments, once the mating extensions of the probe tip (e.g., 10391, 10307, etc.) are fully engaged with the mating fiducial attachment 10352, the spring-loaded plunger 10392 within the probe shaft 10306 can be actuated against the surface of the screw head 10351 of a bone screw, and consequently can elevate the position of the attached TMSM 10336 into an active triggering state.

Some embodiments of the invention include a screw-registration probe system that is able to mate with a fastener with an embedded depth-stop mating interface and register the position and orientation of the fastener's shaft with respect to a 3D-tracking camera system. In this embodiment, the user can mate the probe with the patterned interface attached to a screw shaft and when the probe is fully engaged with the screw mating interface, an internal spring-loaded depressible sliding shaft actuates a TMSM relative to a fixed DRF mounted on the probe to trigger a registration event to the system. In other embodiments, the trigger mechanism of the probe can be actuated by the user, instead of by the successful mating of the probe with the fastener, via systems that include, but are not limited to, those depicted previously in relation to FIGS. 95A-95I, and 98A-98V, etc. Some embodiments of this invention are related to devices and systems described in relation to FIGS. 3A-3C, 10A-10G, 14A-14C, 15A-15C, 29A-29D, 33A-33G, 38A-38G, 44A-44D, 45A-45B, 91A-91C, 101A-101Q, 103A-103Q, and 106A-106F, as well as processes described in relation to FIGS. 58-60, 62A-62D, 63, 64A-64B, 65A-65E, 66A-66B, 68-69, 72, and 113.

FIG. 104A illustrates a front view of a screw-registration probe system 10400 in accordance with some embodiment of the invention. Some embodiments include a screw-registration probe system 10400 comprising a TMSM 10401 (undepressed), and/or DRF 10402, and/or mounting screw 10403, and/or dowel pin 10404, and/or TMSM sliding post 10405 (undepressed), and/or shaft 10406, and/or tool mating tip 10407, and/or tulip head 10408, and/or screw mating attachment 10409, and/or a pedicle screw shaft 10410 (threads not shown). In some embodiments, the tool mating tip 10407 can be a partial-cylinder shape to enable a rod to be implanted into the screw's tulip head, and can maintain the range of motion of the tulip head without losing access to registration sites on the screw. In some embodiments, once the tool mating tip 10407 is completely and substantially rigidly engaged with the screw mating attachment, a depressible sliding shaft (not shown) can be actuated, moving the location of a substantially rigidly-linked TMSM 10401 on a TMSM sliding post 10405 relative to the DRF 10402 of the tool, and signaling to the system that a triggering event of screw registration is occurring. In this embodiment, the screw-registration probe system 10400 is not engaged with the fastener system, and the TMSM 10401 is consequently not in an active triggering position. In some embodiments, the DRF can be modularly attached to the probe device, and can be replaced by other DRF and/or associated tool definition files to change the system's understanding of the probe's function and/or tracking location.

FIG. 104B illustrates a side view of a screw-registration probe system 10415, similar to the systems previously described in relation to FIG. 104A, and using some similar or same components, in accordance with some embodiment of the invention. Some embodiments include a screw-registration probe system 10415 comprising a TMSM 10401 (shown in an undepressed state), TMSM sliding post 10405 (shown in an undepressed state), and tool mating tip 10407. In some embodiments, the tool's geometrical design has the TMSM 10401 that can be located in-line with the 3D-tracked markers of the DRF 10402 to simplify the processing of filtering stray markers, classifying a TMSM, and measuring its relative location for a triggering event as described in at least FIGS. 63, 113.

FIG. 104C illustrates a rear view of a screw-registration probe system 10420, similar to the systems previously described in relation to FIGS. 104A-104B, and using some similar or same components, in accordance with some embodiment of the invention, showing an assembly comprising a TMSM 10401 (in an undepressed state), and/or DRF 10402, and/or TMSM sliding post 10405 (undepressed), and/or shaft 10406, and/or tool mating tip 10407, and/or trigger-retaining screw 10421, and/or a trigger motion-restriction slot 10422. In some embodiments, the spring-loaded trigger mechanism (not shown) can be housed within the TMSM sliding post 10405, and can be restricted in its range of motion of triggering via a trigger-retaining screw 10421 fastened against the probe shaft 10406 within the trigger motion-restricting slot 10422, which is a component of the TMSM sliding post 10405.

FIG. 104D illustrates a front view of a screw-registration probe system 10425, similar to the systems previously described in relation to FIGS. 104A-104C, and using some similar or same components, in accordance with some embodiment of the invention. In some embodiments, the screw-registration probe system 10425 can comprise a TMSM 10426 (in a depressed state), TMSM sliding post 10427 (in a depressed state), and an engaged tool mating tip 10428. In this embodiment, the tool mating tip 10428 can be fully engaged with the screw mating attachment 10409, and the depressible sliding shaft (not shown) can elevate the TMSM 10426 of the TMSM sliding post 10427 away from the DRF 10402 to signal to the system that the registration probe is fully aligned and engaged with the screw mating attachment. In some embodiments, the screw mating attachment can be co-axial with the screw shaft in order to enable the probe to rapidly register the accurate orientation of the screw shaft via the registration of the screw mating attachment location. In other embodiments, the mating attachment of the screw can have features that include, but are not limited to, co-linear mates or ones that are off-angle with the central axis of the screw shaft.

FIG. 104E illustrates a side view of a screw-registration probe system 10430, similar to the systems previously described in relation to FIGS. 104A-104D, and using some similar or same components, in accordance with some embodiment of the invention. In some embodiments, the screw-registration probe system 10430 can comprise a TMSM 10426 (shown in depressed state) and/or TMSM sliding post 10427 (shown in depressed state). In this embodiment, similar to that depicted in FIG. 104D, the screw-registration probe is in an active state via being fully engaged with the mating attachments of the screw.

FIG. 104F illustrates a rear view of a screw-registration probe system 10435, similar to the systems previously described in relation to FIGS. 104A-104E, and using some similar or same components, in accordance with some embodiment of the invention, in accordance with some embodiment of the invention. Some embodiments include a screw-registration probe system 10435 comprising an engaged tool mating tip 10428 and/or a trigger-retaining screw with trigger depressed 10436. In this embodiment, similar to that depicted in FIGS. 104D-104E, the screw-registration probe can be in an active state via being fully engaged with the mating attachments of the screw. In this embodiment, the trigger-retaining screw with trigger depressed 10436 is located within the bottom of trigger motion-restricting slot 10422 because the TMSM sliding post 10427 has elevated relative to the DRF 10402 and probe shaft 10406, which is farther away from the trigger-retaining screw, and which is substantially rigidly attached to the probe shaft 10406.

FIG. 104G illustrates a perspective view of a screw-registration probe system 10440, similar to the systems previously described in relation to FIGS. 104A-104F, in accordance with some embodiment of the invention, showing an assembly comprising an TMSM 10441 (undepressed state), TMSM sliding post 10442 (undepressed state), and a screw mating attachment 10443. In this embodiment, similar to that depicted in FIGS. 104A-104C, the screw-registration probe is in an inactive state.

FIG. 104H illustrates a perspective view of a screw-registration probe system 10450, similar to the systems previously described in relation to FIGS. 104A-104G, in accordance with some embodiment of the invention. Some embodiments include a screw-registration probe system 10450 comprising a tool mating extrusion pattern 10451, and/or spring-loaded plunger (undepressed) 10452, and/or tool mating depth-stop 10453, and/or screw mating pattern 10454, and/or a threaded hole 10455. In this embodiment, the tool mating extrusion pattern 10451 can include different draft angles that complement the screw mating pattern 10454 to enable a unique, well-aligned, and full-engaged mate between the probe and the screw mating attachment. In some embodiments, when the tool mating extrusion pattern is fully engaged with the screw mating pattern 10454, the spring-loaded plunger 10452 is depressed and subsequently elevates the position of the TMSM 10441 until it reaches an active triggering location relative to the DRF 10402. In some embodiments, the threaded holes 10455 within the screw mating pattern 10454 can be utilized in order to substantially rigidly secure the probe mating tip to the screw attachment via fasteners (not shown) that are inserted through the body of the tool mating extrusion pattern 10451.

FIG. 104I illustrates a perspective view of a screw-registration probe system 10460, similar to the systems previously described in relation to FIGS. 104A-104H, in accordance with some embodiment of the invention, showing an assembly comprising an TMSM 10461 (depressed), and/or TMSM sliding post 10462 (depressed), and/or an engaged tool mating tip 10463. In this embodiment, similar to that depicted in FIGS. 104D-104F, the screw-registration probe is in an active state.

Some embodiments of the invention include an adjustable screw interface system of a flexibility assessment device that can mate with fasteners with an embedded depth-stop mating interface and substantially rigidly cross-link with other similar adjustable screw interface systems attached to other anatomical landmarks. In this embodiment, the user can mate a 3D-tracked flexibility assessment device with a vertebra of interest via pedicle screws with depth-stop mates that are engaged at various relative orientations and positions, accounted for via a variable width and angle adjustment mechanism of the screw interface system. In some embodiments, the depicted screw interface system is compatible with flexibility assessment device handles and/or accompanying systems that include, but are not limited to, those depicted previously in relation to FIGS. 40-43 and 95-97. In some embodiments, the flexibility assessment device handles can be adjusted into various handle orientations relative to the screw interface system via a mechanism that includes, but is not limited to, a spring-loaded fastener that can be released or engaged to securely adjust the device handle to a desired orientation relative to the 3D-tracking camera, nearby screw interface devices, other flexibility assessment device handles, DRF-equipped tools, etc. Some embodiments of this invention are related to devices and systems described in relation to FIGS. 34, 34A-34F, 35A-35E, 36A-36I, 37A-37G, 38, 38A-38G, 39A-39F, 40A-40C, 41A-41D, 42A-42K, 43A-43K, 94A-94H, 95A-95I, 96A-96S, 97A-97L, 105A-105G, 106A-106F, as well as processes described in relation to FIGS. 44A-44D, 45A-45B, 58-60, 62A-62D, 63, 64A-64B, 65A-65E, 66A-66B, 68-69, 70, 72, 107A-107D, 108A-108H, 111, and 113.

FIG. 105A illustrates a perspective view of an adjustable screw interface assembly 10500 in accordance with some embodiments of the invention. In some embodiments, the adjustable screw interface assembly 10500 can comprise side arms such as side arm 10501*a* and/or side arm 10501*b*, and/or extension screw 10502, and/or extension screw sleeve 10503, and/or tool mating tip 10504, and/or pedicle screw shaft (threads not shown) 10505, and/or screw mating attachment 10506, and/or threaded hole 10507, and/or tulip head 10508. In some embodiments, the side arm 10501*a* can be a fixed side arm (coupled to shoulder 10513) and/or the side arm 10501*b* can be an adjustable side arm (adjustably positioned in cavity or channel 10519 of adjustment bracket 10518). In some embodiments, the distance between the arms 10501*a* and 10501*b* can be adjusted by sliding arm 10501*b* towards or away from arm 10501*a* using the cavity or channel 10519). In some embodiments, the components of the side arm 10501*a* and side arm 10501*b* can be the same, can use at least some common components, and described similarly. In some embodiments, the screw interface assembly 10500 can substantially rigidly engage with a flexibility assessment system (e.g., see example FIG. 96N). In some embodiments, the screw interface system's tool mating tip 10504 can engage with depth-stop patterns on the screw mating attachment 10506, regardless of whether there is an implanted rod within the tulip head 10508 of the screw. In some embodiments, one of the side arm 10501 assemblies can be linked in a fixed orientation with the adjustable width mechanism of the overall assembly 10500, while the other side arm assembly can vary in its relative width, height, and orientation with respect to the corresponding side arm 10501 assembly. In some embodiments, the extension screws 10502 in the extension screw sleeves 10503 can enable the side arm 10501 and tool mating tip 10504 to substantially rigidly link with the depth-stop interface of the screw mating attachment 10506. In some embodiments, the overall screw interface assembly 10500 includes, but is not limited to, accessory tulip heads that enable for the rigid fixation of two or more flexibility assessment devices (e.g., as depicted below in reference to FIG. 105G) via a rod linkage between the devices that is substantially rigidly linked by way of cap screws inserted on the tulip heads, with the rod within the cavity of the tulip head.

FIG. 105B illustrates a front view of an adjustable screw interface system 10520, similar to the systems previously described in relation to FIG. 105A, and using some similar or same components, in accordance with some embodiment of the invention. Some embodiments include an adjustable screw interface system 10520 comprising at least a side arm 10501*a*, and/or extension screw 10502, and/or extensions screw sleeve 10503, and/or tool mating tip 10504, and/or pedicle screw shaft (threads not shown) 10505, and/or screw mating attachment 10506. In some embodiments, the adjustable orientation of the adjustable side arm (unlabelled) can enable the screw interface system 10520 to mate with pedicle screws that are instrumented into the spine in orientations that are not mirrored about the screw interface system's 10520 central axis.

FIG. 105C illustrates a rear view of an adjustable screw interface system 10530, similar to the systems previously described in relation to FIGS. 105A-105B, in accordance with some embodiments of the invention, showing an assembly comprising a tool mating tip 10504, and screw mating attachment 10506. In some embodiments, the spinal rod implant can be implanted from behind or above the tulip head while the screw interface system 10530 is fully engaged with the pedicle screws.

FIG. 105D illustrates a top view of an adjustable screw interface system 10540, similar to the systems previously described in relation to FIGS. 105A-105C, in accordance with some embodiments of the invention, showing an assembly comprising a tool mating tip 10504, and/or screw mating attachment 10506, and/or threaded hole 10507. In some embodiments, the screw interface system 10540, as depicted, the cap screws and accessory tulip heads of the screw interface system 10540 can be accessed from above via complementary instruments (e.g., screwdriver). Further, FIG. 105E illustrates a side view of an adjustable screw interface system 10550, similar to the systems previously described in relation to FIGS. 105A-105D.

FIG. 105F illustrates a perspective of an adjustable screw interface system 10560, similar to the systems previously described in relation to FIGS. 105A-105D, in accordance with some embodiments of the invention. Some embodiments of the invention include an adjustable screw interface system 10560 comprising an extension screw 10502, and/or a mating-equipped screw (detached from tool) 10561, and/or extension screw threads 10562. In this embodiment, the extension screw threads of the tool mating tip 10504 are not engaged into a mating-equipped screw 10561. In some embodiments, the adjustable side arm sub-assembly can mate with a mating-equipped screw with the orientation-locking fastener not fully engaged, and thus enable the fixed-orientation side arm subassembly to orient itself about the screw interface system 10560 to properly align with the mating interface of the mating-equipped screw 10561.

FIG. 105G illustrates a perspective of an adjustable screw interface system 10565, similar to the systems previously described in relation to FIGS. 105A-105E, in accordance with some embodiments of the invention. In some embodiments, the adjustable screw interface system 10565 can comprise a handle #1 10566, and/or handle #2 10567, and/or device outer tulip head 10568, and/or device inner tulip head 10569, and/or inter-tool connecting rod 10570, and/or device inner tulip head 10571, and/or cap screw 10572, and/or screw-mating attachment 10573, and/or implanted rod for pedicle screws 10574, and/or cap screw 10575, and/or tool-engaged vertebra #1 10576, and/or a tool-engaged vertebra #2 10577. As shown in the non-limiting embodiment of FIG. 105G, in some embodiments, the adjustable screw interface system 10565 illustrates two flexibility assessment devices, substantially rigidly linked via an inter-tool connecting rod 10570 that is substantially rigidly fixed via the device inner tulip head 10571 and cap screw 10572 that are substantially rigidly engaged with vertebrae of interest (10576, 10577), that can be subsequently manipulated into a desired conformation. In other embodiments, instrumented vertebrae, those linked to the flexibility assessment devices and those that are not, can be substantially rigidly linked together via an implanted rod 10574 that ensures the contour of the spine between the flexibility assessment devices can be substantially rigidly fixed in a desired conformation. In some embodiments, the handles (10566, 10567) of the flexibility assessment devices, which are substantially rigidly engaged with vertebrae of interest, can be maneuvered by the user and/or system to manipulate the contour and flexibility of the vertebrae that are linked to and positioned between the flexibility assessment devices. In this embodiment, a desired conformation can be achieved by the flexibility assessment devices (e.g., adjustable screw interface system 10565 can comprise a handle #1 10566, and/or handle #2 10567), and detected by systems including, but not limited to, those described below in reference to FIG. 111. In some embodiments, once one side of the spine has an implanted rod within the instrumented pedicle screws and the rod is substantially rigidly linking the associated vertebrae via tightened cap screws, then the respective handles (10566, 10567) can be detached from the overall screw interface systems, and another rod can be implanted into the contralateral of the spine into the instrumented pedicle screw tulip heads, and thus substantially rigidly fix the overall construct of the manipulated region of the spine. In other embodiments, the two accessory device tulip heads (10568, 10569) on each side of a screw interface system, can enable for multiple constructs to be linked between separately assessed and/or fixed regions of the spine that also have attached screw interface systems. In other embodiments, adjustable side arm and/or the fixed side arm assemblies of a screw interface system can also be adjusted to be able to rotate about the axis of the side arm shaft, enabling the screw interface mating surface to be able to properly align and substantially rigidly engage with the mating patterns of the screw mating attachments of the pedicle screws of interest.

Some embodiments of the invention include a device sub-assembly with a triggering mechanism that contains a lockable mechanism for maintaining the active triggering state of the device. For example, in reference to FIGS. 106A-106F, some embodiments include a trigger mechanism that is compatible with any DRF-equipped system including, but not limited to, devices and systems described in relation to FIGS. 3A-3C, 10A-10G, 14A-14C, 15A-15C, 38, 38A-38G, 44A-57D, 91A-91C, 95A-99O, 101A-103Q, 105A-105G, and 115A-115F, as well as processes described in relation to FIGS. 45A-45B, 58-88F, 91A-91C, 93A-105G, 107A-109D, 111A-113, and 114A-114F.

FIG. 106A illustrates a perspective view of a triggering system 10600 in accordance with some embodiments of the invention. In some embodiments, the triggering system 10600 comprises a TMSM trigger mount 10601, and/or spring-loaded (not shown) TMSM sliding post 10602, and/or screw mount 10603 for substantially rigidly attaching the DRF to the device body, and/or DRF mounting surface 10604, and/or hole for dowel pin 10605 for restricting rotation of the DRF, and/or end cap shaft 10607, and/or sliding trigger body 10608, and/or dowel pin 10609, and/or pivoting trigger lock tab 10610, and/or static trigger tab 10611.

In some embodiments, the trigger system 10600 can contain a mounting surface to enable the selected tool DRF to be modular. In other embodiments, the DRF can be directly embedded within the trigger system 10600 main body. In some embodiments, the sliding trigger body 10608 can contain one or more cutouts to facilitate a reduction in friction with other interfacing components, such as the end cap shaft 10607. It must be noted that FIGS. 106A-106C are non-limiting example embodiments of a triggering mechanism with locking functionality, and although the device body interfacing with the triggering mechanism is most related to the end cap tool used in assemblies related to a rod contour assessment system, such as those depicted in FIGS. 98A-98V, and 99A-99O, this trigger mechanism is compatible with any DRF-equipped system, including, but not limited to, devices and systems described in relation to FIGS. 3A-3C, 10A-10G, 14A-14C, 15A-15C, 38A-38G, 44A-57D, 91A-91C, 95A-99O, 101A-103Q, and 105G, as well as processes described in relation to FIGS. 45A-45B, 58-88F, 91A-91C, 93A-105G, 107A-109D, and 111A-113.

In some embodiments, the spring-loaded (not shown) pivoting trigger lock tab 10610 can be substantially rigidly engaged with the end cap shaft 10607 upon triggering of the sliding trigger body 10608. In other embodiments, a similar trigger locking mechanism, or other alternatives, can be utilized for other TMSM triggering motions than the linear actuation depicted in FIG. 106A, such as rotational actuation, as seen in an example embodiment, such as FIG. 15. In some embodiments, the sliding trigger body 10608 can be designed to wrap around the entire end cap shaft 10607 in order to minimize unwanted rotation and wobble of the trigger body during or after triggering. In some embodiments, a TMSM can be attached to the TMSM trigger mount 10601 to enable the tracking of a marker with respect to the attached DRF for the tool.

FIG. 106B illustrates a rear view of a triggering system 10615, similar to the system 10600 previously described in relation to FIG. 106A, in accordance with some embodiments of the invention. Some embodiments include a triggering system 10615 comprising a TMSM sliding post 10602, and/or end cap shaft 10607, and/or sliding trigger body 10608, and/or pivoting trigger lock tab 10610, and/or static trigger tab 10611, and/or trigger-retaining screw 10616, and/or a trigger motion-restricting slot 10617. In some embodiments, when the trigger-retaining screw 10616 is located at the top of the trigger motion-restricting slot 10617, the TMSM is defined to be in an inactive trigger state, as the sliding trigger body 10608 has not been actuated downward against its internal spring mechanism (not shown).

FIG. 106C illustrates a top view 10625 of a triggering system 10640, similar to the systems previously described in relation to FIGS. 106A-106B, in accordance with some embodiments of the invention, showing an assembly comprising the end cap shaft 10607, and/or sliding trigger body 10608, and/or pivoting trigger lock tab 10610, and/or static trigger tab 10611. In some embodiments, the static trigger tab 10611 includes extensions on both sides of the sliding trigger body 10608 to facilitate compatibility with left or right-hand-dominant users.

FIG. 106D illustrates a side cross-sectional view of a triggering system 10640 shown in view 10625 in a depressed (active) state, similar to the systems previously described in relation to FIGS. 106A-106C, in accordance with some embodiments of the invention. In some embodiments, the triggering system 10625 comprises the end cap shaft 10607, and/or TMSM mount 10626, and/or TMSM sliding post (depressed) 10627, and/or slider trigger body (depressed) 10628, and/or compression spring housing (spring not shown) 10629, and/or dowel pin 10630, and/or locking tab motion-restricting wall 10631, and/or pivoting trigger lock tab (locked) 10632, and/or locking extension 10633, and/or trigger lock receptacle 10634, and/or torsion spring 10635. In some embodiments, the pivoting trigger lock tab 10632 can be engaged into the trigger lock receptacle 10634 when the sliding trigger body is in a depressed state 10628, allowing the locking extension 10633 to be inserted into the receptacle 10634 by actuating against the internal torsion spring 10635 of the pivoting trigger lock tab 10632. In some embodiments, as the sliding trigger body 10608 is depressed via the triggering tabs (e.g., actuating the static trigger tab 10611, pivoting trigger lock tab 10632, etc.), the TMSM (not shown) can be engaged on the TMSM mount 10626, and can change its 3D-tracked location relative to the DRF (not shown), engaged on the DRF mounting surface 10604, and can be subsequently interpreted as a triggering event according to processes including, but not limited to, those described in relation to FIGS. 63, 113. In other embodiments, the locking feature of the trigger mechanism does not have to include a pivoting extension tab that mates with a receptacle. In some embodiments, the trigger mechanism can include, but not be limited to, a spring-loaded detent that is released when the sliding trigger body 10608 is depressed beyond the boundary of the receptacle, and/or a passive latch (either on the sliding trigger body or the end cap shaft) that mates with a receptacle on the opposing mating body (either the end cap shaft or the sliding trigger body, respectively), and that restricts the compression spring from decompressing and returning to its baseline state, etc.

FIG. 106E illustrates a side cross-sectional view of a triggering system 10640 in an undepressed (inactive) state, similar to the systems previously described in relation to FIGS. 106A-106D, in accordance with some embodiments of the invention. In some embodiments, the triggering system 10640 can comprise an end cap shaft 10607, and/or TMSM mount 10626, and/or locking tab motion-restricting wall 10631, and/or trigger lock receptacle 10634, and/or torsion spring 10635, and/or TMSM sliding post (undepressed) 10641, and/or sliding trigger body (undepressed) 10642, and/or pivoting trigger lock tab (unlocked) 10643. In some embodiments, since the sliding trigger body 10608 is undepressed, the TMSM (not shown) engaged on the TMSM mount 10626 can remain at its baseline 3D-tracked location relative to the DRF (not shown), engaged on the DRF mounting surface 10604, and will subsequently be interpreted as a non-triggering inactive tool state according to processes including, but not limited to, those described in relation to FIGS. 63, 113.

FIG. 106F illustrates a perspective exploded view of a triggering system 10650, similar to the systems previously described in relation to FIGS. 106A-106E, in accordance with some embodiments of the invention. Some embodiments include a triggering system 10650 comprising a pivoting trigger lock tab 10610, and/or static trigger tab 10611, and/or locking tab motion-restricting wall 10631, and/or torsion spring 10635, and/or hole for dowel pin 10651 of the pivoting trigger lock tab 10610, and/or dowel pin 10652, and/or hole for dowel pin 10653 of the locking tab motion-restricting wall 10631, and/or TMSM sliding post 10654, and/or end cap shaft 10655, and/or dovetail tracks 10656, and/or trigger lock receptacle 10657, and/or compression spring housing (spring not shown) 10658, and/or DRF mounting hole 10659, and/or hole for dowel pin 10660, and/or locking extension 10661.

In some embodiments of the invention, the torsion spring 10635 can be replaced with any other spring or tensioning system. In addition, in some embodiments, the sliding tracks example embodiment shown in the dovetail tracks 10656 of FIG. 106F can be replaced by any other embodiment that mechanically or electromagnetically enables smooth and unrotated travel of the sliding trigger body 10608 over the end cap shaft 10607. Further, this then facilitates the compression of the spring (not shown) within the compression spring housing 10658 via the actuation of a dowel (not shown), or similar compressing object, substantially rigidly coupled to the TMSM sliding post 10654 of the sliding trigger body 10608.

Some embodiments of the invention include a display interface for a spinal alignment system and display monitor controller. In some embodiments, the system can receive input data from a tracing acquisition of the spine's contour using a 3D-tracked probe, with an example embodiment depicted previously in relation to FIG. 101. The acquired tracing data obtained from this embodiment can then be used to automatically compute spinal alignment parameters and intervertebral angles as described previously in relation to FIGS. 66A-66B and 67. Some embodiments of this invention are related to devices and systems described in relation to FIGS. 101A-101Q, 100A-100F, 91A-91C, 32, 23A-23C, and 2A-15C, as well as processes described in relation to FIGS. 113, 82A-86D, 58-69, and 24-28B.

FIG. 107A displays one embodiment of a display interface 10700 that includes acquiring information regarding the contour of the spine via tracing over anatomical surfaces (e.g., laminae) using a 3D-tracked probe (e.g., example embodiment depicted previously in relation to FIG. 101). Some embodiments of this display interface 10700 include, but are not limited to, a spine drawing 10704, and/or vertebral level label 10705 annotations, and/or live plotting of the 3D-tracked probe's tip 10706 relative to the patient anatomical coordinate system, and/or a selectable button or icon that can be used to clear angle plots 10707, and/or a selectable button or icon that can be used to clear angles 10708, and/or a selectable button or icon that can be used to repeat tracing 10709, and/or a selectable button or icon that can be used to add tracing 10710, and/or a selectable button or icon that can be used to clear all tracings 10711, and/or a selectable button or icon that can be used to initialize trackpad 10712, and/or a live trackpad software display 10701 (active state), and/or live plotting of the 3D-tracked probe's tip on trackpad 10702, and/or a list of measured angles 10703. Further, in some embodiments, the display interface 10700 can include the listbox 10703, and/or a status update box 10744. In other embodiments, the spine drawing 10704 can be replaced by or supplemented with embodiments that include, but are not limited to, patient images (e.g., X-ray, CT, MM, O-arm, fluoroscopy, etc.), 3D renderings of the patient anatomy, drawings of the spinal alignment parameters, etc.

In some embodiments of the invention, the live trackpad software display 10701 can be interfaced using a 3D-tracked probe (e.g., example embodiment depicted previously in relation to FIG. 101) and processes described previously in relation to FIGS. 82A-85. In this embodiment, as the 3D-tracked probe is moved within the initialized trackpad volume, the live probe tip plot 10702 can be scaled in its movement amount and relative location according to scaling processes, such as those described previously in relation to FIGS. 82A-85, that map the position of the 3D-tracked probe tip with respect to the trackpad to the display monitor dimensions and pixel resolution, in which this input from the probe movement is converted into the mirrored live movement of the display's mouse cursor. In some embodiments, the location of the initialized trackpad, relative to the system communicating information to the display interface can remain either static or dynamically adjustable, according to where the relative system is located, where the trackpad may be re-initialized (e.g., initiated via the button to initialize the trackpad 10712), etc. In other embodiments, the trackpad software display 10701 can change colors, or provide another indicator when the 3D-tracked probe is located within the volume defined by the trackpad initialization processes, including, but are not limited to, those described in FIGS. 82A-85. In other embodiments, the listbox 10703 can include, but is not limited to, intervertebral angle and/or distance measurements, 3D or 2D-projected measurements, labels that include anatomical landmarks, labels that include tool positions, identities, and orientations, inter-tool distance and/or angle measurements, etc. In other embodiments, one or more of the buttons or icons 10707, 10708, 10709, 10710,

10711, 10712 on the display interface 10700 can be actuated via user input (e.g., manual mouse clicks, tool-based cursors control as described previously in FIGS. 82A-85, etc.), and control the processes of the display interface outputs, including, but not limited to, the recorded tracing contours, respective measurements per tracing contour, the orthogonal vectors that represent the endplate angle trajectories, etc. In some embodiments, the live plotting of the 3D-tracked probe tip 10706 can actively update its position on the display interface 10700 relative to its relative location with respect to the patient's anatomical coordinate system, which can be initialized via processes that include, but are not limited to, those described previously in relation to FIGS. 61-63.

FIG. 107B illustrates one embodiment of the display interface 10720 that consists of acquiring information regarding the contour of the spine via tracing over anatomical surfaces using a 3D-tracked probe (e.g., example embodiment depicted previously in relation to FIG. 101), in which this display interface embodiment is described previously in relation to FIG. 107A. Some embodiments of this display interface 10720 can include, but is not limited to, a live trackpad software display 10721 (inactive state), a listbox 10703 that includes the prior angular measurement 10722 and the current angular measurement 10723 between the selected anatomical landmarks (e.g., between T7-L2 and C7-T5, respectively), a spinal tracing contour 10724 (e.g., as acquired via a 3D-tracked probe), previously generated vertebral endplate line #1 10725 and line #2 10726, current generated vertebral endplate line #1 10727 and line #2 10728. In this non-limiting embodiment, the live trackpad software display (inactive) 10721 is depicting (as shown) to be in an inactive state by way of the 3D-tracked probe not being located within the volume defined by the trackpad initialization processes that include, but are not limited to, those described in FIGS. 82A-85. In some embodiments, the depicted overlay of endplate lines (10725, 10726, 10727, 10728) involves, but is not limited to, calculating the orthogonal vector from the tracing contour at specific locations along the curve indicated by discrete points inputted by the triggering of the 3D-tracked probe at specific anatomical landmarks of interest (e.g., T7 and L2 vertebrae). In this embodiment, the identified vertebral level involved with the measurement is determined by locating the vertebral segment along the tracing contour with the closest location to the discrete point indicated by the triggering of the 3D-tracked probe. In some embodiments, the calculations illustrated in the listbox (10722, 10723) are intervertebral angles measured between vertebrae as inputted by orthogonal lines along the tracing contour, labelled at discrete vertebral levels by the triggering of a 3D-tracked probe, in which the orthogonal vectors represent the estimated relative angle of the vertebral endplate trajectory for the select vertebrae of interest. In some embodiments, prior measurements (e.g., endplate line #1 10725 and line #2 10726) are illustrated by colors, shapes, transparencies, line types, etc., that are different than those illustrated in the current measurements (e.g., endplate line #1 10727 and line #2 10728).

FIG. 107C illustrates another embodiment of the display interface 10735 that consists of acquiring information regarding the contour of the spine via tracing over anatomical surfaces using a 3D-tracked probe (e.g., example embodiment depicted previously in relation to FIG. 101). Some embodiments of this display interface 10735 includes, but is not limited to, the prior spinal tracing contour 10724 (e.g., as acquired via a 3D-tracked probe) and the new repeat tracing overlaid 10736. In some embodiments, the overlay of multiple tracing contours illustrates the progression of the patient's contour over the course of a procedure and/or during a biomechanical assessment in which the spine is being manipulated. In some embodiments, the measurements depicted in the listbox (10722, 10723) can be color and/or pattern matching to that of the spinal contour overlay so that the user can interpret which measurements correspond with which spinal conformations. In other embodiments, there can be an association between the prior and current spinal contour tracings and/or measurements with the time and/or order in which they were acquired, so that the user, or system can best understand and interpret the progression of the procedure. In some further embodiments, the measurements depicted in the listbox can be updated according to the most recent spinal contour tracings that are acquired as well as the respective angular and/or distance measurements that are made along the spine.

FIG. 107D illustrates one embodiment of the display interface 10740 that consists of acquiring information regarding the contour of the spine via tracing over anatomical surfaces using a 3D-tracked probe (e.g., example embodiment depicted previously in relation to FIG. 101). Some embodiments of this display interface 10740 includes, but is not limited to, the prior spinal tracing contour 10724 (e.g., as acquired via a 3D-tracked probe), and/or the new repeat tracing overlaid 10736, and/or the current generated endplate line #1 10742 and line #2 10743 that are measured with respect to the repeat tracing contour 10736, and/or the measured angle 10741 from tracing #2 10736 listed within the listbox 10703, and/or a status update box 10744 that communicates to the user and/or system the current status of operations of the display interface system and/or its associated algorithms. In some embodiments, the overlay of the new orthogonal vectors represents the vertebral endplate trajectories according to discrete locations along the spinal contour tracing that were labelled by triggering of a 3D-tracked probe at those specific locations. In other embodiments, the orthogonal vectors (10742, 10743) along the contour of tracing #2 emanate from the contour of the associated tracing.

Other embodiments of the display interface 10740 include, but is not limited to, orthogonal vectors and other measurement indicators that are overlaid on multiple tracing contours that have been acquired, not just the most current tracing acquisition 10736. In some embodiments, the system update field 10744 indicates to the user and/or system that it is waiting for discrete point selections to be made on or near the most recent spinal contour tracing to provide inputs to the system with regards for the vertebrae that are desired for the measurement (e.g., intervertebral angle, distance, identities, etc.). In other embodiments, the system does not require any manual inputs from the user or system with regards to a vertebral level to make measurements, as the system can automatically segment vertebral levels, and other information regarding anatomical landmarks, and make a variety of measurements across the spine with all important spinal alignment parameters and/or biomechanical assessments of interest. Other embodiments of the invention include input from discrete and/or continuous tracings acquired of the skin outside of and the bone and tissue within the surgical site. In this embodiment, the system can also accept input from fiducial devices that are initialized to represent anatomical landmarks (e.g., vertebral body of C7) outside of the surgical site but beneath the surface of the skin and/or surgical drapes, for which processes to achieve this input have been previously described in relation to FIGS. 58-60.

Some embodiments of the invention involve a display interface that illustrates the live position of tool-engaged vertebrae while they are being manipulated (e.g., flexibility assessment). Some embodiments of the processes that generate this display interface system include, but is not limited to, the processes depicted below in reference to FIGS. 111A-111C. Some embodiments of the system that interfaces with the display monitor displaying the display interface includes, but is not limited to, one or more flexibility assessment tools (e.g., FIG. 95A) engaged, directly or indirectly, with vertebrae, and/or other anatomical landmarks, of interest. An example embodiment of this system actively manipulating engaged vertebrae is illustrated previously in relation to FIGS. 40A-40C, 96O, etc. Some embodiments of this invention are related to devices and systems described in relation to FIGS. 34, 34A-37G, 39A-43F, 93A-93J, 95A-95I, 97A-97L, 105A-105G, and 106A-106F, as well as processes described in relation to FIGS. 63, 70, and 113.

FIG. 108A displays one embodiment of the invention comprising a display interface 10800 that illustrates a 2D sagittal plane view 10809 of the projected shaft angle of flexibility assessment tool #1 10806 and tool #2 10808 (e.g., depicted in the form of line vectors). Some embodiments of the display interface 10800 include, but are not limited to, posterior 10801, and/or anterior 10802, and/or superior 10803, and/or inferior 10804 axis labels. Other embodiments of the system display 10800 include the screw-end of the flexibility assessment tool #1 10805 and tool #2 10807. Some embodiments of the invention enable the user to toggle between different anatomical planar views of the tracked devices via processes described below in reference to FIG. 111.

FIG. 108B displays one embodiment of the invention consisting of a sagittal plane display interface 10815 in which the flexibility assessment tools are in an active trigger state while engaged with vertebrae. Some embodiments of this display interface can include, but not be limited to, a series of lines representing the 2D projected endplate angles of flexibility assessment tool #1 10819 and tool #2 10821 during dual-triggered acquisition. In some embodiments, the line vectors representing the 2D sagittal projection endplate angles (10819, 10821) illustrate the relative displacement of orientation of the assessment tool handles. Some embodiments include depictions for the screw-end component of the flexibility assessment tool #1 10818 and tool #2 10820. In some embodiments, as the system calculates the intervertebral angles, including the maximum kyphotic angle 10816 and lordotic angle 10817.

FIG. 108C displays one embodiment of the invention comprising a coronal plane 10835 display interface 10830 in which the flexibility assessment tools are in an active trigger state while engaged with vertebrae. Some embodiments of this display interface include, but are not limited to, a series of lines representing the 2D projected endplate angles of flexibility assessment tool #1 10840 and tool #2 10841 during dual-triggered acquisition. In some embodiments, the line vectors representing the 2D coronal projection endplate angles (10840, 10841) illustrate the relative displacement of orientation of the assessment tool handles. Some embodiments include depictions for the screw-end component of the flexibility assessment tool #1 10838 and tool #2 10839. In some embodiments, as the system calculates the intervertebral angles, including the maximum left Cobb angle 10836 and maximum right Cobb angle 10837. In some embodiments, the coronal display interface 10830 can include, but is not limited to, inferior 10832, superior 10831, left 10833, and right 10834 axis labels.

FIG. 108D displays one embodiment of the invention comprising an axial plane 10850 display interface 10845 in which the flexibility assessment tools are in an active trigger state while engaged with vertebrae. Some embodiments of this display interface can include, but is not limited to, a series of lines representing the 2D projected endplate angles of flexibility assessment tool #1 10855 and tool #2 10856 during dual-triggered acquisition. In some embodiments, the line vectors representing the 2D axial projection endplate angles (10855, 10856) illustrate the relative displacement of orientation of the assessment tool handles. Some embodiments include depictions for the screw-end component of the flexibility assessment tool #1 10853 and tool #2 10854. In some embodiments, as the system calculates the intervertebral angles, including the maximum clockwise angle 10851 and maximum counterclockwise angle 10852. In some embodiments, the axial display interface 10845 can include, but is not limited to, anterior 10847, posterior 10846, right 10848, and left 10849 axis labels.

FIG. 108E displays one embodiment of the invention consisting of a sagittal plane display interface 10845 in which the flexibility assessment tools are engaged with vertebrae. Some embodiments of this display interface can include, but not be limited to, rendered vertebrae (10862, 10863) that represent the engaged vertebrae attached to and manipulated by flexibility assessment tool #1 and tool #2. In some embodiments, as the system displays the live relative position of engaged vertebrae, it also calculates and/or displays the current sagittal angle between the vertebral endplates 10861 of engaged anatomy.

FIG. 108F displays one embodiment of the invention consisting of a sagittal plane display interface 10865 in which the flexibility assessment tools are in an active trigger state while engaged with vertebrae during an assessment of sagittal plane flexibility 10866. Some embodiments of this display interface can include, but are not limited to, rendered vertebrae (superior 10870, 10874 and inferior 10872, 10876) that represent the engaged vertebrae attached to and manipulated by flexibility assessment tool #1 and tool #2. In some embodiments, while both flexibility assessment devices are in an active trigger state, the system can display the live relative position of engaged vertebrae and calculate the live and range of intervertebral angles. In some embodiments, the system can compute and display a series of range of motion results including, but not limited to, the superior vertebra's endplate angle relative to vertical at time of maximum kyphosis 10869, and/or the inferior vertebra's endplate angle relative to vertical at time of maximum kyphosis 10871, and/or the superior vertebra's endplate angle relative to vertical at time of maximum lordosis 10873, and/or the inferior vertebra's endplate angle relative to vertical at time of maximum lordosis 10875. In other embodiments, the system can also compute and displays the maximum lordosis intervertebral angle 10868 achieved during acquisition, as well as the maximum kyphosis intervertebral angle 10867 achieved during acquisition. In other embodiments (not shown), the system can calculate and display the estimated position of adjacent vertebrae that may be between or on the outside of the engaged vertebrae. In some other embodiments (not shown), the system can compute and display live renderings and calculations for several simultaneously engaged vertebrae.

FIG. 108G displays one embodiment of the invention consisting of an axial plane display interface 10878 in which the flexibility assessment tools are in an active trigger state while engaged with vertebrae during an assessment of axial plane flexibility 10879. Some embodiments of this display interface can include, but not be limited to, rendered vertebrae (superior 10883, 10887 and inferior 10884, 10888) that represent the engaged vertebrae attached to and manipulated by flexibility assessment tool #1 and tool #2. In some embodiments, while both flexibility assessment devices are in an active trigger state, the system can display the live relative position of engaged vertebrae, and calculate the range of intervertebral angles. In some embodiments, the system can compute and displays a series of range of motion results including, but not limited to, the superior vertebra's endplate angle relative to vertical at time of maximum clockwise twist 10882, the inferior vertebra's endplate angle relative to vertical at time of maximum clockwise twist 10885, the superior vertebra's endplate angle relative to vertical at time of maximum counterclockwise twist 10886, and/or the inferior vertebra's endplate angle relative to vertical at time of maximum counterclockwise twist 10889. In other embodiments, the system can also compute and display the maximum clockwise twist angle 10880 achieved during acquisition, as well as the maximum counterclockwise twist angle 10881 achieved during acquisition. In other embodiments (not shown), the system can calculate and display the estimated position of adjacent vertebrae that may be between or on the outside of the engaged vertebrae. In some other embodiments (not shown), the system can compute and display live renderings and calculations for several simultaneously engaged vertebrae.

FIG. 108H displays one embodiment of the invention comprising a coronal plane display interface 10890 in which the flexibility assessment tools are in an active trigger state while engaged with vertebrae during an assessment of coronal plane flexibility 10891. Some embodiments of this display interface include, but are not limited to, rendered vertebrae (superior 10895*a*, 10895*b* and inferior 10895*c*, 10895*d*) that represent the engaged vertebrae attached to and manipulated by flexibility assessment tool #1 and tool #2. In some embodiments, while both flexibility assessment devices are in an active trigger state, the system can display the live relative position of engaged vertebrae and calculates the live and range of intervertebral angles. In some embodiments, the system can compute and display a series of range of motion results including, but not limited to, the superior vertebra's endplate angle relative to horizontal at time of maximum right cobb angle 10894, and/or the inferior vertebra's endplate angle relative to horizontal at time of maximum right cobb angle 10896, and/or the superior vertebra's endplate angle relative to horizontal at time of maximum left cobb angle 10897, and/or the inferior vertebra's endplate angle relative to horizontal at time of maximum left cobb angle 10898. In other embodiments, the system can also compute and display the maximum left cobb angle 10893 achieved during acquisition, as well as the maximum right cobb angle 10892 achieved during acquisition. In other embodiments (not shown), the system can calculate and display the estimated position of adjacent vertebrae that may be between or on the outside of the engaged vertebrae. In some other embodiments (not shown), the system can compute and display live renderings and calculations for several simultaneously engaged vertebrae.

Some embodiments of this invention involve a display interface that illustrates the registration of a rod contour and the overlay and manipulation of this contour on patient images. Some embodiments of the processes that generate this display interface embodiment include, but are not limited to, the processes depicted below in reference to FIGS. 112A-112C. Some embodiments of the devices that interface with the display monitor include, but are not limited to, a rod contour registration tool (e.g., FIG. 98A) and a rod-engaged registration reference device (e.g., FIG. 98J), with an example embodiment of their combined utilization depicted previously in relation to FIG. 98S. Another embodiment of the rod registration tool that communicate with the display interface includes, but is not limited to, a rod bender tool that can also registration the contour of a rod (e.g., example embodiment depicted previously in relation to FIG. 99M). Some embodiments of this invention are related to devices and systems described in relation to FIGS. 47A-53F, 98A-98V, 99A-99O, and 115A-115F, as well as processes described in relation to FIGS. 63, 73A-78, 113, and 114A-114F.

FIG. 109A displays one embodiment of the invention comprising a display interface 10900 that illustrates the 3D camera view 10906 and 2D projection views (i.e., coronal 10921 and sagittal 10908) of registered rod coordinates and the tools used to register its rod contour. One embodiment of the 3D camera view 10906 includes axes labels for the left 10917 and right 10916 sides of the camera view, the depth axis 10903 away or towards the camera, and the up 10901 or down 10902 directions relative to the camera, as well as the displayed locations of the end cap and slider tool coordinates 10907 relative to the tracking camera coordinate system. Another embodiment of the invention includes 2D projection views of the registered rod contour with respect to the registration reference device's coordinate system, with an example embodiment of the tool's sagittal 10915 and coronal 10922 orientation reference depicted for visual reference. Some embodiments include a 2D sagittal projection view 10908 with anterior 10911 and posterior 10910 axis labels, superior 10912 and inferior 10913 axis labels, an example embodiment of the end cap registration reference device from a sagittal perspective 10915, and a live location of the 2D sagittal projection of the rod-engaging region of the slider tool 10914 with respect to the coordinate system of the end cap registration reference device. Some embodiments include a 2D coronal projection view 10921 with left 10917 and right 10916 axis labels, superior 10918 and inferior 10919 axis labels, an example embodiment of the end cap registration reference device from a coronal perspective 10922, and a live location of the 2D coronal projection of the rod-engaging region of the slider tool 10920 with respect to the coordinate system of the end cap registration reference device.

FIG. 109B displays one embodiment of the invention comprising a display interface 10930 that illustrates the 3D camera view 10936 and 2D projection views (i.e., coronal 10938 and sagittal 10947) of registered rod coordinates and the tools used to register its rod contour. One embodiment of the 3D camera view 10936 includes axes labels for the left 10934 and right 10935 sides of the camera view, the depth axis 10933 away or towards the camera, and the up 10931 or down 10932 directions relative to the camera, as well as the displayed locations of the end cap, slider tool, and registered rod 3D coordinates 10937 relative to the tracking camera coordinate system. Another embodiment of the invention includes 2D projection views of the registered rod contour with respect to the registration reference device's coordinate system, with an example embodiment of the tool's sagittal 10915 and coronal 10922 orientation reference depicted for visual reference. Some embodiments include a 2D sagittal projection view 10938 with anterior 10940 and posterior 10939 axis labels, superior 10941 and inferior 10942 axis labels, an example embodiment of the end cap registration reference device from a sagittal perspective 10915, a live location of the 2D sagittal projection of the rod-engaging region of the slider tool 10943 with respect to the coordinate system of the end cap registration reference device, the registered rod coordinates projected onto the sagittal plane 10945, the end point of the registered rod sagittal coordinates closest to the end cap 10946, and the end point of the registered rod sagittal coordinates farthest from the end cap 10944. Some embodiments include a 2D coronal projection view 10947 with left 10949 and right 10948 axis labels, superior 10950 and inferior 10951 axis labels, an example embodiment of the end cap registration reference device from a coronal perspective 10922, a live location of the 2D coronal projection of the rod-engaging region of the slider tool 10952 with respect to the coordinate system of the end cap registration reference device, the registered rod coordinates projected onto the coronal plane 10954, the end point of the registered rod coronal coordinates closest to the end cap 10955, and the end point of the registered rod coronal coordinates farthest from the end cap 10953.

FIG. 109C displays one embodiment of the invention comprising a display interface 10960 that depicts the 2D views of selected patient images. One embodiment of the system includes a sagittal patient image 10961 oriented for holding the end cap in the user's right hand, as well as a coronal patient image 10962 oriented for holding the end cap in the user's right hand. In some embodiments, illustrations of the end cap registration reference device are adjacent to the patient image, including from its sagittal 10963 and coronal 10964 perspectives.

FIG. 109D displays one embodiment of the invention consisting of a display interface 10970 that depicts the 2D views of selected patient images. One embodiment of the system includes a sagittal patient image 10971 oriented for holding the end cap in the user's right hand, as well as a coronal patient image 10972 oriented for holding the end cap in the user's right hand. In some embodiments, illustrations of the end cap registration reference device are adjacent to the patient image, including from its sagittal 10963 and coronal 10964 perspectives. In some embodiments, the registered rod sagittal projection coordinates 10974 are overlaid on the sagittal image 10971 and the registered rod coronal projection coordinates 10977 are overlaid on the coronal image 10972. Some embodiments include the sagittal projection of the rod contour end point farthest from the end cap 10975, as well as a sagittal projection of the rod contour end point closest to the end cap 10973 (rotation point), overlaid on the sagittal patient image 10971. Some embodiments include the coronal projection of the rod contour end point farthest from the end cap 10976, as well as a coronal projection of the rod contour end point closest to the end cap 10978 (rotation point), overlaid on the coronal patient image 10972.

Other embodiments, involve multiple registered rod contours overlaid onto the patient images, enabling the user to view the progression of adjustments made to the contour of a rod (e.g., via rod contouring with a french bender, robotic bender, etc.). In some embodiments, the user can manipulate the relative translation and rotation of this registered rod contour overlay via processes including, but not limited to, those described below in reference to FIG. 112.

Some embodiments of this invention involve analyzing and annotating a patient's medical images (e.g., X-ray, CT, MRI, etc.) in order to output instructions enabling a user to position an adjustable spinal and pelvic anatomical phantom model to represent a scaled matching contour. For example, FIGS. 110A-110B illustrate a workflow for adjusting the positions of vertebral holders for an adjustable model holder with inputs from patient imaging in accordance with some embodiments of the invention. In some embodiments, the workflow 11001 includes steps or processes that can be used to analyze patient images and generate instructions for how to adjust the conformation of an adjustable phantom spine model to match that of the patient in the images. An example embodiment of the adjustable spine holder system can be depicted in, but is not limited to, FIGS. 90A-90C and 92A-92AD with processes also contained in FIG. 89.

Some embodiments involve scaling adjustments made to analyze a contour of the anatomy in the patient's images. In some embodiments, the processes can operate in reverse order, in which the user uses the workflow 11001 to register the conformation of anatomy of a phantom spine model, and then the system to output a patient image embodiment. Example embodiments of the selected patient image can include, but are not limited to, a virtual rendering or a best-match image selection from a library of patient images that represent the spectrum of spinal contours. In some embodiments, the system-selected patient image can represent the best match for the conformation and/or spinal alignment parameters of the registered phantom spine model.

In some embodiments, any of the above processes, methods, or procedures related to the workflow 11001 can include or be accomplished with one or more of steps or processes such as 11000, 11002, 11004, 11006, 11008, 11010, 11012, 11014, 11016, 11018, 11020, 11022, 11024, 11026, 11028, 11030, 11032, 11034, 11036, 11038, 11040, 11042, 11044, 11046, 11048, 11050, 11052, 11054, 11056, 11058, 11060, 11062, 11064, and 11066. In some embodiments, at least one of the steps can include a decision step, where one or more following steps depend on a status, decision, state, or other condition. In some embodiments, the steps of workflow 11001 can proceed in the order as shown. In some embodiments, any of the steps of the workflow 11001 can proceed out of the order as shown. In some embodiments, one or more of the steps of the workflow 11001 can be skipped.

FIGS. 111A-111C illustrate a workflow 11101 for analyzing and outputting the range of motion results of engaged vertebrae during and after a flexibility assessment in accordance with some embodiments of the invention. Some embodiments of this invention involve the process of displaying the relative alignment and calculated angles of vertebrae. In some embodiments, the workflow 11101 can be used to display 3D and/or 2D views of engaged vertebrae that actively update their displayed positions while the vertebrae are manipulated. In some embodiments, the workflow 11101 describes methods for visualizing the live manipulation of substantially rigidly-engaged vertebrae and calculating their relative 3D and 2D alignments. An example embodiment of the flexibility assessment device can be depicted in, but is not limited to, FIG. 96A. Some relevant figures include example embodiments of devices and systems in FIGS. 34, 34A-37G, 39A-42K, 93A-97L, and 105A-105G and embodiments of processes in FIGS. 63, 70, 79A-79G, 108A-108H, and 113.

Some embodiments involve displaying a live view of rendered vertebrae in one or more of the three anatomical planar views, and then, once both vertebra-engaged devices are triggered, the system can calculate the range of motion and live intervertebral angles between the engaged vertebrae experience during a flexibility assessment. Some embodiments of the available display outputs include, but are not limited to, a live view of rendered tool-engaged vertebrae in all three anatomical planar views at once, and/or a live view of rendered tool-engaged vertebrae in one of three anatomical planar views (e.g., FIGS. 108F-108H), and/or a live view of line vectors representing each tool-engaged vertebra's endplate in one or more of the three anatomical planar views (e.g., FIG. 108A), and/or a live view of line vectors representing each tool-engaged vertebra's endplate in one or more of the three anatomical planar views for the duration of a flexibility assessment (e.g., FIGS. 108B-108D), and/or a live view of rendered tool-engaged vertebrae with overlaid line vectors along the individual endplates in one or more of the three anatomical planar views at once, a live view of concentric circles with radial line vectors extending from each circle that represent the relative endplate angle between the engaged vertebrae in one or more of the three anatomical planar views at once, and a live view of rendered vertebrae and/or line vectors that are displayed over a background reference of rendered vertebrae and/or line vectors from the prior range of motion assessment (if available), etc.

Some embodiments for the system involve calibrating the angle of the device handle relative to its screw-interfacing sleeves, and/or the device's relative position to the engaged vertebrae. In some embodiments, the system can automatically calculate the relative orientation of the handle to the screw interface bodies via measuring the displacement orientation of the handle while the screw interface bodies remain substantially rigidly fixed, and the preset orientation of the handle is known prior to beginning the calibration. In other embodiments, the system can calculate the relative orientation between the assessment device's handle and its screw interface bodies via tracked markers that indicate the position and orientation of the screw interface bodies relative to those of the handles. In other embodiments, the system can receive user inputs regarding the angle of the device handle relative to its screw interface bodies (e.g., tick marks on the angular-adjustment base component).

Some embodiments involve the initialization of the relative angle between the endplates of the engaged vertebrae and the device's screw interface bodies. In some embodiments, if the pedicle screws were instrumented via navigation guidance, the system can automatically compute the angle between the endplates of the engaged vertebrae and the device's handle, which has a mounted DRF.

Some embodiment of the methods for assessing the range of motion and relative alignment of the engaged vertebrae include, but are not limited to, manipulating the spine manually while the vertebrae-engaged assessment devices remain in a triggered state, manipulating the spine directly via the movement of the vertebrae-engaged assessment devices while they are in a triggered state, and manipulating the spine via the insertion of implants (e.g., interbody cages, inserts, rods, screws, etc.) while the vertebrae-engaged devices remain in a triggered state, etc.

Once the trigger state of both devices returns to an inactive state, some embodiments involve the completion of the live alignment feedback and a displayed output of a summary view of the range of motion, along with quantitative relative intervertebral angles, experienced by each engaged vertebra in one or more anatomical planes of interest for the duration of the flexibility assessment. In some embodiments, the user can adjust the selected view of the live and/or summary measurement outputs via user input (e.g., FIGS. 82-85) or device trigger activity (e.g., double-click to switch views, single-click to begin live view, click-and-hold of both devices simultaneously to initiate flexibility measurements of intervertebral range of motion, etc.).

In some embodiments, any of the above processes, methods, or procedures related to the workflow 11101 of FIGS. 111A-111C can include or be accomplished with one or more of steps or processes such as 11100, 11102, 11104, 11106, 11108, 11110, 11112, 11114, 11116, 11118, 11120, 11122, 11124, 11126, 11128, 11130, 11132, 11134, 11136, 11138, 11140, 11142, 11144, 11146, 11148, 11150, 11152, 11154, 11156, 11158, 11160, 11162, 11164, and 11166. In some embodiments, at least one of the steps can include a decision step (e.g., such as step 11110), where one or more following steps depend on a status, decision, state, or other condition. In some embodiments, the steps of workflow 11101 can proceed in the order as shown. In some embodiments, any of the steps of the workflow 11101 can proceed out of the order as shown. In some embodiments, one or more of the steps of the workflow 11101 can be skipped.

Some embodiments of this invention involve the process of registering the contour of a rod implant, overlaying the registered contour on patient images, and updating the overlay with newly modified rod contours. For example, FIGS. 112A-112C illustrate a workflow 11201 for registering and overlaying the contour of a rod and subsequent contours of adjusted rods in accordance with some embodiments of the invention. In some embodiments, the workflow 11201 can include displaying 3D and 2D projection views of a registered rod contour on patient images and then adjusting their displayed position on the images via various available user inputs. In some embodiments, the workflow 11201 describes methods for applying a transformation to 2D projections of a registered rod contour that is overlaid onto patient images. Some embodiments for applying this rigid body transformation include a two-point snap method in which the user inputs two points on the image for the registered rod contour to intersect with, one at the proximal end of the rod and the other along its contour. Other embodiments for this transformation process include using the 3D-tracked end cap tool (e.g., FIGS. 98L-98N) to mirror the relative translation and rotation of the registered rod in the end cap tool onto the patient image (e.g., FIGS. 109C-109D). Some relevant figures include example embodiments of devices and systems in FIGS. 47A-56F, 98A-98V, 99A-99O, 106A-106F, and 115A-115F, and embodiments of processes in FIGS. 45A-45B, 58-60, 63, 64A-64B, 70, 72-78, 87A-87K, 109A-109D, 113, and 114A-114F.

Some embodiments of the system involve a continuous process of adjusting the contour of the rod implant (e.g., contouring the rod with a french rod bender, robotic system, etc.), registering the new contour of the adjusted rod, and then overlaying the new contour on the patient image over the prior rod contour overlays, and repeating until the desired rod contour has been achieved for the patient. Some embodiments involve a separate device for rod contouring (e.g., FIG. 55A) and contour registration (e.g., FIG. 98A), and other embodiments use one device for both processes (e.g., FIGS. 98E, 98K, and 98N). Some embodiments of the rod registration tool involve a mounting interface that enables the DRF to be mounted onto the tool forward and backward, and thus enable it to be utilized by the left or right hand of the user. In some embodiments, the system can automatically detect which side the TMSM is located on the tool relative to the location of the front face of the mounted DRF for the rod registration tool. Other embodiments involve user inputs to identify which hand is holding the rod registration tool. Some embodiments of the hand-identification process involve automatically orienting the patient images to optimize the processes for rod contour registration and live overlays relative to the display monitor and 3D-tracking camera system. Some embodiments for the input of patient images for overlays of the rod contour to be displayed upon include, but are not limited to, pre-operative standing X-ray films, flexion and extension films, CT or MRI slice images, 3D volume reconstructions of the patient, surgical-plan-adjusted X-ray images, intraoperative O-arm scans, fluorosound, ultrasound, cone-beam CT imaging, etc.

In reference to FIGS. 112A-112C, in some embodiments, any of the above processes, methods, or procedures related to the workflow 11201 can include or be accomplished with one or more of steps or processes such as 11200, 11202, 11204, 11206, 11208, 11210, 11212, 11214, 11216, 11218, 11220, 11222, 11224, 11226, 11228, 11230, 11232, 11234, 11236, 11238, 11240, 11242, 11244, 11246, 11248, 11250, 11252, 11254, 11256, 11258, 11260, 11262, 11264, 11266, 11268, 11270, 11272, 11274. Further steps can include 11276, 11278, 11280, 11282, 11284, and 11286. In some embodiments, at least one of the steps can include a decision step (e.g., such as step 11202), where one or more following steps depend on a status, decision, state, or other condition. In some embodiments, the steps of workflow 11201 can proceed in the order as shown. In some embodiments, any of the steps of the workflow 11201 can proceed out of the order as shown. In some embodiments, one or more of the steps of the workflow 11201 can be skipped.

Some embodiments of this invention involve the process of filtering the 3D-tracking camera's output of all visible stray markers and classifying select ones as TMSMs, TSMs, that are associated with particular DRF-equipped tools. For example, FIG. 113 shows a workflow 11301 that can be utilized to filter out undesired stray and phantom markers, classify detected TMSMs with their associated DRF-equipped tools, and then determine if each TMSM-equipped tool is in an active state. In some embodiments, the workflow 11301 describes methods for utilizing the known travel path of a TMSM for a specific tool to filter out visible stray and phantom markers, and then adding a secondary filtering layer by setting a threshold for consecutive frame counts of the TMSM being in a triggered state to mitigate the likelihood of errant marker classification leading to a false, active triggering event for a tool. Some relevant figures include example embodiments of devices and systems in FIGS. 3A-3C, 4A-4I, 10A-10G, 14A-14C, 15A-15C, 29A-29D, 33A-33H, 38, 38A-42K, 44A-57D, 91A-91C, 95A-106F, and 115A-115F, and embodiments of processes in FIGS. 58-88F, 107A-112C, and 114A-114F.

Some embodiments of the system involve the use of location thresholds of stray markers transformed onto a DRF-equipped tool's coordinate system in that the stray marker must be located within a specified tolerance of a tool's known TMSM travel path. Some embodiments of the process for identifying the triggering state of a TMSM of a DRF-equipped tool involve calculating how far along the TMSM is located within the full, known range of the TMSM's possible travel path, and then assessing if this relative location is beyond a preset threshold (e.g., 70% of the full travel path) by the system. In some embodiments, the user is enabled to adjust this preset triggering threshold as a means to adjust the sensitivity of a tool's triggering mechanism, in which tuning the triggering threshold to be more sensitive results in the location threshold being a distance closer to the baseline location of the TMSM. Some embodiments of the system depicted in workflow 11301 involve the filtering and classification of TMSMs, and associated trigger-state thresholding, of several DRF-equipped tools simultaneously (e.g., FIGS. 98S, 95G, etc.) for all acquisition frames of a 3D-tracking camera system that has stored the tool definition files for these tools.

Some embodiments involve TMSMs that exhibit a linear actuation (e.g., FIG. 101A-101Q) and have restricted motion to one axis of the 3D travel path relative to the associated tool's coordinated system. Other embodiments involve TMSMs that exhibit a rotational actuation (e.g., FIGS. 15A-15C, 101A-101Q). The same filtering process depicted in workflow 11301 can be utilized for both single and multi-faced tools in some embodiments.

In some embodiments, any of the above systems, assemblies, processes, methods, or procedures related to the workflow 11301 can include or be accomplished with one or more of steps or processes such as 11300, 11302, 11304, 11306, 11308, 11310, 11312, 11314, 11316, 11318, 11320, 11322, 11324, and 11326. In some embodiments, at least one of the steps can include a decision step (e.g., such as step 11314), where one or more following steps depend on a status, decision, state, or other condition. In some embodiments, the steps of workflow 11301 can proceed in the order as shown. In some embodiments, any of the steps of the workflow 11301 can proceed out of the order as shown. In some embodiments, one or more of the steps of the workflow 11301 can be skipped.

Some embodiments of this invention involve the process of continuously adjusting the contour of a rod (e.g., contouring the rod with a french rod bender, robotic system, etc.) and registering the contour of the adjusted rod. For example, FIGS. 114A-114F shows a workflow 11401 that can be used to detect when a rod has been bent and modify the previously registered rod contour to match the new rod contour. Some relevant figures include example embodiments of devices and systems in FIGS. 47A-57D, 98A-99O, 106A-106F, and 115A-115F and embodiments of processes in FIGS. 63, 73A-81, 87A-88K, 109A-109D, 112A-112C, and 113.

Some embodiments of this system involve registering a rod contour with a rod registration tool (e.g., FIGS. 47A-57D, 63, 73A-81, 87A-88F, 98A-99O, 106A-106F, 109A-109D, 112A-112C, 113, etc.). Some embodiments involve using a 3D-tracked rod bender that can localize the three rod-interface components of the bender, which include the left and right-side rollers and the center rod-contouring surface (e.g., FIGS. 115A-115F). Some embodiments for accurately representing the rod prior to bending include calculating the rod's outer diameter projections onto the current plane of the rod bender's rod-interface components (e.g., FIG. 115A). In some embodiments, this includes an outer surface that comes in contact with the bender's left and right rollers and an inner surface that comes in contact with the bender's rod-contouring surface (e.g., FIG. 115A).

Some embodiments for detecting when a rod is just about to be contoured involve having a spring-loaded (not shown) TMSM that actuates when all three rod-interface components are in contact with a rod. Other embodiments include a mechanism to detect electrical conductivity when all three rod-interface components are in contact with a rod (e.g., FIG. 54). In other embodiments, this step may be bypassed by detecting only when the rod has been contoured or is actively being contoured. Some embodiments for detecting rod bending include assessing whether any of the rod's outer surface coordinates are intersecting the 2D-enclosed areas occupied by the left and right rollers (e.g., FIG. 115B). Other embodiments may include attaching a TMSM to the end of the rod and detecting the relative motion of the TMSM with the end cap device (e.g., FIG. 56). In some embodiments, once rod contouring has been detected, some embodiments for modifying the rod contour include dividing the rod contour into "left unbent", "right unbent", and "bent" segments with each segment having their outer and inner segments (e.g., FIG. 115C). Some embodiments for this include applying a transformation (rotation and translation) to both left and right (or either left or right) unbent rod segments until they are both tangential with their respective rollers (e.g., FIG. 115C). Some embodiments involve reconstructing the outer bent rod segment using the contour of the inner bent rod segment (e.g., FIG. 115D). Some embodiments involve filling in gaps in the newly constructed rod's outer surface coordinates to account for metallurgic stretching of the rod material when the rod is bent (e.g., FIGS. 115E, 115F, etc.). Some embodiments involve removing overlaps in the newly constructed rod's inner surface coordinates to account for metallurgic shrinking of the rod material when the rod is bent (e.g., FIGS. 115E, 115F, etc.). Other embodiments for reconstructing the final rod contour may involve accounting for shape memory of the rod material which causes the rod to spring back slightly towards its previous contour when released from the bender (e.g., FIG. 56).

In reference to FIGS. 114A-114F, in some embodiments, any of the above processes, methods, or procedures related to the workflow 11401 can include or be accomplished with one or more of steps or processes such as 11400, 11402, 11404, 11406, 11408, 11410, 11412, 11414, 11416, 11418, 11420, 11422, 11424, 11426, 11428, 11430, 11432, 11434, 11436, 11438, 11440, 11442, 11444, 11446, 11448, 11450, 11452, 11454, 11456, 11458, 11460, 11462, 11464, 11466, 11468, 11470, 11472, 11474, 11476, 11478, 11480, 11482, 11484, 11486, 11488, 11490, 11492, 11494, 11496, 11498, 11403, 11405, 11407, 11409, 11411, 11413, 11415, 11417, 11419, 11421, 11423, 11425, 11427, 11429, 11431, 11433, 11435, 11437, 11439, 11441, 11443, 11445, 11447, 11449, and 11451. In some embodiments, at least one of the steps can include a decision step (e.g., such as step 11448), where one or more following steps depend on a status, decision, state, or other condition. In some embodiments, the steps of workflow 11401 can proceed in the order as shown. In some embodiments, any of the steps of the workflow 11401 can proceed out of the order as shown. In some embodiments, one or more of the steps of the workflow 11401 can be skipped.

Some embodiments of the invention include the ability to equip a rod bender with tracked markers, such that the 3D coordinates of its rod-interface components can be tracked in space. When coupling this embodiment with the embodiments to assess the contour of the rod prior to implantation, as previously described in relation to FIGS. 47A-56F, 63, 73A-75, 78-80, 98A-98V, 99A-99O, 106A-106F, 109A-109D, and 112A-114F, the acquisition system can interpret when the tracked bender is adjusting the contour of the rod and can reconstruct a rendering of the rod's contour to generate real-time feedback during contouring of the rod.

FIG. 115A displays an embodiment 11500 of the software containing the rod bender's three rod-interface components consisting of the center rod-contouring surface 11508, left roller 11503, and right roller 11504. In some embodiments, the outer roller's path of travel 11512 is displayed as a circle surrounding the centroid 11509 of the center rod-contouring surface. The center of the left roller 11502 and center of the right roller 11505 are located along this path of travel. In some embodiments of the invention, the raw data points of a previously registered rod 11506 can be used to generate a filtered curve 11511 to represent the center curve of the rod, from which the rod's outer surface 11507 and inner surface 11510 are computed based on the known cross-sectional diameter of the rod, and projected onto the plane defined by the rod bender's three rod-interface components, as described previously in relation to FIGS. 114A-114F. This illustration provides an example embodiment of a rod that is not currently being bent, as it is only in contact with the bender's center rod-contouring surface and not in contact with either of the rollers.

FIG. 115B displays an embodiment 11515 representing the software calculations as previously described in relation to FIGS. 114A-114F. The coordinates of the left roller 11521 and right roller 11523 are shown intersecting with the rod's outer segment 11507 and center curve 11511. The left roller 11521, right roller 11523, and center rod-contouring surface 11508 are each segmented by vertical lines as the algorithms utilize these infinitesimally small divisions of each component to assess if the coordinates of the previously-registered rod 11507, 11511, 11510 are intersecting with any of these components, as is the case when the rod is being bent. In this illustration, a region of the rod 11519 is intersecting with the area of the left roller 11521, as well as another area 11520 that is intersecting with the right roller 11523. This intersection is detected via the software's analysis of each vertical line, as previously described in relation to FIGS. 114A-114F. The right roller contains some vertical lines 11517 that are intersecting with the rod's surface and others 11522 that are not. Similarly, the left roller 11521 contains vertical lines 11519 that are intersecting with the registered rod's coordinates, and other vertical lines 11516 that are not intersecting with the rod's coordinates. The area of the center rod contouring surface 11508 is also segmented with multiple vertical lines 11526, one of which is tangential to the rods inner surface 11510.

FIG. 115C displays the partially reconstructed rod to accommodate the geometry of the rod bender previously described in relation to FIG. 115B. This illustration displays the center vertical line 11532 that is coincident with the centroid 11509 of the bender's rod-contouring surface, in addition to the left rotated line 11531 and right rotated line 11533 that can be used to incrementally assess how much the rod is being bent based on the current geometry of the rod bender, as previously described in relation to FIGS. 114A-114F. This illustration displays the left unbent rod segment, consisting of the left outer unbent rod segment 11539, left center unbent rod segment 11540, and left inner unbent rod segment 11541 in addition to the right unbent rod segment consisting of the outer right unbent rod segment 11536, right center unbent rod segment 11537, and inner right unbent rod segment 11538. These unbent segments have been rotated by the angle that enables them to no longer intersect with any of the bender's rod-interface components, but rather be tangential to each as is visualized by the left roller's perimeter 11521 being tangential with the outer left unbent rod segment and the right roller's perimeter 11523 being tangential with the outer right unbent rod segment 11536. The reconstructed inner left bent rod segment 11542 and reconstructed inner right bent rod segment 11543 are defined by the curve of the center rod-contouring surface in between the intersection of its perimeter 11508 and the left 11531 and right 11533 rotated lines. The left and right inner bent rod segments 11542, 11543 are then utilized to compute the left outer bent rod segment 11534 and right outer bent rod segment 11535.

FIG. 115D displays a zoomed-in view 11550 of the embodiment portrayed in FIG. 115C containing the center vertical line 11532, left rotated line 11531, right rotated line 11533, perimeter of center rod-contouring surface 11508 (shown here as circle but does not need to be circular for algorithm to function properly), reconstructed outer left bent rod segment 11534, reconstructed outer right bent rod segment 11535, reconstructed inner left bent rod segment 11542, reconstructed inner right bent rod segment 11543, the left unbent rod segments consisting of the left outer unbent rod segment 11539, left center unbent rod segment 11540, and left inner unbent rod segment 11541, as well as the right unbent rod segments consisting of the right outer unbent rod segment 11536, right center unbent rod segment 11537, and right inner unbent rod segment. The outer surface of the bender's center rod-contouring surface 11508 is visualized, along with its segmenting vertical lines 11553. This closer view allows for a more detailed perspective of the reconstructed inner left bent rod segment 11542 and reconstructed inner right bent rod segment which are defined by the curve of the perimeter of the bender's center rod-contouring surface 11508 in between the intersection of the left rotated line 11531 and right rotated line 11533. This illustration also displays the reconstructed outer left bent rod segment 11534 and reconstructed right outer bent rod segment 11535 at the stage prior to a spline connecting these segments to the right-most point of the left outer unbent rod segment 11539, and the left-most point of the right outer unbent rod segment 11536, as previously described in relation to FIGS. 114A-114F. At the stage of the software algorithm that the illustration displays, there is an outer rod surface gap region 11551 between the outer bent rod segments 11534, 11535 and the outer unbent rod segments 11539, 11536. Additionally, there is an overlap region 11552 of the inner rod surface following the rotation and translation of the right unbent rod segments and prior to the removal of rod coordinates in between the left 11531 and right 11533 rotated lines that enable non-overlapping reconstruction of the inner and outer bent rod segments as previously described in relation to FIGS. 114A-114F.

FIG. 115E displays the fully reconstructed rod for the same bender position previously described in relation to FIGS. 115B-115D containing the perimeter of the bender's center rod-contouring surface 11508, the perimeter of the left roller 11521, perimeter of the right roller 11523, left outer unbent rod segment 11539, left center unbent rod segment 11540, and left inner unbent rod segment 11564 with its coordinates to the right of the left rotated line (not shown) removed, as well as the right outer unbent rod segment 11536, right center unbent rod segment 11537, and right inner unbent rod segment 11565 with its coordinates to the left of the right rotated line (not shown) removed. The reconstructed inner bent rod segment 11561 is made from fusing the left and right inner bent rod segments as shown previously in relation to FIGS. 115C-115D. The reconstructed outer bent rod segment 11563 is calculated from the inner reconstructed bent rod segment 11561 as described previously in relation to FIGS. 114A-114F and any potential gap between the outer unbent rod segments 11539, 11536 and the reconstructed outer bent rod segment 11563 has been filled via a previously fit curve (not shown) between the right-most point of the left outer unbent rod segment 11539, reconstructed outer bent rod segment 11563, and left-most point of the right outer unbent rod segment 11536. This illustration displays the software-rendered updated contour of the rod that would be updated on a display monitor for a user.

FIG. 115F displays a zoomed-in view of that which was shown previously in FIG. 115E containing the perimeter of the bender's center rod-contouring surface 11508, right outer unbent rod segment 11536, right center unbent rod segment 11537, right inner unbent rod segment 11565, left outer unbent rod segment 11539, left center unbent rod segment 11540, left inner unbent rod segment 11564, reconstructed inner bent rod segment 11561 which is utilized to compute the reconstructed center bent rod segment 11562 and reconstructed outer bent rod segment 11563.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general-purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally, or in particular formats that enable the construction or depiction of a physical and tangible object. In some embodiments, the manipulation can be performed by a processor. In such an example, the processor thus transforms the data from one thing to another. Still further, some embodiments include methods can be processed by one or more machines or processors that can be coupled over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A system comprising:

at least one dynamic reference frame, the at least one dynamic reference frame (DRF) configured so that any fixed or mobile portion of the DRF, or any assembly or component coupled to the DRF can be registered in 3D space using a plurality of trackable markers, the plurality of trackable markers including at least one moveable or triggerable marker;

at least one user-actuation trigger or actuator coupled to the at least one moveable or triggerable marker, the at least one user-actuation trigger or actuator configured and arranged to trigger or actuate the at least one moveable or triggerable marker;

at least one 3D tracking camera or imaging system configured to track one or more of the plurality of trackable markers; and a processor and a memory coupled to the processor, the memory storing instructions executable by the processor to track one or more 3D coordinates of one or more of the plurality of trackable markers.

* * * * *